(12) United States Patent
Pugh et al.

(10) Patent No.: US 11,788,136 B2
(45) Date of Patent: Oct. 17, 2023

(54) HYBRID-CAPTURE SEQUENCING FOR DETERMINING IMMUNE CELL CLONALITY

(71) Applicant: UNIVERSITY HEALTH NETWORK, Toronto (CA)

(72) Inventors: Trevor John Pugh, Toronto (CA); David Thomas Mulder, Hamilton (CA); Etienne Raymond G. A. Mahe, Calgary (CA)

(73) Assignee: University Health Network, Toronto (CA)

( * ) Notice: Subject to any disclaimer, the term of this patent is extended or adjusted under 35 U.S.C. 154(b) by 714 days.

(21) Appl. No.: 16/617,826

(22) PCT Filed: May 29, 2018

(86) PCT No.: PCT/CA2018/000104
§ 371 (c)(1),
(2) Date: Nov. 27, 2019

(87) PCT Pub. No.: WO2018/218332
PCT Pub. Date: Dec. 6, 2018

(65) Prior Publication Data
US 2020/0115749 A1    Apr. 16, 2020

Related U.S. Application Data

(60) Provisional application No. 62/512,255, filed on May 30, 2017.

(51) Int. Cl.
| | | |
|---|---|---|
| C12Q 1/6874 | (2018.01) | |
| G16B 30/10 | (2019.01) | |
| C12N 15/10 | (2006.01) | |
| C40B 40/06 | (2006.01) | |

(52) U.S. Cl.
CPC ....... *C12Q 1/6874* (2013.01); *C12N 15/1093* (2013.01); *G16B 30/10* (2019.02); *C40B 40/06* (2013.01)

(58) Field of Classification Search
None
See application file for complete search history.

(56) References Cited

U.S. PATENT DOCUMENTS

| | | | |
|---|---|---|---|
| 2,392,551 | A | 1/1946 | Roe |
| 6,189,282 | B1 | 2/2001 | VanderWerf |
| 9,453,341 | B1 | 9/2016 | Swierad et al. |
| 2007/0292216 | A1 | 12/2007 | Hamel |
| 2008/0125333 | A1 | 5/2008 | Labgold et al. |
| 2010/0018146 | A1 | 1/2010 | Aube et al. |
| 2010/0029498 | A1 | 2/2010 | Gnirke |
| 2011/0072753 | A1 | 3/2011 | MacDonald |
| 2014/0331343 | A1 | 11/2014 | Bradley et al. |
| 2015/0218620 | A1 | 8/2015 | Behlke et al. |

FOREIGN PATENT DOCUMENTS

| | | |
|---|---|---|
| WO | WO 2016/090273 | 6/2016 |
| WO | WO 2017/013436 | 1/2017 |
| WO | WO 2017/177308 | 10/2017 |

OTHER PUBLICATIONS

He et al., "IgH gene rearrangements as plasma biomarkers in Non-Hodgkin's Lymphoma patients," Oncotarget 2011, 2:178-185. (Year: 2011).*
Extended European Search Report issued in Corresponding European Application No. 18810749.4, dated Apr. 19, 2021.
Yaari et al., "Practical guidelines for B-cell receptor repertoire sequencing analysis" Genome Medicine 2015, 7(1), 14 pages.
Bleakley et al., "Recovering probabilities for nucleotide trimming processes for T cell receptor TRA and TRG V-J junctions analyzed with IMGT tools", BMC Bioinformatics, 9:408, 2008.
Jiang et al., "VDJ-Seq: Deep Sequencing Analysis of Rearranged Immunoglobulin Heavy Chain Gene to Reveal Clonal Evolution Patterns of B Cell Lymphoma", J Vis Exp., 106:053215, 2015.
Mamedov et al., "Preparing unbiased T-cell receptor and antibody cDNA libraries for the deep next generation sequencing profiling", Front Immunol., 4:456, 2013.
Matsuda et al., "The complete nucleotide sequence of the human immunoglobulin heavy chain variable region locus", J Exp Med., 188(11):2151-2162, 1998.
Monod et al., "IMGT/JunctionAnalysis: the first tool for the analysis of the immunoglobulin and T cell receptor complex V-J and V-D-J Junctions", Bioinformatics, 20 Suppl 1 :i379-385, 2004.
Partial Supplementary European Search Report Issued in Corresponding EP Patent Application No. 18810749.4, dated Jan. 12, 2021.
Woodsworth et al., "Sequence analysis of T-cell repertoires in health and disease", Genome Med., 5(10):98, 2013.
Gao & Wang, "Ligation-Anchored PCR Unveils Immune Repertoire of TCR-Beta from Whole Blood," BMC Biotechnology, 15-39, 2015.
Yaari & Kleinstein, "Practical Guidelines for B-Cell Receptor Repertoire Sequencing Analysis," Genome Medicine, 7: 121, 2015.
He, J. et al., "IgG gene rearrangements as plasma biomarkers in non-Hodgkin's lymphoma patients." Oncotarget 2011, 2(3), 178-185.

(Continued)

Primary Examiner — Kaijiang Zhang
(74) Attorney, Agent, or Firm — Norton Rose Fulbright US LLP

(57) ABSTRACT

A method of capturing a population of T-Cell receptor and/or immunoglobulin sequences with variable regions within a patient sample, the method comprising: extracting and/or preparing DNA fragments from the patient sample; ligating a nucleic acid adapter to the DNA fragments, the nucleic acid adapter suitable for recognition by a pre-selected nucleic acid probe; capturing DNA fragments existing in the patient sample using a collection of nucleic acid hybrid capture probes, wherein each capture probe is designed to hybridize to a known V gene segment and/or a J gene segment within the T cell receptor and/or immunoglobulin genomic loci.

21 Claims, 19 Drawing Sheets
(18 of 19 Drawing Sheet(s) Filed in Color)
Specification includes a Sequence Listing.

(56) References Cited

OTHER PUBLICATIONS

International Search Report and Written Opinion issued in corresponding application No. PCT/CA2018/000104, dated Sep. 4, 2018.
Bashford-Roger, et al., "Capturing Needles in Haystacks: A Comparison of B-Cell Receptor Sequencing Methods," *BMC Immunology*, 15: 29, 2014.
Bolotin, et al., "Next Generation Sequencing for TCR Repertoire Profiling Platform-Specific Features and Correction Algorithms," *European Journal Immunology*, 42: 3073-3083, 2012.
Brochet et al., "IMGTN-QUEST: the Highly customized and integrated system for IG and TR standardized V-J and V-D-J sequence analysis" *Nucleic Acids Res.*, 2008, 36:W503-508.
Camacho et al., "BLAST+: architecture and applications" *BMC Bioinformatics*, 2009, 10:421.
Extended European Search Report issued in corresponding Application No. 17781661.8, dated Nov. 18, 2019.
Fisher, et al., "Neuroblastoma Killing Properties of V-Delta 2 and V-Delta2 Negative Gamma Delta T Cells Following Expansion by Artificial Antigen Presenting Cells," *Clinical Cancer Research*, 20(22): 5720-5732, 2014.
Gazzola et al., "The evolution of clonality testing in the diagnosis and monitoring of hematological malignancies" *Therapeutic Advances in Hematology.*, 2014, 5(2):35-47.
Halper-Stromberg, et al., "Fine Mapping of V(D)J Recombinase Mediated Rearrangements in Human Lymphoid Malignancies," *BMC Genomics*, 14: 565, 2014.
Herman et al., "Filter-based hybridization capture of subgenomes enables resequencing and copy-number detection" *Nature Methods* 2009, 6(7), 7 pages.
Jiang, et al., "Deep Sequencing Reveals Clonal Evolution Patterns and Mutation Events Associated with Relapse in B-Cell Lymphomas," *Genome Biology*, 15: 432, 2014.
Li, HD "Fast and accurate short read alignment with Burrows-Wheeler Transform" Bioinformatics, 2009, 25:1754-1760.
Lin, et al., "Highly Sensitive and Unbiased Approach for Elucidating Antibody Repertoires," *PNAS*, 113(28):7826-7851, 2016.
Linneman, et al., "High-Throughput Identification of Antigen-Specific TCRs by TCR Gene Capture," *Nature Medicine*, 19(11): 1534-1541, and Supplementary Information, 2013.
Liu et al. "Systematic Comparative Evaluation of Methods for Investigating the TCRβ Repertoire" PLOS One 2016, 18 pages.
Logan, et al., "High-Throughput VDJ Sequencing for Quantification of Minimal Residual Disease in Chronic Lymphocytic Leukemia and Immune Reconstitution Assessment," *PNAS*, 108(52): 21194-21199, 2011.
Mahe, "Design & Validation of a Hybrid-Capture Next-Generation Sequencing-Based T-Cell Clonality Assay," Master of Science Thesis, University of Toronto, Graduate Department of Laboratory Medicine and Pathobiology, 2016.
Mamanova et al. "Target-enrichment strategies for next-generation sequencing" *Nat. Methods*, 2010, 7(2):111-118.
Mamedov, et al., "Quantitative Tracking of T Cell Clones After Haematopoietic Stem Cell Transplantation," *EMBO Mol. Med*, 201-207, 2011.
Mulder, et al., "CapTCR-Seq: Hybrid Capture for T-Cell Receptor Repetoire Profiling," *Blood Advances*, 2(23): 3506-3514, 2018.
Office Action Issued in U.S. Appl. No. 16/093,825, dated Aug. 18, 2020.
Parkinson, et al., "Violation of the 12/23 Rule of Genomic V(D)J Recombination is Common in Lymphocytes," *Genome Research*, 25: 226-234, 2015.
Rosati, et al., "Overview of Methodologies for T-Cell Receptor Repertoire Analysis," *BMC Biotechnology*, 17: 61, 2017.
Ruggiero, et al., "High-resolution analysis of the human T-cell receptor repertoire" *Nature Communications* 2015, 1-7.
Smith et al., "Identification of common molecular subsequences" *J. Mot. Biol.*, 1981, 147(1):195-197.

\* cited by examiner

HYBRID-CAPTURE SEQUENCING FOR DETERMINING IMMUNE CELL CLONALITY

CROSS-REFERENCE TO RELATED APPLICATIONS

This application is a national phase application under 35 U.S.C. § 371 of International Application No. PCT/CA2018/000104 filed 29 May 2018, which claims priority to U.S. Provisional Application No. 62/512,255 filed 30 May 2017. The entire contents of each of the above-referenced disclosures is specifically incorporated by reference herein without disclaimer.

FIELD OF THE INVENTION

The invention relates to methods of capturing and sequencing immune-associated nucleotide sequences, and more particularly to methods of determining clonality of immune cells.

BACKGROUND OF THE INVENTION

The maturation of lymphocytes is a fascinating process that is marked not only by immunophenotypic changes, but also by discrete and regulated molecular events[1-3]. As T-cells mature, an important part of the associated molecular "maturation" involves the somatic alteration of the germline configuration of the T-cell receptor (TR) genes to a semi-unique configuration in order to permit the development of a clone of T-cells with an extracellular receptor specific to a given antigen[1-3]. B-cells undergo a similar maturation process involving different loci that encode the antibody-containing B-cell receptor (BR). These clones, when considered together as a population, produce a repertoire of antigen sensitivity orders of magnitude larger than would be possible by way of inherited immunological diversity alone[3]. Indeed, the somatic rearrangement of the TR and BR genes is one of the key ontological events permitting the adaptive immune response[3].

When molecular carcinogenesis occurs in a lymphoid cell lineage, the result is the selective growth and expansion of the tumoural lymphocytes relative to their normal counterparts[2]. The so-called precursor (historically termed "lymphoblastic") lesions are believed to reflect molecular carcinogenesis in lymphoid cells at a relatively immature stage of maturation[2]. In contrast, if molecular carcinogenesis occurs at a point during or after the process of T-cell receptor gene re-arrangement (TRGR), the result is a "mature" (often also termed "peripheral") T-cell lymphoma in which the tumour contains a massively expanded population of malignant T-cells with an immunophenotype reminiscent of mature lymphocytes, most if not all bearing an identical TR gene configuration[4]. It is this molecular "homogeneity" of the TR configuration within a T-cell neoplasm that defines the concept of clonality in T-cell neoplasia[1,2,4].

The T-cell receptor is a heteroduplex molecule anchored to the external surface of T lymphocytes[5,21]; there the TR, in cooperation with numerous additional signalling and structural proteins, functions to recognize an antigen with a high degree of specificity. This specificity, and indeed the vast array of potential antigenic epitopes that may be recognized by the population of T-cells on the whole, is afforded by (1) the number of TR encoding regions of a given T-cell receptor's genes as present in the germline; and (2) the intrinsic capacity of the TR gene loci to undergo somatic re-arrangement[3]. There are four TR gene loci, whose protein products combine selectively to form functional TRs: T-cell receptor alpha (TRA) and T-cell receptor beta (TRB) encode the α and β chains, respectively, whose protein products pair to form a functional α/β TR; T-cell receptor gamma (TRG) and T-cell receptor delta (TRD) encode the γ and δ chains, respectively, whose protein products pair to form a functional γ/δ TR. The vast majority (>95%) of circulating T-cells are of the α/β type[21,22]; for reasons as yet not fully understood, γ/δ T-cells tend to home mainly to epithelial tissues (e.g. skin and mucosae) and appear to have a different function than the more common a/s type T-cells.

The TRA locus is found on the long arm of chromosome 14 in band 14q11.2 and spans a total of 1000 kilobases (kb)[23]; interestingly, sandwiched between the TRA V and J domains, is the TRD locus (14q11.2), itself spanning only 60 kb[24]. The TRB locus is found on the long arm of chromosome 7 in band 7q35 and spans a total of 620 kb[25]. The TRG locus is found on the short arm of chromosome 7 in region 7p15-p14 and spans 160 kb[26].

Within each TR gene locus are a variable number of variable (V) and join (J) segments[23-26] additional diversity (D) segments are present within the TRB and TRD loci[24,25]. These V, D and J segments are grouped into respective V, D and J regions (see FIG. 1-1). In the germline configuration, a full complement of V (numbering from 4-6 in TRG to 45-47 in TRA), D (2 in TRB and 3 in TRD) and J (numbering as few as 4 in TRD to as many as 61 in TRA) segments can be detected, varying based on inheritance[23-26]. In this configuration, the specificity of any resulting coding sequence would be uniformly based on inherited variation. During maturation, however, somatic mutation (i.e. rearrangement) occurs such that there is semi-random recombination of variable numbers of the V, D and J segments to produce a lineage of cells with a "rearranged" configuration of TR gene segments. This gene re-arrangement, when later subject to gene transcription and translation, produces a TR unique to the given T-lymphocyte (and its potential daughter cells). This process is represented pictorially in FIG. 1-2. Although the specific details of this re-arrangement process are far beyond the scope of this work, the process is at least partly mediated by enzymes of similar function to those used to perform splicing[21,22].

BIOMED-2[29] is a product of several years of collaborative expert study, resulting in a thoroughly studied consensus T-cell clonality assay. The BIOMED-2 assay includes multiplexed primer sets for both Immunoglobulin (IG) and TR clonality assessment and can be implemented with commercially available electrophoresis systems (e.g. Applied Biosystems fluorescence electrophoresis platforms)[29]. These commercially available primer sets have the advantage of standardization and ease of implementation. In addition, by virtue of the extensive study performed by the BIOMED consortium, the BIOMED-2 assay has the well-documented advantage of capturing the mono-clonality of the vast majority of control lymphomas bearing productive T-cell receptors (i.e. flow-sorted positive for either α/β or γ/δ T-cell receptors) using the specified TRB and TRG primer sets[29]. Of note, having been in use for over a decade, the BIOMED-2 has been globally accepted as the diagnostic assay primer set of choice.

The current approach to TRGR testing is subject to a number of technical and practical caveats that dilute the applicability of TRGR testing to the full breadth of real-world contexts.

Because the PCR-based techniques that are employed in TRGR assays are subject to amplicon size restrictions[29,34], the sheer size of the TRA locus prevents a complete assay of the TRA gene in clinical settings. Indeed, although of smaller size, the TRB locus as a whole is also prohibitively large to sequence in its germline configuration. It is therefore of no surprise that much of the published data pertaining to the utility and validity of TRGR assays has stemmed from assays specific to only subparts of TRB as well as TRG, a locus of size much more amenable to a single-assay. In addition, since the TRD locus is often deleted after TR gene rearrangement (since it is contained within the TRA locus and excised whenever the TRA locus is rearranged), assays for TRD have also not been as rigorously studied. For this reason, any BIOMED-2-based T-cell clonality assay aimed at directing immunotherapy, requiring a complete sequence-based understanding of the TR genes involved, would be insufficient.

The BIOMED-2 assay is subject to additional technical challenges. As part of the standard TRGR assay, most laboratories rely on the demonstration of electrophoretic migration patterns for the determination of TR clonality. Interpretation of the assay depends on the demonstration (or lack thereof) of a dominant amplicon of specific (albeit not pre-defined) molecular weight, rather than the normal Gaussian distribution of amplicons of variable size. This approach, as has been described previously[35-47], is subject to interpretative error and other technical problems. Also, given the large amounts of DNA required for the multitude of multiplex tubes making up the assay, the overall assay can very quickly deplete DNA supplies, especially when obtained from limited sample sources.

Finally, and arguably of greatest import, is the issue of diagnostic bias used in the study of TRGR assay performance. More precisely, when laboratories seek to validate a TRGR assay, the requirement of "standard" samples will typically require that the laboratory utilize previously established clonal samples or samples previously diagnosed and accepted to represent clonal entities (e.g. previously diagnosed cases of lymphoma); these samples are in turn compared to "normal" controls. In contrast, the demographics of subsequent "real-life" test samples are unlikely to be so decidedly parsed into "normal" and "abnormal" subsets.

Current T-Cell Receptor (TCR) rearrangement profiling assays rely on targeted PCR amplification of rearranged TCR genomic loci. The simplest method for assessing clonality of T-cells involves qualitative assessment through multiplexed amplification of the individual loci using defined primer sets and interpretation of fragment size distributions according to the BIOMED2 protocol[41,2]. Next-generation sequencing can be used as a read-out to provide quantitative assessment of the TCR repertoire including detection of low abundance rearrangements from bulk immune cells, or even pairing of the heterodimeric chain sequences with single cell preparation methods[43,4]. Hybrid-capture based library subsetting is an alternative method to PCR-based amplification that can improve coverage uniformity and library complexity when sample is not limiting and allows for targeted enrichment of genetic loci of interest from individual genes to entire exomes[45]. In hybrid-capture methods, the formation of probe-library fragment DNA duplexes are used to recover regions of interest[46 7,8].

Similar to T-cells, B-cells involved in adaptive immunity also undergo somatic rearrangement of germline DNA to encode a functional B-cell receptor (BR). Like TRs, these sequences comprise by discrete V, D, J segments that are rearranged and potentially altered during B-cell maturation to encode a diversity of unique immunoglobulin proteins. The clonal diversity of B-cell populations may have clinical utility and, similar to T-cell lymphomas, several cancers are characterized by clonal expansion of specific BR/Ig sequences.

SUMMARY OF THE INVENTION

There is described herein, the development of a novel NGS-based T-cell clonality assay, incorporating all four TR loci. The assay was both analytically and clinically validated. For the former, a series of idealized specimens was used, with combined PCR/Electrophoresis and Sanger Sequencing to confirm NGS-data. The latter validation compared NGS results to the current gold standard for clinical T-cell clonality testing (i.e. the BIOMED-2 primer PCR method) on an appropriately-sized minimally-biased sample of hematopathology specimens. In the latter dataset also, the patterns of T-cell clonality were also correlated with clinical, pathologic, and outcome data.

In an aspect, there is provided, a method of capturing a population of T-Cell receptor and/or immunoglobulin sequences with variable regions within a patient sample, said method comprising: extracting/preparing DNA fragments from the patient sample; ligating a nucleic acid adapter to the DNA fragments, the nucleic acid adapter suitable for recognition by a pre-selected nucleic acid probe; capturing DNA fragments existing in the patient sample using a collection of nucleic acid hybrid capture probes, wherein each capture probe is designed to hybridize to a known V gene segment and/or a J gene segment within the T cell receptor and/or immunoglobulin genomic loci.

In an aspect, there is provided, a method of immunologically classifying a population of T-Cell receptor and/or immunoglobulin sequences, the method comprising:
(a) identifying all sequences containing a V gene segment from the sequences of the DNA fragments by aligning the sequences of the DNA fragments to a library of known V gene segment sequences;
(b) trimming the identified sequences in (a) to remove any sequences corresponding to V gene segments to produce a collection of V-trimmed nucleotide sequences;
(c) identifying all sequences containing a J gene segment in the population of V-trimmed nucleotide sequences by aligning the V-trimmed nucleotide sequences to a library of known J gene segment sequences;
(d) trimming the V-trimmed nucleotide sequences identified in (c) to remove any sequences corresponding to J gene segments to produce VJ-trimmed nucleotide sequences;
(e) identifying any D gene segment comprised in the VJ-trimmed nucleotide sequences identified in (d) by aligning the VJ-trimmed nucleotide sequences to a library of known D gene segment sequences;
(f) for each VJ-trimmed nucleotides sequence identified in (d), assembling a nucleotide sequence comprising the V gene segment, any D gene segment, and the J gene segment identified in steps (a), (e) and (c) respectively;
(g) selecting from the nucleotide sequence assembled in step (f) a junction nucleotide sequence comprising at least the junction between the V gene segment and the J gene segment, including any D gene segment, the junction nucleotide sequence comprising between 18 bp and 140 bp, preferably 40-100 bp, further preferably about 80 bp;

and optionally (h) and (i):
(h) translating each reading frame of the junction nucleotide sequence and its complementary strand to produce 6 translated sequences; and
(i) comparing the 6 translated sequences to a library of known CDR3 regions of T-Cell receptor and/or immunoglobulin sequences to identify the CDR3 region in the DNA fragments.

In an aspect, there is provided, a method of identifying CDR3 regions in T-Cell receptor and/or immunoglobulin sequences, the method comprising:
(a) identifying a V gene segment comprised in the immunoglobulin sequence by aligning the immunoglobulin sequence to a library of known V gene segment sequences;
(b) identifying a J gene segment comprised in the immunoglobulin sequence by aligning the immunoglobulin sequence to a library of known J gene segment sequences;
(c) if V and J gene segments are identified, then comparing the immunoglobulin sequence to a library of known CDR3 regions of T-Cell receptor and/or immunoglobulin sequences to identify any CDR3 region in the immunoglobulin sequence.

BRIEF DESCRIPTION OF FIGURES

The patent or application file contains at least one drawing executed in color. Copies of this patent or patent application publication with color drawing(s) will be provided by the Office upon request and payment of the necessary fee.

These and other features of the preferred embodiments of the invention will become more apparent in the following detailed description in which reference is made to the appended drawings wherein.

DETAILED DESCRIPTION

Figure 1:
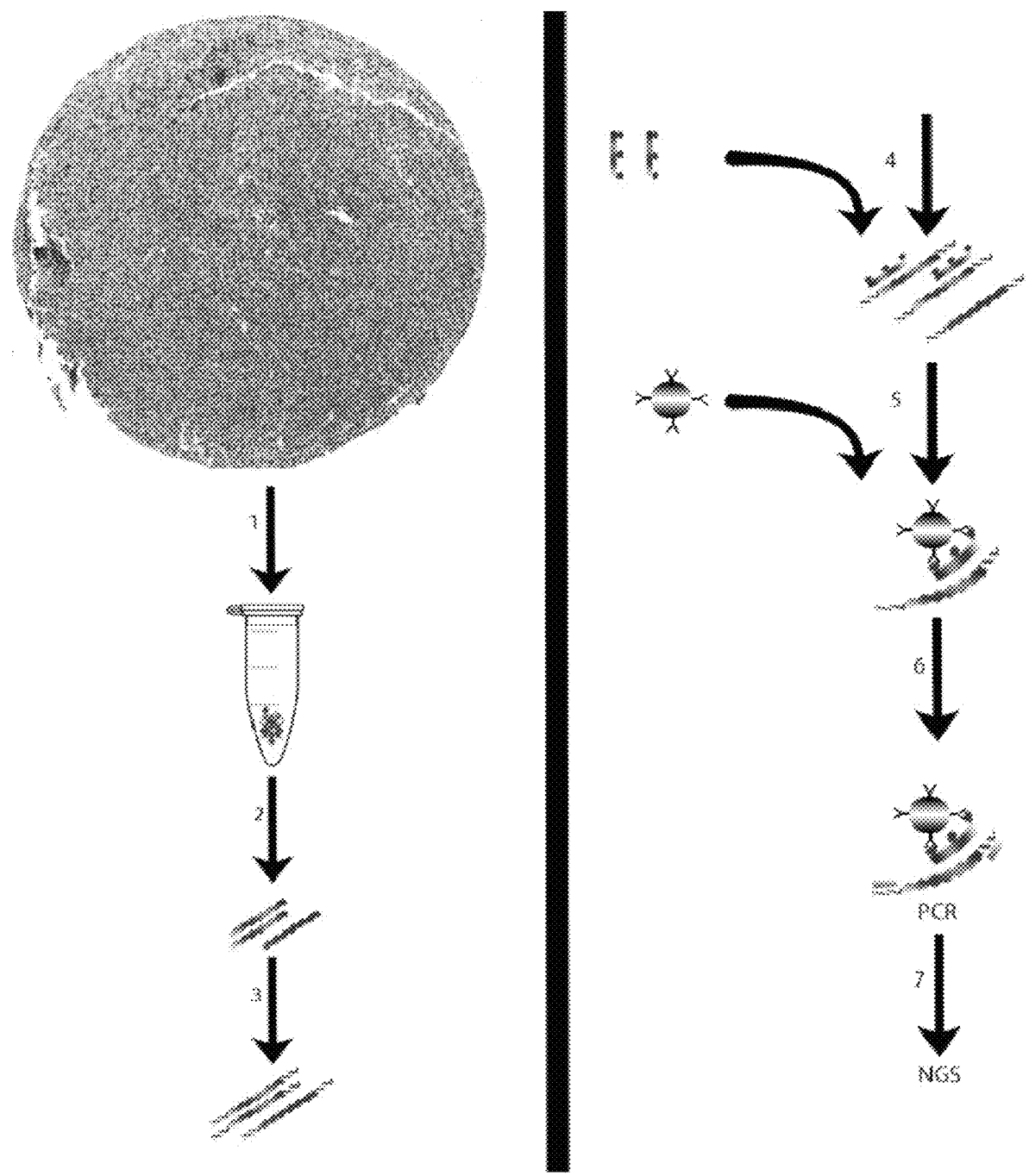
FIG. 1: TRGR Assay Wet-Bench Work-Flow Schematic. 1, DNA isolation; 2, Shearing (~200 bp); 3, Library Production; 4, Hybridization with Biotinylated DNA Probes; 5, Enrichment with Streptavidin-Bound Paramagnetic Beads; 6, PCR; 7, Illumina sequencing.
Figure 2:
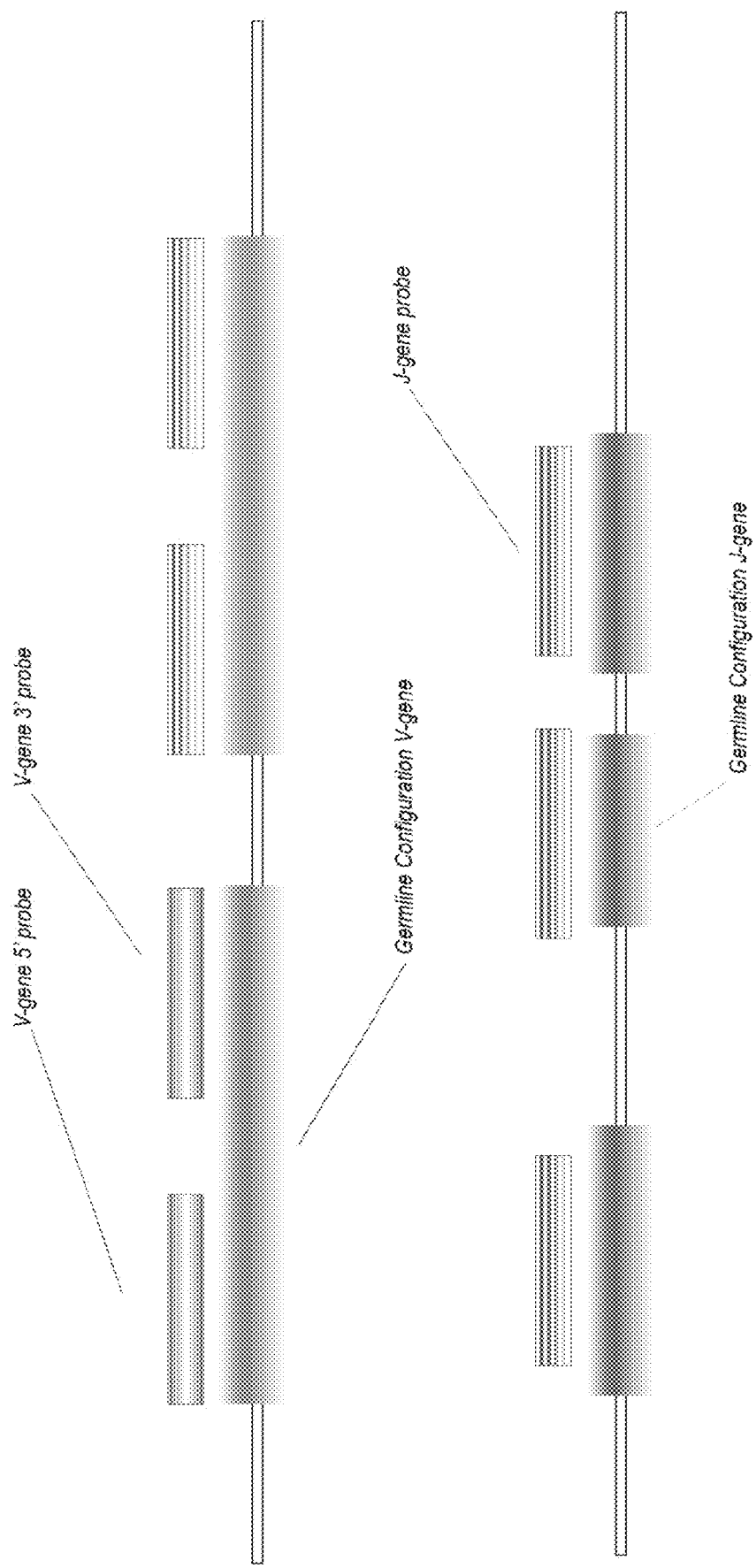
FIG. 2: Schematic Representation of V and J Gene Probe Placement Relative to the Germline. The germline V-genes are highlighted in solid red, with 100 bp probe placement shown above; probes are oriented inward and abut the 5' & 3' ends of the germline V-gene configuration. The germline J-genes are highlighted in solid blue, with 100 bp probe placement shown above; J-gene probes cover the entire J-gene, and on occasion some flanking extragenic sequence.

In the following description, numerous specific details are set forth to provide a thorough understanding of the invention. However, it is understood that the invention may be practiced without these specific details.

The advantages of high-throughput DNA sequencing technologies could potentially be applied to T-cell clonality testing. The nature of T-cell gene diversity, requiring the consideration of potential variability arising from four distinct gene loci, makes obvious the benefit of multiplexing; what has traditionally required multiple separate tests could be combined in a single reaction. The capacity of modern DNA sequencing technologies to query longer contiguous segments of DNA in greater quantities relative to traditional techniques also provides an opportunity to explore the potential meaning of TRA and TRB sequence rearrangements. Sequence-level data might afford a greater ease of assay result interpretation. Indeed, the generation of sequence-level data in a TRGR assay would likely be much more informative than gross estimates of DNA electrophoretic migration patterns when disease trends are being studied; the high-level analysis of such data might help the identification of heretofore hidden patterns of TR rearrangement in specific T-cell lymphoma subtypes. The issue of replicate numbers for establishing test sensitivity/specificity can be easily overcome by exploiting the high-throughput capacity of modern DNA sequencing platforms; for a comparable investment of time (and possibly cost), sequencing-based approach to TRGR could perform a greater number of individual tests, thereby potentially allowing a more statistically robust estimate of test performance.

Traditional sequencing uses PCR-based techniques to markedly amplify input template DNA, thus improving the sensitivity of detection during the sequencing step. Indeed, many sequencing-based technologies still perform directed library preparation using PCR-based techniques to isolate and sequence regions of interest[38]. By this approach, one might employ specific primer sets to enrich for regions of interest in the library preparation step. In the context of TRGR, however, a primer-based approach to library preparation would be challenging: in order to provide the sufficient breath of coverage required to interrogate the status of the vast number of TR genes (especially in the TRA locus), a massive array of primers would be required. Although it is theoretically possible to prime multiple regions in tandem, previous data suggest that such an approach might open the door to the possibility of technical error (for a more thorough review of the details of these errors and the studies that have supported this evidence, see[38]). In the context of TRGR, furthermore, a primer-based approach to library preparation introduces the possibility of allele dropout when the assay attempts to prime a rearranged gene based on the known germline configuration (an easily digestible review to this effect may be found here[39]).

A paradigm shift away from PCR primer-directed amplification of genomic areas of interest was required for sequencing experiments aimed at large numbers of genes. Indeed most sequencing-based technologies rather employ the upfront production of vast libraries of template oligonucleotides followed by a series of template enrichment steps[38]. These latter steps may simply involve the extraction of DNA of specific lengths or quality, or rather the focus may be to enrich DNA containing specific sequences of interest. In the latter scenario, when specific sequence motifs are enriched for during library preparation, the resulting sequencing data will be enriched for the sequences of interest. Additionally, using the above stepwise approach, library preparation may be generalized to permit the enrichment of specific sequences out of a mix of "all" sequences produced from the primary non-specific amplification step; it is easy to see how this approach may be used to permit multiple separate assays using different enrichment approaches applied to a single input library[40].

Hybrid capture is a form of library enrichment in which a library is probed for known sequences of interest using tagged nucleic acid probes followed by a subsequent "pull-down" of the tagged hybrids[38]; for example, DNA probes tagged with biotin can be efficiently enriched when hybridization is followed by a streptavidin enrichment step[38,40-43]. The biotin/streptavidin enrichment procedure is schematized in FIG. 1. In reference to the assessment of TRGR, this approach has the advantage of enriching TR genes based on the available well-defined germline TR gene sequences, which can be performed in a massively parallel fashion using several hundred probes. Notably, this approach also allows for enrichment of rearranged sequences as the hybrid-capture probes can also hybridize to (and therefore enrich for) subsequences of the rearrangement product. This latter "pull-down" of rearranged TR genes would be difficult using a primer-only approach to library preparation.

Rather than restricting the assessment of test performance of the above DNA sequencing approaches to a pre-set (and potentially biased) sample of "malignant" and "benign" T-cell lymphoproliferative disorders, a more prudent sampling rubric might use a "real-world" series of consecutive samples taken from a population as similar to the "test population" as possible. In the context of TRGR validation, such a sample might consist of a series of consecutive tissue samples from patients being worked-up by a hematologist and submitted for molecular (i.e. T-cell clonality) assessment. The overall sample size could be established based on an estimate of the historical incidence of T-cell lymphomas in such a population, such that the total size of the sample is adequately large to include a sufficient "expected" number of clonal T-cell lymphoproliferative disorders.

In many validation studies, the final pathology diagnosis is used as the gold standard against which the novel test is measured[41]. While not unreasonable, there are arguments against employing such an approach. Of foremost concern is the potential for diagnostic or interpretative error, by which "true positivity" of disease could be misappropriated[44]. In the realm of T-cell lymphomas, given at least partly due to their rarity, the frequent lack of pathologist experience might make this problem more likely. Furthermore, evidence indicates that even when diagnoses are based on consensus or panel based interpretation, the possibility of diagnostic bias by dominant opinion should be considered[45].

When a single clearly-defined outcome measure does not exist (or is limited by bias), a composite gold-standard might be more appropriate[46]. Composite gold-standards might include a number of individual test results or clinical observations logically combined to produce "positive" or "negative" composites[46]; of key import is that (1) well-defined rules of composition be set out a priori and (2) the number of samples or subjects with each of the composite test results should be well-described[46]. Ideally, all samples or subjects should be evaluated using each of the composite tests[46].

In order to best study a novel test of TLPDs, rather than limiting the reference test to the gold-standard BIOMED-2 T-cell clonality assay or to pathology diagnoses, a series of both individual and composite references might be considered. From the perspective of analytical validity, one might consider validating an sequencing-based TRGR assay using standard PCR techniques followed by Sanger sequence verification. Since the sequences of each of the TR V and J genes are known, forward and reverse primer sets for each V and J genes, respectively, identified by the capture and sequencing assay could be used to verify that the detected result is valid; this could be followed by Sanger sequencing to validate the result of the DNA sequencing result (with deference specifically to the CDR3 variability-defining region).

In another experiment, one might consider comparing a sequencing-based TRGR result to the BIOMED-2 result (with each test applied to all specimens under study). The primary limitation of this approach would be that the BIOMED-2 assay, as explained above, does not test for any TRA rearrangements; thus this comparison alone would be insufficient. Additional comparisons might involve assessment of the sensitivity and specificity of each of the BIOMED-2 and sequencing-based TRGR assays at identifying benign or malignant TLPDs. For this, a composite gold-standard including histologic features (i.e. pathology diagnosis), immunophenotypic features, additional molecular features (as available, e.g. cytogenetic changes), clinical observations (e.g. presence or absence of features of malignancy), and outcome results (e.g. significant deviation in individual patient survival from the median) might be considered. The clinical validity of the sequencing results could thus be assessed against the current diagnostic standard by means of a much more thorough evaluation.

T-cell lymphomas are cancers of immune cell development that result in clonal expansion of malignant clones that dominate the T-cell repertoire of affected patients. Therefore, clonality assessment of these cell populations is essential for the identification and monitoring of T-cell lymphomas. We have developed a hybrid-capture method that recovers rearranged sequences of T-cell receptor (TCR) chains from all four classes (alpha, beta, gamma, and delta loci) in a single reaction from an Illumina sequencing library. We use this method to describe the TCR V(D)J repertoire of monoclonal cancer cell lines, tumor-derived lymphocyte cultures, and peripheral blood mononuclear cells from a healthy donor, as well as a set of 63 clinical isolates sent for clinical clonality testing for suspected T-cell lymphoma. PCR amplification and Sanger sequencing confirmed cell line and tumor predominant rearrangements, individual beta locus V and J allele prevalence was well correlated with results from a commercial PCR-based DNA sequencing assay with an $r^2$ value of 0.94, and BIOMED2 PCR fragment size beta and gamma locus clonotyping of clinical isolates showed 73% and 77% agreement respectively. Our method allows for rapid, high-throughput and low cost characterization of TCR repertoires that will enhance sensitivity of tumor surveillance as well as facilitate serial analysis of patient samples with a quantitative readout during clinical immunotherapy interventions.

In an aspect, there is provided, a method of capturing a population of T-Cell receptor and/or immunoglobulin sequences with variable regions within a patient sample, said method comprising: extracting/preparing DNA fragments from the patient sample; ligating a nucleic acid adapter to the DNA fragments, the nucleic acid adapter suitable for recognition by a pre-selected nucleic acid probe; capturing DNA fragments existing in the patient sample using a collection of nucleic acid hybrid capture probes, wherein each capture probe is designed to hybridize to a known V gene segment and/or a J gene segment within the T cell receptor and/or immunoglobulin genomic loci.

As used herein, "T-Cell Receptor" or "TCR" means a molecule found on the surface of T lymphocytes (or T cells), preferably human, that is responsible for recognizing fragments of antigen as peptides bound to major histocompatibility complex (MHC) molecules. The TCR is a disulfide-linked membrane-anchored heterodimeric protein normally consisting of the highly variable alpha (α) and beta (β) chains expressed as part of a complex with the invariant CD3 chain molecules. T cells expressing this receptor are referred to as α:β (or αβ) T cells, though a minority of T cells express an alternate receptor, formed by variable gamma (γ) and delta (δ) chains, referred as γδ T cells. Each chain is composed of two extracellular domains: Variable (V) region and a Constant (C) region. The variable domain of both the TCR α-chain and β-chain each have three hypervariable or complementarity determining regions (CDRs). CDR3 is the main CDR responsible for recognizing processed antigen.

The terms "antibody" and "immunoglobulin", as used herein, refer broadly to any immunological binding agent or molecule that comprises a human antigen binding domain, including polyclonal and monoclonal antibodies. Depending on the type of constant domain in the heavy chains, whole antibodies are assigned to one of five major classes: IgA, IgD, IgE, IgG, and IgM. Several of these are further divided into subclasses or isotypes, such as IgG1, IgG2, IgG3, IgG4, and the like. The heavy-chain constant domains that correspond to the difference classes of immunoglobulins are termed α, δ, ε, γ and μ, respectively. The subunit structures and three-dimensional configurations of different classes of immunoglobulins are well known. The "light chains" of mammalian antibodies are assigned to one of two clearly distinct types: kappa (κ) and lambda (λ), based on the amino acid sequences of their constant domains and some amino acids in the framework regions of their variable domains. The variable domains comprise the complementarity determining regions (CDRs). The methods described herein may be applied to immunoglobulin sequences, including B-cell immunoglobulin sequences.

"V gene segments", "J gene segments" and "D gene segments" as used herein, refer to the variable (V), joining (J), and diversity (D) gene segments involved in V(D)J recombination, less commonly known as somatic recombination. V(D)J recombination is the mechanism of genetic recombination that occurs in developing lymphocytes during the early stages of T and B cell maturation. The process results in the highly diverse immune repertoire of antibodies/immunoglobulins (Igs) and T cell receptors (TCRs) found on B cells and T cells, respectively.

The term "nucleic acid" includes DNA and RNA and can be either double stranded or single stranded.

The term "probe" as used herein refers to a nucleic acid sequence that will hybridize to a nucleic acid target sequence. In one example, the probe hybridizes to the RNA biomarker or a nucleic acid sequence complementary thereof. The length of probe depends on the hybridization conditions and the sequences of the probe and nucleic acid target sequence. In one embodiment, the probe is at least 8, 10, 15, 20, 25, 50, 75, 100, 150, 200, 250, 400, 500 or more nucleotides in length.

The term "adapter" as used herein refers a moiety capable of conjugation to a nucleic acid sequence for a particular purpose. For example, the adapter may be used to identify or barcode the nucleic acid. Alternatively, the adapter may be a primer which can be used to amplify the nucleic acid sequence.

The term "hybridize" or "hybridizable" refers to the sequence specific non-covalent binding interaction with a complementary nucleic acid. In a preferred embodiment, the hybridization is under stringent conditions. Appropriate stringency conditions which promote hybridization are known to those skilled in the art, or can be found in Current Protocols in Molecular Biology, John Wiley & Sons, N.Y. (1989), 6.3.1 6.3.6. For example, 6.0× sodium chloride/sodium citrate (SSC) at about 45° C., followed by a wash of 2.0×SSC at 50° C. may be employed.

In some embodiments, the method further comprises sequencing the captured DNA fragments, wherein the sequencing can be used to determine clonotypes within the patient sample. Various sequencing techniques are known to the person skilled in the art, such as polymerase chain reaction (PCR) followed by Sanger sequencing. Also available are next-generation sequencing (NGS) techniques, also known as high-throughput sequencing, which includes various sequencing technologies including: Illumina (Solexa) sequencing, Roche 454 sequencing, Ion torrent Proton/PGM sequencing, SOLiD sequencing. NGS allow for the sequencing of DNA and RNA much more quickly and cheaply than the previously used Sanger sequencing. In some embodiments, said sequencing is optimized for short read sequencing.

In some embodiments, the method further comprises amplifying the population of sequences using nucleic acid amplification probes/oligonucleotides that recognize the adapter prior to said sequencing.

In some embodiments, the method further comprises fragmenting DNA extracted from the patient sample to generate the DNA fragments.

In some embodiments, the ligating step is performed before the capturing step.

In some embodiments, the capturing step is performed before the ligating step.

The term "patient" as used herein refers to any member of the animal kingdom, preferably a human being and most preferably a human being that has AML or that is suspected of having AML.

The term "sample" as used herein refers to any fluid, cell or tissue sample from a subject which can be assayed for nucleic acid sequences. In some embodiments, the patient sample comprises tissue, urine, cerebral spinal fluid, saliva, feces, ascities, pleural effusion, blood or blood plasma.

In some embodiments, the patient sample comprises cell-free nucleic acids in blood plasma.

In some embodiments, the clonality analyses described herein may be use to track clonality across samples types.

In some embodiments, the hybrid capture probes are at least 30 bp in length. In a further embodiment, the hybrid capture probes are between 60 bp and 150 bp in length. In a further embodiment, the hybrid capture probes are between 80 bp and 120 bp in length. In a further embodiment, the hybrid capture probes are about 100 bp in length.

In some embodiments, the hybrid capture probes hybridize to at least 30 bp, preferably 50 bp, more preferably 100 bp of the V gene segment and/or J gene segment.

In some embodiments, the hybrid capture probes hybridize to at least a portion of the V gene segment and/or J gene segment at either the 3' end or the 5' end of the V gene segment and/or J gene segment respectively.

In some embodiments, the screening probes hybridize to at least a portion of the V gene segment.

In some embodiments, the screening probes hybridize to at least a portion of the V gene segment at the 3' end.

In some embodiments, hybridizing comprises hybridizing under stringent conditions, preferably very stringent conditions.

In some embodiments, the collection of nucleic acid hybrid capture probes comprise at least 2, 5, 10, 20, 30, 80, 100, 300, 400, 500, 600, 700, 800 or 900 unique hybrid capture probes.

In some embodiments, the collection of nucleic acid hybrid capture probes is sufficient to capture at least 50%, 60%, 70%, 80%, 90% or 99% of known T-Cell receptor and/or immunoglobulin loci clonotypes.

In some embodiments, the hybrid capture probes are immobilized on an array.

In some embodiments, the hybrid capture probes comprise a label. In a further embodiment, the label is used to distinguish between sequences bound to the screening probes and unbound double stranded fragments, and preferably the capture is performed in solution.

In some embodiments, preparing the DNA fragments comprises extracting RNA from the patient sample and preparing corresponding cDNA.

In some embodiments, the method further comprises a depletion step, comprising depleting the DNA fragments of non-rearranged sequences using probes that recognize nucleic acid sequences adjacent to V and/or J gene segments in the genome. In some embodiments, the capturing of DNA fragments using V gene segment and J gene segment hybrid capture probes is performed in separate steps, and in any order with the depletion step, preferably in the following order: J gene capture, depletion, then V gene capture.

In an aspect, there is provided, a method of immunologically classifying a population of T-Cell receptor and/or immunoglobulin sequences, the method comprising:
  (a) identifying all sequences containing a V gene segment from the sequences of the DNA fragments by aligning the sequences of the DNA fragments to a library of known V gene segment sequences;
  (b) trimming the identified sequences in (a) to remove any sequences corresponding to V gene segments to produce a collection of V-trimmed nucleotide sequences;
  (c) identifying all sequences containing a J gene segment in the population of V-trimmed nucleotide sequences by aligning the V-trimmed nucleotide sequences to a library of known J gene segment sequences;
  (d) trimming the V-trimmed nucleotide sequences identified in (c) to remove any sequences corresponding to J gene segments to produce VJ-trimmed nucleotide sequences;
  (e) identifying any D gene segment comprised in the VJ-trimmed nucleotide sequences identified in (d) by aligning the VJ-trimmed nucleotide sequences to a library of known D gene segment sequences;
  (f) for each VJ-trimmed nucleotides sequence identified in (d), assembling a nucleotide sequence comprising the V gene segment, any D gene segment, and the J gene segment identified in steps (a), (e) and (c) respectively;
  (g) selecting from the nucleotide sequence assembled in step (f) a junction nucleotide sequence comprising at least the junction between the V gene segment and the J gene segment, including any D gene segment, the junction nucleotide sequence comprising between 18 bp and 140 bp, preferably 40-100 bp, further preferably about 80 bp; and optionally (h) and (i):
  (h) translating each reading frame of the junction nucleotide sequence and its complementary strand to produce 6 translated sequences; and
  (i) comparing the 6 translated sequences to a library of known CDR3 regions of T-Cell receptor and/or immunoglobulin sequences to identify the CDR3 region in the DNA fragments.

Alternatively, step (h) may be searching the 6 translated sequences for flanking invariable anchor sequences to define the intervening T-Cell receptor and/or B-cell receptor CDR3 sequences encoded by the DNA fragments.

In some embodiments, the method further comprises, prior to step (a), aligning left and right reads of overlapping initial DNA fragments to produce the DNA fragments on which step (a) is performed.

In some embodiments, steps (a), (c), (e) are performed with BLASTn and step (i) is performed using expression pattern matching to known sequences and IMGT annotated data.

In an aspect, there is provided, a method of identifying CDR3 regions in T-Cell receptor and/or immunoglobulin sequences, the method comprising:
  (a) identifying a V gene segment comprised in the immunoglobulin sequence by aligning the immunoglobulin sequence to a library of known V gene segment sequences;
  (b) identifying a J gene segment comprised in the immunoglobulin sequence by aligning the immunoglobulin sequence to a library of known J gene segment sequences;
  (c) if V and J gene segments are identified, then comparing the immunoglobulin sequence to a library of known CDR3 regions of T-Cell receptor and/or immunoglobulin sequences to identify any CDR3 region in the immunoglobulin sequence.

Alternatively, step (c) may be if V and J gene segments are identified, then searching the immunoglobulin sequence for flanking invariable anchor sequences to define the intervening T-Cell receptor and/or immunoglobulin CDR3 sequences.

In some embodiments, wherein steps (a) and (b) are performed using the Burrows-Wheeler Alignment or other sequence alignment algorithm.

In some embodiments, wherein if a CDR3 region is identified in step (c), then the method further comprises determining whether the identified V and J gene segments could be rearranged in the same locus using a heuristic approach.

In some embodiments, wherein if a CDR3 region is not identified in step (c), then the method further comprises determining if a combination of V(D)J gene segments is present based on Smith Waterman Alignment scores.

In an aspect, there is provided, a method for characterizing the immune repertoire of a subject, the immune repertoire comprising the subject's T-Cell population, the method comprising any of the hybrid capture methods described herein, any of the algorithmic methods described herein, or any combination thereof.

Any of the methods described herein may be used to capture a population of T-Cell receptor sequences, for immunologically classifying a population of T-Cell receptor sequences or for identifying CDR3 regions in T-Cell receptor.

In an aspect, the methods described herein are for characterizing T-cell clonality for a disease in the subject.

In some embodiments, the T-Cell receptor sequences are from tumour infiltrating lymphocytes.

In an aspect, the methods described herein are for identifying therapeutic tumour infiltrating lymphocytes for the purposes of expansion and reinfusion into a patient and/or adoptive cell transfer immunotherapy.

In an aspect, the methods described herein are for monitoring T-cell populations/turnover in a subject, preferably a subject with cancer during cancer therapy, preferably immunotherapy.

In an aspect, the methods described herein are for characterizing the immune repertoire of a subject, the immune repertoire comprising the subject's B-Cell population.

In an aspect, the methods described herein are for capturing a population of B-Cell receptor sequences with variable regions within a patient sample, for immunologically classifying a population of B-Cell receptor sequences, or for identifying CDR3 regions in B-Cell receptor sequences.

In an aspect, the methods described herein are for characterizing B-cell clonality as a feature of a disease in the subject.

The present methods may be used in subjects who have cancer. Cancers include adrenal cancer, anal cancer, bile duct cancer, bladder cancer, bone cancer, brain/cns tumors, breast cancer, castleman disease, cervical cancer, colon/rectum cancer, endometrial cancer, esophagus cancer, ewing family of tumors, eye cancer, gallbladder cancer, gastrointestinal carcinoid tumors, gastrointestinal stromal tumor (gist), gestational trophoblastic disease, hodgkin disease, kaposi sarcoma, kidney cancer, laryngeal and hypopharyngeal cancer, leukemia (acute lymphocytic, acute myeloid, chronic lymphocytic, chronic myeloid, chronic myelomonocytic), liver cancer, lung cancer (non-small cell, small cell, lung carcinoid tumor), lymphoma, lymphoma of the skin, malignant mesothelioma, multiple myeloma, myelodysplastic syndrome, nasal cavity and paranasal sinus cancer, nasopharyngeal cancer, neuroblastoma, non-hodgkin lymphoma, oral cavity and oropharyngeal cancer, osteosarcoma, ovarian cancer, pancreatic cancer, penile cancer, pituitary tumors, prostate cancer, retinoblastoma, rhabdomyosarcoma, salivary gland cancer, sarcoma—adult soft tissue cancer, skin cancer (basal and squamous cell, melanoma, merkel cell), small intestine cancer, stomach cancer, testicular cancer, thymus cancer, thyroid cancer, uterine sarcoma, vaginal cancer, vulvar cancer, waldenstrom macroglobulinemia, and wilms tumor.

In embodiments relating to T-cells, the subject may have a T-cell related disease, such as a T-cell lymphoma.

T-cell lymphomas are types of lymphoma affecting T cells, and can include peripheral T-cell lymphoma not otherwise specified, extranodal T cell lymphoma, cutaneous T cell lymphoma, including Sézary syndrome and Mycosis fungoides, anaplastic large cell lymphoma, angioimmunoblastic T cell lymphoma, adult T-cell Leukemia/Lymphoma (ATLL), blastic NK-cell Lymphoma, enteropathy-type T-cell lymphoma, hematosplenic gamma-delta T-cell Lymphoma, lymphoblastic Lymphoma, nasal NK/T-cell Lymphomas, treatment-related T-cell lymphomas.

In other embodiments relating to B-cells, the subject may have a B-cell related disease, plasma cell disorder, preferably a B-cell lymphoma.

B-cell are types of lymphoma affecting B cells and can include, diffuse large B-cell lymphoma (DLBCL), follicular lymphoma, marginal zone B-cell lymphoma (MZL) or mucosa-associated lymphatic tissue lymphoma (MALT), small lymphocytic lymphoma (also known as chronic lymphocytic leukemia, CLL), mantle cell lymphoma (MCL), DLBCL variants or sub-types of primary mediastinal (thymic) large B cell lymphoma, T cell/histiocyte-rich large B-cell lymphoma, primary cutaneous diffuse large B-cell lymphoma, leg type (Primary cutaneous DLBCL, leg type), EBV positive diffuse large B-cell lymphoma of the elderly, diffuse large B-cell lymphoma associated with inflammation, Burkitt's lymphoma, lymphoplasmacytic lymphoma, which may manifest as Waldenström's macroglobulinemia, nodal marginal zone B cell lymphoma (NMZL), splenic marginal zone lymphoma (SMZL), intravascular large B-cell lymphoma, primary effusion lymphoma, lymphomatoid granulomatosis, primary central nervous system lymphoma, ALK-positive large B-cell lymphoma, plasmablastic lymphoma, large B-cell lymphoma arising in HHVB-associated multicentric Castleman's disease, B-cell lymphoma, unclassifiable with features intermediate between diffuse large B-cell lymphoma and Burkitt lymphoma, B-cell lymphoma, unclassifiable with features intermediate between diffuse large B-cell lymphoma and classical Hodgkin lymphoma, AIDS-related lymphoma, classic Hodgkin's lymphoma and nodular lymphocyte predominant Hodgkin's lymphoma.

In an aspect, the methods described herein are for identifying therapeutic B-cells for the purposes of expansion and reinfusion into a patient.

In an aspect, the methods described herein are for monitoring B-cell populations/turnover in a subject, preferably a subject with cancer during cancer therapy, preferably immunotherapy.

In an aspect, the methods described herein are for detecting minimal residual disease, whereby TCR or immunoglobulin rearrangements may be used as a marker of disease.

In an aspect, there is provided a library of probes comprising the depletion probes in Table D or at least one of the V-gene and J-gene probes set forth in any of Tables 2.1, 4, B1, or B2.

In some embodiments, the clonality analyses described herein may be performed serially.

In some embodiments, the clonality analyses described herein may be used to distinguish between samples.

The advantages of the present invention are further illustrated by the following examples. The examples and their particular details set forth herein are presented for illustration only and should not be construed as a limitation on the claims of the present invention.

Example 1

Methods and Materials
Assay Development

Several important theoretical considerations were entertained during the design phase of our novel sequencing-based TRGR assay (heretofore referred to as the NTRA).

Unlike the current BIOMED approach, we wished to avoid a gene-specific primer-based approach to signal amplification. To accomplish this, we chose a "hybrid capture" target enrichment approach by which input genomic DNA containing the TR genes might be enriched (or "captured") relative to other segments of the genome. Several methodological approaches to target enrichment already exist, with multiple commercially available and rigorously optimized kits capable of enriching nearly any well-defined gene target(s)[47-48].

The NTRA needed to be robust enough to accommodate sample types of variable DNA quality; this requirement reflects the clinical need to apply TRGR assays to a wide variety of specimens in a wide variety of contexts. Knowing that Formalin-fixed paraffin-embedded (FFPE) specimens typically contain degraded and often poor quality DNA (as such representing the "lowest common denominator" of specimen quality)[49], it was deemed necessary to specifically evaluate NTRA performance on FFPE specimens. Furthermore, the use of hybrid capture is also amenable to highly fragmented DNA specimens such as those from circulating cell-free DNA.

Likewise, the most useful NTRA should allow users to both accurately assess the "clonality" of an input sample (as can be done using BIOMED-2 based assays) but also fully characterize the clonotypes of constituent TRGR configurations. Thus it was essential that the NTRA not simply produce a binary "clonal" vs. "polyclonal" result but also provide a much more robust and quantitative data output, including the genes and CDR3 regions present within identified TRGR configurations.

We recognized that much of the utility of the NTRA would depend on the design of a robust bioinformatic analysis pipeline. Of note, at the time at which this project was undertaken, only a single widely-used pipeline existed (the International standard source for ImMunoGeneTics sequences & metadata (IMGT) V-QUEST system), mainly designed around 5'RACE PCR followed by Roche 454 sequencing[51]. As outlined below, several methodological and logistic motivations demanded a novel pipeline of our own design.

Current sequencing-based applications generally require that resultant sequence data (i.e. reads) be mapped to a reference (typically the genome of the organism of interest) using some form of alignment algorithm. Once this alignment is complete, secondary and tertiary tools are used to search for and catalogue sequence deviation from the reference. For our purposes, however, using the entire human genome as a reference map would be unnecessarily cumbersome, especially since the presence of closely juxtaposed V(D)J sequence within a single short (i.e. <500 basepairs (bp)) fragment of DNA is tantamount to evidence of TRGR. Furthermore, aligning to a single reference genome raises the informatics challenge of detecting gene rearrangements from a single alignment step. As such, a strategy of mapping sequence reads to only the reference genes in a parallel fashion (i.e. one mapping procedure to the V genes, and one separate mapping procedure to the J genes) was selected, along with an integrated TRGR detection algorithm This strategy required the theoretical consideration that short sequence read input might result in excessive false negatives (i.e. artificially low TRGR detection rates). This problem might be mitigated, in theory at least, by ensuring that input DNA fragment lengths (and the resulting sequencing read lengths) are carefully set to within a reasonable range of sensitivity for the detection of TRGR in a given sequence. Since all possible TRGRs are combinatorially vast, this process could only be simulated using, for our purposes, an artificial test set of simply-concatenated sequences of all catalogued V, D, and J genes (a test set numbering 197400). By evaluating k-mer subsequences over a range of lengths (k), centred (without loss of generality) about the median of each artificial junction, an estimate of the sensitivity of TRGR detection for variable sequencing windows can be produced. This sequencing window can then be used as an "evidence-based" DNA insert length.

Insert Length Simulation

Appendix 2.0 outlines a MATLAB script designed to estimate the optimal DNA insert length (a value also generalizable to optimal shearing length and minimal Paired-end rEAd mergeR (PEAR)-assembled sequencing length) for the purposes of the NTRA. This optimum is subject to an important restriction: for our purposes, using the Illumina NEXTSEQ platform, read lengths are limited to paired-ended reads of 150 bp each—this translates to <300 bp read lengths when paired-ends are joined by overlapping sequence (using, in our case, the PEAR algorithm[52]). Briefly, the code produces a simulation read set of all possible combinations of V-D-J sequences by way of simple concatenation (with the caveat that a much larger diversity of sequence is found in nature stemming from alterations of junctional sequence by way of splicing inconsistencies); next, the algorithm selects a k-mer (of length from k=32 to 302, in intervals of 30 bp) from within each simulation sequence; the resulting k-mer (centred, without loss of generality, at the junction median) is then subject to Burrows-Wheeler Alignment algorithm (BWA) alignment against the known reference V and J genes (as in the TRSeq pipeline) to evaluate how well the k-mers of each of the artificial reads can be mapped to both V and J genes (representing bioinformatic identification of TRGR within the sequence in question). A histogram of percent detection vs. read length was then produced; analysis of those artificial V-D-J read combinations that could be reliably detected was also performed.

DNA Probe Design

We began by reviewing the sequence and metadata of all reference TR genes obtained by way of a (FASTA-formatted) data download from the IMGT database. All sequences were subjected to a series of Clustal W[53] alignment analyses to verify that sequence alignment was limited to known reference motifs (i.e. the J-gene F/W-G-X-G motif and V-gene conserved Cysteine[54]) and to allele-to-allele overlap.

DNA probe design was then performed using the IMGT reference sequences (including all annotated V and J gene functional, pseudogene and open reading frame sequences) using the XGEN LOCKDOWN probe technology. Briefly, this technology is a hybrid-capture-based technology by which biotin-tagged DNA probes (complementary to known sequences/genomic regions set at a 1×depth of coverage) are allowed to hybridize with sample DNA, followed by a streptavidin elution procedure performed to enrich the target sequences[40-43].

In line with previous studies employing XGEN LOCKDOWN probes[40], each DNA probe was designed to a length as close to 100 bp as possible. Using the IMGT database, germline-configuration sequences were extracted for all alleles of all J-genes, with additional leading and trailing IMGT nucleotides added (as necessary) to obtain 100 bp probe lengths; for those instances in which the IMGT data was insufficient to prepare 100 bp probes, additional random nucleotides were added to the leading and trailing ends of the available sequences. Again using the IMGT database, germline-configuration sequences were extracted for all alleles of all V-genes, with additional leading and trailing IMGT nucleotides added to ensure that the 5' and 3' ends of the germline-configuration genes were covered by a given probe (this design, it was theorized, would be able to account for gene re-arrangement at either end of a V-gene, regardless of strandedness, while still covering the vast majority of the sequence of each gene/allele). With careful placement of the probes as outlined above, we hoped that this design would also limit any specific stoichiometric bias among the V-genes represented in the target pool.

Table 2.1 outlines the complete list of XGEN LOCKDOWN probe design sequences (with relevant associated metadata).

NTRA Work-Flow

Figure 3:
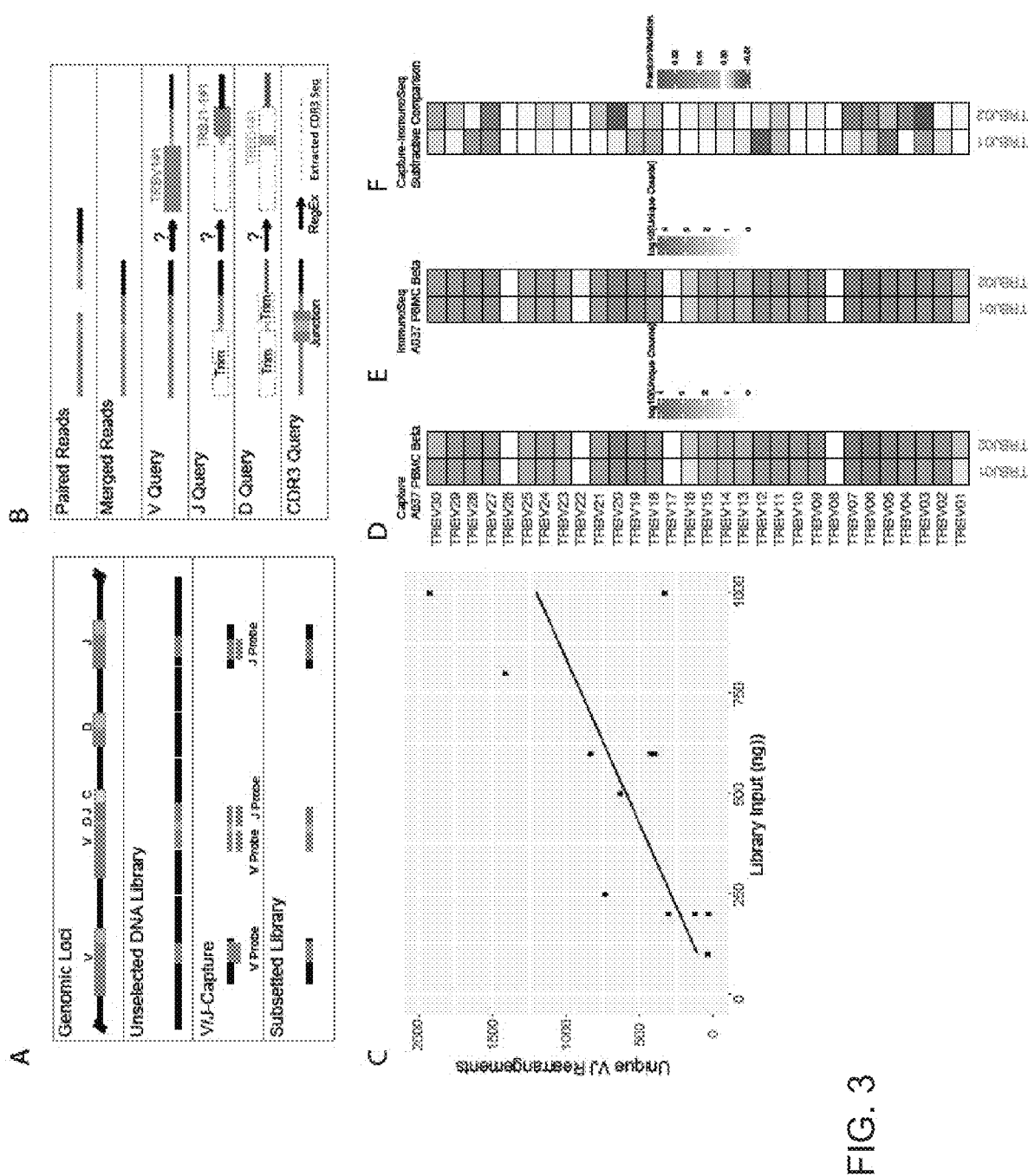
FIG. 3: An overview of the CapTCR-Seq hybrid-capture method. (A) Hybrid-capture method experimental flow diagram. Fragments are colored based on whether they contain V-region targets (blue), J-region targets (red), D-regions (green), constant regions (yellow) or non-TCR coding regions (black). (B) V(D)J rearrangement and CDR3 sequence detection algorithm flow diagram. (C) Number of unique VJ pairs recovered relative to library DNA input amount for one-step V capture of A037 PBMC derived libraries. (D) A037 polyclonal human beta locus VJ rearrangements determined by CapTCR-seq. (E) A037 polyclonal human beta locus VJ rearrangements determined by a PCR-based profiling service. (F) Subtractive comparison between CapTCR-seq and PCR-based profiling service. Red indicates relative enrichment of indicated pair by CapTCR-seq while blue indicates relative enrichment of indicated pair by PCR-based profiling.

The NTRA work-flow is summarized in FIGS. 1 and 3. Briefly, the process begins with DNA isolation, performed for the purposes of this study according to the protocol of Appendix 2.1. Isolated DNA was retrieved from frozen archives and quantified using the QUBIT assay, per Appendix 2.2. Input DNA was shorn using a Covaris sonicator (Appendix 2.3) set to a desired mean DNA length of 200 base pairs; adequate shearing was confirmed using TAPESTATION assessment. Sequence libraries for each specimen were prepared using the protocol outlined in Appendix 2.4; multiplexing was accommodated using either TRUSEQ or NEXTFLEX-96 indices (the latter employed in the final validation run to permit large-scale multiplexing). Library preparation results were validated relative to input short DNA using TAPESTATION assessment. Subsequently, hybrid-capture with the above described XGEN LOCKDOWN probes was performed; captures were performed in pools of 9-13 input libraries, based on a pre-calculated balance of input DNA. The captured library fragments were then repeat-amplified, followed by final QUBIT and TAPESTATION QC-steps. Finally, paired-end 150-bp sequencing was performed on the Illumina NEXTSEQ platform using either a mid- or high-output kit (depending on sample throughput), according to the manufacturer's instructions (Appendix 2.5). The resulting read-pair zipped FASTQ-formatted data files were de-compressed and merged using the publically available PEAR alignment algorithm using a minimum of 25 bp overlap; this allowed the 150-bp sequencing maximum to be expanded to at least 200 bp, as suggest by the results of Section 2.1.2. Non-paired results were also tallied as a means of quality assurance. Subsequent analyses were performed using the custom-designed TRSeq analysis pipeline, as described below.

NTRA Data Analysis: The TRSeq Pipeline

The NTRA TRSeq pipeline was designed around three main algorithmic steps. The first performs local alignment indexed to the TR V and J genes implemented using the Burrows-Wheeler-Alignment (BWA) algorithm[55]. From this algorithm, two important results are obtained: the first is a "reads-on-target" estimate (since the genes enriched for (i.e. the TR V and J genes) are those genes used as the index reference gene set); second, by way of the resulting Sequence Alignment Map (SAM) file output, the original input reads are filtered to exclude those unlikely to contain any of the TR V or J genes. This latter step reduces the informatic burden of input to the (relatively computationally slow) second algorithm step (using either heuristics or the Smith-Waterman Alignment (SWA)). Of note, the BWA algorithm could be implemented on a UNIX-based platform only[55].

The second algorithm step is designed to extract CDR3 sequences wherever present. This algorithm was implemented in MATLAB, guided by previous publications[56], and using a regular-expression (regexp) based search algorithm.

The third step combined the above alignment and CDR3 data (where present), to decide whether a given read contains a TRGR. To do this, one of two decision approaches is used: if a CDR3 is identified in a read, a heuristic approach is employed to decide if the BWA-alignment reference genes could be rearranged within the same locus; the second, in the event that a CDR3 is not detected, relies on the SWA-determined alignment scores to determine if a given combination of V(D)J genes is present.

Bioinformatic Target Enrichment (Burrows-Wheeler-Alignment Algorithm)

Much like the technical aspects of the NTRA function to enrich TR genes at the DNA level, so too can an informatics target-enrichment approach be employed. Using the BWA algorithm[55], a series of FASTQ-formatted reads are first mapped relative to a reference index of IMGT TR V and J genes. Any reads containing sequence mapping to any of the reference genes are flagged as such in the SAM-formatted output file as mapped, whereas those not containing any TR V or J gene mapped sequence are assigned the SAM Flag 4. In this context, unmapped reads are unlikely to contain any detectable TR V(D)J gene rearrangements; this predicate is logical inasmuch as sufficient residual germline sequence of a TR V and/or J gene are required in a read to permit TRGR detection.

Reads-on-target and gene-coverage estimates are also derived using the BWA algorithm, since NTRA input probes consist only of TR V and J genes; this measure is calculated as a percentage of the number of unique reads mapped to the IMGT reference TR V and J gene indices relative to the total number of reads in the input FASTQ-formatted file.

CDR3 Sequence Extraction and SWA Alignment

This part of the TRSeq algorithm was implemented in MATLAB using strategies similar to those employed by the IMGT[56-58]. The IMGTN-QUEST system utilizes a CDR3 sequence extraction algorithm[57,59] and an SWA[60] algorithm performed against the IMGT reference sequences; the IMGT algorithms are all implemented in JAVA and processing is performed on IMGT servers.

As highlighted previously, we were unable to rely solely on the IMGT system for informatics results for several reasons: (1) the export of patient sequence data to an external non-secured network can be risky if insufficiently censored identifying metadata are also included; (2) the IMGT/High V-Quest system has a 500,000 sequence input limit (which may be substantially less than the number of sequence reads that need to be analyzed in the run of even a single high-throughput sequencing run); and (3) the queueing used by the IMGT can be lengthy, requiring a wait of possibly several days for sequence interpretation to begin.

A MATLAB implementation was chosen for convenience, programming familiarity, and because of easy vectorization, parallel computation and object-oriented programming capabilities. In addition, the MATLAB programming and command-line environments are able to easily incorporate UNIX and PERL-based scripts, including the BWA[(Li, 2009)] and CIRCOS software[61] suites, respectively.

The full coding of the analysis algorithm is presented in Appendix 2.6.2. The MATLAB code was written to accommodate FASTQ-formatted data, align each read using BWA to the reference TR V and J gene germline sequences, index the resultant data, test each indexed read for (and extract if present) a CDR3 sequence (using the uniformly present C-X(5 . . . 21)-F/W-G-X-G amino acid motif, per the IMGT canonical sequence motif[62,63]), and perform either an heuristic or SWA alignment-based validation of the reads mapped by BWA as evidence of a rearrangement within the read in question.

The SWA algorithm produces an optimal local alignment[60,64] of two co-input sequences (in this case, a query sequence relative to an IMGT reference sequence), and provides an alignment score (a unit-less measure of the degree to which the alignment perfectly matches an input sequence to its co-input sequence). For the purpose of this instance of the algorithm, for any case in which multiple possible alignments were produced, the alphabetical highest-scoring alignment was selected as the "correct" alignment, provided that this score was at least greater than the minimum cut-off score.

The minimum SWA alignment cut-off score was empirically determined for each of the three V, D, and J-gene gene groups using a large set of confirmed-negative sequences evaluated using the IMGT/HighV-QUEST system[56,57]. The MATLAB code required for implementation of this algorithm is outlined in Appendix 2.6.1. A "practice" set obtained from the IMGT database[65,66] was also employed to test the pipeline, consisting of IMGT PCR-confirmed TRGR sequences with known V-D-J combinations and CDR3 sequences (see Section 3.1.3 for results of this practice set analysis).

Analytical Validation

A selection of 10 "First-Run" samples formed the basis of the analytical validation. These samples included 6 de-identified actual patient samples, obtained from flow-sorted peripheral blood specimens, tumour-infiltrating lymphocyte populations or in vitro cultures of lymphocytes. These samples were each subjected to flow-cytometric evaluation and cell-counting for basic immunophenotyping and cell-input consistency. In addition, four cell lines with known and well-described TR gene rearrangements (based on references cited by the IMGT database[67]) were also included (i.e. Jurkat (Deutsche Sammlung von Mikroorganismen und Zellkulturen (DSMZ) ACC-282), SUPT1 (American Type Culture Collection (ATCC) CRL-1942), CEM (ATCC CCL-119) and MOLT4 (ATCC CRL-1582)).

A three-part analytical validation approach was employed. First, the results obtainable by analysis of the sequencing data using the IMGT/High V-Quest pipeline were directly compared with the results of the TRSeq pipeline. Next, a PCR & Gel Electrophoresis experiment was designed to confirm the presence of the upper $90^{th}$ centile of rearrangement configurations. Finally, the predominant rearrangements with accompanying TRSeq-identified CDR3 sequences were further Sanger-sequenced to validate this latter component of the NTRA analysis.

Comparison with IMGT Results

Given the limited input size capacity of the IMGT/High V-Quest system, a read-by-read comparison of a 10% random subset of the NTRA sequencing data was performed. From the IMGT analysis, a read was assumed to contain evidence of a rearrangement when the IMGT pipeline Junction analysis yielded an in-frame result. In addition, a read-by-read comparison of the alignment results (by gene name, for all V, D and J genes) was also performed.

PCR & Gel Electrophoresis Validation

A PCR-based experiment was deemed a reasonable orthogonal validation approach, given the gold standard BIOMED-2 assay methodology. Knowing that the number of possible rearrangements detected by the NTRA might be substantially large, the PCR validation was arbitrarily limited to those TRSeq-detected rearrangements in the upper $90^{th}$ centile (i.e. percent rearrangement of greater than 10% of total rearrangements). Given this restriction, however, to ensure an adequate denominator of reactions for comparative purposes, all PCR validation experiments were uniformly performed across all 10 first-run samples.

PCR validation primer sets were constructed modeling the standard V-D-J orientation of rearranged TR genes; specifically, the PCR forward primer was set in the V gene and the reverse primer set in the anti-sense strand of the J gene. For each TRSeq-identified rearrangement above 10% of total rearrangements, the V and J genes were identified and the IMGT primer set database searched for gene (not allele) specific primers. While the IMGT primer database did contain a number of suggested primers, many of the TR genes did not have an available appertaining primer. As a result, where necessary, the anticipated rearrangement sequence (containing the V gene sequence artificially positioned before the J gene) was used to derive custom primers using the NCBI Primer-Blast tool[68]. Careful attention was paid to ensure that each resulting theoretical PCR product length was at least 100 bp (the lower limit of fragment size reliably detectable by standard gel electrophoresis) and that a sufficient amount of the anticipated CDR3 region sequence would be preserved in the PCR product. In addition, the theoretical product length was recorded as an approximate size reference for analysis of the resulting electrophoresis migration patterns.

All putative primer pairs were then re-submitted to Primer-Blast M to assess for the possibility of non-specific products; the final set of putative primers pairs was also evaluated using the UCSC in silico PCR algorithm[6]) to confirm that no germline configuration products of less than 4 kb might be produced. Primer set physicochemical characteristics were evaluated using the IDT OligoAnalyzer Tool (v 3.1); Clustal W[55] alignments were used to identify significant primer sequence overlaps (Clustal W alignments note significant overlap of the TRGJ1 and TRGJ2 primers. This overlap was considered acceptable in order to define which of the TRGJ1 and TRGJ2 genes were present (given the presence of 5' end non-homology). Since the PCR/electrophoresis results suggested the presence of both TRGJ1 and TRGJ2 positive products, the dominant TRGJ1 primer was selected for subsequent analyses and the TRGJ2 results excluded). The final primer-set sequences are listed in Table 2.2.

Custom primer set production was performed commercially by IDT and the forward and reverse primers were then mixed according to the design outlined in Appendix 2.7.2. PCR was performed in a 384-well plate on an Applied Biosystems VERITI thermal cycler using the Thermo Scientific 2×REDDYMIX PCR Master Mix kit according to the manufacturer's instructions; several control reactions were included, as highlighted in Appendix 2.7.2. Gel electrophoresis was performed in a 96-well Bio-Rad SUB-CELL Agarose Gel Electrophoresis System (necessitating 4 separate runs); electrophoretic migration was referenced against an Invitrogen TRACKIT 1 kb DNA ladder and visualized using ethidium bromide fluorescence, photographed in an ALPHAIMAGER Gel Imaging System. Electropherograms were digitally rendered, adjusted and composited using ADOBE PHOTOSHOP CC 2014. The resulting electrophoretic results were used in Receiver-Operating Characteristic (ROC) curve analyses relative to the corresponding TRSeq normalized read counts.

Sanger Sequencing Validadon

Based on the results of the above PCR & Gel Electrophoresis experiment, rearrangement-positive PCR products were purified using a QIAQUICK Spin PCR purification kit (100 bp to 1 kb range) according to the manufacturer's instructions (Appendix 2.7.3). Purified PCR products were then quantified by QUBIT and 20 ng equivalent aliquots were taken (with an additional volume reduction step using a SPEEDVAC, as required, for large volumes). The corresponding primer of the original primer pair with the lowest melting point was then selected for the purposes of single-direction Sanger Sequencing (performed at the TCGA Sick Kids Hospital Sequencing Facility).

The resulting sequencing results were analyzed using the FinchTV v 1.4 software suite, with corrections to sequencing error and reverse-complement sequence corrections performed manually as required. The originating TRSeq CDR3 sequences were then compared to the "reference" Sanger Sequence result. This comparison was performed in two ways: first, a basic multi-alignment comparison was performed (using the multialign algorithm of the MATLAB Bioinformatics Toolbox); second, a k-mer based PHRED-quality adjusted comparison was performed.

For the k-mer based approach, for a given V and J gene configuration, the most frequently detected TRSeq CDR3 sequences were aligned to the corresponding Sanger Sequencing result. In this context the Sanger Sequencing results were taken to represent a "consensus" of sequence data produced over all possible V and J configuration CDR3 sequences for that V-J gene configuration (reflecting the possibility of variable TRGR subclones). As such, in order to adjust the Sanger sequencing results to account for the potential alignment of a non-dominant subclone, a quality-based alignment algorithm was employed, based on the methods of[70]. Each input TRSeq CDR3 sequence was aligned along a progressive series of k-mers of the Sanger sequence using a custom quality-based alignment algorithm (code outlined in Appendix 2.8). For each alignment result, if the optimal alignment score occurred within the expected sequencing region (thereby representing an optimal alignment within a region of Sanger sequence expected to contain the actual CDR3 based on flanking primer sets), as outlined in Table 3.1A, the CDR3 sequence was classified as correct (and vice-versa). This classification was then used to perform ROC analysis to determine what number of TRSeq CDR3 sequence read counts might be considered a validated cut-off.

Coverage Analysis

In addition to the above validation results, more detailed assessment of NTRA technical performance was also performed. Specifically, given that the NTRA relies on target enrichment, an assessment of the gene coverage of the NTRA was required. In addition, given that much of the utility of the NTRA might relate to identifying clonal cell populations, it was necessary to assess the dynamic sensitivity of the NTRA to decreasing numbers of cells bearing specific TR gene rearrangement configurations and, conversely, assess how standardized read counts might correlate with approximate input cell numbers.

Coverage Dynamics by Specimen Clonality

Given the nature of TRGR, by which genomic components are excised upon rearrangement, we evaluated the coverage dynamics across the first-run specimens. This analysis served not only as a mean of qualitatively comparing how V and J gene coverage might be expected to vary in specific types of specimens, but also to evaluate which coverage metrics might be most predictive of specimen type (i.e. clonal vs not) and what specific cut-off criteria might be used to this effect. To do this, ROC-based analyses of mean overall and locus-specific coverage data for V and J genes was performed, as well as percent genes at least 100×for each of V and J gene types.

Negative Control Coverage Assessment

For the purposes of this project, a fully germline TR gene configuration was approximated using a cell lines of embryonic origin and a cell line that has been fully sequenced without any known/reported TR gene derangements. The former scenario was approximated using the HEK293 cell line (an embryonic kidney cell line; ATCC CRL-1573) and the latter using a Coriell cell line (whose genome has been well-characterized and is not known to contain TR rearrangements). Use of the latter cell line was incorporated given that, in our hands, this cell line had been previously and purposefully degraded by FFPE treatment, representing a scenario of TR gene coverage assessment in the context of degraded DNA.

Total genomic DNA was extracted from previously cultured HEK293 cells and FFPE treated Coriell cell cultures and subsequently subjected to the NTRA, as outlined in Appendices 2.1 to 2.5. Standard TRSeq analyses were performed for each sample, with special deference paid to the coverage results.

Dilution Series

A rigorous dilution series experiment, in the context of this project, might involve a flow-sort spike of cells with a known TR gene configuration into a population previously determined to be "polyclonal"; this might be approximated, for example, using a well-characterized cell line spiked into a population of lymphocytes obtained from normal blood. Rather than undertaking this more complex and expensive approach, an approximation of this dilution experiment was undertaken with DNA obtained from the Jurkat cell line spiked into a known-polyclonal lymphocyte population DNA isolate (the A037 sample; see Results section 3.2). Specifically, Jurkat DNA was spiked in at log-decrements (as outlined in Table 2.3) based on a lymphocyte total DNA complement assumed to be 0.7 pg, given the results of previous publications[71-73]. The total DNA of each sample in the dilution series was verified (and compared to expected values) using a QUBIT assay; the samples were then subjected to the NTRA, as outlined in Appendices 2.1 to 2.5. Standard TRSeq analyses were performed, with special deference to changes in the raw read counts of Jurkat-specific TRGR configurations across the dilution series.

Alternative Method and Algorithm

Hybrid-Capture Protocol

For T cell receptor (TCR) diversity and clonality analyses we investigated genomic DNA isolated from flow sorted T cells isolated by affinity magnetic bead isolation, peripheral blood mononuclear cells (PBMC) isolated from blood by density gradient separation, cell-free plasma DNA extracted from blood, or scraped and pelleted immortalized cell lines.

Isolated DNA is sheared to ~275 bp fragments by sonication in 130 uL volumes (Covaris). DNA libraries are generated for illumina platform sequencing from 100-1000 ng of sheared DNA by ligation of sequencing library adaptors (NEXTFLEX) using the KAPA library preparation kit with standard conditions. Libraries are visually assessed (Agilent TAPESTATION) and quantified (QUBIT) for quality.

Hybridization with probes specifically targeting the V and J genes is performed under standard SEQCAP (Roche) conditions with XGEN blocking oligos (IDT) and human cot-1 blocking DNA (Invitrogen). Hybridization is performed either at 65 C overnight. The target capture panel consists of 598 probes (IDT) targeting the 3' and 5' 100 bp of all TCR V gene regions, and 95 probes targeting the 5' 100 bp of all TCR J gene regions as annotated by IMGT (four loci, 1.8 Mb, total targeted 36 kb). Hybridization and capture can be performed as a single step with a combined V/J panel, as a single step with only the V panel, or as a three step process when non-rearranged fragment depletion is desired consisting of a V capture, then depletion, then J capture.

For depletion of non-rearranged fragments 500 ng-1000 ng of library is depleted by hybridization with a panel of 137 probes (IDT) targeting the 5' 120 bp of selected TCR V gene region 3' untranslated regions as annotated by IMGT (four loci, 1.8 Mb, total targeted 16.5 kb) and 131 probes (IDT) targeting the 5' 120 bp of selected Ig V gene region 3' untranslated regions as annotated by IMGT (three loci, 3.1 Mb, total targeted 15.7 kb). A modified and truncated SEQCAP protocol is employed wherein following incubation with M-270 streptavidin linked magnetic beads (Invitrogen), the hybridization reaction is diluted with wash buffer I, beads are discarded and the supernatant is cleaned up by standard Agencourt AMPURE XP SPRI bead purification (Beckman).

Algorithm

Figure 5:
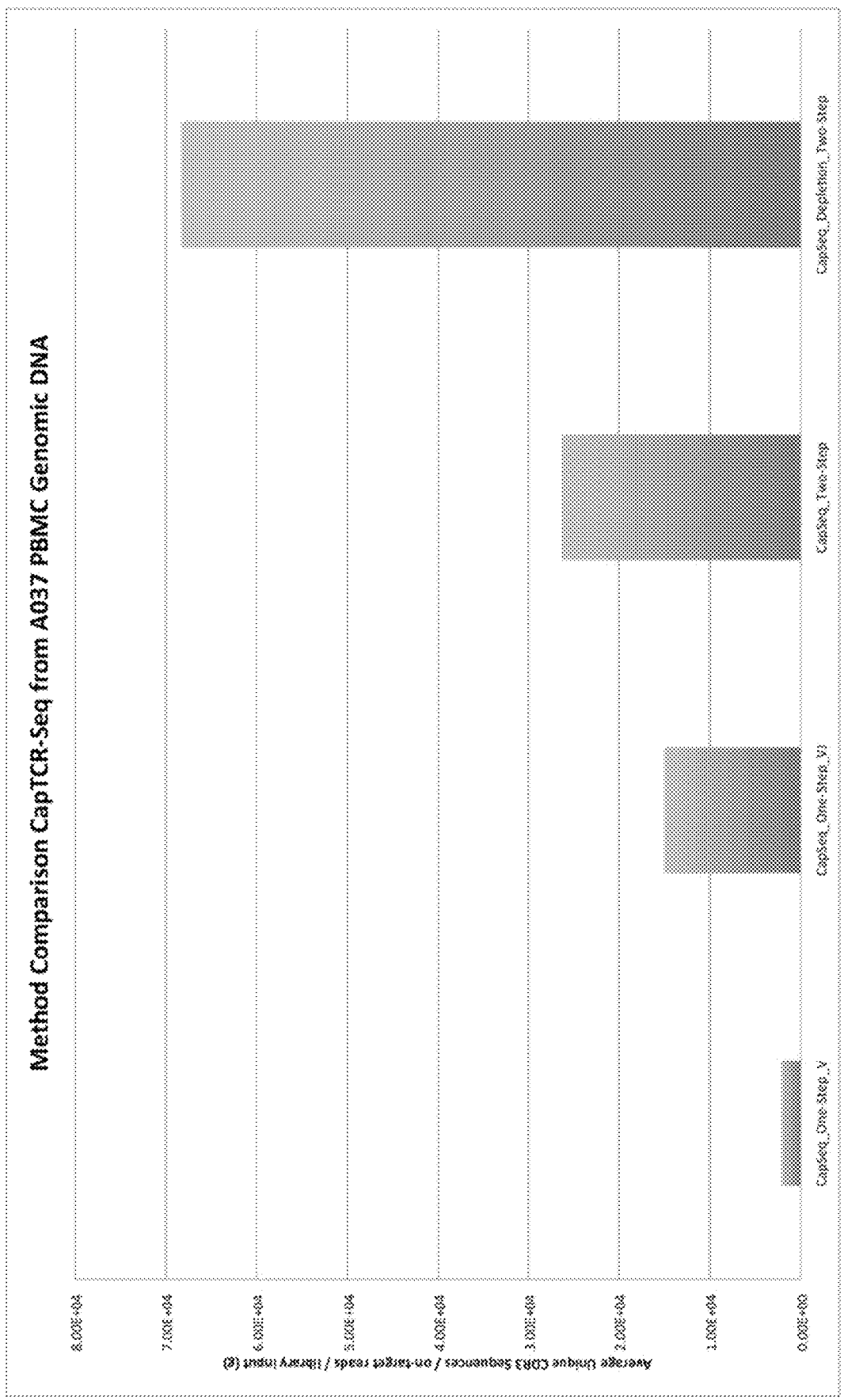
FIG. 5: Comparison of different method variants in terms of yielded average unique CDR3 sequences (normalized to reads and library input).

A custom Bash/Python/R pipeline is employed for analysis of paired read sequencing data generated by Illumina NEXTSEQ 2500 instrument from the hybrid-capture products. Referring to FIG. 5, this pipeline consists of four major steps: (1) Merging of the paired reads; (2) Identification of specific V, J, and D genes within the fragment sequence; (3) identification of the V/J junction position as well as the antigen specificity determining Complementarity Determining Region 3 (CDR3) sequence at this site; (4) Calculation and visualization of capture efficiency and clone frequency within and across individual samples.

(1) 150 bp paired-end reads are merged using PEAR 0.9.6 with a 25 bp overlap parameter. This results in an approximate 275 bp sequence for each fragment and enhances the sensitivity of V,J,D gene detection using the subsequent search strategies.

(2) Individual BLAST databases are created using all annotated V, D, J gene segments from IMGT. These full-length gene sequences are the targets of the hybrid-capture probe panel. Individual merged reads are iteratively aligned using BLASTn with an e value cut-off of 1 to the V database, J database then D database with word size of 5 for D segment queries. Trimming of identified V or J segments in the query sequence is performed prior to subsequent alignment to reduce false positives and increase specificity, particularly for the D gene query.

(3) In order to identify CDR3 sequences, the V/J junction position is extracted from the previous search data for those fragments containing both a V and J search result. 80 bp of DNA sequence flanking this junction is translated to amino acid sequence in all six open reading frames and sequences lacking stop codons are searched for invariable anchor residues using regular expressions specific for each TCR class as determined by sequence alignments of polyclonal hybrid-captured data from a healthy patient as well as TCR polypeptides annotated by IMGT.

(4) Calculation of capture efficiency (on-target/off-target capture ratio) is performed by aligning all recovered, merged reads to the human genome (BWA) and dividing the number of reads aligning to the TCR loci by the total number of reads. The total number of unique TCR clones is determined by finding the unique minimum set of V/J combinations and the number of occurrences of each is tabulated. This data is visualized using R as stacked bar charts to generate figures that can be quickly visually assessed on a sample-by-sample basis for monoclonal or polyclonal signatures or clinically relevant enrichment of particular clones.

Application of the Algorithm to Existing Sequencing Data

The custom pipeline is not dependent on our hybrid-capture protocol and can be performed on non-target captured whole genome or RNA-seq data. In this situation, an in silico capture is performed by extracting reads aligning to the four TCR loci (7:38250000-38450000, 7:141950000-142550000, 14:22000000-23100000) or Ig loci (chr2:89,100,000-90,350,000, chr14:106,400,000-107,300,000, chr22:22,350,000-23,300,000) from DNA (BWA) or RNA (STAR) sequence data (SamTools), followed by paired-end nucleotide sequencing data extraction (PicardTools). These reads are then inserted in to the previously described computational pipeline.

Results and Discussion

Informatics

Insert Length Simulation

The DNA Insert Length Simulation results were generated (data not shown). The analysis suggested a plateau of sensitivity of greater than 99.1% reached after 182 bp. For convenience, an adequately "evidence-based" insert length and informatics read length goal of 200 bp was chosen for the NTRA.

After further analysis excluded extra-locus V-D-J gene combinations (i.e. combinations not likely to result from rearrangements within the same TR locus), the number of missed combinations was reduced from 1752 to 80.

From among the above 80 intra-locus combinations, missed rearrangements originated only from among the TRB and TRG loci, with particular enrichment of TRBV6-2*01 and TRBV6-3*01 within the former (65 of 80) and enrichment of the TRGJ1*02 within the latter (15 of 80).

Analysis by phylogenetic sequence alignment (using the SWA alignment algorithm) within the TRBV6 group showed significant cophenetic linkage between the TRBV6-2*01 and TRBV6-3*01 genes (data not shown). Similarly, analysis by phylogenetic sequence alignment within the TRGJ gene group suggested significant cophenetic linkage between TRGJ1*02 and TRGJ2*01 (data not shown). These results suggest that combinations within the artificial read set involving either of these TRBV genes were likely misaligned to another TRBV gene (likely the next closest cophenetic "cousin," TRBV6-2*02) and that the TRGJ1*02 gene was likely misaligned to the TRGJ1*01 gene. Of note, the observation of closer cophenetic linkage between TRBV6-2*01 and TRBV6-3*01 rather than between TRBV6-2*01 and TRBV6-2*02 (as would be expected for two alleles of the same TR gene) and of closer cophenetic linkage between TRGJ1*02 and TRGJ2*01 rather than between TRGJ1*01 and TRGJ1*02, suggests error on the part of the IMGT classification.

MATLAB SWA Score Cut-Off Determination

The results of the empirical V, D and J-gene MATLAB alignment score cut-off score experiment were generated (data not shown). This experiment employed the code presented in Appendix 2.6.1 run on a test set of 91375 Illumina sequencing reads obtained from anonymized myeloid leukemia samples enriched for sequences outside of the IG/TR loci. These sequences were "confirmed" negative for V, D, and J gene sequences using the IMGT/High V-QUEST system (Brochet et al., 2008; Giudicelli et al., 2011). Given an experimental number of sequencing reads of at least 1 million, a 6-sigma cut-off score for MATLAB TRSeq analysis suggests 53.23 for the V genes; 19.02 for the D genes; and 34.43 for the J genes. It is easily observed that the cut-off values increase respectively from D, to J, to V genes; this observation parallels the mean length of the reference sequences from D to J to V genes.

TRSeq Analysis of IMGT-Produced TRGR Sample Sequence Reads

A sample of 268 short read sequences was downloaded from the IMGT website. These sequences consist of a variety of previously characterized TR and IG gene rearrangements available for download in FASTA format. After re-formatting into FASTQ format (using arbitrary quality scores), the dataset was analyzed using the TRSeq pipeline. Of the 268 short read sequences, 55 were identified by the IMGT as containing TR genes (either V or J genes); to these reads, there was perfect (100%) TRSeq alignment concordance, both in relation to gene name and allele. The TRSeq algorithm identified 50 of the 55 reads as containing evidence of TRGR; the 5 remaining reads were identified by the IMGT as containing rearrangements within the TRD locus, each with a TRSeq CDR3 region correctly identified. These results suggest that the 5 TRSeq "false-negatives" were informatically rejected by the TRSeq algorithm based on insufficient TRD D-gene SWA alignment score values; this form of error is not alarming given the more stringent means by which the TRSeq SWA alignment score cut-off values were determined relative to the IMGT/High V-QUEST pipeline[55,58].

First-Run Results Summary

Table 2.5 outlines the flow-cytometric features of the 6 patient lymphocyte samples. These immunophenotypic features were in keeping with the lymphocyte sample sources of origin (also documented in Table 2.5), varying from normal patient peripheral blood mononuclear cells to highly immune-sensitized lymphocyte cultures from tumour infiltrating lymphocyte specimens. Notably, the A037 sample served as a model of a "polyclonal" lymphocyte population whereas, for the purposes of qualitative assessment at least, the L2D8 sample could be immunophenotypically interpreted as highly "clonal" in nature.

In addition, model "clonal" samples were included, consisting of the Jurkat, CEM, SUPT1 and MOLT4 cell lines. Table 2.6 lists the previously documented rearrangements, as cited in the IMGT database[67].

Prior to target enrichment and sequencing, adequate quality control was assured, as documented by pre and post-library preparation TAPESTATION tracings (data not shown). Post-target enrichment quality control was assured in the same manner.

Illumina NEXTSEQ sequencing was then performed on TAPESTATION-normalized pooled input target-enriched DNA. The appertaining read-pair FASTQ-formatted zipped files were decompressed and the PEAR paired-end merging algorithm was run with a minimum strand sequence overlap of 25 bp. A breakdown of the PEAR results were generated (data not shown). The resulting PEAR-merged FASTQ-formatted read files were input to the TRSeq pipeline.

TRSeq metadata for the first-run sample series were generated (data not shown), including input reads, reads-on-target, summary coverage statistics, and a histogram of read counts for the proportion of each locus contributing to identified TRGR's, respectively.

One important highlight is the variation in coverage seen across the 10 specimens relating to the D locus. As described in the introduction, since the D locus genes are sandwiched within the larger A locus, the D locus genes are often deleted upon A locus rearrangement. The coverage profiles of the D locus therefore paralleled this phenomenon with lower D locus coverage identified in the clearly clonal or oligoclonal samples relative to the polyclonal samples (e.g. 1.2D8 and cell line samples vs. A037 peripheral blood sample).

Composites of the circos plots obtained from the 10 first-run samples were generated (data not shown). Much as the coverage profiles differed across the samples (data not shown), the resulting circos plots demonstrated a clear aesthetic difference from polyclonal to clonal/oligoclonal samples, with emphasis on the number and relative width of the composite circos links (i.e. fewer and broader in width in the more clonal cases and vice versa). Also of note, the color distributions were distinctly different with the more polyclonal cases, containing a larger number of smaller-quantity "subclones" involving a more disparate number of TR genes.

Analytical Validation

IMGT/High V-Quest Comparison

Comparison of the IMGT/High V-Quest pipeline analysis to the TRSeq results were generated (data not shown). The degree of concordance of read-to-read interpretation with respect to identifiable rearrangements (as present or not identified) is excellent (99%), as is the degree of concordance of named D genes (99%). A lower degree of concordance is noted for named V and J genes (68% and 84%, respectively). These results may relate to different initial alignment algorithms employed, as well as different gene-identity cut-off values employed in the SWA algorithms of the IMGT/High V-Quest and TRSeq pipelines. In light of the results seen in Section 3.1.1, the possibility of V and J gene phylogenetic sequence misclassification in the publically-available IMGT sequence databases should also be considered as a possible contributing factor.

The high D-gene concordance relative to the V and J-gene values may relate to both the shorter reference sequences of the D-genes relative to the V and J genes, as well as the lower number of reference D-genes available for rearrangement. It is important to point out the possibility of a theoretical bias against D-gene identification in input reads, given that TRGR reads containing D-genes require 3 rather than 2 composite genes, which could be more difficult to detect in the context of restricted average read lengths. This consideration was brought to bear during the NTRA assay design phase (as described in Section 3.1.1), with the conclusion that adequate flanking 5' and 3' sequence would be available on average in the scenario of read input length of 200 bp or more to reliably identify reads containing V-D-J rearrangements.

PCR & Gel Electrophoresis

PCR primers were mixed and the results by Agarose gel electrophoresis were generated (data not shown). Note that results obtained from PCR reactions using the TRGJ2 reverse primer are excluded, as noted in Section 2.2.2. Two classification approaches may then be entertained, one based on dark-staining PCR bands only, and the other based on any staining (assuming bands to be of appropriate molecular weights, as set out in Table 3.1A). When these classifiers are compared with the read-count-normalized results of the TRSeq algorithm (as set out in Table 3.1A), the ROC curves of are obtained, respectively (data not shown). In the former scenario, the ROC Area-Under-the-Curve (AUC)=0.91 and p-value <0.001, with a TRSeq normalized read count of 6.7 or more. Based on the results, a less stringent classification results in a reduced AUC=0.71 and p-value <0.001, with a TRSeq normalized read count of 1.7 or more.

Sanger Sequencing Results

PCR reactions that were post-PCR purified were submitted for Sanger Sequencing. Alignment of each corresponding TRSeq CDR3 sequence (and associated raw read count) in relation to the manually-verified/corrected Sanger Sequencing Result were generated (data not shown); only those Sanger Sequencing specimens containing TRSeq-identified CDR3 regions, those of sufficient quality for interpretation, and those not rejected based on use of the TRGJ2 reverse primer were further considered.

There appears to be a trend for each distinct primer configuration inasmuch as TRSeq-identified CDR3 sequence configurations having sufficient associated read counts (data not shown), as suggested from Section 3.3.2, show the best contiguous alignments to the corresponding "reference" Sanger Sequences.

To better quantify this relationship, we utilized a k-mer based quality-score adjusted alignment analysis. For each relevant primer configuration, the corresponding CDR3 was aligned using PHRED-based quality-score adjustment across the length of the Sanger "reference" sequence. If the optimal alignment from this process was present within the sequence window in which a CDR3 was theoretically predicted to exist, the CDR3 read configuration was classified as "compatible." The resulting classification analysis is represented by the ROC curve (AUC=0.832, p-value=0.006) (data not shown). Based on this analysis, the optimal TRSeq normalized read count cut-off is 4.9.

Coverage Analysis

Coverage Dynamics by Specimen Clonality

Using the qualitative data of Table 2.5, specimens were classified as either "clonal" or "polyclonal." The resulting ROC curves for the various coverage metrics were prepared (data not shown). Of note, a mean V-gene coverage assessment of the gamma locus appeared to suggest the highest non-unity AUC. Further, the ROC analysis suggested that a mean V-gene coverage of greater than/equal to 4366.4 showed optimal sensitivity and specificity (86% and 67%, respectively) for predicting whether a specimen was unlikely to be clonal. Care should be taken not to use these cut-off points without additional validation, however, given the low number of data points constituting the analysis. Rather, these data stand to suggest a need for further evaluation of the potential predictability of "clonal" status derived from coverage analysis within the gamma locus.

Negative Control Coverage Assessment

The NTRA was tested on samples of previously cultured HEK293 and Coriell cell lines; these analyses aimed mainly at estimating coverage ceilings for the NTRA, but also served as added negative control specimens (i.e. specimens known or expected not to contain any TRGRs).

Applying the PEAR algorithm[52] (with a minimum 25 bp forward-reverse read overlap) resulted in pairing of 83% of input reads in the HEK293 sample and 90% of input reads in the Coriell sample.

In both instances, the number of subsequently identified TRGR configurations did not meet the TRSeq cut-off criteria (TRGRs were identified in 0 of 5,729,205 total input reads in the HEK293 cell line and only 7 of 2,761,466 total input reads in the Coriell cell line). This was in keeping with the anticipated fully-germline configuration of each of these non-lymphoid origin cell types.

For the HEK293 cell line, the percent V and J genes at or above 100×coverage was 100%; the overall TR V gene coverage averaged 29960x; and the overall TR J gene coverage averaged 8789x.

For the Coriell cell line, the percent V and J genes at or above 100×coverage was 100%; the overall TR V gene coverage averaged 13379x; and the overall TR J gene coverage averaged 3925x.

Dilution Series

A dilution experiment was performed at log-reduction intervals, set up according to the design of Table 2.3, and adjusted according to Table 3.2 to account for Jurkat DNA concentration discrepancies. Three Jurkat cell line unique TRGR configurations were selected for inter-dilution comparison, namely the TRAV8-4-TRAJ3, TRGV11-TRGJ1 and TRGV8-TRGJ2 rearrangements identified & confirmed in Section 3.3. The above configurations were confirmed absent in the polyclonal (A037) sample. In addition, each of these configurations showed a specific dominant CDR3 sequence.

The mean of the raw read-counts (i.e. not normalized) across the three tracked V-J configurations (with error bars for standard deviation) vs. expected approximate Jurkat cell numbers (with adjustments for significant digits) from Table 3.2 were generated (data not shown). An exponential trend line could be applied, with R-squared=0.9996.

Of note, when the extremum of the first dilution is excluded, the dilution curve is remarkably linear (data not shown), but with a positive slope. This suggests a linear direct correspondence between read count and number of cells bearing a given V-J configuration at low levels.

In contrast to the reliable low-level detection by way of V-J configuration, detection narrowed to absolute clonotype (by including the CDR3 sequence) was limited to only the first three dilution specimens (i.e. sensitivity down to an approximated 1 in 125 cells; data not shown).

This limited sensitivity speaks to the sensitivity of the TRSeq junction finder to sequencing error. Indeed, if even a single base is changed relative to the canonical regular expression required for detection of a CDR3 sequence, the junction finder will not identify the sequence correctly: likewise, any non-triplicate base insertion will not be detected as an in-frame CDR3 sequence. In contrast, since the TRSeq V and J gene enumeration scheme uses alignment-based algorithms, the TRSeq results relating to V and J gene enumeration are much more forgiving of higher the higher likelihood of sequencing error in clonotypes with low read counts, thus substantially improving the assay sensitivity for characteristically unique V-J gene configurations.

Support for these suppositions is echoed in part by previous work pertaining to core clonotype analyses[27]. Indeed, when the proposed criteria of Bolotin, et. al.[27] for gathering low-level reads of similar but error-prone sequence into common core clonotypes are applied to the dilution experiment (implemented in Appendix 3), it is possible to identify reads comparable to the clonotypes described above in even the most dilute samples.

For example, running the code of Appendix 3 with the input core clonotype of the TRGV8-TRGJ2 configuration, and allowing for a maximum of 3 sequence mismatches, 3 or more reads of satisfactory clonotype can be identified in dilutions 2-5. If the number of sequence mismatches is increased to 4, reads of satisfactory clonotype can be identified in all dilutions (i.e. down to an estimated sensitivity of 1 in 185646 cells).

The importance of these results stems from the applicability of this form of core clonotype analysis to a more accurate identification of minimal-residual disease, for example, at very low levels with remarkable sensitivity, even in the absence of traditional primer-directed sequence enrichment[77].

NTRA—BIOMED-2 Comparison

In keeping with the general approach used to assess BIOMED-2 results, the NTRA TRB and TRG clonotype tables were analyzed to compare the ratio of the dominant clonotype read count relative to the "background" read count. The largest read count not satisfying the normalized TRSeq read count according to the results of Section 3.3 was taken as the background read count value; alternatively, in the case where the dominant clonotype did not satisfy the normalized TRSeq read count cut-off of Section 3.3, the next largest clonotype read count was taken as "background". From among each of the TRB and TRG loci, the largest dominant clonotype-to-background ratios were compared to the overall BIOMED-2 results using a ROC analysis.

The ROC analysis result could be classified as "good"[78] with AUC=0.82, p-value <0.001 (data not shown). Of note, this AUC value appears comparable to those observed in Section 3.3. Of even more impressive note is that the ROC-suggested dominant clonotype-to-background cut-off value was also comparable to that outlined in the current BIOMED-2 TRGR assay interpretation guidelines[79]; indeed, the ROC analysis-suggested value of 3.4, which is effectively the median value of the "indeterminate" range of dominant peak-to-background ratios recommended for BIOMED-2 result interpretation[79].

Interestingly, when the above process was broken down into two separate comparisons of the TRB and TRG loci, the TRG locus was found to be the significant driver: the TRG locus comparison alone yielded a ROC AUC=0.81 (p-value <0.001) whereas the TRB locus comparison alone yielded a ROC AUC=0.60 (p-value=0.17).

NTRA Coverage Metrics—BIOMED-2 Comparison

As in Section 3.4, an analysis of coverage variation in relating to clonal status was undertaken. In contrast to the results of Section 3.4, a far less significant series of areas-under-the-curve were observed from this analysis. The greatest AUC was noted by analysis of mean V-gene coverage (i.e. mean V-gene coverage over all four loci) with AUC=0.59, p-value=0.213.

Furthermore, the data from Section 3.4 suggested that analysis of coverage from the Gamma locus might be predictive of clonal status. Unfortunately, these hypotheses were not substantiated by way of the clinical validation set, from which the AUC for the TRG locus V-gene analysis and TRG locus J-gene analysis were 0.59 and 0.57, respectively.

The clear discordance between these results and those of Section 3.4 likely relates to several factors. First, the sample size in Section 3.4 is one-sixth that of the clinical validation set, making the results of Section 3.4 much more vulnerable to the effects of outliers. Second, the overall coverage in the analytical validation set was lower, owing to base-output restrictions using the mid-output NEXTSEQ kit; as such, coverage correlations made in Section 3.4 might not necessarily be applicable to experiments performed using the high-output NEXTSEQ kit. Thirdly, the clinical validation experiment was not subject to bias of assumption as to the clonality of each input specimen; rather clonality was specifically assayed using an orthogonal method.

SUMMARY

Described above is the first hybrid-capture-based T-cell clonality assay designed to assess clonality and provide clonotype data over all four T-cell gene loci. For this purpose, a custom MATLAB-based analysis pipeline was implemented using optimized object-oriented programming integrating the ultra-fast BWA alignment system and the aesthetically-pleasing circos-based genomic data visualization suite. The latter visualization was designed with current methods in mind, in which electropherographic plots serve as the primary means by which clonotypes are visualized.

Advantages of NTRA Over Traditional T-Cell Clonality Testing Assays

Not only can the NTRA identify clonotypes from all four loci, the use of hybrid capture makes the process platform-agnostic. The laboratory work-flow can be integrated into any standard library preparation work-flow with the addition of a single hybridization step, capable of enriching for sequences containing T-cell genes of a several specimens at a time. In addition, as part of laboratory work-flows already using a hybrid-capture approach for other purposes, the probes used as part of the NTRA are amenable to "spike-in" combined hybridization reactions, provided that there is no significant probe-set sequence overlap or complementarity.

In comparison to the current BIOMED-2 based donality assays, the NTRA adds a dearth of extra data, especially as pertaining to clonotype data from the gene-rich alpha-locus. This locus has traditionally been too diffusely distributed within the genome to be amenable to primer-based amplification, a challenge easily overcome using a hybrid-capture approach. Akin to the requirements of the IMGT, the NTRA outputs a clonotype table containing data specific to the best aligned allele. In contrast, however, visualized data is restricted to gene-level only, thereby providing a means of visualization comparable to electropherographic output. In addition, included with the latter, is the in-frame CDR3 sequence (where detected), data currently not available using either standard PCR-based techniques or the mainstream sequencing-based solutions (e.g. Invivoscribe).

In addition to validating the wet-bench and informatics using a number of orthogonal approaches, the NTRA was also shown to be theoretically sensitive to low-level clonotypes. This latter observation is an important boon to the hybrid-capture approach, suggesting that carefully performed hybrid-capture methods can provide signal amplification comparable to flow-cytometric[81] and molecular approaches[32][82][83].

Assay Cost & Efficiency Considerations

As highlighted in Section 3.8, the assay may be considered cost effective, depending on the specific scenario of interest. In addition, the use of a hybrid-capture approach allows for spike-ins of additional probes for other genomic regions of interest. This allows the possibility of running multiple assays from a single library preparation step, requiring only bioinformatic separation of the resulting enriched sequences.

Applications

Assessment of lymphocyte clonality is integral to the diagnosis of diseases and cancer affecting the immune system. In addition, sequencing of the T-cell repertoire of a patient has gained clinical value with the recent understanding of T-cell mediated recognition and destruction of neoplasms. Further, the development of adoptive cell therapy and recombinatorial engineering of T-cell receptors requires high-throughput molecular characterization of in vitro T-cell populations before transplant. PCR-based methods such as BIOMED-2 and Immunoseq are currently in use for TCR characterization however their costs and complexity remain barriers for clinical deployment requiring high-throughput multi-patient, multi-sample work-flows at low cost. We have therefore developed a hybrid-capture-based method that recovers rearranged TCR sequences of heavy and light TCR chains from all four classes in one tube per sample at low cost. TCR clonality and CDR3 prevalence can be rapidly assessed in a three-day turn-around time with an automated pipeline generating summary figures that can be rapidly assessed by clinicians.

Adaptive T-cell immunotherapy has become a field of great interest in the treatment of multiple solid-tumor cancer types. Non-childhood cancers, particularly those linked to chronic exposure of known carcinogens, are driven by the accumulation of mutations. Some of these mutations drive pro-tumorigenic changes, while others result in non-tumorigenic changes to proteins expressed by the carrier cell. During normal protein turnover these modified proteins are broken down in to short polypeptides and make their way to the surface of the cell in association with molecular surveillance molecules (MHC I). In this context these modified polypeptides are recognized as foreign neo-antigens by the host immune system, and in the context of other signals, lead to the activation of T-cells that direct the destruction of cells expressing these modified proteins.

It is now understood that many solid-tumours exist in a state where their presence recruits neo-antigen specific T-cell lymphocytes to the margins however further advance and effective destruction of the tumor is prevented by expression of checkpoint inhibition molecules on the tumor cell surfaces. Therefore immunotherapy has become a major area of advance in cancer therapy wherein such checkpoint inhibition molecules are masked through transfusion of antibodies. This allows recognition of tumor and its destruction by neo-antigen specific T cells. In order to further enhance such anti-tumor activity, tumor infiltrating lymphocytes (TIL) can be isolated from tumor biopsies and expanded in vitro, followed by subsequent transfusion in great numbers back in to the patient following immunodepletion to enhance transplant colonization thereby driving a durable antitumor response.

T-cell lymphocytes are fundamental to this process, however due to their exquisite specificity, only neo-antigen specific T-cells are capable of driving anti-tumor activity. As a result there is a need for molecular characterization of circulating T-cells in the patient before and after treatment, infiltrating T-cells in the tumor before and after treatment, and screening of expanded populations in vitro for safety and efficacy. Our method provides a high-throughput, low cost and rapid turn-around method for T-cell receptor characterization in order to facilitate clinical deployment and uptake of adoptive cell transfer immunotherapy.

This method is not only of use in immunotherapy applications, as any disease involving expansion of T-cell clones would benefit from its use. The symptoms of autoimmune diseases are driven largely by T-cell mediated cytotoxicity of "self" tissue and therefore the identification and expansion of specific T-cell clones can be monitored using this method. This method would also be useful to follow immune challenges such as infection or immunization in the development of anti-infectives or vaccines.

Example 2

There is also described herein a laboratory and bioinformatic workflow for targeted hybrid-capture enrichment of T-cell receptor loci followed by Illumina sequencing to assess the clonality of a range of specimens with variable T-cell clonal complexity as well as a set of 63 T-cell isolates referred for clinical testing at our institution.

Methods and Materials

Probe design—All annotated V, D, J gene segments were retrieved from the IMGT/LIGM-DB website (www.imgt.org[9]). The 100 bp of annotated 3' V gene coding regions and up to 100 bp, when available, of annotated 5' J gene coding regions were selected as baits. Probes with duplicate sequences were not included.

DNA isolation—CD3+ T cells were isolated by flow assisted cell sorting of PBMC populations separated from whole blood. Peripheral blood mononuclear cells (PBMC) were isolated from whole blood by centrifugation followed by DNA isolation with a GENTRA PUREGENE kit (Qiagen) according to manufacturer protocol. In the case of fresh/frozen tissues, a QIAGEN ALLPREP (Qiagen) kit was employed, according to the manufacturer's instructions. In contrast, for FFPE samples a previously optimized in-house approach was used. First, sample FFPE tissue blocks were cored with a sterilized TISSUE-TEK QUICK-RAY punch (Sakura) in a pre-selected area of representative tissue; alternatively, under sterile conditions, 10×10 µm DNA curls/unstained slides were obtained for each submitted block of FFPE tissue. In a fumehood, 400-1000 µL xylene was aliquot into each tube (volume increased for larger FFPE fragments), followed by vigorous vortexing for 10 sec, incubation in a 65° C. water bath for 5 min, and centrifugation at 13200 rpm for 2 min. The supernatant was then discarded and step an additional xylene treatment step was performed. Subsequently, addition of 400-1000 µL ethanol (volume adjusted for larger input tissue volumes) was performed, followed by vigorous vortexing for 10 sec, and centrifugation at 13200 rpm for 2 min. The supernatant was then discarded and the ethanol treatment step repeated. The resulting pellet was then dried using a SPEEDVAC (Thermo Scientific) for 5 min, after which 150 μL of QIAAMP buffer ATL (Qiagen) was added, followed by 48-hour incubation at 65° C. with 50-150 μL of proteinase K (volume increased for higher input volumes). A final ethanol clean-up step was performed, as above, to produce a purified DNA product. Resuspension in TE buffer (Qiagen) was then performed.

Hybrid capture—Isolated genomic DNA was diluted in TE buffer to 130 uL volumes. Shearing to ~275 bp was then performed on either a Covaris M220 Focused-ultrasonicator or E220 Focused-ultrasonicator, depending on sample throughput, with the following settings: for a sample volume of 130 μL and desired peak length of 200 bp, Peak Incident Power was set to 175 W; duty factor was set to 10%; cycles per burst was set to 200; treatment time was set to 180 s. In addition, temperature and water levels were carefully held to manufacturer's recommendations given the instrument in use.

Illumina DNA libraries were generated from 100-1000 ng of fragmented DNA using the KAPA HYPERPREP Kit (Sigma) library preparation kit following manufacturer's protocol version 5.16 employing NEXTFLEX sequencing library adapters (BIOO Scientific). Library fragment size distribution was determined using the Agilent TAPESTATION D1000 kit and quantified by fluorometry using the Invitrogen QUBIT.

Hybridization with probes specifically targeting V and J loci (Supplemental Table 3) was performed under standard SEQCAP (Roche) conditions with XGEN blocking oligos (IDT) and human Cot-1 blocking DNA (Invitrogen). Hybridization is performed either at 65 C overnight. The target capture panel consists of 598 probes (IDT) targeting the 3' and 5' 100 bp of all TR V gene regions, and 95 probes targeting the 5' 100 bp of all TR J gene regions as annotated by IMGT (four loci, 1.8 Mb, total targeted 36 kb).

Capture Analysis—A custom Bash/Python/R pipeline was employed for analysis of paired read sequencing data generated by Illumina NEXTSEQ 2500 instrument from the hybrid-capture products. First, 150 bp paired reads were merged using PEAR 0.9.6 with a 25 bp overlap parameter[418]. This results in a single 275 bp sequence for each sequenced fragment. Next, specific V, J, and D genes within the fragment sequence were identified by aligning regions against a reference sequence database. Specifically, individual BLAST databases were created using all annotated V, D, J gene segments retrieved from the IMGT/LIGM-DB website (www.imgt.org[49]), as these full-length gene sequences were the source of probes used to design the hybrid-capture probe panel. Individual merged reads are iteratively aligned using BLASTn with an e value cut-off of 1 to the V database, J database then D database with word size of 5 for D segment queries[419]. Trimming of identified V or J segments in the query sequence is performed prior to subsequent alignment. From reads containing V and J sequences, we identified V/J junction position and the antigen specificity determining Complementarity Determining Region 3 (CDR3) sequences. In order to identify CDR3 sequences, the V/J junction position is extracted from the previous search data for those fragments containing both a V and J search result. 80 bp of DNA sequence flanking this junction is translated to amino acid sequence in all six open reading frames and sequences lacking stop codons are searched for invariable anchor residues using regular expressions specific for each TR class as determined by sequence alignments of polyclonal hybrid-captured data from rearranged TR polypeptides annotated by IMGT[9]

Results and Discussion

The CapTCR-seq method employs hybrid capture biotinylated probe sets designed based on all unique Variable (V) gene and Joining (J) gene annotations retrieved from the IMGT database version 1.1, LIGMDB_V12[9]. These probe sets specifically target the 3' regions of V gene coding regions and the 5' regions of J gene coding regions that together flank the short Diversity (D) gene fragment in heavy chain encoding loci and which together form the antigen specificity conferring CDR3 (FIG. 3A). D regions (absent in alpha and gamma rearrangements) were not probed due to their short lengths, high potential junctional diversity introduced by the recombination process, and to permit a single universal probe set for both light and heavy chain loci. These biotinylated probes are hybridized with a fragmented DNA sequencing library, and probe-target hybrid duplexes are subsequently recovered by way of streptavidin-linked magnetic beads. The subsetted library is PCR amplified from the bead-purified hybrid-duplex population using a single set of adapter-specific amplification primers and the resulting library is subjected to paired read 150 bp sequencing on an Illumina NEXTSEQ 500 instrument. A 250 bp fragment size was selected as mid-range between the maximum length of a merged fragment from 150 bp paired-end read sequencing (275 bp) and a lower limit of 182 bp based on alignments of simulated reads centered at the VJ junction with variable insert sizes that had successful V and J alignment sensitivity of >99%.

To identify V(D)J rearrangements from the pool of captured V and J sequences, we used a computational method that performed: (1) Read merging to collapse paired reads in to a single long-read sequence to enhance V(D)J and CDR3 identification, (2) progressive BLASTn-based V, J and D detection utilizing iterative end trimming and (3) CDR3 scoring using regular expression pattern matching (FIG. 3B). This BLAST-based sequence alignment approach was employed due to its tolerance for nucleotide mismatches that could arise from junctional diversity or the presence of allelic variants not present in the reference database. We acknowledge that numerous alternative V(D)J and CDR3 calling algorithms are available[410-16] and these may be used in addition or in lieu of our pipeline to analyze V(D)J fragments captured by our laboratory approach. A head-to-head comparison of these methods is beyond the scope of this proof-of-principle report.

We employed this method to identify V(D)J rearrangements and CDR3 sequences in PBMCs isolated from a healthy human. With a single step hybridization and capture reaction employing the probe panel targeting TCR V genes, the number of detected unique VJ rearrangements increased with increasing amount of sample genomic DNA used to generate the initial library, with 52 times more rearrangements detected with an input of 1,000 ng compared with 100 ng (1925 vs 37) (FIG. 3C). The number of unique VJ rearrangements is dependent on the number of T cells in the original sample with an approximate fourfold increase for CD3+ sorted cells over PBMCs (2475 vs 759) (Supplemental Table 1). Addition of the J probe panel to form a single-step capture using a pooled V and J panel improved recovery of unique CDR3 sequences per 1 ng of library input by 5 fold (single-step V capture mean: 1.7, single-step VJ capture mean: 8.56) (Supplemental Table 1). This modification also increased the ratio of on-target reads, effectively decreasing the amount of sequencing needed to obtain the same number of rearranged fragments (single-step V capture mean: 14.4%, single-step VJ capture mean: 42.9%). Overall, we saw a diverse representation of alleles for all four classes with 2895 alpha, 1100 beta, 59 gamma, 9 delta unique VJ rearrangements observed from 16 independent captures of independent libraries (data not shown). This corresponded to 6257 alpha, 4950 beta, 1802 gamma, 109 delta unique CDR3 sequences. We also submitted a portion of these samples for parallel characterization by a commercial PCR-based TCR profiling service and found similar V/J gene usage and representation with no more than 2% variation (FIG. 3D-F) and correlation with an $r^2$ value of 0.94 (data not shown).

Figure 4:
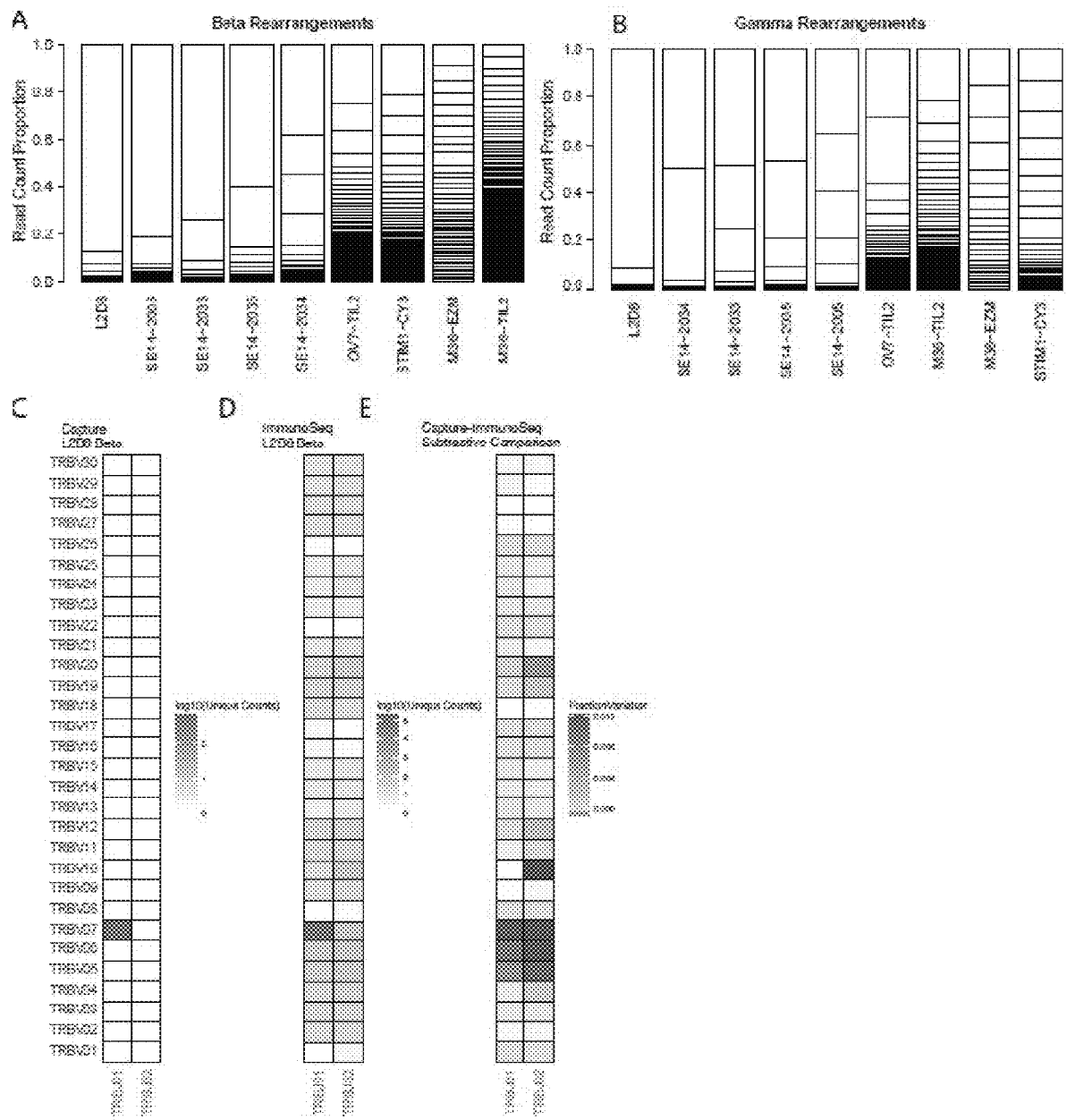
FIG. 4: Cell line and tumor isolate T-cell clonality. Boxes represent individual unique VJ pairs and box size reflects abundance in sample. Samples ordered by decreasing clonality. (A) Beta chain VJ rearrangements. (B) Gamma chain VJ rearrangements. (C) L2D8 Gp100 antigen specific beta locus VJ rearrangements determined by CapTCR-seq. (D) L2D8 Gp100 antigen specific beta locus VJ rearrangements determined by a PCR-based profiling service. (E) Subtractive comparison between CapTCR-seq and PCR-based profiling service. Red indicates relative enrichment of indicated pair by CapTCR-seq while blue indicates relative enrichment of indicated pair by PCR-based profiling.

To test the ability of CapTCR-seq to assess TCR clonality of samples with a range of clonal signatures, we analyzed libraries derived from CD3+ flow-sorted Tumor Infiltrating Lymphocytes (TIL) expanded cultures (oligoclonal) and lymphoblast cell lines (clonal) (FIG. 4A-B: and data not shown). As expected, the cell-lines and antigen-specific cell-sorted samples were more clonal (12-22 unique VJ rearrangements) than the TIL cultures (123-446 unique VJ rearrangements). The predominant alpha rearrangement represented 40-80% of the recovered reads in clonal samples compared to 2.5-17.5% for the latter TIL cultures. Specifically, we detected 12 unique VJ rearrangements in L2D8, a GP100 antigen-specific tumor-infiltrating lymphocyte clone. In OV7, a mixed ovarian tumor-infiltrating lymphocyte population expanded with IL-2 treatment, we found 311 unique VJ rearrangements. We profiled two populations isolated from the same tumor: M36_EZM, a cell suspension of melanoma tumor with brisk CD3 infiltration harbored 123 unique VJ rearrangements, while M36_TIL2, tumor-infiltrating lymphocytes from this tumor expanded in IL-2 harbored 446 unique VJ rearrangements, reflecting a likely expansion of low prevalence T cells. STIM1 is MART1-specific cell line made from peptide stimulation of healthy donor PBMCs, FACS sorting and expansion of tetramer+ cells from which we found 195 unique VJ rearrangements. The cell lines were found to encode previously reported gene rearrangements at the TCR beta and gamma loci, and additional rearrangements not previously reported (Supplemental Table 2)[417]. Targeted PCR amplification of V/J rearrangement pairs, including the most frequently observed for each sample, was performed on these samples. We observed expected product for all prevalent rearrangements with some amplification failures for low prevalence rearrangements (Sample: Observed bands/expected bands; A037: 9/11; L2D8: 4/5; EZM: 3/4; TIL2: 8/9; OV7: 5/9; STIM1: 7/9; SE14 2005: 4/4; SE14 2033: 3/4; SE14 2034: 4/4; SE14 2035: 4/4) (data not shown). We also submitted the GP100 antigen specific L2D8 sample for beta locus profiling by a PCR-based commercial service and found VJ repertoire usage to be highly congruent (FIG. 4C-E), however the commercial service identified extensive low level VJ gene usage not present in the capture data (FIG. 4D). This signal may represent low-level alternative VJ pair antigen specific clones, or sample contamination with non-antigen specific clones.

To demonstrate the potential clinical utility of our approach, we generated DNA sequencing libraries from an unselected cohort of 63 samples submitted for clinical T-cell receptor rearrangement testing and subjected these to capture, sequencing and analysis (Supplemental Table 1). Samples were found to have varying degrees of clonality, with the predominant CDR3 sequence representing up to 40% of the most clonal sample (average 12.2%; median 6.3%%, range 0.8-100%, data not shown). When a clonal population was defined as having the most abundant to third most abundant rearrangements observed at two or more times the level of the next most abundant rearrangement, we observed three groups of samples: 11 with clonal enrichment of both beta and gamma rearrangements, 12 with clonal enrichment of beta or gamma rearrangements, and 41 that were polyclonal for both beta and gamma. When 61 of these samples were assessed by BIOMED2 assay we observed 73% agreement for beta (44/60) and 77% for gamma (46/60), 60% of samples were in agreement for both beta and gamma clonality measures (36/60). For the beta locus, 13 samples that were scored as clonal by BIOMED2 were scored as polyclonal based on relative prevalence when assessed by hybrid capture profiling. Six had low top clone prevalence (predominant rearrangement relative proportion of 1.3%, 1.8%, 2.6%, 3.1%, 3.4%, 3.8%) with a median unique VJ rearrangement count of 185. Seven had higher top clone prevalence (predominant rearrangement relative proportion of 7.6%, 8.4%, 8.5%, 8.8%, 11.9%, 12.1%, 16.9%) with a considerably lower median unique VJ rearrangement count of 44. These 13 samples had variable diversity but no predominant rearrangement was more than twofold enriched relative to the next most common rearrangement. Conversely, three samples that were scored as polyclonal by BIOMED2 at the beta locus were scored as clonal based on relative prevalence (predominant rearrangement relative proportion of 25.9%, 18.6%, 6.5%) with a median unique VJ rearrangement count of 191. These discrepancies could be resolved with deeper sequencing of these libraries to determine whether insufficient depth was distorting the interpretation or whether these represent incorrect interpretations by the BIOMED2 protocol. Improvements in the BIOMED2 primer sets have led to reduced false positives compared to previous generations, and can be further diminished through the use of higher resolution gel separation and additional analyses[42], however if available, sequencing-based methods provide a more quantitative assessment and relative comparison between all rearrangements. To determine whether there was unexpected enrichment in the A037 or lymphoma data sets we compared their gene usages (data not shown). A037 and the lymphoma collection had similar VJ usage profiles with few individual unique VJ rearrangement proportion enriched in A037 of up to 1% and more enrichments amongst the lymphoma set of up to 3% as expected given the clonal enrichment of select rearrangements in T-cell lymphomas.

In summary, CapTR-Seq allows for rapid, inexpensive and high-throughput profiling of all four loci from multiple samples of diverse types from a given DNA sequencing library with fragment size of 250 bp and sequencing length of 150 bp. This method will permit intensive monitoring of TR repertoires of patients with T-cell malignancies as well as monitoring of tumor-infiltrating lymphocytes in tumors from patients undergoing immune checkpoint blockade, adoptive cell transfer and other immunotherapies.

Example 3

Adoptive Cell Transfer (ACT) of in-vitro expanded Tumour-Infiltrating Lymphocytes (TIL) has emerged as an effective treatment for numerous types of solid tumours, often resulting in a durable response and in some cases a complete remission by the patient[B1]. This intervention effectively replaces nearly the entire heterogenous T-cell repertoire of the patient with tumour antigen and patient-specific effector T cells. Effector T-cells are integral for the adaptive immune response due to their roles in cellular cytotoxicity and cytokine production, with specificity conferred by the TCR-MHC interaction[B2]. The CD8+ effector T-cell repertoire consists of alpha/beta and gamma/delta subtypes, both polyclonal and skewing in the incidence of an antigen-specific response or malignancy[B3]. In high mutation load neoplasms, the MHC molecule often presents tumour-associated neo-antigens generated as a result of mutation that lead to clonal expansion and infiltration of tumour-infiltrating lymphocytes (TILs)[B4]. These TILs are largely clonal and distinct from the circulating repertoire in multiple types of neoplasia[B5]. While these TILs are capable of driving an effective anti-tumour response in vitro, they are often exhausted within the tumour microenvironment as a result of expression of immunosuppressive cell-surface proteins by the tumour but their activities can be restored with immune checkpoint blockade therapy[B6]. The combined effect of immunotherapy intervention: immunodepletion, TIL ACT and checkpoint blockade together present an effective treatment for many patients but have a disruptive effect on the endogenous immune repertoire and therefore proper patient care would benefit from longitudinal monitoring of the T-cell repertoire during the course of disease and treatment.

During ACT immunotherapy, both the requisite immunodepletion and T-cell transfer radically disrupt the abundance and diversity of the endogenous T-cell population and therefore molecular profiling methods are required for monitoring of the patient during the course of immunotherapy[B7]. The TCR repertoire consists of cell-specific heterodimeric receptors uniquely rearranged and expressed from either the alpha/beta or gamma/delta genomic loci[B8]. The TCR has unique specificity for an antigen presented in the context of the an MHC molecule as defined by the combined interactions of the amino acid residues encoded at the V-(D)-J junction known as the complementarity determining region 3 (CDR3), and by the CDR1 and CDR2 regions in the upstream V gene fragment.

Methods and Materials

Probe design—All annotated V (V-panel), D, J (J panel) gene segments and V 3'-UTR (depletion panel) sequences were retrieved from the IMGT/LIGM-DB website (www.imgt.org). The 100 bp of annotated 3' V gene coding regions, up to 100 bp, when available, of annotated 5' J gene coding regions, and 120 bp of V 3'-UTR sequences were selected as baits. Probes with duplicate sequences were not included. The V-panel consists of 299 probes (IDT) targeting the 3' and 5' 100 bp of all TR V gene regions, and the J-panel consists of 95 probes targeting the 5' 100 bp of all TR J gene regions as annotated by IMGT (four loci, 1.8 Mb, total targeted 36 kb). The depletion-panel consists of 131 probes targeting the 5' 120 bp of 3'-UTR Immunoglobulin V regions, and 107 probes targeting the 5' 120 bp of 3'-UTR TCR V regions.

DNA Isolation—CD3+ T cells were isolated by flow assisted cell sorting of PBMC populations separated from whole blood. Peripheral blood mononuclear cells (PBMC) were isolated from whole blood by centrifugation followed by DNA isolation with a GENTRA PUREGENE kit (Qiagen) according to manufacturer protocol. In the case of fresh/frozen tissues, a QIAGEN ALLPREP kit (Qiagen) was employed to extract DNA and RNA, according to the manufacturer's instructions. The whole blood plasma fraction was then treated with red blood cell lysis buffer and circulating DNA (cfDNA) was extracted using the QIAGEN NUCLEIC ACID kit (Qiagen) according to manufacturer protocol. cDNA synthesis—mRNA was separated from isolated total RNA using the NEBNEXT Poly(A) mRNA Magnetic Isolation Module (NEB) according to manufacturer's instructions. To generate cDNA, first NEBNEXT RNA First Strand Synthesis Module (NEB) was used followed by NEBNEXT RNA Second Strand Synthesis Module (NEB) according to manufacturer's instructions.

Library preparation—Isolated genomic DNA or synthesized cDNA was diluted in TE buffer to 130 uL volumes. Shearing to ~275 bp was then performed on either a Covaris M220 Focused-ultrasonicator or E220 Focused-ultrasonicator, depending on sample throughput, with the following settings: for a sample volume of 130 µL and desired peak length of 200 bp, Peak Incident Power was set to 175 W; duty factor was set to 10%; cycles per burst was set to 200; treatment time was set to 180 s. In addition, temperature and water levels were carefully held to manufacturer's recommendations given the instrument in use.

Illumina DNA libraries were generated from 100-1000 ng of fragmented DNA using the KAPA HYPERPREP Kit (Sigma) library preparation kit following manufacturer's protocol version 5.16 employing NEXTFLEX sequencing library adapters (BIOO Scientific). Library fragment size distribution was determined using the Agilent TAPESTATION D1000 kit and quantified by fluorometry using the Invitrogen QUBIT.

Hybrid capture—For cDNA derived libraries, hybridization was performed with a pooled panel of probes targeting V and J loci in equimolar concentrations. For genomic DNA derived libraries, hybridization and capture was performed iteratively with probes specifically targeting V loci, 3'-UTR sequences, or J loci under standard SEQCAP (Roche) conditions with XGEN blocking oligos (IDT) and human Cot-1 blocking DNA (Invitrogen). Hybridization is performed at 50 C overnight. The Capture process consisting of bead incubations and washes are performed at 50 C.

For the iterative hybridization and capture process, the first J hybridization and capture is performed in completion with terminal PCR amplification with 4 steps. Following clean-up by Agencourt AMPURE XP SPRI bead purification (Beckman) this product is used as input for a subsequent depletion step. For depletion, a modified and truncated SEQCAP protocol is employed wherein following incubation of the hybridization mixture with M-270 streptavidin linked magnetic beads (Invitrogen), the 15 uL hybridization reaction is separated on a magnetic rack, the supernatant is recovered and diluted to 100 uL with TE buffer, followed by clean up by standard Agencourt AMPURE XP SPRI bead purification (Beckman). The depletion-probe-target-beads are discarded. The purified supernatant is then used as input for a subsequent V-panel capture and hybridization as described above, but with terminal PCR amplification with 16 or amplifications steps to achieve sufficient library for sequencing.

Capture Analysis—A custom Bash/Python/R pipeline was employed for analysis of paired read sequencing data generated by Illumina NEXTSEQ 2500 instrument from the hybrid-capture products. First, 150 bp paired reads were merged using PEAR 0.9.6 with a 25 bp overlap parameter. This results in a single 275 bp sequence for each sequenced fragment. Next, specific V, J, and D genes within the fragment sequence were identified by aligning regions against a reference sequence database. Specifically, individual BLAST databases were created using all annotated V, D, J gene segments retrieved from the IMGT/LIGM-DB website (www.imgt.org), as these full-length gene sequences were the source of probes used to design the hybrid-capture probe panel. Individual merged reads are iteratively aligned using BLASTn with an e value cut-off of 1 to the V database, J database then D database with word size of 5 for D segment queries. Trimming of identified V or J segments in the query sequence is performed prior to subsequent alignment. From reads containing V and J sequences, we identified V/J junction position and the antigen specificity determining Complementarity Determining Region 3 (CDR3) sequences. In order to identify CDR3 sequences, the V/J junction position is extracted from the previous search data for those fragments containing both a V and J search result. 80 bp of DNA sequence flanking this junction is translated to amino acid sequence in all six open reading frames and sequences lacking stop codons are searched for invariable anchor residues using regular expressions specific for each TR class as determined by sequence alignments of polyclonal hybrid-captured data from rearranged TR polypeptides annotated by IMGT.

Results and Discussion

Methods Improvement

We experimented with alternate capture methods, using an iterative three-step hybridization and capture, first with a J panel then molecular depletion of unrearranged V-gene sequences, then subsequently with a V panel (data not shown). The depletion probes (V-gene and J-gene) are shown in Table D. These altered protocols improved recovery of unique CDR3 sequences when normalized to reads. When compared to a one-step V-panel capture, the one-step combined VJ-panel capture increased signal by 6.84×, the two-step J and V iterative capture increased signal by 12×(no significant difference was observed for J-V or V-J iterative order), and the three-step J-depletion-V iterative capture increased signal by 31.2×(FIG. 5).

Figure 6:
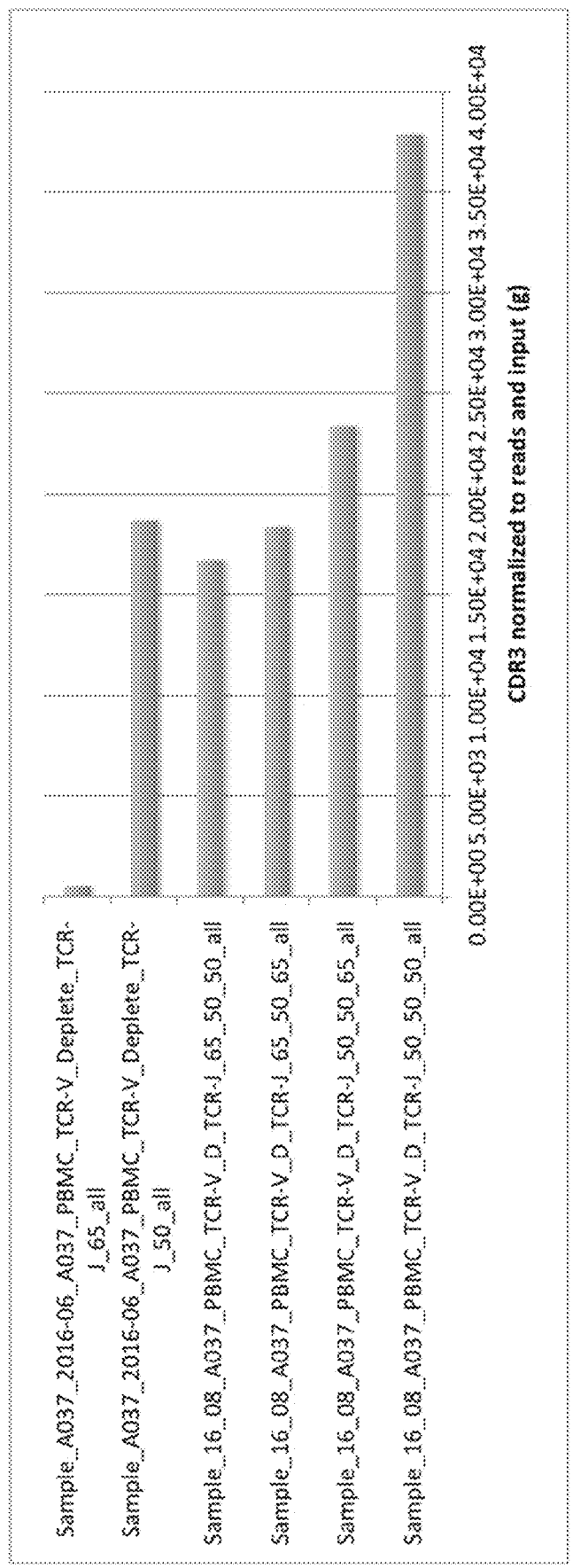
FIG. 6: Comparison of different hybridization and capture temperatures in terms of yielded average unique CDR3 sequences (normalized to reads and library input).

We experimented with reducing hybridization and wash temperatures to improve recovery (FIG. 6). When 50 C to 65 C in 5 C increments were tested at each step of the hybridization and capture, 50 C yielded the highest signal and diversity.

Figure 7:
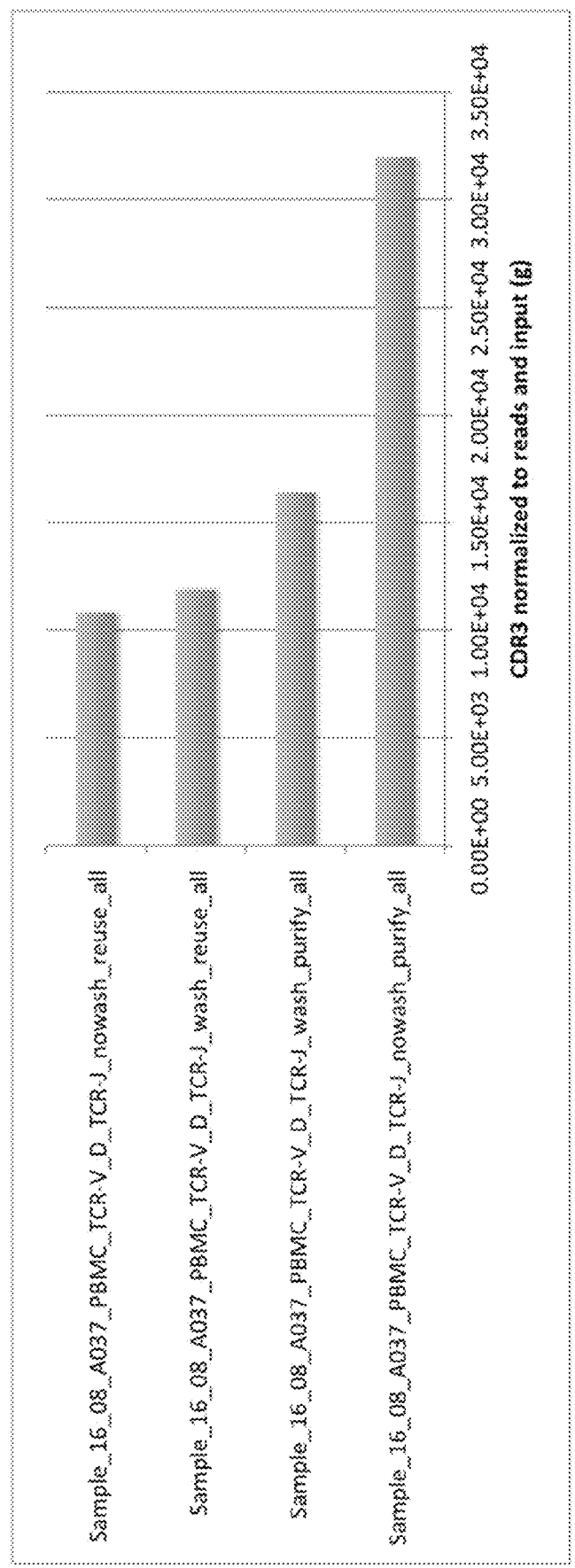
FIG. 7: Comparison of different depletion dean-up steps in terms of yielded average unique CDR3 sequences (normalized to reads and library input).

We determined the best method for depletion (FIG. 7). We found that direct reuse of the hybridization mixture following bead-probe-target separation yielded reduced signal than setting up a new reaction following Agencourt XP bead purification of the supernatant. We also found that direct separation rather than separation of the hybridization following addition of wash buffer yielded increased signal.

Figure 8:
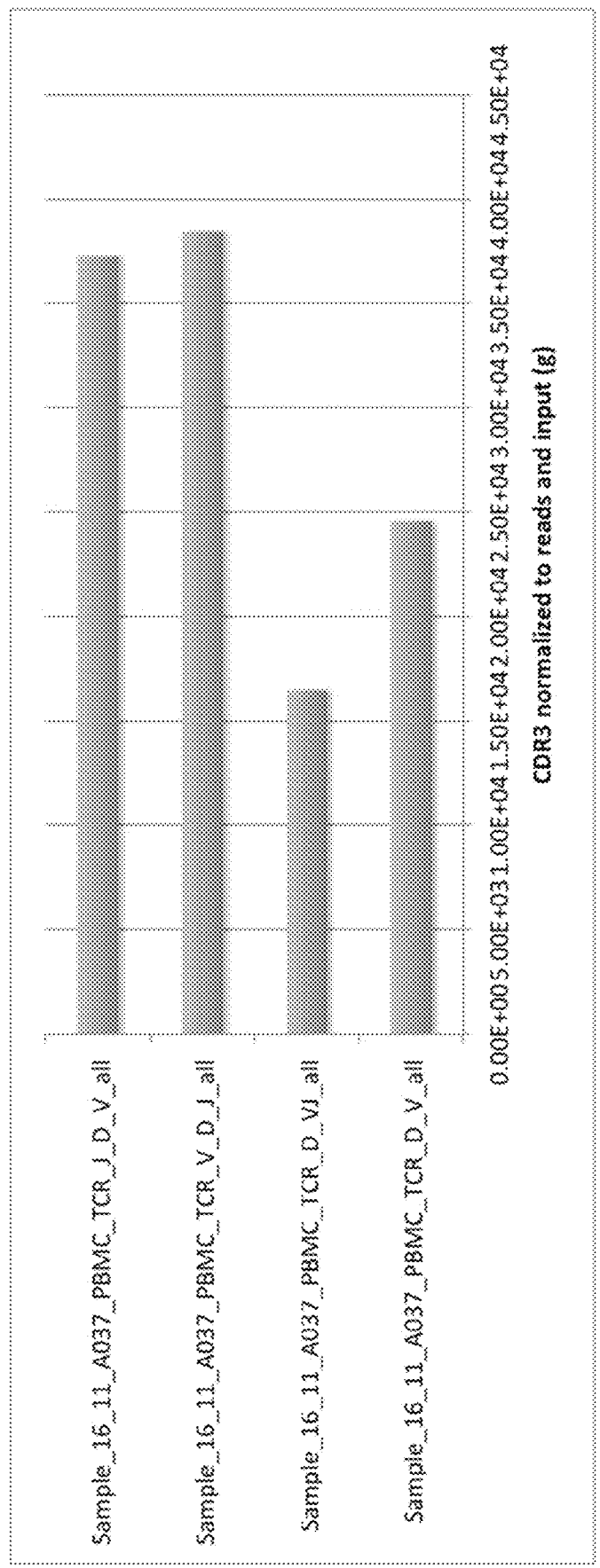
FIG. 8: Comparison of different permutations of iterative captures in terms of yielded average unique CDR3 sequences (normalized to reads and library input).

We tested whether depletion should be preceded by a V or J capture (FIG. 8). We found that direct depletion of the library, followed by V or J capture yielded reduced signal compared to either V-Depletion-J or J-Depletion-V, both of which had increased, yet similar yields.

Input Source Material Comparisons

Figure 9:
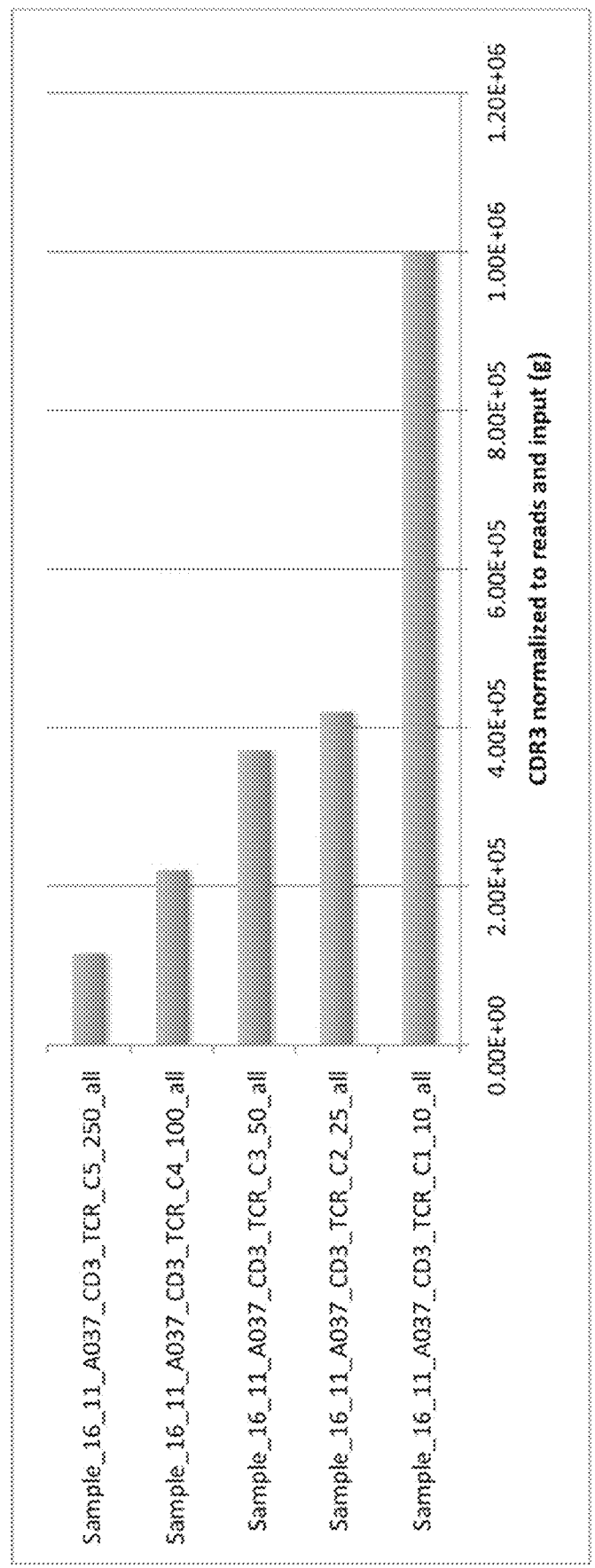
FIG. 9: CD3+ T cell fraction dilution curve. Comparison of average unique CDR3 sequences (normalized to reads and library input) for samples with varying amounts of source material added to generate the library (10 ng-250 ng).
Figure 10:
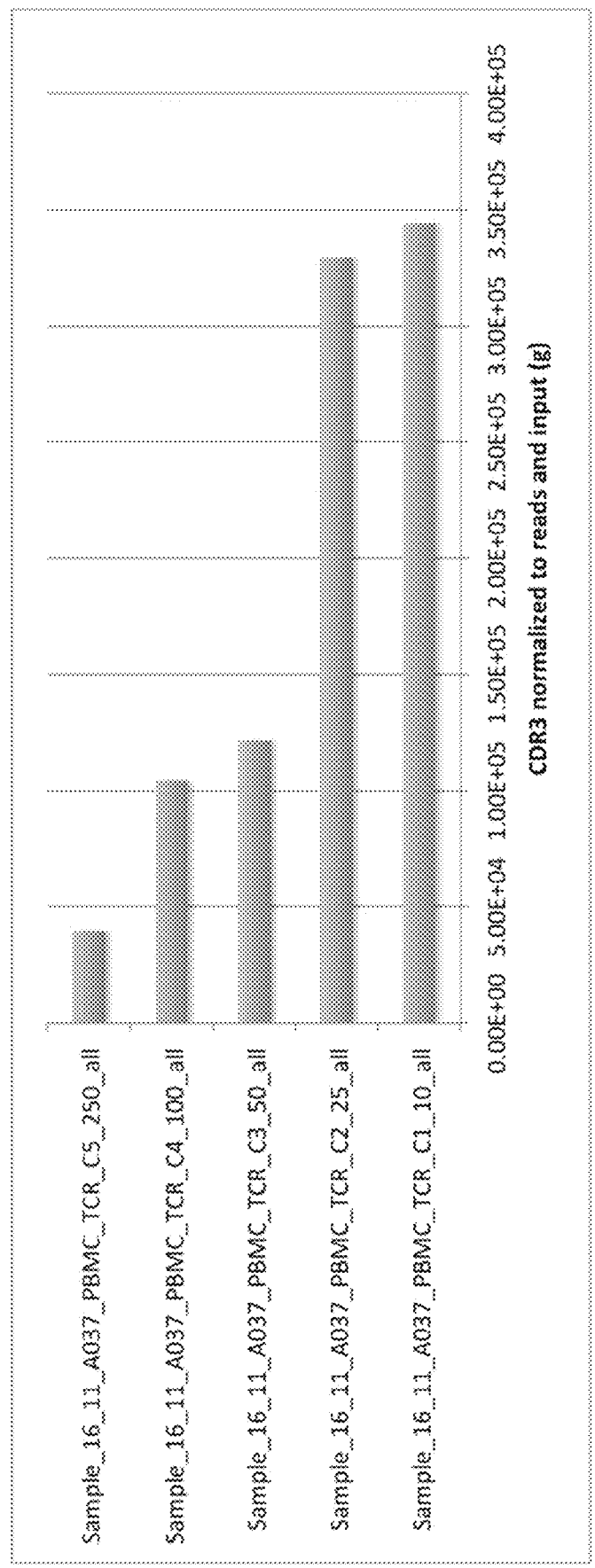
FIG. 10: PBMC fraction dilution curve. Comparison of average unique CDR3 sequences (normalized to reads and library input) for samples with varying amounts of source material added to generate the library (10 ng-250 ng).
Figure 11:
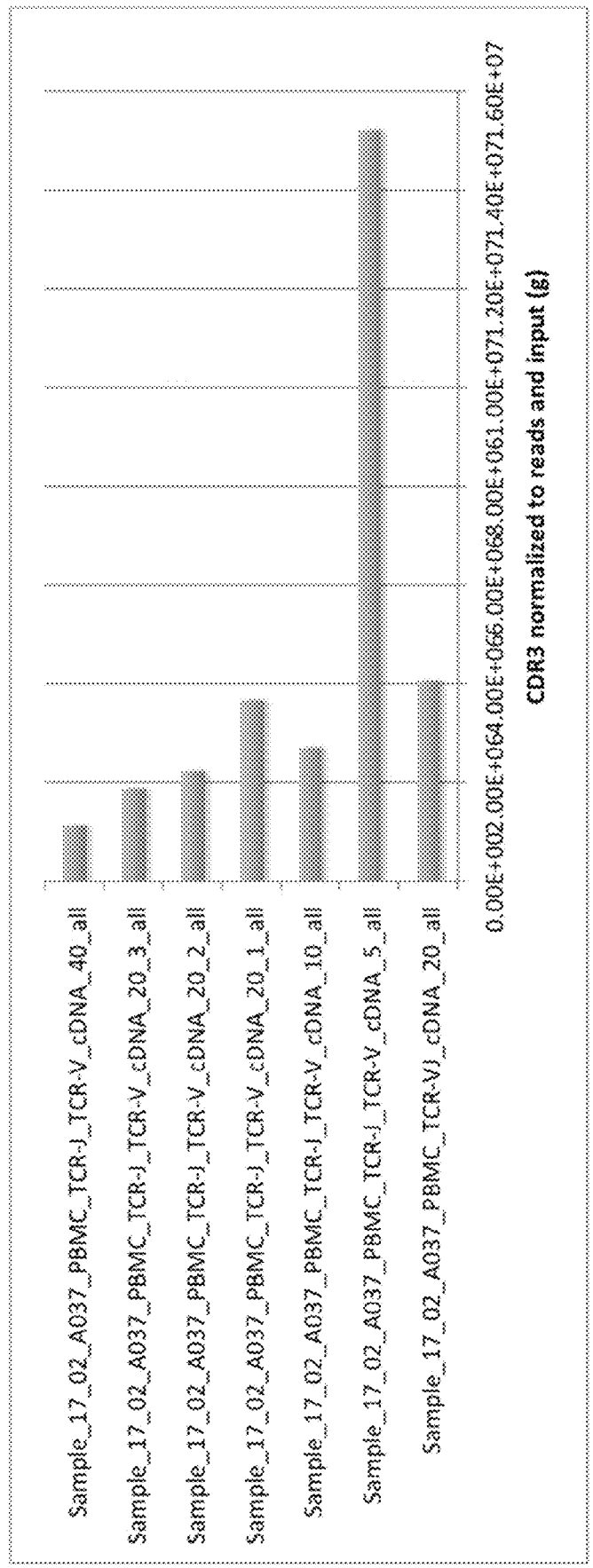
FIG. 11: PBMC fraction cDNA dilution curve. Comparison of average unique CDR3 sequences (normalized to reads and library input) for samples with varying amounts of source material added to generate the library (5 ng-40 ng).
Figure 12:
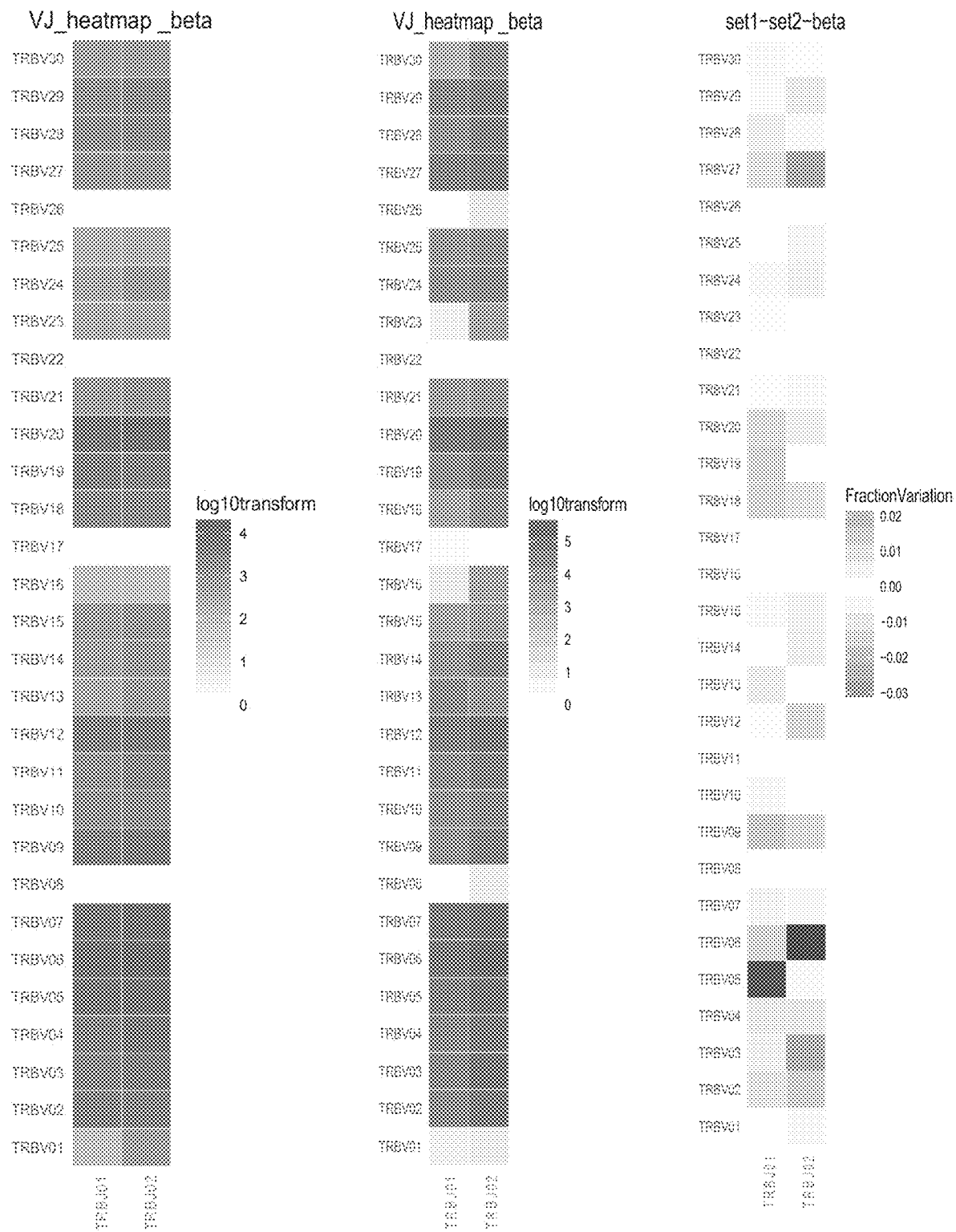
FIG. 12: Comparison of VJ beta locus repertoire for A037 sample derived from genomic DNA (panel 1) and from cDNA (panel 2). A subtractive heatmap is shown in panel 3 that shows differences in overall repertoire between the two samples. Red indicates deviation for genomic, while blue indicates deviation for cDNA.

To determine whether we could characterize the TCR repertoire from both low and high signal samples, we performed a series of dilution curves for CD3+ genomic DNA (FIG. 9), PBMC genomic DNA (FIG. 10), and PBMC derived cDNA (FIG. 11). Less input actually yielded a higher amount of diversity when normalized for input and reads suggesting that high input libraries are being under-sequenced or that probes are being saturated and leaving behind less preferable, but still on-target, targets. Additionally, we observed yields for the cDNA samples to be ~100× that of genomic DNA reflecting enrichment of the TCR signal as a consequence of the high level of transcript expression of the rearranged TCR gene relative to other genes. In contrast, signal from genomic DNA is a related to the fraction of the complete genome of the target sequence and capture efficiency.

Since each sequenced sample represents only a snapshot of the TCR repertoire with the extent dependent on the amount of input material and the complexity of the source repertoire, we were interested in whether the method could assay complete VJ or CDR3 saturation of a patient. We looked at unique VJ pair recovery across multiple samples derived from a single patient blood draw (data not shown). Beta locus VJ saturation was achieved with fewer than ten runs. With sufficient input and sequencing depth, VJ saturation could be achieved in a single run. We also looked at CDR3 saturation across these same samples and were able to achieve approximately 50% beta locus saturation (data not shown). This level could be achieved with fewer samples by using cDNA libraries as input with deeper sequencing.

Figure 19:
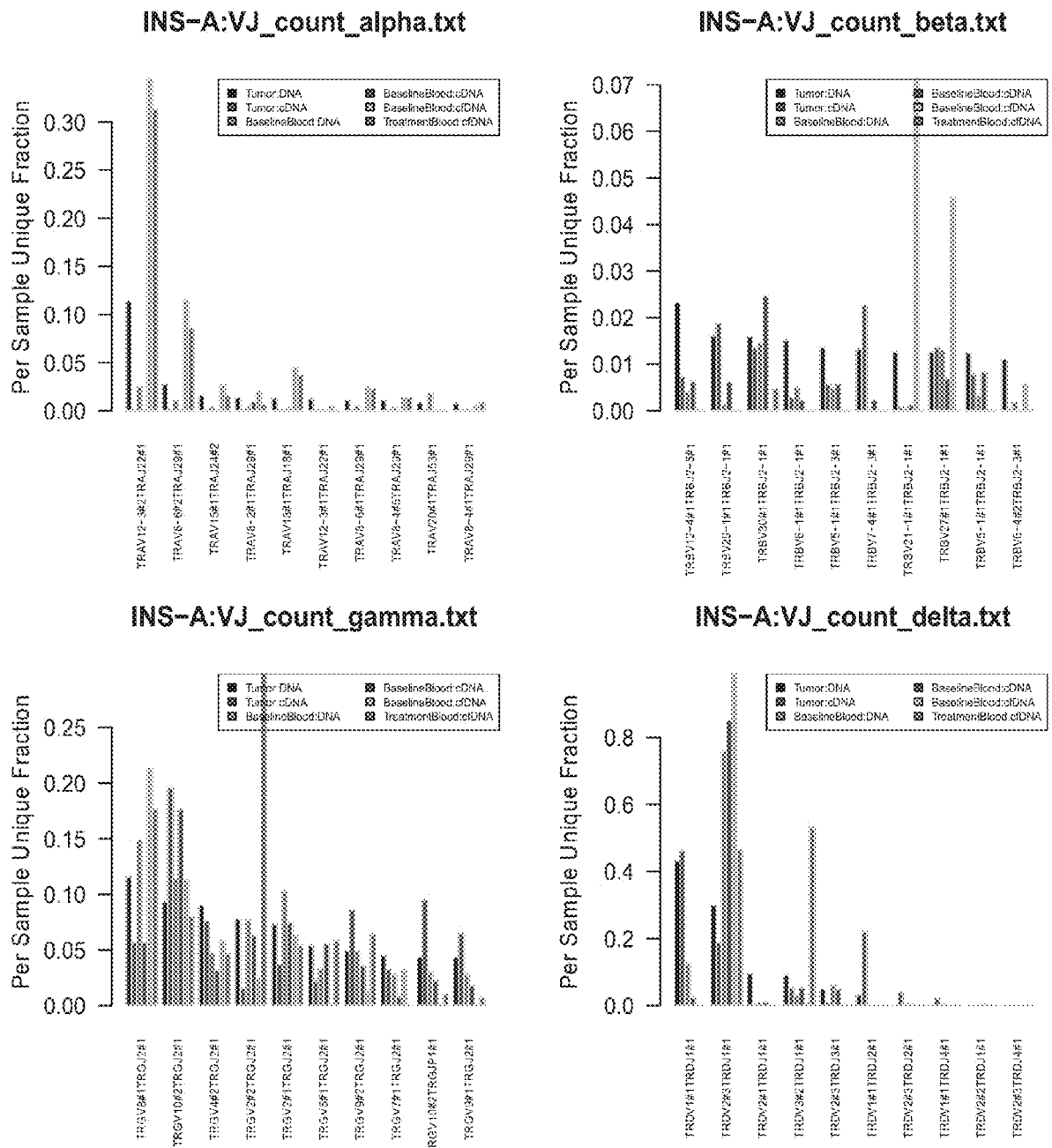
FIG. 19: Sample fractions within all patient A samples for top ten most prevalent VJ rearrangements in tumor. Alpha locus (panel 1), beta locus (panel 2), gamma locus (panel 3), delta locus (panel 4).

We looked at whether the genomic DNA and cDNA samples were recapitulating the same VJ combinations at the beta locus (FIG. 19). This was largely the case with only two discordant VJ pairs showing greater (<3% overall) change.

Figure 13:
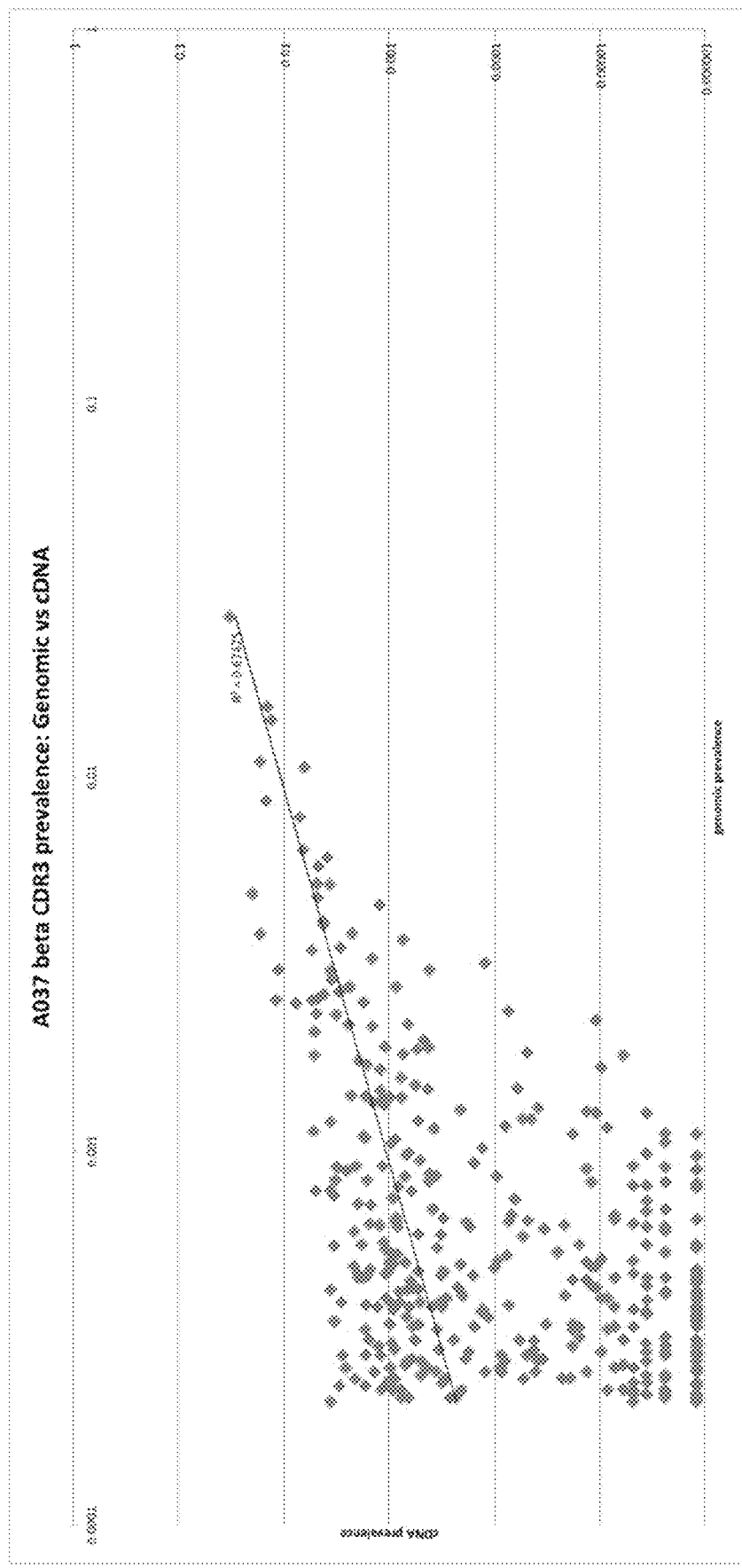
FIG. 13: Prevalence comparison of the top 1000 beta locus CDR3 in the genomic DNA set compared with their prevalences in the cDNA set.

We looked at whether the genomic DNA and cDNA samples were recapitulating the same CDR3 sequences (FIG. 13). For the most prevalent 1000 CDR3 sequences detected from genomic DNA, their correlation with cDNA prevalences had an r squared value of 0.67. Many had similar prevalences however a large number had very low or zero prevalence values in cDNA. This is likely explained by the second group consisting of non-productive rearrangements that are encoded on the alternate chromosome and which are not expressed.

Investigation of Samples from Adoptive Cell Transfer Immunotherapy

Figure 14:
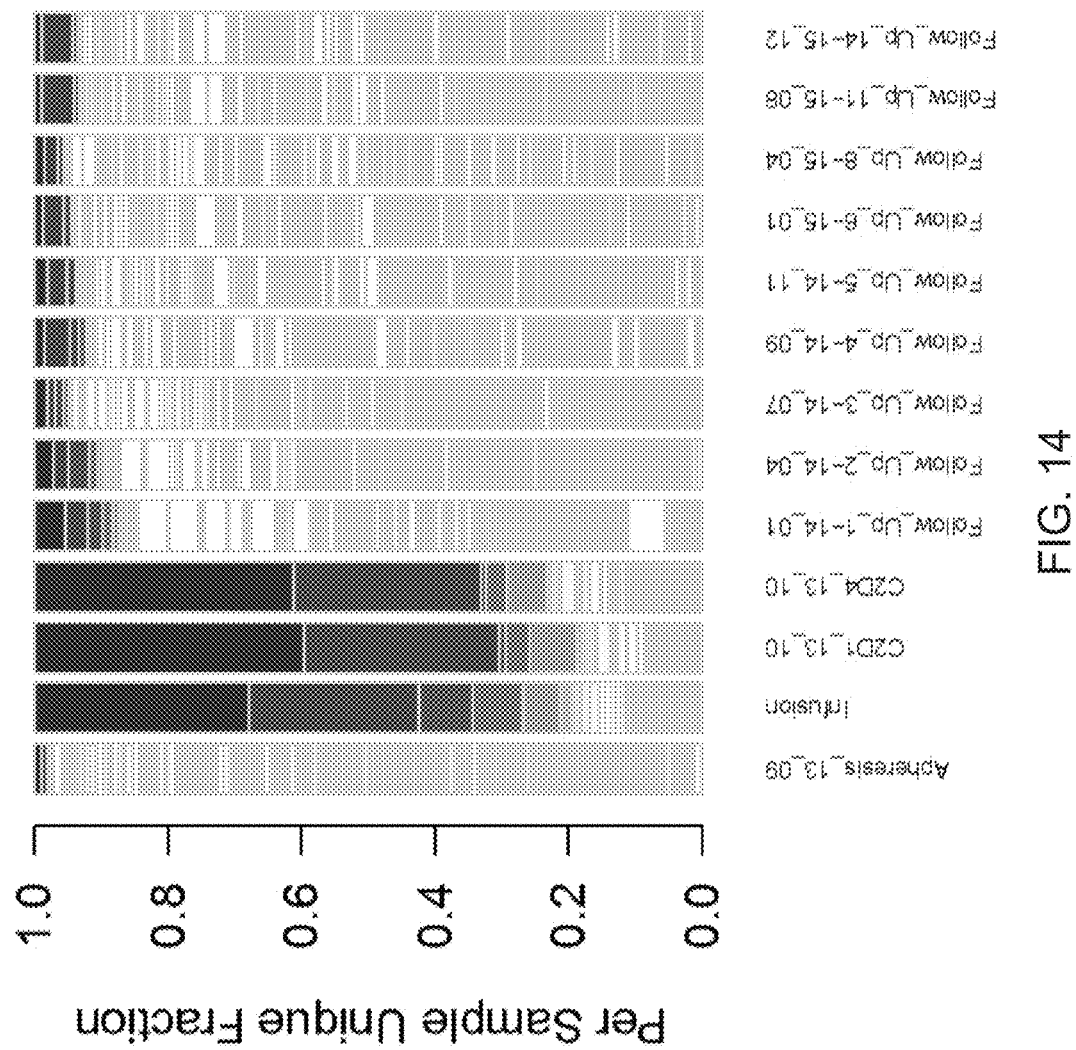
FIG. 14: Beta locus VJ repertoire of an adoptive cell transfer immunotherapy patient over time. Samples are indicated on the X axis ordered by date of sample. VJ clones are ordered in all samples according to prevalence in the TIL infusion product and the top nine most prevalent TIL infusion clones are colored.
Figure 15:
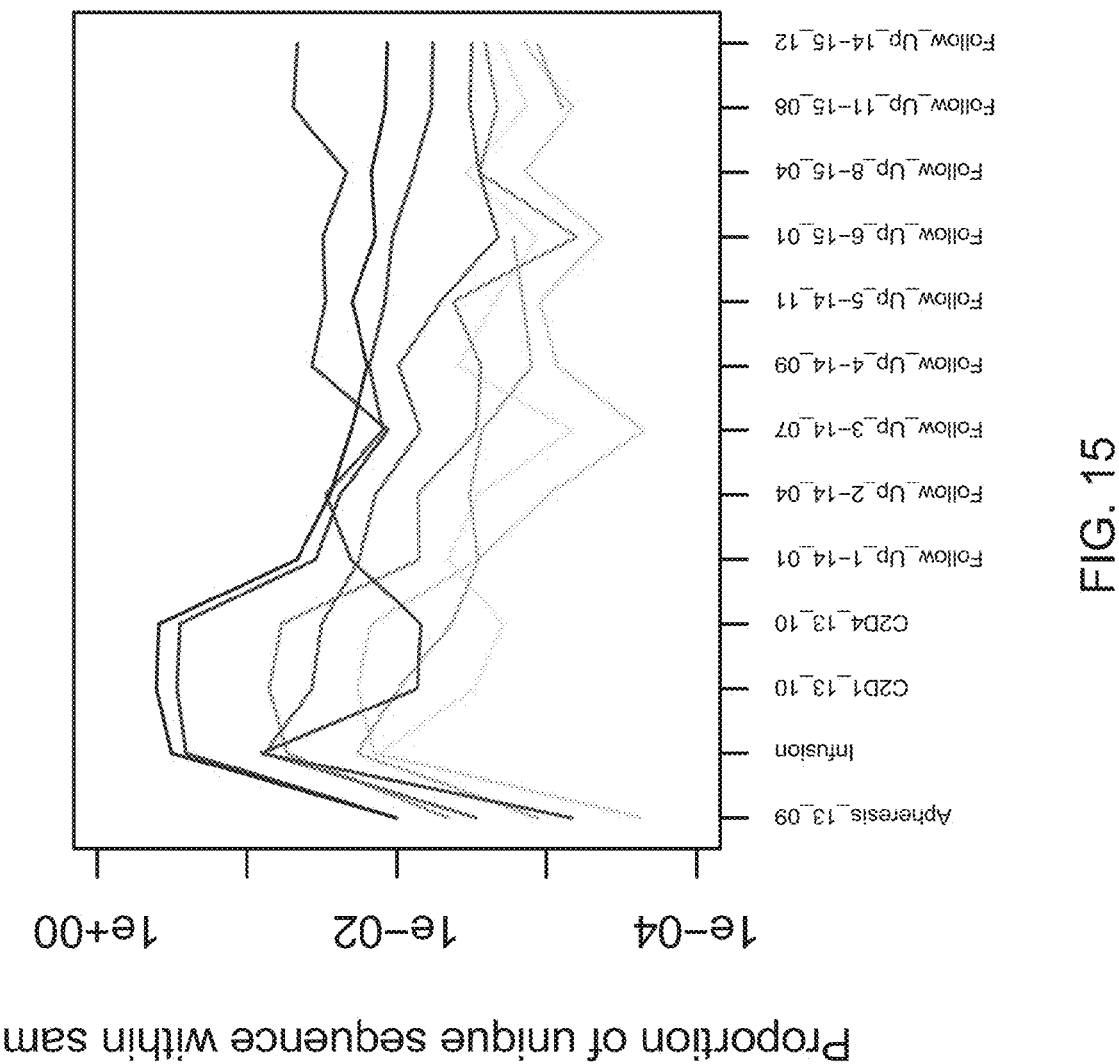
FIG. 15: Nine most prevalent TIL infusion clones at the Beta locus of an adoptive cell transfer immunotherapy patient over time. Samples are indicated on the X axis ordered by date of sample.

We next applied the CapTCR-Seq methodology to samples derived from expanded Tumor Infiltrating Lymphocyte (TIL) infusion populations and PBMCs from serial blood draws from patients undergoing adoptive cell transfer immunotherapy. We wanted to track clones from the TIL culture over time to determine whether they successfully colonized the patient and the extent of their population over time (FIG. 14). Repertoire profiling reveals a polyclonal and diverse baseline repertoire before treatment, a less complex oligoclonal TIL derived culture, less complex oligoclonal repertoires following chemodepletion and transfusion of the TIL infusion, and finally restoration of a more complex polyclonal repertoire over time. When compared to the baseline, highly prevalent clones in the TIL infusion product persist over time albeit in decreasing amounts. The dominant rearrangements decrease in prevalence over time as the native repertoire is reestablished however the TIL product rearrangements persist. We can observe this persistence by graphing the individual profiles for these top nine rearrangements over time (FIG. 15). We can see that while they decrease over time, they remain higher than what was found in the apheresis sample after two years.

Comparison Between Uncaptured and Captured Tumor Samples

We wished to demonstrate the value of this method for interrogating existing cDNA RNA-Seq libraries (data not shown). To do this, Illumina cDNA sequencing libraries were generated from FFPE-derived total RNA and subjected to sequencing followed by analysis using the TCR annotation pipeline to identify unique TCR CDR3 sequences (bulk unique CDR3). Residual library then underwent CapTCR-Seq to identify unique TCR CDR3 sequences (capture unique CDR3). The CapTCR-Seq method yielded a greatly increased number of unique CDR3 sequences (mean: 466 fold, median: 353 fold). When normalized to number of total reads sequenced, we observed a 15fold increase in signal per read sequenced (mean: 15.2, median: 14.5, n=41).

Investigation of Tumor Repertoires from Different Cancer Types

We next wanted to characterize tumor repertoires and investigate highly prevalent TIL clones in the blood repertoire before and during anti-PDL1 immunotherapy treatment. We selected five patients, each with a different tumor type: Patient A: Head and neck; Patient B: Breast; Patient C: Ovarian; Patient D: Melanoma; Patient E: Cervical. Each patient had three sample types: Tumor tissue (extracted DNA and RNA), pre-treatment blood (extracted PBMC DNA, PBMC RNA, and plasma cfDNA), on-treatment blood (extracted plasma cfDNA).

Figure 16:
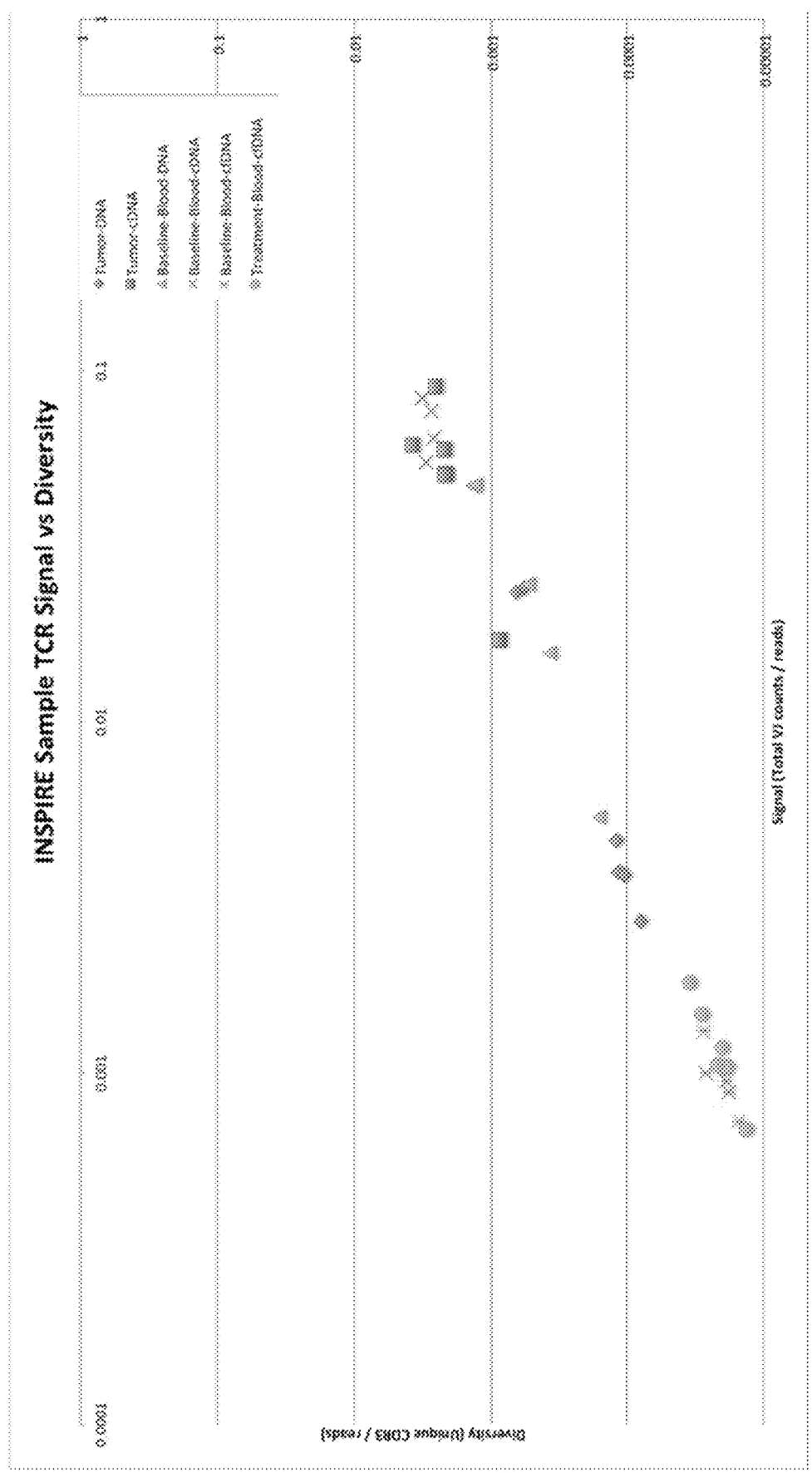
FIG. 16: TCR total signal (VJ counts) and repertoire diversity (unique CDR3 counts) for all samples from five patients.
Figure 17:
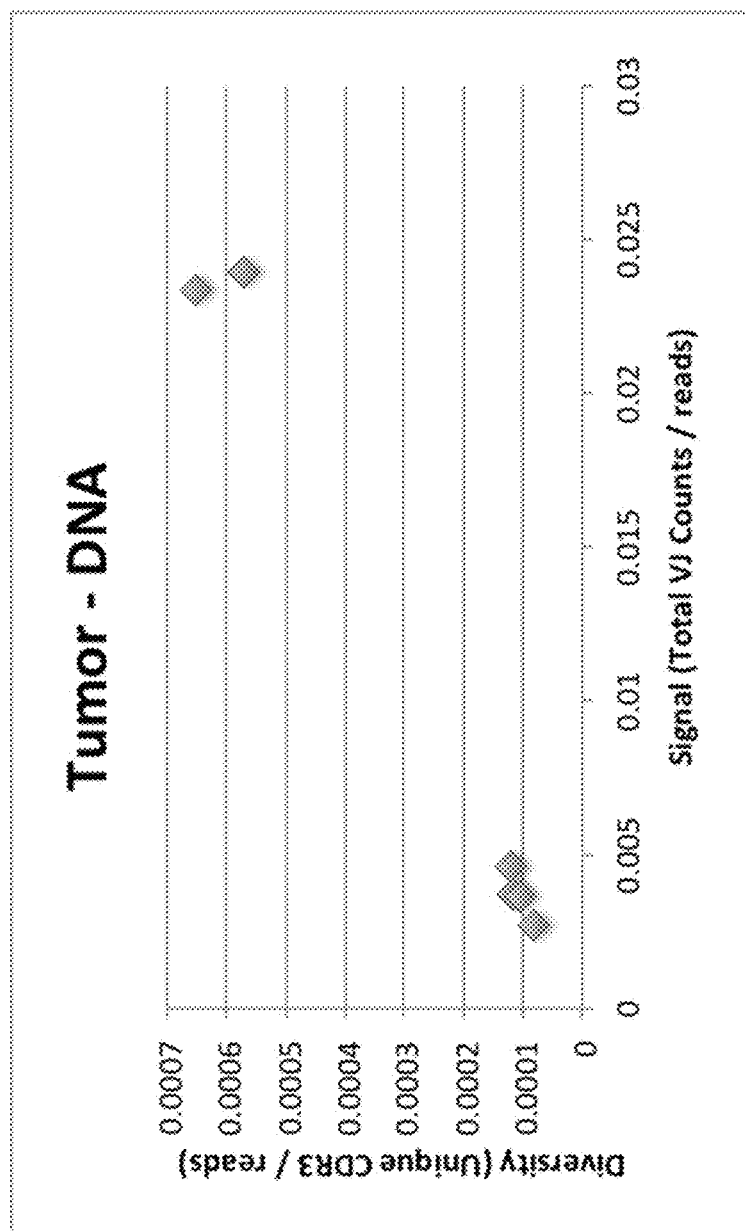
FIG. 17: TCR total signal (VJ counts) and repertoire diversity (unique CDR3 counts) for all tumor samples from five patients.

We first queried the extent of the TCR signal in the tumor samples in terms of infiltration and clonality. TCR signal is defined as the total number of counts of fragments containing both a V and J gene region (non-unique, reads normalized) while diversity is defined as the total number of unique CDR3 sequences detected (unique, reads normalized). Overall, diversity increased with signal (FIG. 16). cfDNA samples had the lowest signal, genomic DNA samples had intermediate signal, while cDNA samples had the highest signal. Blood sample signal and diversity is similar for all five patients, however tumor signal and diversity varied. Two patients had ten-fold higher TCR signal and diversity in their tumors likely reflecting increased infiltration of immune cells (FIG. 17).

Figure 18:
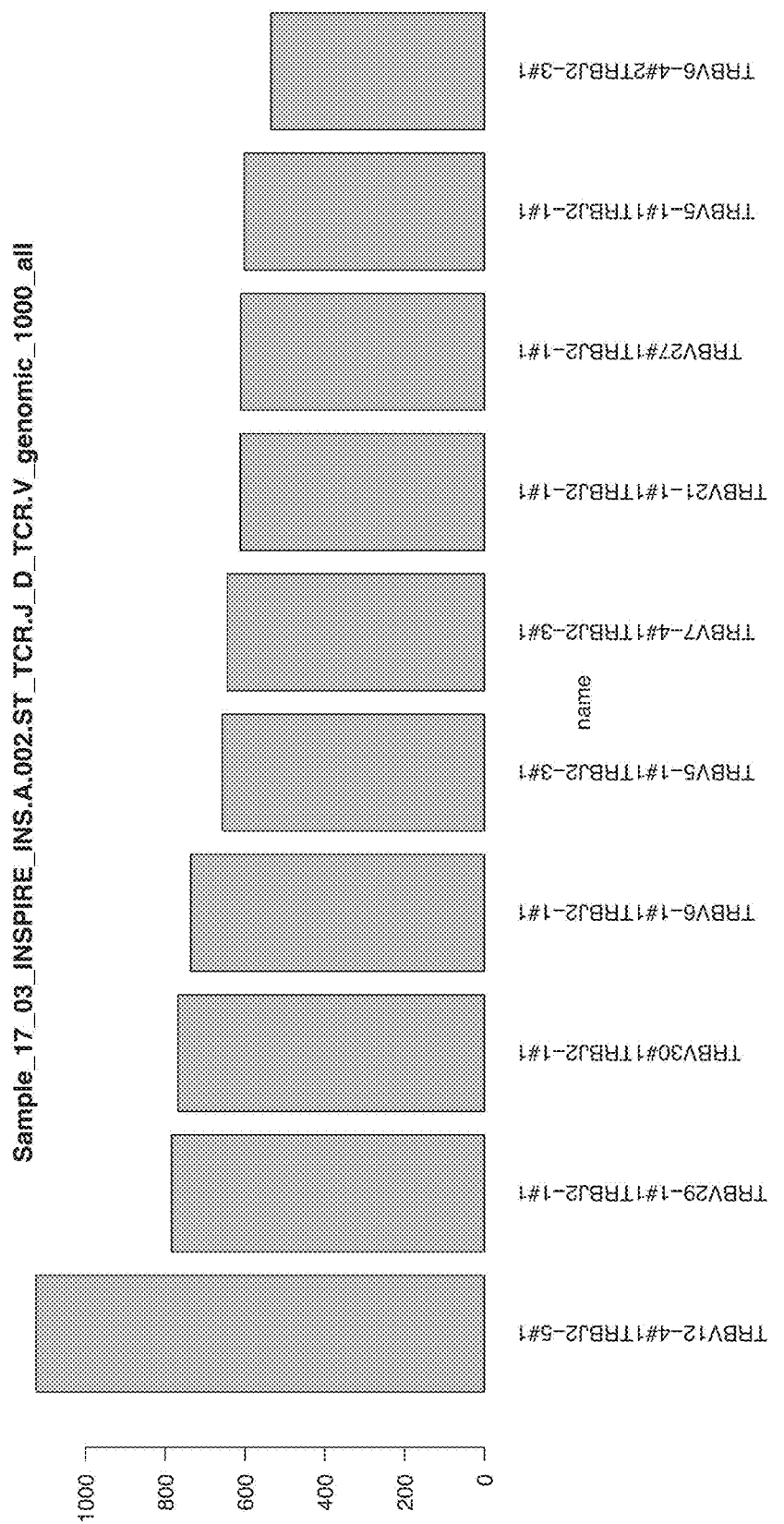
FIG. 18: Top ten most prevalent beta locus rearrangements from patient A tumor.

Next we assessed the clonality of the tumor sample TIL repertoire. Tumors with clonal infiltration have a larger than expected population of one or more VJ rearrangements, the population of which are significantly greater than the next most prevalent clone. Patient A appears to have a large alpha rearrangement population in its tumor compared to baseline blood, while the most prevalent beta rearrangement is only slightly enriched (FIG. 18 and data not shown). The tumor sample for patient B showed both greatly enriched top alpha and beta VJ rearrangements compared to baseline blood (data not shown). The tumor sample for patient C showed both greatly enriched top alpha and beta VJ rearrangements compared to baseline blood (data not shown). The tumor sample for patient D showed both greatly enriched top alpha (2) and beta VJ (1) rearrangements compared to baseline blood (data not shown). The tumor sample for patient E showed only a slightly enriched top beta VJ rearrangement compared to baseline blood (data not shown).

Next we assessed how the most prevalent tumor VJ rearrangements differed in terms of prevalence across the other patient samples (FIG. 19 and data not shown). In general, prevalent TIL clones were not prevalent in the blood repertoire demonstrating clonal expansion within the tumor or selective infiltration. However, for a number of the most prevalent TIL clones, we saw very high levels within the plasma samples suggesting that while these clones are actively undergoing cell death. In combination with their high tumor infiltration, this suggests that these are anti-tumor T-cells undergoing active expansion, anti-tumor cytotoxicity and turnover.

Example 4

We performed similar experiments relating to B-cells. Our design targets more than 500 V-regions and 50 J-regions within the IGH, IGK and IGL loci annotated in the IMmunoGeneTics database. This accounts for all known Ig alleles while maximizing depth of coverage in selected regions. A blast-based informatics pipeline calls V(D)J recombinations and an algorithm combining information from large-insert and soft-clipped reads are used to predict candidate rearrangements which are manually verified in Integrated Genome Viewer.

Candidate V(D)J rearrangements and translocations detected through this approach have been validated in three well-characterized cell-lines with publically available whole genome data; an additional 67 MM cell lines have been annotated for V(D)J rearrangements and translocations into IGH, IGL and IGK genes. The limit of detection was established with a cell-line dilution series. We were also able to translate these techniques to cell-free DNA. These methods are applicable to the detection of MRD in mature B-cell malignancies and immunoglobulin repertoire profiling in a many clinical scenarios including cellular immunotherapy and therapeutics with immunomodulatory effects. V(D)J and complex rearrangement annotations in 70 MM cell-lines are highly relevant in further in-vitro studies.

The B-cell V-gene and J-gene capture probes used are shown in Tables B1 and B2 respectively.

Although preferred embodiments of the invention have been described herein, it will be understood by those skilled in the art that variations may be made thereto without departing from the spirit of the invention or the scope of the appended claims. All documents disclosed herein, including those in the following reference list, are incorporated by reference.

REFERENCE LIST

References

1. Bertness V, Kirsch I, Hollis G, Johnson B, Bunn P A Jr. T-cell receptor gene rearrangements as clinical markers of human T-cell lymphomas. N Engl J Med. 1985 Aug. 29; 313(9):534-8.
2. Swerdlow S H, Cancer I A for R on, Organization W H. WHO classification of tumours of haematopoietic and lymphoid tissues [Internet]. International Agency for Research on Cancer; 2008. Available from: books-.google.ca/books?id=WqsTAQAAMAAJ
3. van Dongen J J, Wolvers-Tettero I L. Analysis of immunoglobulin and T cell receptor genes. Part I: Basic and technical aspects. Clin Chim Acta. 1991 April, 198(1-2): 1-91.
4. Aisenberg A C. Utility of gene rearrangements in lymphoid malignancies. Annu Rev Med. 1993; 44:75-84.
5. Rezuke W N, Abernathy E C, Tsongalis G J. Molecular diagnosis of B- and T-cell lymphomas: fundamental principles and clinical applications. Clin Chem. 1997 October; 43(10):1814-23.
6. Armitage J O. The aggressive peripheral T-cell lymphomas: 2012 update on diagnosis, risk stratification, and management. Am J Hematol. 2012 May; 87(5):511-9.
7. Abouyabis A N, Shenoy P J, Lechowicz M J, Flowers C R. Incidence and outcomes of the peripheral T-cell lymphoma subtypes in the United States. Leuk Lymphoma. 2008 November; 49(11):2099-107.
8. Criscione V D, Weinstock M A. Incidence of cutaneous T-cell lymphoma in the United States, 1973-2002. Arch Dermatol. 2007 July; 143(7):854-9.
9. Ko O B, Lee D H, Kim S W, Lee J S, Kim S, Huh J, et al. Clinicopathologic characteristics of T-cell non-Hodgkin's lymphoma: a single institution experience. Korean J Intern Med. 2009 June; 24(2):128-34.
10. Luminari S, Cesaretti M, Rashid I, Mammi C, Montanini A, Barbolini E, et al. Incidence, clinical characteristics and survival of malignant lymphomas: a population-based study from a cancer registry in northern Italy. Hematol Oncol. 2007 December; 25(4):189-97.
11. Vazquez A, Khan M N, Blake D M, Sanghvi S, Baredes S, Eloy J A. Extranodal natural killer/T-Cell lymphoma: A population-based comparison of sinonasal and extranasal disease. Laryngoscope. 2014 April, 124(4):888-95.

12. Liao J B, Chuang S S, Chen H C, Tseng H H, Wang J S, Hsieh P P. Clinicopathologic analysis of cutaneous lymphoma in taiwan: a high frequency of extranodal natural killer/t-cell lymphoma, nasal type, with an extremely poor prognosis. Arch Pathol Lab Med. 2010 July; 134(7):996-1002.
13. Mitamun W, Suwiwat S, Pradutkanchana J. Epstein-Barr virus-associated extranodal non-Hodgkin's lymphoma of the sinonasal tract and nasopharynx in Thailand. Asian Pac J Cancer Prev Apjcp. 2006 January; 7(1):91-4.
14. Shih L Y, Liang D C. Non-Hodgkin's lymphomas in Asia. Hematol—Oncol Clin N Am. 1991 October; 5(5): 983-1001.
15. Ai W Z, Chang E T, Fish K, Fu K, Weisenburger D D, Keegan T H. Racial patterns of extranodal natural killer/T-cell lymphoma, nasal type, in California: a population-based study. Br J Haematol. 2012 March; 156(5):626-32.
16. Korgavkar K, Xiong M, Weinstock M. Changing incidence trends of cutaneous T-cell lymphoma. JAMA Dermatol. 2013 November; 149(11):1295-9.
17. Weinstock M A. Epidemiology of mycosis fungoides. Semin Dermatol. 1994 September; 13(3):154-9.
18. Weiss L M, Arber D A, Strickler J G. Nasal T-cell lymphoma. Ann Oncol. 1994; 5 Suppl 1:39-42.
19. Zackheim H S, Vonderheid E C, Ramsay D L, LeBoit P E, Rothfleisch J, Kashani-Sabet M. Relative frequency of various forms of primary cutaneous lymphomas. J Am Acad Dermatol. 2000 November; 43(5 Pt 1):793-6.
20. United Nations D of E and SA Population Division. International Migration Report 2009: A Global Assessment. United Nations, New York; 2011.
21. Cossman J, Uppenkamp M, Andrade R, Medeiros U. T-cell receptor gene rearrangements and the diagnosis of human T-cell neoplasms. Crit Rev Oncol-Hematol. 1990; 10(3):267-81.
22. Vantourout P, Hayday A. Six-of-the-best: unique contributions of gammadelta T cells to immunology. Nat Rev Immunol. 2013 February; 13(2):88-100.
23. Lefranc M P. TRA (T cell receptor alpha). Atlas Genet Cytogenet Oncol Haematol. 2003; 7(4):245-8.
24. Lefranc M P. TRD (T cell receptor delta). Atlas Genet Cytogenet Oncol Haematol. 2003; 7(4):252-4.
25. Lefranc M P. TRB (T cell receptor beta). Atlas Genet Cytogenet Oncol Haematol. 2003; 7(4):249-51.
26. Lefranc M P. TRG (T cell receptor gamma). Atlas Genet Cytogenet Oncol Haematol. 2003; 7(4):255-6.
27. Bolotin D A, Mamedov I Z, Britanova O V, Zvyagin I V, Shagin D, Ustyugova S V, et al. Next generation sequencing for TCR repertoire profiling: platform-specific features and correction algorithms. Eur J Immunol. 2012 November; 42(11):3073-83.
28. Linnemann C, Heemskerk B, Kvistborg P, Kluin R J, Bolotin D A, Chen X, et al. High-throughput identification of antigen-specific TCRs by TCR gene capture. Nat Med. 2013 November; 19(11):1534-41.
29. van Dongen J J, Langerak A W, Bruggemann M, Evans P A, Hummel M, Lavender F L, et al. Design and standardization of PCR primers and protocols for detection of clonal immunoglobulin and T-cell receptor gene recombinations in suspect lymphoproliferations: report of the BIOMED-2 Concerted Action BMH4-CT98-3936. Leukemia. 2003 December; 17(12):2257-317.
30. Amagai M, Hayakawa K, Amagai N, Kobayashi K, Onodera Y, Shimizu N, et al. T cell receptor gene rearrangement analysis in mycosis fungoides and disseminated lymphocytoma cutis. Dermatologica. 1990; 181(3): 193-6.
31. Dosaka N, Tanaka T, Fujita M, Miyachi Y, Horio T, Imamura S. Southern blot analysis of clonal rearrangements of T-cell receptor gene in plaque lesion of mycosis fungoides. J Invest Dermatol. 1989 November; 93(5): 626-9.
32. Chan D W, Liang R, Chan V, Kwong Y L, Chan T K. Detection of T-cell receptor delta gene rearrangement by clonal specific polymerase chain reaction. Leukemia. 1997 April, 11 Suppl 3:281-4.
33. Lynch J W Jr, Linoilla I, Sausville E A, Steinberg S M, Ghosh B C, Nguyen D T, et al. Prognostic implications of evaluation for lymph node involvement by T-cell antigen receptor gene rearrangement in mycosis fungoides. Blood. 1992 Jun. 15; 79(12):3293-9.
34. McClure R F, Kaur P, Pagel E, Ouillette P D, Holtegaard C E, Treptow C L, et al. Validation of immunoglobulin gene rearrangement detection by PCR using commercially available BIOMED-2 primers. Leukemia. 2006 January; 20(1):176-9.
35. Bagg A, Braziel R M, Arber D A, Bijwaard K E, Chu A Y. Immunoglobulin heavy chain gene analysis in lymphomas: a multi-center study demonstrating the heterogeneity of performance of polymerase chain reaction assays. J Mol Diagn. 2002 May; 4(2):81-9.
36. Cushman-Vokoun A M, Connealy S, Greiner T C. Assay design affects the interpretation of T-cell receptor gamma gene rearrangements: comparison of the performance of a one-tube assay with the BIOMED-2-based TCRG gene clonality assay. J Mol Diagn. 2010 November; 12(6):787-96.
37. Groenen P J, Langerak A W, van Dongen J J, van Krieken J H. Pitfalls in TCR gene clonality testing: teaching cases. J Hematop. 2008 September; 1(2):97-109.
38. Mamanova L, Coffey A J, Scott C E, Kozarewa I, Turner E H, Kumar A, et al. Target-enrichment strategies for next-generation sequencing. Nat Methods. 2010 February; 7(2):111-8.
39. Bossler A V D V. Chapter 4: Conventional and Real-Time Polymerase Chain Reaction. In: Tubbs R R. S M, editor. Cell and Tissue Based Molecular Pathology. Churchill Livingstone Elsevier; 2009. p. 33-49.
40. Rhodenizer D daSilva C; Skinner N; Hegde, M. One library, many tests: The evolution of Next Generation Sequencing panel testing. In 2014.
41. Bowen D C M; Kautzer, C; Landers, T; Mehta, G; Olivares. Improved Performance of Solution-based Target Enrichment with Spike-in of Individually Synthesized Capture DNA Probes. In 2012.
42. Jarosz M Z Z: Lipson D; Frampton, G; Yalensky, R; Parker A; Cronin, M. High Performance Solution-Based Target Selection Using Individually Synthesized Oligonucleotide Capture Probes. In 2011.
43. Shi W C C; Tang, T; Hipolito, L; Srinivasan, P; Chiang, D; Pend, D; Di Tomaso, E; Tangri, S; Lameh, J; Pollner, R. Development of a Clinical Targeted Next-Generation Sequencing (NGS) Test for Formalin-Fixed Paraffin-Embedded (FFPE) Cancer Samples. In 2014.
44. Schmidt R L, Factor R E. Understanding sources of bias in diagnostic accuracy studies. Arch Pathol Lab Med. 2013 April; 137(4):558-65.
45. Tomaszewski J E, Bear H D, Connally J A, Epstein J I, Feldman M, Foucar K, et al. Consensus conference on second opinions in diagnostic anatomic pathology. Who, What, and When. Am J Clin Pathol. 2000 September; 114(3):329-35.

46. Naaktgeboren C A, Bertens L C, van Smeden M, de Groot J A, Moons K G, Reitsma J B. Value of composite reference standards in diagnostic research. BMJ. 2013; 347:f5605.
47. Duncavage E J, Magrini V, Becker N, Armstrong J R, Demeter R T, Wylie T, et al. Hybrid capture and next-generation sequencing identify viral integration sites from formalin-fixed, paraffin-embedded tissue. J Mol Diagn. 2011 May; 13(3):325-33.
48. Gnirke A, Melnikov A, Maguire J, Rogov P, LeProust E M, Brockman W, et al. Solution hybrid selection with ultra-long oligonucleotides for massively parallel targeted sequencing. Nat Biotechnol. 2009 February; 27(2):182-9.
49. Gilbert M T, Haselkom T, Bunce M, Sanchez J J, Lucas S B, Jewell L D, et al. The isolation of nucleic acids from fixed, paraffin-embedded tissues-which methods are useful when? PLoS One. 2007; 2(6):e537.
50. Bolotin D A, Poslavsky S, Mitrophanov I, Shugay M, Mamedov I Z, Putintseva E V, et al. MiXCR: software for comprehensive adaptive immunity profiling. Nat Methods. 2015 Apr. 29; 12(5):380-1.
51. Li S, Lefranc M-P, Miles J J, Alamyar E, Giudicelli V, Duroux P, et al. IMGT/HighV QUEST paradigm for T cell receptor IMGT clonotype diversity and next generation repertoire immunoprofiling. Nat Commun [Internet]. 2013 Sep. 2 [cited 2016 Jan. 30]; 4. Available from: www.nature.com/doifinder/10.1038/ncomms3333
52. Zhang J, Kobert K, Flouri T, Stamatakis A. PEAR: a fast and accurate Illumina Paired-End reAd mergeR. Bioinforma Oxf Engl. 2014 Mar. 1; 30(5):614-20.
53. Larkin M A, Blackshields G, Brown N P, Chenna R, McGettigan P A, McWilliam H, et al. Clustal W and Clustal X version 2.0. Bioinformatics. 2007 Nov. 1; 23(21):2947-8.
54. Giudicelli V, Chaume D, Lefranc M P. IMGT/GENE-DB: a comprehensive database for human and mouse immunoglobulin and T cell receptor genes. Nucleic Acids Res. 2005 Jan. 1; 33(Database issue):D256-61.
55. Li H D R. Fast and accurate short read alignment with Burrows-Wheeler Transform. Bioinformatics. 2009; 25:1754-60.
56. Brochet X, Lefranc M P, Giudicelli V. IMGTN-QUEST: the highly customized and integrated system for IG and TR standardized V-J and V-D-J sequence analysis. Nucleic Acids Res. 2008 Jul. 1; 36(Web Server issue): W503-8.
57. Giudicelli V, Lefranc M P. IMGTrjunctionanalysis: IMGT standardized analysis of the V-J and V-D-J junctions of the rearranged immunoglobulins (IG) and T cell receptors (TR). Cold Spring Harb Protoc. 2011 June; 2011(6):716-25.
58. Giudicelli V, Brochet X, Lefranc M P. IMGTN-QUEST: IMGT standardized analysis of the immunoglobulin (IG) and T cell receptor (TR) nucleotide sequences. Cold Spring Harb Protoc. 2011 June; 2011(6):695-715.
59. Yousfi Monod M, Giudicelli V, Chaume D, Lefranc M P. IMGT/JunctionAnalysis: the first tool for the analysis of the immunoglobulin and T cell receptor complex V-J and V-D-J JUNCTIONs. Bioinformatics. 2004 Aug. 4; 20 Suppl 1:i379-85.
60. Smith T F, Waterman M S. Identification of common molecular subsequences. J Mol Biol. 1981 Mar. 25; 147(1):195-7.
61. Krzywinski M, Schein J, Birol I, Connors J, Gascoyne R, Horsman D, et al. Circos: an information aesthetic for comparative genomics. Genome Res. 2009 September; 19(9):1639-45.
62. Lefranc M P. Unique database numbering system for immunogenetic analysis. Immunol Today. 1997 November; 18(11):509.
63. Lefranc M P, Pommie C, Ruiz M, Giudicelli V, Foulquier E, Truong L, et al. IMGT unique numbering for immunoglobulin and T cell receptor variable domains and Ig superfamily V-like domains. Dev Comp Immunol. 2003 January; 27(1):55-77.
64. Altschul S, Erickson B. Optimal sequence alignment using affine gap costs. Bull Math Biol. 1986 Sep. 1; 48(5-6):603-16.
65. Lefranc M P. IMGT-ONTOLOGY and IMGT databases, tools and Web resources for immunogenetics and immunoinformatics. Mol Immunol. 2004 January; 40(10):647-60.
66. Lefranc M P. IMGT databases, web resources and tools for immunoglobulin and T cell receptor sequence analysis, imgt.cines.fr. Leukemia. 2003 January; 17(1):260-6.
67. Sandberg Y, Verhaaf B, van Gastel-Mol E J, Wolvers-Tettero I L, de Vos J, Macleod R A, et al. Human T-cell lines with well-defined T-cell receptor gene rearrangements as controls for the BIOMED-2 multiplex polymerase chain reaction tubes. Leukemia. 2007 February; 21(2):230-7.
68. Ye J, Coulouris G, Zaretskaya I, Cutcutache I, Rozen S, Madden T L. Primer-BLAST: a tool to design target-specific primers for polymerase chain reaction. BMC Bioinformatics. 2012; 13:134.
69. Kent W J. S C. W.; Furey, T. S.; Roskin, K. M.; Pringle, T. H.; Zahler, A. M.; Haussler, D. The human genome browser at UCSC. Genome Res. 2002 June; 12(6):996-1006.
70. Malde K. The effect of sequence quality on sequence alignment. Bioinformatics. 2008 Apr. 1; 24(7):897-900.
71. Davidson J N, Leslie I, White J C. Quantitative studies on the content of nucleic acids in normal and leukaemic cells, from blood and bone marrow. J Pathol Bacteriol. 1951 July; 63(3):471-83.
72. Glen A C. Measurement of DNA and RNA in human peripheral blood lymphocytes. Clin Chem. 1967 April; 13(4):299-313.
73. Metais P, Mandel P. [Percentage of desoxypentose-nucleic acid in leucocytes in normal and pathological conditions]. C R Seances Soc Biol Fil. 1950 February; 144(3-4):277-9.
74. Jones S R, Carley S, Harrison M. An introduction to power and sample size estimation. Emerg Med J. 2003 September; 20(5):453-8.
75. Network NCC. NCCN Clinical Practice Guidelines in Oncology. National Comprehensive Cancer Network, Inc.; 2014.
76. Jaffe E S, Organization W H. Pathology and Genetics of Tumours of Haematopoietic and Lymphoid Tissues [Internet]. IARC Press; 2001. Available from: books.google.ca/books?id=XSKqcy7TUZUC
77. Gazzola A, Mannu C, Rossi M, Laginestra M A, Sapienza M R, Fuligni F, et al. The evolution of clonality testing in the diagnosis and monitoring of hematological malignancies. Ther Adv Hematol. 2014 Apr. 1; 5(2):35-47.
78. Tape T. Interpreting Diagnostic Tests [Internet]. University of Nebraska Medical Center; [cited 2015 Nov. 8]. Available from: gim.unmc.edu/dxtests/Default.htm
79. Hu P C, Hegde M R, Lennon P A, editors. Modem clinical molecular techniques. New York: Springer; 2012. 436 p.

80. Brunet J-P, Tamayo P, Golub T R, Mesirov J P. Metagenes and molecular pattern discovery using matrix factorization. Proc Natl Acad Sci USA. 2004 Mar. 23; 101(12):4164-9.
81. Tembhare P, Yuan C M, Xi L, Morris J C, Liewehr D, Venzon D, et al. Flow cytometric immunophenotypic assessment of T-cell clonality by VP repertoire analysis: detection of T-cell clonality at diagnosis and monitoring of minimal residual disease following therapy. Am J Clin Pathol. 2011 June; 135(6):890-900.
82. Sufficool K E, Lockwood C M, Abel H J, Hagemann I S, Schumacher J A, Kelley T W, et al. T-cell clonality assessment by next-generation sequencing improves detection sensitivity in mycosis fungoides. J Am Acad Dermatol. 2015 August; 73(2):228-36.e2.
83. Cazzaniga G, Biondi A. Molecular monitoring of childhood acute lymphoblastic leukemia using antigen receptor gene rearrangements and quantitative polymerase chain reaction technology. Haematologica. 2005 March; 90(3):382-90.
84. Lima M, Almeida J, Santos A H, dos Anjos Teixeira M, Alguero M C, Queirós M L, et al. Immunophenotypic analysis of the TCR-Vbeta repertoire in 98 persistent expansions of CD3(+)/TCR-alphabeta(+) large granular lymphocytes: utility in assessing clonality and insights into the pathogenesis of the disease. Am J Pathol. 2001 November; 159(5):1861-8.
85. Miles J J, Douek D C, Price D A. Bias in the αβ T-cell repertoire: implications for disease pathogenesis and vaccination. Immunol Cell Biol. 2011 March, 89(3):375-87.
86. Society C C. Non-Hodgkin Lymphoma Statistics [Internet]. Cancer Information. 2014. Available from: www.cancer.ca/en/cancer-information/cancer-type/non-hodgkin-lymphoma/statistics/?region=on
87. Canada S. Population by year, by province and territory [Internet]. 2014 September Available from: www.statcan.gc.ca/tables-tableaux/sum-som/IO1/cst01/demo02a-end.htm
88. Information CI for H. DAD Abstracting Manual, 2012-2013 Edition [Internet]. 2012 April Available from: sda.chass.utoronto.ca.myaccess.library.utoronto.ca/sdaweb/cihi/2011to2013/clin/more_doc/DAD_Abstracting_Manual_2012-2013_E.pdf
89. Information CI for H. CIHI Specifications Form for Research Analytical Files [Internet]. 2014 February Available from: sda.chass.utoronto.ca.myaccess.library.utoronto.ca/sdaweb/cihi/2011to2013/clin/more_doc/Specifications-DAD-RAF-EN.pdf
A1. van Dongen, J. J. M. et al. Design and standardization of PCR primers and protocols for detection of clonal immunoglobulin and T-cell receptor gene recombinations in suspect lymphoproliferations: Report of the BIOMED-2 Concerted Action BMH4-CT98-3936. Leukemia 17, 2257-2317 (2003).
A2. Langerak, A. W. et al. EuroClonality/BIOMED-2 guidelines for interpretation and reporting of Ig1TCR clonality testing in suspected lymphoproliferations. Leukemia 26, 2159-2171 (2012).
A3. Han, A., Glanville, J., Hansmann, L. & Davis, M. M. Linking T-cell receptor sequence to functional phenotype at the single-cell level. Nat Biotech 32, 684-692 (2014).
A4. Stubbington, M. J. T. et al. T cell fate and clonality inference from single-cell transcriptomes. Nat Meth 13, 329-332 (2016).
A5. Samorodnitsky, E. et al. Evaluation of Hybridization Capture Versus Amplicon-Based Methods for Whole-Exome Sequencing. Human Mutation 36, 903-914 (2015).
A6. Mamanova, L. et al. Target-enrichment strategies for next-generation sequencing. Nat. Methods 7, 111-118 (2010).
A7. Bodi, K. et al. Comparison of Commercially Available Target Enrichment Methods for Next-Generation Sequencing. J Biomol Tech 24, 73-86 (2013).
A8. Mertes, F. et al. Targeted enrichment of genomic DNA regions for next-generation sequencing. Briefings in Functional Genomics 10, 374-386 (2011).
A9. Giudicelli, V. et al. IMGT/LIGM-DB, the IMGT comprehensive database of immunoglobulin and T cell receptor nucleotide sequences. Nucleic Acids Res. 34, D781-784 (2006).
A10. Bolotin, D. A. et al. MiTCR: software for T-cell receptor sequencing data analysis. Nat Meth 10, 813-814 (2013).
A11. Bolotin, D. A. et al. MiXCR: software for comprehensive adaptive immunity profiling. Nat Meth 12, 380-381 (2015).
A12. Brochet, X., Lefranc, M.-P. & Giudicelli, V. IMGT/V-QUEST: the highly customized and integrated system for IG and TR standardized V-J and V-D-J sequence analysis. Nucleic Acids Res. 36, W503-508 (2008).
A13. Thomas, N., Heather, J., Ndifon, W., Shawe-Taylor, J. & Chain, B. Decombinator: a tool for fast, efficient gene assignment in T-cell receptor sequences using a finite state machine. Bioinformatics 29, 542-550 (2013).
A14. Yu, Y., Ceredig, R. & Seoighe, C. LymAnalyzer: a tool for comprehensive analysis of next generation sequencing data of T cell receptors and immunoglobulins. Nucl. Acids Res. gkv1016 (2015). doi:10.1093/nar/gkv1016
A15. Zhang, W. et al. IMonitor: A Robust Pipeline for TCR and BCR Repertoire Analysis. Genetics 201, 459-472 (2015).
A16. Calis, J. J. A. & Rosenberg, B. R. Characterizing immune repertoires by high throughput sequencing: strategies and applications. Trends Immunol 35, 581-590 (2014).
A17. Sandberg, Y. et al. Human T-cell lines with well-defined T-cell receptor gene rearrangements as controls for the BIOMED-2 multiplex polymerase chain reaction tubes. Leukemia 21, 230-237 (2007).
A18. Zhang, J., Kobert, K., Flouri, T. & Stamatakis, A. PEAR: a fast and accurate Illumina Paired-End reAd mergeR. Bioinformatics 30, 614-620 (2014).
A19. Camacho, C. et al. BLAST+: architecture and applications. BMC Bioinformatics 10, 421 (2009).
B1. Rosenberg, S. A., and Restifo, N. P. (2015). Adoptive cell transfer as personalized immunotherapy for human cancer. Science 348, 62-68.
B2. Hadrup, S., Donia, M., and thor Straten, P. (2013). Effector CD4 and CD8 T Cells and Their Role in the Tumor Microenvironment. Cancer Microenvironment 6, 123-133.
B3. Attaf, M., Huseby, E., and Sewell, A. K. (2015). as T cell receptors as predictors of health and disease. Cell. Mol. Immunol. 12, 391-399.
B4. Gubin, M. M., Artyomov, M. N., Mardis, E. R., and Schreiber, R. D. (2015). Tumor neoantigens: building a framework for personalized cancer immunotherapy. Journal of Clinical Investigation 125, 3413-3421.
B5. Clemente, M. J., Przychodzen, B., Jerez, A., Dienes, B. E., Afable, M. G., Husseinzadeh, H., Rajala, H. L. M., Wodarski, M. W., Mustjoki, S., and Maciejewski, J. P. (2013). Deep sequencing of the T-cell receptor repertoire in CD8+ T-large granular lymphocyte leukemia identifies signature landscapes. Blood 122, 4077-4085.

B6. Topalian, S. L., Drake, C. G., and Pardoll, D. M. (2015). Immune checkpoint blockade: a common denominator approach to cancer therapy. Cancer Cell 27, 450-461.

B7. Novosiadly, R., and Kalos, M. (2016). High-content molecular profiling of T-cell therapy in oncology. Molecular Therapy—Oncolytics 3, 16009.

B8. Abbey, J. L., and O'Neill, H. C. (2007). Expression of T-cell receptor genes during early T-cell development. Immunol Cell Biol 86, 166-174.

B9. Emerson, R. O., Sherwood, A. M., Rieder, M. J., Guenthoer, J., Williamson, D. W., Carlson, C. S., Drescher, C. W., Tewari, M., Bielas, J. H., and Robins, H. S. (2013). High-throughput sequencing of T-cell receptors reveals a homogeneous repertoire of tumour-infiltrating lymphocytes in ovarian cancer. J. Pathol. 231, 433-440.

B10. Gerlinger, M., Quezada, S. A., Peggs, K. S., Furness, A. J. S., Fisher, R., Marafioti, T., Shende, V. H., McGranahan, N., Rowan, A. J., Hazell, S., et al. (2013). Ultra-deep T cell receptor sequencing reveals the complexity and intratumour heterogeneity of T cell clones in renal cell carcinomas. J. Pathol. 231, 424-432.

B11. Restifo, N. P., Dudley, M. E., and Rosenberg, S. A. (2012). Adoptive immunotherapy for cancer: harnessing the T cell response. Nat. Rev. Immunol. 12, 269-281.

B12. Silva-Santos, B., Serre, K., and Norell, H. (2015). γδ T cells in cancer. Nat Rev Immunol 15, 683-691.

B13. Tscharke, D. C., Croft, N. P., Doherty, P. C., and La Gruta, N. L. (2015). Sizing up the key determinants of the CD8(+) T cell response. Nat. Rev. Immunol. 15, 705-716.

B14. Wherry, E. J., and Kurachi, M. (2015). Molecular and cellular insights into T cell exhaustion. Nat Rev Immunol 15, 486-499.

| List of Abbreviations | |
|---|---|
| ATCC | American Type Culture Collection (Biorepository) |
| AUC | Area-under-the-curve |
| bp | basepair |
| BWA | Burrows-Wheeler Alignment algorithm |
| CIHI | Canadian Institutes for Health Information |
| D | T-cell receptor "diversity" type gene |
| DAD | Discharge Abstracts Database (CIHI database) |
| DSMZ | Deutsche Sammlung von Mikroorganismen und Zellkulturen GmbH (German Collection of Microorganisms and Cell Cultures) |
| FDR | False-Discovery Rare |
| FFPE | Formalin-fixed paraffin-embedded |
| ICD-10 | International classification of disease, version 10 |
| IG | Immunoglobulin |
| IMGT | The International standard source for ImMunoGeneTics sequences & metadata |
| J | T-cell receptor gene "join" type gene |
| kb | kilobase |
| LGL | Large-Granular-Lymphocyte (Leukemia/Lymphoma) |
| NGS | Next-generation sequencing (technology) |
| NMF | Non-negative Matrix Factorization |
| NTRA | Novel NGS-based T-cell receptor gene re-arrangement assay |
| PEAR | Paired-end rEAd mergeR |
| PTCL | Peripheral T-cell lymphoma |
| ROC | Receiver-Operating Characteristic (Curve) |
| SAM | Sequence Alignment Map |
| SEER | Surveillance, epidemiology, and end results program (the primary US source of Cancer Statistics) |
| SWA | Smith-Waterman Alignment (algorithm) |
| TGH | Toronto General Hospital |
| TLPD | T-cell lymphoproliferative disorder |
| TR | T-cell receptor |
| TRA | T-cell receptor alpha gene |
| TRB | T-cell receptor beta gene |
| TRD | T-cell receptor delta gene |
| TRG | T-cell receptor gamma gene |
| TRGR | T-cell receptor gene re-arrangement |
| V | T-cell receptor "variable" type gene |
| WHO | World Health Organization |

TABLE 2.1

| SEQ ID NO | Name | Sequence |
|---|---|---|
| SEQ ID NO: 873 | TRAV1-1*01-5' | ggacaaagcctgagcagccctgagtgacagctggaaggagccattgtccagataaactgcacgtaccagacatctggtttttatggctgtcct |
| SEQ ID NO: 874 | TRAV101*01-3' | gttttcttcattcctagtcgtctgataqtatqqtacctccttctacaqqaqtqacaqctqqaaqqaqccattqtccaqataaactqcacqtqaaqactqqctqcctctqcqtqtqaqaqa |
| SEQ ID NO: 875 | TRAV1-1*02-5' | ggacaaagcctgagcagccctgagtgacagctggaaggagccattgtccagataaactgcacgtaccagacatctggtttttatggctgtcct |
| SEQ ID NO: 876 | TRAV1-1*02-3' | caggtcgttttttccttcattcctagtcgtctgatagtatggtacctccttctacaggagtgacagctggaaggagctctgcctcttacttctgcgtgt |
| SEQ ID NO: 877 | TRAV1-2*01-5' | ggacaaacattgaccagcccactgagatgacagctacgagaaggtgccattgtccagatcaactgcacgtaccagacatctggttcaacggctgttct |
| SEQ ID NO: 878 | TRAV1-2*01-3' | gttttcttcattcctagtcggtctgatcaaagggtacagtacctcctttgaaggagtccagttgccattgtccagatgaaagactctgcctcttacctgtgtgtgagaga |
| SEQ ID NO: 879 | TRAV1-2*02-5' | ggacaaacattgaccagcccactgagatgacagctacgagaaggtgccattgtccagatcaactgcacgtaccagacatctggttcaacggctgttct |
| SEQ ID NO: 880 | TRAV1-2*02-3' | catctgggttcaacggctgtctgttaccagcagagtcctcagtccctgatcactctggagggaaagaactgcactcttactacagtggatggtctggaggagaaagtcg |
| SEQ ID NO: 881 | TRAV10*01-5' | aaaaacaagtggagcagagtccttcattctggatgcagacaaagcaagctctgcacatcacagaactctctgaattctactatcagctcctacactgtgagcccctcagcaactaa |
| SEQ ID NO: 882 | TRAV10*01-3' | agtatacagcaactctggatgcagacaaagcaagctctgcacatcacagaactctctgaattctactatcagctcctacactgtgagcccctcagcaactaa |
| SEQ ID NO: 883 | TRAV11*01-5' | ctacatacactgagtccagcagagtccttcattctggatgcatgccgtcgttcctcgagctctccatcgtggagtcagcaccactacttcgtcttg |
| SEQ ID NO: 884 | TRAV11*01-3' | caaatatttaaagaactgcttggaaagaaaattttatagtgttggaatatcgcagtctccaatgtcactgctcttcaactgtacttacagcaacaagtgcttctcagtcttct |
| SEQ ID NO: 885 | TRAV12-1*01-5' | cgaaggaggtgagcagcaggatcctggacctcaatagagccagccagaattctggacctcaatagagccagtatattcctgcatcagagactccagtcagtgattcagccacctacacgcactgttcttcacagtcttct |
| SEQ ID NO: 886 | TRAV12-1*01-3' | aggtttacagcacagtccaatagagccagccagaattctggacctcaatagagccagtatattcctgctcatcagagactccagtcagtgattcagccacctacacgcactgttctctcagtcttct |
| SEQ ID NO: 887 | TRAV12-1*02-5' | cgaaggaggtgagcagcaggatcctggacctcaatagagccagccagaccctcaatagagccagtatattcctgcatcagagactccaagtcagtgattcagccacctacacgcactgttctctcagtcttct |
| SEQ ID NO: 888 | TRAV12-1*02-3' | acagcacactgagtccaatagagccagccagaccctcaatagagccagtatattcctgctcaatcatagagactccaagtcagtgattcagccacctacacgcactgttctcagccacctacttctgtggtgaacattcgcc |
| SEQ ID NO: 889 | TRAV12-2*01-5' | cagaaggaggtgagcagcaggagaatctggacctcaatagagccagtatcctggacccccagtgttccagagggggagccattgcctctccaactgcacttacagtgaccagcactacctgtgccagaggttcccagtcctcct |
| SEQ ID NO: 890 | TRAV12-2*01-3' | aggtttacagcacacagtccaataagccagaattctggacctcaatagagccagtatgttctctgctcatcagagactcccagtgattcagccacttacagtgaccagcactacctgtgccagaggttcccagtcgtgaaca |
| SEQ ID NO: 891 | TRAV12-2*02-5' | cagaaggaggtgagcagcaggagaatctggacctcaatagagccagtatcctggacccccagtgttccagagggggagccattgcctctccaactgcacttacagtgaccagcactacctgtgccagaggttcccagtcctcct |
| SEQ ID NO: 892 | TRAV12-2*02-3' | gtttacagcacacagtccaataagccagaattctggacctcaatagagccagtatgttctctgctcatcagagactcccagtgattcagccacttacagtgaccagcagtttccctcaactgccttcagccacctacttctgtgccgtgtaccac |
| SEQ ID NO: 893 | TARV12-2*03-5' | ggaccccctcagtgttccagcacaggtcctggacctcaataatccagcacttcacactgctcctctttctctcaactgctgcttctctcagagggcagccattgtttctctcaactgcacacatgatgaccagcgagttccagatccccctgtgcgtgaac |
| SEQ ID NO: 894 | TRAV12-3*01-5' | aaggtttacagcacagtccaataagccaggtcctggacctaataatccagcacttcacactgctcctctttctctcaactgctgcttctctcagagggcagccattgtttctctcaactgcacactgtgtcatcagagactccagatccccctgtacgtgac |
| SEQ ID NO: 895 | TRAV12-3*01-3' | cagaaggaggtgagcagaccctaataatccagcactttcacactgctcctctttctctcaactgctgcttctctcagagggcagccattgtttctctcaactgcaccacactgttcatcctcaactgctgcacactgccaacgatcagaggatccagatccccaga |
| SEQ ID NO: 896 | TRAV12-3*01-3' | aggtttacagcacagtccgataaatccagcacttcacactgtccttcacaactgcccgtgtctcatcagagactccagtgattcagccactgccaaatgcctatctgcatcagcaacaacagcagtgcttttcaatactcca |
| SEQ ID NO: 897 | TRAV12-3*02-5' | cagaaggaggtgagcagcctgaccagcagccagtgttccagagggaggagccatgttctctctcctcaactgtccgtgtttctctctcaactgcacactgttcatcctcaactgccacagcaggaggcgttctgcaggagggagccactgccaaatcagagccgataatactgctgcaatgaatacttca |

TABLE 2.1-continued

| SEQ ID NO | Name | Sequence |
|---|---|---|
| SEQ ID NO: 898 | TRAV12-3*02-3' | aggtttacagcagcaggtcgataaatccagcaagtatatctccttgttcatcagagactcacagccagtgattcagccactcacctgtgcaatgagcg |
| SEQ ID NO: 899 | TRAV13-1*02-5' | ggagagaatgtggagcagcatccttcaaccctgagtgtccaggagggagacagcgctgttatcaagtgtacttattcagacagtgcctcaaactacttcc |
| SEQ ID NO: 900 | TRAV13-1*01-3' | cgaattgctgtacattgaacaagacagcagcaaacattctccctgcacatcacagagagagagacgctgttaagacctgaagactcggctgtctactctgtgcagcaagta |
| SEQ ID NO: 901 | TRAV13-1*02-5' | ggagagaatgtggagcagcagtccttcaaccctgagtgtccctgcacatcacagagagagacagccaaacattctccctgcacatcacagagagtgcctcaaactacttcc |
| SEQ ID NO: 902 | TRAV13-1*02-3' | tgttacattgaacaagacagccaaacattctccctgagtgtcccctgagtgtccaggactcacagagaggagacgctgttatcaagtgtctacttctgtgcagcaagtaggaaggac |
| SEQ ID NO: 903 | TRAV13-1*03-5' | ggagagaatgtggagcagcatccttcaaccctgagtgtccaggagggagacagcgctgctggtatcaagtgtacttattcagacagtgcctcaaactacttcc |
| SEQ ID NO: 904 | TRAV13-1*03-3' | gcttatatagacattcgttccaagtgggcgaaaagaagaccaacaattgctgttacattgaacaagacagccaaacattctcctgcagatcaca |
| SEQ ID NO: 905 | TRAV13-2*01-5' | ggagagagtgtggggctgcattcctcacctggagtgtccagtgtccaggaggtgataacctcttattacaactgtgcttattcaaacagcgcctcaaactacttca |
| SEQ ID NO: 906 | TRAV13-2*01-3' | agagtcaccgttttattgaataagacagtgaaacatctctctgagtgtccaggagtgtgacaactcattgcagctcaacctgtcttattcaaacagcgcctcagactacttca |
| SEQ ID NO: 907 | TRAV13-2*02-5' | ggagagagtgtggggctgcattcctcacctggagtgtccaggagtgtgacaactcattgcagctcaacctgtcttattcaaacagcgctcagactacttca |
| SEQ ID NO: 908 | TRAV13-2*02-3' | caaagatcaccgtttattgaataagacagtgaaacatctctctgcagctcaacctgactcagctcagctgtctacttttgtcagaga |
| SEQ ID NO: 909 | TRAV14/DV4*01-5' | gcccagagataactcaaaccccaacaccaggaatgttcgtgcaggaggctgtgactctggactgcacatgacaccagtgatccagtatggtc |
| SEQ ID NO: 910 | TRAV14/DV4*01-3' | actcattgaattccagaaggcaagaaatccgccaacctgtcatctccgcttcatctccgcttcacaactggggactcagcagtgactctgtgccaatgagagggg |
| SEQ ID NO: 911 | TRAV14/DV4*02-5' | gcccagagataactcaaaccccaacaccaggaatgttcgtgcaggaaaaggaggctgtgactctggactgcacatgacaccagtgactgatcaagtatggtc |
| SEQ ID NO: 912 | TRAV14/DV4*02-3' | actcattgaattccagaaggcaagaaatccgccaacctgtcatctccgcttcatctccgcttcacaactggggactcagcagtgatttctgtgcaatgagagggg |
| SEQ ID NO: 913 | TRAV14/DV4*03-5' | gcccagagataactcaaaccccaacaccaggaatgttcgtgcaggaaaaggaggctgtgactctggactgcacatgacaccagtgatccagtatggtc |
| SEQ ID NO: 914 | TRAV14/DV4*03-3' | agtcgctactcattgaatttccagaaggcaagaaatccgccaacctgtcatctccgcttcacaactggggactcagcagtgatcaatgtattctgtcaatg |
| SEQ ID NO: 915 | TRAV14/DV4*04-5' | cagagataactcaaaccccaacaccaggaatgttcgtgcaggaaaaggaggctgtgactctggactgcacatgacaccagtgatcaagtatggtctct |
| SEQ ID NO: 916 | TRAV14/DR4*04-5' | gcaacagaaggtcgctactcattgaattccagaaggcaagaaatccgccaacctgtcatccgcttcacaactggggactcagcagtgactacttct |
| SEQ ID NO: 917 | TRAV15*01-5' | ctccatttctgagtagagctcctcattcattcctgagtatccggagggaatgcacaacattcttaatgcacttatgaggagaactactctcttaa |
| SEQ ID NO: 918 | TRAV15*01-3' | acatttaaagagcgcttgaaaagagaagtttatagtgttttgaatatgtggtctctcatcctggagctgaagtgcaactattcctattctggagtcctgaactct |
| SEQ ID NO: 919 | TRAV16*01-T' | gcccagagagtgactcagctccagcccgagaaagctcctctctgtctttaaaggggcccagtgaagtgcaactattcctattctggagtcctgaactct |
| SEQ ID NO: 920 | TRAV16*01-3' | gcttcactgctgacctaacaaaggcgagacatctttcacctgagaaaccattgctcaagaggaagactcagttacttactgtgctcttaagtgg |
| SEQ ID NO: 921 | TRAV17*01-5' | agtcaacaggagaagaggatcctcaggccttgacatccaagaggcttgacatccaagaggtgaaaatgccaccatgaactgactgcagttacaaaactagtaaacaattacagt |
| SEQ ID NO: 922 | TRAV17*-1-3' | agattaagagtcacgcttgacacttccaagaaagcagtccttgttgatcacggcttccgggcagcagagactgcttcttacttctgtacgacg |

TABLE 2.1-continued

| SEQ ID NO | Name | Sequence |
|---|---|---|
| SEQ ID NO: 923 | TRAV18*01-5' | ggagactcggttaccagacagaaggccagttaccctccctgagagggcagtctgacattaaactgcacttatcagtccagctattcaactttctat |
| SEQ ID NO: 924 | TRAV18*01-3' | gtttcaggccagtcctatcaagagtgacagttccttccacctggagaagctggactctgcagctgtcggactctgcgtctgtactactgagaga |
| SEQ ID NO: 925 | TRAV19*01-5' | gctcagaagtaactcaagcgcagactgaaattctgtgtggtgaaggaggatgtgactcttggactgtgtgatgaaaccgtgatactattact |
| SEQ ID NO: 926 | TRAV19*01-3' | atccttggaacttccagaaatccaccagtccttccttcaactcaccacagctcacactcccagaagtcgtggactcagcagtactctgtctgagtgaggc |
| SEQ ID NO: 927 | TRAV2*01-5' | aaggacaagtgttcagcttcagcctttcacagtgcatcttcagagggagctgtggtggaaatcttctgtaatcactctgtctgttcacaacttctct |
| SEQ ID NO: 928 | TRAV2*01-3' | agggacgatacaacatgacctatgaacggttcctcttccacagtgcctttccttcatcgtcgtcatcgtcagaggtcggggaggcagatgctgtgttactactgtgtggagga |
| SEQ ID NO: 929 | TRAV2*02-5' | aaggacaagtgttcagcttcagcctttcacagtgcctttccttcatcgtcgtcatcgtcagaggtcggggaggcagatgctgtgttactactgtgtgtcaacttctct |
| SEQ ID NO: 930 | TRAV2*02-3' | gggacgtacaacatgacctatgaacggttcctcttccatcgtcgtcatcgtcagaggtcggggaggcagatgctgtgttactactgtgtggaggggctgg |
| SEQ ID NO: 931 | TRAV20*01-5' | gaagaccaggtgacgacgagtcccgagcccgagtccctgagactccagagggagaagctttctgcacatcacagccctaaactgaagactcagccacttatctgtctgtgcagg |
| SEQ ID NO: 932 | TRAV20*01-3' | aaagaaaggctaaaagctacagactcccgagtccccgagcccgagtccctgagactccagagggagaagctttctgcacatcacagccctaaactgaagactcagccacttatctgtctgtgct |
| SEQ ID NO: 933 | TRAV20*02-5' | gaagaccaggtgacgacgagtcccgagcccgagtccctgagactccagagggagaagctttctgcacatcacagtcctcaactcaaacctgaagactcagccacttatctgtctgtgct |
| SEQ ID NO: 934 | TRAV20*02-3' | aaaggagaaagaagctaaaagctacagactcccgagcccgagtccctgagactccagagggagaagctttctgcacatcacagtcctcaactcaaacctgaagactcagccacttatctgtctgtgct |
| SEQ ID NO: 935 | TRAV20*03-5' | gaagaccaggtgacgacgagtcccgagcccgagtccctgagactccagagggagaagctttctgcaccatcaaccgcacagttctcgcagcagtcgagcagtcgagcagcactatctctgt |
| SEQ ID NO: 936 | TRAV20*03-3' | agaaaagaggagaagaaggctaaaagctcacagaagactacgcatcagagtcggcgtcaaactgcagtccaactgcagtgagagactcagcgacttacatcctgtgtgaga |
| SEQ ID NO: 937 | TRAV20*04-5' | gaagaccaggtgacgacgagtcccgagcccgagtccctgagactccagagggagaagctttctgcacatcacagtcctcaactgcagtccaactgcagcagcactatctctgt |
| SEQ ID NO: 938 | TRAV20*04-3' | aaaggagaaagaagctaaaagctacagactcccgagcccgagtccctgagactccagagggagaagctttctgcacatcacagaacttgttctccaactgcagttcactgatagcgcactctcagcaaccctcc |
| SEQ ID NO: 939 | TRAV21*01-5' | aacaggaggtgacgacgagttaatgctctgcgtcgctggatcatcatcaggacgtagtactcatcagagactacttttatcattgacagaagactggttctccaactgtgctgactccacttctttcactgatagcgccactaccctgtgtgtagg |
| SEQ ID NO: 940 | TRAV21*01-3' | aagacttaatgctctgcgtcgctggataaatcatcgcacgctgttgatactttatcatcaggacgtagtactcattacaacatggttctccaactggtttctccaactgttcctccaactggttctccaactgcagttcactgatagcgcactacccctgtgtgtagg |
| SEQ ID NO: 941 | TRAV21*02-5' | aacaggaggtgacacacagttaatgctctgcgtcgctggataaatcatcgcacgctgttgatactttatcatcaggacgtagtactccattatacattgaaactggttctccaactggttctccaactgcagctctccagctgctccagccttcactgatagcgcactaccctgtgtgtagg |
| SEQ ID NO: 942 | TRAV21*02-3' | aagtggagacttaatgctctgcgtcgctggataaatcatcaggacctggaatcatcaggacgtagtactcattacattgaaactggttctccaactggttcctccaactgcgtcctcagcgctccacgctgcggtgcaattcctgacctgcagctgaacattgcagt |
| SEQ ID NO: 943 | TRAV22*01-5' | ggaatacaaagtggagcagagtcctcccagaagtgagtccccagacccgattctcccagacctacagctttattgtacattcctcttcccagaccacagccttattcctcttccgtttattctgtgtggagc |
| SEQ ID NO: 944 | TRAV22*01-3' | agattaagcgccacgactgtcgctacggaccgctacggtattgtacattctcttccgtttattctgtgtggagc |
| SEQ ID NO: 945 | TRAV23/DV6*01-5' | cagcagcaggtgaaacaaagtctcaatctccaatcttgatagtccagaaagaggggattcaattacattcccagcctgcttatgagaacactgcgtttgactacttc |
| SEQ ID NO: 946 | TRAV23/DV6*01-3' | agattcacaatctccttcaataaagtctcaatcttgccaagcagttctcattgcagttcccagcctgcttatgagaacactgcgtttgactacttc |
| SEQ ID NO: 947 | TRAV23/DV6*02-5' | cagcagcaggtgaaacaaagtctcaatctttgatagtccagaaagagggattccaattataaactgcttatgagaacactgtgcttgactacttc |
| SEQ ID NO: 948 | TRAV23/DV6*02-3' | agattcacaatctccttcaataaagtgccaagcagttctcattgcatcatgatccccagcctgcttatgagaacactgcgtttgactacttc |

TABLE 2.1-continued

| SEQ ID NO | Name | Sequence |
|---|---|---|
| SEQ ID NO: 949 | TRAV23/DV6*03-5' | cagcagcaggtgaaacaaagtcctcaatctttgatagtccagaaggaggattcaattataaactgtgcttatgagaacactgcgttgactactttc |
| SEQ ID NO: 950 | TRAV23/DV6*03-3' | agattcacaatctcctcaataaaagtcctcaatctttgatatgccaagcagttctcattgcatatcatgattcccagcctgagactcagcaccactacttctgtgcagcaagca |
| SEQ ID NO: 951 | TRAV23/DV6*04-5' | cagcagcaggtgaaacaaagtcctcaatctcccttaataccaagtgccaagcagtcagtctattgtcatcaaagtccaagctgaagactcagcctactctgt |
| SEQ ID NO: 952 | TRAV23/DV6*04-3' | gaaagaaggaagataagtgccactcttaataccaagtgccaagcagtcagtctattgtacatcaaagtccaagctgaagactcagcctactctgtgcctt |
| SEQ ID NO: 953 | TRAV24*01-5' | aggacgaataagtgccactcttaataccaagtgcaccactcttaataccaagtacatcaaagtccaagctgaagctgaagactcaagactcagccacatactctgtgctttta |
| SEQ ID NO: 954 | TRAV24*01-3' | ggacgaataagtgccactcttaataccaaggtcactcagtcctcagtcctgttcaggagggagacagcaccaattcacctgcagctcccttccagcaatttatgcctac |
| SEQ ID NO: 955 | TRAV24*02-5' | atactgacgtgaacaagtcctcagtcctgttcaggagggagacagcaccaattcacctgcagtcccagctgagatcagccacatactctgtgctttta |
| SEQ ID NO: 956 | TRAV24*02-3' | ggacgaataagtgccactcttaataccaagggtacagtctattgtacatcaaagtccaagctgtcacacgtactgcaattcctcaactacttaagcaatatacagt |
| SEQ ID NO: 957 | TRAV25*01-5' | ggacaacagtaatgcaaattcctcagtcggacatgtacaagaaggaggactccaccgtactcaattcctcaactacttaagcaatatacagt |
| SEQ ID NO: 958 | TRAV25*01-3' | gaaaagactgacatttcagttggagaagcagcaaaaagaacagctccctgcaacatcactccagctgaggaacctacttctgtgcaggg |
| SEQ ID NO: 959 | TRAV26-1*01-5' | gatgctaagaccaccagcccagctccatgattgcgctgaaggagagctgcaaacctgcctgtaatcactcaccactcagtggaatgagtatgt |
| SEQ ID NO: 960 | TRAV26-1*01-3' | gctctctgatcatcacagaagacacagaaaagacagccacacctgatcctgccccacgctacgctgccagagctgcaaacctgctgtatattgcatcgtcagagtcg |
| SEQ ID NO: 961 | TRAV26-1*02-5' | gatgctaagaccaccagccagctccatgattgcgctgaaggagagctgcaaacctgcctgtaatcactcaccagtggaatgagtatgt |
| SEQ ID NO: 962 | TRAV26-1*02-3' | ctctgatcatcacagaagacaccagccacctgatcctgccccacgctacgctgccagagctgcaaacctgcctgtgtactattgcatcgtcagagatgggt |
| SEQ ID NO: 963 | TRAV26-1*03-5' | gatgctaagaccaccagccacccctgatcatcacagaagacacagaaaagacagccacacctgatcctgccccacgctacgctgccagagctgcaaactgcctgtaatcactcaccagtgagtatgt |
| SEQ ID NO: 964 | TRAV26-1*03-3' | caatgaatggctctctgatcatcacagaactcaatgagctaagacacagagcagtaacgaagaagagcctgtcacttgcctgtaacactccacaatcagtggaactgattacatac |
| SEQ ID NO: 965 | TRAV26-2*01-5' | gatgctaagaccacagccagctccatgattgcgctgaaggagagctgcaaacctgcctgtgtactattgcatcctgagagac |
| SEQ ID NO: 966 | TRAV26-2*01-3' | ggcctcctggcaatgctgagcagcaaattcatggagacagaaagtccagtacctgatcctgcacgctgtactgtcatcctgagagac |
| SEQ ID NO: 967 | TRAV26-2*02-5' | gatgctaagaccacacagccaaattcatggagcatgaagagtaacgaagaagagcctgttcacttgcctgtaaccactccacaatcagtggaactgattacatac |
| SEQ ID NO: 968 | TRAV26-2*02-3' | ccctcccagggtccagagtactgatcatgtcttaagcaacaacagaatgcctgtggcaatgctgactgcaactcctcaagtgttctgcactgcctgt |
| SEQ ID NO: 969 | TRAV27*01-5' | accccagctgctgaagcagagccctcagtttctaagcatccaagtttctcaagcaacatcactgtgactgacctcctcaagtttttccagcttacaat |
| SEQ ID NO: 970 | TRAV27*01-3' | aagagactaaccttcagtttggtgatgcaagaaggacagttctctccacatcactgcagcccagcagctactgcaactcctcaagtacaggcctctcagtgcaggag |
| SEQ ID NO: 971 | TRAV27*02-5' | accccagctgctgagcagagcccctcagtttctaagcatccaagtttctcaagcaacatcactgcagcccagcagctactgcaactcctcaagtgtttttccagcttacaat |
| SEQ ID NO: 972 | TRAV27*02-3' | tgaagactaaccttcagtttggtgatgcaagaaggacagtcctctccacatcactgcgccccacatcactgggccacagccagcctgtgatacactactggtacaggccactacctgtcagg |
| SEQ ID NO: 973 | TRAV27*03-5 | accccagctgctgagcagagcccctcagttcctaagcatccaagagggagaaaattcactgtgactgtactgcaactcctcaagtgttctgcactgtcaacttcactactgcaactcctcaagtgttttccagcttacat |

TABLE 2.1-continued

| SEQ ID NO | Name | Sequence |
|---|---|---|
| SEQ ID NO: 974 | TRAV27*03-3' | gctgaagagactaaccttcagttggtgatgcaagaaggacagttctctccacatcactcagccagactggtgatacaggcctctacctctgtgca |
| SEQ ID NO: 975 | TRAV28*01-5' | aaagtgagcagagtcctcaggtcctgatcctcaagaggggaagaaattcattcgtgtgcagttgttcttattacatgatccgtgcagtggtttc |
| SEQ ID NO: 976 | TRAV28*01-3' | gaagactaaaatccgcagtcaaagctgaggaacttatggcactcagatattccagcctgaggactcagcattactccgtgcattactcctgtggggga |
| SEQ ID NO: 977 | TRAV29/DV5*01-5' | gaccagcaagtaagcaaatcaccatcccctgagcgtccaggaaggaagaattccattctgaactgtgactactactaacagcatgttgattattcc |
| SEQ ID NO: 978 | TRAV29/DV5*01-3' | agattcactgtctgtcttcttaaacaaaagtgccaagcaccctctctctgagcctcccagcctgaactgtgactctgcgtcagtgtactctgcaagcg |
| SEQ ID NO: 979 | TRAV29/DV5*02-5' | gaccagcaagtaagcaaatcaccatcccctgagcgtccaggaaggaagaattccattctgaactgtgactactactaacagcatgttgattattcc |
| SEQ ID NO: 980 | TRAV29/DV5*02-3' | agattcactgtttcttaaacaaaagtgccaagcatccctctctctgagcgtccaggaaggaagaattccattctgaactgtgactactactaacagcatgttgattattcc |
| SEQ ID NO: 981 | TRAV29/DV5*03-5' | gaccagcaagtaagcaaatcaccatcccctgagcgtccaggaaggaagaattccattctgaactgtgactactactaacagcatgttgattattcc |
| SEQ ID NO: 982 | TRAV29/DV5*03-3' | agattcactgtttcttaaacaaaagtgccaagcatccctctctctgagcctcccagcctgaactgtgactctgcgtcagtgtactctgcaagcg |
| SEQ ID NO: 983 | TRAV3*01-5' | gctcagtcagtggctcagccggaagatcaggtcaacgttgctgaagggaatcctctgactgtgaaatgcacctattcagtcctctgaaaccctatctttt |
| SEQ ID NO: 984 | TRAV3*01-3' | tttgaagctgaattaacaagagccaaactccttccaactgaagaaaaaccatctgccttgaacgactcgcttgtactctgtgctgagagaca |
| SEQ ID NO: 985 | TRAV3*02-5' | gctcagtcagtggctcagccggaagatcaggtcaacgttgctgaagggaatgcacttcagtctctgaaacctatctttt |
| SEQ ID NO: 986 | TRAV3*02-3' | ctttgaagctgaatttaacaagagccaaactccttcctccacctgaagaaaaccatctgccttgacgctccgcttgtactctgtgctgtgagaccc |
| SEQ ID NO: 987 | TRAV30*01-5' | caacaaccagtcagagtcctcaagcctgatcctcaagaagggaagatgctgtcatcaactgacgtctccaaggcttatatctcgcacagagga |
| SEQ ID NO: 988 | TRAV30*01-3' | aaaatatctgcttcatttaatgaaaaaaagcagcaaagctccctgatcctccagaagggaagatgctgtaccttacgggtcatcaaccactacttctgcggg |
| SEQ ID NO: 989 | TRAV30*02-5' | caacaaccagtcagagtcctcaagcctgatcctcaagccgtgatcctccagaagggaagatgctgtaccttacgggtcatcaaccactacttctgcggg |
| SEQ ID NO: 990 | TRAV30*02-3' | tcgtgaaaaatatctgcttcatttaatgaaaaaagcagcaaagctcccctgtacctcagtcagtactgacgtcctccagctcagtcctccaaggcttatatctcgcacactggt |
| SEQ ID NO: 991 | TRAV30*03-5' | caacaaccagtcagagtcctcaagcctgatcctcaagccgtgatcctccagaagggaagatgctgtaccttacgggtcatcaaccactacttctgcggc |
| SEQ ID NO: 992 | TRAV30*03-3' | tcatgaaaaatatctgcttcatttaatgaaaaaagcggcaaagctccctgatcctccagaagggaagatgctgtaccttacgggtcatcaaccactacttctgcggc |
| SEQ ID NO: 993 | TRAV30*04-5' | caacaaccagtcagagtcctcaagcctgatcctcaagccgtgatcctcaagccgtgatcctccagaagggaagatgctgtaccttacgggtcatcaaccactacttctgcggt |
| SEQ ID NO: 994 | TRAV30*04-3' | tcctgtgatattactgaagggtggagaacagcagtcatgagaggtgagacctgaactggactgtgcatcaaacatatgctcctcgtacctacggc |
| SEQ ID NO: 995 | TRAV31*01-5' | cagagggtcattcaatcccaacagcagcaatatcaaaatctacgtaggaggtgagacctgaactggactgtgcataaacaatattgtatatacatattgt |
| SEQ ID NO: 996 | TRAV31*01-3' | tattctgagctccagaaaactcctatcagcttatcatcatcacagcagaagacctgcaacatattctgtctccaaagagcc |
| SEQ ID NO: 997 | TRAV32*01-5' | aaggatgtgatacagagttattcaaatctaaatgtctaggagagagaatggcgttattaatgacagtatacagatggagcttgaattattctgtt |
| SEQ ID NO: 998 | TRAV32*01-3' | aggctcactgtactgttgaatacaccagtcagaccaccagtaactaggcagaaagactaacatgctccctgcatattacagccaccaaccaggagactcattcctgtacttgtgcagtgagaa |
| SEQ ID NO: 999 | TRAV33*01-5' | gctcagagaagtaaccaagttcagacaccagtcagaaaggagtagctgtgcatgttgaaaccagatagaattgtacactt |

TABLE 2.1-continued

| SEQ ID NO | Name | Sequence |
|---|---|---|
| SEQ ID NO: 1000 | TRAV33*01-3' | gcaaagcctgtgaacttgaaaaagaaaaagttcatcaacctcaccatcaattcctaaaactgactcagccagtacttctgtgtctcaggaatcc |
| SEQ ID NO: 1001 | TRAV34*01-5' | agccaagaactggagcagagtcctcagtcctgatcgtcagtgagaaaagcaagaaactgcacgtcatcaaagacgttatgcttatact |
| SEQ ID NO: 1002 | TRAV34*01-3' | aagataactgccaagttggatcagagtcctcatctatgtttatccaggaaggacagcttccatgatcagatcacttcttcaagcatgcatgtggagcagaca |
| SEQ ID NO: 1003 | TRAV35*01-5' | ggtcaaacagctgctcagtctgtataaccagaaggacagcttccatgatcatccagcatcatacatcattaacacctgctat |
| SEQ ID NO: 1004 | TRAV35*01-3' | aagactgactgctcagtttggtataaccagaaggacagcttccatgatcatccagcatcatacatcattaacacctgctat |
| SEQ ID NO: 1005 | TRAV35*02-5' | ggtcaaacagctgactgctcagtttgtataaccagaaggacagctcctgaatctcagcatccatcagtgatgtaggcatctactctgtgct |
| SEQ ID NO: 1006 | TRAV35*02-3' | aaatggaagactgactgctcagtttggtataaccagaaggacagctcctgaatctcagcatccatcagtgatgtaggcatctactctgtgct |
| SEQ ID NO: 1007 | TRAV36/DV7*01-5' | gaagacaaggtgactgctacaaagccctctatcctggttgtccacgaggagacaccgtaactctcaattgcagttatgaagtgactaacttcgaagcctac |
| SEQ ID NO: 1008 | TRAV36/DV7*01-3' | agactaagtagcatattagataagaaagaactttccaatctccatctcggttgtccacgaggagacattgtaactctcaattgcagttatgaaatgactaacttcgaagcctac |
| SEQ ID NO: 1009 | TRAV36/DV7*02-5' | gaagacaaggtgtacaaagccctctatcctggttgtccacgaggagacctcgaacatcacagccaccagtgaactaactgcagttatgaagtgactaacttcgaagcctac |
| SEQ ID NO: 1010 | TRAV36/DV7*02-3' | ggaagacaaggtgtacaaagccctctatcctggttgtccacgaggagacactgaactgaacatgcagttatgaagtgactaacttcgaagcctac |
| SEQ ID NO: 1011 | TRAV36/DV7*03-5' | gaagacaaggtgtacaaagctaagtagacattagataagaagaaagaccctctatcctggttgtccacgaggagacactttcagcatctgaactgcaccagccacccagagccaccagcacagacgagactcggccgtcacctctgtct |
| SEQ ID NO: 1012 | TRAV36/DV7*03-3' | gtcaggagacaagtagcatattagataagaaagaaccttcagcatctgaactgcagtctaactcacagccacccagagccaccagcacagacgagactcggccgtcacctctgct |
| SEQ ID NO: 1013 | TRAV36/DV7*04-5' | gaagacaaggtgtacaaagccctctatcctggttgtccacgaggagacacttccagcatctgaactgcagttatgaagtgactaacttcgaagcctac |
| SEQ ID NO: 1014 | TRAV36/DV7*04-3' | tcaggagacaagtagcatattagataagaagaaaccttcagcatctgaactgcagtctaactcacagccacccagagccaccagcacagacgagactcggccgtcacctctgtcg |
| SEQ ID NO: 1015 | TRAV37*01-5' | caactgccagtcagccaggcttaaaaaggagaccagcagccagcagcagccacattccctgcgaagtcacagtccccagctccagcgtcacagtcaaatgaactgcacatacagacgtcacacattcttctgcgcaagca |
| SEQ ID NO: 1016 | TRAV37*01-3' | agattccagccagcagccaggcttaaaaaggagaccagcagccagcagccacattccctgcgaagtcacagtccccagctccagcgtgacctgagttgcacatgacaccagtgagaataattattatt |
| SEQ ID NO: 1017 | TRAV38-1*01-5' | gcccagagcactccagtcctcaaccagacagccagcagccagcaaatcctcagtctcagtcctgcgaggaggcagagactgtctgtgacctgagttgcacatgacaccagtgagaataattattatt |
| SEQ ID NO: 1018 | TRAV38-1*01-3' | tctctgtgaacttctgtgaacttccagaaagcagtccagtcctcaaccagacagccagcaaatcctcagtctcagtcctgcgaggaggcagagactgtctgtgacctgagttgcacatgacaccagtgatattctgtgctttcatgaagca |
| SEQ ID NO: 1019 | TRAV38-1*02-5' | gcccagagcactccagtcctcaaccagacagccagcaaatcctcagtctcagtcctgcgaggaggcagagactgtctgtgacctgagttgcacatgacaccagtgatattctgtgctttcatgattattatt |
| SEQ ID NO: 1020 | TRAV38-1*02-3' | gagaatcgttctctgtgaacttccagaaagcagtccagtcctgtgaacttccagaaaaagcagcaaatcctcagtctcagtcctgcgaggaggcagagactgtctgtgacctgagttgcacatgacaccagtcggggacactgggtgatgatattctgtgctt |
| SEQ ID NO: 1021 | TRAV38-1*03-5' | gcccagagcactccagtcctcaaccagacagccagcaaatcctcagtctcagtcctgcgaggaggcagagactgtctgtgacctgagttgcacatgacaccagtggggacactgggtgcatatgacaccagtgagaataattattatt |
| SEQ ID NO: 1022 | TRAV38-1*03-3' | aatcgtttctctgtgaacttctgtgaacttccagaaagcccagcagcaaatcctccagtctcagtcctcaagatctccagatctccagatctcctgcgaggaggcagagactgtctgtgacctgagttgcacatgacaccagtgggggacactgggtgtattctgtcttca |
| SEQ ID NO: 1023 | TRAV38-1*04-5' | gcccagagcactccagtcctcaaccagacagccagcaaatcctcagtctcagtcctgcgaggaggcagagactgtctgtgacctgagttgcacatgacaccagtcggggacactgggtgcatatgacaccagtgagaataattattatt |
| SEQ ID NO: 1024 | TRAV38-1*04-3' | ggagaatcgttctctgtgaacttctgtgaacttccagaaagcagcaaatccttcagtctgaacttccagatcttcagtctcagtcctcaagatctccagatctcagtcctcaagatctccagatctcagtcctcaagatctccagatctcagtcctcaagatctccagatctcagtcctcagagactcagtccagtcctcaagatctccagatctcagtcctcaagatctccagatctcagtcctcaagatctccagatctcagtcctcagagactcagtccagtcctcaagatctccagatctcagtcctcaagatctcagagactcagtccagagactcagtccagagactcagtccagtcctcaagatctccagatctcagagactcagtccagagactcagtccagtcctcaagatctccagatctcagtcctcaagatctcagagactcagtccagagactcagtccagtcctcaagatctccagatctcagagactcagtccagtcctcaagatctccagatctcagagactcagtccagtcctcaagatctccagatctcagagactcagtccagagactcagtccagagactcagtccagagactcagtccagagactcagtccagagactcagtccagagactcagtccagagactcagtccagagactcagtccagagactcagtccagagactcagtccagagactcagtccagagactcagtccagagactcagtccagagactcagtccagagactcagtccagagactcagtccagagactcagtccagtcctcaagatctccagatctcagtcctcaagatctccagatctcagtcctcaagatctccagatctcagagactcagtccagagactcagtcgatgatattctgtgca |

TABLE 2.1-continued

| SEQ ID NO | Name | Sequence |
|---|---|---|
| SEQ ID NO: 1025 | TRAV38-2/DV8*01-5' | gctcagacagtcactcagtctcaaccagagatctctgtgcaggaggcagagaccgtgaccctgagctgcacatgacaccagtgagagtgattatatt |
| SEQ ID NO: 1026 | TRAV38-2/DV8*01-3' | ttctctgtgaattcctgagaaagcagccaaatccttcagtcctgagcatgcaggatgccgcgatgtattctgtctataggagcg |
| SEQ ID NO: 1027 | TRAV39*01-5' | gagctgaaagtgaacaaaaccctgtcctgagcatgcaggagggaaaaactatacatcactactgcaattattcaaccactcagacagctgtatt |
| SEQ ID NO: 1028 | TRAV39*01-3' | cgattaatgctcacttgatacccaagccgtccagcaccctcagcatgccgtgcatgacccctctgccacctacttctgtgccgtggaca |
| SEQ ID NO: 1029 | TRAV4*01-5' | cttgctagacaccccagcctcccatgggactcatatgaaggacaagaagtgaacataacctgtagccacaacaattgctacaaatgattatatca |
| SEQ ID NO: 1030 | TRAV4*01-3' | gcctccctgttatcctgcgacagaaagtccagcactctgagcctgcccgggttccctgaggcgacactgctgtactactgctctgggtgaca |
| SEQ ID NO: 1031 | TRAV40*01-5' | agcaattcagtcagcagcagacgggccaaataacgtctcggaggggagcatctgactctgtgaatatcagtccaggtatcagacctcagcgtgtactactgtctctggaga |
| SEQ ID NO: 1032 | TRAV40*01-3' | aaaactcggaggcggaaatattaaagacaaaaaatccccctgttgaattatcaactcccatcaactgcagtcagttactcggtaggaataagtgccttacact |
| SEQ ID NO: 1033 | TRAV41*01-5' | aaaaatgaagtgagcagagtcctcagaaacctgactgccagaggggagaattatcacacacagctccctgcacatcacagctccgtgttcacatctgtgctgtgtcaga |
| SEQ ID NO: 1034 | TRAV41*01-3' | aagattaattgcacataaaacatacaggagaaagcacagctccctgagtgcggagagtctttcctgagtgtccgagagaacacatgtctctgcgcattgccagagcagcttcacttacattactact |
| SEQ ID NO: 1035 | TRAV5*01-5' | ggagaggatgtgtggagcagattgtgttctattgaataaaagaggataaaacatctgtctctgcgcattgccagagcaccagactgggactcagctatctcacttcttgcagagagta |
| SEQ ID NO: 1036 | TRAV5*01-3' | agactcactgtcttctattgaataaaagaggataaaacatctgtctctgcgcattgccagagcaccagactgggactcagctatctcacttcttcccagcatacttac |
| SEQ ID NO: 1037 | TRAV6*01-5' | agccaaaagataaacagaattcgaggcccgagccctaaaacggcacccctaaaacagttgttcatatcacagctccctgacctgcaactgacatacaaaactattcccagcctctgtgctctagaca |
| SEQ ID NO: 1038 | TRAV6*01-3' | agactgaaggtcacctgaacatcaggagttgttcatcaaacagagttgttcatatcacagctccctgacctgcaactgacatacaaaactattcccagcctctgtgctctagaca |
| SEQ ID NO: 1039 | TRAV6*02-5' | agccaaaagatagaacagaattccgaggcccctgataccaccctaaaacagagttgttcatcaaacagagttgttcaactatacaaaactattcatatcacaagctgacctgcaactgacatacaagctgcaaactacagtgctaccgacagatccagagtgacctgtgt |
| SEQ ID NO: 1040 | TRAV6*02-3' | gaaagaagactgaaggtcacctgaacattcagggaggagtaaaacagagttgttcaactatacaagctgacctgcaactggtaccgacagatccagagtgacctgtgt |
| SEQ ID NO: 1041 | TRAV6*03-5' | gaggcccctgaacattcaggagggtcacctgaacattcaggagggtaaaacagagttgttcaactatacaagctgacctgcaactggtaccgacagatccagagtgacctgtgt |
| SEQ ID NO: 1042 | TRAV6*03-3' | gaaagaagactgaaggtcacctttgatacccgagggtaaaacggcccctgaacctgatactgtgaaatgagaagatgagaaaagagagaagactgcctccatgagctgcacgtgcctgctgtactctgtgctgcaactgaacggtaccagatccagaa |
| SEQ ID NO: 1043 | TRAV6*04-5' | gaggcccctgaacattcaggagggtcacctttgatacccgagggtaaaacggccctgaacctgatactgtgaaatgagaaaagagagaagactgcctccatgagctgcacgtgcctgctgtactctgtgctgcaactgaacggtaccagatccagaa |
| SEQ ID NO: 1044 | TRAV6*04-3' | gaaagaagactgaaggtcaccttgataccccgagggtaaaacagcccctgaacctgatactgtgaaatgagaaaagagagaagactgcctccatgagctgcacgtgcctgctgtactctgtgctgcaactgaacggtaccagatccagaa |
| SEQ ID NO: 1045 | TRAV6*05-5' | gaggcccctgaacattcaggagggtcacctttgatacccgaggcgctcccagccgcctccagcctccccagccgtccccagccgtccagactgcactgctgtaccaaactgctcacctctgtgctgcaactgcactgctgtaccgacagatccagagtaccctgct |
| SEQ ID NO: 1046 | TRAV6*05-3' | gaaagaagactgaaggtcacctttgatacccgagggtaaaacggcccctgaacctgatactgtgaaatgagaaaagagagaagactgcctccatgagctgcacgtgcctgctgtactctgtgctgcaactgaacggtaccagatccagaa |
| SEQ ID NO: 1047 | TRAV6*06-5' | agccaggagggccctgaactgaacggagtaaatgaacagcgtcccagggccctgaacctgatactgtgaaatgagaaaagagagaagactgcctccatgagctgcacgtgcctgctgtactctgtgctgcaactgaacggtaccagatccagaa |
| SEQ ID NO: 1048 | TRAV6*06-3' | ccaggagaggccgctggagcacagccctgaacctgatactgtgaaatgagaaaagagagaagactgcctccatgagctgcacgtgcctgctgtactctgtgctgcaactgaacggtaccagatccagaa |
| SEQ ID NO: 1049 | TRAV7*01-5' | gaaaaccaggtgaagctgaacattactgaagaatggaagcagcttgtacattacagccgtgaagattcagcctgagagctgcacgtactctgtcagtgtttaacaattgc |
| SEQ ID NO: 1050 | TRAV7*01-3' | aaaggaagactaaatgctacattactgaagaatggaagcagcttgtacattacagccgtgaagattcagcctgagagctgcagcctgagattcagcagcctgaagattcagcctgagagctgcacgtactctgtgctgtagatg |

TABLE 2.1-continued

| SEQ ID NO | Name | Sequence |
|---|---|---|
| SEQ ID NO: 1051 | TRAV8-1*01-5' | gcccagtctgtgagccagcataaccaccacgtaattctctgaagcagctcactggagttgggatgcaactattcctatggtgaactgttaatctct |
| SEQ ID NO: 1052 | TRAV8-1*01-3' | gcttttgaggctgaatttataaagagtaaattctcctttaatctctctgaagcagctcactggagttgggatgcaactattcctatggtgaactgttaatctct |
| SEQ ID NO: 1053 | TRAV8-1*02-5' | gcccagtctgtgagccagcataaccaccacgtaattctctgaagcagctcactggagttgggatgcaactattcctatggtgaactgttaatctct |
| SEQ ID NO: 1054 | TRAV8-1*02-3' | ttttcagggatccactggttaaaggcatcaagggcgtgagctctctgaggtcgtgctgaggtaaattctccttaatcgaggaaccctgcagtgga |
| SEQ ID NO: 1055 | TRAV8-2*01-5' | gcccagtcggtgaccagcttgacagccacgtcctgtctctgaaggaccctgcctgaggtgtgctgaggtgacgacggcaactactcatcttcttattcaccatctct |
| SEQ ID NO: 1056 | TRAV8-2*01-3' | gtttgaggctgaatttaagaagagtgaaacctctcctccacctgtctctgaaggagtgaaacctctcagccctgcctgaggtgtgctgaggtgacgacggcaactactcatcttcttattcaccatctct |
| SEQ ID NO: 1057 | TRAV8-2*02-5' | gcccagtcggtgaccagcttagcagccacgtcctgtctctgaaggagtgaaacctctcagccctgcctgaggtgtgctgaggtgacgacggcaactactcatcttcttattcaccatctct |
| SEQ ID NO: 1058 | TRAV8-2*02-3' | ttaagagagtgaaacctctcctccacctgacatcacatctcctgtctctgaaggagtgaaacctctcagccctgcctgaggtgtgctgaggtgacgacggcaactactcatcttcttattcaccatctctcag |
| SEQ ID NO: 1059 | TRAV8-3*01-5' | gcccagtcagtgaccagcctgacatcacatctcctgtctctgaaggagtgaaacctctcactggagtctctgaagcagcctgaggtgtgctgaggtgacgacggcaactactcatcttcttattcaccatctct |
| SEQ ID NO: 1060 | TRAV8-3*01-3' | gctttgaggctgaatttaagaggagtgacatcacatctcctgtctctgaaggagtgaaacctctcactggagtctctgaagcagcctgaggtgtgctgaggtgacgacggcaactactcatcttcttattcaccatctct |
| SEQ ID NO: 1061 | TRAV8-3*02-5' | gcccagtcagtgaccagcctgacatcacatctcctgtctctgaaggagtgaaacctctcactggagtctctgaagcagcctgaggtgtgctgaggtgacgacggcaactactcatcttcttattcaccatctct |
| SEQ ID NO: 1062 | TRAV8-3*02-3' | aggcttgaggctgaatttaagaggagtcaatctccacatcacatctcctgtctctgaacctgaggagcctgaactcactggagtgctgtctgaggtcattggagtgatgcattggagtgaatgtaactattctatgggcaacacctatctgtggtt |
| SEQ ID NO: 1063 | TRAV8-3*03-5' | gcccagtcagtgaccagcctgacatcacatctcctgtctctgaacctgaggagcctgaactcactggagtgctgtctgaggtcattggagtgatgcattggagtgaatgtaactattctatgggcaacacctatctgtgct |
| SEQ ID NO: 1064 | TRAV8-3*03-3' | tattaaaggtcggtgaccagctttgaggctgaccacgtgaaaccctccacctgacctgtctctgaagcagccctgtctgtccaccatatctct |
| SEQ ID NO: 1065 | TRAV8-4*01-5' | gcccagtcggtgaattaagagaagtgaccacgtgaaaccctccacctgtctctgcacctgactgtctgcctgaagcagccctgtctgtccaccatatctct |
| SEQ ID NO: 1066 | TRAV8-4*01-3' | gtttgaggctgaatttaagaagagtgaccacgtgaaaccctccacctgtctctgcacctgactgtctgcctgaagcagccctgtctgtccaccatatctct |
| SEQ ID NO: 1067 | TRAV8-4*02-5' | gcccagtcggtgaccagcttgaccacgtgaaaccctccacctgtctctgacacaacaacctcagccagtgaggacggccaactactcttgtgctgatctgaccga |
| SEQ ID NO: 1068 | TRAV8-4*02-3' | gaatttaagaaagtgaaactcctccacctgtctctgacacaacaacctcagccagtgaggacggccaactactcttgtgctgatctgaccga |
| SEQ ID NO: 1069 | TRAV8-4*03-5' | gcccagtcggtgaccagcttgaccacgtgaaaccctccacctgtctctgcgaggagcctgagccagccgaccctcagccagtgaggacggccaactactcttgtgctcatccgtccaccatatctct |
| SEQ ID NO: 1070 | TRAV8-4*03-3' | catcaacggttgaggctgaatttaagaagagtgaaacctcttccacctgacgaccctcagccagtgaggacggccaactactcttgtgctcatccgtccaccatatctct |
| SEQ ID NO: 1071 | TRAV8-4*04-5' | gcccagtcggtgaccagcttgaccacgtgaaaccctccacctgtctctgacaccctcagccagtgaggacggccaactactcttgtgctctgtttgtgct |
| SEQ ID NO: 1072 | TRAV8-4*04-3' | aggcatcaacggtttgaggctgaattttaagagaacgaaaacctctccacctgacgaaacctccagccctgacgagtcgaacggccaactactcatcgctcgtgtccaccatattgt |
| SEQ ID NO: 1073 | TRAV8-4*05-5' | gcccagtcggtgaccagcttgaccacgtgaaaccctccacctgtctctgaaggagccctgagccctgaggtgcaactactcatcgctcgtgtccaccatatctct |
| SEQ ID NO: 1074 | TRAV8-4*05-3' | ggctgaattttaagagagtgaaaccctcagccactcccaccgaaaccctcagccactccgaaacctccagccctgaagatacacatcagcggccacccctgttaagtgtactcctggtgtactcctggtgagtgagtctcca |
| SEQ ID NO: 1075 | TRAV8-4*06-5' | ctcctcctgtatgcaatacccccaacaaggactctctcctgaagtacacatcagcggccacccctgttaaggcaacaacggtttgaggctg |

TABLE 2.1-continued

| SEQ ID NO | Name | Sequence |
|---|---|---|
| SEQ ID NO: 1076 | TRAV8-4*06-3' | gaatttaagaagagtgaaacctcctccacctgacgaaaccgcagccagtgaggacggctgagtactctgtgctgagtgatctgaacga |
| SEQ ID NO: 1077 | TRAV8-4*07-5' | gttgaaccatatctcttctggtatgtgcaataccccagtcctgaagactccagtttcctgaagtacaacaaggggcacccgctgtaaaggcataacg |
| SEQ ID NO: 1078 | TRAV8-4*07-3' | acggtttgaggctgaattaaaaagagtgaaacctcctccactgacgaaacccagcccatatgaccgacccggctgagtacttctgtgtgaag |
| SEQ ID NO: 1079 | TRAV8-5*01-5' | gcccagtcagtgaccagctgaccatccgcatcaataccctgacctgtctcacctgtctcctgaaggagcctcactggagtgagatgtaactatcctatggggcgatgtgtgggaag |
| SEQ ID NO: 1080 | TRAV8-5*01-3' | tggacacttatcactcccaatcaataccccgtcagcctgtgattcctgatgcctgtctcacttaatcctcagtcgaggaggatgtgtcacc |
| SEQ ID NO: 1081 | TRAV8-6*01-5' | gcccagtcgtgaccagctgacagctgaccaagtccctgtttgaagaagcccctgaagaaaacccctgaagaagccctgagttaccctcagtgtatctct |
| SEQ ID NO: 1082 | TRAV8-6*01-3' | gttttgaggctgaattaacaagagtcaaactccctgtcttccacttgaagaaaacctgacgacgacgctgaactactctgtgctgtgagtga |
| SEQ ID NO: 1083 | TRAV8-6*02-5' | gcccagtcgtgaccagctgacagctgaccaagtccctgtcttgaagaagcccctgaagaagcccctgagtccatataagcgatacggccaatactactctgtttcagtgtatctct |
| SEQ ID NO: 1084 | TRAV8-6*02-3' | gttttgaggctgaattaacaagagtcaaactccctgtcttccacttgaagaaaacctgacgacgctgaactactctgtgctgtgagtga |
| SEQ ID NO: 1085 | TRAV8-7*01-5' | acccagtcgtgaccagcttgatggccacatcacctgtctccctgaggagaaccatcaacccatgagtgagtgctgagtacttctgtgctggtgacagagg |
| SEQ ID NO: 1086 | TRAV8-7*01-3' | aggctgaattaagaagcgaaacctccttcacctgacgaaggccaagtgctccctcgaagtcctatgaaccaacacagtaccctcccttt |
| SEQ ID NO: 1087 | TRAV9-1*01-5' | ggagatcagtgaccctaccgtgaccagatgaagccacataccgtgaaggccacatgcacttggagaaagactcagttcagtgtcctgactataaactgcacgtacacagccgctgtactctgctctgagtga |
| SEQ ID NO: 1088 | TRAV9-1*01-3' | gtttgaagcccatgtgaccctaccgtgaaggccacatgcacttggagaaagactcagttcagtgtcctgactataaactgcacgtacacagccgctgtactctgtgctctgagtga |
| SEQ ID NO: 1089 | TRAV9-2*01-5' | ggaaatcagtgaccctaccgtgaaggccacatgcacttggagaaagaggccttcccactggagaaagaggccttcctgactataaactgcacgtacacagccacagccagtgtactctgtgct |
| SEQ ID NO: 1090 | TRAV9-2*01-3' | gtttgaagcccatgtgaccctaccgtgaaggccacatgcacttggagaaagaggccttcctgactataaactgcacgtacacagccacagccagtgtactctgtgct |
| SEQ ID NO: 1091 | TRAV9-2*02-5' | ggagatcagtgaccctaccgtgaaggccacatgcacttggagaaagaggccttcctgactataaactgcacgtacacagccacagccagtgtactctgtgct |
| SEQ ID NO: 1092 | TRAV9-2*02-3' | caacaaaggtttgaagcccatgtaccacagacaccaaataccggtcagcaatgggagtaaaggacaatgaaactgagactcagtgtcatgattctatgtattggt |
| SEQ ID NO: 1093 | TRAV9-2*03-5' | ggagatcagtgaccctaccgtgaaggccacatgcacttggagaaagaggccttcctgactataaactgcacgtacacagccacagccagtgtactctgtgct |
| SEQ ID NO: 1094 | TRAV9-2*03-3' | caacaaaggtttgaagcccatgtaccacagacaccaaataccggtcactgcgactgcgactgcagcaggaactcagctgcgtatctctgaccagccaaga |
| SEQ ID NO: 1095 | TRAV9-2*04-5' | ggaaatcagtgaccctaccgtgaaggccacatgcacttggagaaagaggccttcctgactataaactgcacgtacacagccacagccagtgtactctgtgct |
| SEQ ID NO: 1096 | TRAV9-2*04-3' | caacaaaggtttgaagcccatgtaccacagacaccaaataccggtcactgcgactgcgactgcagcaggaactcagctgcgtatctctgaccagccaaga |
| SEQ ID NO: 1097 | TRBV1*01-5' | gatactggaattaccagacaccagacaccaaataccggtcagcaatgggagtaaaggacaatgaaactgagactcagctgggacatgattctatgtattggt |
| SEQ ID NO: 1098 | TRBV1*01-3' | acttcacacctgaatgcctgagctctcgttatacctcatgtggtcgactgcagcaggaagactcagctgcgtatctctgaccagccaaga |
| SEQ ID NO: 1099 | TRBV10-1*01-5' | gatgctgaaatcaccccagagcccaagacaccagagaccccaagatcacagagacaggaccctggcgtgtcaccagactggaaccaacaatatgttctt |
| SEQ ID NO: 1100 | TRBV10-1*01-3' | gctacagtgtctctagattaaacacagagcccaagacaccagagacaggaccctcactctgtgcctcctccagacatctgtatttctgcgccagcagtgagtc |
| SEQ ID NO: 1101 | TRBV10-1*02-5' | gatgctgaaatcaccccagagcccaagacacacagagacaggaagcaggtgcgtgtcaccagactggaaccaacaatatgttct |

TABLE 2.1-continued

| SEQ ID NO | Name | Sequence |
|---|---|---|
| SEQ ID NO: 1102 | TRBV10-1*02-3' | agatggctacagtgtctctagatcaaacacagaggacctcccctcattctggagtctgctgtcctcccagactctgtatattctgcgccagagt |
| SEQ ID NO: 1103 | TRBV10-1*03-5' | agcaggtgaccttggcgtgtcaccagactggctcagtgctctagatcaaacacagagaccctccactctgtatcgacaagactggcactgtctgaggctgatcattaccat |
| SEQ ID NO: 1104 | TRBV10-1*03-3' | ctacaaaggagaagtcagatggctcagtgctctagatcaaacacagagacaggaggcaggcaggcagccaggcagacaagtctcttcacctgtagtctgctgtgctcctccagacatctgt |
| SEQ ID NO: 1105 | TRBV10-2*01-5' | gatgctggaatcacccagagcccaagacagagaattcccctcactctggagtcagtcagacactctgattgtcaccagacatctgtatttctgcgccagatatgttct |
| SEQ ID NO: 1106 | TRBV10-2*01-3' | gctatgtgtctcagatcacccagagcccaagacagagaattccccctcactctggagcacagctcagcagctctggatcgacaagactctgtatttctgcgccagtgagtc |
| SEQ ID NO: 1107 | TRBV10-2*02-5' | aaggcaggtgaccttgatgtgtcccgatggctcagtgctgtctccagatcagagacctgagaacagagaattcccctcactctggagtcagcagtaccgcgtcccagacatctgtg |
| SEQ ID NO: 1108 | TRBV10-2*02-3' | agataaaggagaagtcccgatggctcagtgctgtctccagaacacagagaattccccctcactctggagtcagcagtaccgcgtcccagacatctgtg |
| SEQ ID NO: 1109 | TRBV10-3*01-5' | gatgctggaatcacccagagcccaagacacagagagagattcctcctcactctggagtccgctaccagcagtgactcgtgtactctgtgcatcagtgagtc |
| SEQ ID NO: 1110 | TRBV10-3*01-3' | gctatagtgtctctagatcacccagagcccaagacacagagagagattcctcctcactctggagtccgctaccagcagtgactcgtgtactctgtgcatcagtgagtc |
| SEQ ID NO: 1111 | TRBV10-3*02-5' | gctatgtgtctgaatcacccagagcccaagatcaaagacacagagagacaggagattcctcctcactctgagatgctgcaccagcagtgactgagaaccaccgctatatgtact |
| SEQ ID NO: 1112 | TRBV10-3*02-3' | gctatgtgtctgaatcacccagagcccaagatcaaagacacagagagacaggagattcctcctcactctgagatgtcgcaccagcagtgactgagaaccaccgctatatgtact |
| SEQ ID NO: 1113 | TRBV10-3*03-5' | gatgctggaatcacccagagcccaagacacagagagattcctcctcactctgagatgctcgctaccagcagtgactgagaaccaccgctatatgtact |
| SEQ ID NO: 1114 | TRBV10-3*03-3' | agaagtctcagatgtcagtgtctccagatcaaagacacagagagacaggagattcctcctcactctggagtcgctaccagcagtctgagaaccaccgctatatgtact |
| SEQ ID NO: 1115 | TRBV10-3*04-5' | gatgctggaatcacccagagcccaagacacagagagacaggagattcctcctcactctggagtcgctaccagcagtctgagaaccaccgctacatgtact |
| SEQ ID NO: 1116 | TRBV10-3*04-3' | agaagtctcagatgtcagtgtctccagatcaaagacacagagagacaggagattcctcctcactctggagtcgctaccagcagtctgagaaccaccgctacatgtacttctgt |
| SEQ ID NO: 1117 | TRBV11-1*01-5' | gaagctgaagttcgcagagagaggctgccagtgccccagtgtcccagatataagagtccactccagatcagccagctgatccatttttcggctgcatgctcctgtctgccagcttact |
| SEQ ID NO: 1118 | TRBV11-1*01-3' | gattttctgcagagagaggctgccagtgccccagtgtcccagatataagagtccactccagatcagccagctgatccatttttcggctgcatgctcctgtctgccagcttact |
| SEQ ID NO: 1119 | TRBV11-2*01-5' | gaagctgaagtctgcccagtgtcccagatatagagtccactccagatcagccagctgatccatttttcggctgcatgctcctgtctgccagcttact |
| SEQ ID NO: 1120 | TRBV11-2*01-3' | gatttttctgcagagagaggctgccagtgtcccagatatagagtccactccagatcagccagctgatccatttttcggctgcatgctcctgtctgccagcttact |
| SEQ ID NO: 1121 | TRBV11-2*02-5' | gaagctgaagttgcccagtgtcccagatatagagtccactccagatcagccagctgatccatttttcggctgcatgctcctgtctgccagcttact |
| SEQ ID NO: 1122 | TRBV11-2*02-3' | ggatcgattttctgcagagaggctcaaaggagtgcccagtgtcccagatatagagtccactccagatcagccagctgatccatttttcggctgcgtgtatcctgtgccagagt |
| SEQ ID NO: 1123 | TRBV11-2*03-5' | gaagctgaagtctgcccagtgtcccagatatagagtccactccagatcagccagctgatccatttttcggctgcatgctcctgtctgccagcttact |
| SEQ ID NO: 1124 | TRBV11-2*03-3' | ggatcgattttctgcagagaggctcaaaggagagctcccagtgtcccagatcaacgactctcccaagatcaacctcgtggctgtatcctgtgcagcagc |
| SEQ ID NO: 1125 | TRBV11-3*01-5' | gaagctgaagttcagagagaggctcagtgtcccagatataacgtccactccagatcagccagctgatccatttttcggctgcaatccatttctgtgccaacatacccttact |
| SEQ ID NO: 1126 | TRBV11-3*01-3' | gattttctgcagagagaggctcagtgtcccagatataagagtccactccagatcagccagctgatccatttttcggctgcgtgtatcctgtgccagcagtaga |

TABLE 2.1-continued

| SEQ ID NO | Name | Sequence |
|---|---|---|
| SEQ ID NO: 1127 | TRBV11-3*02-5' | gaagctggagtgtcagtctcccagatataagattatagagaaaagcagcctgtggctttttggtgcaatcctatttctgcaaataccttact |
| SEQ ID NO: 1128 | TRBV11-3*02-3' | ggatcgatttctgcagagaggtcaaaggagtagagactccactctgcagctcaagatccagtccactctgagctgggactcggcctgtatttctgtgccagcagc |
| SEQ ID NO: 1129 | TRBV11-3*03-5' | ggctcccagatataagattatagagaaaagcagcctgtggctttttggtgcaatccaattctggccacataccttactggttctgagaactt |
| SEQ ID NO: 1130 | TRBV11-3*03-3' | ggatcgatttctgcagagaggtcaaaggagtagagactccactctgcagatccagtccagcagctgggactcggcctgcatgtatttctgtgccagcagc |
| SEQ ID NO: 1131 | TRBV12-1*01-5' | gatctgtgtatccagtcaccccaggcacaaagtgacagagatgggacaatcagtactctgagatctgaaccaattcaggccaccatgatcttcct |
| SEQ ID NO: 1132 | TRBV12-1*01-3' | gattctcagcacagatgcctgatgtcaccccactctgaggatgggatccagatggaaccagggactgggcctatattctgtgccagcagcttgc |
| SEQ ID NO: 1133 | TRBV12-2*01-5' | gatctgcattatccagtcaccccaggcacatgagtgtgacagaaatggggacagaaacagtgactactgagagtcgagagcagggactcggcctgtatctgaccttgccaattcctttct |
| SEQ ID NO: 1134 | TRBV12-2*01-3' | gattctcagcacagatgcctgatgtcacccacgaggtgacatcctatctctgaggtgacagaatcagcgctgagagcaggggactcggcctgtatgtctgtcaagtcgcttagc |
| SEQ ID NO: 1135 | TRBV12-3*01-5' | gatctgcagttatccagtcaccccgccatgaggtgacagagatgggacaagaagtgactctgagatgtaaaccaattcaggccaccaactcccttttct |
| SEQ ID NO: 1136 | TRBV12-3*01-3' | gattctcagctaagatgctaatgcatcattctccactctgaagatccagtccactctgagagtgacagaatgggacctcagaaccagtcagctgtgactctgtgccagttagc |
| SEQ ID NO: 1137 | TRBV12-4*01-5' | gatgctgagttatccagtcaccccgccatgaggtgacagagatgcagagatgggacaagaagtgacatctgagatgtaaacaattcagctgtgactctgtgccagttagc |
| SEQ ID NO: 1138 | TRBV12-4*01-3' | gattctcagctaagatgctaatgcatcattctccactctgaagatccagtccactctgagaaccagggactgtaaaccaattcaggacactgactactcttct |
| SEQ ID NO: 1139 | TRBV12-4*02-5' | gatgctgagttatccagtcaccccgccatgaggtgacgagagtgacagagatggacagagatgggacaagaagtgactctgagatgtgagatgactctgagaaccagggactgtcagctcagtcagccaattcaggacactgactactcttct |
| SEQ ID NO: 1140 | TRBV12-4*02-3' | tcgattctcagctcagtctaagatgcctaatgcatcattctccactctgaggactcagctctgacagtactcagctgtgactcttctgtgccagttta |
| SEQ ID NO: 1141 | TRBV12-5*01-5' | gatgctgaagtcagagtcacccgacacacaaggtcacacctttagcaccttgagatcactaatgagagatgggaccactgaagatgtcagcccaatttaggccacaactgtacttggtctctagtcgttct |
| SEQ ID NO: 1142 | TRBV12-5*01-3' | gattctcagcagagagcctgatgcaacttagcactctccaagacatctgatcaaagaaaagagggaaacagcccactctgaaatgctatccctatcccctagacacgacactgtcact |
| SEQ ID NO: 1143 | TRBV13*01-5' | gctgctggagtcatccagtcagttcctccaagcatgactacatctgatcattctgatcagactgaacatgagagcctccttggagctggggactgcagccagtgagctcctgtgccagcagcttagg |
| SEQ ID NO: 1144 | TRBV13*01-3' | gattctcagcaacagttcagtcagttcccccaagacatgactacatctgatcattctgatcagacatttgatcagaatcagcccagtgctatccctagacacgacactgtcagcttatt |
| SEQ ID NO: 1145 | TRBV13*02-5' | gctgctggagtcatccagtcatccagtccccaagcatgactacatctgatcattctgatcagacatttgatcagaatcagccactctgagctctatcctagacacgacactgtcact |
| SEQ ID NO: 1146 | TRBV13*02-3' | tgatcgattctcagctgaactcagttcagtctgactatcattctgactgactacacagttcagtgactatcattctggagctggggactgtactctgtgccagcagc |
| SEQ ID NO: 1147 | TRBV14*01-5' | gaagctggagtctcagtctcccagtctccagcacacgtgggggacgtattctactctgaactgaactatagagaaaggccagagatgtgaccagttctggacatgatatcttatt |
| SEQ ID NO: 1148 | TRBV14*01-3' | gattctagctagctgaaaggactgagggactgtgaaggacaaaccagctgaggtgcagcctgaaggtcagaactgagaagggccagactctgagttatttctgtgaccatgatatcttatt |
| SEQ ID NO: 1149 | TRBV14*02-5' | gaagctggagtcactcagtctcccagcacacagcgcacacagccagctgaggtgcagccgagactgaactgagctgaccatgatgaccatgattgatgaggattctgagatgtgaccatgatatcttatt |
| SEQ ID NO: 1150 | TRBV14*02-3' | caatcgattcttagctgcagtcttgaaaggactggaggacatctgaaggtgcagcctgaagttcagcctgaagaactgaggttgcctcagacttgaacataacgtcatgtact |
| SEQ ID NO: 1151 | TRBV15*01-5' | gatgccatggtcatcagaatccaggaggctgaccacttcttttctgcttcttgatatccgctcaccagtgttggaaagccagttgacccagtgagttgttctcagactttgaaccataacgtcatgtact |
| SEQ ID NO: 1152 | TRBV15*01-3' | acttccaatccaggaggccgaacacttcttttctgcttcttgatatccgctcaccagtgttggaaagccagttgaccccagtgagttgttctcagactttgaaccataacgtcatgtact |

TABLE 2.1-continued

| SEQ ID NO | Name | Sequence |
|---|---|---|
| SEQ ID NO: 1153 | TRBV15*02-5' | gatgccatggtcatccagaaccaagatacccaggttaccagttgaaagccagtgacctgagtgttctcagactttgaaccataacgtcatgtact |
| SEQ ID NO: 1154 | TRBV15*02-3' | ggtgaagaagtcgcccagactccaaaacatctgtcagagggaaggacagaaagcaaaatatattgtgcccaataaaggacaagttatgttttt |
| SEQ ID NO: 1155 | TRBV15*03-5' | gatgccatggtcatccagaaccaagatacccaggttaccagttgaaagccagtgacctgagtgttctcagactttgaaccataacgtcatgtact |
| SEQ ID NO: 1156 | TRBV15*03-3' | tgataacttccaatccaggaggcgcccagactccaaaacatctgtgtttctagacatcgtcagaggggaaggacagaaagcatatattgtgcccaataaaagacacagtatgttttt |
| SEQ ID NO: 1157 | TRBV16*01-5' | ggtgaagaagtcgcccagactccaaaacatctgtcagaggggaaggacagaaagcatatattgtgcccaataaaggacacagtatgttttt |
| SEQ ID NO: 1158 | TRBV16*01-3' | gatttcagctaagtgctctcccagactccccaaatcaccctgtagcctgagatgggaaggacagaagctgagattcaggtgcccaatcagcagtgacctgagcagtgacagagtaggttttt |
| SEQ ID NO: 1159 | TRBV16*02-5' | ggtgaagaagtcgcccagactccaaaacatctgtcagaggggaaggacagaagcaaaatatattgtgcccaataaaggacacagtaggttttt |
| SEQ ID NO: 1160 | TRBV16*02-3' | gatttcagctaagtgctctcccagactccccaaatcaccctgtagcctgagatgggaaggacagaagcaaaatatattgtgcccaataaaagacacagtatgttttt |
| SEQ ID NO: 1161 | TRBV16*03-5' | ggtgaagaagtcgcccagactccccaaatcaccctgtagcctgagatgggaaggacagaagcaaaatatattgtgcccaataaaagacacagtatgttttt |
| SEQ ID NO: 1162 | TRBV16*03-3' | ggaaagattttcagtgagttgctctcccaaatcaccctgtagcctgagatgcaggtacgacctgagatctgaagagctcagcagtgcgatccatctctgtcactgtttgtcact |
| SEQ ID NO: 1163 | TRBV17*01-5' | gagcctggagtcagcagctcagacccccagagaactaacgaactcacacctggtcaggacatgggacaagactgagatgcaagacagtgagccaatgacagtcagcgcccatgatgcagtcatgttact |
| SEQ ID NO: 1164 | TRBV17*01-3' | aacgatcacagctcagcagctcagacccccagagaactaacgaactcacacctggtcaggagacatgggacaagactgagatgcaagacagtcagcgcccatgacaatgatgcagtcatgtttact |
| SEQ ID NO: 1165 | TRBV18*01-5' | aatgccggcatgcagaatgccaagactcaggaggggacaagagccccagcatcctggtcaggagagatgagactgagatgcagccaatgagatgcaagacagtcagcgcccatgacaatgatgcagtcatgttact |
| SEQ ID NO: 1166 | TRBV18*01-3' | gattttctgctgaattcccaaagaggggcccccagactcccaaagtacctgtcagaggagtgtgcaggagatcggcagcagttgtgaacacgacagtttctatctctgtgccagtccaccacc |
| SEQ ID NO: 1167 | TRBV19*01-5' | gatggtgaatcactcagtcctcgggagaagaggaatcctttcctctcactgtcagaaagccaagtaaccgacagttgaccctgagttgtgaacagagtttcatctctgtgccagtgtact |
| SEQ ID NO: 1168 | TRBV19*01-3' | ggtacagcgtctctgggagaagaggaatcctttcctctcactgtcagaaaggaagaaagcacagcagaatgttgaccctgagttgacccgagatttgaacagattcatcctctgtgccagtagtataga |
| SEQ ID NO: 1169 | TRBV19*02-5' | gatggtgaatcactcagtcctcgggagaagaggaatcctttcctctcactgtcagaaaggaagaaagcacagcagaatggccccaaagaaccgacagttgaccctgagttgacccgagatttgaacagattgttgaaccagatgccatgtact |
| SEQ ID NO: 1170 | TRBV19*02-3' | ggtacagcgtctctgggagaagaggaatcctttcctctcactgtcagaaaggaagaaagcacagcagaatggccccaaagaaccgacagttgaccctgagtgaacatgcagatatgcagacagtgatgcagtagtaga |
| SEQ ID NO: 1171 | TRBV19*03-5' | gatggtgaatcactcagtcctcgggagaagaggaatcctttcctctcactgtcagaaaggaagaaagcagcacagagatgtgacatcggcccaaagaaccgacagttgtgaacatgcagatatgaacatgatgcagtagtact |
| SEQ ID NO: 1172 | TRBV19*03-3' | tgaagggtacagcgtctctgggagaagaaggaatcctttcctctactgttcctccctctactgtgacatcggccacagagatgtgaccatggccaaagaaccgacatgctcccgacatgctctatctgtggcagtagc |
| SEQ ID NO: 1173 | TRBV2*01-5' | gaacctgaagtcatccagactcccagcatcccagactccacagatgtgaagatctggtcgtctgtccccatcctcaatcacttatactttcatt |
| SEQ ID NO: 1174 | TRBV2*01-3' | aattctcagttgaaggcctgatgatcaaattcacttcactctgaagatctggtcgtccacaaagctggagactcagcagttctgtgccagtgaagc |
| SEQ ID NO: 1175 | TRBV2*02-5' | gaacctgaagtcatccagactcccagcatcccagactccacagatgtgaagatctggtcgtccacaaagctggagaagtgatcttgacatgtcccatctgtccccatctgtcccatctctaatcacttatactttcatt |
| SEQ ID NO: 1176 | TRBV2*02-3' | tgatcaattctcagttgaaggcctgatgatcaaatttcactctgaagatcggcctgatgatcaaatttcactctgaaagatcggagactcagcagttctgtgccagtgt |
| SEQ ID NO: 1177 | TRBV2*03-5' | gaacctgaagtcatccagactcccagcatcccagactccacagatgtgaagatctggtcgtctgtcccatcctcaatcacttatactttcatt |

TABLE 2.1-continued

| SEQ ID NO | Name | Sequence |
|---|---|---|
| SEQ ID NO: 1178 | TRBV2*03-3' | tcaattctcagttgagaggcctgatggatcaaatttcactctgaagatccggtccacaaagctggagactcagcatgtacttctgtgcagcagtgaa |
| SEQ ID NO: 1179 | TRBV20-1*01-5' | ggtgctgtcgtctctcaacatccgagctggggtatctgtaagagtggaacccctgtgaagatcgagtgccgttccctgaacatcgagttcctgactttcaggccacatatgt |
| SEQ ID NO: 1180 | TRBV20-1*01-3' | acaagttctcatcaaccatgcaagcctgaccctgtccactctgacagtgacagtgccatccctgaagacagcagcttcctggacttctacatctgcagtgctagaga |
| SEQ ID NO: 1181 | TRBV20-1*02-5' | ggtgctgtcgtctctcaacatccgagcaggggtatctgtaagagtggaacccctgtgaagatcgagtgccgttccctgaacatcgagttcctgactttcaggccacaactgt |
| SEQ ID NO: 1182 | TRBV20-1*02-3' | gaaggacaagtttctcatcaaccatgcaagcctgaccctgtccactctgacagtgacagtgccatcctgaagacagcagcttcctggacttctacatctgcagtgct |
| SEQ ID NO: 1183 | TRBV20-1*03-5' | ggtgctgtcgtctctcaacatccgagctggggtatctgtaagagtggaacccctgtgaagatcgagtgccgttccctgaagacagcagcttcctggacttctacatctgcagtgct |
| SEQ ID NO: 1184 | TRBV20-1*03-3' | gaaggacaagtttctcatcaaccatgcgagcaggggtatctgtaagagtggaacccctgtgaagatcgacccatctgacagtgacagtgccatccctgaagacagcagcttctacatctgcagtgct |
| SEQ ID NO: 1185 | TRBV20-1*04-5' | ggtgctgtcgtctctcataacatccgagcaagcctgaccctgtccactctgacagtgacagtgccatccctgaagacagcagcttctacatctgcagtgct |
| SEQ ID NO: 1186 | TRBV20-1*04-3' | ggacaagttctctcatcaaccatgcgagcaagcctgaccctgtccactctgacagtgacagtgccatccctgaagacagcagcttctacatctgcagtgctagt |
| SEQ ID NO: 1187 | TRBV20-1*05-5' | ggtgccgtcgtctctcataacatccgagcaagcctgaccctgtccactctgacagtgacagtgccatccctgaagacagcagcttcctggacttctacatctgcagtgctagt |
| SEQ ID NO: 1188 | TRBV20-1*05-3' | ggtgctgtcgtctctcataacatccaactaaccatgcaagcctgaccctgtccactctgacagtgacagtgccatccctgaagacagcagcttccacatctgcagtgct |
| SEQ ID NO: 1189 | TRBV20-1*06-5' | gaaggacaagtttctcgtctctcaacatccgagcaggggtatctgtaagagtggaacccctgtgaagatcgagtgccgttccctgacagtgacagcagtttctacatctgcagtgct |
| SEQ ID NO: 1190 | TRBV20-1*06-3' | ggtgctgtcgtctctcaacatccgagcaggggtatctgtaagagtggaacccctgtgaagatcgagtgccgttccctgaagacagcagcttctacatctgcagtgct |
| SEQ ID NO: 1191 | TRBV20-1*07-5' | ggacaagttctctcatcaaccatgcgagcaagcctgacccttgtccactctgacagtgacagtgccatccctgaagacagcagcttccacatctgcagtgctagt |
| SEQ ID NO: 1192 | TRBV20-1*07-3' | agtgctgtcgtctctcaacatccgagcaggggtatctgtaagagtggaacatctgtaacatcgagtgccgttccctgaacatcgagtgccgttcctgacttctacatctgcagtgctagt |
| SEQ ID NO: 1193 | TRBV20/OR9-2*01-5' | acaagttcctccatcaaccatccaactaaccatgcaaagcctgaccctccgcgttgtaagagtggaacatctgtaacctcgagttctgcaatcagcagcctcaacatcgcagcctgctagtgctagt |
| SEQ ID NO: 1194 | TRBV20/OR9-2*01-3' | ggtgctgtcgtctctcaacatccgagcaggggtatctgtaagagtggaacccctgtgaagatcgagtgccgttccctgaagacagcagcttctacatctgcagtgct |
| SEQ ID NO: 1195 | TRBV20/OR9-2*02-5' | gaaggacaagtttccccatctccaaaactgactctgtgtaagagtctccgcttcggaacatcgagtgccgttcctgacatctttgaacatcgagtgccatctctgaagacagcagcttctacatctgcagtgct |
| SEQ ID NO: 1196 | TRBV20/OR9-2*02-3' | agtgctgtcgtctctcaacatccgagcaggggtatctgtaagagtggaacatctgtaacctgcgcttgtcaaactggaacatgaacatgaacatgacagcgtccccatccgagtgccgttccctgaagacagcagcttctacatctgcagtgctagaga |
| SEQ ID NO: 1197 | TRBV20/OR9-2*03-3' | acaagttccccatccaactaaccttgacccttctcgtctccgcttcggaacatgaacgcctggatgtgttcctataaaagacactagtttact |
| SEQ ID NO: 1198 | TRBV21-1*01-5' | gacaccaagtcacccagagactctggctcaaaactcatcctggtcaaagcctagactgtgtttctgtccagcagcaagc |
| SEQ ID NO: 1199 | TRBV21-1*01-3' | gattttagccaagtccaatgtccagagactcaccccaatgtccaaagactgagtccctgtattctctataaaagacactagtttact |
| SEQ ID NO: 1200 | TRBV21/OR9-2*01-5' | gacaccaagtcacccagagactcaccccaatgtccagagactcaccccaatgtccagagactcaccccaatgcagcaagc |
| SEQ ID NO: 1201 | TRBV21/OR9-2*01-3' | gattttagccaagtccaatgccccagaatgtccaaagactagtttctgtccaatacattctgttact |
| SEQ ID NO: 1202 | TRBV22-1*01-5' | gatgctgacactatcagatgcattccagctcaactgactttcagccccatgcccccagaatgtccccccagagattgagtccctggagtccaagtgaccaatgacaatgacactagtacgctgctagatagtactagcccagcaagc |
| SEQ ID NO: 1203 | TRBV22-1*01-3' | gatgctgacactatcagatgcattccagctcactgggctcactgggatgtgactgtgatggagtggaaacgtgactctggagtggaaacgaattgagaccaatgactactgct |

TABLE 2.1-continued

| SEQ ID NO | Name | Sequence |
|---|---|---|
| SEQ ID NO: 1204 | TRBV22-1*01-3' | aggctacgtgtctgccaagagagaaggggctattctcttcaggtgaagttggccaccacagcaaacagtttgtattctgtcctggagcgcac |
| SEQ ID NO: 1205 | TRBV22/OR9-2*01-5' | gatgctgacatctatcagacgccattccagctcactgggctgtttctccactgggctggatgtgacctggagtagaaacatttgagacacaatgactgtac |
| SEQ ID NO: 1206 | TRBV22/OR9-2*01-3' | ggctacggtgtctgccgagagagaaggggctgtttctccatgtgaagctggccaccacagcaaacagtctgtattctgtcctggagtgcac |
| SEQ ID NO: 1207 | TRBV23-1*01-5' | catgccaaagtcacacagactcccaagactgttggtcccagcctgcaatcctgtccaaaggaaaaagaacaaagatggatgtaccccgaaaaggacatactttgtttatt |
| SEQ ID NO: 1208 | TRBV23-1*01-3' | gattctcatctcaatgcccagactccaggtatttggtcaaaggaagaaggaaagaacaaagatgtattgtaccccaaaacgacatactttgttgtt |
| SEQ ID NO: 1209 | TRBV23/OR9-2*01-5' | catgccaaagtcacacagactcccaggtatctcatctcaatgcccaagctgcaatcctgtccctgcagctgcacccctgtatctctgt |
| SEQ ID NO: 1210 | TRBV23/OR9-2*01-3' | gatgcacaagaagcgattctcatctcaatgcccaggtatttggtcccaagaatgaaggaagaaagaacaaagatgtattgtaccccaaaaacgactactttgttgttt |
| SEQ ID NO: 1211 | TRBV23/OR9-2*02-5' | catgccaaagtcacacagactcccaggtatttggtcaacaagtctcttcagaatgaacaagtgcacaagaagcgattctcatctcaatgcccaagaacgcaccctgcagctg |
| SEQ ID NO: 1212 | TRBV23/OR9-2*02-3' | gtttttgattctccttcagaatgaacaagtctcttcagaagctgcacaagaagcgattctcatctcaatgcccaagaacgcaccctgcagctg |
| SEQ ID NO: 1213 | TRBV24-1*01-5' | gatgctgatgtaccagaccccaagaatacaggcacaggctaaattctccctgtccgagtctgccatccccaacagactctttacttctgtgccaccagtgattg |
| SEQ ID NO: 1214 | TRBV24-1*01-3' | ataccagtgtctctgacaggcacaggctaaattctccctgtccgagtctgccatccccaacagactcttactctgtgccaccagtgattg |
| SEQ ID NO: 1215 | TRBV24/OR9-2*01-5' | gatgctgatgtctctgacaggcacaggcccaagaatacaggcacaggctaaatctccctgtccgagtctgccatctcgtgccaccagctgtcttacttctgtgccaccagtgaatgtact |
| SEQ ID NO: 1216 | TRBV24/OR9-2*01-3' | atacagtgtctctgacaggcacaggcccaagaatacaggcacaggctaaatctccctgtccgagtctgccatctcgtgccaccagctgtcttacttctgtgccaccagtgattg |
| SEQ ID NO: 1217 | TRBV24/OR9-2*02-5' | gatgctgatgtatccagaccccaagaatacaggcacaggcccaagaatacaggcacaggctgtatcagacaggattatgctggcatgtctcagactaaggtcatgatgaatgact |
| SEQ ID NO: 1218 | TRBV24/OR9-2*02-3' | cagttgatctattgctccttgatgtcaaatataaacaaagagagatctgatggatacagtgtctcttgacagtgaacaggctaaattctccctg |
| SEQ ID NO: 1219 | TRBV24/OR9-2*03-5' | gatgctgatgtatccagaccccaagaatacaggcacaggcccaagaatacaggcacaggctgtatcagacaggattatgctggcatgtctcagactaaggtcatgatgaatgact |
| SEQ ID NO: 1220 | TRBV24/OR9-2*03-3' | agtgtctcttgacacatccagaccccaagaatacaggcacaggctcctgtccctgtgtatagggacaggcaagaagatcactctggaatgttccaaaccatggccatgacaaatgtact |
| SEQ ID NO: 1221 | TRBV25-1*01-5' | gaagctgacatctccagatacgcggagcacacggtgttcctctgaccctggagtctgcaggccctcactacctctgtgccaccctgtgccagtgaata |
| SEQ ID NO: 1222 | TRBV25-1*01-3' | agtcaatagtctccagataaggacggagcacacggtgttcctctgaccctgttataggggcaggcattttccctgaccctgagtctgcaggccctcactacctctgtgccagtgaaatgtat |
| SEQ ID NO: 1223 | TRBV25/OR9-2*01-5' | gaagctgaaatctaccagacacccaagacacggagcacacggtgttagggggcaggaagaagatcactctggaatgttccaaaccatggccatgacacaatgtat |
| SEQ ID NO: 1224 | TRB25/OR9-1*01-3' | agtcaacagtctccagaataaggatacggagcacacggtgtttccctgacctgttagggggcaggaagaagatcactctggaatgttccaaaccatggccatgacacaatgtat |
| SEQ ID NO: 1225 | TRBV25/OR9-2*02-5' | gaagctgaaatctaccagacacccaagacacggagcacacggtgttagggggcaggaagaagatcactctggaatgttccaaaccatggccatgacaaatgtact |
| SEQ ID NO: 1226 | TRBV25/OR9-2*02-3' | gagttaattccagagacacaattccaagacacagaatcattgggacacagaaggaaattcattctacagtgttccccagaataaggataagagcgtttcccctgacctggagtctgcagcccctc |
| SEQ ID NO: 1227 | TRBV26*01-5' | gatgctagtacaagaggagatctttgctctgagtcaacaacattgggacacagaaggaatcattcacagtgttgccagactgttacaatgtact |
| SEQ ID NO: 1228 | TRBV26*01-3' | ggtatcatgttcttgaatactatagcatctttcccctgacctgaagtctgccagcagccaacaacgaacatctgtatctctatgcagcagtcatc |

TABLE 2.1-continued

| SEQ ID NO | Name | Sequence |
|---|---|---|
| SEQ ID NO: 1229 | TRBV26/OR9-2*01-5' | gatgctgtagtacacaattctcaagacacagaatcattgggacaggaaaggaattcattctactgtcccagaatgaatcatgtgcaatgtact |
| SEQ ID NO: 1230 | TRBV26/OR9-2*01-3' | ggtatcatgttcttgaaatactatagcatctttctcctgaccctgaagtcgctagcaccaaccagacatgtgtatcctgcagcagttcatc |
| SEQ ID NO: 1231 | TRBV26/OR9-2*02-5' | gatgctgtagtacacaattctcaagacacagaatcattgggacaggaaaggaattcattctactgtcccagaatgaatcatgtgcaatgtact |
| SEQ ID NO: 1232 | TRBV26/OR9-2*02-3' | ggtatcatgttcttgaaatactatagcatctttctcctgaccctgaagtctgctagcaccagacatgtgtatcctgcagcagtcatc |
| SEQ ID NO: 1233 | TRBV27*01-5' | gaagccaagtgaccagaaccccaagatacctcatcacagtgactgactggaaagaagtaacagtgacttgttctcagaatgaacatgactgtcct |
| SEQ ID NO: 1234 | TRBV27*01-3' | ggtacaaagtctctgagaagaggaggaattcccctgatctagtagaaagaggcccagccagacctgctggttctcaggatgtgtcagttatc |
| SEQ ID NO: 1235 | TRBV28*01-5' | gatgtgaaagtaaccccagagctcgagatatctagtgcaaaaggagagaaagtttctcggaatgtgtccgcagcaccagacatcattgtaccctctggccagcagttgtct |
| SEQ ID NO: 1236 | TRBV28*01-3' | ggtacagtgtcctcagagagaaggagcgctctctcaaaagcccaagcagggatatctgtcaagatgcgcagccagtcaccatgaatatgttct |
| SEQ ID NO: 1237 | TRBV29-1*01-5' | agtgctgtcatctccaaaagccaaagcagcgcccaaaactaaactttcaacctctgactgtgagcaacatgagcctgaacatgaacctgactcaagtgccctgacattatcctgcagccgttgaaga |
| SEQ ID NO: 1238 | TRBV29-1*01-3' | acaagttcccatcagcgcgccaaaagcaaacagggatatctgtcaacttcaactctgactctgaacctgtgagcaacatgagcctgaccgcagtcaagtcaccatgatgttc |
| SEQ ID NO: 1239 | TRBV29-1*02-5' | agtgctgtcatctccaaaagcgcgccaaaactaaacctttcaactctgactgttgagcaacatgagcctgaacatgaactctgactctgaagtcaagccatggattatcctgcagcgttgaa |
| SEQ ID NO: 1240 | TRBV29-1*02-3' | tgacaagttcccatcagccgccaagtagccaagtcacaactaaacattcaactctgactgtgagcaaccaagacctgcagcagcagcaactgacactgactctgcagccggca |
| SEQ ID NO: 1241 | TRBV29-1*03-5' | acgatccagtgcaagtcgatagccgcccaaaactaaacctaaccaagcaggatatcttggtatctgtcaactctgactgtcaacctcagcacaagtcaactgacactgactgcaactgcaaatcagggct |
| SEQ ID NO: 1242 | TRBV29-1*03-3' | tgacaagttcccatcagccgccaagtagccaagtcaggatatcttcaactctgactgtcaacctcagcaactcaacctgtgagcaacctgacctgagaactctgagcagaagcaccaagcaccatgatgttct |
| SEQ ID NO: 1243 | TRBV29/OR9-2*01-5' | agtgctgtcatctccaaaagccgcccaaaagcaggaccaaactaagtaacctcgttatctgtcaactctgactgatcaagtgtcaagtcaagcatcctcctcgcagcgttgaaga |
| SEQ ID NO: 1244 | TRBV29/OR9-2*01-3' | acaagttcccatcagccgccaaaagcaaaccaagcaggatatcgtcaactctgcactgacgtgagacaagcagacctcgagaacagcagcatatcctcgcagcgttgaaga |
| SEQ ID NO: 1245 | TRBV29/OR9-2*02-5' | agtgctgtcatctccaaaagccgcccaaaagcaggcaaaccaagcaggatatcgtcaactctgcactgacgtgagacaagcagacctcagtcaacctgaagcaacatccctcgcagcgttgaaga |
| SEQ ID NO: 1246 | TRBV29/OR9-2*02-3' | acaagttcccatcagccgccaaaagcaggcccaaaactaaacctaaccaagcagcaaaactcctgagcacaaggcagagcagaagcagcatatcctcgcagcgttgaaga |
| SEQ ID NO: 1247 | TRBV3-1*01-5' | gacacagttcccaactgttcccagactctccagacaaagtcatgatgtcacacagtcccaaaactaaatgtgacaagaccaagtccattaaatgtgaacactctcctggcttggtgactctgtattctgtgccatgatgatctattatt |
| SEQ ID NO: 1248 | TRBV3-1*01-3' | gcttctcacctaatctccagacactctccagacaaagtcacttaaatccggttcacacagatgtcacttaaatcttcctggagcttggtgactctgtattctgtgccagcaaga |
| SEQ ID NO: 1249 | TRBV3-1*02-5' | gacacagttcccaactgttcccagactctccagacaaagtcatgatgtcacacagtcccaaaactaaatgtgacaagaccaagtccattaaatgtgaacactcacatcaattcccggagcttggtgactctgtgtattctgtgccagc |
| SEQ ID NO: 1250 | TRBV3-1*02-3' | tccaaatcgatctccagatctccagacactctccagacaaagtcacaccaaagtggtcacactcaacatcaattcttcacatcaattaatcttcacatcattaatcttcctggagcttggtgactctgtgtattctgtgccagc |
| SEQ ID NO: 1251 | TRBV3-2*01-5' | gacacagccgttcccagatctccagactctccagacaaagtcatgatgtcacacagatggtcacacagatggtcattaaatcttcctggagcttggtgactctgtgtattctgtgccagc |
| SEQ ID NO: 1252 | TRBV3-2*01-3' | gcttctcacctgactctccagactctccagacactctccagacaaagtcacttaaatcttcctggagcttggtgactctgtgtattctgtgccagcaaga |
| SEQ ID NO: 1253 | TRBV3-2*02-5' | gacacagccgttcccagatctccagactctccagacaaagtcacactcaaaaataccggttcacacagatggtcacacagatggaaaaagaagtctcttaatgaagaaacaaatctggccataatgctatgtatt |
| SEQ ID NO: 1254 | TRBV3-2*02-3' | gcttctcacctgactctccagactctccagacactctccagacaaagtcattttaaatcttcacatcaattaaatcttcctggagcttggtgtattctgtgccagcaaga |

TABLE 2.1-continued

| SEQ ID NO | Name | Sequence |
|---|---|---|
| SEQ ID NO: 1255 | TRBV3-2*03-5' | gacacagccgttcccagactcccaaaatacctggtcacacagacgggaaaaaaggagtctcttaaatgagacaaaatctgggccataatgctatgtatt |
| SEQ ID NO: 1256 | TRBV3-2*03-3' | tcgcttctcacctgactcctccagacaaagttcatttaaatctcacatcaattccctggagcttggtgactctgtgtattctgtgcagcagccaa |
| SEQ ID NO: 1257 | TRBV30*01-5' | tctcagactattcatcagctccagaccggcagcgacccctggtgcagcctggtgcagcctggtgcactgtggagtgcactgtggaggaacatcaaacccaacctat |
| SEQ ID NO: 1258 | TRBV30*01-3' | agaatctctcagctattatcaatggccagaccggcagcgaccctggtgcagcctggtgcagcctggtgagtgcactgtggaggaacatcaaacccaacctat |
| SEQ ID NO: 1259 | TRBV30*02-5' | tctcagactattatcaatggccagaccggcagcgaccctggtgcagcctggtcatcctgagtctcaagaagtctctctgagtcactgtggtcttctatcctgtggagtgt |
| SEQ ID NO: 1260 | TRBV30*02-3' | agaatctctcagctccagaccggcagcgacccctggtgcagcctggtgcagcctgagtctcaagaagtccctctctgagtgcactgtggaggaacatcaaaccctaactggt |
| SEQ ID NO: 1261 | TRBV30*04-5' | actattcatcaatggccagaccggcagcgacccctggtgcagcctggtgcagcctgagtctctctgagtcctaagaagctcctctcgtgtctatcctgtgcctgagt |
| SEQ ID NO: 1262 | TRBV30*04-3' | ccagaatctctcagctccagaccgccccagaccccagaccctgtgcagcctggtcagtcagtcctcccctgagtcagcctgtgcagcctgttgggagcgaccctgtgagtgcactgtggaggaacatcaaaccccaacctat |
| SEQ ID NO: 1263 | TRBV30*05-5' | tctcagactattcatcagctccagaccgctgtgcagcctggtcagctgtgcagcctggtcatcctgagtcatccctgagttctaagaagctctgcttctatcctgtcctgggga |
| SEQ ID NO: 1264 | TRBV30*05-3' | ccagaatctctcagctccagaccgccccagaccaccagaccctgtgcagcctggtcagcctggtcatcctgagttctcagtgactgacaaataagaagtcttttgaaatgtgaacaacatgggcacaggctatgtatt |
| SEQ ID NO: 1265 | TRBV4-1*01-5' | gacactgagttaccagacaccaaaacacctgtcatgggaatgccccaaacagctctctcttaaacctttgaaatgtgaacaactacacgccctgtatcctcgccagcagcaga |
| SEQ ID NO: 1266 | TRBV4-1*01-3' | gcttctcacctgatgccccaacagctctctcttaaacctttgaaatgtgaacaactacacgccctgtatcctctgccagcagccaaga |
| SEQ ID NO: 1267 | TRBV4-1*02-5' | cacctggtcatgggaatgcagagacacccagcccaatatggggccctgcagccagagactcagctctgcgcatgattggtacaagcagaagctaagaagccac |
| SEQ ID NO: 1268 | TRBV4-1*02-3' | tcgctttctcacctgaatgcagagacacccaagcccaacagctctcacttaaacctcacctatgcctcaacctgtgaaatgtgaacaacctgtatctctgccagcagccaa |
| SEQ ID NO: 1269 | TRBV4-2*01-5' | gaaacggagttacgcagacaccaagacaccagccccaagctctcacttatcctcacttatgcctcaacctgtgggatgacaataagaagtctttgaaatgtgaacaacatcgggcataacgctatgtatt |
| SEQ ID NO: 1270 | TRBV4-2*01-3' | gcttctcacctgaatgcagagacacccaagcccaacagctctcacttatcctcacttatgcctcaacctgtgggatgacaataagaagtctttgaaatgtgaacaacatcgggcctgtatcctctgccatgcagcagaaga |
| SEQ ID NO: 1271 | TRBV4-2*02-5' | gaaacggagttacgcagacaccaagacaccagccccaagctctcacttatcctcacttatgcctcaacctgtgggatgacaataagaagtctttgaaatgtgaacaacatcgggcataacgctaatgtatt |
| SEQ ID NO: 1272 | TRBV4-2*02-3' | aagtcgttctcacctgaatgcagacaccaagacccaagccccaagctctcacttatgcctcacttatgcctcaacctgtgggatgacaataagaagactcggcctgtatcctctgccagcacc |
| SEQ ID NO: 1273 | TRBV4-3*01-5' | gaaacggagttacgcagacaccaagacacccaagcccaagctctcacttatcctcacttatgcctcaacctgtgggatgacaataagaagtctttgaaatgtgaacaacctgtatctctgccagcagccaa |
| SEQ ID NO: 1274 | TRBV4-3*01-3' | gcttctcatctgaatgcagacaccaagacacccaagctctcacttatcctcacttatgcctcaacctgtgggatgacaataagaagtctttgaaatgtgaacaacctgtatctctgccagcagca |
| SEQ ID NO: 1275 | TRBV4-3*02-5' | gaaacggagttacgcagacaccaagacacccaagcccaagctctcacttatcctcacttatgcctcaacctgtgggatgacaataagaagtctttgaaatgtgaacaacatcggccctgtatcctctgccgccagcagc |
| SEQ ID NO: 1276 | TRBV4-3*02-3' | aagtcgttctcacctgaatgcagacaccaagacacccaagctctcacttatcctcacttatgcctcaacctgtggtgatgacaaataagaagtctttgaaagtgaacaacatctggtcataacgctatgtatt |
| SEQ ID NO: 1277 | TRBV4-3*03-5' | gaaacggagttacgcagacaccaagacacccaagctccaagctctcacttatgcctcacttatcctcactatccttccttcaaccctacaccctgagacaaaataagaagtctttgaaagtgaacaacatctggtcataacgctatgtatt |
| SEQ ID NO: 1278 | TRBV4-3*03-3' | aagtcgttctcactgactgcagacaccaagacccaacagctctccttcaactaccctgagtcaccctcgccctgtatctctgccagcagc |
| SEQ ID NO: 1279 | TRBV4-3*04-5' | aagaagtctttgaaatgtgaacaacatctgaacaactctggcataacgctatgtattggtacaagcaaagtgctacaagaagtgctaagaagtgcaaagagctcatgagctgagtcatgtttgtctacagtc |

TABLE 2.1-continued

| SEQ ID NO | Name | Sequence |
|---|---|---|
| SEQ ID NO: 1280 | TRBV4-3*04-3' | aagtcgctctcacctgaatgccccaacagtctcacttattcctcacctacacccctgagccagaagactcggcctgtatcctgcgccagcagc |
| SEQ ID NO: 1281 | TRBV5-1*01-5' | aaggctggaatcactcagggcgccagtcctcaaactcaagatatctgatcaaacgagagagacacagcaagtgacactgagctgctccctcctatctctgggcataggagtgtatcct |
| SEQ ID NO: 1282 | TRBV5-1*01-3' | cgattctcagggcgccagtcctcaaactcaagacatctgatcaaacgagagagacacagcaagtgacacctgagctggggggactcggactgtccccttatcttgccagcagcttgg |
| SEQ ID NO: 1283 | TRBV5-1*02-5' | agggctggggtcactcagtctcaaactcaagacatctgatcaaacgagagagacacagcaagtgacacctgagctgtggggggactggctgccccctatctctgggctaggagtgtatcct |
| SEQ ID NO: 1284 | TRBV5-1*02-3' | tcgattctcagggcgccagtcctcaaactcaagacatctgatcaaacgagagagacacagcaagtgacacctggagctggggggactcggccctatctctttgcgccagcgtgc |
| SEQ ID NO: 1285 | TRBV5-2*01-5' | gaggctggaatcaccaagtcaccagtcctcaagacacctgatcaaacagagacccagcaagtgacactgagctgtcccctgctctgggcataactgtgtcct |
| SEQ ID NO: 1286 | TRBV5-2*01-3' | aactgctatgattctcagctgcaccacgtcctcataactattactgatcaaacacgagagtgacactgagccctagggactcagccctgtatcctgtgccaacttg |
| SEQ ID NO: 1287 | TRBV5-3*01-5' | gaggctggagtcaccaaagtcccacaccctgatcaaacagagagacacagcaagtgacactgagctgtctcctcagtctgggcacaacagtgtcct |
| SEQ ID NO: 1288 | TRBV5-3*01-3' | cgattccagggcgccagtcctccatgactgttgctcgtgagatgaatgtgagagacacagcaagtgcctggagctggggggactcggccctgtatcctgtgccagaagcttgg |
| SEQ ID NO: 1289 | TRBV5-3*02-5' | gaggctggagtcaccaaagtcccacaccctgattaaacgagagacacagcaagtgacactgagctgcctgagctgggggactcggccctgtatcctgtgccagcagtgtcct |
| SEQ ID NO: 1290 | TRBV5-3*02-3' | cgattccagggcgccagtcctcaagtccccacaccctgattattgctctgagatgactgtgagagacacagcaagtgcctggagctggggggactcggccctgtatcctgtgccagaagcttgg |
| SEQ ID NO: 1291 | TRBV5-4*01-5' | gagactggagtcaccaaagtcctcccagtcctccagtcccccaccctgatcaaacgagagacacagcaagtgactgagctgtcttctcagtctgggcacaacactgtgtcct |
| SEQ ID NO: 1292 | TRBV5-4*01-3' | agattctcagtctccagtcctccagtcctcctaatttatagctccacacctgatcaaacgagagacacagcaagtgcctggagctggggactgtcctgagctgtctctgccagcagctgg |
| SEQ ID NO: 1293 | TRBV5-4*02-5' | gagactggagtcaccaaagtcctccagtcctccagtcccccacaccctgatcaaacgagagacacagcaagtgacactgagctgtctcctcagtctgggcacaacactgtgtcct |
| SEQ ID NO: 1294 | TRBV5-4*02-3' | tcctagattctcaggtctccagtctcccagtcctccaatatataactctgagctgaatgtgaacacctgctcctgtacaacagccctggcaggcccgtatccctggagactgtccagagc |
| SEQ ID NO: 1295 | TRBV5-4*03-5' | cagcaagtgacactgagatgctcttctcagtctgggcacaacactgtgctgagctgaatgtgaacgcttgcctgtgaacacggtcaggtccccagttatcttcagtatt |
| SEQ ID NO: 1296 | TRBV5-4*03-3' | tcctagattctcaggtctccagtctcccagtcctccaatatataactctgagctgaatgtgaacgcttgagctggacgacctggagactgtctgagcctgtatcctgtgccagagc |
| SEQ ID NO: 1297 | TRBV5-4*04-5' | actgtgtcctggtaccaacaggccctgaggtccagggcccagttatctttcagtattataaggagaggaagaatgagagagaaactccctcctagat |
| SEQ ID NO: 1298 | TRBV5-4*04-3' | tcctagattctcaggtctccagtcctcccagtcctccagtcctccaatatataactctgagctgaatgtgaacgcttgagctggacgactgtgagactgtatcctgtgccagcagc |
| SEQ ID NO: 1299 | TRBV5-5*01-5' | gacgctggagtcaccaaaagtcccacaccctgatcaaacgagagagacacagcaagtgacactgagtctgagatgtctcctcatctctgggcacaagagtgtcct |
| SEQ ID NO: 1300 | TRBV5-5*01-3' | cgattctcagtctccagtctgccagtcccccaaaagtcccacaccctgatcaaacgagagacacagcaagtgacactgagctgtctcctcatctctgtgccagcagctgg |
| SEQ ID NO: 1301 | TRBV5-5*02-5' | gacgctggagtcaccaaaagtcccacaccctgatcaaacgagagagacacagcaagtgacactgagctgtctcctcatctctgggcacaaagagtgtcct |
| SEQ ID NO: 1302 | TRBV5-5*02-3' | tgatcgattctcagtctcgccagtcccccaaactcccacaccctgatcaaactgagtctgaatgtgaacgccttgttgctggggactgcttctcctatctctgtgccagagc |
| SEQ ID NO: 1303 | TRBV5-5*03-5' | gacgctggagtcatccagtctgccaaagtcccacaccctgatcaaactgagtctgaatgtgaacgccttgactgactgagatgactgcttctcctatctctgagcacaagagtgtcct |
| SEQ ID NO: 1304 | TRBV5-5*03-3' | tgatcgattctcagtctcgccagtcccccaaactcccacaccctgatcaaactgagtctgaatgtgaacgccttgttgctggggactgcttgtgggggactcggccctgtatcctgagcacaagagtgtcct |
| SEQ ID NO: 1305 | TRBV5-6*01-5' | gacgctggagtaccccaaagtcccacaccctgatcaaacgagagacacagcaagtgcaacgccttgagatgaactgagatgactgagatgactgagctgtctcctcccttagtctggggcatgtctggcatgtgacactgtgtcct |

TABLE 2.1-continued

| SEQ ID NO | Name | Sequence |
|---|---|---|
| SEQ ID NO: 1306 | TRBV5-6*01-3' | cgattctcaggtcaccagttccctaactaatagctctgagctgaatgtgaacgccttgttgctggggactggccctatctctgtgccagcagcttgg |
| SEQ ID NO: 1307 | TRBV5-7*01-5' | gatgctggagtcacccaaagtcccacacacctgatcaaaacgagaggacacgtgactctgagatgctgtctccctgatcctgagagcagcagtgtcct |
| SEQ ID NO: 1308 | TRBV5-7*01-3' | caattctcaggtcatcagttccctaactatagctctgagctgaatgtgaacgccttgttgctaggggactcggccctctatctctgtgccagcagtgg |
| SEQ ID NO: 1309 | TRBV5-8*01-5' | gaggctggagtcacacaaagtcccacacacctgatcaaaacgagaggacagcaagccttgagctgaatgtgaacgccttgagctgaatgtgaacgccttgagctgaatgtgaacgccttgagctgaatgtgaacgccttgagctgaatgtgaacgccttgttgctcctcctatctctgtgccaccagtgtact |
| SEQ ID NO: 1310 | TRBV5-8*01-3' | agatttctcaggtcgccagttccctaattatagctctgagctgggcaccacctggcacacagtgtactgtgaacgcctgggtctggcctcagctctccttgg |
| SEQ ID NO: 1311 | TRBV5-8*02-5' | aggacagcaagcgactcagatgctctccatatagctctgactgaatgtgaacgcctggagctgagctggaggactcggccctgtatctctgtgccagcagc |
| SEQ ID NO: 1312 | TRBV5-8*02-3' | tcctagatttcaggtcgccagtccccaattatagctctgactgaatgtgaacgcctggagctgagctgcagactcggccctgtatctctgtgccagcagc |
| SEQ ID NO: 1313 | TRBV6-1*01-5' | aatgctggtgtcactcagaccccaaaattccagtcctgaagacaggacagcacatgacactgcagtgcgtctcccccagacatctgtactctgtgccagcagtgaagc |
| SEQ ID NO: 1314 | TRBV6-1*01-3' | gctacaatgtctccagattaaacaaacggagttctccgggtcctgaagacaggacagcatgacactgcagtgcgtctcccccagacatctgtactctgtgccagcagtgaagc |
| SEQ ID NO: 1315 | TRBV6-2*01-5' | aatgctggtgtcactcagaccccaaaattccagtcctgaagacaggacagcatgacactgcagtgcgtctccccaacatctgtactctgtgccagcagtactc |
| SEQ ID NO: 1316 | TRBV6-2*01-3' | gctacaatgtctccagattaaacaaacagaattcctgggtcctgaagacaggacagcatgacactgcagtgcgtctccccaacatctgtactctgtgccagcagtactc |
| SEQ ID NO: 1317 | TRBV6-2*02-5' | aatgctggtgtcactcagaccccaaaatcccgggtcctgaagacaggacagcatgacactgcagtgcgtcctgtccctcgtactctgtactctgtgccagcagtcatgtact |
| SEQ ID NO: 1318 | TRBV6-2*02-3' | tggctacaatgtctccagattaaaaaacagaattcctgggtcctgaagacaggacagcatgacactgcagtgcgtccctcgtactctgtactctgtgccagccct |
| SEQ ID NO: 1319 | TRBV6-3*01-5' | aatgctggtgtcactcagaccccaaaatccgggtcctgaagacaggacagcatgacactgcagtgcgtgtctccccaacatctgtactctgtgccagcatgtactc |
| SEQ ID NO: 1320 | TRBV6-3*01-3' | gctacaatgtctccagattaaaaaacagaattcctgtgtcctgaagacaggacagcatgacactgcagtgcgtcctgtactctgtactctgtgccagccatgtactc |
| SEQ ID NO: 1321 | TRBV6-4*01-5' | attgctgggatcaccaggcaccacatgatattcccccacgttgcccctcacgttgccagacctggcagacatgacactgcagtgcgtcctgtactctgtgcccagccatgactc |
| SEQ ID NO: 1322 | TRBV6-4*01-3' | gttatagtgtctccagagcaccagcaaacacagatgattccccacgttgccccacgttgccccctcagacatctgtgcagacatgagacactgcagtgcgtcctgtacctctgtgccagcatgactc |
| SEQ ID NO: 1323 | TRBV6-4*02-5' | actgctgggatcaccaggcaccaacatgatgtcctccgatgtgattccccacgttgccccacgttgccagatcctggcagagccagcatgacactgcagtgcgtcctgtactctgtgccagccatgactc |
| SEQ ID NO: 1324 | TRBV6-4*02-3' | gttatagtgtctccagagcaccagcaaacacagatgattccccacgttgccccacgttgccagatcctggcagagccagcatgacactgcagtgcgtcctgtactctgtgccagcatgactc |
| SEQ ID NO: 1325 | TRBV6-4*02-5' | aatgctggtgtcactcagaccccaaaattccgggtcctgaagacaggacagcatgacactgcagtgcgtgtctccccaacatctgtactctgtgccagtcct |
| SEQ ID NO: 1326 | TRBV6-4*01-5' | gctacaatgtctccagatcaacaacagaggattttccgcatctgaagatcagtgcgtacctgtactctgtgccagcagtactc |
| SEQ ID NO: 1327 | TRBV6-6*01-5' | aatgctggtgtcactcagaccccaaaattccgcatcaacaacagaggattttccgcatctgaagatcagtgcgtgcagtgcgtccccccagacactctgtgactctgtgccagccataactcatgtact |
| SEQ ID NO: 1328 | TRBV6-6*01-3' | gctacaacgtctccagatcaacaacagaggattttccgcatcctgaagatcagtgcgtggcctcagttggctcgtactctgtgccagcataactcatgtact |
| SEQ ID NO: 1329 | TRBV6-6*02-5' | aatgctggtgtcactcagaccccaaaattccgcatcctgaagatcagtgcgtggcctcagttggctcgtactctgtgccagcataactcatgtact |
| SEQ ID NO: 1330 | TRBV6-6*02-3' | gaatggctcacaacgtcccagatcaaccacagaggatttccgctcaggctgagttcagttggctcgtactctgtacttcttgtgccagcagt |

TABLE 2.1-continued

| SEQ ID NO | Name | Sequence |
|---|---|---|
| SEQ ID NO: 1331 | TRBV6-6*03-5' | aatgctggtgtcactcagaccccaaaattccgcatcctgaagataggacagagcatgacactgcagtgtgcccaggatatgaacaataactacatgtact |
| SEQ ID NO: 1332 | TRBV6-6*03-3' | gaatggctacaacgtctccagatcaaccacagaggattcccgtcaggctggagtaggacagagcatgacactctggagctggtctgtgtacttctgtgccagagt |
| SEQ ID NO: 1333 | TRBV6-6*04-5' | aatgctggtgtcactcagaccccaaaattccgcatcctgaagataggacagagcatgacactgtacctctgtgcccaggatatgaacaatacatgtact |
| SEQ ID NO: 1334 | TRBV6-6*04-3' | tggctacaatgtctccagatcaaccacagaggattcccgtcaggctggagtaggacagagcatcttgtgccagacatctgtgtactctgtgcagcagtcga |
| SEQ ID NO: 1335 | TRBV6-6*05-5' | aatgctggtgtcactcagaccccaaaattccgcatcctgaagataggacagagcatgcagtgtgccccagatatgaaccataactacatgtact |
| SEQ ID NO: 1336 | TRBV6-6*05-3' | gaatggctacaacgtctccagatcaaccacagaggattcccgtcaggctggagtaggacagagcatgacactctgtgtgccaggatgaaccatgtatc |
| SEQ ID NO: 1337 | TRBV6-7*01-5' | aatgctggtgtcactcagaccccaaaatccacgtgtgagagcatgacagagcatcagctgctctccctcaagctggagtctgttacttctgtgccagtactc |
| SEQ ID NO: 1338 | TRBV6-7*01-3' | gctacaatgtctccagatcaaacacagaggattcccactcagtgtgcggctgttgcggctgtgagacatctgtgtactgtgccagtactc |
| SEQ ID NO: 1339 | TRBV6-8*01-5' | aatgctggtgtcactcagaccccaaaatccacatcctgaagacactcaggctggcctcgagaccagagcagctgctccctcagactcgttctccctcagactgtctgcggatgatatgtcct |
| SEQ ID NO: 1340 | TRBV6-8*01-3' | gctacaatgtcctctagattaaacacagaggattcccactcagtgtgcggctgttgcggctggtgctcagagacatctgtgtactgtgcagtactc |
| SEQ ID NO: 1341 | TRBV6-9*01-5' | aatgctggtgtcactcagaccccaaaatccacatcctgaagacacagaggctggagtcaggctggagtcagctgcctcccagagacatctgtatactctgtgccagtactgtcct |
| SEQ ID NO: 1342 | TRBV6-9*01-3' | gctacaatgtatccagatcaaacacagaggattcccgctcctgagactcgagctcagctgcctcccagagacatctgtatactctgtgccagtattc |
| SEQ ID NO: 1343 | TRBV7-1*01-5' | ggtgctggagtctccccagtccctgagacacaaggtagctagcctcagatataatgatccaattcaggtctctgcggggactgcggggactgctcagtctgtgtatctctgtgccagctttatt |
| SEQ ID NO: 1344 | TRBV7-1*01-3' | ggttctctgcacagaggctgagggatccatccaccctgaagtctcagccgcacataagcaggggactgctgctgctgatccaattcaggtgtgtatctctgtgccagcagc |
| SEQ ID NO: 1345 | TRBV7-2*01-5' | ggagctggagtctccccagtcccccagtaacaaggtcacagaggaaaggatccagcgcacacagaggatgtagagctcagctgtgtgatccaattcaggtgtactcgtgccagcttact |
| SEQ ID NO: 1346 | TRBV7-2*01-3' | gcttctctgcagagaggactgggagtccccagtaacaaggtcctccaccctgacgatccagccgcacacagaggatgtagagctcagctgtgtatccaattcaggtctcgtgccagcttagc |
| SEQ ID NO: 1347 | TRBV7-2*02-5' | ggagctggagtctccccagtcccccagtaacaaggtcctccaccctgacgatccagccgcacacagaggatgtagagctcagctgtgtatccaattcaggtgatccatactgcccttact |
| SEQ ID NO: 1348 | TRBV7-2*02-3' | gcttctctgcagagaggactgggagtccccagtaacaaggtccgctccaccctgacgatccagccgcacacagaggatgtagagctcagctgtgtatccaattcaggtctcgtgccagcttagc |
| SEQ ID NO: 1349 | TRBV7-702*03-5' | ggagctggagtctccccagtcccccagtaacaaggtcctccaccctgacgaaggaaaggatccagccgcacacagaggatgtgtagagctcagctgtgtgatccaattcaggtgatccatactgcccttact |
| SEQ ID NO: 1350 | TRBV7-2*03-3' | gcttctctgcagagaggactgggaatccccagtaacaaggtcctccaccctgacgatccagcgcacacagaggaaaggatccagccgcacacagagagctcagctgtgtatccaattcaggtctcgtaccagcttagc |
| SEQ ID NO: 1351 | TRBV7-2*04-5' | ggagctggagtttccccagaggactgggaatccccagtaacaaggtccacagaggaaaggatccagccgcacacagaggatgtagagctcagctgtgtgatccaattcaggtctcatactgcccttact |
| SEQ ID NO: 1352 | TRBV7-702*04-3' | tcgcttctctgcagagaggactgggggactgggacacccccagaccccagacccagaccccagtaacaaggtccgctccaccctgacgatccagcgcacacagaggatgtgagagcagggactgtgtcctatctcaggtctcagctgtatctctgtgccgtagctta |
| SEQ ID NO: 1353 | TRBV7-3*01-5' | ggtgctggagtctccccagacccagaccccagcaacagaccgctccaccctgacgatccagccgcacagacagaccgggaaaatatgagagctcagctgtgtatccaattcaggtctcatactgccctttact |
| SEQ ID NO: 1354 | TRBV7-3*01-3' | ggtcttttgcagtcaggccctgaggcctgaccacccccagacgcctgtctcagctctttgatcaacaggctcgtctactctgaggatcaccagccgtgtgtgatcctgaagatccagcggggactcagccgtgtatctctgtgccagcagctggggactcagccgtgtatctctgtgccagcagcta... |

(Sequences 1353-1356 continue similarly; content extremely dense and some portions unclear)

TABLE 2.1-continued

| SEQ ID NO | Name | Sequence |
|---|---|---|
| SEQ ID NO: 1357 | TRBV7-3*03-5' | ggtgctggagtctcccagacccccagtaacaaggtcacagagaaggaaaaagatgtagagctcaggtgtgatccaattcaggtcatactgcctttact |
| SEQ ID NO: 1358 | TRBV7-3*03-3' | ggttctttgcagtcaggcctgagggatcccagtaacaaggtcacagagaaggaaaatatgtagagctcaggtgtgatccaattcaggtcatactgcctttact |
| SEQ ID NO: 1359 | TRBV7-3*04-5' | ggtgctggagtctcccagacccccagtaacaaggtcacagagaaggaaaatatgtagagctcaggtgtgatccaattcaggtcatactgcctttact |
| SEQ ID NO: 1360 | TRBV7-3*04-3' | cgatcggttctttgcagtgtgatccaattcaggtcatactgcctttactgtgagatccgtctctcactctgaagatcagcacagagccttgcgcgtatcctgtgccagca |
| SEQ ID NO: 1361 | TRBV7-3*05-5' | tgggagtcaggtgtgatccaattcaggtcatactgcctttactgtgagatcagcacagagccttgggcagggcacagagagcgggggactgggactcttcctgtgccagca |
| SEQ ID NO: 1362 | TRBV7-3*05-3' | tgatcggttctttgcagtcaggcctgagggatccgtctctactctgaagatcagcacagagagggggactgggactgtagctcgccaggtgtgatccaattcggtcatcctgtgccagcagc |
| SEQ ID NO: 1363 | TRBV7-4*01-5' | ggtgctggagtctcccagtcccccaaggtacgaaagtcgcaaagagggacgggattgtagctcgccaggtgtgatccaattcggtcatgtatcctctgtgccagtcagt |
| SEQ ID NO: 1364 | TRBV7-4*01-3' | ggttctctgcagagaggcctgagtctcccaaggtacgaaagtcgcaaagagggacgggactgtagctcgccaggtgtgatccaattcggtcatgtatcctctgtgccagtcagt |
| SEQ ID NO: 1365 | TRBV7-4*02-5' | ggtgctggagtctcccccagttctccccaaggtacgaaagtcgcaaagaggacgggatgtagctcgctctccactcagttgtgatccaattcggtcatgtatcctctgtgccagtcaccttatt |
| SEQ ID NO: 1366 | TRBV7-4*02-3' | aacgagacaaatcagggcgggtcctccagtcctcccaaggtacgaaagtcgtctctgcagagatgctgagatcgtctgtatccaattcggtcaggtaaccttatt |
| SEQ ID NO: 1367 | TRBV7-5*01-5' | ggtgctggagtctcccagtcggcccccagtcctcccaaggtacgaagtcacacagagcctgagagtcacacagatcagcgtgatccaattcggtcaggtaaccttatt |
| SEQ ID NO: 1368 | TRBV7-5*01-3' | tcattctccacagagaggtctgaggatcttctcccacctgaagtcacacagagcctgactcggctgtagctcccaattcggtgtatcctctgtgccagagctag |
| SEQ ID NO: 1369 | TRBV7-5*02-5' | ggtgctggagtctcccagtctcccaagtctgaggatctctccaagcctgaagatccagagagggacactccagcgccacagagcgtgatccaattcggtgtatcctctgtgccagagctag |
| SEQ ID NO: 1370 | TRBV7-5*02-3' | caattctccacagagaggtctgaggatctccccaagtctgaggatcttctcccacctgaagatccagcgccacagaggtaagggcgactcagcgctatgctcagtgtatctctgtgcagagctagc |
| SEQ ID NO: 1371 | TRBV7-6*01-5' | ggtgctggagtctcccagtctcccaagtctcccaggtacaagagggacatccagcgatccagcgacagcgcacagaggcaggatgtagctctcaggtgtgatccaattcggtcatgtatcccttatt |
| SEQ ID NO: 1372 | TRBV7-6*01-3' | ggttctctgcagagaggcctgagtctcccaggtacaagagggacgatccagcgagcgacagcgcacagaggcaggatgtagctctcaggtgtgatccaattcggtcatgtatccgtgccagcagc |
| SEQ ID NO: 1373 | TRBV7-6*02-5' | ggtgctggagtctcccagtctcccaagtctcccaggtacaaagaggggacgatccagcgagcgacagcgcacagaggcaggatgtagctctcaggtgtgatccaattcggtcatgtatccttatt |
| SEQ ID NO: 1374 | TRBV7-6*02-3' | tgatcggttctctgcagagaggcctgagtctcccccaggtacaaagaggggacgatccactctgacgatccagcgacagcgcacagaggcacggatgtgagctcggccacatgtatccgtgtgccagcagc |
| SEQ ID NO: 1375 | TRBV7-7*01-5' | ggtgctggagtctcccagtctcccaagtctcccaggtacaaagaggggacgatccactctgatgatccagcgacagcgcacagaggcacggatgtaactctccaattcgagtcatgcaaccttatt |
| SEQ ID NO: 1376 | TRBV7-7*01-3' | ggttctctgcagagaggcctgagtctcccaggtacaaagaggggacgatccactctgatgatccagcgacagcgcacagaggcacggatgtactctccaggtgtgatcccaattcggtcatgtatgccagcagc |
| SEQ ID NO: 1377 | TRBV7-7*02-5' | ggtgctggagtctcccagtctcccaagtctcccaggtacaaagaggggacgatccactctgatgatccagcgacagcgcacagaggcacggatgtaactctccaggtgtgatcgtgaagtcatgtaaccttatt |
| SEQ ID NO: 1378 | TRBV7-7*02-3' | tgatcggttctctgcagaaggcctgagtctcccccaggtacaaagaggggacgatccactctgacgatcagcgacagcgcacagaggcacggactcagcgtatcgcctgtccagcagc |
| SEQ ID NO: 1379 | TRBV7-8*01-5' | ggtgctggagtctctctgcagaaaggctgagtctcccccagtaggtacaaagatgcgaaagaggcgatcctccactctgatgctctccaggtgtgatcaattcgggtcatgtatccctttt |
| SEQ ID NO: 1380 | TRBV7-8*01-3' | gcttctctgcagaaaggctgagtctcccccagtaggtacaaagatgcgaaagaggcgatcctccactctgaagatccagcgccacacagaggagaccccgcgtgtatcctctgtgccagcagc |
| SEQ ID NO: 1381 | TRBV7-8*02-5' | ggtgctggagtctcccagtctcccccagtaggtacaaagatgcgaaagaggcgatcctccactctgaagatccagcgccacacagaggagaccccgcgtgtatcctctgtgccagcagc |

TABLE 2.1-continued

| SEQ ID NO | Name | Sequence |
|---|---|---|
| SEQ ID NO: 1382 | TRBV7-8*02-3' | gctctcttgcagaaaggctctgagggatccgtctccactctgaagatccagcgcacacagaaggactccgcgtgtatctctgtgccagcagcttagc |
| SEQ ID NO: 1383 | TRBV7-8*03-5' | ggtgctggagtctcccagtccccagtacaaagtcgcaaagtgcaaggacaggagatcagctctcaggtgtgatccaattcggtgtcatgtatcccttttt |
| SEQ ID NO: 1384 | TRBV7-8*03-3' | tcgcttctttgcagaaaggctgagggatccgtctccactctgaagatccagagcacacagcaggaggacacacagcacacagaggagactccgcgtgtatctctgtgcagcagcga |
| SEQ ID NO: 1385 | TRBV7-9*01-5' | gatactggagtctcccagaaccccagtacaaagtcacaaagatcacaagatcagcgcacacagaagatccagagcacacagaggggacagatgtaactttcaggtgtgatccaattctgaacacaaccgccttatt |
| SEQ ID NO: 1386 | TRBV7-9*01-3' | ggtctctcgagagagtctcccagaaccctaagggatctttctccacctgaagatcacaagatcagcgcacacagaggggacagatgtaacttcaggtgtgatccaattctgaacacaaccgccttagc |
| SEQ ID NO: 1387 | TRBV7-9*02-5' | gatactggagtctcccagaaccccagtacaaagtcacaaagatcacaagatcagcgcacacagaagatccagagcacacagaggggacagatgtaacttcaggtgtgatccaattctgaacacaaccgccttatt |
| SEQ ID NO: 1388 | TRBV7-9*02-3' | tcggttctctgagagaggcctaagggatctttctccacctgaagatcacaagatcagcgcacacagaggggacagatgtaacttcaggtgtgatccaattctgaacacaaccgccttagc |
| SEQ ID NO: 1389 | TRBV7-9*03-5' | gatactggagtctcccagaaccccagtacaaagtcacaaagatcacaagatcagcgcacacagaagatccagagcacacagaggggacagatgtaacttcaggtgtgatccaattctgaacacaaccgccttatt |
| SEQ ID NO: 1390 | TRBV7-9*03-3' | tgatcggttctctgcagagaggccttgagagtctttcccacctggagatccagcgcacagaggggacagcagatcggccatgtatctctgtgccagagc |
| SEQ ID NO: 1391 | TRBV7-9*04-5' | atatctggagtctcccacaacccagaatcacaagatctttctccacctgaagatcacaagatcagcgcacacagaggggacagatgtaactttcaggtgtgatccaattctgaacacacgccttatt |
| SEQ ID NO: 1392 | TRBV7-9*04-3' | tcggatctctgcagagaggcctaagggatctttctccacctggagatcacaagatcagcgcacacagaggggacagatgtaacttcaggtgtgatccaatgtctctgtgcagcagctct |
| SEQ ID NO: 1393 | TRBV7-9*05-5' | gatactggagtctcccagaaccccagtacaaagtcacaaagatcacaagatcagcgcacacagaggggacagatgtaacttcaggtgtgatccaattctgaacacaccgccttatt |
| SEQ ID NO: 1394 | TRBV7-9*05-3' | tcggttctctgcagagaggccttgagagtctttcccacctggagatccagcgcacagaggggacagcagatcggccatgtatctctgtgcagcaccaaaa |
| SEQ ID NO: 1395 | TRBV7-9*06-5' | gatactggagtctcccagaaccccagtacaaagtcacaaagatcacaagatcagcgcacacagaggggacagatgtaacttcaggtgtgatccaattctgaacacaaaccgccttatt |
| SEQ ID NO: 1396 | TRBV7-9*06-3' | tcggttctctgcagagtcttattgtaccgacagaccctgggcagggccccagagttctgacttactccagaatgaagctcaactagaaaatcaaggctgtgtg |
| SEQ ID NO: 1397 | TRBV7-9*07-5' | cacaaccgcttattgtgtcttctgcagagaggccccaagggatctttctccacctgaagatccagcagggaactccagcgcacagaggagggggactccgcgcacatgtatctctgtgcagcagcagcgtgctca |
| SEQ ID NO: 1398 | TRBV7-9*07-3' | gtctctctgcagagagttcagcagaccagatatccaaggagatccagcgcacagaggggacagatgtaacatctgaattgtcagttagagaccataggcagtgttctgtt |
| SEQ ID NO: 1399 | TRBV8-1*01-5' | gaggcagggatcagcagatctctggaaacaagctcaagatcattccctcaacctgagtgttactagcaccagcagacctcctgtaccttgtggcagtcatc |
| SEQ ID NO: 1400 | TRBV8-1*01-3' | ggaagggtacaatgtcaccagggtgaaaagtcagcgcaaatcatttgtcagaagaaagatgatcctggaatgtgctcagttagcaacagtgtctgatatcgacag |
| SEQ ID NO: 1401 | TRBV8-2*01-5' | gatgctggatcaccagaggcgaagatcagcagatctccctcaacctgagttgctcactgtaccgaccactacctactctgggaatgtgctcagttagcaacactgtctgatatcgacag |
| SEQ ID NO: 1402 | TRBV8-2*01-3' | agaggggtactctgtgttcttgaaacagccccaaaagacacctgagcattccccaatcctgaatcagcaccaccccagacgcatcctgagctctcccccagtctgagcctgtatttctgtgccagcacacag |
| SEQ ID NO: 1403 | TRBV9*01-5' | gattctggagtcacacaaaaccccaaagtcacctgactgtccctgacttgcactctgaactaaaccctgatcagcaacacctgagctctccccagtctgagctctgtgagcctctctgtact |
| SEQ ID NO: 1404 | TRBV9*01-3' | cgattctccgcacacaaaacagttcctgacttgcactctgaactaaaccctgatcagcaacacctgagctctccccagtctgagctctgtgagcctctctgtact |
| SEQ ID NO: 1405 | TRBV9*02-5' | gattctggagtcacacaaaaccccaaagtcacctgactgtccctgacttgcactctgaactaaaccctgatcagcaacacctgagctctccccagtctgagctctgtgagcctctctgtact |
| SEQ ID NO: 1406 | TRBV9*02-3' | cgattctccgcacacaaaacagttcctgacttgcactctgaactaaaccctgatcagcaacactgagctctccccagtctgagctctgtgagcctctctgtagt |
| SEQ ID NO: 1407 | TRBV9*03-5' | gattctggagtcacacaaaaccccaaagtcacctgactgtccctgacttgcactctgaactaaaccctgatcagcaacacctgagctctccccagtctgagctctgtgagcctctctgtact |

TABLE 2.1-continued

| SEQ ID NO | Name | Sequence |
|---|---|---|
| SEQ ID NO: 1408 | TRBV9*03-3' | tgaatgattctccgcataacagttccctgacttgcactgcactgaactaaactgagctcctggagctggggactcagctttgtattctgtgccagagc |
| SEQ ID NO: 1409 | TRBVA*01-5' | gaagctgaagccacctagactctaagcacctgattgcagagacaggaaaggagttctcaagataagtgccaagattcatactggttcacaagaatc |
| SEQ ID NO: 1410 | TRBVA*01-3' | tccctattgaaaatattcctgcaaaaaatagaagttctctttggctcgaaatctgcaactcaggtgtccctgcctgtaccgtcactc |
| SEQ ID NO: 1411 | TRBVA/OR9-2*01-5' | gaagtcaagtcacctagactccccgcaaaaatagcacacctgattgcagagacaggaaaggagttctcaaatctgccaggatatgtgccataattcatactggttctacaagatc |
| SEQ ID NO: 1412 | TRBVA/OR9-2*01-3' | tccctgttgaaaatattcccgcaaaaacagaagttccctttggctctgaaatctgcaaagccctttcagatgtccctgtccctgtgccgtcactc |
| SEQ ID NO: 1413 | TRBVB*01-5' | aatgtcaaagtaacacagacccctgagcagcagcccctgagatgaggcaggaaagttgtatcggaaagtgtttcagatactatcaaccagaccaaaacgtctctgaatccataagatcc |
| SEQ ID NO: 1414 | TRBVB*01-3' | gactctgagacccctcgagcagcagcctatcagtgcagccacatcctctcctggagtcagccgatatgacaaacccaggttgaagcgacctaacctatgagcc |
| SEQ ID NO: 1415 | TRBVC*01-5' | agtgactctaaattggtctatgaagaagcccagtcatcagtaagaagccgcccattcctggagtcgccagtccagacctctctgtacattgcaccagcagttatccacagt |
| SEQ ID NO: 1416 | TRDV1*01-5' | gcccagaaggttactcaagccagtcatcagtatccgtcgcctaaccattcagccttacaagagatcagcctgctcatgaacaagtacttgtgtctctggggact |
| SEQ ID NO: 1417 | TRDV1*01-3' | atctctgccaacttgagtgtgcctgaacaacaaacagtccgtccgtctgctggtgtcatcatcatgcaccatcagcaagtgaaggtcttactactgcctgtgacacc |
| SEQ ID NO: 1418 | TRDV2*01-5' | gccattgagtgacattgataatgcctgaaaaccggtcctgctgtactcactttaagatactcgccactcaataggatcgtgactaagatacttgccagcaagaggaaggtcctactactgcctgtgaca |
| SEQ ID NO: 1419 | TRDV2*01-3' | tttccaaggtgacattgatatgtgcctgaacaaccggtcctgctgtcaaagaaccttcacttgcaccatcagaagatgaaggctcttactactgcctgtgacacc |
| SEQ ID NO: 1420 | TRDV2*02-5' | attgagttggtgcctgaacattgatattgcctgaaaaccagtgcctgctgtcaaagaaccggtcctgctgtcaaagaacagtgctctactactgcctgtgaca |
| SEQ ID NO: 1421 | TRDV2*02-3' | aatttccaaggtgacattgatatgtgcctgaacaaccagtgcctgactcaagaaccttcacttgcaccatcagaagagatgaaggtcttactactgcctgtgaca |
| SEQ ID NO: 1422 | TRDV2*03-5' | gccattgagtggtgcctgaacaacaacagtcctgctgtcaatagggtgtcaatagggtcctgcacccctcaggtgtcctcaggagaagcgatcggtaactact |
| SEQ ID NO: 1423 | TRDV2*03-3' | tttccaaggtgacattgatatgtgcctgaacaaccggtcctgctgtactactaagataatactgcaagtacttaagatactcgtcacttcgccacactgtatattcaaatccagatt |
| SEQ ID NO: 1424 | TRDV3*01-5' | tgtgacaaagtactgacactggaacaccagtcccccgacagagtggcgagtggcagtgatctccaagtgagacagtgccacttactacttgccttag |
| SEQ ID NO: 1425 | TRDV3*01-3' | gacggtttctgtgaaacacattctgacccggaacacagtcccccgacagagtggcgagtggtcagtgaggtgtactgctcactacgacactgtatattcaaatctgccttag |
| SEQ ID NO: 1426 | TRDV3*02-5' | tgtgacaaagtaaccagtgtccccggaacacagtcccccgacagagtggcgagtggtcagtgaggtgtactgctcactacgacactgtatattcaaatccagatt |
| SEQ ID NO: 1427 | TRDV3*02-3' | gacggtttctgtgaaacaccattctgacccggaacacagtcccccgacagagtggcgagtggtcagtgaggtgtactgctcactacgacactgccacttactacttgccttag |
| SEQ ID NO: 1428 | TRGV1*01-5' | tcttccaactgaaggtgaacagaagtcagtcaccagtcgatgatcttcctgaggcaagtacttatcatcc |
| SEQ ID NO: 1429 | TRGV1*01-3' | aaagtatgacactgaaggtgaacagaagtgagcacaaggagcatgcagctgatcctgtgcaaatcaattaaaaatctggttctcattactgtgccacctggacagg |
| SEQ ID NO: 1430 | TRGV10*01-5' | ttatcaaagttgacactggagcagttccagtccagctctccagtttccacttcccatttccaatcctcaatcctaccaagtgacaactggccatctgccttttag |
| SEQ ID NO: 1431 | TRGV10*01-3' | aggcaagaaagattctcaaactccagtccagctctccagtcatgaaacagttccagccatccaccaagtccgtttactacttgctgtcctgaagatagtatcggagcacaaggctgctggtggc |
| SEQ ID NO: 1432 | TRGV10*02-5' | ttatcaaagttgacactggagcagttccagtccagctctccagtcatgaaacagttccagccatccaccaagtccgtttactacttgcaagatagcgaaacagatg |

TABLE 2.1-continued

| SEQ ID NO | Name | Sequence |
|---|---|---|
| SEQ ID NO: 1433 | TRGV10*02-3' | tgaggcaagaagaattctcaactcccacttcaatcctaccatcaagtccgtagagaagaagacatggccgttactactgtgctgcgtggatta |
| SEQ ID NO: 1434 | TRGV11*01-5' | cttgggcagttggaacaacctgacacttccactccacttgaaatatctattccagacagcagcaaataagttccgaggcatccatccaaggcttagcagtaaaa |
| SEQ ID NO: 1435 | TRGV11*01-3' | ggtaagtaaaatgctcacacttccactccactttgaaatatctattccagacagcagcaaataagttcttagagaagaagatgagtggtgtaccactgtgcctgtggattaggcac |
| SEQ ID NO: 1436 | TRGV11*02-5' | cttgggcagttggaacaacctgacacttccactccactttgaaatatctattccagacagcagcaaataagttcttagagaagaagatgagtggtgtaccactgtgcctgtggcttagcagtaaaa |
| SEQ ID NO: 1437 | TRGV11*02-3' | gataagtaaaatgctcacacttccactccactttgaaatatctattccagacagcagcaaataagttcttagagaagaagatgagtggtgtaccactgtgcctgtggattaggcac |
| SEQ ID NO: 1438 | TRGV2*01-5' | tcttccaacttggaagggagaacgaagtcagtcacttgactgaatcactgtgaactcttgaaatcactgtgtcatcctcgtgaaatcaacctttgaaatcagtgaaatcaatgactctgggtctattactgtgcacctgtacatcc |
| SEQ ID NO: 1439 | TRGV2*01-3' | gtattatctacgcaagcacaaggaacaacttgagattgatactgcaggcagtcatcaggcagtcatcatcaggaactgcgaactgagactgactctgggtctattactgtgcaactcttcctacatcc |
| SEQ ID NO: 1440 | TRGV2*02-5' | tcttccaacttggaagggagaacgaagtcagtcacttgactgaatcactgtgaactcttgaaatcactgtgtcatcctcgtgaaatcaacctttgaaatcagtgaaatcaatgactctgggtctattactgtgcacctgtacatcc |
| SEQ ID NO: 1441 | TRGV2*02-3' | gaagtattatctacgcaagcacaaggaacaacttgagattgatactgcaggcagtcatcaggcagtcatcatcaggaactgcgaactgagactgactctgggtctattactgtgccacctgggac |
| SEQ ID NO: 1442 | TRGV3*01-5' | tcttccaacttcatacaccaggaggtgagctgaagtcagtcgagctgagactgcaggcagtcaaaatctaattgaaatgattctgaaatcactgtgctgatcctctgatcttactgtgtaacaataccttctacatcc |
| SEQ ID NO: 1443 | TRGV3*01-3' | gtattatctacgcaaccaggaggtgagctgaagtcagtcgagctgagactgcaggcagtcgatattgagactgcaggcagtcaaaatctaattgaaatgattctgaaatcactgtgctgatcctctgatcttactgtgtaacaataccttctacatcc |
| SEQ ID NO: 1444 | TRGV3*02-5' | tcttccaacttcatacaccaggaggtgagctgaagtcagtcgagctgagactgcaggcagtcgatattgagactgcaggcagtcaaaatctaattgaaatgattctgaaatcactgtgctgatcctctgatcttactgtgtaacaataccttctacatcc |
| SEQ ID NO: 1445 | TRGV3*02-3' | agtattactactgcaaggagaaccaggaggtgagctgaagtcagtcgagctgagactgcaggcagtcgatattgagactgcaggcagtcaaaatctaattgaaatgattctcggagtctgatcttgctgaaggaagtaccgtcacctggacagg |
| SEQ ID NO: 1446 | TRGV4*01-5' | tcttccaacttggaagggagaacgaagtcagtcacttgactgaatcactgtggaatcatcgtgaaatcactgtgctgaaatcactgtgctgaaatcttattgaaatgactgactcgtagtctgatcttgctgaaggaagtaccgtcacctgggatggg |
| SEQ ID NO: 1447 | TRGV4*01-3' | gtatgatactggaagggagaacgaagtcagtcacttgactgaatcactgtggaatcatcgtgaaatcactgtgctgaaatcactgtgctgaaatcttattgaaatgactgactcgtagtctgatcttgctgaaggaagtaccgtcacctgggatggg |
| SEQ ID NO: 1448 | TRGV4*02-5' | tcttccaacttggaagggagaacgaagtcagtcacttgactgaatcactgtggaatcatcgtgaaatcactgtgctgaaatcactgtgctgaaatcttattgaaatgactgactcgtagtctgatcttgctgaaggaagtaccgtcacctgggatggg |
| SEQ ID NO: 1449 | TRGV4*02-3' | gtatgatactggaagggagaacgaagtcagtcacttgactgaatcactgtggaatcatcgtgaaatcactgtgctgaaatcactgtgctgaaatcttattgaaatgactgactcgtagtctgatcttgctgaaggaagtaccgtcacctgggatggg |
| SEQ ID NO: 1450 | TRGV5*01-5' | tcttccaacttcatacaccccaggaggtgagatgaagtcagtcacttgactgaatcactgtggaatcatcaggccagatcactgtgctgaaatcactgtgctgaaatcttattgaaatgactgactcgtgacctactgtaataatgcctctacatcc |
| SEQ ID NO: 1451 | TRGV5*01-3' | gtattactactgcaaggagaatcaggaggtgagatgaagtcagtcacttgactgaatcactgtggaatcatcaggccagatcactgtgctgaaatcactgtgctgaaatcttattgaaatgactgactcgtgacctactgtaataatgcctctacatcc |
| SEQ ID NO: 1452 | TRGV5P*01-5' | tcttccaacttggaagggagaatcaggaggtgagatgaagtcagtcacttgactgaatcactgtggaattgactgtggaatgactgaaatcactgtgctgaaatcactgtgctgaaatcttattgaaatgactgactcgtgacctactgtaataatgcctctacatcc |
| SEQ ID NO: 1453 | TRGV5P*01-3' | gtattactactgcaaggagaatcaggaggtgagatgaagtcagtcacttgactgaatcactgtggaattgactgtggaatgactgaaatcactgtgctgaaatcactgtgctgaaatcttattgaaatgactgactcgtgacctactgtaataatgcctctacatcc |
| SEQ ID NO: 1454 | TRGV5P*02-5' | tcttccaacttggaagggagaatcaggaggtgagatgaagtcagtcacttgactgaatcactgtggaattgactgtggaatgactgaaatcactgtgctgaaatcactgtgctgaaatcttattgaaatgactgactcgtgacctactgtaataatgcctctacatcc |
| SEQ ID NO: 1455 | TRGV5P*02-3' | gtattactactgcaaggagaatcaggaggtgagatgaagtcagtcacttgactgaatcactgtggaattgactgtggaatgactgaaatgactgaaatgactgaaatgactgaaatgattctattgaaatgactgactcgtgacctactgtaataatgcctctacatcc |
| SEQ ID NO: 1456 | TRGV6*01-5' | tctactaacttggaagcgaaagcaggaggtaatcaggaggtaaaagtcaggcaccaggcgaaaataaaagtcaggcaccaggcgaaatttatacctccaaactaaaatgaaaatgaaaatgcctgggttattactgtgatcttcctgtagaaatgccttctacatcc |
| SEQ ID NO: 1457 | TRGV6*01-3' | gcatgacttatggaagcgaaaataaagtcaggcaccaggcgaaatttatacctccaaactaaaatgaaaatgcctgggttattactgtgatcttcctgtagaaatgccacactaggacagg |
| SEQ ID NO: 1458 | TRGV6*02-5' | tctactaacttggaagcgaaaataaagtcaggcaccaggcgaaatggggtcatctgctgctgtaatcaactaaaactgaaaatgccttgctctgtgatctctgggttattactgtgctagaaatgccttctacatcc |

TABLE 2.1-continued

| SEQ ID NO | Name | Sequence |
|---|---|---|
| SEQ ID NO: 1459 | TRGV6*02-3' | gcatgatgacttatgaagtagaaggataagctggaaatttacctccaaaacctaaatgcctctgggctctattactgtgccacctaggacagg |
| SEQ ID NO: 1460 | TRGV7*01-5' | tcttccaacttgcaaggagaggaaggaagtcagtcagtgagctggaaattgatactgcaaatctaattcaaatgattctgatcttactgtccacctggacagg |
| SEQ ID NO: 1461 | TRGV7*01-3' | atatttacttatgcaagcatgaggaggagctggaaattgatactgcaaatctaattgtactgcaaatctaattcaaatgattctgatcttactgtccacctggacagg |
| SEQ ID NO: 1462 | TRGV8*01-5' | tcttccaacttgaaggagaggaacaaagtcagtcaggccaactggtcaccaggccttaaattatactgaaattgaacgtgatcatcactgtgatcttcctgtagaaaatgccgctacaccc |
| SEQ ID NO: 1463 | TRGV8*01-3' | gtatcatacttatgcaagcagcacagggaagagccttaaattatactgaaattgaacgtgatcatcactgtgatcttcctgtagaaaatgccgctacaccc |
| SEQ ID NO: 1464 | TRGV9*01-5' | gcaggtcacctagagcacctcaaattccagtactcagtcagtaaaacgctgtcaaaaacagccctgtcaaaatgacaatgtagagaaacaggacatagctactactgtgccttgtggaataacaattctgcaacat |
| SEQ ID NO: 1465 | TRGV9*01-3' | tgaggtggataggataccctgaaacgtctacatcctccactctcaaattccagtactcagtcagtaaaacgctgtcaaaaacagccctgtcaaaatgacaatgtagagaaacaggacatagctactactgtccttgtgggagtg |
| SEQ ID NO: 1466 | TRGV9*02-5' | gcaggtcacctagagcacctcaaattccagtactcagtcagtaaaacgctgtcaaaaacagccctgtcaaaatgacaatgtagagaaacaggacatagctactactgtgctgatgtctggaataaattctgcaacat |
| SEQ ID NO: 1467 | TRGV9*02-3' | tgaggtggataggataccctgaaacgtctacatcctccactctcaaattccagtactcagtcagtaaaacgctgtcaaaaacagccctgtcaaaatgacaatgtagagaaacaggacatagctactactgtgctgatgtctgggagtg |
| SEQ ID NO: 1468 | TRGVA*01-5' | ctcatcaggccggagcagctgccatgtcgcccatgtcctgcactgtctgtctatctggcagtactgatgaagctggagacagcagccagggcatcagcagggcatgactactgcacaacctgggcctg |
| SEQ ID NO: 1469 | TRGVA*01-3' | agataaaatcatagccaaggatggcagcagtctatctggcagtactgatgaagctggagacagcagccagggcatcagcagggcatgactactgtgtgtcacaacctgaagacttgtaaata |
| SEQ ID NO: 1470 | TRGVB*01-5' | tttaaagcaataaaaatgtcaactacatttttgtcaacagagcaacagataaaactgtctaggtatctgtgtggtgtccactgaagacttgtaaata |
| SEQ ID NO: 1471 | TRGVB*01-3' | cttgaggcaagaacacgggcatgtagtaaagtcaacaatttcaaatgtcactcagtcttcaatgtccagtgtgaaaggaaccagagttccactcttctcccgtacgtctgccatgccca |
| SEQ ID NO: 1472 | TRAJ1*01 | aatagagacacggggcatgatgatactcacggaggaggagaaacaaactcaccttgggacaggcgaattcgggacaggggactatgctccttcctagtctccccaggctacgatgtgaccccatcccc |
| SEQ ID NO: 1473 | TRAJ10*01 | gaggcatcaaacactgtgatactcacggaggaggagaaacaaactcaccttgggacaggcgaattcgggacaggggactatgctccttcctagtctccccaggctacgatgtgaccccatcccc |
| SEQ ID NO: 1474 | TRAJ11*01 | tatgggattttgctatagtgtgaattcaggatacagcagtctaggatacagcagtctcttctagtctccaggtacagtcaggctggaaattgaccccatccc |
| SEQ ID NO: 1475 | TRAJ12*01 | actgactaagaacactgtggattgatggatagcagtgtataaattgatcttcgggagtgggaccagactgctggtcaggcctggtaagtaaggtcagagag |
| SEQ ID NO: 1476 | TRAJ13*01 | aagcaggcattacagtgtcagtgtcatcgggtgaattctggggtaccagaaagtgaattgaactggagacaagatcatcagtgaacctgtaagtgagtccaattccatg |
| SEQ ID NO: 1477 | TRAJ13*02 | aaaggcaggcattacagtgtcagtgtcatcgggtgaattctggggtaccagaaagtcatcatccttggagtgggaagaggaaccaccttatcagtgagtccaagtaggcaatatgtcactaa |
| SEQ ID NO: 1478 | TRAJ14*01 | tttgtcaggcagctgatctgtgttgattatgacacattcatctttggagtgggaagaggaaccaccttatcagtgagtccagtaggcaatatgtcactaa |
| SEQ ID NO: 1479 | TRAJ15*01 | cagggcctcattcactgtcgccaaccaggcaggcaggcaggcaggaactgctctgatctttgatctttggagtgggaagaggaaccactctatcagtgagttccagtaagtccagtaccgataattatt |
| SEQ ID NO: 1480 | TRAJ15*02 | cagggcctcattcactgtcgccaaccaggcaggcaggcaggcaggaactgctctgatctttgatctttggagtgggaagaggaaccactctatcagtgagttccagtaagtccagtaccgataattatt |
| SEQ ID NO: 1481 | TRAJ16*01 | tgtacaatagatcactgtgggttttcagatgccagaagctgtcagaagctgtcagaagtcctcttgcaaggggaaccatgttaaggtggatcttagtaaggttattactaatga |
| SEQ ID NO: 1482 | TRAJ17*01 | cctgtggttttgctgggcttaaatcattgtgatcaaagctgaggcaggcaacaagctaactttggaggagaacaagctaacttgggaggagaacaagtaactttgtagttaaaccagtga |
| SEQ ID NO: 1483 | TRAJ18*01 | agggacacagcattgtgccgacagaggctaccaccctgggaagtgctatacttggaagagaacaagttcagtgaactcagtgagtgctgctcggcctgtcggcctggtgagtcgcttc |

TABLE 2.1-continued

| SEQ ID NO | Name | Sequence |
|---|---|---|
| SEQ ID NO: 1484 | TRAJ19*01 | tttgcagaggacagatggctatcaaagatttacaagattcacctttggaagggatccaaacataagtcactccaagtaagtgagcagccttttgt |
| SEQ ID NO: 1485 | TRAJ2*01 | tggtgtcacctacgctgtatgaatactggaggaacaattgataaactcacattgggaaaggacccatgtattcatctattatcttggtagtcatcccaggtg |
| SEQ ID NO: 1486 | TRAJ20*01 | tgtaggcgacctcgcactgtggttctaacgactacaagctcagcttgactttggagccgatcggcacagtaactaccacagtaagcaagtaagaaagtcca |
| SEQ ID NO: 1487 | TRAJ21*01 | tgtaatgccaataaacatgtgtactgtacaacttcaacaaatttactttgctacttggatctgggaccaaactcaatgtaaaaccaagtaagtatagttgcctagaaga |
| SEQ ID NO: 1488 | TRAJ22*01 | gttgagcaaatcatagtgtttctctgttctgtcaaggcaactgaccttggatctcggacaatggagttatctgtgaaacccagtgttttacctgtaggctgctcaattaaa |
| SEQ ID NO: 1489 | TRAJ23*01 | aggatatgtaacacagtgtgattataacaggaggaaagctatctcggacacaggagaaagctatcttcggacagggaacgagctatctgtgaaatgtatc |
| SEQ ID NO: 1490 | TRAJ23*02 | gactggatgtgttttgacaggatatgtaacacagtgtgatttataaccagggaaaatcgagttgagcaggaccaggtgtggtcaccccagttaagccatcctggagc |
| SEQ ID NO: 1491 | TRAJ24*01 | gaggtgtttgtcacagtgtgacaactgacagtgggggaaattcgagttggagcagtgaccaggttgagtgaggaccaggttgtgtcaccccagtaagccagttcccgga |
| SEQ ID NO: 1492 | TRAJ24*02 | gaggtgtttgtcacagtgtgacaactgacagtgggggaaattcgagttggagcagtgaccaggttgagtgaggaccaggttgtgtcaccccagtaagccaccttccctgga |
| SEQ ID NO: 1493 | TRAJ25*01 | atgctgagataatcactgagaaggacaaggctctccttatctttggaagggacaaagctgcttgtcaagccaagtaagtgacatataatttat |
| SEQ ID NO: 1494 | TRAJ26*01 | ctgagcccagaaacactgtggggataactgtaacaccaatgcaggcaaatcaacttttgtcttgtcccggaaccagatgtccgtgctgtcccctgtccaagtaagtacagtaagtggag |
| SEQ ID NO: 1495 | TRAJ27*01 | caatagcactaagactgtgtaacactgtctgggatgggcaaatcaactctgcactacgtcactcgtgaagccaagtaagtgttgtcttcttgc |
| SEQ ID NO: 1496 | TRAJ28*01 | agaaaggaaactctgtgcatatcctgggctgggagttaccaacttcaccttcggagagtggacacacaaactctcggtcatacaagtaagttcttcttctg |
| SEQ ID NO: 1497 | TRAJ29*01 | ttatggaggaaatcactgtgggaattcaggaaacacacacctctgtcttttggaaagggcacagagctcacaagactttctgtcgattgcaagtaagtgttctagccatcc |
| SEQ ID NO: 1498 | TRAJ3*01 | aaagacttacccacagtggggggtacagcagtgctgaaattctttggatcaaggaccagcaggagaccacgactcatatctcccccagtaagtgctgttatgtgattt |
| SEQ ID NO: 1499 | TRAJ30*01 | gttatgtcccaatcacagtgtgaacaagtgaacagagatgacaagatgccagatacaacatgtggaatctcatgtgttggaagccccagtcagctgcagtaagtgccatgttttattga |
| SEQ ID NO: 1500 | TRAJ31*01 | agtaaagcgagcattgtgatgtgtgaattatgggtgtgaattatgggtgctactacaaacagtctctctttgggactgtcagctgcactctgttgaactacgtaagtaagtggcca |
| SEQ ID NO: 1501 | TRAJ32*01 | ggctctgaaggactgtgtgaattatggggtgtactacaagcttggcaaacacaagtaatcttcttgaactggatctcagcctgcactctgcttgctgtcgcaagtacgtaagtagtggca |
| SEQ ID NO: 1502 | TRAJ32*02 | gtgattcagccacctacctctgtgccgatggtggtactacaactatcagttacaccaagctaatcggggcgctgggaccaagtaagtcaggtaagtgcctgtgtctcagccaaataatccagaaccc |
| SEQ ID NO: 1503 | TRAJ33*01 | gttaaggttttttgtgtctgtggatagcaactactactgtcttataaccaccgacaagctcatcttttgggactgggacagttaaagccaggtaagtcaggtaagtgtcagagagtgactg |
| SEQ ID NO: 1504 | TRAJ34*01 | aggttttttgtagatctcagtactccactgtggataggcttgggaatgtgctgcattgcgggtccggcactcaagtgatgttttaccacgtaagtatctttctcatt |
| SEQ ID NO: 1505 | TRAJ35*01 | taaaagaatgagccattgtgaaactgtcaaactggggcaaacaccctctcttgggactgaacgagactccacgtattcctgtaagtcctaagtcctgaca |
| SEQ ID NO: 1506 | TRAJ36*01 | tactgggcagaaacactgtgtcaaactggggtctcgcaacacaggcaaacaatcttcttgggcaaggacaactaaccaggtaggtaggtctggatgtttcca |
| SEQ ID NO: 1507 | TRAJ37*01 | aaagtacagcattagagtggtgtctctgcctctgcaacacaggcaaactaatcttggcaaggacaactatcttaccaagtaaaacaggtaggtaggacttaccaagatccagaac |
| SEQ ID NO: 1508 | TRAJ37*02 | ctcagccgtgtacttctgtgctcttcatgctctagcaacacaaccgaagctgattgggggacaagctggaacaagcctggcagtcttgggcagtcttcgtgtaact |
| SEQ ID NO: 1509 | TRAJ38*01 | aaagcttctatgactgtaatgctggcaacaaccgcaagctgattgggggattgggaacaagcctggcagaatccgagtgagtcttcgtgtaact |

TABLE 2.1-continued

| SEQ ID NO | Name | Sequence |
|---|---|---|
| SEQ ID NO: 1510 | TRAJ39*01 | cagccgaagatcactgtgtgaataatgcaggcaacatgctcacctttggaggggaacaaggttaatgtcaaacccgtgagtatctctgctgaat |
| SEQ ID NO: 1511 | TRAJ4*01 | aagcaccatctgattgtgttttctgtggtggctacaataagctgattttgagctggacaggaccagctggctgtacacccatgtgagtgaccctgcaag |
| SEQ ID NO: 1512 | TRAJ40*01 | tatgttggttatgtagagacacataacactgtgactaccctcaggaacctacaaatacatctttggaacaggcacccaggctgaaggtttagcaagt |
| SEQ ID NO: 1513 | TRAJ41*01 | ttagggagaacgactgtgaatcaaattccggtatgcacttcggcaaggagctgtcact caggaaaactctcatctttgaaacaggggtcacaccccgtgtgtcacacccgtgagttttgtggtttac |
| SEQ ID NO: 1514 | TRAJ42*01 | agccccataggactgtgtgaattatgggaaggaagccaaggaaatctcatctttgagacagggacccagatgacatgcgcttggagcagggacagagtagagcacaaactcctgtgtcaaaccaagtaagttggggaatgggtcaat |
| SEQ ID NO: 1515 | TRAJ43*01 | tgttaagcatgtattactgtgacaataacaatgactaccggcactcaggtaaataccggcactccacctgggactgaacaagacttcagtcagtcggt |
| SEQ ID NO: 1516 | TRAJ44*01 | agtttctgttagaagcatctcacagtgtaaataccggcactccacctgggactgaacaagacttcagtcagtcggt |
| SEQ ID NO: 1517 | TRAJ45*01 | agggttggcccagagtgtattcaggaggagtgctgacgatgcggagacaaagcagcggagacagtgacttcttgggaccctgattttgtcaaaggacccggggaccaatctgtttgcagtatgtcctgtgagtaagtcgtgagcagaaagt |
| SEQ ID NO: 1518 | TRAJ46*01 | aagctgcctgacagccgtgagagaaaagcacgcggagaacaaattggtctcttggcgcaggaaccattctgagagtcaagtcctgtgagtctatatccagaaccctgacctg |
| SEQ ID NO: 1519 | TRAJ47*01 | gtagaggagttgacgtgtgtggaatatggaaacaagtgtcttggccaggaaccattctgagagtcaagtcctgtgagtctatatccagaaccctgacctg |
| SEQ ID NO: 1520 | TRAJ47*01 | gtgtactattgacatctccggcctgtatctaacttggaatggaatgagaaataaccagtcttatcttgggacaggggagacaagtttgacgtgcattcaccatcatccaagtaagtcaacaagtcctcatcatcctggg |
| SEQ ID NO: 1521 | TRAJ48*01 | atgactagaacactgtgtatcttggaaccggtaacgtccctacgacagtgacgggcaggagcattcactttgggacaggagcaagttgacggtcattccaagtaagtcaacaagtaagtaccaaactaggc |
| SEQ ID NO: 1522 | TRAJ48*01 | tgtgagcttcctatcacagtggagcctgtgtgaaaactcctacgacagtatggagaagcatgagaaataaactgcaatctaaactgactgcatttgactgtcctcaagtaagtgccctggggtgct |
| SEQ ID NO: 1523 | TRAJ5*01 | tactgtgatgtccatcacagtggctgctgtgaccagggagcgtgacagtgtactagctagtagcaactataaactgcaattggaaaggagatgacattgacaagtgacgcatctcttaaccgtgaatccaagtaagttgaaggagt |
| SEQ ID NO: 1524 | TRAJ50*01 | aaactccctgagtgcaggtgctgtaatgctgagaatgagagtgacaccgtggtaatgctgagaatgagagtcgtgacagtgtactagctagtagcacctggctgtattgccggaagaaccaccggagctagcaccttcaaggattgaaggggagtaagctctgaatccaagtaagttgaaggagt |
| SEQ ID NO: 1525 | TRAJ51*01 | gcctcagtgcagtgctgtgagaatagtgaggtgtacatatactgcaactataaactgcattggaaaggaccatctcttaaccgtgaatccaagtaagtcacaagtaagttgagggagt |
| SEQ ID NO: 1526 | TRAJ52*01 | agccttctgtgctgctgtgtgtaattcagggagcctgcaagtgctcttcaggttgcctgattgcccaagaagtggctgtattgccggaagaaccaccggagctagcaccttcaaggactgactactactactactactcaaccgtactatcaaccaagtaagtgacaggggtgaag |
| SEQ ID NO: 1527 | TRAJ53*01 | taaagcctcgtcgtgctgtgtaattcaggagcctgtaatctgcctccgttgggaaagtgctgaagctgacattggaaaagggagcattgacgaatgggaagaaggaaatgagaaatcgaaactgactggaagcttggaaaaggaaatcaactctcgagtgttagaccagtgacaggggtgaag |
| SEQ ID NO: 1528 | TRAJ54*01 | gaggatggatccctgtcagtgacaagtgctgtgatcgcaagtcctgtgatcgcaagtctccctgtcagtgacaagtgctgtgatgactacaaaatataacctcgagtgttagaccagtgacaggggtgaag |
| SEQ ID NO: 1529 | TRAJ55*01 | agatcctcgtcattgttcattgtttactgagccaatagtaagctgacattgaaaaggaaaaggaatataatcaactcgagtgttagaccagtgtatgttttaatgaatgtt |
| SEQ ID NO: 1530 | TRAJ56*01 | aagcagctgtgtggggtgtaactcagggtgatctgaaaagctgtcttgaaaaggaatgtgaagaaaaggaatgtgaagaaaaggaacaaaagtgacacagtaaaccatgaaactgaataatcgaatattgctt |
| SEQ ID NO: 1531 | TRAJ57*01 | aagccccacagcagtgtttaagaaacacagtggctcaggttgctgacctgttggaagaaaggacagtggctctggaatattggaagaaaaggaaggaacacagctcacagtgatcctgtaagtctcctgtaagtctcttggagaggagcatt |
| SEQ ID NO: 1532 | TRAJ58*01 | atgtaaaggcagcccctgtaagtgcagcccctgtgggaaggaagaaattacatttggaattggaacacggagtatacctactacctggaggagggacaagag |
| SEQ ID NO: 1533 | TRAJ59*01 | atgtaaaggcagcccctgtaagtgcagcccctgtgggaaggaagaaattacatttggaattggaacacggagtatacctactacctggaggagggacaagag |
| SEQ ID NO: 1534 | TRAJ6*01 | caggtttatcaaggctgtcctcactgtgtcatcaggaggaagctacatacattgttcatccgtgtaagt |

TABLE 2.1-continued

| SEQ ID NO | Name | Sequence |
|---|---|---|
| SEQ ID NO: 1535 | TRAJ60*01 | gtaaagggctggcactatgtgaagatcacctagatgtcaacttggaaggggactgagtaattgtgagcctggtgagtacctcaactccagagg |
| SEQ ID NO: 1536 | TRAJ61*01 | taaaggtgcccactcctgtgggtaatacagactgacattggagctcagaaactcatgaaactcagccagcaagtaatattggcagaa |
| SEQ ID NO: 1537 | TRAJ7*01 | tgtaatacacttacacagtgactgactatggaacagactcgcttttgggaagggaaccaagtggtcatccaagtaagtgagctggatcctcc |
| SEQ ID NO: 1538 | TRAJ8*01 | tacagagttatgtcagagtgtgaacacaggcttcagaaactgtattggaactgacctgacaggcaagtaagtcaaatctgcagaa |
| SEQ ID NO: 1539 | TRAJ9*01 | cgcagtgcaaatcactgctgggaaatactggaggcttcaaaactatcttggacaggcaggaactatgttaaagcaagtaagtccatgaaataacc |
| SEQ ID NO: 1540 | TRBJ1-1*01 | tttcacctgacccctgtcactgtgaactgtgaagctcttcttggacaagtgtcaggtaggtaagacatttcaggtctttgc |
| SEQ ID NO: 1541 | TRBJ1-2*01 | tttagagtggcatattcttatgtgctaactactgctcggaaactcactgtatattggagagggaagttggctcactgtgtagtgagtaagcaggtctcaggagggg |
| SEQ ID NO: 1542 | TRBJ1-3*01 | tttgaagtggcctgagcctgtgctctggaagctgaaacaccatatcttggagaggggaagttggctcactgtggctcactgtggctcactgtgactggacagct |
| SEQ ID NO: 1543 | TRBJ1-4*01 | tccttccagtcttaatgtgtgcaactaatgaaaaactgttttggaaccaggtcgcagtggaactggaatggatggtatgtaaagactctttcggat |
| SEQ ID NO: 1544 | TRBJ1-5*01 | tttgcccactcatgatgcactgtagcaatcagcccagcatttggtgatgactccacttggtgatgggaatggcagaatcagggtggta |
| SEQ ID NO: 1545 | TRBJ1-6*01 | ttatctaagcctctgcagctgtgcactgtgctgctctgctctataattcaccctccactttggaatggaacggacaggcttggggtccactcttgactc |
| SEQ ID NO: 1546 | TRBJ1-6*02 | ttatctaagcctctgcagctgtgctgctctgctctataatccaccctccactttggaatggaacggacaggcttggggtcagcagtatggggtatgggctcactcttgactc |
| SEQ ID NO: 1547 | TRBJ2-1*01 | tctgggcagccccttccactgtctcctacaatgagcagtctcctcgggcagttgaggagcggagacacggctctaggctgcgaccggaccccccagtaggtctcaggtggag |
| SEQ ID NO: 1548 | TRBJ2-2*01 | tgcgccaggtgcccaggtgcccaggggctgcgaacacccggagacaggagctgtttttcggggacttcggggctgtggctgggctgcggtggtgggctgcgga |
| SEQ ID NO: 1549 | TRBJ2-2P*01 | agctgcccactctgagagggctgtgtgctgagcacagatacgcagatattggcccaggccccggaccggtccagtgctcagtcagtaagcggggcgatgggctccag |
| SEQ ID NO: 1550 | TRBJ2-3*01 | ttttgtcctgggcgcgtccggggctcggggctgtgagcaaacattcagtactcggcgctccacttggcccaaggccccggtccgtgctccggtgggtaagcggggtcggggagccg |
| SEQ ID NO: 1551 | TRBJ2-4*01 | tcctgtgcgcgtcccggggctcggggctgtgggggccgtgacagaccaagagaccccaaggagcacccggagccgtccaggccagcaggggcaggagccggcgtgtgccggtgtgcggggcgggg |
| SEQ ID NO: 1552 | TRBJ2-5*01 | tttgtcgcggggtcccccaggggctcccccggagctgtgctctcgggcagccgagacactttcggacagcacagcggtctcacaggtgagattcggggcgtctcccaccttc |
| SEQ ID NO: 1553 | TRBJ2-6*01 | tgcggggagtccccggggtgcacctcgtgctccgtgctcctagacagtagtgagaccccaacgtcctagagtactcggacttcggggccccggccccggccccggaccccggccggtcacaggtcacagggtggttcggggaccacaccgg |
| SEQ ID NO: 1554 | TRBJ2-7*01 | tttgcatgcggggtgcacctcaagtgccgtgaccccgtgctcctagacagtagtgaggagccgataaactcatccttgaccaggtcaccggtcacagggtcacagcggccaccaggtcaccaggtcaccggtcacagggttcggggcgtctccccacttc |
| SEQ ID NO: 1555 | TRBJ2-7*02 | tttgcatgcggggatgcgacctcaagtgcctgtgacaccgataaactcatccttgataccacaactcatcgtgactggaaccaagtgaaccaggtaactcattattctga |
| SEQ ID NO: 1556 | TRDJ1*01 | ttttggaactgtcctcaagctctgtgtgacaccgataaactcatccttgatagcacaactcatccttgatagcacaactcatcgtgaacaactggaaagggaacaactcatcggaaccaggtgaaccaggtgaaccaggtaactcattatctga |
| SEQ ID NO: 1557 | TRDJ2*01 | ttttctcttaatgactgtcataatgctctgtcctgggacaccgacagtgttcttcggacactggcatcaaactcttcgtgagccgtgagtgatcttttcctat |
| SEQ ID NO: 1558 | TRDJ3*01 | tgaggcactgtcatatgctctgggacaccgacagtgttttcggacactggcatcaaactcttcgtgagccgtgagtgatcttttcctat |
| SEQ ID NO: 1559 | TRDJ4*01 | atgagacatacaaaaagtaatgccgccccagaacccctgatcttggcaaaggaacctatctggaggtacaacaac |
| SEQ ID NO: 1560 | TRGJ1*01 | tttttgatgactgaatcactgtggaattattataagaaactctttggcagtggaacaactctttggcagtggaacaactctttggcagtatcgaagaatacaacatt |

TABLE 2.1-continued

| SEQ ID NO | Name | Sequence |
|---|---|---|
| SEQ ID NO: 1561 | TRGJ1*02 | tactgtgccttgtgggaggtgcttattataagaaactctttggcagtggaacaacacttgttgtcacaggt |
| SEQ ID NO: 1562 | TRGJ2*01 | tttgatatggactgaatcactgtggaattattataagaaactctttggcagtggaacaacactgttgtcacaggtaagtaagtatcgaagaatacaacatt |
| SEQ ID NO: 1563 | TRGJP*01 | ataaaggcttctcagtggtgggcaagagtgggcaaaaaatcaaggtatttggtcccggaacaaagcttatcattacacaggtaagttttctttaaattt |
| SEQ ID NO: 1564 | TRGJP1*01 | gatttttctagaagcttagaccggtggtgataccactggttggtcaagatatttgctgaagggactaagctcatagtaacttcacctggtaagt |
| SEQ ID NO: 1565 | TRGJP2*01 | gattttgtagaagcttagaccagtgatgatagtgattgatcaagacgtttgcaaaaggactaggctcatagtaacttcgcctggtaagt |

TABLE 2.3

Dilution Series Design

| Dilution | Total desired number of cells in 50 μL | Desired cell fraction of Jurkat-configuration lymphocytes | Number of desired Jurkat cells | Required polyclonal cells | Equivalent Jurkat DNA required (μL)‡ | Equivalent polyclonal (A037) DNA required (μL) | Water (μL) | Theoretical final dilution DNA concentration (ng/μL) |
|---|---|---|---|---|---|---|---|---|
| 1 | 2.00E+05 | 1 | 2.00E+05 | 0 | 13.21 | 0.00 | 36.79 | 2.80 |
| 2 | 2.00E+05 | 0.1 | 2.00E+04 | 1.80E+05 | 13.21 of 1 in 10 dilution of Dilution 1 | 2.79 | 34.00 | 2.80 |
| 3 | 2.00E+05 | 0.01 | 2.00E+03 | 1.98E+05 | 13.21 of 1 in 10 dilution of Dilution 2 | 3.07 | 33.72 | 2.80 |
| 4 | 2.00E+05 | 0.001 | 2.00E+02 | 2.00E+05 | 13.21 of 1 in 10 dilution of Dilution 3 | 3.09 | 33.70 | 2.80 |
| 5 | 2.00E+05 | 0.0001 | 2.00E+01 | 2.00E+05 | 13.21 of 1 in 10 dilution of Dilution 4 | 3.10 | 33.69 | 2.80 |
| 6 | 2.00E+05 | 0.00001 | 2.00E+00 | 2.00E+05 | 13.21 of 1 in 10 dilutiono f Dilution 5 | 3.10 | 33.69 | 2.80 |

‡Assumptions of note: Stock Jurkat Cell Line DNA Concentration: 10.6 ng/μL; Presumes lymphocyte DNA content: 0.0007 ng/cell

TABLE 2.4

Clinical, Pathology & Outcome Data Parameters

| Clinical Data Parameters | Pathology Data Parameters | Treatment Data Parameters | Outcome Data Parameters |
|---|---|---|---|
| Age at Diagnosis | Morphology (small cell, large cell anaplastic) | First-line therapy | Birthdate |
| Gender | Background (mixed or uniform inflammatory infiltrates) | Transplant (Yes/No) | Diagnosis Date |
| Primary Site of involvement | Bone Marrow Status of Diagnosis (% of involvement by tumor, if applicable) | Second-line or subsequent additional therapies | Date of Last Follow-up |
| Performance Status | Primary Specimen immunohistochemistry (positive/negative) | | Disposition (0 = Alive; 1 = Deceased) |
| B symptoms | CD2 | | |
| International Prognostic Index | CD3 | | |
| Stage | CD4 | | |
| CBC at diagnosis | CD5 | | |
| Hb | CD7 | | |
| MCV | CD8 | | |
| Plt | CD10 | | |
| Neut | CD21 | | |
| Mono | CD23 | | |
| Eo | CD30 | | |
| Lymph | CD56 | | |
| Other | CD57 | | |
| Chemistry | BCL6 | | |
| LDH | KI67 | | |
| Uric Acid | EBER | | |
| Albumin | ALK | | |
| Alk-Phos | PD1 | | |
| ALT | CXCL-13 | | |
| AST | Primary Speciment Flow Cytometry (positive/negative) | | |
| BUN | CD45 | | |
| Calciura | CD2 | | |
| Chloride | CD3 | | |
| CO2 | CD5 | | |
| Creatinine | CD4 | | |
| Glucose | CD7 | | |
| Potassium | CD8 | | |

TABLE 2.4-continued

Clinical, Pathology & Outcome Data Parameters

| Clinical Data Parameters | Pathology Data Parameters | Treatment Data Parameters | Outcome Data Parameters |
|---|---|---|---|
| Sodium | CD10 | | |
| Total Bilirubin | CD19 | | |
| Total protein | CD20 | | |
| | CD30 | | |
| | TCR alpha/beta | | |
| | TCR gamma/delta | | |
| | Molecular | | |
| | Clonality (clonal/polyclonal) | | |
| | Other | | |
| | Cytogenetics (normal/abnormal) | | |
| | Classical | | |
| | FISH | | |
| | Serology (positive/negative) | | |
| | HIV | | |
| | HTLV-1 | | |

TABLE 2.5

Sample descriptions and flow cytometry data of the 6 actual patient lymphocyte specimens used for analytical validation

| Sample Name | Description | Flow-cytometry Features (if available) | Number of Cells Input for DNA Isolation | "Clonal/Oligoclonal" vs "Polyclonal" |
|---|---|---|---|---|
| A037 | Healthy Donor Patient Peripheral Blood Mononuclear Cells | N/A | 10,000,000 | Polyclonal |
| OV7 | Mixed Ovarian Tumour-Infiltrating Lymphocytes expanded with IL-2 treatment | 90% CD3+ 10% CD4+ 70% CD8+ | 10,000,000 | Polyclonal |
| EZM | Cell suspension of melanoma tumour with brisk CD3 infiltration | N/A | 10,000,000 (possible admixed tumour cells) | Uncertain |
| TIL2 | Melanoma tumour-infiltrating lymphocytes expanded in IL-2 | 97% CD8+ | 10,000,000 | Oligoclonal |
| STIM1 | MART1-specific cell line made from peptide stimulation of healthy donor PBMCs, FACS sorting and expansion of tetramer+ cells | 99% CD8+ | 10,000,000 | Clonal/Oligoclonal |
| L2D8 | gp100-specific tumour-infiltrating lymphocyte clone | ~100% CD8+ | 10,000,000 | Clonal/Oligoclonal |

TABLE 2.6

Cell lines used for analytical validation

| Cell Line | Reference Collection # | Previously Documented/Known TRGR Configurations |
|---|---|---|
| CEM (CCRF-CEM) | ATCC CCL-119 | TRBV3-1*01-TRBD1*01-TRBJ2-3*01<br>TRBJ1-5-TRBJ2-1 (partial rearrangement)<br>TRBV9-TRBD2 (partial rearrangement)<br>TRGV3-TRGJ1/TRGJ2<br>TRGV4-TRGJ1/TRGJ2 |
| Jurkat | DSMZ ACC-282 | TRAV8-4-TRAJ3<br>TRBV12-3-TRBJ1-2 (partial rearrangement) |
| MOLT4 | ATCC CRL-1582 | TRBV20-1*01-TRBD2*01-TRBJ2-1*01<br>TRBV10-3-TRBD1*01-TRBJ2-5<br>TRGV2-TRGJP1<br>TRGV2-TRGJP2 |
| SUPT1 | ATCC CRL-1942 | TRBV9*01-TRBD2*01-TRBJ2-1*01<br>TRGV3-TRGJ1/TRGJ2<br>TRGV4-TRGJ1/TRGJ2 |

TABLE 1.1

Capture Sample Method Data

| Sample | Sample | Protocol Type | Library input (ng) |
|---|---|---|---|
| A037 healthy reference | | | |
| Sample_A037_PBMC_TCR_A_all | A037_PBMC | CapSeq_One-Step_V | 100 |
| Sample_A037_PBMC_TCR_B_all | A037_PBMC | CapSeq_One-Step_V | 200 |
| Sample_A037_PBMC_TCR_D_all | A037_PBMC | CapSeq_One-Step_V | 600 |
| Sample_A037_PBMC_TCR_E_all | A037_PBMC | CapSeq_One-Step_V | 800 |
| Sample_A037_PBMC_TCR_F_all | A037_PBMC | CapSeq_One-Step_V | 1000 |
| Sample_A037_PBMC_TCR_G_all | A037_PBMC | CapSeq_One-Step_V | 200 |
| Sample_A037_PBMC_TCR_H_all | A037_PBMC | CapSeq_One-Step_V | 600 |
| Sample_A037_PBMC_TCR_J_all | A037_PBMC | CapSeq_One-Step_V | 200 |
| Sample_A037_PBMC_TCR_K_all | A037_PBMC | CapSeq_One-Step_V | 600 |
| Sample_A037_PBMC_TCR_L_all | A037_PBMC | CapSeq_One-Step_V | 1000 |
| Sample_16_01_A037_PBMC_TCR_F_all | A037_PBMC | CapSeq_One-Step_V | 500 |
| Sample_16_01_A037_PBMC_TCR_H_all | A037_PBMC | CapSeq_One-Step_V | 250 |
| Sample_A037_S1_all | A037_PBMC | CapSeq_One-Step_VI | 100 |
| Sample_A037_PBMC_1S_all | A037_PBMC | CapSeq_One-Step_VI | 100 |
| Sample_16_11_A037_PBMC_TCR_VI_all | A037_PBMC | CapSeq_One-Step_VI | 100 |
| Sample_A037_CD3_1S_all | A037_CD3 | CapSeq_One-Step_VI | 100 |
| Cell lines and flow sorted | | | |
| M36_EZM | flow_sorted | CapSeq_One-Step_VI | 100 |
| M36_TIL2 | flow_sorted | CapSeq_One-Step_VI | 100 |
| DV7-TIL2 | flow_sorted | CapSeq_One-Step_VI | 100 |
| SE14-2005 | cell_line | CapSeq_One-Step_VI | 100 |
| SE14-2033 | cell_line | CapSeq_One-Step_VI | 100 |
| SE14-2034 | cell_line | CapSeq_One-Step_VI | 100 |
| SE14-2035 | cell_line | CapSeq_One-Step_VI | 100 |
| STIM1 | flow_sorted | CapSeq_One-Step_VI | 100 |
| L2D8 | flow_sorted | CapSeq_One-Step_VI | 100 |
| Patient samples | | | |
| M14-10124 | patient_tumor | CapSeq_One-Step_VI | 100 |
| M14-11153 | patient_tumor | CapSeq_One-Step_VI | 100 |
| M14-11567 | patient_tumor | CapSeq_One-Step_VI | 100 |
| M14-11587 | patient_tumor | CapSeq_One-Step_VI | 100 |
| M14-11721 | patient_tumor | CapSeq_One-Step_VI | 100 |
| M14-11770 | patient_tumor | CapSeq_One-Step_VI | 100 |
| M14-12217 | patient_tumor | CapSeq_One-Step_VI | 100 |
| M14-12649 | patient_tumor | CapSeq_One-Step_VI | 100 |
| M14-12728 | patient_tumor | CapSeq_One-Step_VI | 100 |
| M14-12753 | patient_tumor | CapSeq_One-Step_VI | 100 |
| M14-13167 | patient_tumor | CapSeq_One-Step_VI | 100 |
| M14-13300 | patient_tumor | CapSeq_One-Step_VI | 100 |
| M14-13750 | patient_tumor | CapSeq_One-Step_VI | 100 |
| M14-14570 | patient_tumor | CapSeq_One-Step_VI | 100 |
| M14-14625 | patient_tumor | CapSeq_One-Step_VI | 100 |
| M14-14907 | patient_tumor | CapSeq_One-Step_VI | 100 |
| M14-14951 | patient_tumor | CapSeq_One-Step_VI | 100 |
| M14-14962 | patient_tumor | CapSeq_One-Step_VI | 100 |
| M14-1508 | patient_tumor | CapSeq_One-Step_VI | 100 |
| M14-15119 | patient_tumor | CapSeq_One-Step_VI | 100 |
| M14-3271 | patient_tumor | CapSeq_One-Step_VI | 100 |
| M14-4454 | patient_tumor | CapSeq_One-Step_VI | 100 |
| M14-5819 | patient_tumor | CapSeq_One-Step_VI | 100 |
| M14-5875 | patient_tumor | CapSeq_One-Step_VI | 100 |
| M14-6143 | patient_tumor | CapSeq_One-Step_VI | 100 |

TABLE 1.1-continued

Capture Sample Method Data

| Sample | Sample | Protocol Type | Library input (ng) |
|---|---|---|---|
| M14-6430 | patient_tumor | CapSeq_One-Step_VI | 100 |
| M14-6443 | patient_tumor | CapSeq_One-Step_VI | 100 |
| M14-6502 | patient_tumor | CapSeq_One-Step_VI | 100 |
| M14-6885 | patient_tumor | CapSeq_One-Step_VI | 100 |
| M14-7046 | patient_tumor | CapSeq_One-Step_VI | 100 |
| M14-7049 | patient_tumor | CapSeq_One-Step_VI | 100 |
| M14-7053 | patient_tumor | CapSeq_One-Step_VI | 100 |
| M14-7107 | patient_tumor | CapSeq_One-Step_VI | 100 |
| M14-7554 | patient_tumor | CapSeq_One-Step_VI | 100 |
| M14-7568 | patient_tumor | CapSeq_One-Step_VI | 100 |
| M14-7691 | patient_tumor | CapSeq_One-Step_VI | 100 |
| M14-7700 | patient_tumor | CapSeq_One-Step_VI | 100 |
| M14-7782 | patient_tumor | CapSeq_One-Step_VI | 100 |
| M14-7862 | patient_tumor | CapSeq_One-Step_VI | 100 |
| M14-7884 | patient_tumor | CapSeq_One-Step_VI | 100 |
| M14-7992 | patient_tumor | CapSeq_One-Step_VI | 100 |
| M14-8132 | patient_tumor | CapSeq_One-Step_VI | 100 |
| M14-8272 | patient_tumor | CapSeq_One-Step_VI | 100 |
| M14-8639 | patient_tumor | CapSeq_One-Step_VI | 100 |
| M14-8668 | patient_tumor | CapSeq_One-Step_VI | 100 |
| M14-8740 | patient_tumor | CapSeq_One-Step_VI | 100 |
| M14-8913 | patient_tumor | CapSeq_One-Step_VI | 100 |
| M14-8914 | patient_tumor | CapSeq_One-Step_VI | 100 |
| M14-9212 | patient_tumor | CapSeq_One-Step_VI | 100 |
| M14-9801 | patient_tumor | CapSeq_One-Step_VI | 100 |
| M15-1195 | patient_tumor | CapSeq_One-Step_VI | 100 |
| M15-1330 | patient_tumor | CapSeq_One-Step_VI | 100 |
| M15-1470 | patient_tumor | CapSeq_One-Step_VI | 100 |
| M15-1556 | patient_tumor | CapSeq_One-Step_VI | 100 |
| M15-1825 | patient_tumor | CapSeq_One-Step_VI | 100 |
| M15-1867 | patient_tumor | CapSeq_One-Step_VI | 100 |
| M15-1883 | patient_tumor | CapSeq_One-Step_VI | 100 |
| M15-237 | patient_tumor | CapSeq_One-Step_VI | 100 |
| M15-2603 | patient_tumor | CapSeq_One-Step_VI | 100 |
| M15-2779 | patient_tumor | CapSeq_One-Step_VI | 100 |
| M15-3091 | patient_tumor | CapSeq_One-Step_VI | 100 |
| M15-587 | patient_tumor | CapSeq_One-Step_VI | 100 |
| M15-795 | patient_tumor | CapSeq_One-Step_VI | 100 |
| M15-933 | patient_tumor | CapSeq_One-Step_VI | 100 |

TABLE 1.2

Capture Sample Read Counts

| Sample | total reads | on-target reads | off-target reads | on-target ratio | merged reads | reads after threshold |
|---|---|---|---|---|---|---|
| A037 healthy reference | | | | | | |
| Sample_A037_PBMC_TCR_A_all | 1961529 | 96884 | 1864620 | 0.049392081 | 1961504 | 1900159 |
| Sample_A037_PBMC_TCR_B_all | 9915634 | 865444 | 9050165 | 0.087280753 | 9915609 | 9488814 |
| Sample_A037_PBMC_TCR_D_all | 11554469 | 359807 | 11194637 | 0.031140072 | 11554444 | 10839947 |
| Sample_A037_PBMC_TCR_E_all | 8208382 | 4019972 | 4188385 | 0.489739878 | 8208357 | 8069762 |
| Sample_A037_PBMC_TCR_F_all | 13434420 | 3925996 | 9508399 | 0.292234127 | 13434395 | 13076224 |
| Sample_A037_PBMC_TCR_G_all | 11585206 | 217323 | 11367558 | 0.018758665 | 11585181 | 11162632 |
| Sample_A037_PBMC_TCR_H_all | 8680363 | 1631345 | 7048993 | 0.187935113 | 8680338 | 8302862 |
| Sample_A037_PBMC_TCR_J_all | 17147171 | 504177 | 16642969 | 0.029402926 | 17147146 | 14908072 |
| Sample_A037_PBMC_TCR_K_all | 8812446 | 518449 | 8293972 | 0.055831453 | 8812421 | 7851064 |
| Sample_A037_PBMC_TCR_L_all | 21053845 | 429885 | 20623935 | 0.020418361 | 21053820 | 17568322 |
| Sample_16_01_A037_PBMC_TCR_F_all | 4457394 | 958772 | 3498597 | 0.215096983 | 4457369 | 4389100 |
| Sample_16_01_A037_PBMC_TCR_H_all | 6835579 | 1719308 | 5116246 | 0.25152339 | 6835554 | 6750376 |
| Sample_A037_S1_all | 1920124 | 1082540 | 837559 | 0.563786505 | 1920099 | 1867339 |
| Sample_A037_PBMC_15_all | 4368959 | 2120537 | 2748397 | 0.435521638 | 4768430 | 4706036 |
| Sample_16_11_A037_PBMC_TOR_VJ_all | 1433221 | 413057 | 1020139 | 0.288201889 | 1433196 | 1427599 |
| Sample_A037_CD3_15_all | 4701054 | 2361517 | 2339512 | 0.502337774 | 4701029 | 4651006 |
| Cell lines and flow sorted | | | | | | |
| M36_EZM | 2318060 | 1380043 | 937992 | 0.595349951 | 2318035 | 2255858 |
| M36_TIL2 | 1569122 | 769525 | 799572 | 0.490417571 | 1569097 | 1518502 |
| OV7-TIL2 | 2392656 | 1271622 | 1121009 | 0.531468795 | 2392631 | 2320790 |

TABLE 1.2-continued

Capture Sample Read Counts

| Sample | total reads | on-target reads | off-target reads | on-target ratio | merged reads | reads after threshold |
|---|---|---|---|---|---|---|
| SE14-2005 | 1291244 | 476090 | 815129 | 0.368706457 | 1291219 | 1216685 |
| SE14-2033 | 1339529 | 662257 | 677247 | 0.494395418 | 1339504 | 1293618 |
| SE14-2034 | 1278441 | 564484 | 713932 | 0.441540908 | 1278416 | 1240462 |
| SE14-2035 | 1678562 | 743158 | 935379 | 0.442734912 | 1678537 | 1611636 |
| STIM1 | 1880814 | 900492 | 980297 | 0.478777806 | 1580789 | 1827853 |
| L2D8 | 1651306 | 910355 | 740926 | 0.551293946 | 1651281 | 1603088 |
| Patient samples | | | | | | |
| M14-10124 | 3874239 | 1363917 | 2510297 | 0.352047718 | 3874214 | 1641564 |
| M14-11153 | 4921789 | 1618479 | 3303285 | 0.328839574 | 4921764 | 4871138 |
| M14-11567 | 4961317 | 1742809 | 3218483 | 0.351279509 | 4961292 | 4808248 |
| M14-11587 | 4284116 | 1363269 | 2920822 | 0.318214773 | 4284091 | 4230674 |
| M14-11721 | 5480831 | 1885151 | 8595655 | 0.343953499 | 5480806 | 5423859 |
| M14-11770 | 5405827 | 415885 | 4989917 | 0.076932725 | 5405802 | 5177500 |
| M14-12217 | 5135793 | 1690789 | 3444979 | 0.329216734 | 5135768 | 5098364 |
| M14-12649 | 7798007 | 2759564 | 5038418 | 0.353880677 | 7797982 | 7715502 |
| M14-12728 | 5006452 | 739003 | 4267424 | 0.147610124 | 5006427 | 4799839 |
| M14-12753 | 5044768 | 1512141 | 3532602 | 0.299744408 | 5044743 | 4998359 |
| M14-13167 | 2912824 | 980216 | 1932583 | 0.336517414 | 2912799 | 2891403 |
| M14-13300 | 6403753 | 976423 | 5427305 | 0.15247668 | 6403728 | 6226299 |
| M14-13750 | 6648103 | 894302 | 5753776 | 0.134519877 | 6648078 | 6520478 |
| M14-14570 | 4577658 | 964191 | 3613442 | 0.210629759 | 4577633 | 4516409 |
| M14-14625 | 4919394 | 671943 | 4247426 | 0.136590604 | 4919369 | 4678232 |
| M14-14907 | 6045676 | 1996999 | 4048652 | 0.330318562 | 6045651 | 5967138 |
| M14-14951 | 4339950 | 334232 | 4005693 | 0.077012869 | 4339925 | 4253000 |
| M14-14962 | 2621464 | 397567 | 2223872 | 0.151658386 | 5799400 | 5552790 |
| M14-1508 | 6616839 | 3224927 | 3391887 | 0.487381815 | 6616814 | 6538041 |
| M14-15119 | 4825285 | 658203 | 4167057 | 0.136407072 | 4825260 | 4721235 |
| M14-3271 | 7352598 | 3438740 | 3913833 | 0.467690468 | 7352573 | 7230944 |
| M14-4454 | 7015117 | 3588858 | 3426234 | 0.511589187 | 7015092 | 6912945 |
| M14-5819 | 6427168 | 2297299 | 4129844 | 0.357435654 | 6427143 | 6377748 |
| M14-5875 | 6466993 | 2244807 | 4222166 | 0.347117318 | 6466973 | 6357148 |
| M14-6143 | 5149354 | 740986 | 4408343 | 0.143898827 | 5149329 | 4979117 |
| M14-6430 | 7717729 | 4019388 | 3698316 | 0.520799318 | 7717704 | 7610950 |
| M14-6443 | 5310114 | 1719071 | 3591018 | 0.323735234 | 5310089 | 5258149 |
| M14-6502 | 6854324 | 449983 | 6404316 | 0.065649505 | 6854299 | 6571525 |
| M14-6885 | 4473140 | 636717 | 3836398 | 0.142342292 | 4473115 | 4255663 |
| M14-7046 | 2901414 | 389561 | 2511828 | 0.134265913 | 2901389 | 2690711 |
| M14-7049 | 4194422 | 328956 | 3866041 | 0.078283969 | 4194397 | 4104557 |
| M14-7053 | 4534911 | 634273 | 3900613 | 0.139864487 | 4534886 | 4132215 |
| M14-7107 | 3653179 | 489927 | 3163227 | 0.134109771 | 3653154 | 3443643 |
| M14-7554 | 6905643 | 3346628 | 3558990 | 0.484622214 | 6905618 | 6814973 |
| M14-7568 | 5989679 | 2953254 | 3036400 | 0.49305714 | 5989654 | 5933921 |
| M14-7691 | 4715544 | 2109689 | 2605830 | 0.447390375 | 4715519 | 4633852 |
| M14-7700 | 6664469 | 2293770 | 4370674 | 0.344178959 | 6664444 | 6605136 |
| M14-7782 | 6155725 | 3173681 | 2982019 | 0.515565754 | 6155700 | 6034814 |
| M14-7862 | 5025139 | 361053 | 4664061 | 0.071849356 | 5025114 | 4886216 |
| M14-7884 | 5190944 | 361315 | 4829604 | 0.069604873 | 5190919 | 5085124 |
| M14-7992 | 5745439 | 2514128 | 2931286 | 0.489802055 | 5745414 | 5649598 |
| M14-8132 | 5328896 | 1787753 | 3541118 | 0.335482809 | 5328871 | 5288026 |
| M14-8272 | 6030251 | 3161144 | 2869082 | 0.524214332 | 6030226 | 5874655 |
| M14-8639 | 7376555 | 3887519 | 3489011 | 0.527010102 | 7376530 | 7249500 |
| M14-8668 | 5401734 | 2916998 | 2484711 | 0.540011411 | 5401709 | 5338260 |
| M14-8740 | 5346366 | 233692 | 5112649 | 0.043710438 | 5346341 | 5202430 |
| M14-8913 | 6495674 | 3372030 | 3123619 | 0.51911934 | 6495649 | 6455304 |
| M14-8914 | 6562054 | 3324004 | 3238025 | 0.506549321 | 6562029 | 6458959 |
| M14-3212 | 4503869 | 1426322 | 3077522 | 0.316688163 | 4503844 | 4452847 |
| M14-9801 | 5502711 | 387341 | 5115345 | 0.07039094 | 5502686 | 5398233 |
| M15-1195 | 6305701 | 392089 | 5913587 | 0.062180081 | 6305676 | 6065963 |
| M15-1330 | 8302037 | 2704496 | 5597516 | 0.325762942 | 8302012 | 8107829 |
| M15-1470 | 3834967 | 292000 | 3542942 | 0.076141464 | 3834942 | 3767575 |
| M15-1556 | 6935912 | 3615566 | 3320321 | 0.521281989 | 6935887 | 6892616 |
| M15-1825 | 6078396 | 1963007 | 4115364 | 0.322948192 | 6078371 | 6014071 |
| M15-1867 | 6865892 | 3557974 | 3307893 | 0.518210016 | 6865867 | 6816073 |
| M15-1883 | 6227227 | 3087220 | 3139982 | 0.495761597 | 6227202 | 6169114 |
| M15-237 | 6215041 | 2213245 | 4001771 | 0.356111086 | 6215016 | 6155386 |
| M15-2603 | 5639514 | 2766020 | 2873469 | 0.490471342 | 5639489 | 5564062 |
| M15-2779 | 5680891 | 2792325 | 2888541 | 0.49152941 | 5680866 | 5628837 |
| M15-3091 | 6906018 | 3575635 | 3330358 | 0.517756397 | 6905993 | 6843330 |
| M15-587 | 3920359 | 589850 | 3330484 | 0.15045816 | 3920334 | 3808959 |
| M15-795 | 4275264 | 769512 | 3505727 | 0.179991692 | 4275239 | 4205077 |
| M15-933 | 6551470 | 3277319 | 3274126 | 0.500241778 | 6551445 | 6481344 |

TABLE 1.3

Capture Sample V and J Calls

| Sample | alpha VJ calls | beta VJ calls | gamma VJ calls | delta VJ calls | unmatched VJ calls | single V or J | absent V and J |
|---|---|---|---|---|---|---|---|
| A037 healthy reference | | | | | | | |
| Sample_A037_PBMC_TCR_A_all | 30 | 111 | 46 | 0 | 0 | 171866 | 1728107 |
| Sample_A037_PBMC_TCR_B_all | 473 | 806 | 538 | 0 | 0 | 1634949 | 7852049 |
| Sample_A037_PBMC_TCR_D_all | 298 | 244 | 127 | 1 | 0 | 583395 | 10255883 |
| Sample_A037_PBMC_TCR_E_all | 4470 | 1956 | 2916 | 82 | 5 | 5486404 | 2573930 |
| Sample_A037_PBMC_TCR_F_all | 3932 | 1815 | 3169 | 84 | 6 | 5949549 | 7117670 |
| Sample_A037_PBMC_TCR_G_all | 101 | 186 | 78 | 15 | 0 | 420033 | 10742220 |
| Sample_A037_PBMC_TCR_H_all | 1607 | 1125 | 252 | 12 | 4 | 2160797 | 6139066 |
| Sample_A037_PBMC_TCR_J_all | 323 | 139 | 135 | 4 | 2 | 1112523 | 13794947 |
| Sample_A037_PBMC_TCR_K_all | 352 | 169 | 200 | 6 | 0 | 1027278 | 6823060 |
| Sample_A037_PBMC_TCR_L_all | 259 | 111 | 136 | 8 | 3 | 1057487 | 16510319 |
| Sample_16_01_4037_PBMC_TCR_F_all | 325 | 363 | 628 | 25 | 1 | 3437777 | 949382 |
| Sample_16_01_A037_PBMC_TCR_H_all | 1397 | 763 | 1015 | 21 | 2 | 4575171 | 2172015 |
| Sample_A037_S1_all | 1052 | 606 | 734 | 12 | 2 | 1255308 | 609626 |
| Sample_A037_PBMC_15_all | 1008 | 599 | 834 | 26 | 1 | 2536312 | 2167257 |
| Sample_16_11_A037_PBMC_TCR_VJ_all | 340 | 161 | 329 | 11 | 0 | 934369 | 492390 |
| Sample_A037_CD3_15_all | 6368 | 3264 | 4805 | 123 | 7 | 2753833 | 1882607 |
| Cell lines and flow sorted | | | | | | | |
| M36_EZM | 138 | 94 | 94 | 0 | 0 | 1521931 | 733602 |
| M36_TIL2 | 2136 | 1579 | 1963 | 4 | 7 | 1015956 | 496858 |
| OV7-TIL2 | 2619 | 1879 | 1918 | 52 | 1 | 1515855 | 798467 |
| SE14-2005 | 2450 | 1293 | 2070 | 0 | 0 | 818261 | 392612 |
| SE14-2033 | 1389 | 924 | 1344 | 0 | 0 | 895089 | 394873 |
| SE14-2034 | 1910 | 2833 | 1377 | 0 | 0 | 856362 | 377981 |
| SE14-2035 | 3031 | 2017 | 2157 | 0 | 0 | 1020846 | 583586 |
| STIM1 | 3068 | 1524 | 2503 | 0 | 0 | 1192227 | 628532 |
| L2D8 | 2074 | 962 | 948 | 0 | 0 | 1060361 | 538744 |
| Patient samples | | | | | | | |
| M14-10124 | 1971 | 1098 | 1674 | 48 | 0 | 2380500 | 1256274 |
| M14-11153 | 585 | 283 | 623 | 9 | 0 | 2811142 | 2058492 |
| M14-11567 | 1423 | 001 | 1278 | 8 | 6 | 2599812 | 2204821 |
| M14-11587 | 182 | 251 | 142 | 0 | 2 | 2473198 | 1756900 |
| M14-11721 | 210 | 65 | 192 | 0 | 3 | 3272558 | 2150832 |
| M14-11770 | 17 | 36 | 25 | 0 | 0 | 768985 | 4408438 |
| M14-12217 | 343 | 141 | 2481 | 643 | 0 | 2982597 | 2112155 |
| M14-12649 | 1267 | 857 | 1327 | 4 | 3 | 4868928 | 2843117 |
| M14-12728 | 986 | 607 | 967 | 14 | 0 | 1069367 | 3727899 |
| M14-12753 | 1600 | 960 | 2053 | 40 | 1 | 2485050 | 2508656 |
| M14-13167 | 215 | 87 | 248 | 22 | 0 | 1710714 | 1180118 |
| M14-13300 | 1620 | 688 | 2344 | 13 | 1 | 1571492 | 4650142 |
| M14-13750 | 1995 | 1039 | 2144 | 108 | 7 | 1527402 | 4987784 |
| M14-14570 | 155 | 163 | 290 | 45 | 0 | 1742539 | 2773218 |
| M14-14625 | 1083 | 562 | 967 | 7 | 1 | 1084783 | 3590830 |
| M14-14907 | 981 | 247 | 494 | 15 | 0 | 3030809 | 2934593 |
| M14-14951 | 166 | 84 | 174 | 4 | 3 | 613083 | 3639487 |
| M14-14962 | 623 | 332 | 545 | 7 | 0 | 1160605 | 4390679 |
| M14-1508 | 3489 | 2654 | 3136 | 19 | 1 | 4047376 | 2481367 |
| M14-15119 | 4218 | 1546 | 1551 | 0 | 3 | 986010 | 3727908 |
| M14-3271 | 4607 | 2563 | 3523 | 64 | 6 | 4297650 | 2922532 |
| M14-4454 | 197 | 904 | 1199 | 11 | 6 | 4479570 | 2429285 |
| M14-5819 | 186 | 86 | 271 | 2 | 1 | 2435125 | 3942078 |
| M14-5875 | 484 | 371 | 533 | 12 | 0 | 3411599 | 2944150 |
| M14-6143 | 575 | 241 | 481 | 1 | 0 | 1235788 | 3742032 |
| M14-6430 | 863 | 471 | 705 | 39 | 0 | 4942133 | 2666740 |
| M14-6443 | 0 | 0 | 0 | 0 | 0 | 2721814 | 2536336 |
| M14-6502 | 119 | 77 | 140 | 0 | 0 | 913846 | 5657347 |
| M14-6885 | 1274 | 727 | 888 | 4 | 3 | 985106 | 3267662 |
| M14-7046 | 497 | 190 | 442 | 5 | 4 | 615177 | 2074397 |
| M14-7049 | 5 | 2 | 396 | 61 | 0 | 630487 | 3473057 |
| M14-7053 | 40 | 228 | 420 | 23 | 0 | 936724 | 3194412 |
| M14-7107 | 1122 | 577 | 915 | 2 | 1 | 797093 | 2643934 |
| M14-7554 | 901 | 469 | 861 | 24 | 1 | 1741112 | 5071606 |
| M14-7568 | 2181 | 861 | 1674 | 141 | 2 | 3472975 | 2456088 |
| M14-7691 | 5077 | 4087 | 4193 | 0 | 0 | 2889813 | 1730683 |
| M14-7700 | 536 | 342 | 860 | 6 | 0 | 4144765 | 2458628 |
| M14-7782 | 682 | 417 | 223 | 21 | 0 | 3850370 | 2182602 |
| M14-7862 | 264 | 104 | 232 | 0 | 2 | 735636 | 4149979 |
| M14-7854 | 340 | 228 | 434 | 0 | 0 | 739308 | 4344815 |
| M14-7992 | 1987 | 1338 | 1755 | 12 | 0 | 3223885 | 2420622 |

TABLE 1.3-continued

Capture Sample V and J Calls

| Sample | alpha VJ calls | beta VJ calls | gamma VJ calls | delta VJ calls | unmatched VJ calls | single V or J | absent V and J |
|---|---|---|---|---|---|---|---|
| M14-8132 | 229 | 150 | 287 | 3 | 0 | 3138235 | 2149123 |
| M14-8272 | 273 | 223 | 299 | 0 | 0 | 3574689 | 2299172 |
| M14-8639 | 638 | 335 | 605 | 29 | 0 | 4327667 | 2920227 |
| M14-8668 | 140 | 107 | 117 | 0 | 2 | 3224632 | 2113263 |
| M14-8740 | 741 | 374 | 842 | 0 | 0 | 643355 | 4557119 |
| M14-8913 | 451 | 268 | 447 | 12 | 0 | 3838965 | 2615162 |
| M14-8914 | 868 | 350 | 718 | 1 | 1 | 4020234 | 2436788 |
| M14-9212 | 1208 | 712 | 1318 | 7 | 0 | 2691103 | 1758500 |
| M14-9801 | 407 | 183 | 387 | 2 | 0 | 779518 | 4617737 |
| M15-1195 | 119 | 84 | 83 | 0 | 0 | 767911 | 5297767 |
| M15-1330 | 8600 | 3192 | 5559 | 101 | 7 | 5264470 | 2825901 |
| M15-1470 | 327 | 203 | 562 | 0 | 1 | 561308 | 3205175 |
| M15-1556 | 446 | 253 | 453 | 6 | 2 | 3805780 | 3085647 |
| M15-1825 | 969 | 508 | 1009 | 13 | 0 | 3034468 | 2977105 |
| M15-1567 | 269 | 127 | 256 | 34 | 0 | 2887666 | 3927692 |
| M15-1883 | 2011 | 885 | 1324 | 82 | 4 | 3843001 | 2321808 |
| M15-237 | 276 | 191 | 275 | 0 | 1 | 3558414 | 2596230 |
| M15-2603 | 1559 | 821 | 1398 | 24 | 0 | 3448607 | 2111654 |
| M15-2779 | 1475 | 761 | 1463 | 41 | 3 | 3503916 | 2121179 |
| M15-3091 | 200 | 34 | 143 | 9 | 0 | 3519287 | 3323608 |
| M15-587 | 547 | 375 | 627 | 11 | 2 | 931289 | 2876009 |
| M15-795 | 360 | 159 | 355 | 7 | 3 | 1064180 | 3140014 |
| M15-933 | 1187 | 596 | 1118 | 13 | 3 | 2942292 | 3536136 |

TABLE 1.4

Capture Sample Unique V and J Calls

| Sample | alpha unique VJ counts | beta unique VJ counts | gamma unique VJ counts | delta unique VJ counts | total unique VJ | Unique VJ normalized to input |
|---|---|---|---|---|---|---|
| A037 healthy reference | | | | | | |
| Sample_A037_PBMC_TCR_A_all | 11 | 20 | 6 | 0 | 37 | 0.37 |
| Sample_A037_PBMC_TCR_B_all | 44 | 65 | 18 | 0 | 127 | 0.64 |
| Sample_A037_PBMC_TCR_D_all | 213 | 158 | 25 | 1 | 397 | 0.66 |
| Sample_A037_PBMC_TCR_E_all | 955 | 405 | 49 | 3 | 1412 | 1.77 |
| Sample_A037_PBMC_TCR_F_all | 1343 | 527 | 49 | 6 | 1925 | 1.93 |
| Sample_A037_PBMC_TCR_G_all | 8 | 18 | 5 | 1 | 32 | 0.16 |
| Sample_A037_PBMC_TCR_H_all | 502 | 305 | 24 | 2 | 833 | 1.39 |
| Sample_A037_PBMC_TCR_J_all | 192 | 90 | 21 | 3 | 306 | 1.53 |
| Sample_A037_PBMC_TCR_K_all | 268 | 122 | 32 | 4 | 426 | 0.71 |
| Sample_A037_PBMC_TCR_L_all | 220 | 85 | 24 | 3 | 332 | 0.33 |
| Sample_16_01_A037_PBMC_TCR_F_all | 414 | 175 | 41 | 2 | 632 | 1.26 |
| Sample_16_01_A037_PBMC_TCR_H_all | 463 | 235 | 34 | 3 | 735 | 2.94 |
| Sample_A037_S1_all | 446 | 22 | 36 | 3 | 712 | 7.12 |
| Sample_A037_PBMC_15_all | 466 | 253 | 36 | | 759 | 7.59 |
| Sample_16_11_A037_PBMC_TCR_VJ_all | 263 | 125 | 36 | 3 | 427 | 4.27 |
| Sample_A037_CD3_15_all | 1704 | 710 | 54 | 7 | 2475 | 24.75 |
| Cell lines and flow sorted | | | | | | |
| M36_EZM | 67 | 41 | 15 | 0 | 123 | 1.23 |
| M36_TIL2 | 244 | 163 | 38 | 1 | 445 | 4.46 |
| OV7-TIL2 | 143 | 114 | 49 | 5 | 311 | 3.11 |
| SE14-2005 | 6 | 13 | 5 | 0 | 24 | 0.24 |
| SE14-2033 | 14 | 3 | 5 | 0 | 22 | 0.22 |
| SE14-2034 | 5 | 16 | 7 | 0 | 28 | 0.28 |
| SE14-2035 | 9 | 9 | 6 | 0 | 24 | 0.24 |
| STIM1 | 101 | 71 | 23 | 0 | 195 | 1.95 |
| L2D8 | 6 | 3 | 3 | 0 | 12 | 0.12 |
| Patient samples | | | | | | |
| M14-10124 | 225 | 142 | 33 | 2 | 402 | 4.02 |
| M14-11153 | 137 | 63 | 28 | 2 | 230 | 2.30 |
| M14-11567 | 242 | 147 | 39 | 1 | 429 | 4.29 |
| M14-11587 | 37 | 39 | 15 | 0 | 91 | 0.91 |
| M14-11721 | 35 | 14 | 21 | 0 | 70 | 0.70 |
| M14-11770 | 14 | 16 | 8 | 0 | 38 | 0.38 |

TABLE 1.4-continued

Capture Sample Unique V and J Calls

| Sample | alpha unique VJ counts | beta unique VJ counts | gamma unique VJ counts | delta unique VJ counts | total unique VJ | Unique VJ normalized to input |
|---|---|---|---|---|---|---|
| M14-12217 | 59 | 32 | 15 | 1 | 107 | 1.07 |
| M14-12649 | 174 | 132 | 34 | 1 | 341 | 3.41 |
| M14-12728 | 433 | 229 | 47 | 4 | 713 | 7.13 |
| M14-12753 | 178 | 104 | 25 | 4 | 311 | 3.11 |
| M14-13167 | 44 | 19 | 21 | 2 | 85 | 0.86 |
| M14-13300 | 221 | 146 | 33 | 2 | 402 | 4.02 |
| M14-13750 | 410 | 20 | 46 | 5 | 662 | 6.62 |
| M14-14570 | 34 | 33 | 18 | 5 | 88 | 0.38 |
| M14-14625 | 485 | 242 | 50 | 2 | 779 | 7.79 |
| M14-14907 | 227 | 62 | 26 | 2 | 317 | 3.17 |
| M14-14951 | 73 | 43 | 24 | 1 | 141 | 1.41 |
| M14-14962 | 327 | 173 | 41 | 3 | 544 | 5.44 |
| M14-1508 | 352 | 208 | 46 | 5 | 606 | 6.06 |
| M14-15119 | 19 | 18 | 7 | 0 | 44 | 0.44 |
| M14-3271 | 798 | 405 | 53 | 4 | 1260 | 12.60 |
| M14-4454 | 260 | 132 | 31 | 2 | 425 | 4.25 |
| M14-5819 | 53 | 23 | 24 | 1 | 101 | 1.01 |
| M14-5875 | 99 | 79 | 32 | 1 | 211 | 2.11 |
| M14-6143 | 278 | 113 | 40 | 1 | 432 | 4.32 |
| M14-6430 | 173 | 112 | 29 | 3 | 317 | 3.17 |
| M14-6443 | 0 | 0 | 0 | 0 | 0 | 0.00 |
| M14-6502 | 66 | 37 | 27 | 0 | 130 | 1.30 |
| M14-6885 | 513 | 262 | 32 | 3 | 810 | 8.10 |
| M14-7046 | 157 | 70 | 23 | 1 | 251 | 2.51 |
| M14-7049 | 3 | 1 | 3 | 3 | 10 | 0.10 |
| M14-7053 | 148 | 89 | 35 | 4 | 276 | 2.76 |
| M14-7107 | 456 | 205 | 45 | 1 | 707 | 7.07 |
| M14-7554 | 164 | 103 | 29 | 5 | 301 | 3.01 |
| M14-7568 | 480 | 8 | 39 | 5 | 710 | 7.10 |
| M14-7691 | 237 | 146 | 43 | 0 | 426 | 4.26 |
| M14-7700 | 105 | 64 | 26 | 1 | 196 | 1.96 |
| M14-7782 | 150 | 99 | 34 | 2 | 285 | 2.85 |
| M14-7862 | 76 | 32 | 22 | 0 | 130 | 1.30 |
| M14-7884 | 171 | 106 | 39 | 0 | 316 | 3.16 |
| M14-7992 | 258 | 160 | 34 | 2 | 454 | 4.54 |
| M14-8132 | 34 | 25 | 23 | 1 | 54 | 0.84 |
| M14-8272 | 73 | 60 | 29 | 0 | 161 | 1.61 |
| M14-8639 | 25 | 77 | 27 | 3 | 237 | 2.32 |
| M14-8668 | 44 | 32 | 19 | 0 | 95 | 0.95 |
| M14-8740 | 17 | 9 | 13 | 0 | 39 | 0.39 |
| M14-8913 | 90 | 61 | 30 | 2 | 183 | 1.83 |
| M14-8914 | 177 | 75 | 29 | 1 | 282 | 2.83 |
| M14-9212 | 190 | 128 | 27 | 3 | 348 | 3.48 |
| M14-9801 | 85 | 41 | 29 | 1 | 156 | 1.56 |
| M15-1195 | 45 | 32 | 24 | 0 | 101 | 1.01 |
| M15-1330 | 1019 | 362 | 55 | 0 | 1442 | 14.42 |
| M15-1470 | 50 | 353 | 28 | 0 | 118 | 1.16 |
| M15-1556 | 120 | 59 | 24 | 1 | 204 | 2.04 |
| M15-1825 | 214 | 121 | 30 | 1 | 366 | 3.66 |
| M15-1867 | 90 | 46 | 32 | 2 | 170 | 1.70 |
| M15-1883 | 435 | 194 | 33 | 6 | 668 | 6.68 |
| M15-237 | 51 | 36 | 21 | 0 | 105 | 1.08 |
| M15-2603 | 294 | 169 | 57 | 3 | 523 | 5.23 |
| M15-2779 | 349 | 185 | 31 | 5 | 570 | 5.70 |
| M15-3091 | 44 | 25 | 15 | 1 | 85 | 0.85 |
| M15-587 | 309 | 159 | 39 | 4 | 511 | 5.11 |
| M15-795 | 174 | 73 | 38 | 2 | 287 | 2.87 |
| M15-933 | 353 | 170 | 57 | 1 | 581 | 5.81 |

TABLE 1.5

Capture Sample Unique CDR3 Calls

| Sample | alpha total unique CDR3 | beta total unique CDR3 | gamma total unique CDR3 | delta total unique CDR3 | total unique CDR3 | Unique CDR3 normalized to input |
|---|---|---|---|---|---|---|
| A037 healthy reference | | | | | | |
| Sample_A037_PBMC_TCR_A_all | 12 | 27 | 9 | 0 | 48 | 0.48 |
| Sample_A037_PBMC_TCR_B_all | 63 | 104 | 31 | 0 | 198 | 0.99 |

TABLE 1.5-continued

| | Capture Sample Unique CDR3 Calls | | | | | |
|---|---|---|---|---|---|---|
| Sample | alpha total unique CDR3 | beta total unique CDR3 | gamma total unique CDR3 | delta total unique CDR3 | total unique CDR3 | Unique CDR3 normalized to input |
| Sample_A037_PBMC_TCR_D_all | 229 | 188 | 65 | 2 | 484 | 0.81 |
| Sample_A037_PBMC_TCR_E_all | 1367 | 778 | 348 | 21 | 2514 | 3.14 |
| Sample_A037_PBMC_TCR_F_all | 2066 | 1100 | 540 | 24 | 3730 | 3.73 |
| Sample_A037_PBMC_TCR_G_all | 11 | 23 | 11 | 3 | 48 | 0.24 |
| Sample_A037_PBMC_TCR_H_all | 633 | 482 | 62 | 3 | 1180 | 1.97 |
| Sample_A037_PBMC_TCR_J_all | 216 | 104 | 48 | 4 | 372 | 1.86 |
| Sample_A037_PBMC_TCR_K_all | 297 | 14 | 82 | 5 | 532 | 0.89 |
| Sample_A037_PBMC_TCR_L_all | 242 | 99 | 63 | 8 | 412 | 0.41 |
| Sample_16_01_A037_PBMC_TCR_F_all | 482 | 229 | 155 | 14 | 880 | 1.76 |
| Sample_16_01_A037_PBMC_TCR_H_all | 555 | 330 | 158 | 4 | 1047 | 4.19 |
| Sample_A037_S1_all | 509 | 303 | 141 | 5 | 958 | 9.58 |
| Sample_A037_PBMC_15_all | 533 | 34 | 157 | 13 | 1053 | 10.53 |
| Sample_16_11_A037_PBMC_TCR_VJ_all | 293 | 142 | 114 | 8 | 557 | 5.57 |
| Sample_A037_CD3_15_all | 2840 | 1672 | 691 | 47 | 5250 | 52.50 |
| Cell lines and flow sorted | | | | | | |
| M36_EZM | 70 | 48 | 26 | 0 | 144 | 1.44 |
| M36_TIL2 | 310 | 25 | 101 | 2 | 435 | 4.38 |
| OV7-TIL2 | 219 | 92 | 83 | 9 | 503 | 5.03 |
| SE14-2005 | 32 | 29 | 21 | 0 | 82 | 0.82 |
| SE14-2033 | 32 | 21 | 10 | 0 | 63 | 0.63 |
| SE14-2034 | 10 | 66 | 8 | 0 | 84 | 0.84 |
| SE14-2035 | 33 | 39 | 23 | 0 | 95 | 0.95 |
| STIM1 | 160 | 36 | 55 | 0 | 351 | 3.51 |
| L2D8 | 14 | 21 | 10 | 0 | 45 | 0.45 |
| Patient samples | | | | | | |
| M14-10124 | 279 | 201 | 101 | 3 | 584 | 5.84 |
| M14-11153 | 151 | 80 | 54 | 2 | 287 | 2.87 |
| M14-11567 | 287 | 193 | 97 | 1 | 578 | 5.78 |
| M14-11587 | 41 | 57 | 30 | 0 | 128 | 1.28 |
| M14-11721 | 39 | 17 | 28 | 0 | 84 | 0.84 |
| M14-11770 | 14 | 16 | 11 | 0 | 41 | 0.41 |
| M14-12217 | 66 | 43 | 52 | 18 | 179 | 1.79 |
| M14-12649 | 206 | 185 | 89 | 1 | 481 | 4.81 |
| M14-12728 | 494 | 323 | 183 | 7 | 1007 | 10.07 |
| M14-12753 | 223 | 164 | 79 | 10 | 476 | 4.76 |
| M14-13167 | 55 | 23 | 32 | 6 | 116 | 1.16 |
| M14-13300 | 253 | 216 | 102 | 6 | 577 | 5.77 |
| M14-13750 | 516 | 313 | 167 | 20 | 1016 | 10.16 |
| M14-14570 | 35 | 40 | 34 | 8 | 117 | 1.17 |
| M14-14625 | 56 | 321 | 193 | 3 | 1079 | 10.79 |
| M14-14907 | 255 | 75 | 66 | 3 | 399 | 3.99 |
| M14-14951 | 76 | 47 | 42 | 2 | 167 | 1.67 |
| M14-14962 | 371 | 224 | 140 | 5 | 740 | 7.40 |
| M14-1508 | 448 | 314 | 163 | 8 | 933 | 3.33 |
| M14-15119 | 83 | 67 | 10 | 0 | 16 | 1.60 |
| M14-3271 | 1084 | 714 | 275 | 12 | 2085 | 20.85 |
| M14-4454 | 303 | 17 | 84 | 4 | 561 | 5.61 |
| M14-5819 | 57 | 31 | 40 | 1 | 129 | 1.29 |
| M14-5875 | 114 | 101 | 68 | 3 | 286 | 2.86 |
| M14-6143 | 308 | 14 | 108 | 1 | 557 | 5.57 |
| M14-6430 | 202 | 139 | 71 | 5 | 417 | 4.17 |
| M14-6443 | 0 | 0 | 0 | 0 | 0 | 0.00 |
| M14-6502 | 69 | 38 | 50 | 0 | 157 | 1.57 |
| M14-6885 | 613 | 381 | 164 | 3 | 1161 | 11.61 |
| M14-7046 | 177 | 78 | 72 | 3 | 330 | 3.30 |
| M14-7049 | 3 | 1 | 13 | 11 | 28 | 0.28 |
| M14-7053 | 162 | 109 | 79 | 10 | 360 | 3.60 |
| M14-7107 | 532 | 290 | 158 | 1 | 981 | 9.81 |
| M14-7554 | 189 | 129 | 78 | 13 | 409 | 4.09 |
| M14-7568 | 583 | 252 | 138 | 10 | 983 | 9.83 |
| M14-7691 | 317 | 301 | 99 | 0 | 717 | 7.17 |
| M14-7700 | 123 | 82 | 74 | 1 | 280 | 2.80 |
| M14-7782 | 166 | 125 | 75 | 4 | 370 | 3.70 |
| M14-7862 | 82 | 38 | 37 | 0 | 157 | 1.57 |
| M14-7884 | 181 | 125 | 102 | 0 | 408 | 4.08 |
| M14-7992 | 306 | 231 | 118 | 3 | 658 | 6.58 |
| M14-8132 | 37 | 34 | 33 | 3 | 105 | 1.05 |
| M14-8272 | 77 | 73 | 50 | 0 | 200 | 2.00 |
| M14-8639 | 140 | 99 | 65 | 8 | 312 | 3.12 |

TABLE 1.5-continued

Capture Sample Unique CDR3 Calls

| Sample | alpha total unique CDR3 | beta total unique CDR3 | gamma total unique CDR3 | delta total unique CDR3 | total unique CDR3 | Unique CDR3 normalized to input |
|---|---|---|---|---|---|---|
| M14-8668 | 45 | 35 | 26 | 0 | 106 | 1.06 |
| M14-8740 | 31 | 21 | 16 | 0 | 68 | 0.68 |
| M14-8913 | 114 | 78 | 53 | 5 | 250 | 2.50 |
| M14-8914 | 212 | 100 | 78 | 1 | 391 | 3.91 |
| M14-9212 | 224 | 168 | 85 | 3 | 480 | 4.80 |
| M14-9801 | 104 | 52 | 42 | 1 | 199 | 1.99 |
| M15-1195 | 48 | 36 | 32 | 0 | 116 | 1.16 |
| M15-1330 | 1469 | 619 | 279 | 15 | 2382 | 23.82 |
| M15-1470 | 57 | 44 | 50 | 0 | 151 | 1.51 |
| M15-1556 | 127 | 71 | 56 | 1 | 255 | 2.55 |
| M15-1825 | 259 | 147 | 108 | 2 | 516 | 5.16 |
| M15-1867 | 96 | 54 | 59 | 4 | 213 | 2.13 |
| M15-1883 | 520 | 284 | 120 | 11 | 935 | 9.35 |
| M15-237 | 58 | 45 | 32 | 0 | 135 | 1.35 |
| M15-2603 | 351 | 220 | 123 | 4 | 698 | 6.98 |
| M15-2779 | 408 | 247 | 123 | 7 | 785 | 7.85 |
| M15-3091 | 47 | 29 | 25 | 2 | 103 | 1.03 |
| M15-587 | 346 | 214 | 113 | 6 | 679 | 6.79 |
| M15-795 | 188 | 85 | 87 | 3 | 363 | 3.63 |
| M15-933 | 418 | 242 | 162 | 3 | 825 | 8.25 |

TABLE 2

Cell Line Identified VJ Rearrangements

| Cell Line | Internal | Reference Collection # | Alpha | Beta | Gamma | Delta |
|---|---|---|---|---|---|---|
| | | | | Previously Documented/Known TCR Configurations | | |
| CEM | SE14-2035 | ATCC CCL-119 | NA | TRBV3-1*01-TRBD1*01-TRBJ2-3*01 TRBJ1-5-TRBJ2-1 (partial rearrangement) TRBV9-TRBO2 (partial rearrangement) | TRGV3 TRG1/TRG2 TRGV4 TRG1/TRG2 | NA |

| | Observed | | | |
|---|---|---|---|---|
| | Alpha (Counts) | Beta (Counts) | Gamma (Counts) | Delta |
| | TRAV27#1TRU40#1 (987) | TRBV3 1#1TRB7 3#1 (1087) | TRGV4#2TRGJ2#1 (809) | ND |
| | TRAV29_DVS#1TRAJ4#1 (765) | TRAV3-2#3TRBJ2-3#1 (512) | TRGV3#2TRGJ2#1 (604) | |
| | TRAV29_DVS#3TRAJ4#1 (45) | TRAV3-2#3TRBJ2-4#1 (45) | TRGV3#1TRGJ2#1 (228) | |
| | TRAV27#3TRAJ40#1 (3) | TRBV3-1#1TRBJ2-5#J (8) | TRGVS#2TRGJ2#1 (106) | |
| | TRAV27#2TRAJ40#1 (1) | TRBV3-1#1TRBJ2-4#1 (4) | TRGV4#1TRGJ2# | |
| | TRAV8-G#2TRAJ20#1 (2) | TR8V3-1#1TRBJ2-6#1 (2) | | |
| | | TRBV3-2#3TRBJ2-6#1 (2) | | |
| | | TRBV9#2TRBJ2-1#1 (2) | | |

| | | | Previously Documented/Known TCR Configurations | | | |
|---|---|---|---|---|---|---|
| Jurkat | SE14-2033 | DSMZ ACC-282 | TRAV8-4 TRAJ3 | TRBV12-3 TRBJ1-2 (partial rearrangement) | TRGV8-TRG2 | NA |
| | | | | | TRGV-1 TRGJ | |

| | Observed | | | |
|---|---|---|---|---|
| | TRAV8-4#6TRAJ3#1 (1000) | TRBV12-4#1TRBJ3-2#1 (608) | TRGVB#1TRGJ2#3 | ND |
| | TRAV8-4#2TRAJ3#2 (118) | TRBV12-4#2TRBJ2-2#1 (137) | TRGV11#1TRGJ1#1 (272) | |
| | TRAV12-3#2TRAJ26#1 (16) | TRBV12-3#1TRB8J1-2#1 (16) | TRGV11#2TRGJ1#1 (202) | |

TABLE 2-continued

| | | | Cell Line Identified VJ Rearrangements | | |
|---|---|---|---|---|---|
| | | | TRAV17#1TRAJ24#2 (7) | | TRGV11#1TRGJ2#1 (12) |
| | | | TRAV17#1TRAJ16#1 (4) | | TRGV11#2TRGJ2#1 (1) |
| | | | TRAV17#1TRAJ29#1 (3) | | |
| | | | TRAV14_DV4#2TRAJ224#2 (2) | | |
| | | | TRAV26#2TRAJ29#1 (1) | | |
| | | | TRAV17#1TRAJ32#1 (1) | | |
| | | | TRAV29_DV5#1TRAJ4#1 (1) | | |
| | | | TRAV9-2#1TRAJ29#1 (1) | | |

| | | | Previously Documented/Known TCR Configurations | | |
|---|---|---|---|---|---|
| MCLT4 | SE14-2034 | ATCC CRB-1582 | NA | TRBV20-1*01-TRBD2*01-TRBJ2-1*01 | TRGV2-TRGIP1 TRGV2 TRGIP2 | NA |

| | | | | TRBV10-3-TRBD1*01-TRBJ2-5 Observed | | |
|---|---|---|---|---|---|---|
| | | | TRAV1-1#1TRAJ33#1 (799) | TRBY20-1#1TRBJ2-1#1 (937) | TRGV2#1 TRGJP2#1 (524) | ND |
| | | | TRAV1-1#1TRAJ23#2 (621) | TRBV10-3#2TRBJ2-5#1 (724) | TRGV2#2TRGIP1#1 (496) | |
| | | | TRAV1-1#2TRAJ24#2 (79) | TRBV20_DR9-283TR8J2-1#1 (384) | TRGV8#2TRGIP1#1 (1) | |
| | | | TRAV1-1#2TRAJ33#1 (1) | TRBV10-3#2TRBJ2-6#1 (91) | | |
| | | | | TR5V20-1#7TRBJ2-1#1 (8) | | |
| | | | | TR8V20_OR9-2#8THBJ2-2#2 (2) | | |
| | | | | TR8V20-1#1TRBJ2-2#1 (1) | | |
| | | | | TRBV20-1#3TR8J2-1#1 (1) | | |

| | | | Previously Documented/Known TCR Configurations | | |
|---|---|---|---|---|---|
| SUPT2 | SE14-2005 | ATCC CRL-1942 | NA | TRBV9*01-TRBD2*01-TRVJ-1*01 | TRGV3 TRGJ1/ TRGBJ2 | NA |

| | | | | | TRGV11-TRGJ1/TRG2 | |
|---|---|---|---|---|---|---|
| | | | | Observed | | |
| | | | TRAV1-1#3TRAJ12#1 (1120) | TRBV9#2TRBJ2-1#1 (971) | TRGV3#2TRGJ2#1 (683) | ND |
| | | | TRAV2-1#2TRAJ8#1 (836) | TRBV9#1TRBJ2-1#1 (137) | TRGV4#1TRGJ2#1 (449) | |
| | | | TRAV2-1#2TRAJ8#1 (263) | TRBV9#2TRBJ2-2#2 (9) | TRGV4#2TRGJ2#1 (367) | |
| | | | TRAV2-1#2TRAJ8#1 (263) | TRBV9#2TRBJ2-2#2 (9) | TRGV3#1TRGJ2#1 (198) | |
| | | | TRAV2-1#2TRAJ8#1 (263) | TRBV9#2TRBJ2-2#2 (9) | TRBV9#2TRBJ2-2#2 (9) | |
| | | | TRAV2-1#2TRAJ8#1 (263) | TRBV9#2TRBJ2-2#2 (9) | | |
| | | | | TRBV9#2TRBJ2-2#2 (9) | | |
| | | | | TRBV9#2TRBJ2-2#2 (9) | | |
| | | | | TRBV9#2TRBJ2-2#2 (9) | | |

Unique VJ TCR configurations correspond to sequences recorded at the following IMGT location:
www.imgt.org/IMGTrepertoire/Probes/Rearrangements%20and%20junctions/human/Hu_TRrea.html

TABLE 3

Sanger Sequencing Results

| Primer Combination | Expected PCR Product Size When Present (bp) ¥ | PCR & Electro- phoresis Result † | Reads with Detected Primer Combination | Total Number of Rearranged Reads Detected A037 | Reads on Target | Total Number of Input Reads | PCR & Electro- phoresis Result † | Reads with Detected Primer Combination | Total Number of Rearranged Reads Detected L2D8 | Reads on Target | Total Number of Input Reads |
|---|---|---|---|---|---|---|---|---|---|---|---|
| TRAV1-1 & TRAJ12 | 275 | Negative | 0 | 877 | 1155401 | 1370124 | Weak | 0 | 1384 | 985843 | 1182258 |
| TRAV1-1 & TRAJ33 | 282 | Weak | 0 | 877 | 1155401 | 1370124 | Weak | 0 | 1384 | 985843 | 1182258 |
| TRAV1-1 & TRAJ49 | 278 | Weak | 0 | 877 | 1155401 | 1370124 | Weak | 0 | 1334 | 985843 | 1182258 |
| TRAV12-2 & TRAJ45 | 285 | Weak | 0 | 877 | 1155401 | 1370124 | Negative | 0 | 1384 | 985843 | 1182258 |
| TRAV17 & TRAJ52 | 103 | Negative | 1 | 877 | 1155401 | 1370124 | Positive | 425 | 1384 | 985843 | 1182258 |
| TRAV27 & TRAJ17 | 326 | Negative | 0 | 877 | 1155401 | 1370124 | Negative | 0 | 1384 | 985843 | 1182258 |
| TRAV27 & TRAJ40 | 327 | Weak | 0 | 877 | 1155401 | 1370124 | Weak | 0 | 1334 | 985843 | 1182258 |
| TRAV29/DV5 & TRAJ26 | 327 | Negative | 0 | 877 | 1155401 | 1370124 | Negative | 0 | 1384 | 985843 | 1182258 |
| TRAV29/DV5 & TRAJ4 | 315 | Weak | 0 | 877 | 1155401 | 1370124 | Negative | 0 | 1384 | 985843 | 1182258 |
| TRAV35 & TRAJ48 | 333 | Negative | 0 | 877 | 1155401 | 1370124 | Positive | 316 | 1384 | 985843 | 1182258 |
| TRAV8-3 & TRAJ42 | 333 | Negative | 0 | 877 | 1155401 | 1370124 | Negative | 0 | 1384 | 985843 | 1182258 |
| TRBV10-3 & TRBJ2-5 | 296 | Negative | 0 | 877 | 1155401 | 1370124 | Weak | 0 | 1384 | 985843 | 1182258 |
| TRBV12-3 & TRBJ1-2 | 103 | Weak | 0 | 877 | 1155401 | 1370124 | Negative | 0 | 1384 | 985843 | 1182258 |
| TRBV18 & TRBJ2-2 | 264 | Negative | 0 | 877 | 1155401 | 1370124 | Negative | 0 | 1384 | 985843 | 1182258 |
| TRBV20-1 & TRBJ2-1 | 349 | Positive | 6 | 877 | 1155401 | 1370124 | Negative | 0 | 1384 | 985843 | 1182258 |
| TRBV5-7 & TRBJ2-2 | 133 | Weak | 0 | 877 | 1155401 | 1370124 | Negative | 0 | 1384 | 985843 | 1182258 |
| TRBV7-8 & TRBJ1-6 | 257 | Negative | 0 | 877 | 1155401 | 1370124 | Positive | 315 | 1384 | 985843 | 1182258 |
| TRBV7-8 & TRBJ2-5 | 240 | Weak | 2 | 877 | 1155401 | 1370124 | Negative | 0 | 1384 | 985843 | 1182258 |
| TRBV9 & TRBJ2-1 | 336 | Positive | 2 | 877 | 1155401 | 1370124 | Weak | 0 | 1384 | 985843 | 1182258 |
| TRGV11 & TRGJ1 | 297 | Negative | 8 | 877 | 1155401 | 1370124 | Negative | 0 | 1384 | 985843 | 1182258 |
| TRGV2 & TRGJP2 | 325 | Positive | 13 | 877 | 1155401 | 1370124 | Negative | 0 | 1384 | 985843 | 1182258 |
| TRGV3 & TRGJ1 | 241 | Weak | 3 | 877 | 1155401 | 1370124 | Positive | 0 | 1384 | 985843 | 1182258 |
| TRGV4 & TRGJ1 | 254 | Positive | 17 | 877 | 1155401 | 1370124 | Positive | 161 | 1384 | 985843 | 1182258 |
| TRGV8 & TRGJ1 | 263 | Positive | 8 | 877 | 1155401 | 1370124 | Negative | 4 | 1384 | 985843 | 1182258 |
| TRGV8 & TRGJP1 | 266 | Positive | 2 | 877 | 1155401 | 1370124 | Negative | 0 | 1334 | 985843 | 1182258 |
| TRGV9 & TRGJ1 | 182 | Positive | 9 | 877 | 1155401 | 1370124 | Negative | 0 | 1384 | 985843 | 1182258 |

| Primer Combination | Expected PCR Product Size When Present (bp) ¥ | PCR & Electro- phoresis Result † | Reads with Detected Primer Combination | Total Number of Rearranged Reads Detected EZM | Reads on Target | Total Number of Input Reads | PCR & Electro- phoresis Result † | Reads with Detected Primer Combination | Total Number of Rearranged Reads Detected TIL2 | Reads on Target | Total Number of Input Reads |
|---|---|---|---|---|---|---|---|---|---|---|---|
| TRAV1-1 & TRAJ12 | 275 | Negative | 0 | 115 | 1377194 | 1595646 | Negative | 0 | 2095 | 926207 | 1145281 |
| TRAV1-1 & TRAJ33 | 282 | Negative | 0 | 115 | 1377194 | 1595646 | Weak | 0 | 2095 | 926207 | 1145281 |
| TRAV1-1 & TRAJ49 | 278 | Negative | 0 | 115 | 1377194 | 1595646 | Weak | 0 | 2095 | 926207 | 1145281 |
| TRAV12-2 & TRAJ45 | 285 | Negative | 1 | 115 | 1377194 | 1595646 | Weak | 0 | 2095 | 926207 | 1145281 |
| TRAV17 & TRAJ52 | 103 | Negative | 0 | 115 | 1377194 | 1595646 | Negative | 0 | 2095 | 926207 | 1145281 |
| TRAV27 & TRAJ17 | 326 | Negative | 0 | 115 | 1377194 | 1595646 | Weak | 0 | 2095 | 926207 | 1145281 |
| TRAV27 & TRA140 | 327 | Weak | 0 | 115 | 1377194 | 1595646 | Weak | 0 | 2095 | 926207 | 1145281 |
| TRAV29/DV5 & TRAJ26 | 327 | Negative | 0 | 115 | 1377194 | 1595646 | Positive | 37 | 2095 | 926207 | 1145281 |
| TRAV29/DV5 & TRAJ4 | 315 | Negative | 0 | 115 | 1377194 | 1595646 | Negative | 0 | 2095 | 926207 | 1145281 |
| TRAV35 & TRAJ48 | 333 | Negative | 0 | 115 | 1377194 | 1595646 | Negative | 0 | 2095 | 926207 | 1145281 |
| TRAV8-3 & TRAJ42 | 333 | Negative | 0 | 115 | 1377194 | 1595646 | Negative | 0 | 2095 | 926207 | 1145281 |
| TRBV10-3 & TRBJ2-5 | 296 | Negative | 0 | 115 | 1377194 | 1595646 | Weak | 0 | 2095 | 926207 | 1145281 |
| TRBV12-3 & TRBJ1-2 | 103 | Negative | 0 | 115 | 1377194 | 1595646 | Negative | 0 | 2095 | 926207 | 1145281 |
| TRBV18 & TRBJ2-2 | 264 | Negative | 0 | 115 | 1377194 | 1595646 | Negative | 0 | 2095 | 926207 | 1145281 |
| TRBV20-1 & TRBJ2-1 | 349 | Negative | 0 | 115 | 1377194 | 1595646 | Weak | 8 | 2095 | 926207 | 1145281 |
| TRBV5-7 & TRBJ2-2 | 133 | Weak | 0 | 115 | 1377194 | 1595646 | Negative | 0 | 2095 | 926207 | 1145281 |
| TRBV7-8 & TRBJ1-6 | 257 | Negative | 0 | 115 | 1377194 | 1595646 | Negative | 0 | 2095 | 926207 | 1145281 |
| TRBV7-5 & TRBJ2-5 | 240 | Negative | 0 | 115 | 1377194 | 1595646 | Weak | 0 | 2095 | 926207 | 1145281 |
| TRBV9 & TRBJ2-1 | 336 | Weak | 0 | 115 | 1377194 | 1595646 | Weak | 6 | 2095 | 926207 | 1145281 |
| TRGV11 & TRGJ1 | 297 | Negative | 0 | 115 | 1377194 | 1595646 | Negative | 3 | 2095 | 926207 | 1145281 |
| TRGV2 & TRGJP2 | 325 | Positive | 6 | 115 | 1377194 | 1595646 | Positive | 10 | 2095 | 926207 | 1145281 |
| TRGV3 & TRGJ1 | 241 | Positive | 0 | 115 | 1377194 | 1595646 | Positive | 17 | 2095 | 926207 | 1145281 |
| TRGV4 & TRGJ1 | 254 | Positive | 3 | 115 | 1377194 | 1595646 | Positive | 56 | 2095 | 926207 | 1145281 |
| TRGV8 & TRGJ1 | 263 | Positive | 4 | 115 | 1377194 | 1595646 | Positive | 63 | 2095 | 926207 | 1145281 |
| TRGV8 & TRGJP1 | 266 | Weak | 0 | 115 | 1377194 | 1595646 | Positive | 0 | 2095 | 926207 | 1145281 |
| TRGV9 & TRGJ1 | 182 | Weak | 0 | 115 | 1377194 | 1595646 | Positive | 11 | 2095 | 926207 | 1145281 |

TABLE 3-continued

Sanger Sequencing Results

| Primer Combination | Expected PCR Product Size When Present (bp) ¥ | PCR & Electro-phoresis Result † | Reads with Detected Primer Combination | Total Number of Rearranged Reads Detected | Reads on Target | Total Number of Input Reads | PCR & Electro-phoresis Result † | Reads with Detected Primer Combination | Total Number of Rearranged Reads Detected | Reads on Target | Total Number of Input Reads |
|---|---|---|---|---|---|---|---|---|---|---|---|
| | | | | OV7 | | | | | STIM1 | | |
| TRAV1-1 & TRAJ12 | 275 | Negative | 4 | 2074 | 1379128 | 1675034 | Negative | 0 | 2796 | 1066413 | 1315476 |
| TRAV1-1 & TRAJ33 | 282 | Weak | 0 | 2074 | 1379128 | 1675034 | Negative | 0 | 2796 | 1066413 | 1315476 |
| TRAV1-1 & TRAJ49 | 278 | Weak | 0 | 2074 | 1379128 | 1675034 | Negative | 0 | 2796 | 1066413 | 1315476 |
| TRAV12-2 & TRAJ45 | 285 | Negative | 0 | 2074 | 1379128 | 1675034 | Weak | 238 | 2796 | 1066413 | 1315476 |
| TRAV17 & TRAJ52 | 103 | Weak | 0 | 2074 | 1379128 | 1675034 | Negative | 0 | 2796 | 1066413 | 1315476 |
| TRAV27 & TRAJ17 | 326 | Negative | 0 | 2074 | 1379128 | 1675034 | Negative | 0 | 2796 | 1066413 | 1315476 |
| TRAV27 & TRAJ40 | 327 | Negative | 0 | 2074 | 1379128 | 1675034 | Weak | 0 | 2796 | 1066413 | 1315476 |
| TRAV29/DV5 & TRAJ26 | 327 | Positive | 298 | 2074 | 1379128 | 1675034 | Negative | 2 | 2796 | 1066413 | 1315476 |
| TRAV29/DV5 & TRAJ4 | 315 | Negative | 0 | 2074 | 1379128 | 1675034 | Negative | 0 | 2796 | 1066413 | 1315476 |
| TRAV35 & TRAJ48 | 333 | Negative | 0 | 2074 | 1379128 | 1675034 | Negative | 0 | 2796 | 1066413 | 1315476 |
| TRAV8-3 & TRAJ42 | 333 | Negative | 0 | 2074 | 1379128 | 1675034 | Weak | 185 | 2796 | 1066413 | 1315476 |
| TRBV10-3 & TRBJ2-5 | 296 | Negative | 0 | 2074 | 1379128 | 1675034 | Negative | 0 | 2796 | 1066413 | 1315476 |
| TRBV12-3 & TRBJ1-2 | 103 | Weak | 0 | 2074 | 1379128 | 1675034 | Negative | 0 | 2796 | 1066413 | 1315476 |
| TRBV18 & TRBJ2-2 | 264 | Negative | 0 | 2074 | 1379128 | 1675034 | Negative | 0 | 2796 | 1066413 | 1315476 |
| TRBV20-1 & TRBJ2-1 | 349 | Negative | 1 | 2074 | 1379128 | 1675034 | Negative | 0 | 2796 | 1066413 | 1315476 |
| TRBV5-7 & TRBJ2-2 | 133 | Negative | 0 | 2074 | 1379128 | 1675034 | Negative | 0 | 2796 | 1066413 | 1315476 |
| TRBV7-8 & TRBJ1-6 | 257 | Negative | 0 | 2074 | 1379128 | 1675034 | Negative | 0 | 2796 | 1066413 | 1315476 |
| TRBV7-8 & TRBJ2-5 | 240 | Weak | 85 | 2074 | 1379128 | 1675034 | Negative | 0 | 2796 | 1066413 | 1315476 |
| TRBV9 & TRBJ2-1 | 336 | Positive | 0 | 2074 | 1379128 | 1675034 | Weak | 0 | 2796 | 1066413 | 1315476 |
| TRGV11 & TRGJ1 | 297 | Negative | 0 | 2074 | 1379128 | 1675034 | Negative | 23 | 2796 | 1066413 | 1315476 |
| TRGV2 & TRGJP2 | 325 | Weak | 0 | 2074 | 1379128 | 1675034 | Positive | 11 | 2796 | 1066413 | 1315476 |
| TRGV3 & TRGJ1 | 241 | Negative | 7 | 2074 | 1379128 | 1675034 | Positive | 13 | 2796 | 1066413 | 1315476 |
| TRGV4 & TRGJ1 | 254 | Weak | 5 | 2074 | 1379128 | 1675034 | Positive | 40 | 2796 | 1066413 | 1315476 |
| TRGV8 & TRGJ1 | 263 | Positive | 14 | 2074 | 1379128 | 1675034 | Positive | 24 | 2796 | 1066413 | 1315476 |
| TRGV8 & TRGJP1 | 266 | Positive | 197 | 2074 | 1379128 | 1675034 | Negative | 0 | 2796 | 1066413 | 1315476 |
| TRGV9 & TRGJ1 | 182 | Negative | 15 | 2074 | 1379128 | 1675034 | Positive | 120 | 2796 | 1066413 | 1315476 |

| Primer Combination | Expected PCR Product Size When Present (bp) ¥ | PCR & Electro-phoresis Result † | Reads with Detected Primer Combination | Total Number of Rearranged Reads Detected | Reads on Target | Total Number of Input Reads | PCR & Electro-phoresis Result † | Reads with Detected Primer Combination | Total Number of Rearranged Reads Detected | Reads on Target | Total Number of Input Reads |
|---|---|---|---|---|---|---|---|---|---|---|---|
| | | | | SE14-2005 (SUPT1) | | | | | SE14-2033 (Jurkat) | | |
| TRAV1-1 & TRAJ12 | 275 | Positive | 460 | 2371 | 837044 | 1096080 | Negative | 0 | 1554 | 817921 | 995632 |
| TRAV1-1 & TRAJ33 | 287 | Negative | 0 | 2371 | 837044 | 1096080 | Weak | 0 | 1554 | 817921 | 995632 |
| TRAV1-1 & TRAJ49 | 278 | Weak | 0 | 2371 | 837044 | 1096080 | Negative | 0 | 1554 | 817921 | 995632 |
| TRAV12-2 & TRAJ45 | 285 | Negative | 0 | 2371 | 837044 | 1096080 | Negative | 0 | 1554 | 817921 | 995632 |
| TRAV17 & TRAJ52 | 103 | Negative | 0 | 2371 | 837044 | 1096080 | Negative | 0 | 1554 | 817921 | 995632 |
| TRAV27 & TRAJ17 | 326 | Negative | 0 | 2371 | 837044 | 1096080 | Negative | 0 | 1554 | 817921 | 995632 |
| TRAV27 & TRAJ40 | 327 | Weak | 0 | 2371 | 837044 | 1096080 | Weak | 0 | 1554 | 817921 | 995632 |
| TRAV29/DV5 & TRAJ26 | 327 | Weak | 0 | 2371 | 837044 | 1096080 | Weak | 0 | 1554 | 817921 | 995632 |
| TRAV29/DV5 & TRAJ4 | 315 | Weak | 0 | 2371 | 837044 | 1096080 | Negative | 1 | 1554 | 817921 | 995632 |
| TRAV35 & TRAJ48 | 333 | Negative | 0 | 2371 | 837044 | 1096080 | Negative | 0 | 1554 | 817921 | 995632 |
| TRAV8-3 & TRAJ42 | 333 | Negative | 0 | 2371 | 837044 | 1096080 | Negative | 0 | 1554 | 817921 | 995632 |
| TRBV10-3 & TRBJ2-5 | 296 | Negative | 0 | 2371 | 837044 | 1096080 | Weak | 0 | 1554 | 817921 | 995632 |
| TRBV12-3 & TRBJ1-2 | 103 | Weak | 0 | 2371 | 837044 | 1096080 | Positive | 138 | 1554 | 817921 | 995632 |
| TRBV18 & TRBJ2-2 | 264 | Negative | 0 | 2371 | 837044 | 1096080 | Negative | 0 | 1554 | 817921 | 995632 |
| TRBV20-1 & TRBJ2-1 | 349 | Negative | 0 | 2371 | 837044 | 1096080 | Negative | 0 | 1554 | 817921 | 995632 |
| TRBV5-7 & TRBJ2-2 | 133 | Weak | 0 | 2371 | 837044 | 1096080 | Negative | 0 | 1554 | 817921 | 995632 |
| TRBV7-8 & TRBJ1-6 | 257 | Negative | 0 | 2371 | 837044 | 1096080 | Negative | 0 | 1554 | 817921 | 995632 |
| TRBV7-8 & TRBJ2-5 | 240 | Negative | 0 | 2371 | 837044 | 1096080 | Negative | 0 | 1554 | 817921 | 995632 |
| TRBV9 & TRBJ2-1 | 336 | Positive | 538 | 2371 | 837044 | 1096080 | Negative | 0 | 1554 | 817921 | 995632 |
| TRGV11 & TRGJ1 | 297 | Negative | 0 | 2371 | 837044 | 1096080 | Weak | 242 | 1554 | 817921 | 995632 |
| TRGV2 & TRGJP2 | 325 | Weak | 0 | 2371 | 837044 | 1096080 | Negative | 0 | 1554 | 817921 | 995632 |
| TRGV3 & TRGJ1 | 241 | Positive | 22 | 2371 | 837044 | 1096080 | Negative | 0 | 1554 | 817921 | 995632 |
| TRGV4 & TRGJ1 | 254 | Positive | 25 | 2371 | 837044 | 1096080 | Negative | 0 | 1554 | 817921 | 995632 |

TABLE 3-continued

| | | Sanger Sequencing Results | | | | | | | | |
|---|---|---|---|---|---|---|---|---|---|---|
| TRGV8 & TRGJ1 | 263 | Negative | 0 | 2371 | 837044 | 1096080 | Weak | 146 | 1554 | 817921 | 995632 |
| TRGV8 & TRGJP1 | 266 | Negative | 0 | 2371 | 837044 | 1096080 | Negative | 0 | 1554 | 817921 | 995632 |
| TRGV9 & TRGJ1 | 182 | Weak | 0 | 2371 | 837044 | 1096080 | Negative | 0 | 1554 | 817921 | 995632 |

| Primer Combination | Expected PCR Product Size When Present (bp) ¥ | PCR & Electro-phoresis Result † | Reads with Detected Primer Combination | Total Number of Rearranged Reads Detected | Reads on Target | Total Number of Input Reads | PCR & Electro-phoresis Result † | Reads with Detected Primer Combination | Total Number of Rearranged Reads Detected | Reads on Target | Total Number of Input Reads |
|---|---|---|---|---|---|---|---|---|---|---|---|
| | | | | SE14-2034 (MOLT4) | | | | | SE14-2035 (CEM) | | |
| TRAV1-1 & TRAJ12 | 275 | Negative | 0 | 1723 | 741549 | 906513 | Negative | 0 | 1744 | 981779 | 1283677 |
| TRAV1-1 & TRAJ33 | 282 | Positive | 347 | 1723 | 741549 | 906513 | Weak | 0 | 1744 | 931779 | 1289677 |
| TRAV1-1 & TRAJ49 | 278 | Negative | 0 | 1723 | 741549 | 906513 | Negative | 0 | 1744 | 981779 | 1289677 |
| TRAV12-2 & TRAJ45 | 285 | Negative | 0 | 1723 | 741549 | 906513 | Negative | 0 | 1744 | 981779 | 1289677 |
| TRAV17 & TRAJ52 | 103 | Negative | 0 | 1723 | 741549 | 906513 | Positive | 0 | 1744 | 981779 | 1289677 |
| TRAV27 & TRAJ17 | 326 | Negative | 0 | 1723 | 741549 | 906513 | Negative | 0 | 1744 | 981779 | 1289677 |
| TRAV27 & TRAJ40 | 327 | Negative | 0 | 1723 | 741549 | 906513 | Positive | 506 | 1744 | 981779 | 1289677 |
| TRAV29/DV5 & TRAJ26 | 327 | Negative | 0 | 1723 | 741549 | 906513 | Negative | 0 | 1744 | 981779 | 1289677 |
| TRAV29/DV5 & TRAJ4 | 315 | Negative | 0 | 1723 | 741549 | 906513 | Positive | 751 | 1744 | 981779 | 1289677 |
| TRAV35 & TRAJ48 | 333 | Negative | 0 | 1723 | 741549 | 906513 | Negative | 0 | 1744 | 981779 | 1283677 |
| TRAV8-3 & TRAJ42 | 333 | Negative | 0 | 1723 | 741549 | 906513 | Weak | 0 | 1744 | 981773 | 1289677 |
| TRBV10-3 & TRBJ2-5 | 298 | Positive | 379 | 1723 | 741549 | 906513 | Negative | 0 | 1744 | 981779 | 1289677 |
| TRBV12-3 & TRBJ1-2 | 103 | Negative | 0 | 1723 | 741549 | 906513 | Negative | 0 | 1744 | 981779 | 1289677 |
| TRBV18 & TRBJ2-2 | 264 | Negative | 0 | 1723 | 741549 | 906513 | Negative | 0 | 1744 | 981779 | 1289677 |
| TRBV20-1 & TRBJ2-1 | 349 | Positive | 551 | 1723 | 741549 | 906513 | Negative | 0 | 1744 | 981779 | 1289677 |
| TRBV5-7 & TRBJ2-2 | 133 | Negative | 0 | 1723 | 741549 | 906513 | Weak | 0 | 1744 | 981779 | 1289677 |
| TRBV7-8 & TRBJ1-6 | 257 | Negative | 0 | 1723 | 741549 | 906513 | Negative | 0 | 1744 | 981779 | 1289677 |
| TRBV7-8 & TRBJ2-5 | 240 | Negative | 0 | 1723 | 741549 | 906513 | Negative | 0 | 1744 | 981779 | 1289677 |
| TRBV9 & TRBJ2-1 | 336 | Negative | 0 | 1723 | 741549 | 906513 | Positive | 1 | 1744 | 981779 | 1283677 |
| TRGV11 & TRGJ1 | 297 | Negative | 0 | 1723 | 741549 | 906513 | Weak | 0 | 1744 | 981779 | 1289677 |
| TRGV2 & TRGJP2 | 325 | Positive | 275 | 1723 | 741549 | 906513 | Weak | 0 | 1744 | 981779 | 1289677 |
| TRGV3 & TRGJ1 | 241 | Negative | 0 | 1723 | 741549 | 906513 | Positive | 222 | 1744 | 981779 | 1289677 |
| TRGV4 & TRGJ1 | 254 | Negative | 0 | 1723 | 741549 | 906513 | Positive | 0 | 1744 | 981779 | 1289677 |
| TRGV8 & TRGJ1 | 263 | Negative | 0 | 1723 | 741549 | 906513 | Negative | 0 | 1744 | 981779 | 1289677 |
| TRGV8 & TRGJP1 | 266 | Negative | 0 | 1723 | 741549 | 906513 | Negative | 0 | 1744 | 981779 | 1289677 |
| TRGV9 & TRGJ1 | 182 | Negative | 0 | 1723 | 741549 | 906513 | Weak | 0 | 1744 | 981779 | 1289677 |

TABLE 4

| SEQ ID NO | Name | Sequence |
|---|---|---|
| SEQ ID NO: 1566 | TRAV10*02-RIGHT | caggtcgttttcttcattcctagtcgtcctgatagttatggttacctccttcacagagagctccagatgaaagactctgcctcttacttctgcctgt |
| SEQ ID NO: 1567 | TRAV1-2*02-RIGHT | catctgggttcaacggctgttctgtaccagcaacatgctggcgaagcaccacattctcgtcttacaatgttcctgattgtctggagagaaaggtcg |
| SEQ ID NO: 1568 | TRAV12-1*02-RIGHT | acagcacagtcaatagagccagccagtatatttccctgctcatcagagactccagctcagtgattcagcaccacctgtgtgttggtgaacattcgcc |
| SEQ ID NO: 1569 | TRAV12-2*02-RIGHT | gtttacagcacagctcaataaagccagccagtatgttctctgctcgtcctgatgactcccagccagtcagccacctgtgccgtgtaccac |
| SEQ ID NO: 1570 | TRAV12-2*03-RIGHT | aaggtttacagcacagtcaataaagccagccagtatgttctctgctcatcagagactcccagccagtcagccaccaccactctgtgccgtgaac |
| SEQ ID NO: 1571 | TRAV12-3*02-RIGHT | aggtttacagcacagtcgataaatccagccaagtatatctccttgttcatcagagactcagcgccagtcagccacctctgtgcaatgagcg |
| SEQ ID NO: 1572 | TRAV13-1*02-RIGHT | tgttacattgaacagacagccaaacattctccctgcacatcacagagaccaacgaattgctgttacattgaacaagacagccaaacattctccctgcagaaggac |
| SEQ ID NO: 1573 | TRAV1301*03-RIGHT | gcttattatagacattcgtcaaatgggcgaaagaaagaccaacatctctctcgcaaattgctagctcaacctggagactcagctgtctactttgtgcatcaca |
| SEQ ID NO: 1574 | TRAV13-2*02-RIGHT | caaagagtcaccgttattgaatagacagtgaaacatctctctccgccaacctggtcatctccgttcacaactggggactcagtcatatttcgtgagaga |
| SEQ ID NO: 1575 | TRAV14/DV4*03-RIGHT | aggtcgctactactcattgaattccagaaggcaagcaagaaatccgccaacctgtcatctccgttcacaactgggggactcagcaatgcaatg |
| SEQ ID NO: 1576 | TRAV14/DR4*04-RIGHT | gcaacagaaggtcgtactcfattgaattccagaaggcaagaaatccgccaacctgtctgttactactgtgctgtggtactttct |
| SEQ ID NO: 1577 | TRAV2*02-RIGHT | gggacgatacaacatgaacctgtctctttcatcgtcgtcatcccagtgcgggaggcagatgctgcttactactgtgctgtggcctgg |
| SEQ ID NO: 1578 | TRAV20*02-RIGHT | aaaagagaagaaaggctaaaagtccacattaacaaagaagaaagctttctgcacatcacagccctaaacctgaagactcagcaccttatctctgtgct |
| SEQ ID NO: 1579 | TRAV20*03-RIGHT | agaaaggagaagaaggctaaaagccacattaacaaagaagaaagctttctgcacatcacagccctaaacctgaagactcagcacttatctctgt |
| SEQ ID NO: 1580 | TRAV20*04-RIGHT | aaaggagaaagaaaggctaaaacacattaacaaagaagaaagctttctgcacatcacagccctaaacctgaagactcagcaccttatctctgtgct |
| SEQ ID NO: 1581 | TRAV21*02-RIGHT | aagtggaagactaatgcctgctgataatcatcaggacgtagttatacattgcagtctcagcctggctgactcagccacctacctctgtgct |

TABLE 4-continued

| SEQ ID NO | Name | Sequence |
|---|---|---|
| SEQ ID NO: 1582 | TRAV23/DV6*02-RIGHT | agattcacaatctccttcaataaagtgccaagcagtctcattgatcatcatggattcagcctcagccacctacttctgtgcagcaagcg |
| SEQ ID NO: 1583 | TRAV23/DV6*03-RIGHT | agattcacaatctccttcaataaagtgccaagcagtctcattgatcatcatggattcagcctcagccacctacttctgtgcagcaagca |
| SEQ ID NO: 1584 | TRAV23/DV6*04-RIGHT | gaaagaaggagattcacaatctccttcaataaagtgccaagcagtctcattgcatatcatggattcccagcctggagactcagccacctacttctgt |
| SEQ ID NO: 1585 | TRAV24*02-RIGHT | ggacgaataagtgccactcttaataccaaggaggttacagtctattgtacatcaaggatcccagcctgaagattcagccacataccctg |
| SEQ ID NO: 1586 | TRAV26-1*02-RIGHT | ctctgatcatcacagaagacagaaagtccagcacccttgatcctgcccacgtacgctgagagacactgctgtgtactattgcatcgtcagagattgggt |
| SEQ ID NO: 1587 | TRAV26-1*03-RIGHT | caatgaatgcctctctgatcatcacagaagacagaaagtccagcaccctgatcctgcccacgtacgctgagagacactgctgtgtactattgcatc |
| SEQ ID NO: 1588 | TRAV26-2*02-RIGHT | ccctcccagggtccagagtacgtgattcatggtcttacaagcaatgaacaacagaatggcctgtgtggcaatcgtgaagacagaaagtccagtacct |
| SEQ ID NO: 1589 | TRAV27*02-RIGHT | tgaagagactaaccttcagtttggtgatgcaagaaaggacagtctctccacatcactgctggtgcccagcctgatacaggccactacctcgtgcagg |
| SEQ ID NO: 1590 | TRAV27*03-RIGHT | gctgaagagactaaccttcagtttggtgatgcaagaaaggacagtctctccacatcactgctggtgatacaggcctctacctctgtgca |
| SEQ ID NO: 1591 | TRAV29/DV5*02-RIGHT | agattcactgctttctcttaaacaaaagtgccaagcacctctctctgacattgtgccctccagcctgcactgtgcctccagcctggagactgcagtgtacttctgtgcagcaagc |
| SEQ ID NO: 1592 | TRAV29/DV5*03-RIGHT | agattcactgctttctcttaaacaaaagtgccaagcacctctctctgacattgtgccctccagcctgcactgtgcctccagcctggagactgcagtgtacttctgtgcagtaagcg |
| SEQ ID NO: 1593 | TRAV3*02-RIGHT | ctttgagctgaattaacagagcaaacctcctccacctgaagaaccatctgccctgtgagcgactccgcttgtacttgtgtgtgagaccc |
| SEQ ID NO: 1594 | TRAV30*02-RIGHT | tcgtgaaaaatatctgcttcatttaatgaaaaaagcagcaaagtccctgtacctacggccctccccagctcagtacctcagtaccagacctacttct gcggg |
| SEQ ID NO: 1595 | TRAV30*03-RIGHT | tcatgaaaaatatctgcttcatttaatgaaaaaagcggcaaagtcccgtacctacggcctccagtcactcagtaccagaacctacttctgcggc |
| SEQ ID NO: 1596 | TRAV30*04-RIGHT | tcctgatattactgaaggtggagacagaagcgtcatgaaaaatatctgcttcatttaatgaaaaagcagcaaagtccctgtaccttacggc |
| SEQ ID NO: 1597 | TRAV35*02-RIGHT | aaatgaagactgactgctcagtttggtatcaccagaagaacttttcagcatcctgaatatctcagcattagtgatgaaggcatctactctgtgct |
| SEQ ID NO: 1598 | TRAV36/DV7*02-RIGHT | ggaagactaagtagcatattagataagaaagaaccggagaccggccgctctacctctggtgctgtgg |

TABLE 4-continued

| SEQ ID NO | Name | Sequence |
|---|---|---|
| SEQ ID NO: 1599 | TRAV36/DV7*03-RIGHT | gtcaggaagactaagtagcatattagataagaagaactttcagcatcctgaacatcacagccaccagaccgagactcggcgtctacctctgtgct |
| SEQ ID NO: 1600 | TRAV36/DV7*04-RIGHT | tcaggaagactaagtagcatattagataagaagaactttcagcatcctgaacatcacagccaccagaccgagactcggcgtctacctctgtgctg |
| SEQ ID NO: 1601 | TRAV38-1*02-RIGHT | gagaatcgttctctgtgaacttccagaaagcagccaaatccttcagtctccaagatctcagactcacagctgggggacactgcgatgtattctgc |
| SEQ ID NO: 1602 | TRAV38-1*03-RIGHT | aatcgttctctgtgaacttccagaaagcagccaaatccttcagtctccaagatctcagactcacagctgggggacactgcgatgtattctgtgctttca |
| SEQ ID NO: 1603 | TRAV38-1*04-RIGHT | ggagaatcgttctctgtgaacttccagaaagcagccaaatccttcagtctccaagatctcagactcacagctggggacactgcgatgtattctgtgca |
| SEQ ID NO: 1604 | TRAV6*02-RIGHT | gaagaaagactgaaggtcaccctttgataccaccctttaaacagagttgtttcatatcacagcctcccagcctgcagactcagactcctacctctgtgct |
| SEQ ID NO: 1605 | TRAV6*03-RIGHT | gaagaaagactgaaggtcaccctttgataccaccctttaaacagagttgtttcatatcacagcctcccagcctgcagactcagactcctacctctgtgct |
| SEQ ID NO: 1606 | TRAV6*04-RIGHT | gaaagaaagactgaaggtcaccctttgataccaccctttaaacagagttgtttcatgtcacagcctccccagcctgagactagctcagtcctacctctgtgct |
| SEQ ID NO: 1607 | TRAV6*05-RIGHT | gaaagaaagactgaaggtcaccctttgataccaccctttgataccaccctttaaacagagttgtttcatatcacagcctcccagcctgcagactcagactcctacctctgtgct |
| SEQ ID NO: 1608 | TRAV6*06-RIGHT | ccaggaagaggcccctgttttctgctactcatacgtgaaatgagaaagggtgaaatgagaaagagactgaaggtcacctttgataccaccctttaaccaga |
| SEQ ID NO: 1609 | TRAV8-1*02-RIGHT | tttcagggaatccactggtaaaggcatccaagggcgtgaggctgaattataagagtaaattctccttaatctgaggaaccctctgtgcagtgga |
| SEQ ID NO: 1610 | TRAV8-2*02-RIGHT | tttaagagagtgaaacctccttccacctgacgaaaccctcagccatgacgacggctgatctctgttgttgaccctcacgagctttcag |
| SEQ ID NO: 1611 | TRAV8-3*02-RIGHT | aggctttgaggctgaatttaagagagtcaatctctccttcaacctgaggaaaccctctgtgcattggagtgatgctgtagtacttctgtgtggtt |
| SEQ ID NO: 1612 | TRAV8-3*03-RIGHT | tattaaggctttgaggctgaattttaagagagtcaattctcctgacgaaaccctcctgtgcattggagtgatgctgtgagtacttctgtgct |
| SEQ ID NO: 1613 | TRAV8-4*02-RIGHT | gaatttaagagagtgaaacctcctccacctgacaaacctcagccatgacgacggctgatgctctgtgctgtgatctcgaaccga |
| SEQ ID NO: 1614 | TRAV8-4*03-RIGHT | catcaacggtttgaggctgaatttaagagagtgaaacctccttccacctgacgaaacctcagccccatatgagcgaccggctgagtactctgtgct |
| SEQ ID NO: 1615 | TRAV8-4*04-RIGHT | aggcatcaacggtttgaggctgaattaagaagagtgaaacctccttccacctgacgaaacccctcagcccactgacgaaccccctcagcccatatgagcgacgcggctgagtacttctctgt |

TABLE 4-continued

| SEQ ID NO | Name | Sequence |
|---|---|---|
| SEQ ID NO: 1616 | TRAV8-4*05-RIGHT | ggctgaatttaagaagagtgaacctcctccacctgacgaaacctcagccatatgagcgacgggctgagtacttctgtgctgtgagtgagtctcca |
| SEQ ID NO: 1617 | TRAV8-4*06-RIGHT | gaattaagaagagtgaacctcctccacctgacgaaacctcagccagcccatatgagcgacgacggtcggtgagtacttctgtgctgtgagtgatctcgaaccga |
| SEQ ID NO: 1618 | TRAV8-4*07-RIGHT | acggtttgaggctgaattaaaaggagtgaaacctccttccacttgacgaaaccctcagccatgaccgagaaccctcagcgaccggtgagtacttctgtgctgtgtgag |
| SEQ ID NO: 1619 | TRAV9-2*02-RIGHT | caacaaggtttgaagccacataccgtaagaaaccacttcttccacttggagaaaggctcagtcaagtcagactcagcggtacttctgtgct |
| SEQ ID NO: 1620 | TRAV9-2*03-RIGHT | caacaaggtttgaagccacatccgtaaggaaaccacttcttccacttggagaaggctcagtcaagtcagactcagcggtacttctgtgct |
| SEQ ID NO: 1621 | TRAV9-2*04-RIGHT | caacaaggtttgaagcccacataccgtaaggaaaccacttcttccacttggagaasaaggctcagtcagttcaagtgtcagactcagcggtgtacttctgtgct |
| SEQ ID NO: 1622 | TRBV10-1*03-RIGHT | ctaacaaaggagaagtctcagatggctacagtgtctctagatcaaacacagaggactccccctcactgtagtctgtgctcctccagacatctgt |
| SEQ ID NO: 1623 | TRBV10-2*02-RIGHT | agataaggagaagtcccgatgctacgttgtctccagatccaagacagagaattccccctcactctggagtcagtcagtaccgctaccccagacatctgtg |
| SEQ ID NO: 1624 | TRBV10-3*03-RIGHT | agaagtctcagatggctatagtgtctctagatcaaagacagaggattcctcctcactctggagtccgtctaccagctccagactctgtacttctgt |
| SEQ ID NO: 1625 | TRBV10-3*04-RIGHT | agaagtctcagatggctatagtgtctctagatcaaagacagaggattcctcctcactctggagtccgtctaccagctccagacatctgtacttctgt |
| SEQ ID NO: 1626 | TRBV11-2*02-RIGHT | ggatcgattttctgcagagaggctcaaaggagtagactccactccaagatccagctccaacctcgcaaagttgagaactcggccgtatctctgtgccagcagt |
| SEQ ID NO: 1627 | TRBV11-2*03-RIGHT | ggatcgattttctgcagagaggctcaaaggagtagactccactccaagatccaacctgcaaagctgaggactgccgtgtatctctgtgccagcagc |
| SEQ ID NO: 1628 | TRBV11-3*02-RIGHT | ggatcgattttctgcagagaggctcaaaggagtagactccactccaagatccagtctgcagagctgggactggactggactcctctgtgccagcagc |
| SEQ ID NO: 1629 | TRBV11-3*03-RIGHT | ggatcgattttctgcagagaggctcaaaggagtagactccactccaagatccagtctccaagaaccccaggactcagcgttgtacttctgtgccagcagc |
| SEQ ID NO: 1630 | TRVV12-4*02-RIGHT | tcgattctcagctaagatgccttaatgcatcattccacttgaggatgaacatgagtcctggagctggggactcccgagctgggactcagccctgtacttctgtgccagcagccagcagtgttta |
| SEQ ID NO: 1631 | TRBV13*02-RIGHT | tgatgcttccagtctcaacagttcagtgactactcattctgaactgatactctgaaggtgcaccctgtacttctgccagcagt |
| SEQ ID NO: 1632 | TRBV14*02-RIGHT | caatcgattctagctgaaggactggaggacgctattctactctgaaggtgcagcctgagaactggaggattgaggattcctgtgccagcagc |

TABLE 4-continued

| SEQ ID NO | Name | Sequence |
|---|---|---|
| SEQ ID NO: 1633 | TRBV15*02-RIGHT | tgataacttccaatccaggaggccgaacacttcttctgctttctgacatccgctcaccaggcctggggacgcagccatgtactgtgccaccagc |
| SEQ ID NO: 1634 | TRBV15*03-RIGHT | tgataacttccaatccaggaggccgaacacttcttctgctttctgacatccgctcaccaggcctggggacgcagccatgtaccagtgtgccaccagc |
| SEQ ID NO: 1635 | TRBV16*03-RIGHT | ggaaagatttcagtcaagtgcctcccaaattcaccctgagcctgagatccaggctacgaagttgaggattcagcagtgatttttgtgccagcagc |
| SEQ ID NO: 1636 | TRBV19*03-RIGHT | tgaaggtacagcgtctctcgggagaagaggaatccttctcctcactgtgacatcggccaaaagaaccgacagctttctatctctgccagtagc |
| SEQ ID NO: 1637 | TRBV2*02-RIGHT | tgatcaattccagtgaaggctgatggatcaaattcactctgaagatccggtcccacaaagtggaggactcagcagtactctgtgccagtgt |
| SEQ ID NO: 1638 | TRBV2*03-RIGHT | tcaattctcagtgagaggctgatgatcaaattcactctgaagatccggtcccacaaagtggaggactcagcagtactctgtgcagcagtgaa |
| SEQ ID NO: 1639 | TRBV20-1*02-RIGHT | gaaggacaagttctcatcaaccatgcaagcctgacctgtccactctgacagtgaccagtgccatcctgaagacagcagcttctacatctgcagtgct |
| SEQ ID NO: 1640 | TRBV20-1*04-RIGHT | ggacaagttctcatcaaccatgcaagcctgacctgtccactctgacagtgaccagtgccatcctgaagacagcagcttctacatctgcagtgctagt |
| SEQ ID NO: 1641 | TRBV20-1*05-RIGHT | ggacaagttctcatcaaccatgcaagcctgacctgtccactctgacagtgaccagtgccatcctgaagacagcagcttctacatctgcagtgctaga |
| SEQ ID NO: 1642 | TRBV20-1*06-RIGHT | gaaggacaagttctcatcaaccatgcaagcctgacctgtcccactctgacagtgaccagtgccatcctgaagacagcagcttctacatctgcagtgct |
| SEQ ID NO: 1643 | TRBV20-1*07-RIGHT | ggacaagttctcatcaaccatgcaagcctgacctgtccactctgatagtgaccagtgccatcctgaagacagcagcttctacatctgcagtgctaga |
| SEQ ID NO: 1644 | TRBV20/OR9-2*02-RIGHT | gaaggacaagttcccatcaaccatccaaacctgacctgtccgctcctgacctgcctgccatcctgaagacagcagcttctacatctgcagtgct |
| SEQ ID NO: 1645 | TRBV23/OR9-2*02-RIGHT | gtttttgatttcctttcagaatgaacaagttcttcaagaaatgaagatgcacaagaagcgattcctatcctcaatgccccaagaaccgcaccctgagcctg |
| SEQ ID NO: 1646 | TRBV24/OR9-2*02-RIGHT | cagttgatctattgcctttgatctcaaatatataaacaaaagagagatctcgatgatacagtgtcttgacagaacaggctaaattctcccctg |
| SEQ ID NO: 1647 | TRBV25/OR9-2*02-RIGHT | gagttaattccacagaagggagatctttgtctgagtcaacagtctccagaataaggatagagcgtttcccctgaccctggagtctgccagcccctc |
| SEQ ID NO: 1648 | TRBV29-1*02-RIGHT | tgacaagttcccatcagcgccccaaaccctaacattctcaagtctgactgtgagcaacatgagcctgaagacagcagcatatctctgcagcgttgaa |
| SEQ ID NO: 1649 | TRBV29-1*03-RIGHT | tgacaagttcccatcagccgcccaaaccctaacattctcaactctgactgtgagcaacatgagcctgaagacagcagcatatctctgcagcgcgggc |

TABLE 4-continued

| SEQ ID NO | Name | Sequence |
|---|---|---|
| SEQ ID NO: 1650 | TRBV3-1*02-RIGHT | tccaaatcgattctcacctaaatctccagacaaagctaaattcctgagcttggtgactctgtgtatttctgtgccagc |
| SEQ ID NO: 1651 | TRBV3-2*03-RIGHT | tcgcttctcacctgactctccagacaaagttcattaaatcttccatcaattcctgagcttgtgactctgtgtattctgtgcagcagccaa |
| SEQ ID NO: 1652 | TRBV30*02-RIGHT | agaatctcagcctccagacccccaggacccagtcatcctgagtctcctcctcagtgactctggcttctatctctgcctggagtgt |
| SEQ ID NO: 1653 | TRBV30*04-RIGHT | ccagaatctcagcctccagacccccaggacccagtcatcctgagtctcattctgagtctcttaagaagctcctccagtgactctggcttctatctctgcctggagt |
| SEQ ID NO: 1654 | TRBV30*05-RIGHT | ccagaatctcagcctccagacccccaggacccagtcatcctgagtctcatcctgagtctcttaagaagctcctccagtgactctggcttctatctctgcctgggga |
| SEQ ID NO: 1655 | TRBV4-1*02-RIGHT | tcgcttctcacctgaatgcccaacagctctcacttatgccttcacctacacgcccctacacactgcagcagaagactcagccctgtatctctgcagcagccaa |
| SEQ ID NO: 1656 | TRBV4-2*02-RIGHT | aagtcgttctcacctgaatgcccaacagctctcacttatgccttcacctacacctgcagcagaagactcagccctgtatctctgcagcagccacc |
| SEQ ID NO: 1657 | TRBV4-3*02-RIGHT | aagtcgttctcacctgaatgcccaacagctctcacttatccctcacctatcctcacttatccactacacccgcagcagaagactcggccctgtatctctgcgccagcgcagc |
| SEQ ID NO: 1658 | TRBV4-3*03-RIGHT | aagtcgttctcacctgaatgcccaacagctctcacttatccctcacttatccacttcttcacctacacacacccgcagcagagaactcggccctgtatctctgcgccagcgcagc |
| SEQ ID NO: 1659 | TRBV4-3*04-RIGHT | aagtcgttctcacctgaatgcccaacagctctcacttatccctcacttatcttcacctacacacacccgcagcagagaactcggccctgtatctctgcgccagcgcagc |
| SEQ ID NO: 1660 | TRBV5-1*02-RIGHT | tcgattctcagggcgccagtctctcaactctcgctctgagatgaatgtgagcacctggagctgggggactggagctgaacgccttatctttgccagcgcttgc |
| SEQ ID NO: 1661 | TRBV5-4*02-RIGHT | tcctagattctcaggtctccagtctccagtccctaattataactctgagctgaatgtgaacgccttggagctggacgactggacgcctgtatcctgtatccctgtatccctgtgccagcagc |
| SEQ ID NO: 1662 | TRBV5-4*03-RIGHT | tcctagattctcaggtctccagtctccagtccctaattatagctctgagctgaatgtgaacgccttggagtggacgactggagctgacctgtatctctgtgccagcagc |
| SEQ ID NO: 1663 | TRBV5-4*04-RIGHT | tcctagattctcaggtctccagtctccagtccctaattatagctctgagctgaatgtgaacgccttggagtggacgactggagctgacctgtatctctgtgccagcagc |
| SEQ ID NO: 1664 | TRBV5-1*02-RIGHT | tgatcgattctcagctcgccagtccctaactagctctgagctgaatgtgaacgccttgttgctgggggactggagctgacctgtatctctgtgccagcagc |
| SEQ ID NO: 1665 | TRBV5-5*03-RIGHT | tgatcgattctcagctcgccagtccctaactagctctgagctgaatgtgaacgccttgttgctgggggactggagctgacctgtatctctgtgccagcagc |
| SEQ ID NO: 1666 | TRBV5-8*02-RIGHT | tcctagattttcaggtcgccagtccctaattagctctgagctgaatgtgaacgccttggagctggagactggacctgtatctctgtgccagcagc |

TABLE 4-continued

| SEQ ID NO | Name | Sequence |
|---|---|---|
| SEQ ID NO: 1667 | TRBV6-2*02-RIGHT | tggctacaatgtctccagattaaaaaacagaattcctgctggggttcggctgcctcccctccaaacatctgtgtacttctgtgccagca gccct |
| SEQ ID NO: 1668 | TRBV6-3*03-RIGHT | gaatgctacaacgtctccagatcaaccacagaggatttccgcctcaggctgagttgctgtcctcccagacatctgtgtactctgtgcca gcagt |
| SEQ ID NO: 1669 | TRBV6-6*04-RIGHT | tggctacaatgtctccagatcaaccacagaggatttccgcctcaggctgagtgtggctgtccctcccagacatctgtgtactctgtgccagca gtcga |
| SEQ ID NO: 1670 | TRBV6-6*05-RIGHT | gaatgctacaacgtctccagatcaaccacagaggatttccgcctcaggctgagtggctgctgctcccagacatctgtgtactctgtgcca gcagc |
| SEQ ID NO: 1671 | TRBV6-2*03-RIGHT | gcttctctgcagagaggactgggatccgtctccactctgacgatccagcctgacatcagcgacacagaggactcggcctgtatctctgtaccagca gcttagc |
| SEQ ID NO: 1672 | TRBV7-2*04-RIGHT | tcgcttctctgcagagaggactgggatccgtctccactctgacatccagcctgacatccagcgacacagaggactcggccgtgtatctctgtgcagc agctta |
| SEQ ID NO: 1673 | TRBV7-3*04-RIGHT | cgatcggttctttgcagtcaggcctgagtcaggcctgagtctctactctgaagatccagaagatccagcgacacagaggactcagcctgtatctctgtgcca gcagc |
| SEQ ID NO: 1674 | TRBV7-3*05-RIGHT | cgatcggttctttgcagtcaggcctgagtcaggcctgagtctctactccgaagatccagaagatccagcgacacagaggactcagcctgtatctctgtgcc agcagt |
| SEQ ID NO: 1675 | TRBV7-4*02-RIGHT | aacgagacaaatcagggcgccagtggtcggtcggttctctgagagaggcctgagatcgtctccactccgaagatccagcgacacagagcag ggggactca |
| SEQ ID NO: 1676 | TRBV7-6*02-RIGHT | tgatcggttctctgcagagaggcctgagggatccatctccactctgacgatccagcgcacagagcagcgggactccggcctgtatcgtgcc agcagc |
| SEQ ID NO: 1677 | TRBV7-7*02-RIGHT | tgatcggttctctgcagagaggcctgagggatccatctccactctgacgattcagcgcacagagcagcgggactccagctcagcctgtatcgtgcc agcagt |
| SEQ ID NO: 1678 | TRBV7-8*03-RIGHT | tcgcttctctttgcagagaaggcctgagggatccgtctccactccacctgaagatccgaagatccgacacagagcagcgggactccgcctgtatctctgtgcagc agccga |
| SEQ ID NO: 1679 | TRBV7-9*02-RIGHT | tcggttctctgcagagaggcctaaggatctttccaccttggagatccgaaggatccgacacagagcagcggggactccggccatgtatctctgtgccagc agctta |
| SEQ ID NO: 1680 | TRBV7-9*04-RIGHT | tcggatctctgcagagaggcctaaggatctttccaccttggagatctctccaccttggagatccgacacagagcagcggggactccggccatgtatctctgtgccagc agctct |
| SEQ ID NO: 1681 | TRBV7-9*05-RIGHT | tcggttctctgcagagaggcctaaggatccttccaccttggagatctctccaccttggagatccgacacagagcagcggggactccggccatgtatctctgtgccagc accaaa |
| SEQ ID NO: 1682 | TRBV7-9*06-RIGHT | tcggttctctgcagaggcctaaggatctcttttccaccttggagatccgacacttggagatccgacacagagagcagggggactccggccatgtatctctgtgccagc acgttg |
| SEQ ID NO: 1683 | TRBV7-9*07-RIGHT | gttctctgcagaggcctaagggatcttcctccaccttggagatcagcgcacagagagcaggggggactccggccatgtatcctctgtgcagcagc agcagt |

TABLE 4-continued

| SEQ ID NO | Name | Sequence |
|---|---|---|
| SEQ ID NO: 1684 | TRBV9*03-RIGHT | tgaacgattccgcacacagttccctgactgactctgaactaaacctggactgcactgaactaaacctggagctctcggagctggggactcagcttgtattctgtgccagcagc |
| SEQ ID NO: 1685 | TRGV2*02-RIGHT | gaagtattatacttacgcaagcacaaggaacaactgagattgatactgcaaatctaattgaaatgactctgggtctcttactgtgccacctgggac |
| SEQ ID NO: 1686 | TRGV20-1*03-RIGHT | gaaggacaagttctcatcaaccatgcaagcctgacctgtccactcgacagtgaccagtgccatcctgaagacagcagctctacatctgcagtgct |
| SEQ ID NO: 1687 | TRGV6*01-RIGHT | gcatgtaacttatgaagtagaagataagctgaaattatacctccaaaactaatgaaaatgctctgggtctattactgtgccacctaggacagg |
| SEQ ID NO: 1688 | TRGV4*02-RIGHT | gtatgatacttacggaagcacaaggaagaacttgagaatgatactcgaaatcttattgaaaatgactctggagtctattactgtgccacctggatggg |
| SEQ ID NO: 1689 | TRGV5P*01-RIGHT | gtattactactcatacaccgaggaggtggagctggaatttgagactgcaaatgtcaattgaaaatgattctgggtctattactgtgccacctggggcagg |
| SEQ ID NO: 1690 | TRBV10-3*02-RIGHT | gctatagtgtctctagatcaaagacagagattcctcctcactctggatccgctaccagtcccagactctgtactctgtgccatcagtgagtc |
| SEQ ID NO: 1691 | TRBV24/OR9-2*01-RIGHT | atacagtgtctctcgacaggcacaggctaaattccctgtcctcagagtctgccatcccaaccagacagctcttactctgtgccaccagtgatttg |
| SEQ ID NO: 1692 | TRBV20/OR9-2*01-RIGHT | acaagttccatcaaccatccaaacctgaccttctccgctctgacagtgaccagtgccatcctgaagacagcagcttctacatctgcagtgctagaga |
| SEQ ID NO: 1693 | TRGV11*01-RIGHT | ggtaagtaaaaatgctcacactctccactccactttgaaaataagttctctagagaaagaagatgaggtggtaccactgtgctgctggattaggcac |
| SEQ ID NO: 1694 | TRBV7-8*02-RIGHT | gctccttgcgaaagccctgagggctccagccgtctcgagggatccgcgcacagaggaggactccgcgtatctctgtgccagcagcttagc |
| SEQ ID NO: 1695 | TRBV7-3*02-RIGHT | ggttcctgcagtcaggcctgagggatccgcctgtctctactctgaagatccagccagacagcaggggactgcagggtatccgtgccagcttaac |
| SEQ ID NO: 1696 | TRGV10*01-RIGHT | aggcaagaagaattctcaaactctcactcttacatcttaccatcttcaccattcacaatgtagagaaacaggacatagctacctactgtgtcgttactactgcgttattactacctgtgtgtggtgggc |
| SEQ ID NO: 1697 | TRGV9*02-RIGHT | tgaggtggataggatacctgaaacgtctaaaacctgaaacaatgtagagaaacaggacagaaactatgtaggactggaagacagtgccactactgtgtggagtg |
| SEQ ID NO: 1698 | TRDV3*02-RIGHT | gacggtttctgtgaacacattctgaccagagctttcactggtgatctctccagtaaggactgaagacagtgccactactgcctttag |
| SEQ ID NO: 1699 | TRDV2*02-RIGHT | aattccaaggtgacattgatattgcaaagaacctggctgtacttaagatacttcaccatcagagagatactgtgacttactactgtgcctgtgaca |
| SEQ ID NO: 1700 | TRGV3*02-RIGHT | agtattatactcatcacacccaggaggtggagctgatattgagactgcaaatctaattgaaaatgattctgggtctattactgtgccacctgggacag |

TABLE 4-continued

| SEQ ID NO | Name | Sequence |
|---|---|---|
| SEQ ID NO: 1701 | TRDV2*01-RIGHT | tttccaaggtgacattgatattgcaagaacctggctgctactaagatactgcactaagatactactcagagagagatgaagggtcttactactgtgctgtgacacc |
| SEQ ID NO: 1702 | TRBV19*02-RIGHT | ggtacagcgtctctcgggaagaaggaatccttccttcctcactgacatcggccaaagaaccgacagttctatctctgtgccagtagtataga |
| SEQ ID NO: 1703 | TRAV14/DV4*01-RIGHT | actcattgaatttccagaaggcaagaaaatccgcaaccctgtcatctccgcttcacaactggggactcagcaatgtactctgcaatgagagaggg |
| SEQ ID NO: 1704 | TRBV3-2*02-RIGHT | gcttctcacctgactctccagacaagtcattaaatctcacatcatttaaatctcctgagctggtgactctgtgtatttctgtgccagcagcaaga |
| SEQ ID NO: 1705 | TRGV10*02-RIGHT | tggagcaagaaagaattctcaaactctcacttcatcctccatcaagtccgtagagaagaagacatggccgttactactgtgctgcgtgggatta |
| SEQ ID NO: 1706 | TRAV11*01-RIGHT | caaatatttaaagactgctggaaagaaaattttatagtgttggaatatcgcagctctcatctggagattcagcacctacttctgtgcttg |
| SEQ ID NO: 1707 | TRBV5-2*01-RIGHT | aactgcctaattgattctcgctcaccagtccataactattactgagtcaaaacgagctaggggactcagcctgtatctctgtgccagcaacttg |
| SEQ ID NO: 1708 | TRBV8-1*01-RIGHT | ggaaggtacaatgtctctgaaacaagctcaagcattctccctcaaccctggagtctacagcagcagaccctctgtacctctggcagtgcatc |
| SEQ ID NO: 1709 | TRAV38-1*01-RIGHT | tctctgtgaacttccagaaagcagccaaatccctcagtctccaagatctcagactcatagctggggacactgcgatgtatttctgttttcatgaagca |
| SEQ ID NO: 1710 | TRAV22-1*01-RIGHT | aggctacgtgctctgccaagaggagaagggctatttcttctcagggtgaagttggccccaaccagccaaacagcttgtgtactctgtcctggagcgac |
| SEQ ID NO: 1711 | TRBV16*01-RIGHT | gatttcagctaagtgcctcccaaattcacctgagcttgagatccaggctacgaagcttgagattcagcagtgatttttgccagcagccaatc |
| SEQ ID NO: 1712 | TRBV30*01-RIGHT | agaatctcagcctcagccccaggacccccaggagcccaaacctccttccacctgagttctaagaagctcccttctcagtgactactctgcctggagtgt |
| SEQ ID NO: 1713 | TRAV3*01-RIGHT | tttgaagctgattaacaagagcaagaaatccaacaccctgatcctgcccacgtgagagacactgtgtgactcctgtacttctgtgtgagagaca |
| SEQ ID NO: 1714 | TRAV26-1*01-RIGHT | gcctctctgatcatcagaagacagaagtctaataaatgctaaacatgtctcctgatattacagccacccaaccaggagactcattcctgtacttctgtgcagtgagttg |
| SEQ ID NO: 1715 | TRAV32*01-RIGHT | aggctcactgctgaactttgaataaaagaaaaagttcatcaacttccttaaaactgactcagcagctacttcctgtgtacttctgtgcagtgagaa |
| SEQ ID NO: 1716 | TRAV33*01-RIGHT | gcaaagcctgtgaactttgaaaagaaaagtcatcaacctcaccatccaccatccttaaaactgactcagcagtactcagccctgtacttctgtgctctcaggaatcc |
| SEQ ID NO: 1717 | TRBV13*801-RIGHT | gattctcagctcaacagtcagtgactatcattctgaactgaacatgaactgacctcccttggagctggggactcagccctgtacttctgtgcagcagcttagg |

TABLE 4-continued

| SEQ ID NO | Name | Sequence |
|---|---|---|
| SEQ ID NO: 1718 | TRBV15*01-RIGHT | acttccaatccaggaggccgaacacttcttctgctttcttgacatccgtcttcaccaggcctggggacacagcctgtacctgtgccaccagcagaga |
| SEQ ID NO: 1719 | TRAV2*01-RIGHT | agggacgatacaacatgaccctatgaacggttctctcttcatgctgtcgctgctctccagtgcgggaggcagatgctgttactactgctgtggagga |
| SEQ ID NO: 1720 | TRBV7-1*01-RIGHT | ggttcctgcacagaggtctgagggatccactctccactctgaagttccagcgcacacagcaggggactggctgtgtatctctgtgccagcagctcagc |
| SEQ ID NO: 1721 | TRBV23-1*01-RIGHT | gattcatctcaatgcccaagaacgcaccctgcgcctggcaatcctgtcctcagaacccggagacacgcactgtatctctgccagcagtcaatc |
| SEQ ID NO: 1722 | TRBV23/OR9-2*01-RIGHT | gatgcacaagaagcgattctcatctcaatgcccaagaaccaccctgcagcctggcaatcctgtcctcggaaccggagacaccgcactgtatctctgt |
| SEQ ID NO: 1723 | TRBVA*01-RIGHT | tccctattgaaatatttcctggcaaaaatagaagttctctttggctctgaaatctgcaactcccttcaggtgtccctgtcctgtactgcactgcactc |
| SEQ ID NO: 1724 | TRBVA/OR9-2*01-RIGHT | tccctgtgaaatatttcccggcaaaaaacagaagttccctttggctctgaaatctgcagacctgaggatccagccatgggacctatattctgtgccagcactc |
| SEQ ID NO: 1725 | TRBV12-1*01-RIGHT | gattccagcacagatgcctagtcttcccactctgaggatccagccatgggacctatattctgtgccagcagtttgc |
| SEQ ID NO: 1726 | TRBV26/OR9-2*01-RIGHT | ggtatcatgtttcttgaaatactataagcatctttctcctgaccctgaagtctgctcagcaacccagagacatgtgtatctctgccagcagttcatc |
| SEQ ID NO: 1727 | TRGV9*01-RIGHT | tgaggtggataggatacctgaaacgtctacactccactccaccattcacaatgtagagaaacaggacatagactacctactgtgcctgtgggaggtg |
| SEQ ID NO: 1728 | TRGVB*01-RIGHT | cttgagcaagaacaaatttcaaatgtctactcagtctttaccataaacttcataggaaaggaagatgaggccattactactgcacctgttaggacc |
| SEQ ID NO: 1729 | TRBV7-3*01-RIGHT | ggttctttgcagtctcaggcctgaggatccagccatgggacctctctactctgaagatccagccagccgtgtatctctgtgccagcagcttaac |
| SEQ ID NO: 1730 | TRBV7-9*01-RIGHT | ggttcctgcagagaggatctggggatctttcctcaccttggagatccagccagtgacctgagatcagcccatgtatctctgtgccagcagcttagc |
| SEQ ID NO: 1731 | TRBV7-2*01-RIGHT | gcttcctgcagagaggacctggggatcgggatccagccgtctcacactctgacgatccagccgccacagcaggagactcggcgtatctctgtgccagca |
| SEQ ID NO: 1732 | TRBV7-2*02-RIGHT | gcttcctgcagagaggactggggatctgggatccagccgtctcacactctgacgatccagccgccacagcaggagactcggcgtatctctgtgccagcagcttagc |
| SEQ ID NO: 1733 | TRBV7-7*01-RIGHT | ggttcctgcagagagggctgagggatccgtcgaggatccactctcgacgattcagcgcacagagcgcggactcagcgtatctgtgccagcagcttagc |
| SEQ ID NO: 1734 | TRBV7-8*01-RIGHT | gcttctttgcagaaaggcctgagggatccgtctccactctgaagatccagccgcacatagcaggaggactccgcgtatctctgccagcagcttagc |

TABLE 4-continued

| SEQ ID NO | Name | Sequence |
|---|---|---|
| SEQ ID NO: 1735 | TRBV17*01-RIGHT | aacgattcacagctgaaagacctaacgaacgtcttccacgtgaagatccatcccgcagagccgaggactcagccgtgatcctcacagtagcggtgg |
| SEQ ID NO: 1736 | TRBV5-8*01-RIGHT | agatttcagtcgccagtccctaattatagctctgagctgaatgtgaacgcctggagctggaggactcggcctgtatctctgtgccagcagttgg |
| SEQ ID NO: 1737 | TRBV5-7*01-RIGHT | caattcagtcaccagtccctaactatagctctgagctgaatgtgaacgcctgttgctgggggactcggcctgtatctctgtgccagcagttgg |
| SEQ ID NO: 1738 | TRBV5-6*01-RIGHT | cgattccagtcaccagtccctaactatagctctgagctgaatgtgaacgcctgttgctggggactcggcctgtatctctgtgccagcagttgg |
| SEQ ID NO: 1739 | TRBV5-5*01-RIGHT | cgattccagctcgccagtccctaactatagctctgagctgaatgtgaacgcctgttgctgggggactcggcctgtatctctgtgccagcagttgg |
| SEQ ID NO: 1740 | TRBV5-4*01-RIGHT | agattccagtctccagtccctaattatagctctgagtgaatgtgaacgtggagctggacgactcggcctgtatctctgtgccagcagtttgg |
| SEQ ID NO: 1741 | TRBV-1*01-RIGHT | cgattccagggcgccagtctctaactctcgctcgagatgaatgtgagcacctggagctggggggactcggccctttatcttgcgcagcagcttgg |
| SEQ ID NO: 1742 | TRBV3-1*01-RIGHT | gcttccacctaaatccagacaaagctcactaaatcttcacatcaattccctggagctggtgactctgctgtgtattctgtgccagcagccaaga |
| SEQ ID NO: 1743 | TRBV1*01-RIGHT | acttcacacctgaatgccctgacagctccgcttatacctcatggtcgcactgcagctgcgtatctctgcaccagcagcaaga |
| SEQ ID NO: 1744 | TRBV5-3*01-RIGHT | cgattccagggcgccagtccatgactgttgctctgagatgaatgtgagtgcctggagctggggactcggccctgtatctctgtgccagcagaag |
| SEQ ID NO: 1745 | TRBV5-3*02-RIGHT | cgattccagggcgccagtccatgactattgctctgactgaatgaatgtgagtgcctggagctggggactcggccctgtatctctgtgccagcagaag |
| SEQ ID NO: 1746 | TRBV9*01-RIGHT | cgattccgcacacagtccctgactgcctgaactaaacctgagctctcggagctggggagctggggactcggccctgtattctgtgccagcagccgtag |
| SEQ ID NO: 1747 | TRBV3-2*01-RIGHT | gcttccacctgactctccagacaaagctcattaaatctcacttattcctcacctcgaagatccggtccacacacccctggagctggtgactctgctgtgtatttctgtgccagcagccaaga |
| SEQ ID NO: 1748 | TRBV2*01-RIGHT | aatttcagtgaaaggcctgatgaaccaaattcactcagctcctcacttattccttcacctcaaaagtggaggactcagaaaccctggagactcggccatgtactctgtgccagcagtgaagc |
| SEQ ID NO: 1749 | TRBV4-3*01-RIGHT | gcttctcacctgaatgcccaacagtgccccaacagtctctcttcacctacacacccctgcagcagagactcggcccctgtatctctgcgccagcagcaaga |
| SEQ ID NO: 1750 | TRBV4-1*01-RIGHT | gcttctcacctgaatgcccaacagtgccccaacagtctctcttaaacctcacctactacacccctgcagcagagactcggcccctgtatctctgcgccagcagcaaga |
| SEQ ID NO: 1751 | TRBV4-2*01-RIGHT | gcttctcacctgaatgcccaacagtgcctcacttattcctcacctacacaccctgcagcagaagactcggcccctgtatctctgcgccagcagcaaga |

TABLE 4-continued

| SEQ ID NO | Name | Sequence |
|---|---|---|
| SEQ ID NO: 1752 | TRAV34*01-RIGHT | aagataactgccaagttggatgagaaagcagcaaagttccctgcgatatcacagcctcccagccatgcaggcatctacctctgtgagcagaca |
| SEQ ID NO: 1753 | TRBV28*01-RIGHT | ggtacagtgctcagagagaagaggagcgcttctccctgattctggagtccgcagcaccaacagacatctatgtacctctgtgccagcagtttatg |
| SEQ ID NO: 1754 | TRBV20-1*01-RIGHT | acaagttcctcatcaaccatgcaagcctgaccttgtccactctgacagtgaccagtgcccatctgaagacagcagcttctacatctgagtgctagaga |
| SEQ ID NO: 1755 | TRBV20/OR9-2*03-RIGHT | acaagttcccatcaaccatccaaacctgaccttctccgctgacagtgaccagtgcccatctgaagacagcagcttctacatctgagtgctagaga |
| SEQ ID NO: 1756 | TRBV6-6*02-RIGHT | gaatgctacaacgtctccgatcaaccacagaggattccccgctcaggctggtgtcctcccagactctgacttctgtgccagtgcagt |
| SEQ ID NO: 1757 | TRBV6-6*01-RIGHT | gctacaacgtctccgatcaaccacagaggattccccgctcaggctggtgtgctcctgcgtcctcccagacatctgtgtacttctgtgccagcagtactc |
| SEQ ID NO: 1758 | TRBV6-5*01-RIGHT | gctacaatgtctccagatcaaccacagaggattccccgctcaggctgtgctcggctcggtgctgctcctgctcctcccagacatctgtgtacttctgtgccagcagtt |
| SEQ ID NO: 1759 | TRBV6-8*01-RIGHT | gctacaatgtctctagattaaacagagaggatttccccgctcaggctgtgctcggctcggtgctgctcctgctcctcccagacatctgtgtactgtgccagcagtt actc |
| SEQ ID NO: 1760 | TRBV6-9*01-RIGHT | gctacaatgtatccagatcaaaacagagaggattcccgctcaggctgtgctcggctcagtgctgctcctgctcctcccagacatctgtatacttctgtgccagcagt tattc |
| SEQ ID NO: 1761 | TRBV6-7*01-RIGHT | gctacaatgtcttcagatcaaacagagaggatttccccccaagtggagtcagtgctgctcctctgagattctgtttacttctgtgccagcagt actc |
| SEQ ID NO: 1762 | TRBV12-3*01-RIGHT | gattccagctaagctgcctaatgcatcattctccactctgaagatccagccctgaagacccaggagactcagtgtgtactctgtgccagcagt ttagc |
| SEQ ID NO: 1763 | TRBV12-4*01-RIGHT | gattccagctaagctgcctaatgcatcattctccactctgaagatctccactctgaagatccagccctgaagaaccagcagtgtgactctgtgccagcagt ttagc |
| SEQ ID NO: 1764 | TRBV12-5*01-RIGHT | gattccagcagagatgcctgatgcaacttagcactcagctccactctgaagatccagccctgaagaaccagggactcagctgtgtattttgtagtggt ttggt |
| SEQ ID NO: 1765 | TRBV12-2*01-RIGHT | gattccagctgagaggcctgatgatcattctccactctgaagatccagccctgaagactccagccctgagagaggcaggagggactccggccgtgatgtctgcaagtcg cttagc |
| SEQ ID NO: 1766 | TRBV6-1*01-RIGHT | gctacaatgtctccagattaaacaacggagttctcgctcaggcggagtcggctcggtgctcctcccagacactgtgagtcagctgtgtactctgtgccagcagt gaagc |
| SEQ ID NO: 1767 | TRBV7-4*01-RIGHT | ggttcctgcagagaggcctgagagatccgtctctccactctgaagatccagcagcagtgtgtatctctgccagca gcttagc |
| SEQ ID NO: 1768 | TRBV7-5*01-RIGHT | tcaattctccacagagagtctgaggatctttctccacctgaagatccagagcgcacagagcaagggcgactcggctgtgtatctctgtgccagaa gcttag |

TABLE 4-continued

| SEQ ID NO | Name | Sequence |
|---|---|---|
| SEQ ID NO: 1769 | TRAV20*01-RIGHT | aagaaaggctaaaagccacattaacaagaaggaagcttctgcacatcacagccccctaaacctgaagactcagccacttatctctgtct gtgcagg |
| SEQ ID NO: 1770 | TRBV11-1*01-RIGHT | gattttctgcagagaggctcaaaggagtagactccactctcaagatccagctgagactgggactggcctgatgtatctctgcagcag cttagc |
| SEQ ID NO: 1771 | TRAV15*01-RIGHT | acatttaaagaagcgcttggaaaagagaagtttatagtgtttgaatatgctgtctctcatcctggagattcaggcaccacttctgcttt gagg |
| SEQ ID NO: 1772 | TRAV7*01-RIGHT | aaaggaagactaaatgctacattactgaagaatgaagcagttgtacattacagccgtgcagcctgaagattcagccacctattctgctg tagatg |
| SEQ ID NO: 1773 | TRAV16*01-RIGHT | gcttcactgctgacctaacaaaggcgagacatcttttccactgaagaaaccattgctcaagaggaagactcagccatgtattactgtctct aagtgg |
| SEQ ID NO: 1774 | TRAV6*01-RIGHT | agactgaagtgcaccttttgataccaccccctaaacagagttgttctcatatacagactcagctactacctctgtctcta gaga |
| SEQ ID NO: 1775 | TRBV19*01-RIGHT | ggtacagcgtctctcggagagaaggaatcctttcctctcactgtgacatcggccaaagaaccgacagttctatcctgtgccagtag tataga |
| SEQ ID NO: 1776 | TRAV14/DR4-02-RIGHT | actcattgaattccagaaggcaagaaatccgccaacctgtcatctccgcttcacaactggggactcagcaatgtattctgcaatgag agaggg |
| SEQ ID NO: 1777 | TRAV9-1*01-RIGHT | gttttgaagccatgtaccgtaaagaaccactctctttccactggagaagactcagttcaagatcagacagactccgtgtacttctgtgctctg agtga |
| SEQ ID NO: 1778 | TRAV9-2*01-RIGHT | gtttgaagccacacataccgtaagaacccactctcttcccactggagaaaggctcagtcagtgtcagactcagcggtgtacttctgtgctctg agtga |
| SEQ ID NO: 1779 | TRAV1-1*01-RIGHT | gtttttcttcattcctagctcgctctgatagtcctcctctacaggagtccagatgaaagactctgccccttacttctgcgctgtgaga ga |
| SEQ ID NO: 1780 | TRAV38-8*01-RIGHT | ttctctgtgacttccagaagcagccaaatcctcagtctccagatctcagactcacagtggggatgcgcgatgtattctgcttatag gagcg |
| SEQ ID NO: 1781 | TRAV19*01-RIGHT | attcttggaacttccagaaatccagcagtcctccttcaacttcattatcacagcccctcaacttcagcagtatacttctgcttgagtg aggc |
| SEQ ID NO: 1782 | TRAV30*01-RIGHT | aaaatatctgcttcattaatgaaaaaagcagcaagccccgtaccttacggctccagtactcaggacctactctgcggca cagaga |
| SEQ ID NO: 1783 | TRGV7*01-RIGHT | agtatttacttatgcaagcatgaggaggctggaaatgatactgcaaatcttattgaaatgattgagactgcaaatctaattaaaaagattgtgccacctggg acagg |
| SEQ ID NO: 1784 | TRGV1*01-RIGHT | aaagtatgacactggaagcacaaagcaattggaattgagactgcaaatctaattaaaatcaattaaaaagattgtctattactgccacctgg gacagg |
| SEQ ID NO: 1785 | TRGV3*01-RIGHT | gtattataccatacacccaggaggtggagctggatattgagactgcaaatctaattgaaaatgattctgggtctattactgccacctgg gacagg |

TABLE 4-continued

| SEQ ID NO | Name | Sequence |
|---|---|---|
| SEQ ID NO: 1786 | TRGV5*01-RIGHT | gtattaactcatacaccaggaggtggagctggatattgatactgaaaatgattctgggtctattactgtgccacctgggacagg |
| SEQ ID NO: 1787 | TRGV8*01-RIGHT | gtcatcacttatgcaagcacagggacgagcctaaatttatactgaacgtgactctgggctctattactgtgccacctgggatagg |
| SEQ ID NO: 1788 | TRGV4*01-RIGHT | gtatgatacttatggaagcacaggaagaactgagaatgtactgaaatctattgaaaatgactctgggtctattacgtgccacctgggatggg |
| SEQ ID NO: 1789 | TRGV2*01-RIGHT | gtattaacttacgcaagcacaaggaacaacttgagattgataactgaaaatctaattgaaaatgctctgggtctattactgtgcacctgggacggg |
| SEQ ID NO: 1790 | TRGV5P*02-RIGHT | gtattaactcatacaccgaggaggtggagctggaatttgagactgcaaaatctaattgaaaatgattctgggtttatactgtgccacctgggcagg |
| SEQ ID NO: 1791 | TRAV21*01-RIGHT | aagacttaatgcctcgctggtataatcatcaggacgtagtacttatacattgcagctccttcagcctgactcagccactctctgctgtgagg |
| SEQ ID NO: 1792 | TRBV29/OR9-2*01-RIGHT | acaagttcccatcagccgcccaaactaacattctcaactctgactgtgagcaacaggagacctgaagacagcagcatatacctctgcagcgttgaaga |
| SEQ ID NO: 1793 | TRAV37*01-RIGHT | agattcacagccaggctgaatttaaacagcttaaaagagaccagcacattccctgacatacaggatcccagctccatgactcaaccacattcttctgcagcaagca |
| SEQ ID NO: 1794 | TRBV21/OR9-2*01-RIGHT | gatttcagccaatgccccaaatctcaccctgacctgtacctggagatccagtccagtgagtccacggagtccacgcagtccaggagacacagcactgtatttctgccaacagccaaagc |
| SEQ ID NO: 1795 | TRBV21-1*01-RIGHT | gattttagccaatgctccaaaactcatcctgacctggagatccagtccagtgagtccagggacagggacagaccagggtcagggggacaacagcactgtatttctgtgcagcagccaaagc |
| SEQ ID NO: 1796 | TRAVB-6*01-RIGHT | gttttgaggctgaattaacaagagtcaaactctcctccactgaggaaaccctcagtccatataagcgacacggtgagtactcctgtgctgtgagtga |
| SEQ ID NO: 1797 | TRAV8-3*01-RIGHT | gctttgaggctgaattaagaggatcaatctctccttcaatctgaggaaaccctctgtcattggaagtgatgtgctgagtactctgtgtgggtgc |
| SEQ ID NO: 1798 | TRBV29-1*01-RIGHT | acaagttcccatcagccgcccaaactaacattctcaactctgactgtgagcaacatgagccccggagtctgcagcctgaagacagtagcacatctcagtacctctgcagcgttgaaga |
| SEQ ID NO: 1799 | TRBV25/OR9-2*01-RIGHT | agtcaacagtctccagaataaggacggagcagtttcccctgaccctggagtctgcagcctgcaggccctcacataccctcagtacctctgcagcagtgaata |
| SEQ ID NO: 1800 | TRBV25-1*01-RIGHT | agtcaacagtctccagaataaggacggagcatttcccctgaccctggagtctgcaggcctgcaggacagcctcacatccagcatccataccctagtgatgaggcatctcagtacctctgcagcagtgaata |
| SEQ ID NO: 1801 | TRAV35*01-RIGHT | aagagactgactcagtttggtataaccagaaagacagcttcctgcaatctccgaatatctcagcatccataccctgcacatcacagccaccccagactacagatgtaggaacctacttctggcag |
| SEQ ID NO: 1802 | TRAV25*01-RIGHT | gaaaagactgacattcagtttggagaagcaaaaagaacagctccctgcacatcacagactaccccagactacagatgtaggaacctacttctgtgcaggggtgcaggg |

TABLE 4-continued

| SEQ ID NO | Name | Sequence |
|---|---|---|
| SEQ ID NO: 1803 | TRAV12-2*01-RIGHT | aggtttacagcacagctcaataaagccagccagtatgtttctgtcatcagagactcccagccagtgattcagccactacctctgccgtgaaca |
| SEQ ID NO: 1804 | TRAV12-1*01-RIGHT | aggtttacagcacagctcaatagagccagccagtcagctatatttccctgctcatcagagactccaagctcagtgattcagccactactctgtggt gaaca |
| SEQ ID NO: 1805 | TRAV12-3*01-RIGHT | aggtttacagcacacaggtcgataatccagcagtatatctccttgtcatcagagactcacagccagtgattcagccactacctctgtcaat gagcg |
| SEQ ID NO: 1806 | TRAV23/DV6*01-RIGHT | agattcacaatctccttcaatcaaaagtgccaagcagtctcattgatatcatgattcccagcctggagctcagccactctgtgcagc aagca |
| SEQ ID NO: 1807 | TRAV22*01-RIGHT | agataagcgccacgactgtcgctacggaacgctcagctattgtacattcctcttcccagaccacagactcaggcgttatctctgctgtg gagc |
| SEQ ID NO: 1808 | TRAV41*01-RIGHT | aagattaattgccacataaacatacaggaaaagtagtccctgcacatcacagctccccatcccagagactctgccgtctacatctgtct gtcaga |
| SEQ ID NO: 1809 | TRAV39*01-RIGHT | cgattaatggcctcacttgataccaaagcccgtctcagcaccctccacatcacagtgccgtgcatgacctctgtgccactactctgtccgt ggaca |
| SEQ ID NO: 1810 | TRAV36/DV7*01-RIGHT | agacaagtagcatattagataagaagaacttccagtatcctgaacatcacagccaccagacagagaccggccatctacctctgtgct gtggagg |
| SEQ ID NO: 1811 | TRAV29/DV5*01-RIGHT | agattcactgtctttctaaacaaaagtgccaagcaccactctctctgcatattgtgcctccacctggagactctgcagtgtactctgtgcagca agcg |
| SEQ ID NO: 1812 | TRAV27*01-RIGHT | aagagactaaccttcagttggtgatgcaagaaaagacagtctctccacatcactgcagcccagcctggtgatataggcctcacctctgtg caggag |
| SEQ ID NO: 1813 | TRBV6-4*01-RIGHT | gttatagtgctccagagcaaacacagatgattccccctcacgttggcgtctgctgtaccctcagacatgtgactctgtgccagcagtg actc |
| SEQ ID NO: 1814 | TRBV10-1*01-RIGHT | gctacagtgtctctagatcaaacacagagaccctccactcactggagtctgcctccttctgcctgcgcagacatcgtatattctgccagagt gagtc |
| SEQ ID NO: 1815 | TRBV10-2*01-RIGHT | gctatgttgctccagatccaagacagagaattccccctcactcttggagtcagtcaccgtccgtgctccctcccagacatctgtatttctgcgcagagt gagtc |
| SEQ ID NO: 1816 | TRBV6-2*01-RIGHT | gctcaaatgtctccagattaaaaaacagaatttcctgcggttggtcgctgctcctcccaaaatcgtgtactctgtgccagagt tactc |
| SEQ ID NO: 1817 | TRBV10-3*01-RIGHT | gctatagtgtctctagatcaagacagagattcctcctcactctggagtccgctaccagctcccagacatctgtactctgtgccatcagttg agtc |
| SEQ ID NO: 1818 | TRAV24*01-RIGHT | ggacgaataagtgccactcttaataccaagaggtacagtatttgtacatcaaaggatcccagcctgaagactcagccacatccctctgt gccttta |
| SEQ ID NO: 1819 | TRBV14*01-RIGHT | gattcttagctgaaggactggagggacctattctactctgaaggtgcagcctgagaactggagattcctggagtttatttctgcagcag ccaaga |

TABLE 4-continued

| SEQ ID NO | Name | Sequence |
|---|---|---|
| SEQ ID NO: 1820 | TRBV24-1*01-RIGHT | atacagtgtctctcgacaggcacaggctaaattctccctgtccctagagtctgcatcccaaccagacagctcttacttctgtgccacagtgatttg |
| SEQ ID NO: 1821 | TRBV24/OR9-2*03-RIGHT | agtgtctctgacaggaacaggctaaattctccctgtgcaccccaaccagacagcttctaggtactcagtgccacagtgatttc |
| SEQ ID NO: 1822 | TRAV8-2*01-RIGHT | gtttgaggctgaattaagaagagtgaaactccttccactgacgaaactcttcaagcccatatgagcgacggctgagtacttctgtgctgtgagtga |
| SEQ ID NO: 1823 | TRAV8-4*01-RIGHT | gttttgaggctgaattaagaagagtgaaactccttccactgacgaaactcagcgcccatatgagcgacggctgagtacttctgtgctgtgagtga |
| SEQ ID NO: 1824 | TRBV22/OR9-2*01-RIGHT | ggctacggtgtctcccgagagaggggctgttcttcatgtgaagctggccacacagctctgtacttctgtcctgggagtgcac |
| SEQ ID NO: 1825 | TRAV26-2*01-RIGHT | ggcctcctctgcaatcgctgaagacagaaagtccagtacctgatcctgacccgtctacctgagagatgctgtgtgtactactgcatcctgagagac |
| SEQ ID NO: 1826 | TRBV11-2*01-RIGHT | gatttctgcagagaggctcaaaggagtagactccactctcaagatccagctcgagagttggagactcggctgtatctctgtgccagcagcttaga |
| SEQ ID NO: 1827 | TRBV11-3*01-RIGHT | gatttctgcagagaggctcaaaggagtagactccactctcaagatccagctcgagagctggggactcggctgtatctctgtgccagcagcttaga |
| SEQ ID NO: 1828 | TRAV8-1*01-RIGHT | gctttgaggctgaattataaagagtaaattctccttaatctgaggaaccctctgtgtcagtgtgacacagctgagtacttctgtgccgtgaatgc |
| SEQ ID NO: 1829 | TRBV7-5*02-RIGHT | caattctccacagagaggtctgagatctttctccactgaagatccactccactcgacgtccagcgcacagagcagcggactcggctgtgtatctctgtgcagaagcttagc |
| SEQ ID NO: 1830 | TRBV7-6*01-RIGHT | ggttctctgcagagaggcctgagggatgcctgagggaatccatccactttgaaaataaagttcttagagaagaagataggtgtgtaccactgcctgctgattgcttagc |
| SEQ ID NO: 1831 | TRGV11*02-RIGHT | gataagtaaaaatgtccacacttccactttgacactttcctgttgttgatcacgattcctcacggttccctgatccggagtcgcccagcccaaccagacctcctcgtacttctgtacaggcac |
| SEQ ID NO: 1832 | TRAV17*01-RIGHT | agattaagagtccacgcttgacacttccctgttgttgatcacggttcctcttgtgatcacggttccgggcagcagacactgcttcttacttctgtctacggacg |
| SEQ ID NO: 1833 | TRBV27*01-RIGHT | ggtacaaagtcctcgaaagagaaggaggaatttcccccgatccggagtcgcccagcccaaccagacctcctgtacttctgtgccagcagtttatc |
| SEQ ID NO: 1834 | TRDV1*01-RIGHT | attctgcaacttcaagaaagcagcgaaatccgtcgcctaaccattcagccttacagctagaagattcagcaaagtactttgtctcttgggaact |
| SEQ ID NO: 1835 | TRBV18*01-RIGHT | gatttctgctgaatttcccaaagggcccagcatcctgaggatccagcaggtagtgcgaggagattcggcagctcgctcaaccagtcaccacc |
| SEQ ID NO: 1836 | TRAV5*01-RIGHT | agactcactgtctctattgaataaaaggataaacatctgtctctcgcattgcagacaccagatgggactcagtatcagtctacttctgtgcagagagta |

TABLE 4-continued

| SEQ ID NO | Name | Sequence |
|---|---|---|
| SEQ ID NO: 1837 | TRAV13-2*01-RIGHT | agagtcaccgtttattgaataagacagtgaaacatctctctgaaattgcagtactcaacctggagactcagcgtcacttttgtgcagagaata |
| SEQ ID NO: 1838 | TRDV2*03-RIGHT | tttccaaggtgacattgatattgcaagaaccttgctgctgcttaagatacttgcaccatcagagagagatgaaggtcttactactgtgccgtgacacc |
| SEQ ID NO: 1839 | TRAV1-2*01-RIGHT | gtctttcttcattccttagtcggttcaaagggtacagttacctcctttgaaggagctccagatgaaagactcgcctcttacctctgctgtgagaga |
| SEQ ID NO: 1840 | TRDV3*01-RIGHTS | gacggtttctgtgaacacattctgacccagaaagctttcacttggtgatctctccagtaaggactgaagacagtgccattactactgccttag |
| SEQ ID NO: 1841 | TRAV31*01-RIGHT | tattctgagcttccagaaaacaactaaaactattcagcttatcatatcatcacagccagagaccctgcaacatattctgtgtctcaaagagcc |
| SEQ ID NO: 1842 | TRAV10*01-RIGHT | agatatacagcaactctggatgcagacacaaagcaaagctctctgcacatacacagcctcccagctcagcgattcagcctcctacatctgtgtggtgagcg |
| SEQ ID NO: 1843 | TRAV28*01-RIGHT | gaagactaaaatccgagtcagtctgagaacttatgccacctatacacagattcccagcctgagactcagctattactctgctgtggga |
| SEQ ID NO: 1844 | TRAV40*01-RIGHT | aaaactcggaggcggaaatattaaagacaaaactcccccattgaaatattcagtcaggtatcagactcagccgtgactacgtcttctgggaga |
| SEQ ID NO: 1845 | TRGV6*02-RIGHT | gcatgatacttatggaagtagaagtagaagagatcgacagtccttcctccacctgagaagccctcgggtctattactgtgccacctagagcagg |
| SEQ ID NO: 1846 | TRAV18*01-RIGHT | gtttcaggcagtcctatcaagagtgacagttcttcctccacctgagaagcctggtgcagctgtgcggactgtgactactgcctctgagaga |
| SEQ ID NO: 1847 | TRBV26*01-RIGHT | ggtatcatgttctttgaaatactatagcatcttttcccctgacccttgaagtctgccagcaccaacagacatcgtgtatctctatgcagcagttcatc |
| SEQ ID NO: 1848 | TRBV8-2*01-RIGHT | agagggtactgtgttcttgaaacaagcttgagcattcccaatcctggcatccaccagcacccagccctatctgtaccactgtggcagcacatc |
| SEQ ID NO: 1849 | TRGVA*01-RIGHT | agataaaatcatagcaaggatgcagcagctctatcttggcagtactgaagttggagacaggcatcgagggcatgaactactgcacaacctgggcctg |
| SEQ ID NO: 1850 | TRAV4*01-RIGHT | gcctccctgttatcctgccgacagaaagtccgacactctgagcctgccgggttccctgacgacactgctgtgactactgcctcgtgggtgaca |
| SEQ ID NO: 1851 | TRAV8-7*01-RIGHT | aggctgaattaagaagagcgaaacctccttctacctgaggaaacatcaaccatgtgagtgctgctgagtacttctgtgctgtgggtgacaggag |
| SEQ ID NO: 1852 | TRAV13-1*01-RIGHT | cgaattgctgttacattgaacaagcagcaaacattcccctgcacatcacagagaccaaactgaagactcggctgtctacttctgtgcagcaagta |
| SEQ ID NO: 1853 | TRBVB*01-RIGHT | gactcgagaccctctgcagcagcagccctatcagtgcagccatatcctcctgaggcggatgatgacaacccccaggttgaagcgacctaacctatgagcc |

TABLE 4-continued

| SEQ ID NO | Name | Sequence |
|---|---|---|
| SEQ ID NO: 1854 | TRAV8-5*01-RIGHT | tggacacttatcacttcccaatcaatacccctgtgatttctagcctgtctttacttaatcttcctatgcctgagtcttaatcctgcagctgaggaggatgtatgtcacc |
| SEQ ID NO: 1855 | TRBV16*02-RIGHT | gatttcagtcagtaagtgcctccaaattcacctgtagcctgagatcccagctgagattgaggattcagcagcttacgaagttgaggatcagcagcttagcgcagtagtcagtgtattttctgcagcagccaatc |
| SEQ ID NO: 1856 | TRBV26/OR9-2*02-RIGHT | ggtatcatgttctgaaatactagcatctttctccctgaccctgaagtctgtcagcacaccaaccagacatgtgtatctctcgcagcagttcatc |
| SEQ ID NO: 1857 | TRBV7-3*03-RIGHT | ggtccttgcagtcagcctgagggatccgtctctactctgaagatctgaagcagcagagacaggggactcagcgcgtatcccgtatccgtcagcagcttaac |
| SEQ ID NO: 1858 | TRBV7-9*03-RIGHT | tgatcgttcctgcagagagaggcctaaggatctttctccaccttggagatccagccagccagacagaggggactggccatgtactctgtgccagcagc |
| SEQ ID NO: 1859 | TRBV9*02-RIGHT | cgattcccgcacaacagtccctgacttgcazctctgaactaaacctgagctctgggactggggactcagtttgtatttctgtgcagcagcgtag |
| SEQ ID NO: 1860 | TRBV29/OR9-2*02-RIGHT | acaagttcccatcagccgccccaaactaacattctcaactctgactgtgagcaacagaggacctgaagacagcagcatatacctgcagcgttgaaga |
| SEQ ID NO: 1861 | TRAV8-6*02-RIGHT | gtttttgaggctgaattaacagagtcaaactccttccactgaggaaacctcagtcagtccatataagcgacacggctgagtactctgtgctgtgagtga |
| SEQ ID NO: 1862 | TRBV6-4*02-RIGHT | gttatagtgtctccagagcaaacagatgattccccctcacgttggcgtctgtgctgtatccctctcagacatctgtgtacttctgtgcagcagtgactc |
| SEQ ID NO: 1863 | TRBV10-1*02-RIGHT | agatggctacagtgtctctagatcaaacagagacctcccccactctggagtctgtcgctgtcgctctgccctcccaaacatctgtactctgtgcagcagtgcagt |
| SEQ ID NO: 1864 | TRBV6-3*01-RIGHT | gctacaatgtctccagattaaaaacagaattcctgctgggttggagtcggctgcgcctcctcccaaacatctgtacttctgtgcagcagttactc |
| SEQ ID NO: 1865 | TRAJ1*801 | aatagagacacggggcatggtgatgaagttgaagtattacctcccagtgcaattggcaaggaaccagagttccacttctccccgtactgtcccatgccca |
| SEQ ID NO: 1866 | TRAJ10*01 | gaggcatcaaacactgtgatactccacggggaggaggaaacaaactcacccttgggacacagccacttgggacacagccactcagctaaagtgaacctcagtaagtatgagattctat |
| SEQ ID NO: 1867 | TRAJ11*01 | tatgggattgctatagtgaattcagatgcgatggaaggggactatgttctagtctccagtacatgttgaccccatccc |
| SEQ ID NO: 1868 | TRAJ12*01 | actgactaagaacactgtgggatgatagcagctataattgatctcggagtgggaccagactgctgtcagcctgtaagtaaggtgtcagagag |
| SEQ ID NO: 1869 | TRAJ13*01 | aaggcaggcattacagtgtgaattctgggggttaccagagaagttacctttgaattggaacaaagcttccaagtcatccccaagtgagtccaatttcctatg |
| SEQ ID NO: 1870 | TRAJ13*02 | aaaggcaggcattacagtgtgaattcggggggttaccagaagaagttaccctttggaactggaacaaagctccaagtcatcccaagtgagtccaatttccctat |

TABLE 4-continued

| SEQ ID NO | Name | Sequence |
|---|---|---|
| SEQ ID NO: 1871 | TRAJ14*01 | tttgtcaggcagcagtgctgtgattatagcacattcatctttgggagtgggacaagattatcagtaaacctgtaagtaggcaatgtcactaaa |
| SEQ ID NO: 1872 | TRAJ15*01 | cagggcctcattcacgtgccaaccaggcaggaactgctctcgatcttggaagggaaccacctatcagtgagttccagtagtacctgataattatt |
| SEQ ID NO: 1873 | TRAJ15*02 | cagggcctcattcactgtgccaaccaggcaggaactgctctgatcttgggaagggaaccacctatcagtgagttccagtaagtacctgataattatt |
| SEQ ID NO: 1874 | TRAJ16*01 | tggtacaatgatcactgtggtttcagatggccagaagctgctctttcaagggaaccatgttaaggtggatcttagtaagtattattactaatga |
| SEQ ID NO: 1875 | TRAJ17*01 | cctgtggttttgctgggcctaaatcattgtgatcaaagctcaggcaacaagctaacttttggaggagaaccaggtgctagtaaaccaagtga |
| SEQ ID NO: 1876 | TRAJ18*01 | aggggaccagcattgtgccgacagaggctcaaccctgggaggctatacttggagaggaactcagttgactgctggcctggtgagtgagtcgcttc |
| SEQ ID NO: 1877 | TRAJ19*01 | tttcagaggacagatgtggctatcaaagatttcacctgaaaggatccaaacataatgtcactccaagtgagcagcctttgt |
| SEQ ID NO: 1878 | TRAJ2*01 | tggtgtcacctacggtgatgaatactggaggaacaattgataaactcacattggaaagggaccccattgtatccattatctggtgagtcatcccaggtg |
| SEQ ID NO: 1879 | TRAJ20*01 | tgtaggcgacctcgcactgtggttctcaacgactacaagctcagtttgggagccgaaccacagtaactgtaagagcaagtaagaaagaaaagtcca |
| SEQ ID NO: 1880 | TRAJ21*01 | tgtaatgccaataaacatggtgtacaactccaacaaattttacttggatctggaccaaactcaatgtaaaaccaagtaagtatagtgcctagaaga |
| SEQ ID NO: 1881 | TRAJ22*01 | gttgagcaaatcatagtgttcttctggtctgcaaggcaactgaccttggacacaattgactgttttacctgtaggctgcctcaattaaa |
| SEQ ID NO: 1882 | TRAJ23*01 | aggatatgtaacacagtgtgattataaccaggaggaaagctatctctccgacagggaacggagtatctgtgaaaccccagtaagtataaattgtatc |
| SEQ ID NO: 1883 | TRAJ23*02 | gactgatgtgtttttgacaggatatgtaacacagtgtgattataaccaggaggaaaagcttatcttccggacagggaacggagtatctgtgaaaccca |
| SEQ ID NO: 1884 | TRAJ24*01 | gaggtttgtcacagtgacaattgacactgtggggaattcagttggagcagggaccccaggtgtggtcaccaggtaagccattcctggagc |
| SEQ ID NO: 1885 | TRAJ24*02 | gaggtgttgtcacagtgacaactgacactgtggggaattcagttcagtctggagcagggaccccaggtgtggtcaccaggtaagccatccctgga |
| SEQ ID NO: 1886 | TRAJ25*01 | atgctgagataatcactatgcagaaggacactgtggggataactgtccctttatctttgggaagggacaaggctcttgtcagccagtaagtgacatataatttat |
| SEQ ID NO: 1887 | TRAJ26*01 | ctgagcccagaaacactgtggggataactggtcagaatttgctttggtcccgaaccagattgtccgtgtccgtgtaagtacagttaagtggag |

TABLE 4-continued

| SEQ ID NO | Name | Sequence |
|---|---|---|
| SEQ ID NO: 1888 | TRAJ27*01 | caatagcactaaagactgtgtaacaccaatgcaggcaaatcaaccttgggatggactacgctcactgaagcaagtaagtgtgttctttctttgc |
| SEQ ID NO: 1889 | TRAJ28*01 | agaaaggaaactctgtgcatactctggggctgggagttaccaactcacttcggaagggaccaaactcctcggtcataccaagtaagttcttctttctg |
| SEQ ID NO: 1890 | TRAJ29*01 | ttatggaggaaatcactgtgggaatcaggaaaacactggtccttgtcttggaaaggcacaagactttctgattgcaagtaagtgttctagccatcc |
| SEQ ID NO: 1891 | TRAJ3*01 | aaagaccttaccacagtggggtacagcagtgcttccaagataatcttgatcagggacaagactcagcatccggcaagtaagtagaatgaagcagg |
| SEQ ID NO: 1892 | TRAJ30*01 | gttatgtgtcccaatcacagtgtgaacagatgcaacagatcatcttgaaaagggacacgactcatattctcccagtaagtgctgttatgtgattt |
| SEQ ID NO: 1893 | TRAJ31*01 | agtaaaggcaggaagtgctgtggaataacaatgccagactcatgttggagatggaactcagctgtggtgaagcccagtaagtggccatgttttattga |
| SEQ ID NO: 1894 | TRAJ32*01 | ggctctgaaggactgtgtgaattatggcgtgctacaaacaagctcatcttgaactggcactctgctgtcagccaagtacgtaagtagtggca |
| SEQ ID NO: 1895 | TRAJ32*02 | gtgattcagccaccctcctgtgccgatgtggtgctacaaacaagctcatcttggaactggcactctgctgtcagccaaatatccagaaccc |
| SEQ ID NO: 1896 | TRAJ33*01 | gttaaggtttttgtgctgtgtggatagcagctatcagtcaatcgggcgctggaccaagctaattataaagcaggtaagtctcagagatgtgactg |
| SEQ ID NO: 1897 | TRAJ34*01 | aggtttttgtagatccagtatcactgtgtcttataacaccgacaagctcatcttgggactggaccagattacaagtctttccaagt |
| SEQ ID NO: 1898 | TRAJ35*01 | taaaagaatgagccattgtggataggctttgggaatgtgctgcattgcgggtccgcactcaagtgatgtttaccacgtaagtatcctttctcatt |
| SEQ ID NO: 1899 | TRAJ36*01 | tactggcagaaacactgtcaaactggcaactctcttggactgaaacgagactcaccgttatccctgtaagtccttacctcttgaca |
| SEQ ID NO: 1900 | TRAJ37*01 | aaagtacagcattagagtggctctggcaacacaggcaaactaatcttggcaagggacaacttacaagtaaaccaggtaggtctggatgtttccca |
| SEQ ID NO: 1901 | TRAJ37*02 | ctcagccggtgtacttcctgtctcatgctgtcttcagcaacaggcaaactaactctttggcaaggacaacttacaagtaaaccagatatccagaac |
| SEQ ID NO: 1902 | TRAJ38*01 | aaagtttctatgactgtgtaatgctggcaacaaccgtaagctgattgggagttgggaacaagctgcagtaaatcgagtgagtcttcgtgttaact |
| SEQ ID NO: 1903 | TRAJ39*01 | cagccgaagatcactgtgtgaataatcaggcaacatgctccacttcacctttggagggggaacaagttaatggtcaaacccgtgagtatcctgctgaat |
| SEQ ID NO: 1904 | TRAJ4*01 | aagcaccatctgattgtgtcttttctggtgctacaataagctgattttggagcagggacaggcaggctgctacaccatgtgagtatgaccctgcaag |

TABLE 4-continued

| SEQ ID NO | Name | Sequence |
|---|---|---|
| SEQ ID NO: 1905 | TRAJ40*01 | tatgtggtttatgtagagacacataacactgtgactacctcaggaacctacaaatacatctttgaacaggcaccaggctgaaggtttagcaagt |
| SEQ ID NO: 1906 | TRAJ41*01 | ttagggagaacgcactgtggaactcaaatccgggtatgcactcaacttcggcaaaggcacctcgtcgttggtcacccctgagtttttgtggtttac |
| SEQ ID NO: 1907 | TRAJ42*01 | agcccataggactgtgtgaattatggaggaagccaaggaaatctcatcttggaaaggcatctaaactctcgttaaaccaagtaagtgttggggattc |
| SEQ ID NO: 1908 | TRAJ43*01 | ttgtagagcatgtattactgtgacaataacaatgacatgcgtcttggagcaggaccagcagtgactgacagtaaaaccaagtaagtggggaatgggtcaat |
| SEQ ID NO: 1909 | TRAJ44*01 | aggttctcgttatgaagtcatccacagtgtaaatacccgcactgcagtaaactcaccttgggactgaacaagactcaggtcacgctcggt |
| SEQ ID NO: 1910 | TRAJ45*01 | agggttggccagagtgtgtattcaggagaggtgctgacggaccaccttggcaaaggactcatctaatcatccagcctgtaagtgctttgcctg |
| SEQ ID NO: 1911 | TRAJ46*01 | aagctgctgacagccgtgagagaaagcagcgagacaagctgactttgggaccgggactcgcttagcagtcgttagcccagtaagtctgagcagaaagt |
| SEQ ID NO: 1912 | TRAJ47*01 | gtagaggagtgacgctgtgtggaatatggaaacaaactgtctcttggcgcaggaaccattctgagagtcaagtcctgtgagtataaaacacactccaag |
| SEQ ID NO: 1913 | TRAJ47*02 | gtgtactattgcattccggccctgaatatggaaacaagtggtcttggcgcaggaaccattcctgagagtcaagtcctatccagaaccctgaccctg |
| SEQ ID NO: 1914 | TRAJ48*01 | atgactagaacactgtgtatctaacttggaaatgagaaattaaccttgggactggaacaagactccaccatcataccagtaagttcttcatccttgg |
| SEQ ID NO: 1915 | TRAJ49*01 | tgtgagcttcctatcacagtggaaccaccgtaaccagttctatttggacaggacaagttgacgcattccaagtaagtcaaagaaatttccca |
| SEQ ID NO: 1916 | TRAJ5*01 | tactgtgatgtaccagggtgtggacacggtggacacggaggagcacttacttttggagtggaacaagactcccaagtgtcaaccaagtagtaccccaaacttaggc |
| SEQ ID NO: 1917 | TRAJ50*01 | taaagtttgatggctgtgtgaaaacctcctacgacaagtgtatattgggccaggacaagcttatcagtcattcccagtaagtgtcctgggtgct |
| SEQ ID NO: 1918 | TRAJ51*01 | aaactccctgaagcagggagtcgtgacagctatattgaaaggagacatgactaactgtgaagcaagcaagctggaaagacctaa |
| SEQ ID NO: 1919 | TRAJ52*01 | gcctccagtgcagtgctaatgctggtgtactagtctatggaggtagcaactataaactgacattggaaaggaccatcttgactgtcctccagtaagtaacaagac |
| SEQ ID NO: 1920 | TRAJ53*01 | agcctctgtgctgtgagaatagtggaggtagcaactataaactgacatttggaaaagggaactctcttaacgtgaatccaagtaagtttgaagggagt |
| SEQ ID NO: 1921 | TRAJ54*01 | taaagcctcgtgctggtgtaattcaggagcccaagagccgaagctgtatttggccaaggaaccaggctgactatcaacccagtaagtatgacagggtgaag |

TABLE 4-continued

| SEQ ID NO | Name | Sequence |
|---|---|---|
| SEQ ID NO: 1922 | TRAJ55*01 | gaggatggatccctgttagtgacaagtgctggtaatgctcctgtgggaaggggatgagtacaaaataatccaagtaagtggaggg acaagaag |
| SEQ ID NO: 1923 | TRAJ56*01 | agatcctcgtgcattgtgttatactggagccaatagtagctgacattggaaaggaataacctcgagtgttagaccaggtatgttttaatga atgtt |
| SEQ ID NO: 1924 | TRAJ57*01 | aagcagtcctgtggggtgtaactcagggcggatctgaaaagctggtctcttggaaaggaactgacgaactgacagtaaaccatgaagtctgaa taatgctt |
| SEQ ID NO: 1925 | TRAJ58*01 | aagccctcagcacagtgtttaagaaaccagtgctctaggtgaccttgggaaggaacacagtcacagtgaatcctggtaagtggaag ggagcatt |
| SEQ ID NO: 1926 | TRAJ59*01 | atgtaaggcagcagctcctgtggaaggaaggaaacaggaaattacattggaatgggacgcaagtagagagtgaagctatctttaaacc aaaggtgt |
| SEQ ID NO: 1927 | TRAJ6*01 | caggttttatcaaaggctgctcctcactgtgctgcatcaggaggaagctacacctacattggaagaggaaccaccttattgtcatccgtgta agt |
| SEQ ID NO: 1928 | TRAJ60*01 | gtaaagggcctgggcactatgtgaagatcactagtgctcaacttggaagggactgagttaattgtgagctggtgagtacctcaact ccagagg |
| SEQ ID NO: 1929 | TRAJ61*01 | taaaggtgcccactcctgtgggtaccggttaatagaaactgacattggagccaacactagagaatcatgaactcagcaagtaatatt ggcagaa |
| SEQ ID NO: 1930 | TRAJ7*01 | tgtaatacacttacacagtgtgactatatggaacaacagactcgcttttgggaagggaaccaagtggtgtcatacaagtaagtgagctggg atcctcc |
| SEQ ID NO: 1931 | TRAJ8*01 | tacagagttatgtcagagtgtgaacacagcctttcagaaactgtattggaactggcaccgactctggtcagtcaagtaagtcaaatctg cagaaa |
| SEQ ID NO: 1932 | TRAJ9*01 | cgcagtgcaaatcactgtgggaaatactgtgaggcttcaaaactatcttgagcaggaacaagactattgttaaagcaagtaagtccatga aataacc |
| SEQ ID NO: 1933 | TRBJ1-1*01 | ttttcacttgaccctgtcactgtgacactgaagcttcttggacactgaagctcacagttgtaggtgaagacattttcaggttcttt tgc |
| SEQ ID NO: 1934 | TRBJ1-2*01 | ttttagagtgctatattcttatgtctaactatggctacacctccggtccgggaccaggttaaccgtgtaggtaaggctgggggtctagga gggg |
| SEQ ID NO: 1935 | TRBJ1-3*01 | tttgaagtggccctgggagctgtgctctggaaaaccacatatttggagaggaaagttggctcactgtgtaggtgatgaagtcaaggctgg atagct |
| SEQ ID NO: 1936 | TRBJ1-4*01 | ttcctccagtcttaatgttgtgcaactaatgaaaactgttttttggcagtggaaccccagctctctgtctcttgggtatgtaaagactctttcgg gat |
| SEQ ID NO: 1937 | TRBJ1-5*01 | tttgcacactcatgatgcactgtgagcaatcagccccagcattttggttgatggactcgactctccatcctaggtaagttggcagaatcaggg tggta |
| SEQ ID NO: 1938 | TRBJ1-6*01 | ttatctaagcctctgcagctgctcctctataattcacccctccacttgggaatggaccaggctcactgtgaccaggtatggggctccactcttg actc |

TABLE 4-continued

| SEQ ID NO | Name | Sequence |
|---|---|---|
| SEQ ID NO: 1939 | TRBJ1-6*02 | ttatctaagcctctgcagctgtgtcctctataattcacccccactttgggaacggaccaggctcactgacaggtatgggggctccactcttgactc |
| SEQ ID NO: 1940 | TRBJ2-1*01 | ttctggcagcagccccctccactgtgctcctacaatgagcagttctcgggcaggacagctcaccgtgctagtaagaaggggctccaggtgggag |
| SEQ ID NO: 1941 | TRBJ2-2*01 | tgcgccagggtcccaggggtgtgcgaacaccggggagctgttttttggagaaggctctaggctgaccgtactgggtaaggaggcggctgggctccgga |
| SEQ ID NO: 1942 | TRBJ2-2P*01 | agctgcccactctgagaggggctgtgctgagaggcgctgctgacgcgtctggcggaggactcctggttctgggtctgggagagcgatgggctctcag |
| SEQ ID NO: 1943 | TRBJ2-3*01 | ttttgtcctgggcctccaggctgtgagcacagatacgcagtatttggccccaggcaccggctgacagtgctcgtaagcggggctccccgctgaagccc |
| SEQ ID NO: 1944 | TRBJ2-4*01 | ttctgtccgcgtctcggggctgtgagccaaaaacattcagtactcggcgcccaggaccccgggctctcagtgctggaagctgggccgcccgggggaccg |
| SEQ ID NO: 1945 | TRBJ2-5*01 | tttttgtgcgggctcgggggcctgtcgggggccagtcaggcacgcggctcctggctgtcgtgagcgcgggctgctgggggcgggg |
| SEQ ID NO: 1946 | TRBJ2-6*01 | tgcggggagtccccgggctgtgctgtggtagtcttgacagtgacccgtgccgtgtggttcgcgggaccacccgg |
| SEQ ID NO: 1947 | TRBJ2-7*01 | tttgcatgcggggtgcacctccgtgtgctctcctacgagcagtacttcgggccgggcggcccgggcaccaggtcacaggtgagattcggctcggctctcccaccttc |
| SEQ ID NO: 1948 | TRBJ2-7*02 | tttgcatgcggggatgcacctccgtgtctcctacgagcagtacgtcgggcacccgggcaccaggtcacaggtgagattcggggcgtctccccaccttc |
| SEQ ID NO: 1949 | TRDJ1*01 | ttttgaacgtcctccaagtgctgtgacatcgataaactcatctttgaaaaggaaccgtgactgtgaaccaagtaagtaactcattattatctga |
| SEQ ID NO: 1950 | TRDJ2*01 | ttttcgtaatgacgcctgtggtagtcgttgacagcacaactcatcgtgaaaggaacaactcatcgtgaaccaggtaagttatgcatttact |
| SEQ ID NO: 1951 | TRDJ3*01 | tgaggcactgtcataatgtgctcctggacacccgacagtgttttcggactgcatcaaacttcttcgtggagccccgtgagtgatctttttcctat |
| SEQ ID NO: 1952 | TRDJ4*01 | atgagacatacaaaaggtaatgcgccccagaccctgatcttggcaaaggaacctatctggaggtacaacaac |
| SEQ ID NO: 1953 | TRGJ1*01 | ttttgatatgactgaatcactgtgaattattataagaaactcttggcagtgtgaacaacactggttgtcacagttaagtatcggaagaatacaacatt |
| SEQ ID NO: 1954 | TRGJ1*02 | tactgtgcctgtgggaggtgcttattataagaaactcttggcagtggaacaacacttgtgtcacaggt |

TABLE 4-continued

| SEQ ID NO | Name | Sequence |
|---|---|---|
| SEQ ID NO: 1955 | TRGJ2*01 | ttttgatatgactgaatcactgtgaattattaagaaactctttggcagtggaacaacactgttgtcacaggtaagtatcggaagaataca<br>acatt |
| SEQ ID NO: 1956 | TRGJP*01 | ataaaggcttctcagtggtgggcaagagttggcaaaaaatcaaggtatttgtcccgaacaaagcttatcattacagtaagttttcttt<br>aaattt |
| SEQ ID NO: 1957 | TRGJP1*01 | gattttctagaagcttagaccggtgataccagtggttcaagatattgctgaagggactaagctcatagtaacttcacctggtaagt |
| SEQ ID NO: 1958 | TRGJP2*01 | gattttgtagaagcttagaccagtgtgatagtagtgatcaagacgttgcaaaagggactaggctcatagtaacttcgctggtaagt |

TABLE B1

| SEQ ID NO | Name | Sequence |
|---|---|---|
| SEQ ID NO: 239 | IGHV(II)-1-1*01 | CACACTTGAGCCCAGCCTTTCTGGGCCAACTCTCCATCTGTAGAGACATCCAAGGCCCAGTTATCCCTGCAGCTGAGCTCCGTGAT GGCCAAGGGCAGGCCCACATTCCCGTGGGA |
| SEQ ID NO: 240 | IGHV(II)-20-1*01_IGHV(II)-20-1*02 | GCTTGTTGCTCATGTAGCTCAGCAGCCATAGGAAGAGCTGCCCCGGCGGACATAGATCTGAGGTGGCGACTGGACTCTTGAGGAGTG GGTTGGAATTTTTGCTGCCTTCATGACCTGTGCAC |
| SEQ ID NO: 241 | IGHV(II)-22-1*01_IGHV(II)-23-2*01 | AATCCAACCACTCCTCCAAGAGTCCAGTGACCATCTCCAGATCCACATCCAAAAACAGTTTCTCCTACAGCTGAGCTACCTTAACAA GGAGTACAACAACCATGATTTTTATACAAAAGA |
| SEQ ID NO: 242 | IGHV(II)-26-2*01 | CATCATGCACCCTCCACCAGTTCCATGTCCCCATCAACAAGTGACTCCAACACAGTGACTCCTGTGAAGCTCAGTCCATGACCA CCTAGGACACGGCTGAGTATTACTGTGAAAGA |
| SEQ ID NO: 243 | IGHV(II)-28-1*02_IGHV(II)-28-1*03 | GTGAAGGGAGCACAAATTACAACCACTGCTCAAGAGTCCATATCCAAGATCCATGTCCTTACAGCTCTTACAGCTGAGCTCTGTGCCCA GTGAACACACACGCATTTTTAAGCAAAAGA |
| SEQ ID NO: 244 | IGHV(II)-30-1*01_IGHV(II)-30-1*02_IGHV(II)-30-32*01_IGHV(II)-30-51*01 | TTACTCCCCTCTTCTCCAAGAGTCCAGTGACCATCTCCAGATCTCACCATCTCCAAGATCCAGTCCAAAAAGTAGTTCTTTACAGCTGAACTATGTGAGGAAC AAACACATAGCAAAAGATGCAATGAAGGGCCTT |
| SEQ ID NO: 245 | IGHV(II)-30-21*01 | TTACAACCCACTGCTCATATCCGGATCCAAGAAACAGTTCTTACAGCTGAGCTCTGTGCCCAGTGAACACAACTACG CATTTTGAAGCAAAAGATGCAATGAAGGGCCTT |
| SEQ ID NO: 246 | IGHV(II)-30-41*01 | TTACAACCCACTGCTCAAGAGTCCATATCCAGATCCAAGAAACAGTTCTTACAGCTGAGCT CTGTGCCCAGTGAACACAACTACG CATTTTAAGCAAAAGACGCAATGAAGGGCCTT |
| SEQ ID NO: 247 | IGHV(II)-30-51*02_IGHV(II)-33-1*-1 | TTACTCCCCTCTTCTCCAAGAGTCCAGTGACCATCTCCAGATCCATGTCAAAAAGTACTTCTTCTTACAGGTGAACTATGTGAGCAACA AACACATAGCAAAAGCCATGTATTTTAGAGCAAAAGA |
| SEQ ID NO: 248 | IGHV(II)-31-1*01 | TTACATCCCACTTCTCAAGAGTCCATATCCAGATCCAAGAAACAGTTCTTACAGCTGAGCTCTGTGCCCAGTGAACACAACTACAC ATTTTGAAGCAAAAGACGCAATGAAGGGCCTT |
| SEQ ID NO: 249 | IGHV(II)-40-1*01 | AGCCTGGTGAAGCCCTTGCAAACCCCCCACTCACTCCTCAAGAGTCCTGCCTCTGTCACACATCAGTGCTTCCTG |
| SEQ ID NO: 250 | IGHV(II)-43-1*01 | CATGAAGGGAGCACAAATTCTAACCACTCCTCAAGAGTCCAGTCAGTTCCAGATCCACCACCTCCAGATCTATGTCCAAAAACAGCTCTTCGTATGGC TGAGTGACATTAGCAACAGCACCAGCCATGT |
| SEQ ID NO: 251 | IGHV(II)-43-1D*01 | CATGAAGGGAGCACACAAATTCACCCACTCCTCAAGAGTCCAGTCCAGTCCAGTCCACCACCTCCAGATCTATGTCCAAAAACAGCTCTTCGTATGGC TGAGTGACATTAGCAACAGCAACACCATGT |

TABLE B1-continued

| SEQ ID NO | Name | Sequence |
|---|---|---|
| SEQ ID NO: 252 | (IGHV(II))-44-2*01 | ACGATGATCCATCTCTGCAGAGCCAACTCTCCTTCTCCAGAGATTCATCCAAGAGACAATTTGACTATACCTGAGCTCTGTGACATC TGAGGACATGGTTTGTATTACTGTGCAAGACA |
| SEQ ID NO: 253 | IGHV(II)-46-1*01 | GACCTGAATAGCACACACTTACCCTCTGCCTCCACCTCACTGTTACTGGCCACTCCGTCACAACCAGTCCTTACTAGTGGACCTGGAT CTGCCGGCTCTTCAGGAGGGGCTGCAATGGAT |
| SEQ ID NO: 254 | IGHV(II)-49-1*01 | ACGCAACCACCGCTCCAGAGTCCAGTCACCATCTCFAGATCCACATCCAAAACACAGTTTCTTCTACAGCTGAGCTACCTGAGCAAC GAGTACACCATGAATTTTTACACAAAGA |
| SEQ ID NO: 255 | IGHV(II)-51 2*01 | AATTCTAACCCACTCCTCATGAGCTCAGTCACCATCTCCAGATCCACGTCCAAGAACCAAATTTCTTTTAGCTGAGTTCTGTGACCAA CAATGCCACAACCTTGTATTACTGTGAGAGG |
| SEQ ID NO: 256 | IGHV(II)-53-1*01 | ATTCCAACCCACTCCTCCAAGAGTCCAGTCACCATCTCCAGATCCATGTCCAAAAAGCAGTTCTTCCTACAGCCGAGCTAAGTGAGTCA CAAGCACACAGCCATGTATTTTTAACAAAGA |
| SEQ ID NO: 257 | IGHV(II)-60-1*-1 | AAATTCCACCCACTCCTTATGAATCCAGTCACCATCTCCAAATTCGGGTCCAAAAAACACTGTTTTTACAGTGGAGCTATGTGAGC AACAAGCTCAGAGCCATGTTTAAAGAGAGA |
| SEQ ID NO: 258 | IGHV(II)-62-1*-01 | ATTACTCCCCTTTCTCAAGAGTCCAGTCACCATCCCCAGATCCACCATGTCCAAAAAAACAGTTCTTCCTACAGCTGAGCTACATGAGCAAC AATCACATAGCCATATATTTTCAGCAATAGA |
| SEQ ID NO: 259 | IGHV(II)-65-1*01 | TTCCAACCCACTCCTCCAGTCAGTCACTATCTCCAGATCCACATCCAAAAAAACACAGTGTTTCCTGTAGCTGAGCTACCTGAGCAAC AAGTACACAACCATGTAATTTTAATACAAAGA |
| SEQ ID NO: 260 | IGHV(II)-67-1*-1 | ATGCCTAGGTGTGAAGATCACACACTGACCTCACCCATGCTGTCTCTGGCCACTTCATCACACAACCATGCTTAATATTGACGTGGAT CTGCCAGTCCCCGGGAATGGGTGAATGGAT |
| SEQ ID NO: 261 | IGHV(III)-11-1*01 | GGGCAACACAGGGAGAAATTCAAGAGAGAAGTTCTTACATGCACCCCTACGTGCACGGTCTCACTGAGATCTTTACTCTTCCTTATCAC GTTTGTCTGTAAATCACAACGAATGGTGCATT |
| SEQ ID NO: 262 | IGHV(III)-13-1*01 | TGGGACTTCCTTCCTTGAGTAAAAAGATGATTAACAATGATTAACAATCCTCAAATACACTCAGTTCAGGAGAGATTCTCTTTAAGATGATTAACCTGAGA GCTCAGGAAAAGTCCGTGTATTACTTTGAGGGA |
| SEQ ID NO: 263 | IGHV(III)-16-1*01 | TCAGAGTTACTCTCCATGAGTACAAATAAATTAACAGTCCCAAGCGACACCTTTTCATGTGCAGTCTACCTAAAGGGACCAAACTG AAAGTCAAGGACAAGGCCTTGTAATACTGTGAG |
| SEQ ID NO: 264 | IGHV(III)-20-2*01 | ACCAAGAGAATGCTATCATCATCTTTCTGTTCTTTTTGGAAGGAATGCCCCCCTCCTTTAAGTGCAGTCTGCCTACAATGACCAATCTGAAAG TCTTTGCTTTTCAGCAGTTTAATAAGATT |
| SEQ ID NO: 265 | IGHV(III)-2-1*01 | GGGTTACTTTCCATGAGTACAAATAAATAACATCCAAGCAACACACCCTTTTAAGTGCAGTCTGCCTACAATGACCAATCTGAAAAG CCAAGGACAAGGTCATGTATTACTGTGAGTGA |
| SEQ ID NO: 266 | IGHV(III)-25-1*01 | GCAAGCTCCAGGACCAGGGTTGATGTGGGCAGCAACAGGGAGAAATTGAAGAGGAAGCTCTCAGTGGTGCCCTCATGAATACAA AGAATCTTTCACAGTCCCCAGGACACCCTTACGTGC |
| SEQ ID NO: 267 | IGHV(III)-25-1*02 | AGAGGAGCTCTCAGTGTGCCCTCCATGAATACAAAGAATCTTCACAGTCCCCAGGACACCCTTACGTGCATGGTCTCACTGATAT CTTTACTTCCTTTATCACTTTTGTTTGTAAAT |
| SEQ ID NO: 268 | IGHV(III)-25-1*01_IGHV(III)-26-1*02 | GGGTTACTCTCCATGAGTACAGATAAATCAACATTCCCAAGTGACAAGTGCAGTCTGCAGTCCTTACAAGGACCAACCTGAAA GCCAAGGCAAGGCCGTATATTACAGTGAGGGA |

TABLE B1-continued

| SEQ ID NO | Name | Sequence |
|---|---|---|
| SEQ ID NO: 269 | IGHV(III)-38-1*01 | AATGGGACTCGCCTTCAGTACAAAGAAGATTAACAGTCCTCAGAGACACTGTTCAGAAGATTCTCTTTAAGATAATAAAACTGAGAGCCCAAGACAAGTCTGTATTACTGTGAGGGA |
| SEQ ID NO: 270 | IGHV(III)-38-1*02 | AATGGGACTCGCCTTCAGTACAAAGAAGATTAACAGTCCTCAGAGACACTGTTCAGAAGATTCTCTTTAAGATAATAAAACTGAGAGCCCAAGACAAGTCTGTGTATTACTGTGAGGGA |
| SEQ ID NO: 271 | IGHV(III)-38-1D*01 | AGTGGGACTCTCCTTCAGTACAAAGAAGATTAACAGTCCTCAGAGACACTGTTCAGAAGATTCTCTTTAAGATAATTAAACCAAGAGCCCAAGACAAGTCTGTGTATTACTGTGAGGGA |
| SEQ ID NO: 272 | IGHV(III)-44*01 | TTTTAGGAAGAATGCCCCCTCAACTCATCTCCACTTGTCTGCATGTATTTCTATTTGTCTTGGACGTTCCCACAGCCTCNCGAACACTCACCTCACCCTACAATGCTGCTCGAGGGGTC |
| SEQ ID NO: 273 | IGHV(III)-44D*01 | ATTTTCCTTGCTTATAAGGTTTTAACCAGAAGAATGCTGTCATCATCTTTCCTGTTCTTTTAGAAGGAATGCCCCCTCAACTCATCTCCACTTGTCTGCATGTATTTCTATTTGTCTT |
| SEQ ID NO: 274 | IGHV(III)-5-1*01 | GATTTATCATCTCAAGAGACAATGTCAAGAGATGCTGTTTCTGCAAATGGGCAATCTGCAAACCAAGGACACGTCACTACATTACTGTCAAGAGAAG |
| SEQ ID NO: 275 | IGHV(III)-51-1*01 | CAATGCAGACTATGTTAGGGCAGACTCACCACTTCCAGAGACAACAACCAAGTACATGCTGTACATGCAAATGAACAGCCTGAGAACCCAGAACCATGGCAGCATTTAACTGTGCAGGAAA |
| SEQ ID NO: 276 | IGHV(III)-5-2*01 | GGTGCTCTGCTCCAGCACAAAGAAGATTCACAGTTCCTGGGGACAACACTTAACATCACAATCTCCCTTAAAATTATCTACTGGAAAGCTGAGGAGTAGGCAGTGCAGTATTACTGTGAGAGA |
| SEQ ID NO: 277 | IGHV(III)-67-2*01 | GATTTATTGTCTCCAGAGACAATGTCAAGAATATGCTATATCTGCAATGGGCGATCTGTAAACCAAGGACACATCAGTATATCACTGTCAAGAGAG |
| SEQ ID NO: 278 | IGHV(III)-67-3*01 | AGCATATAATGAAGATTCACAATTCCCAGGGACACCAATTACCGCACAGTCTCCCTTAAAATAATCTACTTGGAAGCTGAGGGGGCTCTCACCAGGGTAGGCAGTGATTATTACTGTGAGAGA |
| SEQ ID NO: 279 | IGHV(III)-76-4*-1 | AGGTTTACTCTTCATGAGTACAAATAAATTAACTGGTCAGCGGACGACACCCTTTCACGTGCACTCTACCTTACAATGACTAACCTGAAAGCCAAGGACAAGGTTGTGTAAATACTGTGAGCTT |
| SEQ ID NO: 280 | IGHV(III)-1*01 | TGGTACCCTCCATCAATACAAAGAAAAATCATAATCCTCAGGGACACCCTTGTCAGCACAGTCTCCCTCAAAATGACCACCTGAGAGCCGAGGAGAAGGCCATGTATTACTGTGAGAGA |
| SEQ ID NO: 281 | IGHV(III)-82*01 | GGGTTACTCTCCATGAGTACAAGTAAATTAACAGTCCCAAGCAACAACACCCTTTCAAGTGCAGTCTACCTTAAAATGACCAATGTGAAAGCCAAGGACAAGACCTTGTATTACTGTGA |
| SEQ ID NO: 282 | IGHV(IV)-44-1*01 | CTAAGCCCCCAACCTTCAGGGCAGAGCTAGCATCTCCAGAAACCATCTAAAAAACATAGTAAAAAACACATTACAGCCTGAGAGTGTGATGGCTGGGGATGCAGGCGTGATTATTACTGTGCTCAAGG |
| SEQ ID NO: 283 | IGHV1/OR15-1*01 | AACTATGCACAGAAGTTTCAGGGCAGAGTCACCATGACCAGTCCATCAGCAGCACGGGACACGTCCATCAGCACACCGGAGCTGAGCAGCCTGAGAGATCTGAGGACACGCCACGTATTACTGTGCGAGA |
| SEQ ID NO: 284 | IGHV1/OR15-1*02 | CTATGCACAGAAGTTTCAGGGCAGAGTCACCATGACCAGGGACACGTCCATCAGCAGCCTGCACGGAGCTGAGCAGCCTGAGATCTGAGGACACGGCCACGTATTACTGTGCGAGAGA |
| SEQ ID NO: 285 | IGHV1/OR15-1*03 | CTATGCACAGAAGTTTCAGGGCAGAGTCACCATGACCAGGGACACGTCCATCAGCACAGCCTACATGCAGCTGAGCAGCCTGAGAGCTGAGCAGCCTGAGAGCTGAGCAGCCTGAGA |

TABLE B1-continued

| SEQ ID NO | Name | Sequence |
|---|---|---|
| SEQ ID NO: 286 | IGHV1-1*04 | CTATGCACAGAAGTTTCAGGGCAGAGTCACCATTGACCAGGGACACGTCCATCAGCAGCCTACATGGAGCTGAGCAGCCTGAGAT CTGAGGACACGGCCACGTATTACTGTGCGAGAGA |
| SEQ ID NO: 287 | IGHV1/OR15-2*01 | AACTACCCACAGAAGCTCCAGGGCAGAGTCACCATGACCAGGGACACATCCACGAGCACAATCCGAGACAGCCTGAGCAGCCTGA GATCTGACGACATGGCCGTGTATTACTGTGCGAGA |
| SEQ ID NO: 288 | IGHV1/OR15-2*02_IGHV1/OR15-2*03 | CTACCCACAGAAGCTCCAGGGCAGAGTCACCATGACCAGGGACACATCCACGAGCACAATCCACGAGCACAGCCTACATGGAGCTGAGCAGCCTGAGA TCTGAGGACATGGCCGTGTATTACTGTGCGAGAGA |
| SEQ ID NO: 289 | IGHV1/OR15-3*01 | AAATATTCACAGAAGCTCCAGGGCAGAGTCACCATTACCAGGGACACATCTTCGAGCACAACAGCCTACATGCAGCTGAGCAGCCTGAG AATCTGAGACACGGCCGTGTATTACTGTGCGAGA |
| SEQ ID NO: 290 | IGHV1/OR15-3*02 | ATATTCACAGAAGCTCCAGGGCAGAGTCACCATTACCAGGGACACATCTTCGAGCACAACAGCCTACATGCAGCTGAGCAGCCTGAGAT CTGAGGACACGGCCGTGTATTACTGTGCGAGA |
| SEQ ID NO: 291 | IGHV1/OR15-3*03 | AAGTATTCACAGAAGCTCCAGGGCAGAGTCACCATTACCAGGGACACATCTGCGAGCACACATCTGCGAGCAGCTACATGCAGCTGAGCAGCCTGAGA ATCTGAGGACACGGCCGTGTATTACTGTGCGAGA |
| SEQ ID NO: 292 | IGHV1/OR15-4*01 | CGTTTCTCTGGCTCTGGCTCTGCGACAAACACGGCCTCTCCCTGACAATCTCTGGGCTCCAGGGCTGAGGACAGGAGATTATTACTGCAGT TCATATACAGCCACTCCCATATTCCTGATT |
| SEQ ID NO: 293 | IGHV1/OR15-5*02 | AGCTATGCACAAAAAGTTCCAGGCCAGAGTCACCATAACCAGGGACACATCCACGGGACACATCCATGAGCAGCCTACATGGAGCTAAGCAGTCTGAG ATCTGAGGACACGGCCATGTATTACTGTGAGA |
| SEQ ID NO: 294 | IGHV1/OR15-6*01 | TATATGCACAGAATTCCAGGGCAGAGTCACCATGACCAGGGACACGTCTACAGACACAGCCTACATGGAGCTGAGCAGCCTGAGAT CTGAGGACACAGCCGTATATTAATGTCAAGACA |
| SEQ ID NO: 295 | IGHV1/OR15-9*01 | CTATGCACAGAAGTTCCAGGGCAGAGTCACCATCAGGGACACATCCATGGGCACAGCACATCCATGGGCACAGCAGCCTGAGCAGCCTGAGA TCTGAGGACACGGCCATGTATTACTGTGAGAGA |
| SEQ ID NO: 296 | IGHV1/OR16-2*01 | CTATGCACAGAAGTTCAGGGCAGAGTCACCATGACCAGGGACACATGTCCACGAGCACAGCCTACATGAGCTGAGCAGTCAGAGA TCTGAGGACATAGATGTGTACTACTGTGCGAGACA |
| SEQ ID NO: 297 | IGHV1/OR21-1*01 | CTATGCACAGAAGTTCCAGGCCAGAGTCACCATTACCAGGGACACATCCACGAGCACAGCCTACATGGAGCTAAGCAGTCTGAGAT CTGAGGACACGGCCATGTATTACTGTGTGAGA |
| SEQ ID NO: 298 | IGHV1-12*01 | GTCCCTGACCGATTCTCTGGCTCCAAGTCTGGCCACCTCAACCTCCCTGGCCATCAGTGGGCTCCGGTCCGAGTAGAGGCTGATTAT TACTGTGCAGCATGGGATGACAGCCTGACTGGT |
| SEQ ID NO: 299 | IGHV1-12*02 | GTGAAGAAGCCTGGGGCCTCAGTGAAGGTCTCCTGCAAGGCTTCTGGATACACCTTCACCTACTGCACTGGGTATGCA GGCCCCCTGACAGGGCTTGAATGACAGGATTT |
| SEQ ID NO: 300 | IGHV1-14*01 | CTATGCACAGAAGTTCAGGGCAGAGTCACCATGACCAGGGACACGTCCACGAGCACAGCCTACATGGAGCTGAGCAGTCAGAGA TCTGAGGACATAGATGTGTACTACTGTGCGAGACA |
| SEQ ID NO: 301 | IGHV1-17*02 | CTACGCACAGAAGTTCCGGGGCAGAGTCACCATTACCAGTGACACAGCCTGCGTGAGCAGGTCCGTGAGCACAGCCTACATGGAGCTGAGCAGCCTGAGA TCTGAAGACATGGTCGTGTATTCCTGTGTGAGAGA |
| SEQ ID NO: 302 | IGHV1-18*01 | CACTGCTGACCTCGACCCTCAGCGGCAGAGTCTCCATGACCAGAACAGTCTACATGACCTGAGGTGAAGAGCCTAAGAT CTGACGACACGGCCACATCCAAAACAGTCTACATGACCTGAGGTGAAGAGCCTAAGAT |

TABLE B1-continued

| SEQ ID NO | Name | Sequence |
|---|---|---|
| SEQ ID NO: 303 | IGHV1-18*03 | CTATGCACAGAAGCTTCCAGGGCAGAGTCACCATGACCACAGACACATCCACGAGCACAGCCTACATGGAGCTGAGGAGCCTGAGA TCTGACGACATGGCCGTGTATTACTGTGCGAGAGA |
| SEQ ID NO: 304 | IGHV1-18*04 | CTATGCACAGAAGTTCCAGGGCAGAGTCACCATGACCACAGACACATCCACGAGCACAGCCTACATGGAGCTGAGGAGCCTGAGA TCTGACGACACGGCCGTGTATTACTGTGCGAGAGA |
| SEQ ID NO: 305 | IGHV1-2*01 | CCTGACCGATTCTCTGGCTCCAAGTCTGCCACCTCAGCCTCTCCTGGCCATCACTGGGCTCCAGGCTGACGATGAGGCAGATTATTAC TGCCAGTCCTATGACAGGGGTCTGAGTGTCTC |
| SEQ ID NO: 306 | IGHV1-2*02 | AACTATGCACAGAAGTTTCAGGGCAGGGTCACCACGACAGTCCATCAGCAGCCTACATGGACCTGAGCAGCTGAGACAGGCTGA GATCTGACGACACGGCCGTGTATTACTGTGCGAGA |
| SEQ ID NO: 307 | IGHV1-2*03 | CTATGCACAGAAGTTTCAGGGCAGGGTCACCGTGACCAGGGACACGTCCATCAACACAGTCTACATGGAGCTGAGCAGACTGAGA TCTGACGACACGGCCGTGTATTACTGTGCGAGAGA |
| SEQ ID NO: 308 | IGHV1-2*04 | CTATGCACAGAAGTTTCAGGGCTGGGTCACCATGACCAGGGACACGTCCATCATGAGCTGAGCAGGCTGAGA TCTGACGACACGGCCGTGTATTACTGTGCGAGA |
| SEQ ID NO: 309 | IGHV1-2*05 | ATCCCTGAGCGATTCTCTTGGCTCCAGTCAGGACAACAGCTGACCATCAGTGGAGTCCAGGCAGAGAGACGAGGTTGACTA TTACTGTCAATCAGCAGACAGCAGTGGTACTCCG |
| SEQ ID NO: 310 | IGHV1-24*01 | GTACGCACAGAAGTTCCAGGGCAGAGTCACCATGACCGAGGACACATCTACAGACACAGCCTACATGGAGCCGGTCAGCCTGAGA TCTGACGACACGGCCGTCTATTACTGTGCAACAGA |
| SEQ ID NO: 311 | IGHV1-3*01 | AAGTATTCACAGAAGTTCAGGGGAGAGTCACCATTACCAGGGACACATCGGCGAACACAGCCTATGAGCTGAGTAGCCTAA GATCTGAAGACACGGCTGTGTATTACTGTGCAAGA |
| SEQ ID NO: 312 | IGHV1-3*02 | ATATTCACAGGAGTTCCAGGGCAGAGTCACCATTACCAGGGACACATTCACCAGGGACACATCCGCGACAGCCTACATGGAGCTGAGCAGCCTGAGAT CTGAGGACATGGCTGTGTATTACTGTGCGAGAGA |
| SEQ ID NO: 313 | IGHV1-38-4*01 | CGGGGTCCCTGACCAGGTTCAGTGGCAGTGGATCGGGCACAGATTTTACACTGAAGATCAGCAGAGTGAGCCTGAGGACATTGGG GTTTATTACTGTATGCAGTCTCTCCAAACTCCTCA |
| SEQ ID NO: 314 | IGHV1-45*01 | CTACGCAGAAATTCCAGGACAGAGTCACCATTACTAGGGACAGTCTATGAGCACAGCCTACATGGAGCTGAGCAGCCTGAGAT CTGAGGACACAGCCATGTATTACTGTGCAAGANA |
| SEQ ID NO: 315 | IGHV1-45*02 | CCAACTACGCACAGAAATTCCAGGACAGAGTCACCATTACCAGGGACAGGTCTATGAGGACACAGCCTACATGGAGCTGAGCAGCCTG AGATCTGAGGACACAGCCATGTATTACTGCAA |
| SEQ ID NO: 316 | IGHV1-46*01 | GCTACGCACAGAAGTTCCAGGGCAGAGTTCTCCAGTCACCATTGACCAGGGACAGTCCATCAGCGGACACGTTCCACGAGCACAGTCTACATGGAGCTGAGCAGCCTGAG ATCTGAGGACACGGCCGTGTATTACTGTGCGAGAG |
| SEQ ID NO: 317 | IGHV1-46*02 | ATCCCTGAGAGATTCTCTGGCTCCAGTCAGGGACAATGGCCACCTTGACCATTAGTGGGCCCAGGTGGAGGATGAAGCTGACTA CTACTGTTACTCAACAGACACTAATGATAATCGG |
| SEQ ID NO: 318 | IGHV1-46*03 | AAGTTCGCACAGAAGTTCCAGGGCAGGGTCACCATTACGAGGGACACGTCCACGAGCACAGTCTACATGAAGCTGAGCAGCCTTAA GATCTGAGGACACGGCCGTGTATTACTGTGCGACA |
| SEQ ID NO: 319 | IGHV1-58*01 | CTACGCCACAGAAGTTCCAGGAAAGAGTCACCATTACCAGGAGCCTACATGTCCACAAGTACAGCCTACATGGAGCTGAGCAGCCTGAGAT CCGAGGACACGGCCGTGTATTACTGTGCGGGCA |

TABLE B1-continued

| SEQ ID NO | Name | Sequence |
|---|---|---|
| SEQ ID NO: 320 | IGHV1-58*02 | CTACGCACAGAAGTTCCAGGAAAGAGTCACCATTACCAGGGACATGTCCACAAGCACAGCCTACATGGAGCTGAGCAGCCTGAGAT<br>CCGAGGACACGGCCGTGTATTACTGTGCGGCAGA |
| SEQ ID NO: 321 | IGHV1-67*01_IGHV1-67*02 | AGCTACGCACAGAAGTTCCAGGGCAGAGTCACGATTACCGCGGACACATCCACGAGCACAGCCTACATGGAGCTGAGCAGCCTGA<br>GATCTGAAGACACGGCCATGTATTACTGTGGGAGA |
| SEQ ID NO: 322 | IGHV1-68*01 | CTATGCAAAGAAGTTCCAGGGCAGAGTCACCATTACCAGGGACAGATGTCCCTGAGGACAGCCTACATAGAGCTGAGCAGCCTGAGAT<br>CTGAGGACTCGGCTGTGTATTACTGGGCAAGATA |
| SEQ ID NO: 323 | IGHV1-69*01 | ATCCAGCCAGGTTCAGTGGCAGTGGGTCTGGGACAGATTTCACTCTCACCATCAGCAGCCTGAGCCTGAAGATTTTGCAGTTTAT<br>TACTGTCAGCACCGGAGCAACTGGCTAATCGCC |
| SEQ ID NO: 324 | IGHV1-69*02_IGLV3-2*02 | TCCGGGTCCCTGACAGGTTCAGTGGCAGTGGATCAGGCACAGATTTTACACTGAAAATCAGTAGAGTGGAGGCTGAGGATGTTG<br>GGGTTTATTATTGCATGCAAGCTCTACAAGGGGA |
| SEQ ID NO: 325 | IGHV1-69*04 | AATACCGCACAGAGGTTCGAGGACAGAGTCACGATTACCGCGGACACATCGACGAGCACAGTCTTCATGGAACTGAGCAGCCTGA<br>GATCTGAAGACACGGCCGTGTATTACTGTGCGAGA |
| SEQ ID NO: 326 | IGHV1-69*05 | AGACTACGCACAGAAATTCCAGGGCAGAGTCACGATTCACGGACAGAGTCACGGACGAATCGACGGACACATCCTACATGGAAGTGAAGAGCCTG<br>AGATCTGAAGACACGGCCGTGTATTATTGTGCGAG |
| SEQ ID NO: 327 | IGHV1-69*06 | ACTACGCACAGAAGTTCCAGGGCAGAGTCACGATTCACCGCGCAGACCAAATCCACGAGCCTACATGGAGCTGAGCAGCCTGAG<br>ATCTGAGGACACGGCCCGTGTATTACTGTGCGAGA |
| SEQ ID NO: 328 | IGHV1-69*07 | GACTACGCACACAGAAGTTCAGGCCAGAGTCACAATAAGCGCGCACAGAATTCACGCCCCATAGTTTATAGGAGTTGAGAAGCCTGAG<br>ATCCGACCAGCACGCACCCATATTACTGTGCGACA |
| SEQ ID NO: 329 | IGHV1-69*08 | AGACTACGCACAGAACTTCCAGATAGAGTCAACATTAATGCGGACCAATCTACGAACACAGTCTACATGGAACTGAGCAGGCTGA<br>CATCTGACGACACGGCCGTCTATTACTGTGCGAG |
| SEQ ID NO: 330 | IGHV1-69*09 | CTCCGCTCAGAAGTTCCAAGACAGAGTCACCATTAGTGTCGACAGAGTCACCGAGTCCGCGGGCACAGTATACATGGACCTGGACAGCCTGACCT<br>CTGAAGACACGGCCATGTATTACTGTGCGAAAGA |
| SEQ ID NO: 331 | IGHV1-69*10 | AACTACGCACCGAAGTTCCAGGGCAGAGTCACGATTACCGCGGACATTACCGCGGACAGCACGAATCCACGAGCACAGCCTACATGGAGCTGAGCAGCCTGAG<br>ATCTGAGGACACGGCCGTCGTGTATTACTGTGCGAGA |
| SEQ ID NO: 332 | IGHV1-69*11_IGHV1-69*12_IGHV1-69D*01 | CTACGCACAGAAGTTCCAGGGCAGAGTCACGATTACCGCGGACGAATCCACGAGCACAGCCTACATGGAGCTGAGCAGCCTGAGA<br>TCTGAGGACACGGCCGTGTATTACTGTGCGAGAGA |
| SEQ ID NO: 333 | IGHV1-69*13 | ACTACGCACAGAAGTTCCAGGGCAGAGTCACGATTACCGCGGACGAATCCACGAGCACAGCCTACATGGAGCTGAGCAGCCTGAG<br>ATCTGAGGACACGGCCGTGTATTACTGTGCGAGAG |
| SEQ ID NO: 334 | IGHV1-69*14 | CTACGCACAGAAGTTCCAGGGCAGAGTCACGATTACCGCGGACAAATCCACGAGCACAGCCTACATGGAGCTGAGCAGCCTGAGA<br>TCTGAGGACACGGCCGTGTATTACTGTGCGAGAGA |
| SEQ ID NO: 335 | IGHV1-69-2*01 | TGCTCGCACAGAAATTCGGGGCAGAATTCCATAACCGCGGACACGTCCAGACAACTTACGGCGCTGAGCAGCCTGACC<br>TCTGATGACGACGTCTATTACTGTGTTCAACAG |

TABLE B1-continued

| SEQ ID NO | Name | Sequence |
|---|---|---|
| SEQ ID NO: 336 | IGHV1-8*01 | GGCTATGCACAGAGAAGTTCCAGGGCAGAGTCACCATGACCAGGAACACTCCATAAGCACAGCCTACATGGAGCTGAGCCTGA GATCTGAGGACACGGCCGTGTATTACTGTGCGAGA |
| SEQ ID NO: 337 | IGHV1-8*02 | CTATGCACAGAGTTCCAGGGCAGAGTCACCATGACCAGGAACACCTCCATAAGCACAGCCTACATGGAGCTGAGCCTGAGAT CTGAGGACACGGCCGTGTATTACTGTGCGAGAG |
| SEQ ID NO: 338 | IGHV2/OR16-5*01 | ACAGCACGTCTCTGAAGAACAGGCTCATCATCTCCAAGGACACCTCCAAAAGCCAGGTGGTCTTACCATGACCAACATGGACCCTG TGGACACAGCCCACGTATTACTGTGCATGAGAG |
| SEQ ID NO: 339 | IGHV2-10*01 | ACAGCCCATCTCTGAAGAGTAGGCTCATTATCTCCAAGGACACCTCCAAGGATGAAGTGGTTCTAACAGTGATCAACATGGACATTG TGGACACAGCCACATATTACTGTGCAAGGAGAC |
| SEQ ID NO: 340 | IGHV2-25*01 | TACAGGACATCTCTGAAGAGCAGGCTCTCCATCTCCAAGGACACCCTCCAAAAGCCTGTGGCCTTACCATGACCAACATGGACCCT GTGGACACAGCCACGTATTATTGTGCACGGATA |
| SEQ ID NO: 341 | IGHV2-5*01_IGHV3-30*13_IGHV4-30-4*01 | TCCGGGGTCCCTGACAGGTTCAGTGGCAGTGGATCAGGCACAGATTTTACACTGAAAATCAGTAGAGTGGAGGCTGAGGATGTTG GGATTTATTACTGCATGCAAGCTCTACAAACCCCA |
| SEQ ID NO: 342 | IGHV2-5*02_IGHV2-5*03 | ACAGCCCATCTCTGAAGAGCAGGCTCACCATCACCAAGGACACCTCCAAAAACCAGGTGGTCTTACAATGACCAACATGGACCCTG TGGACACAGCCACATATTACTGTGCACACAGAC |
| SEQ ID NO: 343 | IGHV2-5*05_IGHV2-5*09 | ACGGCCCATCTCTGAAGAGCAGGCTCACCATCACCAAGGACACCTCCAAAAACCAGGTGGTCTTACAATGACCAACATGGACCCT GTGGACACAGCCACATATTACTGTGCACACAGAT |
| SEQ ID NO: 344 | IGHV2-5*06 | TACGGCCCATCTCTGAAGAGCAGGCTCACCATCACCAAGGACACCTCCAAAAACCAGGTGGTCCTTACAATGACCAACATGGACCCT GTGGACACAGCCACATATTACTGTGCACACAGA |
| SEQ ID NO: 345 | IGHV2-5*07 | AGGCGCTACAGACCCTCTCTGAAGACCAGACTCACCATTCACCCAGGACACATGTCCAGGAACCAGGTGTCCTTAGACTGACCAACTT GGACCCACTGGACACAGGCACATATTTTGTGCA |
| SEQ ID NO: 346 | IGHV2-5*10 | AGCGCTACAGACCCATCTCTGAAGAGCAGGCTCACCATCACCAAGGACACCTCCAAAAAACCAGGTGGTCCTTACAATGACCAACGTG GACCCTGTGGACACAGCCACATATTACTGCAC |
| SEQ ID NO: 347 | IGHV2-70*01 | CTACAGCACATCTCTGAAGACCAGGCTCACCATCTCCAAGGACACCTCCAAGGACACCTCCAAGGACACCTTCCAAAAACCAGGTGGTCCTTACAATGACCAACATGACCCC TGTGGACACAGCCACGTATTACTGTGCACGGAT |
| SEQ ID NO: 348 | IGHV2-70*04 | TACAGCACATCTCTGAAGACCAGGCTCACCATCTCCAAGGACACCTCCAAAAACCAGGTGGTCCTTACAATGACCAACATGGACCCT GTGGACACAGCCACGTATTACTGTGCACGATA |
| SEQ ID NO: 349 | IGHV2-70*06 | TGATAAATTCTACAGCACATCCTGAAGACCAGGCTCACCATCTCCAAAAACCAGGACACCTCCAAAAACCAGGTGGTCCTTACAATGACCAA CATGGACCCCTGTGGACACGGCCGTATTACTG |
| SEQ ID NO: 350 | IGHV2-70*10_IGHV2-70*11_IGHV2-70D*04_IGHV2-70D*14 | ACAGCACATCTCTGAAGACCAGGCTCACCATCTCCAAGGACACCTCCAAAAACCAGGTGGTCCTTACAATGACCAACATGGACCCTG TGGACACAGCCACGTATTACTGTGCACGGATAC |

TABLE B1-continued

| SEQ ID NO | Name | Sequence |
|---|---|---|
| SEQ ID NO: 351 | IGHV2-70*12 | ACAGCACATCTCTGAAGACCAGGCTCACCATCTCCAAGGACACCTCCAAAAACCAGTGGTCCTTACAATGACCAACATGGACCCTG<br>TGGACACAGCCACATATTACTGTGCACACAGAC |
| SEQ ID NO: 352 | IGHV2-70*13 | ACAGCACATCTCTGAAGACCAGGCTCACCATCTCCAAGGACACCTCCAAAAACCAGTGGTCCTTACAATGACCAACATGGACCCTG<br>TGGACACAGCCCACGTATTATTGTGCACGGATAC |
| SEQ ID NO: 353 | IGHV3/OR15-7*01 | GAATATGCTGCCTCTGCGTCTGAAAGGCAGACTTACCATCTCAAGAGAGGATTCAAAGAACACGATGTATCTGCAAATGAGCAACCTGAA<br>AACCGAGGACTTGGCCGTGTATTACTGTGCTAGA |
| SEQ ID NO: 354 | IGHV3/OR15-7*02_IGHV3/OR15-7*03 | GAATATGCTGCCTCTGCGTCTGAAAGGCAGACTTACCATCTCAAGAGAGGATTCAAAGAACACGCTGTATCTGCAAATGAGCAGCCTGAA<br>AACCGAGGACTTGGCCCGTGTATTACTGTCTAGA |
| SEQ ID NO: 355 | IGHV3/OR15-7*04 | TATGTCGCGTCTGTGAAAGGCCAGACTTACCATCTCAAGAGAACACGCTGTATCTCAAATGAGACAGCCTGAAAA<br>CCCGAGGACTTGGCCCGTGTATTACTGTGCTAGAGA |
| SEQ ID NO: 356 | IGHV3/OR15-7*05 | ATATGCTGCGTCTGTGAAAGGCAGACTTACCATCTCAAGAGAGGATTCAAAGAACACCGCTGTATCTGCAAATGAGCAACCTGAAAA<br>CCGAGGACTTGGCCGTGTATTACTGTGCTAGAGA |
| SEQ ID NO: 357 | IGHVE/OR16-10*01_IGHV3/OR16-10*03_IGHV3/OR16-11*01 | CTATGCAGACTCCGTGAAGGCCGATTCACCATCTCCAGAGACAATGCCAAGAACTCCTTGTATCTTCAAATGAACAGCCTGAGAGC<br>CGAGGACATGGCTGTGTATTACTGTCAAGAGA |
| SEQ ID NO: 358 | IGHV3/OR16-10*02 | TACTATGCAGACTTCCGTGAAGGGCCGATTCACCATCTCCAGAGACAATGCCAAGAACTCCTTGTATCTTCAAATGAACAGCCTGAGA<br>GCCGAGGACATGGCTGTGTATTACTGTCAAGA |
| SEQ ID NO: 359 | IGHV3/OR16-12*01 | AACTACGCAGACTCTGTGAAGGGCCAGATTCACCATCTCCAGACAACTCAAAGAACACGCTCTACCTGCAAATGAACAGCCTGAG<br>AGTGGAGGACACATGGCCGTGTATTACTGTGCAAGA |
| SEQ ID NO: 360 | IGHV3/OR16-13*01 | AGCTACGCAGACTCCATGAAGGGCCAATTCACCATCTCCAGAGACAATGCTAAGAACACGCTGTATCTGCAAATGAACAGTCTGAG<br>AGCTGAGGACATGGCTGTGTATTACTGTACTAGA |
| SEQ ID NO: 361 | IGHV3/OR16-14*01 | AGCTACGCAGACTCCTTGAAGGGCCAATTCACCATCTCCAGAGACAATGCTAAGAACACGCTGTATCTGCAAATGAACAGTCTGAG<br>AGCTGAGGACTATGGCTGTGTATTACTGTACTAGA |
| SEQ ID NO: 362 | IGHV3/OR16-15*01 | CTATGTGACTCCGTGAAGGGCCAATTTTCCATCTCCAGAGACAATTCCAGCAGTCCCTGTATCTGCAAAGAACAGACAGAGAG<br>CCAAGGACATGGCCGTGTATTACTGTGAGAAA |
| SEQ ID NO: 363 | IGHV3/OR16-15*02 | CACTATGTGGACTCCGTGAAGGGCCAATTTACCATCTCCAGAGACAATTCCAGCAGTCCCTGTATCTGCAAAAGAACAGACAGAG<br>AGCCAAAGACATGGCCGTGTATTACTGTGAGA |
| SEQ ID NO: 364 | IGHV3/OR16-16*01 | CACTATGTGGACATCCGTGAAGGGCCAATTTACCATCTCCAGAGACAATTCCAGACAATTCCCGTATCTGCAAAAGAACAGACAGAG<br>AGCCAAGGACATGGCCGTGTATTACTGTGAGA |
| SEQ ID NO: 365 | IGHV3/OR16-7*01 | CTACGCTGCACCTGTGAAGGCAGATTCACCATCTCAAGAGTTGATTCAAAAAAACACGCTGTATCTGCAAATGAACAGCCTGAAAAC<br>CGAGGACACGGCCGTGTATTACTGTACCACAGA |

TABLE B1-continued

| SEQ ID NO | Name | Sequence |
|---|---|---|
| SEQ ID NO: 366 | IGHV3/OR16-7*02 | GACTACGCTGCACCTGTGAAAGGCAGATTCACCATCTCAAGAGTTGATTCAAAAAACACGCTGTATCTGCAAATGAACAGCCTGAAAACCGAGGACACGGCCGTGTATTACTGTACCACA |
| SEQ ID NO: 367 | IGHV3/OR16-8*01 | AACTACCGAGACTCTGTGAAGGGCCGATTCACCATCTCCAGGGACAACGCCAATAACTCACCGTATCTGCAAATGAACAGCCTGAGAAGTGAGGACACGGCTGTGTATTACTGTGAAA |
| SEQ ID NO: 368 | IGHV3/OR16-8*02 | CTACGCAGACTCTGTGAAGGGCCGATTCACCATCTCCAGGGACAACGCCAATAACTCACCGTATCTGCAAATGAACAGCCTGAGAGCTGAGGACACGGCTGTGTATTACTGTGAAACA |
| SEQ ID NO: 369 | IGHV3/OR16-9*01 | GGGGTCCATCAAGGTTCACCGCCAGTGGATCTGGGACAGAATTCACTCTCAATATCAGCAGCCTGCACCCTGACGATTTGCAACTTATTACTGCCAGCAATATGAGCCTTATACCCC |
| SEQ ID NO: 370 | IGHV3-11*01 | GTATGGAGACTCTGTGAAGGGCCGATTCACCATCTCCAGAGACAACGCCAAGAACGCCCTGTATTTACAGATGAACAGCCTGAGAGCCCGAGGACACGGCTGTCTATTACTGTGCAGACA |
| SEQ ID NO: 371 | IGHV3-11*02 | GGGGATCCCTGATCGCTTCTCAGGCTCAGTCTGGGCTGAGCTCTACCCTCACCATCTCGAGCCCTCCAGTCTGAGGATGAGGCTGACTATTACTGTCAGACCTGGGGCACTGACATTCAG |
| SEQ ID NO: 372 | IGHV3-11*03 | AACTACCGAGACTCTGTGAAGGGCCGTTCACCATCTCCAGAGACAACGCCAACAACTCACTGTTTCTGCAAATGAACAGCCTGAGAGCCCGAGGACGCGCGCCGTGTATGACTGTGCGAGA |
| SEQ ID NO: 373 | IGHV3-11*04 | CCTGACCGATTCTCTGGCTCAGTCTGGCCATCTCAGCCTCTCCTGGCCATCAGTGGCCTCCAGTCTGAGGATGAGGCTGATTATTACTGTGCACCATGGGATGACAGCCTGAATGGTCCG |
| SEQ ID NO: 374 | IGHV3-11*05 | CTACGCAGACTCTGTGAAGGGCCGATTCACCATCTCCAGAGACAACGCCAAGAACTCACTGTATCTGCAAATGAACAGCCTGAGAGCCCGAGGACACGGCTGTATTCTGTGCGAGAG |
| SEQ ID NO: 375 | IGHV3-11*06 | CTACGCAGTCTCTGTGAAGGGCCGATTCACCATCTCCAGAGACAACGCCGCTAACTACAGTGTATCTGCAAATGAACAGCCTGCGAGACCGAGGACACGGCTGTGTATTCTGTGCGAGA |
| SEQ ID NO: 376 | IGHV3-13*01 | ACTATCCAGGCTCCGTGAAGGGCCGATTCACCATCTCCAGAGAAAATGCCAAGAACTCCTTGTATCTTCAAATGAACAGCCTGAGAGCCGGGGACACGGCTGTGTATTACTGTGCAAGAG |
| SEQ ID NO: 377 | IGHV3-13*02 | CTATCCAGGCTCCGTGAAGGGCCGATTCACCATCTCCAGAGAAAATGCCAAGAACTCCTTGTATCTTCAAATGAACAGCCTGAGAGCCGGGGACACGGCTGTGTATTACTGTGCAAGA |
| SEQ ID NO: 378 | IGHV3-13*03 | TACTATCCAGGCTCCGTCGTGAAGGCCAATTCACCATCTCCAGAGAAAATGCCAAGAACTCCTTGTATCTTCAAATGAACAGCCTGAGAGCCGGGGACACGGCTGTGTATTACTGTCAAGA |
| SEQ ID NO: 379 | IGHV3-13*04 | CTATCCAGGCTCCGTGAAGGGCCGATTCACCATCTCCAGAGAAAATGCCAAGAACTCCTTGTATCTTCAAATGAACAGCCTGAGAGCCGGGGACACGGCTGTGTATTACTGTGCAAGA |
| SEQ ID NO: 380 | IGHV3-13*05 | ACTATCCAGACTCCGTGAAGGGCCGATTCACTATTCTCCAGAGAAAATGCCAAGAACTCCTTGTATCTGCAAATGAACAGCCTGAGAGCCGGGGACACGGCTGTATATTACTGTGCAAGA |
| SEQ ID NO: 381 | IGHV3-15*01 | GACTACGCTGCATCCGTGAAAGACAGATTCACCATCTCAAGAGATGATTCAAAAATACGGTGTTTCTGCAACTGAACAGCCTGAAAACCGAGGACACAGCCGTCTATTACTGTACCACA |
| SEQ ID NO: 382 | IGHV3-15*02 | ACTACGCTGCACCCATTAAAGGCAGATTCACCATCTCAAGAGATGATTCAAGAAAAACACACTGTTTCTGCAAATGAACAGCCTGAAAAACGAAGACACAGCCATGTATTTGTACCACAG |

TABLE B1-continued

| SEQ ID NO | Name | Sequence |
|---|---|---|
| SEQ ID NO: 383 | IGHV3-15*03 | CTACGCTGCACCTGTGAAAGGCAGATTCACCATCTCAAGAGTTGATTCAAAAAACACGCTGTATCTGCAAATGAACAGCCTGAAAAC<br>CGAGGACACAGCCGTGTATTACTGTACCACAGA |
| SEQ ID NO: 384 | IGHV3-15*04_IGHV3-15*06 | CTACGCTGCACCCGTGAAAGGCAGATTCACCATCTCAAGAGATGATTCAAAAAACACGCTGTATCTGCAAATGAACAGCCTGAAAA<br>CCGAGGACACAGCCGTGTATTACTGTACCACAGA |
| SEQ ID NO: 385 | IGHV3-15*05 | ATAGACTATGCTCACCCGTGAAAGGCAGATTCATCATTTCAAGAGATGATTCAAAAAGTACGGTGTATTACAAATGAACAGACTG<br>AAATTGAGGACACAGCCGTATATTATTGTGTC |
| SEQ ID NO: 386 | IGHV3-15*07 | ACTACGCTGCACCTGTGAAGGCAGATTCACCATCTAAGAGATGATTCAAGAGATGATTCAAGAACACGCTGTATTTAACATGAACAGCCTGAAA<br>ACCGAGGACACAGCCGTGTATTGTCTTTCAG |
| SEQ ID NO: 387 | IGHV3-15*08_IGHV3/OR16-6*01_IGHV3/OR16-6*02 | CTACGCTGCACCTGTGAAAGGCAGATTCACCATCTCAAGAGATGATTCAAAAAACACGCTGTATCTGCAAATGATCAGCCTGAAAAC<br>CGAGGACACGGCCGTGTATTACTGTACCACAGG |
| SEQ ID NO: 388 | IGHV3-16*01_IGHV3-16*02 | CTATGTGACTCCGTGAAGCGCCGATTCATCATCTCCAGAGACAATTCCAGGAACTCCCTGTATCTGCAAAGAACAGACGGAGAG<br>CCGAGGACATGGCTGTGTATTACTGTGTGAGAAA |
| SEQ ID NO: 389 | IGHV3-19*01 | CTATGCAGACTCTGTGCAGGCCGATTCATCATCTCCAGAGACAATTCCAGGAACTTCCTGTATCAGCAAATGAACAGCCTGAGGCC<br>CGAGGACACGGCCTGTGTATTACTGTGCGAGAA |
| SEQ ID NO: 390 | IGHV3-20*01 | TTATGCAGACTCTGTGCAGGGCCGATTCACCATCTCCAGAGACAACGCCAAGAACTCCCTATATCTGCAAATGAACTCTGAGAGC<br>CGAGGACACGGCCTTGTATTACTGTGCGAGAG |
| SEQ ID NO: 391 | IGHVE-20*02 | TTATGCAGACTCTGTGAAGGGCCGATTCACCATCTCCAGAGACAACGCCAAGAACTCCCTGTATCTGCAAATGAACAGTCTGAGAGC<br>CGAGGACACGGCCTTGTATCACTGTGCGAGAG |
| SEQ ID NO: 392 | IGHV3-21*01 | ATTACGCAGACTCAGCGAAGGGCCGATTCACCATCTCCAGAGACAACGCCAAGAACACAATGTATCTGCAAATGAACAGCCTGAGA<br>GCCGAGGACACGGCTATGTATTACTGTGCGACCG |
| SEQ ID NO: 393 | IGHV3-21*02 | TATACTATGCAGACTCACTGAGGGCCGATTCACCATCTCCAGAGACAACGCCAGAATTCACTGTCTCTGCAAATCAACGACCTGC<br>GACCCGACACGGCTATATATTATTGTGCGA |
| SEQ ID NO: 394 | IGHV3-21*03 | CTACGCAGACTCAGTGAAGGGCCGATTCACCATCTCCAGAGACAACGCCAAGAACTCACTGTATCTGCAAATGAACAGCCTGAGAG<br>CCGAGGACACAGCCGTGTATTACTGTGCGAGAGA |
| SEQ ID NO: 395 | IGHV3-21*04 | CTACGCAGACTCAGTGAAGGGCCGATTCACCATCTCCAGAGACAACGCCAAGAACTCACTGTATCTGCAAATGAACAGCCTGAGAG<br>CCGAGGACACGGCCGTGTATTACTGTGCGAGAGA |
| SEQ ID NO: 396 | IGHV3-22*02 | ATAGACCACACGTCTGAAAGGCAGATCACCATCTCAAGAGATGATTCCAAAAAGCATCACCTATCTGCAAAATGAAGAGCCTGAAAA<br>CCGAGGACACGGCCGTGTATTACTGTTCCAGA |
| SEQ ID NO: 397 | IGHV3-23*01 | ATACTACGCAGATCCCGTGAAGGGCCGTTCACCATCTCCAAGAGACAATTCCAAGAACACGCTGTATCTGCAAATGAACAGCTGA<br>GAGCCGAGGACACGGCCGTATATTACTGTGCGAA |

TABLE B1-continued

| SEQ ID NO | Name | Sequence |
|---|---|---|
| SEQ ID NO: 398 | IGHV3-23*02 | CTACGGAGACTCCGTGAAGGGCCGGTTCACCATCTCAAGAGACAATTCCAAGAACACGCTGTATCTGCAAATGAACAGCCTGAGAG CCGAGGACACGGCCGTATATTACTGTGCGAAAGA |
| SEQ ID NO: 399 | IGHV3-23*03_IGKV1/OR-4*01 | ATCCAGCCAGGTTCAGTGGCAGTGGGTCTGGGACAGACTTCACTCTCACCATCAGCAGCCTGGAGCCTGAAGATTTTGCAGTTTAT TACTGTCAGCAGCGTAGCAACTGGCTAATCGCC |
| SEQ ID NO: 400 | IGHV3-23*04 | ACTACGCAGACTCCGTGAAGGGCCGGTTCACCATCTCCAGAGACAATTCCAAGAACACGCTGTATCTGCAAATGAACAGCCTGAGA GCCGAGGACACGGCCGTGTATTACTGTGCGAAAG |
| SEQ ID NO: 401 | IGHV3-23*05 | TATTACCGAGACTCCGTGAAGGGCCGGTTCACCATCTCAAGAGACAATTCCAGGAACACACTGTTTGCAATTGAATAGCCTGAGA GTCGAGGACACGGCCATATATTATTGTGCGAAA |
| SEQ ID NO: 402 | IGHV3-23D*01_IHGV3-23D*02 | CTACGCAGACTCCGTGAAGGGCCGGTTCACATCTCCAGAGACAATTCCAAGAACACGCTGTATCTGCAAATGAACAGCCTGAGAG CCGAGGACACGGCCGTATATTACTGTGCGAAAGA |
| SEQ ID NO: 403 | IGHV3-25*01_IGHV3-25*02_IGHV3-25*05 | CCTCATAGACTCCGTAAGGACCGATTCAATACCTCCAGAGATAACGCCAAGAACGCCAAGAACACTTCATCTGCAAATGAACAGCCTGAAAAC CGAGGACACGGCCCTCTTATTAGTGTACCAGAGA |
| SEQ ID NO: 404 | IGHV3-25*03 | CCTCATAGACTCCGGTAAGGACCGATTCAATACCTCCAGAGATAACGCCAAGAACGCCAAGAACACTTCATCTGCAAATGAACAGCCTGAAAAC CGAGGACACGGCCCTGTATTAGTGTACCAGAGA |
| SEQ ID NO: 405 | IGHV3-25*04 | ACTGGTATCCCAGCCAGGTTCAGTGGCAGTGGGTCTGGGACAGAGTTCACTCTCACCATCAGCAGCCTGCAGTCTGAAGATTTGC AGTTTATTACTGTCAGCAGTATAATAACTGGCAG |
| SEQ ID NO: 406 | IGHV3-29*01_IGHV3-30-42*01 | ATGCAGACTCTGTGAAGGGCAGATTCTCCATCTCCAAAGACAATGCTAAGAACTCTCTGTATCTGCAATGAACAGTCAGGAACTG AGGACAATGCTGTGTATGCTGCTACATAAGGTT |
| SEQ ID NO: 407 | IGHV3-30*01 | CTACGCAGACTCCGTGAAGGGCCGATTCACCATCTCCAGAGACAATTCCAAGAACACACTGTATCTGGCAATGAACAGCCTGAGAG TTGAGGACACGGCTGTGTATTACTGTGTGAGAGA |
| SEQ ID NO: 408 | IGHV3-30*02 | CTACGCAGAGTCCGTGAAGGGCCGATTCACCATCTCCAGAGACAATTCCAAGAACACACCCTGTATCTTCAACTGAACAGCCTGAGAGC TGAGGACACGGCTGTGTATTATTGTGCGAAAGA |
| SEQ ID NO: 409 | IGHV3-30*03 | CTATGCAGACTCCGTGAAGGGCCGATTCACCATCTCCAGAGACAATTCCAAGAACACCCTGTATCTGCAAATGAACAGCCTGAGAG CTGAGGACACGGCTGTGTATTACTGTGCGAGAGA |
| SEQ ID NO: 410 | IGHV3-30*04_IGHV3-30*07 | TCCGGGGTCCCTGACAGGTTCAGTGGCAGTGGATCAGGCACAGATTTTACACTGAAAAATCAGTAGAGTGGGGCTGAGGATGTTG GGGTTTATTACTGCATGCAAGCTCTACAAACCCCA |
| SEQ ID NO: 411 | IGHV3-30*08 | CCTGAGCGATTCTCTGCTCCAACTCTGGCAACACAGCCACTCTGACCATCAGCGGGACCCAGGCTATGGATGAGGCTGACTATTAC TGTCAGGCGTGGGACAGCACTGCCGATGTG |
| SEQ ID NO: 412 | IGHV3-30*09 | ACACTATGCAGACTCCGTTCAGGGCCGATTCGGCGTCTCCAGAGACACAATTCAACTACACGGCGTACGTGCAACTGAACAGCCTGA GACCAGACGACACGGCTGTTTATTTTGTGCGAG |

TABLE B1-continued

| SEQ ID NO | Name | Sequence |
|---|---|---|
| SEQ ID NO: 413 | IGHV3-30*10 | TCTACACAGACTCCGTGAAGGGCCGATTCACCATCTCCAGAGACAATTCCAAGAACACAGTGATTTGCAGATGACTAACCTGAGC GATGACGACACGGCTGTGTACTTCTGTGCGAAAG |
| SEQ ID NO: 414 | IGHV3-30*12 | CTACGCAGACTCCGTGAAGGGCCGATTCACCATCTCCAGAGACAATTCCAAGAACACGGCTGTATTACTGTGCGAGAGCCTGAGAG CCGAGGACACGGCTGTGTATTACTGTGCGAGAGA |
| SEQ ID NO: 415 | IGHV3-30*14 | TTATGCAGACTCCGTGAAGGGCCGATTCACCATCTCCAGAGACAATTCCAAGAACACATTGTTCCTCAAATGAACAGCCTGAGAGT AGAGGACACGGCTCTCTATTACTGTGCGAAAGA |
| SEQ ID NO: 416 | IGHV3-30*15 | CTACGCAGACTCCGTGAAGGGCCGATTCACCATCTCCAGAGACAATTCCAAGAACACGCTGTATCTGCAAATGAGCAGCCTGAGAG CTGAGGACACGGCTGTGTATTACTGTGCGAGAGA |
| SEQ ID NO: 417 | IGHV3-30*16 | TTTACGCAGACTCCATGAAGGGCCGCTTCACCATCTCCAGAGAGACTCCAAGAACACGCTGTATCTGCACATGAACAGCCTGAGA CCTGAGGACACGGCTGTCTATTACTGTGCGAGAG |
| SEQ ID NO: 418 | IGHVE-30*19 | TTTTACTCAGACTCCATGAAGGGCCGGTGCACATTCCAGGACAACTCCAAGCAGACAGTGTATTTGAAATAGACACCCTGGA AACTGAAGACACGGCGGGTATTCCTGTGAAA |
| SEQ ID NO: 419 | IGHV3-30-2*01_IGHV3-30-52*01 | TTATGCATAATCTTTGAAGAGCAAATTCACCATCTCCAAAGAAAATGCCAAGAACTCACTGTATTGCTAATGAACAGTCTGAGAGC AGCGGGCACAGTGTGTGTTACTGTATGTGAGG |
| SEQ ID NO: 420 | IGHV3-30-22*01 | ATGCAGACTCTGTGAAGGGCCAGATTCTCCATCTCCAAAGACAATGCTAAGACAATTCCAGAGACAACGCTGTATCTGCAAATGAACAGCCTGAGAG AGGACACATGGACGGTGTCAGTGGCTGTACATAAGGTC |
| SEQ ID NO: 421 | IGHV3-30-3*01_IGHV3-30-3*03_IGHV3-30*06_IGHV3-30*11_IGHV3-30*17 | CTACGCAGACTCCGTGAAGGGCCGATTCACCATCTCCAGAGACAATTCCAAGAACACGCTGTATCTGCAAATGAACAGCCTGAGAG CTGAGGACACGGCTGTGTATTACTGTGCGAGAGA |
| SEQ ID NO: 422 | IGHV3-30-3*02 | GGGGTCCATCAAGGTTCAGTGCAGTGATCTGGGACAGATTTCACTCTCCACCATCAGCAGTCTGCAACCTGAAAATTTGCAACT TACTACTGTCAACAGAGTTACAGTACCCCTTGG |
| SEQ ID NO: 423 | IGHV3-30-33*01 | TTATGCATAATCTTTGAAGAGCAAATTCACCATCTCCAAAGAAAATGCCAAGAACTCACTGTATTTGCTAATGAACAGTCTGAGAGC AGAGGGACACAGCTGTGTGTTACTGTATGTGAGG |
| SEQ ID NO: 424 | IGHV3-30-5*01_IGHV3-30-5*02_IGHV3-30*18_IGHV3-NL1*01 | CTATGCAGACTCCGTGAAGGGCCGATTCACCATCTCCAGAGACAATTCCAAGAACACGCTGTATCTGCAAATGAACAGCCTGAGAG CTGAGGACACGGCTGTGTATTACTGTGCGAAAGA |
| SEQ ID NO: 425 | IGHV3-32*01 | ATGCAGACTCTGTGAAGGGCCGATTCTCCATCTCCAAAGACAATGCTAAGACACTCTGTATCTGCAAATGAACACTCAGAGAGCTG AGGACGTTGGCCGTGTATGGCTATACATAAGGTC |
| SEQ ID NO: 426 | IGHV3-33*01 | CTATGCGAGACTCCGTGAAGGGCCGATTCACCATCCCCGAGAGGCAATTTCAAGAACACGCTGTATCTGCAAATGAACAGCCTGAGTG CCGAGGACACGGCTGTGTATTACTGTGCGAGAGA |

TABLE B1-continued

| SEQ ID NO | Name | Sequence |
|---|---|---|
| SEQ ID NO: 427 | IGHV3-33*02 | CTATGCAGACTCCGTGAAGGGCCGATTCACCATCTCCAGAGACAATTCCAAGAACACGCTGTTTCTGCAAATGAACAGCCTGAGAG CCGAGGACACGGCTGTGTATTACTGTGCGAGAGA |
| SEQ ID NO: 428 | IGHV3-33*03 | ATCCAGACAGGTTCAGTGGCAGTGGGTCTGGGACAGACTTCACTCTCACCATCAGCAGACTGGAGCCTGAAGATTTTGCAGTGTA TTACTGTCAACACTATCGTAGTTCACCTCGAAG |
| SEQ ID NO: 429 | IGHV3-33*04 | CTATGCAGACTCCGTGAAGGGCCGATTCACCATCTCCAGAGACAATTCCAAGAACACGCTGTATCTGCAAATGAACAGCCTGAGAG CCGAGGACACGGCTGTGTATTACTGTGCGAGAGA |
| SEQ ID NO: 430 | IGHV3-33*05 | TTACGCAGACTCCGTGAAGGGCCGATTCATCATCTCCAGAGACAATTCCAGGGACACGGTGTTTCTGCAGATGAGCAGCCTGAGAC TCGAGGACACGGCTGTCTATTACTGTGCGACAGA |
| SEQ ID NO: 431 | IGHV3-33*06 | CTATGCAGACTCCGTGAAGGGCCGATTCACCATCTCCAGAGACAATTCCAAGAACACCCTGTATCTGCAAATGAACAGCCTGAGAG CCGAGGACACGGCTGTGTATTACTGTGCGAAAGA |
| SEQ ID NO: 432 | IGHV3-332*01 | TTATGCCCAATCTGTGAAGAGACAAATTCACCATCTCCAAAGAAAATGCCAAGAACTCACTGTATTTGCAAATGAACAGTCTGAGAGC AGAGGGCACAGCTGTGTGTTACTGTATGTGAGG |
| SEQ ID NO: 433 | IGHV3-35*01 | CACTATGCAGACTCTGTGAAGGGCCGATTCATCATCTCCAGAGACAACCCCTGTATCTGCAAACGAATAGCCTGAGG GCGAGGACACGGCTGTGTATTACTGTGTGAGA |
| SEQ ID NO: 434 | IGHV3-36*01_IGHV3-36*02_IGHV3-36*03 | AGCTATGCAGACTCTGTGAAGGTCGATTCACCCTCCCAGAGATGCCAAGAAATCACTGTATCTGCAAATGAACAGCGTCAG AGCCGAGGATAGTCTGTGTATTACTGTGGTGGC |
| SEQ ID NO: 435 | IGHV3-37*01 | GGTAGTCTATATATGCAGACTGAGGGTAGATTCACCATCTCTAGAGACAATGCCAAGAACATGCTGTTCTTGCAAATGAACA GTCTGAGAGATGAGGACTCGGTTGTGTTGAGAGA |
| SEQ ID NO: 436 | IGHV3-37*02 | TGGTAGCCTATACTATGCAGACACTGAGGGTAGATTCACATCTCTAGAGACAATGCCAAGAACATGCTGTACTTGCAAATGAAC AGTCTGAGAGATGAGGAGACTCGGCTGTGTGAGAGA |
| SEQ ID NO: 437 | IGHV3-38*01 | ACCCAGAGACTCCAGGAAGGGCAGATTCACCATCTCCAGAGACAATTCCAAGAACACGCTGTATCTTCAAATGAACAACCTGAGAGCT GAGGGCACGGCCGCCGTATTACTGTGCCAGAGA |
| SEQ ID NO: 438 | IGHV3-38*02_IGHV3-38*03 | ACGCAGAGACTCCAGGAAGGGCAGATTCACCATCTCCAGAGACAATTCCAAGAACACGCTGTATCTTCAAATGAACAACCTGAGAGCT GAGGGCACGGCCGCCGTGTATTACTGTGCCAGATATA |
| SEQ ID NO: 439 | IGHV3-3803*01 | CTATGCAGACTCCAAGGAGGGCAGATTCACCATCTCCAGAGACAACAATTCCAAGAGACACGCTGCATCTTCAAATGAACAGCCTGAGAG CTGAGGACACGGCTGTGTATTACTGTAAGAAAGA |
| SEQ ID NO: 440 | IGHV3-41*01 | ATACTATGCAGACTCTGTGAAGGGCCGATTCACAATCTCCGAGACAATTCTAAGAGACATGCTCTATCTGCAAATGGACAGTCTGAAA GCTAAGGACACGGCCATGTATTACTGTACCAGA |
| SEQ ID NO: 441 | IGHV3-42*02_IGHV3-42D*01 | ATGCGCTGCATCTGTGAAGGCAGGTTCACCATCTCAAGAGATGATTCAAAGAACCACCGACTGTATATGCAAATGAATACCCTGAAAA CCAAGTACACGCCGCCATCTATTACTGTACTAGAGA |

TABLE B1-continued

| SEQ ID NO | Name | Sequence |
|---|---|---|
| SEQ ID NO: 442 | IGHV3-42*03 | ATGCGCTGCATCTGTGAAAGGCAGGTTCACCATCTCAAGAGATGATTCAAAGAACACTGTATCTGAAGTGAATACCCTGAAAACCGAGTACACGGCCATCTATTACTGTAGTAGAGA |
| SEQ ID NO: 443 | IGHV3-43*01 | ATTATGCAGCCTCTGTGAAGGGTCGATTCACCATCTCCAGAGACAACTCCAAAAACTCCCTGTTTTGCCAAATGAACAGTCTGAGAGTTGAAGATTCCGCCTTCTATTACTGTGAAAAG |
| SEQ ID NO: 444 | IGHV3-43*02 | TACTATGCAGACTCTGTGAAGGGCCGATTCACCATCTCCAGAGACAACAGCAAAAACTCCCTGTATCTGCAAATGAACAGTCTGAGAACTGAGGACACCGCCTTGTATTACTGTGCAAAA |
| SEQ ID NO: 445 | IGHV3-43D*01 | ATGCAGACTCTGTGAAGGGTCGATTCACCATCTCCAGAGACAACAGCAAAAACTCCTGTATCTGCAAATGAACAGTCTGAGAGCTGAGGACACCGCCTTGTATTACTGTGCAAAGATA |
| SEQ ID NO: 446 | IGHV3-47*01 | TACTATGCAGACTCCGTGATGGGCCGATTCACCATCTCCAGAGACAACGCCAAGAAGTCCTTGTATCTTCATATGAACAGCCTGATAGCTGAGGACATGGCTGTGTATTATTGTGCAAGA |
| SEQ ID NO: 447 | IGHV3-47*02 | TACTATGCAGACTCCGTGATGGGCCGATTCACCATCTCCAGAGACAACGCCAAGAAGTCCTTGTATCTTCAAATGAACAGCCTGATAGCTGAGGACATGGCTGTGTATTATTGTGCAAGA |
| SEQ ID NO: 448 | IGHV3-48*01 | TACTACCGAGACTCTGTGAAGGGCCGATTCACCATCTCCAGAGACAATGCCAAGAACTCACTGTATCTGCAAATGAACAGCCTGAGAGCCGAGGACACGGCTGTGTATTACTGTGCGAGA |
| SEQ ID NO: 449 | IGHV3-48*02 | TACTACCGAGACTCCGTGAAGGGCCGATTCACCATCTCCAGAGACAATGCCAAGAGTCACTGTATCTGCAAATGACCAGCCTGAGAGTCGAGGACACGGCTGTGTATTACTGTGCGAGG |
| SEQ ID NO: 450 | IGHV3-48*03 | TACTACCCAGACTCTGTGAAGGGCCGATTCACCATCTCCAGAGACAGTGCCAAGAATTCACTGTATCTGCACATGCACAGCCTGAGAGCCGAGGACACGGCTGTTTATTACTGTGCGAGA |
| SEQ ID NO: 451 | IGHV3-48*04 | CTACGCAGACTCTGTGAAGGGCCGATTCACCATCTCCAGAGACAACGCCAAGAACTCACTGTATCTGCAAATGAACAGCCTGAGAGCCGAGGACACGGCTGTGTATTACTGTGCGAGAG |
| SEQ ID NO: 452 | IGHV3-49*01 | ATACACCGCGTCTGTGAAAGGCAGATTCACCATCTCCAAGAGATGGTTCCAAAAGCATCGCCTATCTGCAAATGAACAGCCTGAAAACCGAGGACACAGCCAGCTATTACTGTACTAGAGA |
| SEQ ID NO: 453 | IGHV3-49*02_IGHV3-49*03 | ATACCCCGCGTCTGTGAAAGGCAGATTCACCATCTCAAGAGATGATTCCAAAAGCATCGCCTATCTGCAAATGAACAGCCTGAAAACCGAGGACACAGCCAGCTATTACTGTACTAGA |
| SEQ ID NO: 454 | IGHV3-49*04 | AAATACGCCGCGTCTGTGAAAGGCAGATTCACCATCTCAAGAGAGTGATTACAAAAGCGTCGTCTATCTGCAAATGAACAGCCTGAAAAGCGAGGACACACCGGCTATTACTGTACTAGA |
| SEQ ID NO: 455 | IGHV3-49*05 | GAATACGCCGCGTCTGTCGTCAGATTCACCATCTCAAGAGATGATTCCAAAAGCATCCAAAAGCATCGCCTATCTGCAAATGAACAGCCTGAAAACCGAGGACACACAGCCGTATTACTGTACTAGA |
| SEQ ID NO: 456 | IGHV3-50*01 | ATGCAGACTCTGTGAAGGTCAGATTCACCATCTCCAAAGACAATGCCAAGACACAGGTTGTATCTGCAAATGAACAGTCTGAGAGCTGAGAATATGGCTCTGTATTATTGAGTCAAAGGTA |
| SEQ ID NO: 457 | IGHV3-52*01 | CTATGTAGACTCTGTGAAGGGCCGATTGACCATCTCCAGAGACAATGCCAAGAACTCCCTATCTGCAAGTGAACAGCCTGAGAGCTGAGGACATGACCGTGTATTACTGTGTGAGAGG |
| SEQ ID NO: 458 | IGHV3-52*03 | TACTATGCTAGACTCTGTGAAGGGCCGATTACTGTCACCATCTCCAGAGACAATGCCAAGAACTCCCTCTATCGAGTGAACAGCCTGAGAGCTGAGGACATGACCGTGTATTACTGTGAGA |

TABLE B1-continued

| SEQ ID NO | Name | Sequence |
|---|---|---|
| SEQ ID NO: 459 | IGHV3-53*01 | CTACGCAGAGACTCCGTGAAGGGCCGATTCACCATCTCCAGAGACAATTCCAAGAACACGCTGTATCTTCAAATGAACAGCCTGAGAG<br>CCGAGGACACGGCCGTGTATTACTGTGCGAGAGA |
| SEQ ID NO: 460 | IGHV3-53*02 | TACTATGCAGACTCTGTGAAGGGCCGATTCACCATCTCCAGAGACAACAGCCAAAACTCCCTGTATCTGCAAATGAACAGTCTGAAA<br>ACTGAGGACACACCGCCTTGTATTACTGTGTGAAA |
| SEQ ID NO: 461 | IGHV3-53*03 | CTACGCAGACTCTGTGAAGGGCCGATTCACCATCTCCAGAGACAATTCCAAGAACACGCTGTATCTTCAAATGAACAGCCTGAGAGC<br>CGAGGACACGGCCGTGTATTACTGTGCTAGGGA |
| SEQ ID NO: 462 | IGHV3-53*04 | GTTTCTCATCGTTCTCTGGCTCCAAGTCTGGCAACACACGGCCTCCCTGACCATCTCTGGGCTCCGGGCTGAGGACGAGGGTGATTAT<br>TACTGCACCTCATATACAATCAATAGCGATTTT |
| SEQ ID NO: 463 | IGHV3-54*02 | TTATGCACAATCTGTGAAGAGCAGATTCACCATCTCCAGAGACAATGCCAAGAACTCACTCCCTTTGCAAATGAACAGTCTGAGAGC<br>AGAGGGCACGGCCGTGTATTACTGTATGTGAGG |
| SEQ ID NO: 464 | IGHV3-54*04 | TTATGCACAATCTGTGAAGACCAGATTCACCATCTCCAAAGAAAATGCCAAGAACTCACTCCCTGTTTGCAAATGAACAGTCTGAGAGA<br>AGAGGGCACGGCCGTGTATTACTGTATGTGAGT |
| SEQ ID NO: 465 | IGHV3-57*01 | GAACAGCCTGAGAGCTGAGGACGCCGAGGGCACAAATTAACAGTCCCAAGGCGACACCTTTTCATGTGCAGTCTACCTTACAATGACCAACCTGAA<br>AGCCAAGGACACAAGGCTGTGTATTACTGTGAGGA |
| SEQ ID NO: 466 | IGHV3-57*02 | GAGTTACTCTCCATGAGTACAAATAACAGTCCCAAGGCGACACCTTTTCATGTGCAGTCTACCTTACAATGACCAACCTGAAAG<br>CCAAGGACACAAGGCTGTGTATTACTGTGAGGGA |
| SEQ ID NO: 467 | IGHV3-6*01 | CTACGCAGACTCTGTGAAGGGCCGATTCACCATTCACCAAAAACTCACTGTATCTGAAATGAACAGACAGTCTGAGGG<br>CAGAGGATGCAGCTGACATGGCTGTATTACTGTGAGAGA |
| SEQ ID NO: 468 | IGHV3-60*01 | CTACGCAGACTCTGTGAAGGGCTGATTCACCATCTCTAGAGACAATTCACTGTATCTGCAAATGAACAGCCTGAGAGC<br>CGACGACACAGTGGCTGTGTATTACTGTGAAAGA |
| SEQ ID NO: 469 | IGHV3-62*01 | CTACACAGACTCTGTGAAGGGCCGATTCACCATCTCCAGAGACAATTCACTGTCTCTGCAAATGAACAGCCTGAGAGC<br>CGAGGGCACAGTTGTGACTGTGTATTACTGTGAAAGA |
| SEQ ID NO: 470 | IGHV3-63*01 | ATGCAGACTCTGTGAAGGGCCAGATTCACCATCTCCAAAGACAATGCTAAGAACTCACCGTATCTCCAAACGAACAGTCTGAGAGCT<br>GAGGACATGACCATGGCTGTATTACTGTGAGAGA |
| SEQ ID NO: 471 | IGHV3-64*01 | ATTTCATGCAGACTCTGTGAAGGGCAGATTCACCATCTCCAGAGACAATTCCAAGAGACACATGTTTCAAATGGGCAGCCTGAG<br>AGCTGAGGACTGAGGCTGTGTATTACTGTGCGAGA |
| SEQ ID NO: 472 | IGHV3-64*02 | TTATGCAGACTCTGTGAAGGGCAGATTCACCATCTCCAGAGACAATTCCAAGAACACCTGTATCTTCAAATGGGCAGCCTGAGAG<br>CTGAGGACACAGTGGCTGTGTATTACTGTGCGAGAG |
| SEQ ID NO: 473 | IGHV3-64*03 | CTACGCAGACTCAGTGAAGGGCAGATTCACCATCTCCAGAGACAATTCCAAGAACACGCTGTATGTCCAAATGAGCAGTCTGAGAG<br>CTGAGGACACGGCTGTGTATTACTGTGTGAAAGA |
| SEQ ID NO: 474 | IGHV3-64*04 | CATTCTACGCAGAACTCCGCGAAGGCAGATTCACCATCTCCGAGAACAATCCAAGAGACACTCTGCATCTTCAAATGAACAGTCTGA<br>GACCTGAGGACTCGGCTGTCTTATTACTGTGTGA |
| SEQ ID NO: 475 | IGHV3-64*05 | ACTACGCAGACTCCGTGAAGGGCAGATTCACCGTCTCCAGAGACGATGCCAAGAGACCCTCTTTCTTCAAGTGAGCGGTCTGCGA<br>GCTGAGGGACACGGCTGCTATTACTGCGAAAG |

TABLE B1-continued

| SEQ ID NO | Name | Sequence |
|---|---|---|
| SEQ ID NO: 476 | IGHV3-64D*06 | AAGTACCGGACTCCGTGAAGGGCCAGATTCATTACTCCAAGAACACGTTGTATCTTCAAATGAGCAGTCTGAGACCTGAGGACACGGCTATTTATTGTGTGAAA |
| SEQ ID NO: 477 | IGHV3-65*01 | CTTTCTAATCGCTTCTCTGGCTCCAAGTCTGGCTCCAACACGGCCTCCCTGACCATCTCTGGGCTGAGGACGGGCTGATTATTTCTGCAGCTCATATACAACCAACAAGGGG |
| SEQ ID NO: 478 | IGHV3-65*01 | ATACGCCGCGTCTGTGAAAGGCAGATTCACCATCTCAAGCGATGATTCAAAAGCATCGCCTATCTGCAAATGAACAGCCTGAAAACCGAGGACACGGCCGTGTATTACTATACCAGAGA |
| SEQ ID NO: 479 | IGHV3-66*01 | CTACGCAGACTCCGTGAAGGGCCAGATTCACCATCTCCAGAGACAATTCCAAGAACACGCTGTATCTTCAAATGAACAGCCTGAGACCGAGGACACGGCTGTGTATTACTGTGCGAGAGA |
| SEQ ID NO: 480 | IGHV3-66*02 | TATTACAGACTCCGTGAAGGGCCGATTCACCATCTCCAGAGACAATTCCAAGAACACGCTGTATCTTCAAATGAACAGCCTGAGAGCTGAGGACACGGCTGTGTATTACTGTGCGAGA |
| SEQ ID NO: 481 | IGHV3-66*03 | CTACGCAGACTCCGTGAAGGGCCGATTCACCATCTCCAGAGACAATTCCAAGAACACGCTGTATCTTCAAATGAACAGCCTGAGAGCTGAGGACACGGCTGTGTATTACTGTGCGAGAG |
| SEQ ID NO: 482 | IGHV3-66*04 | CTACGCAGACTCCGTGAAGGGCCAGATTCACCATCTCCAGAGACAATTCCAAGAACACGCTGTATCTTCAAATGAACAGCCTGAGACCGAGGACACGGCTGTGTATTACTGTGCGAGACA |
| SEQ ID NO: 483 | IGHV3-69-1*01 | GGGGTTTCTAATCGCTTCTCTGCTCCAAGTCTGCCAACACGGCCTCCCTGACAATCTCTGGACTCAGCAGGCTGAGAGCGAGGCTGATTATTACTGCTGCTCATATGCAGAAGTAAGACT |
| SEQ ID NO: 484 | IGHV3-69-1*02 | CATCCCAGACAGGTTCAGTGGCAGTGGGTCTGGGACAGACTTCACTCTCAGCATCAGCAGGCTGGAGCCTGAAGACTTTGCAGTGTATTACTGTCAGCAGTATGGTAGCTCACCTCCGA |
| SEQ ID NO: 485 | IGHV3-7*01 | CTATGTGGACTCTGTGAAGGGCCGATTCACCATCTCCAGAGACAACGCCAAGAACTCACTGTATCTGCAAATGAACAGCCTGAGAGCCGAGGACACGGCTGTGTATTACTGTGCGAGA |
| SEQ ID NO: 486 | IGHV3-7*02 | ATACTATATGGACTCTGTGAAGGGCCGATTCACCATCTCCAGAGACAACGCGAAGAACTCAGTGAACTCCAATCAACAGCCTGAGAGGCGAGGACACGGCTGTCTATTACTGTGCGAG |
| SEQ ID NO: 487 | IGHV3-7*03 | CTATGTGGACTCTGTGAAGGGCCGATTCACCATCTCCAGAGACAACGCCAAGAACAACGCCAAGAACTCACTGTATCTGCAAATGAACAGCCTGAGGG |
| SEQ ID NO: 488 | IGHV3-71*01 | GAATAGACCACGTCTGTGAAAGGCAGATTCACAATCTCAAGAGATGATTCAAAAGCATCACCTATCTGCAAATGAACAGCCTGAGAGCCGAGGACACGGCCGTGTATTACTGTGCGAGA |
| SEQ ID NO: 489 | IGHV3-71*02 | ATAGACCACGTCTGTGAAAGGCAGATTCACAATCTCAAGAGATGATTCAAAAGCATCACCTATCTGCAAATGAACAGCCTGAGAGCCGAGGACACGGCCGTGTATTACTGTGCGAGA |
| SEQ ID NO: 490 | IGHV3-71803 | ATAGACCACGTCTGTGAAAGGCAGATTCACCATCTCAAGAGATGATTCCAAAGATGATTCCAAAGATGATTCCAAAGATGATTCCAAAGATGATTCAAAGAACTCACCTATCTGCAAATGAACAGCCTGAGAGCCGAGGACACGGCCGTGTATTACTGTGCGAGA |
| SEQ ID NO: 491 | IGHV3-72*01 | AATACGCCGCGTCTGTGAAAGGCAGATTCATCATCTCAAGAGATGATTCAAAGAACTCACTATATCTGGAAATGAACAGCCTGAAAACGAGGACACGGCCGAGTATTACTGTGCTAGAG |
| SEQ ID NO: 492 | IGHV3-73*01 | ACATCTTACGCTCCGTCGATAAAAGGCAAGTTCATCATTTCCAGAGATGATTCCAGCAATATGTTGTATCTTCAAATGAACAACCTGAAAACCGAGGAGACAGGCCCTCTATTTTGTACT |

TABLE B1-continued

| SEQ ID NO | Name | Sequence |
|---|---|---|
| SEQ ID NO: 493 | IGHV3-73*02 | GCATATACTGCCTCGTGAGAGGCAGTTCACCATCTCCAGAGATGATTCAAAGAACACGGCGTGGCTGCAAATGAGCAGCCTGG AAACCGAGGACACGGCCGTATATTACTGTATTAGA |
| SEQ ID NO: 494 | IGHV3-74*01 | CTACGCGGACTCCGTGAAGGGCCGATTCACCATCTCCAGAGACAACGCCAAGAACACGCTGTATCTGCAAATGAACAGTCTGAGAG CCGAGGACACGGCTTTGTATTACTGTGTAAGAGA |
| SEQ ID NO: 495 | IGHV3-74*02 | AACTACGCGGACTCCGTGAAGGGCCGATTCACCATCTACAGAGACGACGCCAAGAACACACTGAATCTGCAAATGAACAGTCTGAG AGTCGAGGACACGGCAGTGTATTATTGTGTAAGA |
| SEQ ID NO: 496 | IGHV3-74*03 | AACTTACGCGGACTCCATGAAGGGCCGATTCACCATCTCCAGAGACAATGCCAAAAACACGCTGGATCTGCAAATGAACAGCCTGA GAGTCGAGGACACGGCTGTGTATTACTGTGTAAG |
| SEQ ID NO: 497 | IGHV3-75*01 | TCCTACTAGCCTGTGGCAAATGGAAGCATCTCTTTTTTATCAGACTGAATAATATTGTAGTGTTTCTTATACCACATTACTTCATCCC TTTGTGCATTAACACTTAGGTTGTTTTAT |
| SEQ ID NO: 498 | IGHV3-76*01 | TACTATCCAGACTCTGTGAAGGGCCGGTTGACCATCTCCAGAGAAAAACACCAAGAACTCACTGTATCTGCAAATAAACAGTTTCATT GCTGACACCATGGCCGTCTATTACTGTGAAGAGA |
| SEQ ID NO: 499 | IGHV3-79*01 | TACCACCCACTCCTCAAGTGTCCAGTCACCATCTCCCAGATCCCGTGTCCAAAAAAGCAGTTCTTCCTACAGCTGAGCTACATGAGCAAC AAGCACATAGCCATGTATTTTAAGCCAAGA |
| SEQ ID NO: 500 | IGHV3-9*01 | TAGGCTATGTGACTCTGTGAAGGGCCGATTCACCATCTCCAGAGACAACGCCAAGAACTCCCTGTATCTGCAAATGAATAGTCTGA GAGCTGAGGACACGGCCTTATATTACTGTGCAA |
| SEQ ID NO: 501 | IGHV3-9*02 | ATGCGGACTCTGTGAAGGGCCGATTCACCATCTCCAGAGACAACGCCAAGAACTCCCTGTATCTGCAAATGAACAGTCTGAGAGCT GAGGACACGGCCTTGTATTACTGTGCAAAGATA |
| SEQ ID NO: 502 | IGHV3-9*03 | ATGCGGACTCTGTGAAGGGCCGATTCACCATCGCCAGAGACAACGCCAAGAACTCCCTGTATCTGCAAATGAACAGTCTGAGAGCT GAGGACATGGCCTTGTATTACTGTGCAAAGATA |
| SEQ ID NO: 503 | IGHV4/OR15-8*01 | CTACAACCCGTCCCTCAAGAGTCGAGTCACCATATCAGTAGACAAGTCCAAGAACCAGTTCTCCCTGAAGCTGAGCTCTGTGACCGC CGCGGACACGGCCGTGTATTACTGTGCGAGAGA |
| SEQ ID NO: 504 | IGHV4/OR15-8*02 | TACTACGCAGAGTCTGTGAAGGGCCGATTCACCATCTCCAGGGACAACGCCAAGAACTCACTGTATCTGCAAATGAACAGCCTGAG AGCCGAGGACACGGCCGTGTATTACTGTGCGAGA |
| SEQ ID NO: 505 | IGHV4/OR15-8*03 | CTACAACCCATCCCTCAAGAGTCGAGTCACCATATCAGTAGACAAGTCCAAGAACCAGTTCTCCCTGAAGCTGAGCTCTGTGACCGC CGCGGACACGGCCCTGTATTACTGTGCGAGAGA |
| SEQ ID NO: 506 | IGHV4-28*01 | TACTACAACCCGTCCCTCAAGAGTCGAGTCACCATGTCAGTAGACACGTCCAAGAACCAGTTCTCCCTGAAGCTGAGCTCTGTGACC GCTGGACACGGCCGTGTATTACTGTGCGAGA |
| SEQ ID NO: 507 | IGHV4-28*02_IGHV4-28*05_IGHV4-28*07 | CTACAACCCGTCCCTCAAGAGTCGAGTCACCATGTCAGTAGACACGTCCAAGAACCAGTTCTCCCTGAAGCTGAGCTCTGTGACCGC CGTGGACACGGCCGTGTATTACTGTGCGAGAAA |
| SEQ ID NO: 508 | IGHV4-28*03 | CTACAACCCGTCCCTCAAGAGTCAGTCACCATGTCAGTAGACACGTCCAAGAACCAGTTCTCCCTGAAGCTGAGCTCTGTGACCGC CGTGGACACGGCCGTGTATTACTGTGCGAGAGA |

TABLE B1-continued

| SEQ ID NO | Name | Sequence |
|---|---|---|
| SEQ ID NO: 509 | IGHV4-28*04 | TACTACAACCCGTCCCTCAAGAGTCGAGTCACCATGTCAGTAGACACGTCAGTAGACCAGTTCTCCCTGAAGCTGAGCTCTGTGACC GCCGTGGACACGGCCGTGTATTACTGTGCGAGA |
| SEQ ID NO: 510 | IGHV4-28*06 | CTACAACCCGTCCTCCAAGAGTCGAGTCACCATGTCACCATGTCAGTAGACACGTCCAAGAACCAGTTCTCCFTGAAGCTGAGCTCTGTGACCGC CTTGGACACGGCCGTGTATTACTGTGCCAGAAA |
| SEQ ID NO: 511 | IGHV4-30-2*01 | ACTTCAACCCGTCCTCCAAGAGTCGAGTCACCTATCAGTTGACAGGTCCGAGAACCAGTTCTCCTGAAGCTCAGCTCTGTGACCG CCCGGACACGGCCGTGTATTACTGTGCCAGAG |
| SEQ ID NO: 512 | IGHV4-30-2*03 | CTACAACCCGTCCCTCAAGAGTCGAGTCACCATATCCGTAGAGACACGTCCAAGAACCAGTTCTCCTGAAGCTGAGCTCTGTGACCGC TGCAGACACGGCTGTGTATTACTGTGCGAGACA |
| SEQ ID NO: 513 | IGHV4-30-2*05 | CTACAACCCGTCCCTCAAGAGTCGAGTTACCATATCAGTAGACACGTCCAAGAACCAGTTCTCCTGAAGCTGAGCTCTGACTGC CGCAGACACGGCCGTGTATTACTGTGCCAGAGA |
| SEQ ID NO: 514 | IGHV4-30-2*06 | CTACAACCCGTCCCTCAAGAGTCGAGTCACCATATCAGTAGACACGTCCAAGAACCAGTTCTCCTGAAGCTGAGCTCTGTGACCGC CGCGGACACGGCCGTGTATTACTGTGCCAGAGA |
| SEQ ID NO: 515 | IGHV4-30 4*02 | CTACAACCCGTCCCTCAAGAGTCGAGTTACCATATCAGTAGACACGTCCAAGAACCAGTTCTCCTGAAGCTGAGCTCTGTGACCGC AGCAGACACGGCCGTGTATTACTGTGCCAGAGA |
| SEQ ID NO: 516 | IGHV4-30 4*03 | ATTATAACCCGCCCTCAGGAGTCGAGTAACCATATCAGCAGATCAGGTCTCCCTGGAGCTGAGTCCTATGACTG CCGGGACACGGCCGTGTATTACTGTGCCAGAG |
| SEQ ID NO: 517 | IGHV4-30 4*07 | CTACAACCCGTCCCTCAAGAGTCGAGTCACCATATCAGTAGACACGTCCAAGAACCAGTTCTCCTGAAGCTGAGCTCTGTGACCGC CGCGGACACGGCCGTGTATTACTGTGCCAGAGA |
| SEQ ID NO: 518 | IGHV4-31*01 | CCTACTACAACCCGTCCAACCGTCTAGTTACCATATCAGTAGACACGTCTAAGAACACCAGTTCTCCCTGAAGCTGAGCTCTGTGAC TGCTGCGACACGGCCGTGTATTACTGTGCGA |
| SEQ ID NO: 519 | IGHV4-31*02 | CTACAACCCGTCCCTCAAGAGTCGAGTTAACCATATCAGTAGACACGTCCTAAGAACCAGTTCTCCTGAAGCTGAGCTCTGTGACTGC CGCGGACACGGCCGTGTATTACTGTGCGAGAGA |
| SEQ ID NO: 520 | IGHV4-31*03 | TTACTACAACCCCTCCCTCAAGGGGCGAGTTACCATATCAGTAGACACGTCTGAGACCAGTTCTCCCTGAGGCTGAGCTCTGTGAC TGCCGCGACACGGCCGTGTATTACTGTGCGG |
| SEQ ID NO: 521 | IGHV4-31*04 | ACCGACTACACACCCGTCCCTCCCTCCAGGAGTCCAGTTACCATATCAGTAGACATGTCTAAGAACACCAGTTCTCCCTGAAACTGAGGTCTGTG ACTGCCGCGACAGGCCCGTCTATTATTGTGCG |
| SEQ ID NO: 522 | IGHV4-31*06 | ACTACAACCCGTCCCTCAAGAGTCGAGTTACCATATCAGTAGACACGCCTAAGAACCAGTTCTCCTCTGGAGTTGAGCTCTGTGACTG CCCGCGACACGGCCGTGTATTACTGTGCGAGAG |
| SEQ ID NO: 523 | IGHV4-31*07 | ACTATAACCCGTCCCTCCAAGAGTCGAGTCGAGCCTCCATCTCACAAGACACGTCTGAGAACCAGTTCTCCGTTTCCTGAGGCTGACCTCTGTGACTG CCGCGGACACGGCCGTGTATTTCTGTGCGAG |
| SEQ ID NO: 524 | IGHV4-31*08 | ACTACAACTCGTCCCTCAAGAGTCGACTTACCATATCCGTAGAGACACCAGTTCTCCGAGAACCAGTTCTCCCTGAAGCTGAGCTCTGTGACCG CTGCGGACACGGCCGTGATTACTGTGCGAGA |
| SEQ ID NO: 525 | IGHV4-31*10 | CTACAACCCGTCCCTCAAGAGTCGAGTTACCATATCAGTAGACCCGTCCAAGAACCAGTTCTCCCTGAAGCCGAGCTCTGTGACTGC CGCGGACACGGCCGTGGATTACTGTGCGAGAGA |

TABLE B1-continued

| SEQ ID NO | Name | Sequence |
|---|---|---|
| SEQ ID NO: 526 | IGHV4-34*01 | ACTACAACCGTCCCTCAAGAGTCGAGTCACCATATCAGTAGACACGTCCAAGAACCAGTTCTCCCTGAAGCTGAGCTCTGTGACCG CCGCGGACACGGCTGTGTATTACTGTGCGAGAG |
| SEQ ID NO: 527 | IGHV4-34*02 | GACTACAACCCGTCCCTCAAGAGTCGAGTCACCATATCAGTGGACACGTCCAAGAACCAGTTCTCCCTGAAGCTGAGCTCTGTGACC GCCGCGGACACGGCTGTGTATTACTGTGCGAGA |
| SEQ ID NO: 528 | IGHV4-34*03 | ACTACAACCCGTCCCGTCTCAAGAGTCGAGTTACCATATCAGTAGACACGTCTAAGAACCAGTTCTCCCTGAAGCTGAGCTCTGTGACTG CCGCGGACGGCCGTGTATTACTGTGCGAGAG |
| SEQ ID NO: 529 | IGHV4-34*04 | GAGTTCCTGATCGCTTCCAGGCTCGAGTCACCATATCAGTGGGCTGACCGTCCACCATCTCCAACCTCCAGTCTGAGGATGAGGCTGATT ATTACTGTGAGACCTGCACAGTAACACTCATG |
| SEQ ID NO: 530 | IGHV4-34*05 | CAACACCCGTCCCTCAAGAGTCGAGCCACCATATCAGTAGACACGTCCAAGAACCAGTTCTCCCTGAAGCTGAGCTCTGTGACCGC CGCGGACACGGCTGTGTATTACTGTGCGAGAG |
| SEQ ID NO: 531 | IGHV4-34*08 | ACCAACTACAAAGTTCCCTCGAGAGTCGAGTCACCATATCAATTGACACGTCTAAGAACCGATTCTCCCTGAGGGTGAGGGCCGTG ACCGCCGCGGACACGGCTAAATACTTCTGTGCG |
| SEQ ID NO: 532 | IGHV4-34*09 | AAGTACAACCCGTCGCTCAGAGAGTCGGGTCACCATATCAATAGACACGTCCAAGGAACCACTTCTCCCTGAACCTGAGCTCAGTGACC GCCGCGGACACGGCTGTCTATATTTCTGTGCGAGA |
| SEQ ID NO: 533 | IGHV4-34*10 | AACTACAACCCGTCCCTCAAGAGTCGAGTCACCATATCAATAGACACGTCCAAGAGGCAATTCTCCCTGAGGCTGACTTCTATGACC GCCGCGGACACGGCTGTCTATTTCTGTGCGAGA |
| SEQ ID NO: 534 | IGHV4-34*11 | ATCCCACCCCAGGCTCAGTGGCCGTCTCCCTGAGAGTCGAGTCACCATATCAATAGACACGTCCACTCTCCAACCAGCTGGAGCTGAGAGATTTCTGCAGTTTAT TACTGTCAGGCTTAGCAACTGCAATCGCC |
| SEQ ID NO: 535 | IGHV4-34*12 | TTACAACCCGTCCCTCCAGAGTCGAGTCACCATATCAATAATAGACACGTCCAAGCACCAATTCTCCCTGAGGGTGATTCTTTGACCGCC GCGGACACGGCTAGATATTTCTGTGCGAGAGG |
| SEQ ID NO: 536 | IGHV4-34*13 | ACTACAACCCGTCCCTCAAGAGTCGAGTCACCATATCAGTAGACACGTCCAAGAAACAGCTCCCTGAAGTTGAGCTCTGTGAACG CCGCGGACACGGCTGTGTATTACTGTGCGAGAG |
| SEQ ID NO: 537 | IGHV4-38-2*01 | CACTACAACCCGTCCCTCAAGAGTCGAGTCTCCATATCAGTTGTCACGTCCAAGAACCAGCTCTCCCTGAGGCTGAGTTTGTGACT GCCGCAGACACGGCCGTCTATTACTGTGCGAGA |
| SEQ ID NO: 538 | IGHV4-38-2*02 | TACTACAACCCGTCCCTCAAGAGTCGAGTCACCATATCAGTAGACACGTCCAAGAACCAGTTCTCCCTGAAGCTGAGCTCTGTGACC GCCGCAGACACGGCCGTGTATTACTGTGCGAGA |
| SEQ ID NO: 539 | IGHV4-39*01 | AGTGGGGTTCCCATCAAGTTCAGTGCCGGTGTCTGTGGACAGATTTCACCCTCACCATCAGCAGTCTGCAATCTGAAGATTTTGCA ACTTACTATCTGTCAACAGAGTTATAGTCCCCG |
| SEQ ID NO: 540 | IGHV4-39*02 | TACTACAATCCCTCCCTCAAGAGCCGAGTCACCATATCCGTAGACACGTTGAAGAATAACTTCTCCCTGAAGCTGAGTTCTGTGACCG CCGCAGACACGGCTGTTTATTACTGTACGAGA |
| SEQ ID NO: 541 | IGHV4-39*03 | GTCTACAATCCGTCCCTCAAGAGTCGAGTCACCATATCCGTAGACACGTCCAAGAACCTGTTCTCCCTGAAACTGACCTCTGTGACCG CCGCAGACAGGCTGGTATATTTCTGTGCGAGA |
| SEQ ID NO: 542 | IGHV4-39*05 | CACCTTCTACAACCCGTCCCTCAAGAGTCGAGTCACCATATCCGTGGACACGTCCAAAAACCAGATCTCCCTGAGGCTGAACTCTGT GACCGCCGCCAGACGGCTGTGTATTATTGTGC |

TABLE B1-continued

| SEQ ID NO | Name | Sequence |
|---|---|---|
| SEQ ID NO: 543 | IGHV4-39*06 | CTACAACCCGTCCCTCAAGAGTCGAGTCACCATATCAGTAGACACGTCCAAGAACCAGTTCCCTGAAGCTGAGCTCTGTGACCGC CGCGGACACGGCCGTGTATTACTGTGCGAGAGA |
| SEQ ID NO: 544 | IGHV4-39*07 | ACTATAACCCGTCTCTGAGTCGAGTCGCCATATCAGTAGACACGTCCAGGAACCAGTTCTCCTGAAGCTGAACTCTGTGACCG CCGCGGACACGGCCGTTTATTACTGTGCCAGAG |
| SEQ ID NO: 545 | IGHV4-4*01 | GGGGTCCCATCAAGGTTCAGTGGCAGTGATCTGGGACAGATTTCACTCTCACCATCAGCAGTCTGCAACCTGAAGATTTTGCAACT TACTACTGTCAACAGAGTTACAGTACCCCCCG |
| SEQ ID NO: 546 | IGHV4-4*02 | ACTACAACCCGTCCCTCAAGAGTCGAGTCACCATATCAGTAGACAAGTCCAAGAACCAGTTCTCCCTGAAGCTGAGCTCTGTGACCG CCGCGGACACGGCCGTGTATTACTGTGCGAGAG |
| SEQ ID NO: 547 | IGHV4-4*03 | CTACAACCCTCCCTCAAGAGTCGAGTCACCATGTCAGTAGACACGTCCAAGAACCAGTTCTCCCTGAAGCTGAGCTCTGTGACCGC CGCGGACACGGCCGTGTATTACTGTGCGAGAGA |
| SEQ ID NO: 548 | IGHV4-4*07 | ACTACACCCTCCCTCAAGAGTCGAGTCACCATGTCAGTAGACACGTCCAAGAACCAGTTCTCCCTGAAGCTGAGCTCTGTGACCG CCGCGGACACGGCCGTGTATTACTGTGCGAGAG |
| SEQ ID NO: 549 | IGHV4-4*08 | CTACACCCCTCCCTCAAGAGTCGAGTCACCATATCCGTAGACACGTCCAAGAACCAGTTCTCCCTGAAGCTGAGCTCTGTGACCGC CGCAGACACGGCCGTGTATTACTGTGCGAGAG |
| SEQ ID NO: 550 | IGHV4-55*01 | CTACAACCCGTCCCTCAAGAGTCGAGTCACCATATCCGTAGACACGTCCGTAGACACGTCCAAGAACCAGTTCTACCTGAAGCTGAGCTCTGTGACCGC CGCGGACACGGCCGTGTATTACTGTGCGAGAGA |
| SEQ ID NO: 551 | IGHV4-55*02 | CTACAACCCGTCTCCCTCAAGAGTCGAATCACCATGTCAGTAGACACGTCCAAGAACCAGTTCTACCTGAAGCTGAGCTCTGTGACCGC CGCGGACACGGCCGTGTATTACTGTGCGAGAGA |
| SEQ ID NO: 552 | IGHV4-55*08 | CTACAACCCGTCCCTCAAGAGTCGAAT6CACCATGTCAGTAGACACGTCCAAGAACCAGTTCTACCTGAAGCTGAGCTCTGAACCGC CGCGGACACGGCCGTGTATTACTGTGCGAGAG |
| SEQ ID NO: 553 | IGHV4-55*09 | CTACAACCCGTCCCTCAAGAGTCGAATCACCATGTCCGTAGACACGTCCAAGAACCAGTTCTCCCTGAAGCTGAGCTCTGTGACCGC CGTGGACACGGCCGTGTATTACTGTGCGAGAAA |
| SEQ ID NO: 554 | IGHV4-59*01_IGHV4-59*07 | AACTACAACCCCTCCCTCAAGAGTCGAGTCACCATATAGACACGTCCAAGAACACGTCCCTGAAGAACCAGTTCTCCCTGAAACTCAGCTCTGTGACC GCTGCGACACGGCCGTGTATTACTGTGCCAGAG |
| SEQ ID NO: 555 | IGHV4-59*02 | AGTATAACCCCTCCCTCAAGAATCGAGTCACCATATCATTAGACACGTCCGAGAACCAGTTCTCCCTGAAACTCAGCTCTGTGACCGC CGCGGACACGGCCCTATTACTGTGCCAGAG |
| SEQ ID NO: 556 | IGHV4-59*03 | ACTACAACCCCCTCCCCTCCCGCAAGAGTCGGGTCACCATATCACCATATCAGCGCACACGTCCACGAATCAATTCCCTGAACCTGTTCTCTGTGACCGC TGCGGACACGGCCGTGTATTACTGTCGAGAG |
| SEQ ID NO: 557 | IGHV4-59*04 | AAGTATAACCCGTCCCTCAAGAGTCGACTCACCCCTGTCCATTGACACGTCCAGAGAGCCAGTTCTCCCTGAAGTTGAGGTCTGTGACC GCCGCCCGACACGGCCGTCTATTACTGTGCCGA |
| SEQ ID NO: 558 | IGHV4-59*08 | CTTTATATAATCCCTCCCTCGAGAGTCGAGTCACCATGTCAGTAGACAATCCAAGGACCAGTTCTCCATGAAGCTGACCTCTGTGACCG CCCGAGACACGGCCATATATTACTGTGCGAGA |
| SEQ ID NO: 559 | IGHV4-59*10 | CAGTTCTCCCTCCCTCCCAGGAGGCGAGTCACCATGTCAACAGACACGTCCAGAAATCAGTTCTCCCAATTGACTTCTGTGACCGCT GCGGACACGGCCGTCTATTACTGTGCGAGAGA |

TABLE B1-continued

| SEQ ID NO | Name | Sequence |
|---|---|---|
| SEQ ID NO: 560 | IGHV4-61*01 | CTACAACCCCTCCCTCAAGAGTCGAGTCACCATATACAGTGACACGTCCAAGAACCAGTTCTCCCTGAAGCTGAGCTCTGTGACCGC TGCGGACACGGCCGTGTATTACTGTGCGAGAGA |
| SEQ ID NO: 561 | IGHV4-61*02 | CAACTACAACCCCTCCCTCAAGAGTCGAGTCACCATATCAGTGACACGTCCAAGAACCAGTTCTCCTGAAGCTGACTGAGCTCTGTGAC CGCCGCAGACACGGCCGTGTATTACTGTGCGAG |
| SEQ ID NO: 562 | IGHV4-61*03 | AACTACAACCCCTCCCTCAAGAGTCGAGTCACCATGTCAGTAGACACGTCCAGGAACCACTTCTCCCTGAACCTGAACTCTGTGACC GCCGCAGACACGGCCGTCTATTACTGTGCGAGA |
| SEQ ID NO: 563 | IGHV4-61*04 | GGGTACACCAGGTACACCCCCTCCTCAAGAGTCGAGTCACCATATCAATAGACTCGTCCAAGAACCAGTTGTCCCTGAATCTGAAC TCTGTGACCGCCGCCGACACGGCCGTCTACTAC |
| SEQ ID NO: 564 | IGHV4-61*05 | AACTACAACCCCTCCCTCAAGAGTCGAGTCACCATATCAGTAGACAAGTCCAAGAACCAGTTCTCCCTGAAGCTGAGCTCTGTGACC GCCGCGGACACGGCCGTGTATTACTGTGCGAGA |
| SEQ ID NO: 565 | IGHV4-61*08 | AACTACAACCCCTCCCTCAAGAGTCGAGTCAGCATATCAGTAGACACGTCTAAGAACCAATTCTCCCTGAAGCTGACCTCTGTGACC GCTGCGGACACGGCCGTCTATTACTGTGCGAGA |
| SEQ ID NO: 566 | IGHV4-80*01 | ATTGGATACATCTATTATAGTGGGAGGAGCTACTACACCCCGTCCCTCAGGAGTTGAGTCATGTCAATGAAACGTCCAAGAAC CAGTTTCCCTGAAGCTGAGCTCTGTGACCGCA |
| SEQ ID NO: 567 | IGHV4-10 1*01 | AACTACAGCCCGTCTCCTTCCAAGGCCACGTCCACCATCTCAACTGACAAGTCCATCAACACTGCCTCGAGTGGACAGCCTGAAG GCCTCGGACACCGCCATCTATTATTGTGCGAGA |
| SEQ ID NO: 568 | IGHV4-10 1*02 | CAATACAGCCCGTCTCTTTCAAGGCCACGTCCACCATCTCAGCTGACAAGTCCATCACACTGCCTACTTGCAGTGGAGCAGCCTGAAG GCCTCGGACACCGCCATATATTATTGTGCGAGA |
| SEQ ID NO: 569 | IGHV4-10 1*03 | AACTACAGCCCGTCTCCTTCCAAGGCCACTGCAGTCACCATCTCAGCATCTCAGCTGACAGTCCATCAGCACTGCTACTGCAGTGGAGCAGCCTGAAG GCCTCGGACACCGCCATGTATTTCTGTGCGAGA |
| SEQ ID NO: 570 | IGHV4-10 1*04 | TACAGCCCCATCTCTGGAGGGTAGACTCACCATCACCAAGGACACCTCCAAAAACCAGGTGGTTCCTTACAATGACCGACATGGACCCT GTGGACACAGGCACATATTACTGTGCACACAGA |
| SEQ ID NO: 571 | IGHV5-51*01 | ATATAGCCCGTTCTTCCAAGGCCAGTTCACCATGTCACCATGTCAGCGACAAGTCCATCAGCAGCCGCCTACCTACAGTGGAGCAGCCTGCGGG CCTCGGACACCGCCATGTATTACTGTGCGAGACA |
| SEQ ID NO: 572 | IGHV5-51*02 | GATACAGCCCGTTCTTCGAAGGCCAGGTCACCATGTCAGCGACGAGTCCCTTCAGCACCGTCTACCTCCAATGAGCAGCCTGAAG CCCTTCGGACAGCGCCATGTATTTCTGTGCGGC |
| SEQ ID NO: 573 | IGHV5-51*03 | AGATACAGCCCGTTCTTCCAAGGCCAGTGCAGTCACCATCTCAGCCGACAAGTCCATCAGCACCGCCTACCTGCAGTGGAGCAGCCTGAA GGCCTCGGACACCGCCATCTATTTCTGTGCGAGA |
| SEQ ID NO: 574 | IGHV5-51*04 | AGATATAGCCCGTCTTCCAAGGCCAGTGCAGTCACCATCTCAGCCGACAAGTCCATCAGTACCGCCTACCTGCAGTGGAACAGCCTGAG GGCCTCGGACACCGCCATCTATTACTGTGCGAGA |
| SEQ ID NO: 575 | IGHV5-78*01 | ATACAGCCCATCTTCCAAGGCCACGTCACCATTCAGCGACCACGTCCAGCAGCAGCTCCAGCAGCACCGCGCCTACCTGCAGTGGAGCAGCCTGAAGG CCTCGGACGCCGCCATGTATTATTGTGAGAGG |
| SEQ ID NO: 576 | IGHV5-78*02 | CAGATACAGCCCACCTTCCAAGGCCACGTCACCATCTCAGCCGACAGCTCCAGCAGCAGCTCCAGCAGCTCCAGCGACAGCTCCAGCGACAGCTCCAGCAGCACCGCCTACCTGCGAGTGGAGCAGCCTGAA GGCCTCGGACGCCGCCATGTATTATTGTGAGA |

TABLE B1-continued

| SEQ ID NO | Name | Sequence |
|---|---|---|
| SEQ ID NO: 577 | IGHV6-1*01 | ATTATGCAATATCTGTGAAAAGTCGAATAGCCATCAACCCAGACACATCCAAGAACCAGTTCTCCCTGCAGCTGAACTCTGTGACTC CCGAGGACACGGCTGTGTATTACTGTGCAAGAG |
| SEQ ID NO: 578 | IGHV6-1*02 | ATCCCAGACAGGTTCAGTGGCAGTGGGTCTGGGACAGACTTCACTCTCACCATCAGCAGACTGGAGCCTGAAGATTTTGCAGTGTA TTACTGTCAGCAGTGTAGTAGCTCACCCTGGATG |
| SEQ ID NO: 579 | IGHV7-27*01 | ACTGGGAACCTAACGTATGCCCAGGGCTTCACAGGACGGTTTGTCTTCTCCATGGACACCTCCAGCAGCATGCATATCTTCATATC AGCAGCCTAAAGGCTGAGGACACGTGCAAGAGG |
| SEQ ID NO: 580 | IGHV7-34-1*01_IGHV70 34-1*02 | GTATACCCACGGCTTCACAGGATGGTTTGTCTTCTCCATGGACACGTCTGTCAGCACGGCTGTGTCTTCAGATCAGCAGCCTAAAGGC TGAGGACACGGCCGAGTATTACTGTGCAAGTA |
| SEQ ID NO: 581 | IGHV7-40*01 | CCTGACCGCTTCTCGGCTTCCAAGTCTGGCACGTCTGCCACCCTGGGCATCACTGGACTCCAGACTGGAGACGAGGCCCATTATTAC TGCGCCACATGGGATAGTGGCCTGAGTGCCGGA |
| SEQ ID NO: 582 | IGHV47-40*03 | ATATACCACGGCTTCACAGGACGGTTTCTATTCTCCATGGACACCTCTGTCAGCATGGCTATCTGCAGATCAGCAGCCTAAAGGC TGAGGACACGGCCGTGTATGACTGTATGAGAGA |
| SEQ ID NO: 583 | IGHV47-40*04 | ATATACCACGGCTTCACAGGACGGTTTCTATTCTCCATGGACACCTCTGTCAGCATGGCTATCTGAAGATCAGCAGCCTAAAGGC TGAGGACACGGCCGTGTATGACTGTATGAGAGA |
| SEQ ID NO: 584 | IGHV7-40D*01 | GTATACCCACGGCTTCACAGGACGGTTTGTCTTCTCCATGGACATGGCTATCGCTATCTGCAGCATGGCCTATCGCAGCCTAAAGGC TGAGGACACGGCCGTGTATTACTGTGCAGAGA |
| SEQ ID NO: 585 | IGHV7-4-1*01 | ACGTATGCCCAGGGCTTCACAGGACGTTTGTCTTCCTTGGACACCTCTGTCAGCACGGCATATCTGCAGATCTGCAGCCTAAAG GCTGAGGACACTGCCGTGTATTACTGTCGAGA |
| SEQ ID NO: 586 | IGHV7-4-1*02 | CAACATATGCCCAAGACTTCACAGGGCGATTGTCTTCTCCCGGACACCTCTGTCAAACAGGCATTTCTGCAGATCAGCAGCCTACA GGCTGAAGACACTGCCGTCTATTACTGTGCA |
| SEQ ID NO: 587 | IGHV7-4-1*04 | GTATGCCCAGGGCTTCACAGGACCGGTTTGTCTTCTTCCATGGACATGGCATATCTGCAGATCAGCAGCCTAAAGGC TGAGGACACTGCCGTGTATTACTGTGCAGAGA |
| SEQ ID NO: 588 | IGHV7-4-1*05 | GTATGCCCAGGGCTTCACAGGACGTTTGTCTTCTCCTTGGACACCTCTGTCAGCATGGCATATCTGCAGATCAGCAGCCTAAAGGC TGAGGACACTGCCGTGTTACTGTGCAGAGA |
| SEQ ID NO: 589 | IGHV7-56*02 | TGTATGCCCACAGATTCACACACGGTTTGTCTTCTCCATGGACACCTCTGTCAGCACGGCGATCTGCAGACTAGCTGCCTAAAGAC TGAGGATGCAGCCATTATTACTGTGTAGGTA |
| SEQ ID NO: 590 | IGHV7-81*-01 | ATATGCCCAGGGCTTCACAGGACGTTTGTCTTCTCCATGGACACCTCTGCCAGACATCTGCAGAGATCAGCAGCCTAAAGGC TGAGGACATGGCCATGTATTACTGTGCAGATA |
| SEQ ID NO: 591 | IGK1/OR10-1*01_IGKV1/OR10-1*01 | TGGGATTCCCTCTCGGTTCAGTGACAGTGGATCTGGGACAGACAGATTACACTCTCACCATCAGCAGCCTGCAGCCTGAAGATTTTGCAAC TTATTACTGTCAACAGAGTGACAGTACCTCTC |
| SEQ ID NO: 592 | IGKV1/OR1-1*01 | TGGGATTCCCTCTCGGTTCAGTGACAGTGGATCTGGGCAGACTACACTCTCACCATCCGCAGCCTGCAGCCTGAAGATTTGCAAG TTATTACTGTCAACAGAGTGACAGTACCCCTCC |

TABLE B1-continued

| SEQ ID NO | Name | Sequence |
|---|---|---|
| SEQ ID NO: 593 | IGKV1-118*01 | TGGGATTCCCTCTCGGTTCAGTGACAGTGGATCTGGGCAGATTACACTCTCACCATCCGAGCCTGCAGCCTGAAGATTTTGCAACTTATTAGTGTCAACAGAGTGACAGTAACCCTCC |
| SEQ ID NO: 594 | IGKV1/OR-2*01 | TGGGATTCCCTCTCGGTTCAGTGACAGTGGATCTGGGACAGATTACACTCTCACCATCAGCCTGCAGCCTGAAGATTTTGCAACTTATTACTGTCAACAGAGTGACAGTAACCCTCC |
| SEQ ID NO: 595 | IGKV1/O42-0*01 | TGGGATTCCCTCTCGGTTCAGTGACAGTGGATCTGGGCAGATTAACTCTCACCATCCGCAGCCTGCAGCCTGAAGATTTTGCAACTTATTACTGTCAACAGAGTGACAGTAACCCTCC |
| SEQ ID NO: 596 | IGKV1/OR2-1*01_IGKV1/OR2-2*01 | TGGGATTCCCTCTCGGTTCAGTGACAGTGGATCTGGGCAGATTACACTCTCACCATCAGCCTGCAGCCTGAAGATTTTGCAGCTTATTACTGTCAACAGAGTGACAGTACCCCTCC |
| SEQ ID NO: 597 | IGKV1/OR2-108*01 | GGGGGTCCCATCTCGGTTCAGTGGCAGTGGATCTGGGACAGATTTCACTCTCACCATCAGCAGCCTGCAGCCTGAAGATGTTGCAACTTATTACTGTCTACAGGATTATACTACCCCATT |
| SEQ ID NO: 598 | IGKV1/OR2-11*01_IGKV1/OR2-9*01 | GGCGATGCCATCTCAGTTCAGTGGCAGCGGATATGGAAGAGATTTCACTCTCACCGTCAGCAGCCTGCAGCCTGAAGATTTTGCAACTTATAATGTCAACAAGAGACATTTTCCCTCC |
| SEQ ID NO: 599 | IGKV1/OR2-118*01 | TGGGATTCCCTCTCGGTTCAGTGACAGTGGATCTGGGGCAGATTACACTCTCACCATCCGCAGCCTGCAGCCTGAAGATTTTGCAAATTATTACTGTCAACAGAGTGACAGTACCCCTCC |
| SEQ ID NO: 600 | IGKV1/OR22-1*01 | CCATCCTGGTTCAGTAGCAGTCAATCTGGGACAGATTTCACTCTCCACCATCAGCAGCCTGCAGCCTGAGCGTGATGATTGGCCACTTATTACTGTCAACAGCATTACAGTACCCTCC |
| SEQ ID NO: 601 | IGKV1/OR22-5*01 | TGGGATTCCCTCTCAGTTCAGTGACAGTGGGACAGATCTCCACCATCAGCAGCCTGCAGCCTGAAGATTTTGCAACTTATTACTGTCAACAGAGTTACAGTACCCCTCC |
| SEQ ID NO: 602 | IGKV1/OR22-5*02 | TGGGATTCCCTCTCAGTTCAGTGACAGTGGATCTGGGACAGATTAGACTCTCACCATCAGCAGCCTGAAGATTTTACAACTTATTACTGTCAACAGAGTTACAGTACCCCTCC |
| SEQ ID NO: 603 | IGKV1/OR2-3*01 | GGGGATGCCATCTCAGTTCAGTGGCAGCGGATATGGAAGAGATTTCACTCTCACTGTCAGCAGCCTGCAGCCTGAAGATTTTGCAACTTATTAATGTCAACAAGAGACATTTTCCCTCT |
| SEQ ID NO: 604 | IGKV1/OR2-6*01 | GTTTGCAAACGGGGGTTCCATCTCTGTTCAGTGTAGTGAATCTGGTAGTGAATCTGGGACAGATTTCACTCTAACCATCAGCAGCCTGCAGCCTGATGATGATGCAACTTACTGTCAACAGTAACTCC |
| SEQ ID NO: 605 | IGKV1/OR-3*01 | TGGGATTCCCTCTCGGTTCAGTGACAGTGGATCTGGGACAGATTACACTCTCACCATCAGCCTGCAGCCTGAAGATTTTGCAGCTTATTACTGTCAACAGAGTGACAGTAACCCTCC |
| SEQ ID NO: 606 | IGKV1/OR9-1*01_IGKV1/OR9-2*01 | TGGGATTCCCTCTCGGTTCAGTGACAGTGGATCTGGGACAGATTACACTCTCACCATCAGCCTGCAGCCTGAAGATTTTGCAACCTATTACTGTCAACAGAGTGACAGTAACCCTCC |
| SEQ ID NO: 607 | IGKV1/ORY-1*01 | TGGGATTCCCACTCGGTTCAGTGACAGTGGATCTGGGACAGATTACACTCCCCACCATCAGCCTGCAGCCTGAAGATTTTGCAACTTACTACTGTCAACAGAGTGACAGTAACCCTCC |
| SEQ ID NO: 608 | IGKV1-12*01 | TGGGGTCCCATCAAGGTTCAGCGGCGGTTCAGCGGCAGTGGATCTGGGACAGATTTCACTCTCCACCATCAGCAGCCTGCAGCCTGAAGATTTTGCAACTTACTATTGTCAACAGGCTAACAGTTTCCCTCC |

TABLE B1-continued

| SEQ ID NO | Name | Sequence |
|---|---|---|
| SEQ ID NO: 609 | IGKV1-12*02 | TGGGGTCCCATCACAAGGTTCAGCGGCAGTGGATCTGGGACAGATTTCACTCTCACCATCAGCAGCCTGCAGCCTGAAGATTTTGCAAC TTACTATTGTCAACAGGCTAACAGTTTCCCTTC |
| SEQ ID NO: 610 | IGKV1-13*01_IGKV1D-13*01 | TGGGGTCCCATCACAAGGTTCAGCGGCAGTGGATCTGGGACAGATTTCACTCTCACCATCAGCAGCCTGCAGCCTGAAGATTTTGCAAC TTATTACTGTCAACAGTTTAATAATAGTTACCCTA |
| SEQ ID NO: 611 | IGKV1-13*02_IGKV1D-13*02 | TGGGGTCCCATCACAAGGTTCAGCGGCAGTGGATCTGGGACAGATTTCACTCTCACCATCAGCAGCCTGCAGCCTGAAGATTTTGCAAC TTATTACTGTCAACAGTTTATAGTTACCCTCA |
| SEQ ID NO: 612 | IGKV1-16*01 | AGTGGGGTCCCATCAAGGTTCAGTGGCAGTGGATCTGGGACGGATTACACTCTCACCATCAGCAGCCTGAAGATTTTGC AACTTATTACTGTCAACAGTATTATAGTACCTCT |
| SEQ ID NO: 613 | IGKV1-16*02 | AAGTGGGGTCCCATCAAAGTTCAGCGGCAGTGGATCTGGGACAGATTCACTCTCACCATCAGCAGCCTGAGCCTGAAGATTTTG CAACTTATTACTGCCAACAGTATAATAGTTACCC |
| SEQ ID NO: 614 | IGKV1-17*01 | AGGTGGGGTCCCATCAAGGTTCAGCGGCAGTGGATCTGGGACAGAATTCACTCTCACAATCAGCAGCCTGCAGCCTGAAGATTTTG CAACTTATTACTGTCTACAGCATAATAGTTACCC |
| SEQ ID NO: 615 | IGKV1-17*02 | TGGGGTCCCATCACAAGGTTCAGCGGCAGTGGATCTGGGACAGAATTCACTCTCACAATCAGCAACCTGCAGCCTGAAGATTTTGCAA CTTATTACTGTCTACAGCATAATAGTTACCC |
| SEQ ID NO: 616 | IGKV1-17*03_IGKV1D-17*01 | TGGGGTCCCATCAAGGTTCAGCGGCAGTGGATCTGGGACAGAATTCACTCTCACAATCAGCAGCCTGCAGCCTGAAGATTTTGCAA CTTATTACTGTCTACAGCATAATAGTTACCCTCC |
| SEQ ID NO: 617 | IGKV1-22*01 | GGGTCCCGACACGGTTCAGTGGCAGTAGGTCTGGGACACACATTTCACCATCAGGAGCCTGCAACCTGAAGAGATGTTATA ACTTATTGCTGTCTATAGACTTACAGCAGCCAT |
| SEQ ID NO: 618 | IGKV1-27*01 | ATCAGGGGTCCCATCTCGGTTCAGTGGCAGTGGATCTGGGACAGATTTCACTCTCACCATCAGCAGCCTGCAGCCTGAAGATGTTGC AACTTATTACTGTCAAAATATAACAGTGTCCC |
| SEQ ID NO: 619 | IGKV1-32*01 | GGGGTCCCTGATCGTCTTCTGGCTCCAAGTCTGGCAACAGGCCTCCCTGACCGTCTCTGGGCTGAGGATGAGGCTGA TTACTGCAGTTCATATGCTGGCGACAACATT |
| SEQ ID NO: 620 | IGKV1-33*01 | TGAAAACAGGGGTCCCATCAAGGTTCAATGGAAGTGGATCTGGGACAGATTTTACTTTCACCATCAGCAGCCTGAAGAT ATTGCAACATATTACTGTCAACGTATGATAATC |
| SEQ ID NO: 621 | IGKV1-35*01_IGKV1D-35*01 | TGGGGCTCCTTCGCGGTTCGGTGGCAGTGGATCTGGGACAGATTTACTCTCACCATCAGAATCCTGCAGCTAAAGATGTTGCAAC TTATTACTGTCAACAGTATAAAATTACCCTAT |
| SEQ ID NO: 622 | IGKV1-37*01_IGKV1D-37*01 | TGGAGTCCCATCTCGGTTCAGTGGCAGTGGATCTGGGACAGATTTCACTCTCACTATCAGCAGCCTGCAGCCTGAAGATGCCCCTCC TTATTACGGTCAACGGATTACAATGCCCCTCC |
| SEQ ID NO: 623 | IGKV1-39*01 | TGGGGTCCCATCAAGGTTCAGTGGCAGTGGATCTGGGACAGATTTCACTCTCACCATCAGCAGTCTGCAACCTGAAGATTTTGCAAC TTACTACTGTCAACAGAGTTACAGTACCCCTCC |

TABLE B1-continued

| SEQ ID NO | Name | Sequence |
|---|---|---|
| SEQ ID NO: 624 | IGKV1-39*02 | TGGGGTCCCATCAAGGTTCAGTGGCAGTGGATCTGGGACAGATTTCACTCTCACCATCAGCAGTCTGCAACCTGAAGATTTTGCAACTTATTACTGTCAGTGTGTTACAGTACACCTCC |
| SEQ ID NO: 625 | IGKV1-5*01 | TGGGGTCCCACCAACCTTCAGCGGCAGTGGATCTGGGACAGATTTCGCTCTCACCATCAGCAGACTGGAGCCTGAAGATTTTGCAACTTATTACTGCCAACAGTATGATAGTTATTCGAC |
| SEQ ID NO: 626 | IGKV1-5*02 | TGGGGTCCCATCAAGGTTCAGCGGCAGTGGATCTGGGACAGATTCACTCTCACCATCAGCAGCCTGCAGCCTGATGATTTTGCAACTTATTACTGCCAACAGTATAATAGTTATTCTC |
| SEQ ID NO: 627 | IGKV1-5*03 | GTCCCTGATCGTTCTCTGGCTCCATCCTTGGGAACAAAGCTGCCCTCACCATCAGCGGCCCAGGCAGATGATTCTGACTATTACTGTGTACTATATATGGTGATGCCTGGGCG |
| SEQ ID NO: 628 | IGKV1-6*01 | GTGGGGTCCCATCAAGGTTCAGCGGCAGTGGATTTGGCACAGATTTCACTCTCACCATCAGCAGCCTACAGCCTGAAGATTTTGCAACTTATTACTGTCTACAAGATTACAGTTACCCTCC |
| SEQ ID NO: 629 | IGKV1-6*02 | TGGGGTCCCATCAAGGTTCAGCGGCAGTGGATCTGGCACAGATTTCACTCTCACCATCAGCAGCCTGCAGCCTGAAGATTTTGCAACTTATTACTGTCTACAAGATTACACATTACCCTCC |
| SEQ ID NO: 630 | IGKV1-8*01 | GTGGGGTCCCATCAAGGTTCAGCGGCAGTGGATCTGGGACAGATTTCACTCTCACCATCAGCGGCCTGCAGTGTGAAGATTTTGCAACTTATTACTGTCGACAGTATAATAGTTACCCTC |
| SEQ ID NO: 631 | IGKV19*01 | TTGGGTCCCATCAAGGTTCAGCGGCCGTGGATCGGGACAGATTCACCCTCACAATCACCGAATTCACTCTGAAGATTTTGCAACTTATTACTGTCAACAGCTTAATCGTTACCCTCC |
| SEQ ID NO: 632 | IGKV1D-12*01 | AAGTGGGGTCCCATCAAGGTTCAGCGGCAGTGATCTCTCACTCACTCTCACTATCAGCAGTCTGCAGCCTGAAGATTTTGCAACTTACTACTGTCAACAGGCTAACAGTTTCCC |
| SEQ ID NO: 633 | IGKV1D-16*01 | AAGTGGGGTCCCGTCAAGGTTCAGCGGCAGTGGATCTGGGACAGATTTCACTCTCACCATCAGCAGCCTGCAGCCTGAAGATTTTGCGACTTATTACTGCCAACAGTATAATAGTTACCC |
| SEQ ID NO: 634 | IGKV1D-16*02 | TGGGGTCCCATCAAGGTTCAGCGGCAGTGGATCTGGGACAGATTTCACTCTCACCATCAGCAGCCTGCAGCCTGAAGATTTTGCAACTTATTACTGCCAACAGTATAATAGTTACCCTCC |
| SEQ ID NO: 635 | IGKV1D-17*02 | AAGTGGGGTCCCATCGAGGTTCAGCGGCAGTGATCTGGGACAGAATTCACTCTCACAATCAGCAGCCTGCAGCCTGAAGATTTTGCAACTTATTACTGTCTACATATAATTACCC |
| SEQ ID NO: 636 | IGKV1D-22*01 | GGCTCCCCGTCACGGTTCAGTGGCAGTAGGTCTGGGACACATTTCACACATTCTCACCATCAGCAGCCTGCAACCTGAAGATGTTATAACTTATTACTGTCTATAGACTTACAGCAGCAT |
| SEQ ID NO: 637 | IGKV1D-27*01 | GGGGGTCCCATCTCGGTTCAGTGGCAGTGGATCTGGGACAGATTCACTCTCACCATCAGCAGCCTGCAGCCTGAAGATGTTGCAACTTATTACTGCCAAAAGTATAACAGTGCCCCTCC |
| SEQ ID NO: 638 | IGKV1D-32*01 | GTCCCATTGCAGTTATGTGGCATTGGATCCAGGACAGATTTGATTCTCACCATTAGCATCCTGAAGTCTGCAACTTCTTATTTGGTCAACAGTATAAAAGTGACCCTCT |
| SEQ ID NO: 639 | IGKV1D-33*01 | AGCAGGGGTCCCATCAAGGTTCAGTGGAAATAGAATCTGGGACAGATTTACTTTCACCATCAACAGCCTGCAGTCTGAGATATCGCAACATATTACTGTCAACATATGATGATCTCCC |
| SEQ ID NO: 640 | IGKV1D-39*01 | AGTGGGGTCCCATCAAGGTTCAGTGGCAGTGGATCTGGGACAGATTTCACTCTCACCATCAACAGTCTGCAACCTGAAGATTTTGCAACTTACTACTGTCAACAGAGTTACAGTACCCC |

TABLE B1-continued

| SEQ ID NO | Name | Sequence |
|---|---|---|
| SEQ ID NO: 641 | IGKV1D-42*01_IGKV1D-42*02 | TGGGGTCTCATCAGAGTTCAGTGGCAGTGGATCTGGGACGGATTTCACTCTCACCATCATCAGCCTGAAGCCTGAAGATTTTGCAGCTTATTACTGTGTAAACAGGACTTCAGTTACCCCTCC |
| SEQ ID NO: 642 | IGKV1D-43*01 | TGGGGTCCATCAAGGTTCAGCGGCAGTGGATCTGGGACGGATTACACTCTCACCATCAGCCTGCAGCCTGAAGATTTTGCAACTTATTACTGTCAACAGTATTATAGTACCCCTCC |
| SEQ ID NO: 643 | IGKV1D-8*01 | AGTGGGGTCCCATCAAGATTCAGTGGCAGTGGATCTGGGACAGATTCACTCTCACCATTAGTGCCTGCAATCTGAAGATTTTGCAACTTATTACTGTCAACATATTATAAATTTCCCT |
| SEQ ID NO: 644 | IGKV1D-8*02_IGKV1D-8*03 | TGGGGTCCCATCAAGGTTCAGTGGCAGTGGATCTGGGACAGATGGACAGATTTCACTCTCACCATCAGCTGCCTGCAGTCTGAAGATTTTGCAACTTATTACTGTCAACAGTATTATAGTTTCCCTCC |
| SEQ ID NO: 645 | IGKV1-NL1*01 | TGGGGTCCCATCCAGGTTCAGTGGCAGTGGATCTGGGACGGATTACACTCTCACCATCAGCAGCCTGCAGCCTGAAGATTTTGCAACTTATTACTGTCAACAGTATTATAGTACCCCTCC |
| SEQ ID NO: 646 | IGKV2/OR2-1*01 | GGGTCCCAGACAGGTTCAGTGGCAGTGGGTCAGGCATTGATTTCACACTGAAAATCAGCCCGGTGAGGCTGAGGATGTTGGGGTTTATATTACTGCAAGCTACACACTGGCCCCC |
| SEQ ID NO: 647 | IGKV2/OR2-10*01_IGKV2/OR2-2*01_IGKV2/OR2-7*01_IGKV2/OR2-8*02 | CTCGAGTCCCAGACAGGTTCAATGCAGTGGGTCAGGCATCTCTGCAGCTCTGATTTCACACTGAAAATCAGCCGGGTCGAGCTGAAGATGTTGGGGTTTATTACTGCAGCTCTGCAGTCTCCTCC |
| SEQ ID NO: 648 | IGKV2/OR22-3*01 | TGCAGTCCCAGACAGGCTCAGTGGCAGTGGGTCAGGCACTGATTTCACACTGAAATCAGCCGGGTCGGGTGAGGCTGAAGATGTGGGGTTTATCACTGCATGCATGCAAGCTCTACAACTCCTCC |
| SEQ ID NO: 649 | IGKV2/OR22-4*01 | TGGAGTTCCAGACAGGTTCAGTGGCAGTGGGTCAGGCACTGATTTCACACTGAAAATCAGCCCGATTGATTCTCTGAAAATCAGTGGGGTGAGGCTTAGGATGTTGGGGTTTATTACTGCAAGCTCTACAAACTCCGCC |
| SEQ ID NO: 650 | IGKV2/OR2-4*01_IGKV2/OR2-7*01_IGKV2/OR2-7D*01 | GGGTCCCAGACAGGTTCAGTGGCAGTGGGTCGGGCATTGATTGATTTCACACTGAAAATCAGCCGGCCCGGGTGTGCGGAGGCTGCGGATGTTGGGGTTTATATTACTGCAAGCTACAACACTGGTCCCC |
| SEQ ID NO: 651 | IGKV2-10*01 | CTCGAGTCCAGACAGGTTCAGTGGCAGTGGGTTGGGGACAGATTTCATGCTGAAATCTGAAATCAGGAGGATGGATGCTGAGGATGTTGGGGTTTATTGCTGCCAGCAAGTACACATTATCCTCC |
| SEQ ID NO: 652 | IGKV2-14*01_IGKV2D-14*01 | TGGAGTCCCAGACAGGTTCAGTGGCAGTGGGTCGGGGACAGAGATTTCATGTTTAAAATAAGGAGGATGATGTCGAGGATGTTGGGGTTTATTGCTGCCAGCAAAGTACACATTATTCTCC |
| SEQ ID NO: 653 | IGKV2-18*01 | AATCCCTTCTCTGGCTCCAAGTCTGGCAACACGGCCCTTCCCCTGACCATCTCTGGGCTCCAGGCTGAGGACGAGGCTGATTATTACTGCGCCTATATACAAGCAGCAGCACTCTTTATATC |
| SEQ ID NO: 654 | IGKV2-19*01 | TCTGGGGTCTCGGGCACAGGCAGTTCAGCAGCAGTGGTTCAGGGACAGAGATTTCATATTGAAAATCAGCAGGGGTAGAGCGTTGAGGACGTTGGGGTTTATTACTGCCTGCAAGGTACAAGTGCCT |

TABLE B1-continued

| SEQ ID NO | Name | Sequence |
|---|---|---|
| SEQ ID NO: 655 | IGKV2-23*01 | TGGTAATGGATACACCTATTTGTATTAGTTCCTGCAGAAGCCAGGCCACTCTCCACAGCTCCTGATCGTAGAGACTTCCATCAGTTT<br>TCTGCCTTCCCACACAGTTCTCCCCAGTGGG |
| SEQ ID NO: 656 | IGKV2-24*01 | CTCTGGGGTCCCAGACAGATTCAGTGGCAGTGGGCAGGGACAGAGATTTCACACTGAAAATCAGGCTGGAAGCTGAAGGCTGAGGATGTC<br>GGGGTTTATTACTGCATGCAAGCTACACAATTCCC |
| SEQ ID NO: 657 | IGKV2-26*01 | TGGAGTGCCAGATAGGTTCAGTGGCAGCGGGTCAGGGACAGATTTCACACTGAAAAATCAGCCCGGGTGGAGGCTGAGGATGTTGG<br>AGTTTATTACTGCAAGATGCAAGATGCACAAGATCCTCC |
| SEQ ID NO: 658 | IGKV2-28*01 | CGGGGTCCCTGACAGGTTCAGTGGCAGTGGATCAGGGACACAGATTTTACACTGAAAATCAGCAGAGTGGAGGCTGAGGATGTTGGG<br>GTTTATTACTGCATGCAAGCTCTACAAACTCCTCC |
| SEQ ID NO: 659 | IGKV2-29*01 | TGGAGTGCCAGATAGGTTCAGTGGCAGCGGGTCAGGGACAGAGATTTCACACTGAAAAATCAGCCCGGTGAGGCTGAGGATGTTGG<br>GGTTTATTACTGCAAGGTATACACCTTCCTCC |
| SEQ ID NO: 660 | IGKV2-29*02_IGKV2-29*03 | TGGAGTGCCAGATAGGTTCAGTGGCAGCGGGTCAGGGACAGAGATTTCACACTGAAAAATCAGCCCGGTGAGGCTGAGGATGTTGG<br>GGTTTATTACTGCATGCAAGGTATACACCTTCCTCC |
| SEQ ID NO: 661 | IGKV2-30*01 | CTCTGGGGTCCCAGACAGATTCACCGGCAGTGGGTCAGGCAGTGGGTCAGGGAAATCAGCAGGGTGAGGCTGAGGCTGAGGATGTTT<br>GGGGTTTATTACTGCATGCAAGCTACACACTGGCC |
| SEQ ID NO: 662 | IGKV2-30*02_IGLV7-46*01 | CTCTGGGGTCCCAGACAGATTCAGCGGCAGTGGGTCAGGCAGTGATTCACACTGAAAAATCAGCCAGGTGAGGCTGAGGATGTT<br>GGGGTTTATTACTGCAAGCTACAAGTACACTGGCC |
| SEQ ID NO: 663 | IGKV2-36*01 | ATTTATGAGGTTTCCAACCAAGCCTCCGAATTCTCAGACAGTTCAGGGGTAATGGGTCAGTGAGTTTACACTGAAAGTCAGT<br>AGGACGGAGACCAAGGATGTTGGAGTTTATTAG |
| SEQ ID NO: 664 | IGKV2-38*01 | TCTGGAGTCCCAGACAGCAGTTCAATAGCAGTGGGTCAGGCACACATATTTAAACTCAAAATTAGCAGGGTGGAGGCTGAGGATATTCG<br>ACTTTATTAATACATGCAAGCTACACAGTTCCT |
| SEQ ID NO: 665 | IGKV2-4*01 | TGGAGTCCCAAACAAGTTCAGTGGCAGCAGGTCAGGGACAGAGTTTCACACTTAAATTCAGCACAAGTGGAGGCTGAGGATGTTGGG<br>GTTTATTGCTGTAAACAGGGTCTGCAAGGTCCTCA |
| SEQ ID NO: 666 | IGKV2-40*01 | CCTGATCGCTTCTCTGGCTCCAAGTTGGCAACACGGCCCTCCCTGACCATCTCTGGGCTCCTGGCTGAAGATGAGGCTGATTATCACT<br>GCTGCTCATATGCGGGCAGCTTCACTGTGATC |
| SEQ ID NO: 667 | IGKV2D-10*01 | CTGGAGTCCCAGACAAGTTCAGTGGCAGTGGGTCGGGGACAGATTTCATGCTAAAATCAGGAGGATGATGCTGAGGATGTTGGG<br>GTTTATTGCTGCCAGCAAAGTACACATTATCCTCC |
| SEQ ID NO: 668 | IGKV2D-18*01 | TCTGGGGTCCCAGACAGTTTAGTGGCAGTGGGTCAGGCAGTGATTCACACTGAAAATCACTGGGTGGAGGCTGAGGATGTTG<br>GGGTTTATTACTGCATGCAAGCTACACAGTTTCCT |
| SEQ ID NO: 669 | IGKV2D-19*01 | GGGGTTTCTAATCGCTTCTCTGGCTCCAAGTCTGGCAACACCGGCCTCCCTGACCATCTCTGCTCCAGGCTGAGGACGAGGCTGAT<br>TATTACTGCTGTCATATGCAAACAGCGACTCC |
| SEQ ID NO: 670 | IGKV2D-23*01 | ACCACATAACCGTGAGTTTGCAGTGGTTGCAGGGACAGATTTTATGCTTAAGATCAGTAGGGTGGAGGCTGAGGATCTTGG<br>CTATTACAACTGCCACCACTCTACAATATCCT |

TABLE B1-continued

| SEQ ID NO | Name | Sequence |
|---|---|---|
| SEQ ID NO: 671 | IGKV2D-24*01 | TGGGGTCCCAGACAGATTCAGTGGCAGTGGGCAGGGACAGATTTCACACTGAAAATCAGCAGGTGAAGCTGAGGATGTCGG GGTTTATTACTGCACGCAAGCTACACAATTTCCTCA |
| SEQ ID NO: 672 | IGKV2D-26*01_IGKV2D-26*03 | TGGAGTGCCAGATAGGTTCAGTGGCAGCGGGTCAGGGACAGATTTCACACTGAAAATCAGCCGGTGAGGCTGAGGATTTTGAA GTTTATTACTGCATGCAAGATGCACAAGATCCTCC |
| SEQ ID NO: 673 | IGKV2D-26*02 | TCTGGAGTGCCAGATAGGTTCAGTGGCAGCGGTCAGGGACACTGGGACACTGAAAATCAGCCGGTGGAGGCTGAGGATTTTG GAGTTTATTACTGCATGCAAGATGCACAAGATCCT |
| SEQ ID NO: 674 | IGKV2D-28*01 | TCCGGGGTCCCTGACAGTTCAGTGGCAGTGGATCAGGCACAGATTTTACACTGAAAATCAGCAGAGTGGAGGCTGAGGATGTTG GGGTTTATTACTGCCATGCAAGCTCTACAAACTCCT |
| SEQ ID NO: 675 | IGKV2D-29*01 | CTCTGGAGTGCCAGATAGGTTCAGTGGCGCGGGTCAGGGACAGATTTCACACTGAAAATCACCGAAAATCAGCCGGTGAGGCTGAGGATCCT GGGGTTTATTACTGCATGCAAGTATACAGCTTCC |
| SEQ ID NO: 676 | IGKV2D-29*02 | ACGCAGACTCCGTGAAGGCCGGTTCACCATCTCCAGAGACAATTCCAAGAGAAGAACACTCTGTATCTGCAAATGAACAGCCTGAGA GTCCGAGGACACGGCCGTATATTACTGTGCGAAAG |
| SEQ ID NO: 677 | IGKV2D-30*01 | CTGGGGTCCCAGACAGATTCAGCGGCAGTGGGTCAGGCACTGAGTTCACACTGAAAATCAGCAGGGTGGAGCTGAGGATGTTGG GGTTTATTACTGCATGCCAAGTACATACTGGCCTC |
| SEQ ID NO: 678 | IGKV2D-38*01 | TCTTACCGCTCCCTCGATAAAAGCAAGTTCATCATTTCCAGAGATGATTCCAGCAATATGTTGTATCTTCAAATGAACAACCTGAAAA CCGAGGACACGGCCGTCTATTTTGTACTCGC |
| SEQ ID NO: 679 | IGKV2D-40*01 | TGGAGTCCCAGACAGGTTCAGTGGCAGTGGGTCAGGCACTGATTTCACACTGAAAATCAGCAGGGTGAGGCTGAGGATGTTGGA GTTTATTACTGCATGCAACGTATAGAGTTTCCTTC |
| SEQ ID NO: 680 | IGKV3/OR22-2*01 | CCTGGAAAAGCTCCCTGGTTCTCATCTAAGGCACATCCAACAGGGCCACTAGCATCCTGGGGTTTAGTGTCATGGATTGGAGAC AGACTTTACTATCCAGCTGCCTGAAGCCT |
| SEQ ID NO: 681 | IGKV3/OR2-268*01 | TGGCATCCCAGCCAGGTTCAGTGGTAGTGGGTCTGGGACAGACTTCACTCTCACCATCAGCAGCCTGCAGCCTGAAGATTTTGCAGT TTATTACTGCAGCAGGATTATAACTTACCTCC |
| SEQ ID NO: 682 | IGKV3/OR2-5*01 | TGACATCCCAGTGGGGCTCAGTAGCTGTGAATCTGGGATGTACTTTACTCTCACCAACAGTAACCTGGAACCTGAAGATTTTGCACT TGATTACTTCTTATCTGTATAGTAGTTGAATTT |
| SEQ ID NO: 683 | IGKV3-11*01 | CCGCTGGCGTCCCAGCCAGGTTCAGTGGCAGTGGGTCTGGGACAGACTTCACTCTCACCATCAGCAGACTCGAAGATTTTG CAGTTTATTACTGTCAACACTGTAGGAACTGGC |
| SEQ ID NO: 684 | IGKV3-11*02 | TACTACCGAGACTCCGTGAAGGGCCGATTCACCATCTCCAGAGACAACGCCAAGAACACGCTGTATCTTCAAATGAACAGCCTGAGA GCTGAGGACACGGCCGTGTATTACTGTGCGAGA |
| SEQ ID NO: 685 | IGKV3-15*01 | GGTATCCCAGCCAGGTTCAGTGGCAGTGGGTCTGGGACAGAGTTCACTCTCACCATCAGCAGCCTGCAGTCTGAAGATTTTGCAGT TTATTACTGTCAGCAGTATAATAACTGGCCTCCG |
| SEQ ID NO: 686 | IGKV3-20*01 | CACTGGGCATCCCAGACAGGTTCAGTGGCAGTGGGTCTGGGACAGACTTCACTCTCACCATCAGCAGACTGGAGCCTGAAGATTTTG CAGTGTTATTACTGTCAGCAGTATGGTAGTCACC |
| SEQ ID NO: 687 | IGKV3-20*02 | GTCCATCCAGCAGGGCCACTGCATCCCAGCCAGGTTCAGTGGCAGTGGGTCTGGGACAGACTTCACTCTCACCATCAGCAGACTG GAGCCTGAAGATTTGCAGTTTATTACTGTCAGC |

TABLE B1-continued

| SEQ ID NO | Name | Sequence |
|---|---|---|
| SEQ ID NO: 688 | IGKV3-25*01 | TACAGCCTGATTTGTGATAGTGGGTCGGGACAGGGCTTACTCTCACCATCGGCAGCCTGGAGCCTGGAGATTTGCAC TTCATCACTGTTATCAGCATAGTAGTTGGTGTCC |
| SEQ ID NO: 689 | IGKV3-31*01 | ATCCCAGCCAGGTTCAGTGGCAGTGGGTCTGGGACAGACTTCACTCTCACCATCAGCAGCCTGGAGCCTGAAGATTTGCAGTTTAT TACTGTCAGCACCGTAGCAACTGGCTAATCGCC |
| SEQ ID NO: 690 | IGKV3-34*01_IGKV3D-34*01 | AGCATCCCAGCCCGGTTCAGTGTGTGGGCCTGAGGCAGCAGACTTTACCCCACCATCAACAGCCTAGACCCTGAAGATGTCACAAT TTTATTACCCTCATCAGTACAGCAGTGGGTGTCC |
| SEQ ID NO: 691 | IGKV3-7*01 | TAGCATCCCAGCCAGGTTCAGTGGCAGTGGGTCTGGGACAGAGACTTCACTCTCACCATCAGCAGCCTGCAGCCTGAAGATTTTGCAGT TTATTACTGTCAGCAGGATCATAACTTACCTCC |
| SEQ ID NO: 692 | IGKV3-7*02_IGKV3/OR2-268*02_IGKV3D-7*01 | TGGCATCCCAGCCAGGTTCAGTGGCAGTGGGTCTGGGACAGAGACTTCACTCTCACCATCAGCAGCCTGCAGCCTGAAGATTTTGCAG TTTATTACTGTCAGCAGGATTATAACTTACCTCC |
| SEQ ID NO: 693 | IGKV3-7*03 | TAGCATCCCAGCCAGGTTCAGTGGCAGTGGGTCTGGGAGAGACTTCACTCTCCACCATCAGCAGCCTGAAGATTTTGCAG TGTATTACTGTCAGCAGGATCATAACTTACCTCC |
| SEQ ID NO: 694 | IGKV3-7*04 | TAGCATCCCAGCCAGGTTCAGTGGCAGTGGGTCTGGGACAGAGACTTCACTCTCACCATCAGCAGCCTGCAGCCTGAAGATTTGCAGT TTATTACTGTCAGCAGGATTATAACTTACCTCC |
| SEQ ID NO: 695 | IGKV3D-11*01_IGKV3D-11*02 | TGGCATCCCAGCCAGGTTCAGTGGCAGTGGGCCTGGGACAGAGTTCACTCTCACCATCAGCAGCCTAGAGCCTGAAGATTTTGCAG TTTATTACTGTCAGCAGCGTAGCAACTGGCATCC |
| SEQ ID NO: 696 | IGKV3D-11*03 | TGGCATCCCAGCCAGGTTCAGTGGCAGTGGGCCTGGGACAGAGTTCACTCTCACCATCAGCAGCCTAGAGCCTAGAGCCTGAAGATTTGCAG TGTATTACTGTCAGCCGTAGCAACTGGCATCC |
| SEQ ID NO: 697 | IGKV3D-15*01 | TATCCCAGCCAGGTTCAGTGGCAGTGGGTCTGGGACAGAGAGTTCACTCTCACCATCAGCCTGCAGTCTGAAGATTTGCAGTTTA TTACTGTCAGCAGTATAATAACTGGCCTCAGAG |
| SEQ ID NO: 698 | IGKV3D-15*02 | TGGCATCCCAGCCAGGTTCAGTGGCAGTGGGTCTGGGACAGAGAGTTCACTCTCACCATCAGCAGCCTGCAGTCTGAAGATTTTGCAG TTTATTACTGTCAGCAGTATAATAACTGACCTCC |
| SEQ ID NO: 699 | IGKV3D-15*03 | TGGCATCCCAGCCAGGTTCAGTGGCAGTGGGTCTGGGACAGAGAGTTCACTCTCACCATCAGCCATCCTCCAGTCTGAAGATTTTGCAGT TTATTACTGTCAGCAGTATAATAACTGGCCTCC |
| SEQ ID NO: 700 | IGKV3D-20*D1 | ACTGGCATCTCAGACAGGTTCAGTGGCAGTGGGTCTGGGACAGACTTCACCTCCCAGCAGAGCTGAAGCCTGAAGATTCTGC AGTGTATTTCTGTCAGCAGTATGGATCATCCCT |
| SEQ ID NO: 701 | IGKV3D-20*02 | TGGCATCCCAGACAGGTTCAGTGGCAGTGGGTCTGGGACAGACTTCACTCTCACCATCAGCAGACTGAGCCTGAAGATTTTGCAG TCTATTACTGTCAGCGGCTAGCAACTGGCATCC |
| SEQ ID NO: 702 | IGKV3D-25*01 | ATCTATGGTACAGCCCTGATTTGTGATAGTGGGTCAGGACAGGGCTTACTCTCACCATCGGCAGGCTGGAGCCTGGAGATTTGCAC TTCATCACTGTTATCAGCATAGTAGTTGGTGTCC |

TABLE B1-continued

| SEQ ID NO | Name | Sequence |
|---|---|---|
| SEQ ID NO: 703 | IGKV3D-31*01 | CAATGTCCCAGCCTGGTGGAGTGGCAGTGGGTTCGGGGAAAGCTTCAGTCTCATTATCAGCAGGCTGAGCATGAAGATTTGCAC<br>TTTAACACTGTTATCAGCATAGTGGTGGGTATTC |
| SEQ ID NO: 704 | IGKV4-1*01 | ATCCGGGGTCCCCTGACCATTCAGTGGCAGCGGGTCTCGGACAGAGATTTCACTCTCACCATTAGCTGCAGACTGAAGATGTGG<br>CAGTTTATTCTTGTCAGCAATTTCATAGTTTTCC |
| SEQ ID NO: 705 | IGKV5-2*01 | CCTGGAATCTCACCCTCGAGTTCAGTGGCAGCGGGTATGGAACAGATTTTACCCTCACAATTAATAACATAGAATCTGAGGATGCTGCA<br>TATTACTTCTGTCTACAACATGATAATTTCCCG |
| SEQ ID NO: 706 | IGKV6-21*01_IGKV6-6-21*02-IGKV6D-21*01 | AGGGGTCCCCTCGAGGTTCAGTGGCAGTGGATCTGGGACAGATTCACCCTCACCATCAATAGCCTGGAAGCTGAAGATGCTGCAA<br>CGTATTACTGTCATCAGAGTAGTAGTTTACCTCA |
| SEQ ID NO: 707 | IGKV6D-21*02 | AGGGGTCCCCTCGAGGTTCAGTGGCAGTGGATCTGGGACAGATTTCACCCTCACCATCAATAGCCTGGAAGCTGAAGATGCTGCAG<br>CGTATTACTGTCATCAGAGTAGTAGTTTACCTCA |
| SEQ ID NO: 708 | IGKV6D-41*01 | TCAGGGGTCCCCTCGAGTTCAGTGGCAGTGGATCTGGGACAGATTCACCTTTACCATCAGTAGCCTGGAAGCTGAAGATGCTGC<br>AACATATTACTGTCAGCAGGGCAATAAGCACCCT |
| SEQ ID NO: 709 | IGKV7-3*01 | TGGAATCCACCTCGATTCAGTGGCAGCGGGTATGGAACAGATTTTACCCTCACAATTAATAACATAGAATCTGAGGATGCTGCATA<br>TTACTTCTGTCTACAACATGATAATTTCCCTCT |
| SEQ ID NO: 710 | IGLV(I)-20*01 | GTCCCTGATGGCTTCTCTGGCTCCAAGTCTGGCAACTCTGGAAACACAGCCTCCCATGACCATCTCTGGGTTCCAGGCTGAGGATGAGGCTGATTAT<br>TACTGCAACTCACATAGAGAGTGGCACTTTC |
| SEQ ID NO: 711 | IGLV(I)-38*01 | TCCAGAACTGATTCTGAGTGATCAGTCTGGCAAGGAGGCCTTCCTGAGCATATCTGGGCTCCAGGCTGAGGACAAGGCTGATCAC<br>TAACGTTGGATTTGGACAGTTCTCTGGAGGCCCC |
| SEQ ID NO: 712 | IGLV(I)-42*01 | TTTCAGGACAGACGCCTCAGGCTACCAGTCTTGCATGAAGCCCTTCTAAGCATCTCTGGGCTTTAGGCTGAGGACAAGGCTGATCACT<br>CCTGTTGGCTTCAGACAGCCCCCTGGAGGTCCA |
| SEQ ID NO: 713 | IGLV(I)-56*01 | CCTCAGGGAATTTCCCAGCCCCATGTTAGGCAGTTTGGCCTCCCCTGGCCATCTCGGCTCCAGGCTGGCGACGTGCTGATTTTCA<br>CTATTAGCACAGAATGGCAGCCTCGCTGATTA |
| SEQ ID NO: 714 | IGLV(I)-63*01 | TCCCTGACAATTCTCTGGCTTCAAGTCTGGCAACTCCATTTCTGACAATCACTGTGCTACAGCCTCAAGATGAGGCTGATTATCAC<br>TGCCAATTCTACAAAACAGCCTGAGTGCTTT |
| SEQ ID NO: 715 | IGLV(I)-68*01 | CATAGGCCCAATGCTGAGGCTCCAGGTTGGAGAACATGGCCTCTCTGGACTCTCAGGCAGAGGAAAAGGCTGATTTT<br>TATTCTCAGCTTGGGACACAAGCACCAAGGCTCA |
| SEQ ID NO: 716 | IGLV(I)-70*01 | CCCTGACCGCTTCTCTGGCTCAAAGTCTGGCAACCACAGCCTCCGACTATCTCGGGCCTTCAGCCTCGAGGACGAGGCTGATTATTA<br>CTGTTCAACATGGGACTACAGCCTCAGTGCTCA |
| SEQ ID NO: 717 | IGLV(IV)-53*01 | CAGACAATTCTCTGGTTGAGAGGCTCTCCAGAGTCTCAAGTTATTTGTCTCTCGGCCTTCACCTTGAGGATGGAGCAGATCA<br>TCTCTCAACCTCAGATGGCTGACAGGGCATGCTTA |
| SEQ ID NO: 718 | IGLV(IV)-59*01 | CTAAATCCAAAGATGCCTTGGCCAGTGCAGGCAATTGCTCATCTCTGGGGTCCAGCCAGAGGACAAGACTATCTGTCTATCTATT<br>ACTGTCAGACCTCAGATATTGATACTTCAGTTA |

TABLE B1-continued

| SEQ ID NO | Name | Sequence |
|---|---|---|
| SEQ ID NO: 719 | IGLV(IV)-64*01 | TCTGGATTAATGAAGGCCGGTCCATAAAGGGCTCTTGCTCATATCTGATCTCCAGTCTGAGGATGAGGCTTACTATTACTGTATGATCGAGCAGCAGAGCTTCTCATGCTGACACA |
| SEQ ID NO: 720 | IGLV(IV)-65*01 | GTTCCCCATCCACTTCTCTGGAATCCAATGATACATTAGCCAATGCAGGGATTCTGTACATTCTGTACATTCCGTTGGCTGAAGCCTGAGGGTGAGGCTATTACTGTGTAGTGTCACAAGCAGCTCAAGT |
| SEQ ID NO: 721 | IGLV(IV)-66-1*01 | GTCACTTCTGTGAATCCAAAGATCCCTCGGGCAATGTGCAGGGATTCTGCACATTTCTGAGCAGCCTGAGATCAAGTCCGACTATTACTATTTACATATCACAGCAACAGTGCACTTT |
| SEQ ID NO: 722 | IGLV(V)-58*01 | TACAGTTCTCAGGATCCAGCTATGGGGCTATGCGGTAGGTCCACCATTCCCAACATCCAGTTTGAGGATGAAGCTGATTGTATCTGTGGTGCAGATCATAGCATTGGTGTACATTGGGT |
| SEQ ID NO: 723 | IGLV(V)-66*01 | ATTCCCAGTCACTAGTTCTCAGTCTCCAAGACTGGAGCTGACCACTATAGTGTCATTTCTACAATCCCGTCTGAGGATGGAGCTGACTATATCTGTGGTACAGATTGTAGCATTGGTGTG |
| SEQ ID NO: 724 | IGLV(VI)-22-1*01 | AGAGACATAAGACTCATTCTCAGGCTCCAAGTCTGACCAGTCTTCTTTGAGACTCCCTGGAGCTCCCTGGATCCCAGCAGTGACACTGATCACTATTGCTGTCCCACACATCCCAAGTGATGAGGA |
| SEQ ID NO: 725 | IGLV(VI)-25-1*01 | AGAGACATAAGATTGATTCTCAGGCTCCATATCAGGAGAAACACAGCCTCCCTGACCATTACTGGACTCCAGCCTCAGCCTCCCTGGATCCCAGCAGTGACACTGATCACTATTATGTTGCTGTTCCACACATCCCAAGTGATGAGGA |
| SEQ ID NO: 726 | IGLV10-54*01 | CTCAGAGAGATTATCTGCATCATATCAGGAGAAACAGCTCCCCTGACCATTACTGGACTCCAGCCTCAGCCTCCCTGGAGACGAGCTGACTATTACTGCTCAGCATGGGACAGCAGCCTCAGTGCT |
| SEQ ID NO: 727 | IGLV10-54*02 | ACTCAGAGAGAATCTCTGCATCCAGTCAGGAAACACAGCTCCCTGACCATTACTGGACTCCAGCCTCAGCCTCCCTGGAGACGAGCTGACTAGTATTACTGCTCAGCATGGGACAGCAGCCTCAGTGCT |
| SEQ ID NO: 728 | IGLV10-54*03 | AAAGAAAAGGACATATTCCTGAGGGGTACAGTGTCTCTAGAGAGAAAGAAGGAGCGTTCTCCCTGATTCTGAGTCCGCCAGCACCAACCACATCTATGTACCCTGTGCCAGCAGC |
| SEQ ID NO: 729 | IGLV10-67*01 | GCTTCTAATCGCTTCTCTGGCTCCAAGTCTGGCAACACGGCCTCCCTGACCATCTCTGGGCTTCAGGCTGAGAACGAGGCTGATTATTACTGCAGTTCATATACAAGACAGCCTCACACTCTC |
| SEQ ID NO: 730 | IGLV10-67*02 | TCTCAGAGAGATTCCCTGCTCCGGTTAGGAACATGGACATTCTGACCATCTCTGGCCTCCAGACCAAGGACAAGCCTGCCTATTACTGCTCTCAGCCTGGGACAGCAGCCTCAGTGCTCA |
| SEQ ID NO: 731 | IGLV110_55*01_IGLV11-1-55*02 | CCCAGTCCAGTCTCTGGCTCTCAGGAGGAGACCTCAAGTAACAACAGCGTTTTGCTCATCTCTGGCCTCGAGGACGAGGCCGATTATTACTGCCAGTGGCAGTTCCAGTGTACGAAAGTAGTGCTAAT |
| SEQ ID NO: 732 | IGLV1-36*01 | CTCTGACCGATTCTCTGGCTCCAAGTCTGGCACCTCAGCCTCCTGGCCAATCAGTGGCCTCCAGTCTGAGGATGAGGCTGATTATTACTGTGCAGCATGGGATGACAGCCTGAATGGTCC |
| SEQ ID NO: 733 | IGLV1-40*01 | CCCTGACCGATTCTCTGGCTCCAAGTCTGGCACCTCAGCCTCCCTGGCCATCACTGGACTCCAGGCTGAGGATGAGGCTGATTATTACTGCCAGTCCTATGACAGCAGCCTGAGTGGTTC |
| SEQ ID NO: 734 | IGLV1-40*02 | GTCCCTGACCGATTCTCTGGCTCCAAGTCTGGCACCTCAGCCTCCCTGGCCATCACTGGGCTCCAGGCTGAGGATGAGGCTGATTATTACTGCCAGTCCTATGACAGCAGCCTGAGTGGT |
| SEQ ID NO: 735 | IGLV1-40*03 | GTCCCTGACCGATTCTCTGGCTCCAAGTCTGGCGCCTCAGCCCTCCCAGCCTCCCTGGCCATCACTGGGCTCCAGGCTGAGGATGAGGCTGATTATTACTGCCAGTCCTATGACAGCAGCCTGAGTGGT |

TABLE B1-continued

| SEQ ID NO | Name | Sequence |
|---|---|---|
| SEQ ID NO: 736 | IGLV1-41*01 | ATTCCTGACCGATTCTCTGGCTCCAAGTCTGGCTCCAAGTCTGGCACCTCAGCACTCACTGGCCTCTGGCCTCTGAGGACGAGGCCGATTAT<br>TACTGCTTAGCATGGGATACCAGCCCGAGAGCT |
| SEQ ID NO: 737 | IGLV1-41*02 | TCCTGACCGATTCTCTGGCTCCAAGTCTGGCTCCACCTCAGCACCTCAGCCTCTGGCCTCTGAGGACTAGGCCGATTATTA<br>CTGCTTAGCATGGGATACCAGCCTGAGAGCTTG |
| SEQ ID NO: 738 | IGLV1-44*01 | CCCTGACCGATTCTCTGGCTCCAAGTCTGGCTCCAGCCTCAGCCTCTGGCCTCCAGTGGGCTCCAGTCTGAGGATGAGGCTGATTATTA<br>CTGTGCAGCATGGGATGACAGCCTGAATGGTC |
| SEQ ID NO: 739 | IGLV1-44*01 | GTCCCTGCCCGATTCTCTGGCTCCAAGTCTGGCTCCAGCCTCAGCCTCCCTGGCCATCCGTGGGCTCCAGTCTGACGATGAGGGTGATTAT<br>TTCTGTTCGGCATGGGATGACAGCCTGAATCAT |
| SEQ ID NO: 740 | IGLV1-47*01 | GGGTCCCTGACCGATTCTCTGGCTCCAAGTCTGGCACCTCAGCCTCCTGGCCATCAGTGGGCTCCGAAGATGAGGCTGTTT<br>ATTACTGTGGAGCGTGGGATGCGGCCTGAGTG |
| SEQ ID NO: 741 | IGLV1-47*02 | CCCTGACCGATTCTCTGGCTCCAAGTCTGGCACCTCAGCCTCCTGGCCATCAGTGGGCTCCGGTCCAGAGGATGAGGCTGATTATTA<br>CTGTGCAGCATGGGATGACAGCCTGAGTGGTCC |
| SEQ ID NO: 742 | IGLV1-50*01 | CCCTGACCATTCTCTGGCTCCAAGTCTGGCACCTCAGCCTCCCTGGCCATCACTGGACTCCAGTCTGAGGATGAGGCTGATTATTAC<br>TGCAAAGCATGGGATAACAGCCTGAATGCTCA |
| SEQ ID NO: 743 | IGLV1-51*01 | ATTCCTGACCGATTCTCTGGCTCCAAGTCTGGCCACGTCAGCGCACCTCAGCCCCGGACTCCAGACTGGGACGAGGCCGATTAT<br>TACTGCGAACATGGGATAGCAGCCTGAGTGCT |
| SEQ ID NO: 744 | IGLV1-51*02 | TCCTGACCGATTCTCTGGCTCCAAGTCTGGCACAGTCTGCCACCCTGGCACTGCCAGACTCCAGAGGACGAGGCCGATTATTA2<br>TTGCGGAACATGGGATAACAATCTGCGTGCGGG |
| SEQ ID NO: 745 | IGLV1-62*01 | TATCTGACCGAATTCTCTGGTTCCAAGTCTGGCAGTCTGGCCTTGGCCTCCCTGGGCACCACTGGGCTGAGGACAAGACTGATTATC<br>ACTGCCAGTCCCGGACATCTGCTGAGTGCTTG |
| SEQ ID NO: 746 | IGLV2-11*01 | GGGTCCCTGATCGCTTCTCTGCTCCAAGTCTGGCTCCAAGTCTGGCAACACGGCCTCCCCTGACCATTCTCTGGGCTCCAGGCTGAGGATGAGGCTGATT<br>ATTACTGCTGCTCATATGCAGGCAGCTACACTT |
| SEQ ID NO: 747 | IGLV2-11*02 | GTCCCTGATCGCTTCTCTGGCTCCAAGTCTGGCTCCAAGTCTGGCAACAATCTCTGGGCTCCAGGCTGAGGATGAGGCTGATTAT<br>TACTGCTGCTCATATGCAGGCAGCTACACTTTC |
| SEQ ID NO: 748 | IGLV2-14*01 | GTCTCTAATCGCTTCTCTGGTTCCAAGTCTGGCAACAGTCTGGCAACACGGCCTCCCTGACCAATCTCTGGGCTCCAGCCTGAGGACGAGGCTGATTAT<br>TACTGCAACTCATATCAACCAGCGACACTCTC |
| SEQ ID NO: 749 | IGLV2-14*02 | GTTTCTAATCGCTTCTCTGGCTCCAAGTCTGGCTCCAAGTCTGGCAACACGGCCTCCAACATCTCTGGGCTCCAGCCTGAGGACGAGGCTGATTATT<br>ACTGCAGTCCATATACAAGCAGCAGCTCTC |
| SEQ ID NO: 750 | IGLV2-18*01 | AAGTACGCCGACTCCGTGAAGGGCCGATTCACCATCTCCAGAGACAACGCCAGGAACACGCTGTATCTGCAGATGAACAGTCTGAG<br>AGCCGAGGACACCGCTGTGTATTATTGTGCAAGA |
| SEQ ID NO: 751 | IGLV2-18*02 | TCTTGGACCCCTGCCCGGTTCTCAGGCTCCTCCTCGGGGGCAAAGCTGTCCTGACACTGTCAGGTGTGCAGCCTGAGGACGAGGC<br>TGAGTATTACTGCATGCTCTACTCTAGTGGTCCT |
| SEQ ID NO: 752 | IGLV2-18*03 | GTCCCTGATCGCTTCTCTGGGTCCAAGTCTGGCAACACAGCAGCTCCCTGACCACCTCTGGGCTCCAGGCTGAGGACGAGGCTGATTAT<br>TACTGCAGTCTCATATACAAGCAGCAGCTTTC |

TABLE B1-continued

| SEQ ID NO | Name | Sequence |
|---|---|---|
| SEQ ID NO: 753 | IGLV2-18*04 | GTCCCTGATCGTCTCCTGGGTCTCCAAGTCCGGCAACACGGCCTCCCTGACCATCTCTGGGCTCCAGGCTGAGGACGAGGCTGATTAT TACTGCAGCTCATATACAAGCAGCAGCACTTTC |
| SEQ ID NO: 754 | IGLV2-23*01 | TTTCTAATCGCTTCTCTGGCTCCAAGTCTGGCAACACGGCCTCCCTGACAATCTCTGGGCTCCAGGCTGAGGACGAGGCTGATTATT ACTGCTGCTCATATGCAGGTAGTAGCACTTTAC |
| SEQ ID NO: 755 | IGLV2-23*02 | GTTTCTAATCGCTTCTCTGGCTCCAAGTCTGGCAACACGGCCTCCCTGACAATCTCTGGGCTCCAGGCTGAGGACGAGGCTGATTAT TACTGCTGCTCATATGCAGGTAGTAGCACTTTC |
| SEQ ID NO: 756 | IGLV2-23*03 | GGGTTTCTGATCGCTTCTCTGGCTCCAAGTCTGGCAGCACGGCCTCCCTGACACGTCTGGGCTCCAGGCTGAGGATGAGGCTGATT ATTACTGCTGCTCATATGTTGGCAGTCACACTT |
| SEQ ID NO: 757 | IGLV2-28*01 | TCTCTGATCACTTCTCTGGCTCCAGCTCTGGCAACATGGCCTCCCTGACAATCTCTGGGCTTCCAGGCTGAGGACGAGGCTGATTATT ACTGCAGTTCATATACAAGCAGCACAATTTTC |
| SEQ ID NO: 758 | IGLV2-33*01_IGLV2-33*02 | ATCTCTGACCTCTCTCAGGCTCCAAGTCTGGCAACATGGCTTCCCTGACCATCTCTGGGCTCCAAGTCCGAGTTGAGGCTAATTATC ACTGCAGCTTATATTCAAGTAGTTACACTTTC |
| SEQ ID NO: 759 | IGLV2-33*03 | ATCTCTGACCTCTCTCAGGCTCCAAGTCTGGCAACATGGCTTCCCTGACCATCTCTGGGCTCCAAGTCCGAGTTGAGGCTAATTATC ACTGCAGCTTATATTCAAGTAGTTACACTTTC |
| SEQ ID NO: 760 | IGLV2-34*01_IGLV2-NL1*01 | GCCCCTGGTTGCTTCTCTGGCTCCAAGTCTGGCAACACGGCCTCCCTGACAATCTCTGGGCTCCAGGCTGAGACCATCTCTGGACTCCAGGCTGAGGACGAGGCTGATTAT TACTGCAGCTCATATGCAGGCAGTACAATTTC |
| SEQ ID NO: 761 | IGLV2-5*01 | GTCCCTGATCGTTCTTCTGGCTCTCCAAGTCTGGCAATACGGCCTCCATGACCATCTGGACTCCAGGCTGAGGACGAGGCTGATTAT TAGTGCTGCTCATAAGCAGTGCCACTAA |
| SEQ ID NO: 762 | IGLV2-5*02 | TCCCTGATCGTTTCTCTGGCTCCAAGTCTGGCAACACTGGCAACACAGTGCCACTTAAC |
| SEQ ID NO: 763 | IGLV2-8*01 | GGTCCCTGATCGCTTCTCTGGCTCTCCAAGTCTGGCAACACGGGCCTCCCTGACCGTCTGTGGGCTCCAGGCTGAGGACCAGAGCTGATTA TTACTGCAGCTCATATGCAGGCAGCAACAATTT |
| SEQ ID NO: 764 | IGLV2-8*02 | GTCCCTGATCGCTTCTCTGGCTCCAAGTCTGGCAACACGGCCTCCCTGACCGTCTCTCTGGGCTCTCCAGGCTGAGGATGAGGCTGATTAT TACTGCAGCTCATATGCAGGCAGCAACAATTTC |
| SEQ ID NO: 765 | IGLV3-1*01 | AGGGATCCCTGAGCGAATCTGTGGCTCCAAGTCTGGGAACACAGCCACTCTGACCATCAGCGGGACCCAGGCTATGATGAGGCTG ACTATTACTGTCAGGCGTGGGACAGCAGGGCTGC |
| SEQ ID NO: 766 | IGLV3-10*01 | CCCTGAGAGATTCTCTGGCTCCAGGCAGGGACAATGGCCACCTTGACTATCAGTGGGGCCCAGGTGAGGATGAAGCTGACTACT ACTGTTACTCAACAGACAGCAGTGGTAATCATTG |
| SEQ ID NO: 767 | IGLV3-12*01 | CCCTGAGCGATTCTCTGGCTCCAACCCAGGGACAGCAGCACCACCCTGGACTAGTAGTGATCCCCC ACTGTCAGGTGTGGGACAGTAGTGATCATTC |
| SEQ ID NO: 768 | IGLV3-12*02 | CCCTGAGCGATTCTCTGGCTCCAACCCAGGGAACACCGCCACCCTGACCATCAGCAGGATCGAGGCTGGGATGAGGCTGACTATT ACTGTCAGGTGTGGGACAGTAGTGATCATCC |

TABLE B1-continued

| SEQ ID NO | Name | Sequence |
|---|---|---|
| SEQ ID NO: 769 | IGLV3-13*01 | TGGAATCCCTGAGCGATTCTCTGGCTCCACCTCAGGGAACAACCGCCCTGACCATTAGCAGGGTCCTGACCAAAGGCGGGGCTG ACTATTACTGTTTTCTGGTGATTAGAACAATCT |
| SEQ ID NO: 770 | IGLV3-15*01 | GGATCTCTGAGAGATTCTCTGGCTCCAACTCGGGGACTTGGACAACGTGGCCACCTGACCATCAACAGGACCCCAGGGTGGGACAAGGCTATT ACTGTAAGATGTGGGACATTAGGACTCCTCATCC |
| SEQ ID NO: 771 | IGLV3-16*01 | ATCCCTGAGCGATTCTCTGGCTCCAGTCAGGGACACAATAGTCACATTGACCATCAGTGGAGTCCAGGCAGAGAGAGGCTGGACTA TTACTGTCTATCAGACAGACAGCAGTGTACTTAT |
| SEQ ID NO: 772 | IGLV3-17*01 | TCCCAGACCGATTCTCTGGCTCCAAGTCAGGAACACAGCCCTGACCATCACTGGGGCTCAGGTTGAACATGAAGCTGACTATTA CCGTCACTCATGGGACACAGTGTACTCATCT |
| SEQ ID NO: 773 | IGLV3-19*01 | CGGGCCTCCGGGGTTCCCTGACAGGTTCAGTGGCCAGTGGATCAGGCACAGATTTACTGACAGTGGAGGCTGAGG ATGTTGGGGTTTATTACTGCACATGCAAGCTCTACAT |
| SEQ ID NO: 774 | IGLV3-2*01 | AGTGATTCCTGACCAATTTCTGACTGCATATCAGAGGACATGGCCACCTTGATTATTAATGGGGCACAGGATGGAAACAAGCTA TTACTGTCGCTCGGAACAGCACTGCTTCTCATCT |
| SEQ ID NO: 775 | IGLV3-21*01 | GGATCCCTGACCGATTCTCTGGCTCCAATTCTGGGAACACGGGCCCACCCTGACCATCAGCAGGTCGAAGCGCGGGATGAGGCCGAC TATTACTGTCAGGTGTGGGATGTGAATAGTGATC |
| SEQ ID NO: 776 | IGLV3-21*02 | ATCCCTGAGCGATTCTCTGGCTCCAACTCTGGGAACACGGGCCCACCCTGACCATCAGCAGGTCGAAGCGCGGGATGAGGCCGACTA TTACTGTCAGGTGTGGGATAGTAGTAGTGATCAT |
| SEQ ID NO: 777 | IGLV3-21*03 | CCCTGAGCGTTCTCTGGCTCCCAACTCTGGGAACACGGGCCCACCCTGACCATCAGCAGGTCGAAGCGCGGGATGAGGCCGACTATT ACTGTCAGGTGTGGGAGTAGTAGTAGTGAACCACC |
| SEQ ID NO: 778 | IGLV3-22*01 | TGGAATCCCTGACCGATTCTCTGGCTCCACCTCAGGGAACCTCAGGGAACACACCCCTGACCATCAGCAGGGTCCTGACCGAAGACGAGGCTG ACTATTACTGTTTGTCTGGGAATGAGGACAATCC |
| SEQ ID NO: 779 | IGLV3-22*02 | TGGAATCCCTGACCGATTCTCTGGCTCCACCTCAGGGAACCTCAGGGAACACACCCCTGACCATCAGCAGGGTCCTGACCGAAGACGAGGCTG ACTATTACTGTTTGTCTGGGAATGAGGATAATCC |
| SEQ ID NO: 780 | IGLV3-24*01 | CAGGGATCCCTGACCGATTCTCTGAGATTCTCTGGCTCCAAACTCAGGGACCTCAGGGAACCTCAGGAGACAGGACCCCAGGCTGGGACCAGGCTATT ACTGTAAGATGTGGGACATTAGGACTCCTCATCC |
| SEQ ID NO: 781 | IGLV3-24*02 | AGGGGATTCTCTGAGATTCTCTGGCTCCAAACTCAGGGAACAGGAACACCCCTGGCCATCAACAGGGCCCAGGCTGGGGACCAGGCTATT ACTGTAAGATGTGGGACATTAGGACTCCTCATCC |
| SEQ ID NO: 782 | IGLV3-25*01 | CCCTGAGCGATTCTCTGGCTCCAGTCAGGGACAAAGTCACGTTGACCATCAGTGGAGTCCAGGCAGAAGATGAGGCTGACTATT ACTGTCAATCAGACAGACAGCAGTGGTACTTATCC |
| SEQ ID NO: 783 | IGLV3-25*02 | GCGACAATATATCTGCGTCGGTGAAAGGCAGATTCACCATCTCCAGAGATGATTCAAAAACATGGCGTTTCTCAAATGGACAG CCTGAGACCCGACGACACGGCCCTGTATTACTGT |
| SEQ ID NO: 784 | IGLV3-25*03 | CTCAGGGATCCCTGAGCGATTCTATGCTCCACCTCAGGGACACCAGAACACAGTCACGTTGACCATCAGTGGAGTCCAGGCAGAAGACGAGG CTGACTATTACTGTCAATCAATTGACAAAAGTGG |
| SEQ ID NO: 785 | IGLV3-26*01 | TCCCAGACCAATTCTCTGGCTCCAAGTCAGGAACACAGCCACCCCTGACCATCACTGGGCTCAGGTTGAACATGAAGCTGACTATTA CCATCACTCATGGGACAGTGCTACTCACCT |

TABLE B1-continued

| SEQ ID NO | Name | Sequence |
|---|---|---|
| SEQ ID NO: 786 | IGLV3-27*01 | AGGGATCCCTGAGCGATTCTCCGGCTCCAGCTCAGGGACTCCAGCTCACCTTGACCATCAGCGGGGCCCAGGTTGAGGATGAGGCT GACTATTACTGTTACTCTGCGCTGACAACAATCT |
| SEQ ID NO: 787 | IGLV3-29*01 | CTTCAGGGATCCTAAGTGATTCCAGCTCCAACTCGGGGAACATGTCATCCCTGACCATCAGTGAGCCCAGGCTGGGACGAG GCTTTCCTCCTCAGTGTGGGGCAGTGGCACTGCA |
| SEQ ID NO: 788 | IGLV3-30*01 | AGTGATTCTCTGGCTCCAACTTGTGGAACACAGCCACTTCTGACCATTAGTGGGCCCAGGCCAGGGACGAGGCTATTACTGTAGCA CCTATGATGGCTGAGGGAGCAGGACCAGTGGCT |
| SEQ ID NO: 789 | IGLV3-30*02 | AGTGATTCTCTGGCTCCAACTTGTGGAACACAGCCACTTCTGACCATTAGTGGGCCCAGGCCAGGGACGAGGCTATTACTGTAGCA CCTATGATGGCTGAGGGAGCAGGACCAGTGGCT |
| SEQ ID NO: 790 | IGLV3-31*01_IGLV3-31*02 | TCCTAAGAAATTCTCTGGCTCCAGCTCAGGGACATGCCACCCTGACCATCACTGGGATTCAGGTTGAAGACAAGGCTGACTATTA CTGTCAGTCATGGGACACAGTCTGTACTTCATTC |
| SEQ ID NO: 791 | IGLV3-32*01 | AAGGATCCCTGAGCGATTCTCTGGCTCCAAATCAGGCAACACAACACCCTGACCATCACTGGGGCCTGAGGATGAGGCTG ATTATTACTCAGTTGATAGACAACCATGCTAC |
| SEQ ID NO: 792 | IGLV3-4*01 | GCTCAGAGATCACTGAGCGATCCTGTTCTGCTCAGGGGGAACAGCCACACTGACCATTACTGGGGAACAGCCACACTGACCATTACTGGGACTGAAGACGAG GCTATTTTGTTTTCTGGAGATAAAAACACATT |
| SEQ ID NO: 793 | IGLV3-6*01 | GAATTTCTGATTTTCTGAGTCCAGCTCAGGGAACATGCCACCCTGACCATCAGCAGGGCTCAGACTGAGGACGAGGCTGACTATT ACTGTCACAGGTACAATAGAAACAGTGATGAGCC |
| SEQ ID NO: 794 | IGLV3-6*02 | GAATTTCTGATTTTCTGAGTCCAGCTCAGGGAACATGCCACCCTGACCATCAGGGCTCAGACTGAGGACGAGGCTGACTATTA CTGTCACAGGTACAACAGAAACAGTGATGAGCC |
| SEQ ID NO: 795 | IGLV3-7*01 | TGATTCCTGAACACTCTCTGACTCCATATCAGAGAACATGGCCACCCTGATAATCAATGGGCCCCAGGCTGGAAACAAGGCTATTA CTGTCAATCATGAGACAGCACTGATACTCATCT |
| SEQ ID NO: 796 | IGLV3-9*01_IGLV3-9*03 | GGGATCCCTGAGCGATTCTCTGCCTCCAACTCGGGAACACCGGCACCCTGACCATCAGCAGAGCCCAAGCGGGGATGAGGCTG ACTATTACTGTCAGGTGTGGGACAGCAGCACTGCA |
| SEQ ID NO: 797 | IGLV3-9*02 | CCCTGAGCGATTCTCTGCTCCAACTCGGGAACACCGGCACCCTGACCATCAGCAGAGCCCAAGCGGGGATGAGGCTGACTATT ACTGTCAGGTGTGGGACAGCACTGCACCCC |
| SEQ ID NO: 798 | IGLV4-3*01 | TACTACGCAGACTCAGTGAAGGGCCGATTCACCATCTCCAGAGACAACGCCAAGAACTCACTGTATCTGCAAATGAACAGCCTGAG AGCCGAGGACACGGCTGTGTATTACTGTGCGAGA |
| SEQ ID NO: 799 | IGLV4-60*01 | AGCGGAGTTCCTGATCGCTTCTCCAGCTCCAGCTTCTGGGGCTGACCGGTCCTACCTCACCATCTCCAACCTCCAGTTAGAGGATGAGGCT GATTATTACTGTGAGACTTGGGACAGTAACACT |
| SEQ ID NO: 800 | IGLV4-60*02 | GGAGCGGAGTTCCTGATCGCTTCTCAGCTCCAGCTTCTGGGGCTGACCGCTCCTACCTCACCATCTCCAACCTCCAGTTGAGGATGAGG GTGATTATTACTGTGAGACCTGGGACACTAACA |
| SEQ ID NO: 801 | IGLV4-60*03 | GGCGGAGATCCGAATCGCTTCTCCAGCTCCAGCTTCTGGGGCTGACCGCTACCTCACCGCTACTCACCATCTCCAACCTCCAGTCTCCAGTCTGACGATCAGGCT GATTATTACTGTGAGACCTGGGACAGTGACACT |

TABLE B1-continued

| SEQ ID NO | Name | Sequence |
|---|---|---|
| SEQ ID NO: 802 | IGLV4-69*01 | GAGACGGGATCCCTGATCGCTTCTCAGGCTCCAGTTCTGGGGCTGAGCGCTACCTCACCATCTCAGCTCCAGTCTGAAGATGAGGCTGAGTATTACTGTCAGACCTGGGGCCCTGGCA |
| SEQ ID NO: 803 | IGLV4-69*02 | GGGTCCCATCAAGGTTCAGTGCAGTGATCTGGGACAGAGATTTCACTCTCACCATCAGCAGTCTGCAACCTGAAGATTTTGCAACTTACTACTGTCAACAGAGTTACAGTACCCCTGGAT |
| SEQ ID NO: 804 | IGLV5-37*01 | CCCAGCCGCTTCTCTGGATCCAAAGATGCTTCAGCAGCATACAGGGATTTACTCATCTCCGGCTCCAGTCTGAGGATGAGGCTGACTATTACTGTGTATATGATTGGCCAAGCCAATGCTTCT |
| SEQ ID NO: 805 | IGLV5-39*01 | TCCCCAGCCGCTTCTCTGGATCCAAAGATGTTTCAACCAATGCAGGCCTGTTACTCATCTCTGGGCTCCAGTCTGAAGATGAGGCTGACTATTACTGTGCCATTTGGTACAGCAGTCTT |
| SEQ ID NO: 806 | IGLV5-39*02 | CCCAGCCGCTTCTCTGGATCCAAAGATGCTTCAACCAATGCAGGCCTTTACTCATCTCTGGGCTCCAGTCTGAAGATGAGGCTGACTATTACTGTGCCATTTGGTACAGCAGCACTTCT |
| SEQ ID NO: 807 | IGLV5-45*01 | CTGGCCATCCAGACAGGTTCAGTGGCAGTGGGTCTGGGACAGAGACTTCACTCTCACCATCAGCAGACTGGAGCCTGAAGATTTTGCAGTGTATTACTGTCAGCAGTATGGTGACTCACCTC |
| SEQ ID NO: 808 | IGLV5-45*02 | TCCCCAGCCGCTTCTCTGGATCCAAAGATGCTTCGGCCAATGCAGTGGGTCTGGGACAGACTTCACTCTCAGTCTGCAACCTGAAGATTTTGCACTATTACTGTATGATTTGGCACAGCGCTT |
| SEQ ID NO: 809 | IGLV5-45*03 | AGTGGGGTCCCATCAAGGTTCAGTGGCAGTGGGTCTGGGACAGACTTCACTCTCTCACCATAAAGCAGTCTGAACCTGAAGATTTTGCAACTTACTACTGTCAACAGACTTATCCGGAAGCCGG |
| SEQ ID NO: 810 | IGLV5-45*04 | CCCAGCCGCTTCTCTGGATCCAAAGATGCTTCAGGGGATTTTACTCATCTCTGGGCTCCAGTCTGAGGATGAGGCTGACTATTACTGTATGATTTGGCACAGTGCTTCT |
| SEQ ID NO: 811 | IGLV5-48*01 | CCCAGCCGCTTCTCTGGATCCAAAGATGCTTGAGCAATGCAGGAGATTTTAGTCATCTCTGGGCTCCAGTCTGAGGATGAGGCTGACTATTACTGTATGATTTGGCACAGTGCTTCT |
| SEQ ID NO: 812 | IGLV5-48*02 | CCCAGCCGCTTCTCTGGATCCAAAGATGCTTGACCAATGCAGGGATTTATTCATCTCTGGGCTCTAGTCTGAGGATGAGGCTGACTATTACTGTATGATTTGGCACAGTGCTTCT |
| SEQ ID NO: 813 | IGLV5-52*01 | CGCTTCTCTGGATCCAACGATGCATCAGCAGTTCTGCGTATCTGGGCTCCAGCCTGAGGATGAGGCTGACTATTACTGTGGTACATGGCACAGCAACTCTAAGACCCCT |
| SEQ ID NO: 814 | IGLV6-57*01_IGLV6-57*02 | CCCTGATCGGTTCTCGGCTCCAGACAGCTCCTCCAACTCTGCCTCCCCCACCATCTCTGACTGAAGACTGAGGACGAGGCTGACTACTACTGTCAGTCTTATGATAGCAGCAATCA |
| SEQ ID NO: 815 | IGLV7-35*01 | GGACCCCTGCCCAGTCTTCAGGCTCCAGTTCTGGGAGGCAGCAAAGCTGCCCAGACACTTGGGTGTGCAGCCCAGAGAGTGAAGCTGAGTACTACTGCTTACTGCACCATATGTGCTTGG |
| SEQ ID NO: 816 | IGLV7-43801 | TGGACCCCTGCCCAGTTCTCAGGCTCCTCCTCCTTGGGGCAAAGCTGCCCTGACACTGTCAGTGTGCAGCCTGAGGTGAAGCGGAGCTGAGTATTACTGCCTGCTCTACTATGGTGGTGCTCAG |
| SEQ ID NO: 817 | IGLV7-46*02 | TGGACACCTGCCCGGTTCTCAGGCTCCTCCTTTGGGGCAAAGCTGCCCTGACACTGCTTGCCCTTTTGGGTGCGCAGCCTGAGGATGAGGCTGAGTATTACTGCTTACTGCCTCCTATAGTGGTGCTCGG |
| SEQ ID NO: 818 | IGLV7-46*03 | CTTGGACACCTGCCCGGTTCTCAGGCTCCTCCTCCTTGGGGCAAAGCTGCCCTGACCTTTTCGGTGCGCAGCCTGAGGATGAGGCTGAGTATTACTGCTTGCTCTCCTATAGTGGTGCTCGG |

TABLE B1-continued

| SEQ ID NO | Name | Sequence |
|---|---|---|
| SEQ ID NO: 819 | IGLV8/OR8-1*01 | CCTGGTCGCTTCTCTGGCTCCATCCTTGGGAACAAAGCTGCCCTCACCATCACGGGGACTCAGTAGATGATGACTCTGATCATTACT GTGTGCTGTACATGGGTAGTGGCAATTCCACAG |
| SEQ ID NO: 820 | IGLV8/OR8-1*02 | GGGGTCCCTGGTCGCTTCTCTGGCTCCATCCTTGGGAACAAAGCTGCCCTCACCATCACGGGGACTCAGGTAGATGATGACTCTGAT CATTACTGTGTGCTGTACATGGGTAGTGGCAAT |
| SEQ ID NO: 821 | IGLV8-61*01 | CTTCTGGGGTCCCTGATCGCTTCTCTGGCTCCATCCTTGGGAACAAAGCTGCCCTCACCATCACGGGGGCCCAGGCAGATGATGAAT CTGATTATTACTGTGTGTATATGGGTGGTG |
| SEQ ID NO: 822 | IGLV8-61*02 | GGTCCCTGATTGCTTCTCTGGCTCCATCCTTGGGAACAAAGCTGCCCTCACCATCACGGGGGCCCAGGCAGATGATGAATCTGATTA TTACTGTGTGCTGTATATGGGTAGTGGCATTTC |
| SEQ ID NO: 823 | IGLV9-49*01 | TGATCGCTTCTCAGTCTTTGGGCTTCAGGCCTGAATCGGTACCTGACCATCGAGACATCGAGACATCCAGGAAGAGGATGACAGTGACTTCCACT GTGGGGCAGACCATGGGCAGTGGGAGCAACTTCGT |
| SEQ ID NO: 824 | IGLV9-49*02 | CTTCTCAGTCTTGGGCTCAGGCCTGAATCGGTACCTGACCATCAAGAGACATCAAGGAAGAAGATGAGAGTGACTACCACTGTGGGG CAGACCATGGGCAGTGGGAGCAACTTCGTGTAACC |
| SEQ ID NO: 825 | IGLV9-49*03 | CTTTCAGTCAGTCTTGGGCTCAGGCCTGAATCGGTACCTGACCATCAAGAGACATCAAGGAAGAAGAGGATGAGAGTGACTACCACTGTGGGG CAGACCATGGCAGTGGGAGCAACTTCGTGTAACC |
| SEQ ID NO: 826 | VPREB1*01 | TCCAAAGATGTGCCAGGAACAGGGGTATTTGAGCATCTCTGAGCTGCAGCCTGAGGACGAGGCTATGTATTACTGTGCTATGG GGGCCCCAGCTCGGAGAAGGAGGAGAGGAGAGG |

TABLE B2

| SEQ ID NO | | | | Name | Sequence |
|---|---|---|---|---|---|
| SEQ ID NO: 827 | | 89161040 | 89161073 | IGKJxxx-211891 | TACACTTTTGGCCAGGGGACCAAGCTGGAAATCAG ACGTAAGTACTTTTTTCCACTGATTCTTCACTGTT GCTAATTAGTTTACTTTGTGTTCCTTTGTGTGGAT TTTCATTAGTCGG |
| SEQ ID NO: 828 | | 89160080 | 89160117 | IGKJ5*01-X67858 | GATCACCTTCGGCCAAGGGACACGACTGGAGATTA AACGTAAGTAATTTTTCACTATTGTCTTCTGAAAT TTGGGTCTGATGGCCAGTATTGACTTTTAGAGGCT TAAATAGGAGTTTGG |
| SEQ ID NO: 829 | 2 | 89160398 | 89160435 | IGKJ5*01-X67858 | GCTCACTTTCGGCGGAGGGACCAAGGTGGAGATCA AACGTAAGTGCACTTTCCTAATGCTTTTTCTTATA AGGTTTTAAATTTGGAGCGTTTTTGTGTTTGAGAT ATTAGCTCAGGTCAA |
| SEQ ID NO: 830 | 2 | 89160733 | 89160770 | IGKJ3*01-X67858 | ATTCACTTTCGGCCCTGGGACCAAAGTGGATATCA AACGTAAGTACATCTGTCTCAATTATTCGTGAGAT TTTAGTGCCATTGTATCATTTGTGCAAGTTTTGTG ATATTTTGGTTGAAT |
| SEQ ID NO: 831 | 2 | 89161037 | 89161075 | IGKJ2*01-X67858 | TGTACACTTTTGGCCAGGGGACCAAGCTGGAGATC AAACGTAAGTACTTTTTTCCACTGATTCTTCACTG TTGCTAATTAGTTTACTTTGTGTTCCTTTGTGTGG ATTTTCATTAGTCGG |
| SEQ ID NO: 832 | 2 | 89161398 | 89161435 | IGKJ1*01-X67858 | GTGGACGTTCGGCCAAGGGACCAAGGTGGAAATCA AACGTGAGTAGAATTTAAACTTTGCTTCCTCAGTT GTCTGTGTCTTCTGTTCCCTGTGTCTATGAAGTGA TCTATAAGGTGACTC |
| SEQ ID NO: 833 | 2 | 89161398 | 89161433 | IGKJ1*01-X63370 | GGACGTTCGGCCAAGGGACCAAGGTGGAAATCAAA CGTGAGTAGAATTTAAACTTTGCTTCCTCAGTTGT CTGTGTCTTCTGTTCCCTGTGTCTATGAAGTGATC TATAAGGTGACTCTG |
| SEQ ID NO: 834 | 2 | 23235961 | 23235998 | IGLJ1*01-X51755 | GGCTCCTGCTCCAGCCCAGCCCCCAGAGAGCAGAC CCCAGGTGCTGGCCCCGGGGGTTTTGGTCTGAGCC TCAGTCACTGTGTTATGTCTTCGGAACTGGGACCA AGGTCACCGTCCTAG |
| SEQ ID NO: 835 | 2 | 23235961 | 23235998 | IGLJ1*01-X51755 (2) | TTATGTCTTCGGAACTGGGACCAAGGTCACCGTCC TAGGTAAGTGGCTCTCAACCTTTCCCAGCCTGTCT CACCCTCTGCTGTCCCTGGAAAATCTGTTTTCTCT CTCTGGGGCTTCCTC |
| SEQ ID NO: 836 | 22 | 23241798 | 23241835 | IGLJ2*01-X51755 | CAGCTTCCTCCTTCACAGCTGCAGTGGGGGCTGGG GCTGGGGCATCCCAGGGAGGGTTTTGTATGAGCC TGTGTCACAGTGTGTGGTATTCGGCGGAGGGACCA AGCTGACCGTCCTAG |
| SEQ ID NO: 837 | 22 | 23241798 | 23241835 | IGLJ2*01-X51755 (2) | TGTGGTATTCGGCGGAGGGACCAAGCTGACCGTCC TAGGTGAGTCTCTTCTCCCCTCTCCTTCCCCACTC TTGGGACAATTTCTGCTGTTTTTGTTGTTTCTGT ATCTTGTCTCAACTT |
| SEQ ID NO: 838 | 22 | 23241801 | 23241835 | IGLJ3*02-D87023 | CAGCTTCCTCCTTCACAGCTGCAGTGGGGGCTGGG GCTGGGGCATCCCAGGGAGGGTTTTGTATGAGCC TGTGTCACAGTGTTGGGTGTTCGGCGGAGGGACCA AGCTGACCGTCCTAG |
| SEQ ID NO: 839 | 22 | 23241801 | 23241835 | IGLJ3*02-D87023 (2) | TTGGGTGTTCGGCGGAGGGACCAAGCTGACCGTCC TAGGTGAGTCTCTTCTCCCCTCTCCTTCCCCGCTC TTGGGACAATTTCTGCTGTTTTTGTTGTTTCTGT ATCTTGTCTCAACTT |
| SEQ ID NO: 840 | 22 | 23247168 | 23247205 | IGLJ3*02-D87023 | AGCTTCCTCCTTCACAGCTGCAGTGGGGGCTGGGG CTAGGGGCATCCCAGGGAGGGTTTTGTATGAGCC TGTGTCACAGTGTTGGGTGTTCGGCGGAGGGACCA AGCTGACCGTCCTAG |
| SEQ ID NO: 841 | 22 | 23247168 | 23247205 | IGLJ3*02-D87023 (2) | TTGGGTGTTCGGCGGAGGGACCAAGCTGACCGTCC TAGGTGAGTCTCTTCTCCCCTCTCCTTCCCCGCTC TTGGGACAATTTCTGCTGTTTTTGTTGTTTCTGT ATCTTGTCTCAACTT |

TABLE B2-continued

| SEQ ID NO | | | | Name | Sequence |
|---|---|---|---|---|---|
| SEQ ID NO: 842 | 22 | 23247171 | 23247205 | IGLJ3*01-X51755 | AGCTTCCTCCTTCACAGCTGCAGTGGGGCTGGGG<br>CTAGGGGCATCCCAGGGAGGGTTTTGTATGAGCC<br>TGTGTCACAGTGTGTGGTATTCGGCGGAGGGACCA<br>AGCTGACCGTCCTAG |
| SEQ ID NO: 843 | 22 | 23247171 | 23247205 | IGLJ3*01-X51755<br>(2) | TGTGGTATTCGGCGGAGGGACCAAGCTGACCGTCC<br>TAGGTGAGTCTCTTCTCCCCTCTCCTTCCCCGCTC<br>TTGGGACAATTTCTGCTGTTTTTGTTTGTTTCTGT<br>ATCTTGTCTCAACTT |
| SEQ ID NO: 844 | 22 | 23252740 | 23252777 | IGLJ4*01-X51755 | GTATTTGGTGAGGAACCCAGCTGATCATTTTAGA<br>TGAGTCTCTTCTTCCCTTTCTTTCCCTGCCAAGTT<br>GGTGACAATTTTATTCTGATTTCGATCTTTGTCTG<br>TGACTTGCCACAGCC |
| SEQ ID NO: 845 | 22 | 23252740 | 23252777 | IGLJ4*01-X51755<br>(2) | TTTTGTATTTGGTGGAGGAACCCAGCTGATCATTT<br>TAGATGAGTCTCTTCTTCCCTTTCTTTCCCTGCCA<br>AGTTGGTGACAATTTTATTCTGATTTCGATCTTTG<br>TCTGTGACTTGCCAC |
| SEQ ID NO: 846 | 22 | 23256443 | 23256480 | IGLJ5*02-D87017 | CAGAGAGGGTTTTGTATGAGCCTGTGTCACAGCA<br>CTGGGTGTTTGGTGAGGGACGGAGCTGACCGTCC<br>TAGATGAGTCTTTTCCCCCTCCTTCCCTGGTCTCC<br>CCAAGGTACTGGGAA |
| SEQ ID NO: 847 | 22 | 23256443 | 23256480 | IGLJ5*02-D87017<br>(2) | CTGGGTGTTTGGTGAGGGACGGAGCTGACCGTCC<br>TAGGATGAGTCTTTTCCCCCTCCTTCCCTGGTCTC<br>CCCAAGGTACTGGGAAATTTTCTGCTGCTTTTGTT<br>CTTTTCTGTATCTTG |
| SEQ ID NO: 848 | 22 | 23260336 | 23260373 | IGLJ6*01-X58181 | GGAGGGTTTGTGTGCAGGGTTATATCACAGTGTAA<br>TGTGTTCGGCAGTGGCACCAAGGTGACCGTCCTCG<br>GTGAGTCCCCTTTTCTATTCTTTTGGGTCTAGGGT<br>GAGATCTGGGGAGAC |
| SEQ ID NO: 849 | 22 | 23260336 | 23260373 | IGLJ6*01-X58181<br>(2) | TAATGTGTTCGGCAGTGGCACCAAGGTGACCGTCC<br>TCGGTGAGTCCCCTTTTCTATTCTTTTGGGTCTAG<br>GGTGAGATCTGGGGAGACTTTTCTGTCCTTTCTGT<br>TCTCTCTAGGGTAGA |
| SEQ ID NO: 850 | 22 | 23263570 | 23263607 | IGLJ7*01-X57808 | TCACTGTGTGCTGTGTTCGGAGGAGGCACCCAGCT<br>GACCGTCCTCGGTAAGTCTCCCCGCTTCTCTCCTC<br>TTTGAGATCCCAAGTTAAACACGGGGAGTTTTTCC<br>CTTTCCTGTCTGTCG |
| SEQ ID NO: 851 | 22 | 23263570 | 23263607 | IGLJ7*01-X57808<br>(2) | TGCTGTGTTCGGAGGAGGCACCCAGCTGACCGTCC<br>TCGGTAAGTCTCCCCGCTTCTCTCCTCTTTGAGAT<br>CCCAAGTTAAACACGGGGAGTTTTTCCCTTTCCTG<br>TCTGTCGAAGGCTAA |
| SEQ ID NO: 852 | 22 | 23263570 | 23263607 | IGLJ7*02-D87017 | TCACTGTGTGCTGTGTTCGGAGGAGGCACCCAGCT<br>GACCGCCCTCGGTAAGTCTCCCCGCTTCTCTCCTC<br>TTTGAGATCCCAAGTTAAACACGGGGAGTTTTTCC<br>CTTTCCTGTCTGTCG |
| SEQ ID NO: 853 | 22 | 23263570 | 23263607 | IGLJ7*02-D87017<br>(2) | TGCTGTGTTCGGAGGAGGCACCCAGCTGACCGCCC<br>TCGGTAAGTCTCCCCGCTTCTCTCCTCTTTGAGAT<br>CCCAAGTTAAACACGGGGAGTTTTTCCCTTTCCTG<br>TCTGTCGAAGGCTAA |
| SEQ ID NO: 854 | 22 | 106329408 | 1.06E+08 | IGHJ6*03-M63030 | TACTACTACTACTACATGGACGTCTGGGGCAA<br>AGGGACCACGGTCACCGTCTCCTCAGGTAAGAATG<br>GCCACTCTAGGGCCTTTGTTTTCTGCTACTGCCTG<br>TGGGGTTTCCTGAGC |
| SEQ ID NO: 855 | 22 | 106329408 | 1.06E+08 | IGHJ6*03-M63030<br>(2) | ATTACTACTACTACTACATGGACGTCTGGGGC<br>AAAGGGACCACGGTCACCGTCTCCTCAGGTAAGAA<br>TGGCCACTCTAGGGCCTTTGTTTTCTGCTACTGCC<br>TGTGGGGAATTC |
| SEQ ID NO: 856 | 14 | 106329408 | 1.06E+08 | IGHJ6*04-AJ879487 | ATTACTACTACTACTACGGTATGGACGTCTGGGGC<br>AAAGGGACCACGGTCACCGTCTCCTCAGGTAAGAA<br>TGGCCACTCTAGGGCCTTTGTTTTCTGCTACTGCC<br>TGTGGGGTTTCCTGA |

TABLE B2-continued

| SEQ ID NO | | | | Name | Sequence |
|---|---|---|---|---|---|
| SEQ ID NO: 857 | 14 | 106329409 | 1.06E+08 | IGHJ6*03-X86359 | TGATGCTTTTGATATCTGGGGCCAAGGGACAATGG TCACCGTCTCTTCAGGTAAGATGGCTTTCCTTCTG CCTCCTTTCTCTGGGCCCAGCGTCCTCTGTCCTGG AGCTGGGAGATAATG |
| SEQ ID NO: 858 | 14 | 106329626 | 1.06E+08 | IGHJ3P*02-X97051 | CTTGCAGTTGGACTTCCCAGGCCGACAGTGGTCTG GCTTCTGAGGGGTCAGGCCAGAATGTGGGGTACGT GGGAGGCCAGCAGAGGGTTCCATGAGAAGGGCAGG ACAGGGCCACGGACA |
| SEQ ID NO: 859 | 14 | 106330024 | 1.06E+08 | IGHJ4-U42590 | GACTATTGGGGCCAGGGAACCCTGGTCACCGTCTC CTCAGGTGAGTCCTCACAAGCTCTCTCCTACTTTA ACTCAGAAGACTCTCACTGCATTTTTGGGGGAGA TAAGGGTGCTGGGTC |
| SEQ ID NO: 860 | 14 | 106330024 | 1.06E+08 | IGHJ4*02-X97051 | ACTACTTTGACTACTGGGGCCAGGGAACCCTGGTC ACCGTCTCCTCAGGTGAGTCCTCACAACCTCTCTC CTGCTTTAACTCTGAAGGGTTTTGCTGCATTTTTG GGGGAAATAAGGGT |
| SEQ ID NO: 861 | 14 | 106330024 | 1.06E+08 | IGHJ4-U42588 | AACTGGTTCGACCCCTGGGGCCAGGGAACCCTGGT CACCGTCTCCTCAGGTGAGTCCTCACCACCCCCTC TCTGAGTCCACTTAGGGAGACTCAGCTTGCCAGGG TCTCAGGGTCAGAGT |
| SEQ ID NO: 862 | 14 | 106330024 | 1.06E+08 | IGHJ5-M18810 | CAGTGCTTCGACCCCTGGGGCCAGGGAACCCTGGT CACCGTCTCCTCAGGAGATTCCTCACCACCCCCTC TCTGAGTCCTCTTAGTGAGACTCAGTTTGCCGGAC TCTCAGGGTCAGAGT |
| SEQ ID NO: 863 | 14 | 106330024 | 1.06E+08 | IGHJ5*02-X97051 | ACAACTGGTTCGACCCCTGGGGCCAGGGAACCCTG GTCACCGTCTCCTCAGGTGAGTCCTCACCACCCCC TCTCTGAGTCCACTTAGGGAGACTCAGCTTGCCAG GGTCTCAGGGTCAGA |
| SEQ ID NO: 864 | 14 | 106330425 | 1.06E+08 | IGHJ5*02-X97051 | TACTTTGACTACTGGGGCCAGGGAACCCTGGTCAC CGTCTCCTCAGGTGAGTCCTCACAACCTCTCTCCT GCTTTAACTCTGAAGGGTTTTGCTGCATTTCTGGG GGGAAATAAGGGTGC |
| SEQ ID NO: 865 | 14 | 106330425 | 1.06E+08 | IGHJ4-U42588 | TTTGACTGCTGGGGCCAGGGAACCCTGGTCACCGT CTCCTCAGGTGAGCCCTCACAACCTCTCTCCTGGG TTAACTCTGAAGGGTTTTGCTGCATTTTTGGGGGG AAATAAGGGTGCTGG |
| SEQ ID NO: 866 | 14 | 106330797 | 1.06E+08 | IGHJ3*01-M25625 | TGATGCTTTTGATGTCTGGGGCCAAGGGACAATGG TCACCGTCTCTTCAGGTAAGATGGGCTTTCCTTCT GCCTCCTTTCTCTGGCCCCAGCGTCCTCTGTCCTG GAGCTGGGAGATAAT |
| SEQ ID NO: 867 | 14 | 106330797 | 1.06E+08 | IGHJ3*02-X97051 | TGATGCTTTTGATATCTGGGGCCAAGGGACAATGG TCACCGTCTCTTCAGGTAAGATGGCTTTCCTTCTG CCTCCTTTCTCTGGGCCCAGCGTCCTCTGTCCTGG AGCTGGGAGATAATG |
| SEQ ID NO: 868 | 14 | 106330797 | 1.06E+08 | IGHJ3*02-X97051 (2) | GATGCTTTTGATATCTGGGGCCAAGGGACAATGGT CACCGTCTCTTCAGGTAAGATGGCTTTCCTTCTGC CTCCTTTCTCTGGGCCCAGCGTCCTCTGTCCTGGA GCTGGGAGATAATGT |
| SEQ ID NO: 869 | 14 | 106331001 | 1.06E+08 | IGHJ2P*01-X97051 | GCTACAAGTGCTTGGAGCACTGGGGCCAGGGCAGC CCGGCCACCGTCTCCCTGGGAACGTCACCCCTCCC TGCCTGGGTCTCAGCCCGGGGGTCTGTGTGGCTGG GGACAGGGACGCCGG |
| SEQ ID NO: 870 | 14 | 106331409 | 1.06E+08 | IGHJ2*01-X97051 | CTACTGGTACTTCGATCTCTGGGGCCGTGGCACCC TGGTCACTGTCTCCTCAGGTGAGTCCCACTGCAGC CCCCTCCCAGTCTTCTCTGTCCAGGCACCAGGCCA GGTATCTGGGGTCTG |

TABLE B2-continued

| SEQ ID NO | | | | Name | Sequence |
|---|---|---|---|---|---|
| SEQ ID NO: 871 | 14 | 106331617 | 1.06E+08 | IGHJ1*01-X97051 | GCTGAATACTTCCAGCACTGGGGCCAGGGCACCCT<br>GGTCACCGTCTCCTCAGGTGAGTCTGCTGTCTGGG<br>GATAGCGGGGAGCCAGGTGTACTGGGCCAGGCAAG<br>GGCTTTGGCTTCAGA |
| SEQ ID NO: 872 | 14 | 106331834 | 1.06E+08 | IGHJ1P*01-X97051 | AAAGGTGCTGGGGGCCCCTGGACCCGACCCGCCCT<br>GGAGACCGCAGCCACATCAAGCCCCCAGCCCCACA<br>GGCCCCCTACCAGCCGCAGGGTTTTGGCTGAGCTG<br>AGAACCACTGTGCTA |

TABLE D

| SEQ ID NO | Name | Sequence |
|---|---|---|
| SEQ ID NO: 1 | IGKV1/OR2-3*01 | cccagtgcgacaagtcataacatcaaccgctaggatagcagatgagtgaggccgggttgc<br>cctagatgctcctcctggtgcctcaatctgctgagttgttttccagatgcagccaagttt |
| SEQ ID NO: 2 | IGKV1-22*01 | cctagagtgttacaggtcataaaataaaccccccagggaagcagaagtatgactcatggct<br>gccccaggtgcttccactggtgcctccatctgctgagagtgtttctcaggtgcagccaag |
| SEQ ID NO: 3 | IGKV1-27*01 | cactgtgatacaagcccgaacataaaccatggaggaagtagatgtgtgaggctgggctg<br>ccccagctgctcctcctggtgccgccctctgctgacagcagttctcagatgcagccaagg |
| SEQ ID NO: 4 | IGKV1D-37*01 | cacagtgttacaaggcataacataaaccccccaaggaagcagatgtatggggctggcctg<br>ccccagatactcctcctactgcctccagctgctcagagcgtttctcatattccagtcaag |
| SEQ ID NO: 5 | IGKV1-39*01 | cacagtgttacaagtcataacataaacctccaaggaagcagatgtgtgaggacgagccac<br>cccagatgctcctcctggtgcctccatctgctgagagcatttctcaaactcagtcaggtt |
| SEQ ID NO: 6 | IGKV1-35*01 | cacagtgttacaaaccataacaaacccccccaggaaagcagacatgtgacgctgggctg<br>ccccacctgctcttctttgtgcagccatctggtgacaacacttctcagactcagcctgag |
| SEQ ID NO: 7 | IGKV1-32*01 | cacagtgttacaaacccaataagctcccccaaggaagcagatatgtgagggtgggctgccc<br>cagctgcttctcctgtttcctccatctgctgagagtgtttctcagactcagccacactct |
| SEQ ID NO: 8 | IGHV7-81*01 | caccatgtggaaacccacatcctgagagtgtcagaaatcctgatgtgggaggcagctgtg<br>ctgagctgaggcagtgatgcagcagtttccttaacttccatcttatctcattttgcatcg |
| SEQ ID NO: 9 | IGHV1-14*01 | cacagtgtgaaacccacatcctgagagtcagaaatcctgagggaggtggcagcagtg<br>ctaggcttgagagatgacagggattttatttgctttaaaggctttttttagaaagcgagg |
| SEQ ID NO: 10 | IGHC1-69*01 | gacacagtgtgaaacccacatcctgagagtgtcagaaacctgagggagaaggcagctg<br>tgccgggctgaggagatgacaggggtttattaggtttaaggctgtttacaaaatgggtat |
| SEQ ID NO: 11 | IGHV1-67*01 | cacagtgtgaaaactcatatcctgagagtgtcagtaaccctgagggaggaagcagctgtc<br>ccagttttcaggatatgacaggatttatggggtttaatgttgtttagaaaataggttata |
| SEQ ID NO: 12 | IGHV1/OR21-1*01 | cacaatgtgaaacccacatcttgagagttcagaaactgcagggaggaggcagctgtgt<br>tcctgcagaggagatgacaggaagatgaggtttaaagttgtttagaaaatgggtcaagt |
| SEQ ID NO: 13 | IGHV1/OR15-3*03 | gacacagagtgaaacccacatcctgagagtgtcagaaaccccaaggaggagcagctgta<br>ctggagctgaggaaatggacaaagattattcagattgaagactttctacgaaaatgacct |
| SEQ ID NO: 14 | IGHV1-3*02 | cacagtgtgaaacccacatcctgagagtgtcagaaacccaggggggaagcagctgtgc<br>tggcatggaggaaatgacaaagattattagattgaagactttctcagaaaatgatattaa |
| SEQ ID NO: 15 | IGHV1-17*01 | gacacagtgcgaaacccacatcctgagagtgtcagaaacccaggaaggaggcacctgt<br>gctgacacagagggagatgacaaagattattagattaacgattttcttaga |
| SEQ ID NO: 16 | IGHV1-17*02 | cacagtgcgaaacccacatcctgagagtgtcagaaacccaggaaggaggcacctgtgc<br>tgacacagaggagatgacaaagattattagattaaagattttcttagaaaatgacactaa |
| SEQ ID NO: 17 | IGHV1-38-4*01 | cacagtgtgaaacccacatcctgagagtgtcagaaagcctgaggaaggaggcagctgtg<br>ctggggctgaggagatgacagggattacttgattgaagactttcttagaaaacgaggtta |
| SEQ ID NO: 18 | IGHV5-51*01 | cacagtgagagaaaccagccccgagcccgtctaaaaccctccacaccgcaggtcagaat<br>gagctgctagagactcactcccaggggcctctctattcatctggggaggaaacactggc |
| SEQ ID NO: 19 | IGHV5-78*01 | gaccatctaaaaccttccgcggtgcaggtgcagagtgagctgccagacacaccctcccca<br>ggggcctctctattcatccggggaggaaacactggctgtttgtgtcctcaggagcaaaaa |
| SEQ ID NO: 20 | IGHV3-50*01 | gcgaataatggagaacttgagatatggagtgtgagtggatatgagtgaaaaaacagtgat<br>tctgtgtggcaggttctgactcagatgtctctgtgcttgtaggtgtctagtgtggggtgc |

TABLE D-continued

| SEQ ID NO | Name | Sequence |
| --- | --- | --- |
| SEQ ID NO: 21 | IGHV(III)-76-1*01 | cacaggagatatccgtgtggcaacctaacacaggggacacctgtatttgtgtctgagccc agacacaaacctccctgcagggagacaggaggggaccgtgtgacagacactgctcagaac |
| SEQ ID NO: 22 | IGHV3-30-22*01 | ccaagtgagagctgaggacatggctgtgcatggctgtacataaggtcccaagtgagcaaa catcggtgtgagtccagacacaacacttcctgcaaaaacaagaaaggagtctgggccgaa |
| SEQ ID NO: 23 | IGHV(III)-22-2 | acaagagtcagaaaagtgtgcaggaggccgggtgaggctgtagacactgtcagcccacta tgccaatcccaccacgagtgctggagaaggtgggagtctgatgaagcttactaacaaacc |
| SEQ ID NO: 24 | IGHV(II)-44-1D*01 | gccgagattgcgccactgcactcagcctgggcgacagagcgagacttcgtctcaaaaaaa caaaaaaaaaaatcaatcattggaatactgttgttcattacaattaatgaacgcttgata |
| SEQ ID NO: 25 | IGLV(IV)-64*01 | cacaggtggggaagtgggacaaaatctcagcctgctcagagtcttgttctctgatgaaat ttagatcttaaaataacttatatcacttgtgtgggatgagtgagatatcccgagctcaca |
| SEQ ID NO: 26 | IGHV(II)-23-2*01 | cacagcgaggggaagccattgtgcgctcagaacactctacaaattttcctccctagtgtt ttaccaaaactggtatatatttcagatactgaaatatttacaa |
| SEQ ID NO: 27 | IGLV(VI)-22-1*01 | agtaagaccaaaaccctcctgagattcctggcttgtgtcctgacactggggctgttggga ttcctgtctttccttcaagattgttcaaataagcaccgacaatcacttccatgtgagata |
| SEQ ID NO: 28 | IGLV(V)-58*01 | aaggcaaagtgacccagtgaatgaggaagcaggacaaaaactgttttctctgctccact atgaaggctgccacgtggccctgagaaacagtgcctgttttccttactactcaagaaaga |
| SEQ ID NO: 29 | IGLV(V)-66*01 | ccgtttgggtaaagcacagataaatggggaaatgaggcaaaaactgttttttctactctgc taccaaggttgaaaaatggctctcagaaccagtgtctgctgacctgcatactcaaatatg |
| SEQ ID NO: 30 | IGHV(II)-20-3*01 | taaaataaaataaaatgtaaaaaatgatcaataaatgaaattactatcagttgaaactca ttaaatttaaagacattttctactcaagtaactataagaacatgaatgtcaagtttcaga |
| SEQ ID NO: 31 | IGLV(IV)-59*01 | cacaggcagatgagaaagtgagacgaaactcagcctactaagaatggaactatggctctt ttttccaattgtcaaataattttcacatacacaaactattttggaagtagctactgattca |
| SEQ ID NO: 32 | IGLV7-46*02 | cacagtgacagatccatgagaggaaccaagacataaacctccctcggcccttgtgatgtg gagatcacatgatcagacatgccagatcccaagatagcctacatgtggaccagccataga |
| SEQ ID NO: 33 | IGLV8-61*01 | cacagtgatttaaacctatgaggaagtgcaactaaaacctctttatatactgagaacagt tcagcccttacagacaggagggaaagtgagagggtggaaatggtcaacacggtgagtgag |
| SEQ ID NO: 34 | IGLV8/OR8-1*01 | tttaaacccatgaggaggtgcaactaaaacctctttacatactcagaaagattcagccct tagaagcaagagagaagttgagagggtgggaatgtcaacaccatgagctgggaacctcct |
| SEQ ID NO: 35 | IGLV(I)-56*01 | ttctctgattatctggatgctctgtgactccttctgtgcatctctgggatcatcattcag actcacctgcaccctgagcagtaacatcaatgttgtttgctatgacatttactggaaaca |
| SEQ ID NO: 36 | IGKV3-31*01 | cacagtgattccacaggaaaccaaacctccacaagacagctggtgttttttcctcaagcc ttctgtttacttatgggaagctactatggtggctgcttagttattgagagaaaacaatggg |
| SEQ ID NO: 37 | IGKV3-34*01 | cacagtaattcaacatgaaacaaaaactttcacaaaaccattgatttttttttctaaaa ccagcagctttatgggctgcagctatgatggctgcccagttttagcaactgtgcctctat |
| SEQ ID NO: 38 | IGKV3D-25*01 | catactgattcaacatgcaacaaaaacctccaggagacctaaggtgtttatttgattata ccacctgcttcctttttagtcatctgatgtggtgctgctcagttttagcatctctgcttt |
| SEQ ID NO: 39 | IGKV3-11*01 | cacagtgattccacatgaaacaaaaaccccaacaagaccatcagtgtttactagattatt ataccagctgcttcctttacagacagctagtgggtggccactcagtgttagcatctcag |
| SEQ ID NO: 40 | IGHV2-70*13 | cacagagacacagcccagggcgcttcctgtacaagaacccaggtgttttttcagtggtgct ccctcccacttctgcagaacaggatagtgtggctgagatgccatttcctgcccagggcg |
| SEQ ID NO: 41 | IGHV2-70D*04 | cacagagacacagcccagggcgcctcctgtacaagaacccaggctgcttctcagtggtgc tccctcccacctctgcagaacaggatagtgtggctgagatgccatttcctgccagggcc |
| SEQ ID NO: 42 | IGLV(VI)-25-1*01 | agtaagaccaaaaccctcctgagattcctgacttgtgtcctgacaccaggtctgttcttc cctcccctagaataaaacatctcttaagcacaaggctgaagaaatgtggcctcctcctttt |
| SEQ ID NO: 43 | IGHV(II)-22-1*01 | cacagcgaggggaagccattgtgcgctcagaacactctacaaattttcctccctagtgtt ttaccaaaactggtatatatttcagatactgaaatatttacaacctacgttattatgcta |
| SEQ ID NO: 44 | IGHV(II)-30-31*01 | caaacaaaacgacacaaaaaattccaaagttgtgcaccctctaaaagcatatgtacttaa ttctcattttttaatttattaaacagctctaataagttcaatgttcctgccttctcagttg |
| SEQ ID NO: 45 | IGKV2D-36*01 | aaaacttgaacttccatcaatgataaatattccttttgcctcaagcacatatttgaggaa ttttccattgagtagatcctaccgataaggtcacattttttctgtctgtttttaatctgaata |
| SEQ ID NO: 46 | IGHV1-12*02 | tagttatttgagagattttttcatacaacatttattctgtaagcaaatttcagggattgtt gaatgaatcatattaacaaatctgacacagaacttcctctgaatcaatctttgtaaacat |

TABLE D-continued

| SEQ ID NO | Name | Sequence |
|---|---|---|
| SEQ ID NO: 47 | IGHV(II)-44-2D*01 | tgcctggccgtaagttaccatgtgcttttttaaaaaaatcatagcaaaggggtgtcttctg<br>gaaatgacattttgaaatggtgttattagaccacccctggaagggacacagtaaccacac |
| SEQ ID NO: 48 | IGHV(II)-74-1 | agtgatggtgggggtcctactagcctgtggcaaatggaagcatctcttttttatcagact<br>gaataatattgtagtgttttcttataccacatttacttcatcccttttgtgcattaacact |
| SEQ ID NO: 49 | IGHV(II)-46-1*01 | aaaatccattgctagtggtggtgggagtccatttgtcttgtggaaaatggcagcatttcc<br>ttattttataaggcataataatgctatgttgtgtacacataccacattgtctttatccat |
| SEQ ID NO: 50 | IGHV(II)-67-1*01 | aaaatgcatggctagtgctgctggaaacccattcctactgtggcaaatggcagcatctct<br>tttaaaaggctaaataatattctattctgtatacataccacattgccattatccttttg |
| SEQ ID NO: 51 | IGHV(II)-23-1*01 | atagatggataaactaacctaggcctttgaaaataaaacccttatctgagagtgaaaagat<br>aagccatagatttggagagtttgcttgcaaatcaaatatttggaaaaggacttttattac |
| SEQ ID NO: 52 | IGHV(II)-40-1*01 | taggcactggatggaaagcacaggagtgggtcaggtgcatacgtgatgagtggaggatga<br>attccagcccacttatcatgaattcagacaagcccacatgttcccacatgcactatatct |
| SEQ ID NO: 53 | IGHV(IV)-44-1*01 | cactgtgactcgaatccagagtgaactcagacacaaacctgccctgcaggggttcttggg<br>accacaaggggaaggatcaggtcaccagggtgtacttaggaaccactgaactgggtcagg |
| SEQ ID NO: 54 | IGHV(II)-28-1*02 | cgcaatgaagggccttcattgtgagcctagacacaaccctccctgcagggtgaatagga<br>gcagcaggggcattcggggcagtatgggggcttaggatgattgttaggggtcaggatga |
| SEQ ID NO: 55 | IGHV(II)-30-41*01 | cattgtgagcctagacacaaccctccctgcaggggtgaataggagcagcagggggcattc<br>ggggcagtatgggggcttaggatgattgttaggggtcaggatgagcaggatcaaggcttc |
| SEQ ID NO: 56 | IGHV(II)-65-1*01 | cacaacgaggggaagtcattgtgagcccagatacaaacctccctgcagggagctcagaa<br>agagcaggaggcactcaggacaccagggaacactctggacacatcaaggcaggtgcaatg |
| SEQ ID NO: 57 | IGHV(II)-51-2*01 | aacagaagagatgtcagtgtgatcccagacacaaacttccctggagaggggcccaggacc<br>accaaagagcactcaggcccatgaaaacagggcccaagctggagaacgggtttcctgtca |
| SEQ ID NO: 58 | GHV(II)-15-1*01 | cacagaaggggaggtcattgtgaggccagacacaaacctccctgcaggaagctcaggac<br>accaggggtgctcagacaccaagggctctcaggacacatcaaggcaggtgcaagagggg |
| SEQ ID NO: 59 | IGHV6-1*01 | cacagtgaggggaagtcagtgtgagcccagacacaaacctccctgcagggatgctcagga<br>ccccagaaggcacccagcactaccagcgcagggcccagaccaggagcaggtgtggagtta |
| SEQ ID NO: 60 | IGHV(II)-60-1*01 | cagagtgaggggaccacggtgcgagctcacacccaaaccttcctggagggggtgcacagga<br>cagcaggagtcccgatgatggaaggggggtggtctggattccaggtcactctcaagatcat |
| SEQ ID NO: 61 | IGHV(II)-53-1*01 | cacagtaaggtaaccacagtgggaactcacacccaaacctccctgtggggtgcacagga<br>cagccacagttactcaggaccccaggattcctcaggacaccaaggggcactcaaggccat |
| SEQ ID NO: 62 | IGHV(II)-20-1*01 | cacagtgaggggacatcagtgtgagcccagacacaaacctccctatgcggttcacagga<br>cagcatgggtgctgaggacagaggtgggcactcaggaaccagcagggaaacccagggg |
| SEQ ID NO: 63 | IGHV3-41*01 | agtgagaggaagtccgtgtgagcccagacacaaacctccctgcaggggcacgcggggcca<br>ccagagggtgcccaggatcccctgaagacagggacagcccaaaggcaggtgcagatggat |
| SEQ ID NO: 64 | IGHV3-52*01 | cacagtgaggggaggtcagtgtgagcccagacacaaacctcctgcaggggcatctggagc<br>cacaaggggcgctcaggatacacagaggacaggggcagcccaggggcaggtgcaggtgg |
| SEQ ID NO: 65 | IGHV3-73*02 | cacagtgaggggaggtcagtgtgagcccggacacaaacctccctgcagggggcgcgcgggg<br>ctaccaggggcgctcgggactcactgagggcgggacaggtcccaggaacaggtgcagcg |
| SEQ ID NO: 66 | IGHV3-42*03 | cagtgaggggaggttaacgtaggcccatacacaaatctccctgcaggggcgcgcagggc<br>caactgggggcgctcgggacccactgaggatgggacaggtcccaggggcgggtgcagggg |
| SEQ ID NO: 67 | IGHV3-6*01 | tacggtaaggagaagtcagtgtgagcccagacacaaacctcccttcagggtacctgggac<br>aaccaggggaaagcctgggacactgtgcactgtgctgacccagggggcaagtgcaggtgct |
| SEQ ID NO: 68 | IGHV3/OR16-9*01 | cacagagtgagggaagtcagtgagagcccaggcacaaacctccctgaaggggtcccaga<br>aacgactaggggggcgccaggacactgtgcacggggctgtctccagggcaggtgcaggtgc |
| SEQ ID NO: 69 | IGHV(II)-44-2*01 | aacagtgagaggaagtcaatgtgagtccagacataaaccttcctgctgagaacaatggaa<br>agcttttcttctaagataaggaataagaaaagaatgcccagtcttaataattctaatcag |
| SEQ ID NO: 70 | IGHV3-25*02 | cacagtgaggggaggtcagtgtgagcccagacacaaacctccctgcagggccatgcgggt<br>ggtttcctttctcagctgcaggaggcgggcttattgttgcaggactctggagacttatta |
| SEQ ID NO: 71 | IGHV(II)-26-2*01 | ctcagtgaggaggtgtccttatgagccctgacacaaacctgtcagggcacttaggacctc<br>caggaagactcaagaccaccaaggggactcacgaccactggggaagggcaggttgcagta |
| SEQ ID NO: 72 | IGHV(III)-67-3*01 | cacagcgagggacatttctgtgagtccagacagaaacctccctgcaggagacaagagag<br>gactttgtgataaatggtgcttaggacaccagggggcactcaggacagcagagggtgctc |

TABLE D-continued

| SEQ ID NO | Name | Sequence |
|---|---|---|
| SEQ ID NO: 73 | IGHV(III)-47-1 | cacggtgaggggacatctgtgtgagctcagacacaaacctgcctgcagggagacacaaac<br>ctccctgcatggtagatgcttctcagaaccaccaggggggtgcacaggaaaccagaaggtg |
| SEQ ID NO: 74 | IGHV(III)-82*01 | cataggagcaggaacatctgcgtgagcccagacacaaaatcctctgcagggagacaggag<br>ggaatcgcatggtagatgctgattggaactaccatgtgtcgctcagaactaccaggaggt |
| SEQ ID NO: 75 | IGHV(III)-67-4*01 | cacaggagagagattatctgcacaagcccagacacaaaaatctgcagggagacaggaggg<br>aactgcatggtagatgctgctcagaagcaccaggggggcactcaacacaaggggggcgctca |
| SEQ ID NO: 76 | IGHV(III)-16-1*01 | agacacaggagagggaatatctgcgtgagcccagacagaaaaatctgcaggaagacag<br>gagggagctgcatggtagatgctcctcagaaccaccagggcaccttggggacaaacctggg |
| SEQ ID NO: 77 | IGHV3-57*02 | cacaggagagggaatatctgtgtgagcccagacacaaaaatctctgcagagagacaggag<br>ggaactgcatggtagatgctcctcataaccacaaaggggcagtcaggaccatcaggagga |
| SEQ ID NO: 78 | IGHV(III)-5-1*01 | cacatgaggaaaggccggtgtgagacacaaacctccaggaacacctgggctaatgagctg<br>caggggggcgctcaggacccactgatcagtcaaccacagagggggagtgcaaaggttaggac |
| SEQ ID NO: 79 | IGHV3-63*01 | ccaagtgaggaaacatcggtgtgagtccagacacaaaatttcctgcagaaagaagaaagg<br>attctgggccgaaggggacactcagcactcacaaaacaggtggagcccccagggcaggtac |
| SEQ ID NO: 80 | IGHV3-54*01 | gtcaccaggtaagaagacatcagtgtgatcacagacacagaatttcctgaaataagggag<br>gagtctgggctaaaagggcactcaggacccacagaaaacagcggaagctctagggc |
| SEQ ID NO: 81 | IGHV3-54*04 | caccaggtaagaagacatcagtgtgaacacagacacagaatttcctgaaataagggagga<br>gtctgggctaaaagggcactcaggacccacagaaaacaggggaagctctagggcaggtgc |
| SEQ ID NO: 82 | IGHV3-79*01 | agaagacatcagtgtgaacacagacacagaggttcctgtaatgataagggaggaggctgg<br>gataaagggagcactcaagacccacagaaaacaggggaagctctagggcaggtgcagacg |
| SEQ ID NO: 83 | IGHV3-30-33*01 | caccaggtaagaagacatcagtgtgaacacagacacagagtttcctgcaatgataaggga<br>ggaggctgggctaaaagggcactcaggacccactgaaaacgggcagctctagggcaggt |
| SEQ ID NO: 84 | IGHV3-30-2*01 | ccaggtaagaagacatcagtgtgaacacagacacagtttcctgcaatgataagggaggag<br>gctgggctaaaagggcactcaggacccactgaaaacgggcagctctagggcaggtacag |
| SEQ ID NO: 85 | IGHV3-9*01 | cacagtgaggggaagtcagcgagagcccagacacaaaacctcctgcaggaagacaggaggg<br>gcctgggctgcagagggcactcaagacacactgaaaacacggttaacactgggacaagtt |
| SEQ ID NO: 86 | IGHV(III)-51-1*01 | catcgtgatgggaagtccacgtgggctcagagacagactgccatgcaggacacagggggt<br>ggcttggctgaaggggcactcagcacccacagaagacaggagcagcccagggcaggggc |
| SEQ ID NO: 87 | IGHV3-62*01 | cgcagtgagaagtcagtgtgagcccagacacaaacctcctgcagggtacctgggacaatc<br>agggaaagcctgggacactgtatactgggctgtccccaggggcaagtccaggtgatataa |
| SEQ ID NO: 88 | IGHV3-19*01 | cactgtgagaggacggaagtgtgagcccagacacaaacctcctgcaggaacgttgggga<br>aatcagctgcaggggggcgctcaagacccactcatcagagtcaaccccagagcaggtgcac |
| SEQ ID NO: 89 | IGHV3-76*01 | cacagtgaggagaagtcagtgtgagcccagtcacaaacctcctacaggaacgctgggagg<br>aaaatcagctacagggctcactcaaggcccactgatcagagtccactccagagggaggtt |
| SEQ ID NO: 90 | IGHV3-37*01 | catggtgaggggaaatcagtatgagcccagccagaaacctccctgcaggaaccctgggggt<br>ggggggaaatcagctgcaggggcactcaggacccactgatcagaatcaaccccagaagg |
| SEQ ID NO: 91 | IGHV3-23D*01 | cacagtgaggggaagtcattgtgagcccagacacaaacctccctgcaggaacgatggggg<br>tgaaatcagcggcaggggcgctcaggacccgctgatcagagtcatccgcagaggcaggt |
| SEQ ID NO: 92 | IGHV3-53*02 | cacagtgaggggaggccattgtgcgcccagacacaaacctccctgcaggaacgctgggga<br>aatcagcggcaggggcgctcaggagccactgatcagagtcagcccccggaggcaggtgca |
| SEQ ID NO: 93 | IGHV4-39*07 | cacagtgaggggaggtgagtgtgagcccagacacaaaacctccctgcagggaggctgaggg<br>cgcggtcgcaggtgcagctcagggccagcaggggggcgcgcggagctcacggaatacaagg |
| SEQ ID NO: 94 | IGHV4-55*02 | tacacagtgagggaggtgagtgtgagcccagacacaaaccctccctacagataggcagag<br>ggggcgggcacaggtgctgctcaggaccaacaggggggcgcgcgaggcacagagcccgagg |
| SEQ ID NO: 95 | IGLV11-55*01 | cacagtgagacagatgaggaagtcggacaaaaaccaaggttttaagcttgtcattttttac<br>tgaactggttaagaacttcagtggttaataaaatcacattaaatacaggattgttgttaa |
| SEQ ID NO: 96 | IGLV(IV)-53*01 | cactgtgctctaggccaatgggaaaatcccctctgcttgtgctgcctgggctcccactag<br>gccctgctgttttgtgacaacagccagcactggtggtgacgcttcagccatgtatgccct |
| SEQ ID NO: 97 | IGKV6D-41*01 | cactgtgctacaaccccaaaacaaaaattagctcagcctggcggaacagagaaactgaaca<br>ataccccgttttatgatccttgcaggtgcagttggggaaataatttaccaaataccatc |
| SEQ ID NO: 98 | IGKV7-3*01 | cacagtgctttaggtctaaacaaaaacctcccagggagcagctgctccctgaggctcaaatc<br>cctcagatgtggctttttatgcaggtccatcagcctgctgtcataggcttgtttgaacaa |

TABLE D-continued

| SEQ ID NO | Name | Sequence |
| --- | --- | --- |
| SEQ ID NO: 99 | IGKV2-23*01 | cacaatggttcagcaccaaacaaaagcctcctgcttggattgtcccagctgcccaaatta<br>gttccttcactgaggagtagacagggtatatgctctaaatctatgtaacaggaagatgtt |
| SEQ ID NO: 100 | IGKV2-18*01 | cacagtggtacaaccctgaacagaaacctcccttcttgctgtggttcagctgcccaaatg<br>tgttgtttatctggaaagcagacactgtctattatcttgggagagtaaagagaggaagat |
| SEQ ID NO: 101 | IGKV2-4*01 | cacagtggtaaaaccctgaacacaaacctcccctacttgggatggcccagccatccacaag<br>tgtttgcacgtggactgtctgcatggcagattctgagttggcttcacaggtagatgttag |
| SEQ ID NO: 102 | IGKV2/OR22-4*01 | cacagtgctacatcctcgaacagaaacctccctgctggttgacccagctcgcgcatgggc<br>tgcttgtctgagggaacagctgagcagagtctttgagtctgcagaggagaaggctgttgg |
| SEQ ID NO: 103 | IGKV4-1*01 | cacagtgcttcagcctcgaacacaaacctcctccccatacgctgggccagtaggtctttg<br>ctgcagcagctgcttcctctgcacacagcccccaacatgcatgcttcctctgtgtgttgg |
| SEQ ID NO: 104 | IGHV4-80*01 | gggaggcggaggggcgggcgcaggtgccgctcaggaccagcaggggcgcgcggggccc<br>acagagcaggaggccgggtcaggagcaggtgcaggagggcggggcttcctcatctgctc |
| SEQ ID NO: 105 | IGLV2-11*01 | ctcagcctcctcactcagggcacaggtgacacctccagggaaagggtcacaggggtctct<br>gggctgatccttggtctcctgctcctcaggctcacctgggcccagcactgactcactaga |
| SEQ ID NO: 106 | IGLV(I)-70*01 | tgcccttggcctgtcccgaggctgatcactccatacttgcctatgacaaacaaagagggt<br>gcctgtggctgatcgtacagtttaagcaagggaggaagtgagactcagccacaggcccct |
| SEQ ID NO: 107 | IGLV(IV)-66-1*01 | cactgtgctccagacttacggggaagtgagattagaacctcccctgcattctctctgcct<br>tgtgcaggcaacaatacactgtctgggaccgagtgtggctcatcagtagcagctttgttg |
| SEQ ID NO: 108 | IGLV5-52*01 | cacagtgctccagacccatgaggaagtaagacaaaaccctcccctctactctcctggtct<br>agtgaaatcaccctgctggtggctctgaccaaatctagctcaggggtgacatctgttg |
| SEQ ID NO: 109 | IGLV1-62*01 | tacagtgctccaggcttgcagggagtgagacaagaaccccttcctcctttcccaggag<br>ggtgagtgcccagcagctactgcacaggcctggcctgtggcttctgcagttgctgtttcc |
| SEQ ID NO: 110 | IGLV6-57*01 | cacagtgctccagacccatggggaagtgagacagaaactcccagagcatctctacctgg<br>gccagtctcagcctgtctccaccagagagggtagctctcccatctctcctgtctaagtgc |
| SEQ ID NO: 111 | IGLV(I)-20*01 | caccgtggtccaagttcatggggaattgagacccaaacctgccctgggctctcagcctct<br>ctcttgttctgaagatgcttcctcaccctgtgcaaggggcttcttgcagcactgccttga |
| SEQ ID NO: 112 | IGLV8/OR8-1*02 | tccacagtgatttaaacccatgaggaggtgcaactaaaacctctttacatactcagaaag<br>attcagcccttagaagcaagagagaagttgagagggtgggaatgtcaacaccatgagctg |
| SEQ ID NO: 113 | IGLV3-17*01 | cacagtgacacagacagattggaaagtgagatctaaagaccttcactgtctgtatcaccc<br>tctttctccagccatagcaggactgagcagggctggcccgggtcacctggatcgaagccc |
| SEQ ID NO: 114 | IGLV3-26*01 | cactcatgggacagcagtgctactcacctcacaatgacacagacagattggaagtgaga<br>tctaaagaccttcactgtctgtgtcaccctcttcctccagccatagcaggactgtggaga |
| SEQ ID NO: 115 | IGLV3-29*01 | cacagtgacagaggcagacaaggaagtaagacacagacccctttccccatctgtgctgctg<br>tcgtcctccagcccggcaacactgtggacaaagccatgagcatgcatgacccagttcacc |
| SEQ ID NO: 116 | IGLV4-60*02 | cacagtgatacaggcagatgaggaagtgggacaaaatcctcaacctgctgaggctattgt<br>tcagtgacaattttttaattttaaaacattttctgtatgtaaaaaatctatctggatgcat |
| SEQ ID NO: 117 | IGLV10-54*02 | cacagtgcctcaggccagtggggaagtgagataaaaactcaagagctccctcggcctcac<br>tgaacaggcctcacagagcactgtttaaactggaccacccaaaagacaagggatgcattc |
| SEQ ID NO: 118 | IGLV10-67*01 | cacagcgcctcagggggaagtgagacgaaaactcaggagctcccctagcttcactcggtat<br>gcgggggcgtcatagagcactgtttaaactaaaccaaaaatgacaagggctggtttccac |
| SEQ ID NO: 119 | IGLV(I)-42*01 | aacagtgctgcagtctgggaaagtgagatgagaacacgccaggtctcctaggagcatgac<br>cttccaatggcaccacccacaaccaggacacgctggtcttgttttaccatttgtgtggat |
| SEQ ID NO: 120 | IGLV2-28*01 | cacagtggacataagattgattctcaggctccaagtctggccagtgagcttctttgagac<br>tccctgggatcccagcagtgacactgatcactattgctgtcccacacatcccaagtgatg |
| SEQ ID NO: 121 | IGLV(IV)-65*01 | cagcactccagacccactggggaggttacaaaaacctcttctctgatctcctggcctggtg<br>tagtcactcctgctggtggctctaataaagtctatctcactgggtgacttatattttaga |
| SEQ ID NO: 122 | IGLV(I)-63*01 | cacagtgctccggggttgaagtaagtcagaccaaaacacacagtgtgcccagccatgaagc<br>tctcccatgcacccctactctgcagctaagtcaatgtgttctctcacttgtttgtccta |
| SEQ ID NO: 123 | IGLV(I)-68*01 | ggcagtacttcaggccagtggggaagtgggagaaaaagctgctgcccatccagcaatgga<br>gcttctctgtgcagccccacttcttgggcaagtcagctgattaacgttgcttttcattt |
| SEQ ID NO: 124 | IGHV(II)-28-2*01 | acacctggcctcttcgttttattcatatattccttcagcagccactatgtcttcccact<br>gatttcttcagtttctgcctttttcctttgaataaggctgttactcctgagggaagatgg |

TABLE D-continued

| SEQ ID NO | Name | Sequence |
|---|---|---|
| SEQ ID NO: 125 | IGHV(II)-44-3*01 | ggcaggccaccaagtccagctaattttgtattttagtagacactgggtttcacaatat tggtctggctggtctcaaactcctgatctcagcctcccaaagtgctgggattaaagccgt |
| SEQ ID NO: 126 | IGHV3-36*01 | attgtgtgcatcccttgtttaggtacatgcagagatgctgctttggtgtgttcaggggct cctgttttggggacaccaattttggagtttgcagtatccttgagtccagtacgttcatgg |
| SEQ ID NO: 127 | IGHV(III)-25-1*01 | atggtctcactgatatctttacttcttttatcacttttgttatgtaaatcacaatgaata gtgtattcctcatctattatacatttgttaagtctttttggtgtcttttaaaaaaactga |
| SEQ ID NO: 128 | IGHV(III)-25-1*02 | cacaatgaatagtgtattcctcatctattatacatttgttaagtctttttggtgtcttt aaaaaaactgataactttatagtatgtaatatccttaagtcctgaaagtgttttttgatg |
| SEQ ID NO: 129 | IGHV(III)-11-1*01 | cttcatctattatacacttgttaagtctttttggcatcttttaaaaaactggtaacttt atcctgtgtaatatccctgttaagtcctaaaagtcttttttgatgtctattttttcttaa |
| SEQ ID NO: 130 | IGHV(III)-20-2*01 | tacctaaatgtgtgtgggggaagcaggggggtgttattctgttgttctgtgttctctgaga tgcatggattcaccatttactctgcctccatttttggggaacacagttagaaaaaatgtca |
| SEQ ID NO: 131 | IGHV(III)-44D*01 | tggttttcagcagttttaataagattcacctaaatgtgtgtgtgtgtcgaggggtgtt atgctattgttctgtgttctctgagatgcatggattcaccgtttactctgtctccatttt |
| SEQ ID NO: 132 | TRGV1*01 | cacagtgattcagacactgaaaatctgcctgtggttgcttctggtacacaagatagacca gccaactctcatttcctgccctgaatttactgtattctgtacaaagagaaacacagctta |
| SEQ ID NO: 133 | TRGV4*01 | cacagtgattcagatccgccctacaccacactgaaaacctgccttgtggctgcttctggt acacaagatagagctgccccctctcatttcctgccaccaaatttaccgtgtgctgaacaa |
| SEQ ID NO: 134 | TRGV9*01 | cacagcagcagacagtttgagccatcccattcaataaatgtttattgagtctttgtttat aattacgaattgggaagccacagttaccaccagtgtgcttgtaaacagttttttaagataa |
| SEQ ID NO: 135 | TRGVA*01 | cgcagccttgcatgctgccccagccctacacaaaaggactcttcctcccgatccaacaag gccttgggcattttcacttactcttggtcccttgggtttccctgtggcatagaagaaaaa |
| SEQ ID NO: 136 | TRBV8-1*01 | caataatggcaatgtggcagtttccatacatatgtttgtgctagcttttttattattata tagtaaacttctttgcctcttttttatagttattgtcttgaaatatattttatctgatata |
| SEQ ID NO: 137 | TRBV22-1*01 | cacaatggaagcacaaccattgtctctctgtgcgaaatgtgtcctcaccctacagcccc cacccatcctctagcttaattttttcattttaatattttcttgagattttactatgtc |
| SEQ ID NO: 138 | TRAV1-1*01 | cacagtgactatgaggcctccttaactgtgccaaaattcaaaagacaatcagtggagtac aggtgggcttgagaagttctagaacttcctgagtgtatctttgcttaccgtctaatttta |
| SEQ ID NO: 139 | TRAV1-2*01 | cacggtgactatgaggcctcttttagctgcaccaaaattcaaaaggcaaccacagcagcga gaagctgtatttcctgagtgtatgcctgctgtgagttaagactggggactttggaaccag |
| SEQ ID NO: 140 | TRAV8-5*01 | tcaggaccctgtgataattgtgttaactgcacaaattatagagcatgtgtgttcaaacaa tatgaaatctgggcacctgaaaaaagaacaggataacagcaatgttcagggaataagag |
| SEQ ID NO: 141 | TRBV21/OR9-2*01 | cacagtgccgaatgttagccctttcttagaacacaaactcattatggacccagctcaggaa ataagtgtatgtcaggttggtacacactataataacagaaagccaacttgaaagacaata |
| SEQ ID NO: 142 | TRBV16*01 | cacaatgttaaatattagctaatcttaggacacagactcatcacggactcagctcaggaa gcaggtggtatactaggttggaaggaaataacagaaactagagctagcttaagccaaagg |
| SEQ ID NO: 143 | TRBV23-1*01 | cacagcactgaaatgtcagttcctcttagcacacaaacttgtcacagacccagctcagga agcaggtgatgtattaggctggaagggagtaacagaaaataactggagccagcttaagcc |
| SEQ ID NO: 144 | TRAV40*01 | cactgtgttaaaagcacagtgggagctatacaaaaaccctcaaaggctcagagagaagtatg tagtgaggctggaaaacccaggttgtagagccctgttctctcttttcacagacagtcctgt |
| SEQ ID NO: 145 | TRDV3*01 | cactatgatgcaggtgcccaggaagtcataacacaaactcctggggcacagctcagcaga gctgcctcttagggcaggtcatgtctgggacttggcatccttctcttagccattttgggt |
| SEQ ID NO: 146 | TRAV2*01 | cacagaggcagggaacccatgaagagctgaacagaaacagagatcacagcctttgcagga ggcaaaacagagatgagcaataacttttcctccttaattcagtattacccaagctttttt |
| SEQ ID NO: 147 | TRAV16*01 | cacagtagctggttttgcaaggaagcagaacacaaaccctttaaatacaggaaatatttc tttgcaaactctctgtatggccacagcagggcattcttttccagaaattaatattgagt |
| SEQ ID NO: 148 | TRAV8-7*01 | gactgtgcctgggactgcaggaggagctgaacacaaacttcctgagacactgaggttttc aggaactcaagggcacagcctgacctatttgtagcaaggtctctcatttgatgaaagtga |
| SEQ ID NO: 149 | TRAV8-6*01 | cacagtgcctgagactgcaggagagctgaacacaaacctcctgagatgctgagactttct gtgactcaagaactcaacctgtggagctttcaagagggtccctttttttctgtgcccgttt |
| SEQ ID NO: 150 | TRAV3*01 | cacactgataggggctgcaggggagcagaacacaaactcttgagtctggtaaagcccat tttcttgaagtctttgttccttcacatgagaacggtgtgcttccaggatatgtcacttat |

TABLE D-continued

| SEQ ID NO | Name | Sequence |
|---|---|---|
| SEQ ID NO: 151 | TRAV8-1*01 | cacagtgtctgggactgcaaagggagctgaacacaaacttcctaaggtgctagggagaat aactgcctctgaaagattttggattctgtcacagtagaaaccatgatgttagtatttta |
| SEQ ID NO: 152 | TRAV18*01 | cagagtggggagggactgcagcgagagcccagcacaaaccctggggaacgcaggtggggcc tgggtgtgagccgctttgggagatgaatgaatatggactcttgttcgctgggaccccaaa |
| SEQ ID NO: 153 | TRAV9-1*01 | cacagtgacagggactgcaggggaagctgagcacaaactctgagcagcacgagggcctg gctgctgagtgtaagccactgtgatcccctctggttagggaccaggaactactctactat |
| SEQ ID NO: 154 | TRAV31*01 | cactgtgaagaacatgttagaagagccttacaaaaagatcggaactcaacctgaggcaat tgcctattcccacattctcaggaaaaactcacaaaccttacccaggcatttgttagcagc |
| SEQ ID NO: 155 | TRAV38-1*01 | cacaatgagatgagcagcagggagaggcttacagaaacctcagacctcagcatctgtgca aaggtcacaggggtgagagggaagtggtagggtaataggtatagaaaatcattgacttctc |
| SEQ ID NO: 156 | TRAV19*01 | cacagtgagatgggtgcctgtgggagccctacaaaaacctcaacaagaggcagggctcct ggggagagactctgtcacagacaggaagaagcaaggagggtctgtgtcagcacaggtggt |
| SEQ ID NO: 157 | TRAV14/DV4*01 | cacagtgacagaactgtcggagggaggtgtacaaaagcccctgggggacctgcttgagacct ccacctgctggagaaccaaggcgggaaatcaacatcacagacaggaagtggcta |
| SEQ ID NO: 158 | TRAV33*01 | cacagaagtagaaatgacagtggaagataaacaaaaaccttagcactccataaaggaagc cacctgctcaggagcttagggaaaatacatgaagcacagacaggaagaaggcacattagt |
| SEQ ID NO: 159 | TRDV1*01 | cacagtgtttgaagtgatagtaaaagcaaaacaaaaacccctagggctcaataagagaacc cctctactccccatcctttgctacaggagccaatctgaaatgcacacctgcagatctcag |
| SEQ ID NO: 160 | TRDV2*03 | cacccctgctgcagctctacttctgagcagctcaaaaaccactgaccaggcgcggtggctc acacctgtaatcccagcactttgggaggccgaggtgggtggatcacgaggtcaggagatc |
| SEQ ID NO: 161 | TRBV30*01 | cacactgagctgggtggggcagacatctgtgcaaaaaccccaccctctcctgagccctaa ccatactcccaggggccttcacttagggactgggtggaggatatttgtaagtaggtttc |
| SEQ ID NO: 162 | TRBV20-1*01 | cacagcgccaggagggggatcagacaccgcggcaagaacccctgcagctgccctccgcccc agcgggccccctgagtgctgagaggggaagcgtggagaatggaaaaccacagctttcctg |
| SEQ ID NO: 163 | TRBV29/OR9-2*01 | cacagtgcagggcacagatcaaagatctaagcaagaacctcagctcccttctacccagct cccctcacatgaacctgagggccctgtcaaggtgggacagaagaggaaaccacagctctt |
| SEQ ID NO: 164 | TRBVB*01 | gccacacacactcaagatgcccagacaccctgcactccgatcttactcgttcctttact gttttcatcctaattgccctcttacacattttgaccacacattttttggtcttggtggttgt |
| SEQ ID NO: 165 | TRGV10*02 | accatactagaactgttgaaacaacatgcacaaaatcccctcccagggtctgtgcccacc acatccttcccaacaggggcaaccacagccagtccccagctgggctcccagactcaggct |
| SEQ ID NO: 166 | TRGVB*01 | cacagcatcagtgccacactgtcccacacaacaacctctgtttgggtctctgcccaaccac atccttcccatgggagcaaactctatggactcctagctgggctcccacccctcagccttgc |
| SEQ ID NO: 167 | TRGV11*02 | cacagtgttagagttgtcaagataacctacacagaaactatctccgagtctgtgcctgtc cacatccttctccatgtgggcaaccacagcggtttgctcagctgggtgcccagccggagc |
| SEQ ID NO: 168 | TRAV4*01 | ctcgtgggtgacacacagtgagacagatgggcctgcacctgtgccgttttcctctgtggg gtgggagtcacagcctagaaagaagtccaaaagtgctttctaaaatttttattttcaaaa |
| SEQ ID NO: 169 | TRAV26-1*01 | cacactgggacagatggggctgcacctgtgcaatatctccctggtggcaagtgaggagga gggtagcattcacctagagcaaaatgtcgataggagtcaaaaagtaacaagaaaagagga |
| SEQ ID NO: 170 | TRAV26-2*01 | cacagtgggacagatggggctgcagctgtgcaatatctccctggtgatgaaagggaaggc atctaacgaggccactgcacaagaaggagcagaagtttaatagaggaagaagaaaattta |
| SEQ ID NO: 171 | TRBV10-1*01 | cacagtgctgcacagctgcctcctctctgcacataaagggcagttagaatgactgaggtt gcctgtgctcccaagtcccagccttcacaggagtcggagagccctggctagcctgggggc |
| SEQ ID NO: 172 | TRBV10-2*01 | cacagtgctgcacagctgcctcctctctgcacggaaacggcagttagaaaaactgaggtt gcctgtgcaccccaagtctgggcccaccctgggacgtctcagcccccataggagtcacag |
| SEQ ID NO: 173 | TRBV10-3*01 | cacagtgctgcatggctgcctcctctctgcacgtaaacagcagttagaaagactgaggtt gctctgtgtctatccccacccttggaagtccaggcctccatagaagtcagagggccctgg |
| SEQ ID NO: 174 | TRBV28*01 | cacagcgcagcacagctgcatcctctctgcacaaaagagcggacgtaagagagaagggg ccctaactcagggctggtgctggctccgatggcacattcgtgctaaatagaaaaaaagcg |
| SEQ ID NO: 175 | TRBV6-2*01 | cacagtgctgcacgctgtctcctctctgcacagaaaggcaagggaaggtgctgccctcc tccgcagcacagattcagcgatgcccttggtcctagcaccgaaaactttggagccccaat |
| SEQ ID NO: 176 | TRBV6-4*01 | cacagtgctgcacagccatcctctctgtacataaatgcaggggaggctctgccctcct ccccgaccccagactcaaccatgtccttggcagagttctcagcactgggaatcttggaag |

TABLE D-continued

| SEQ ID NO | Name | Sequence |
| --- | --- | --- |
| SEQ ID NO: 177 | TRBV6-9*01 | cacagcgctgcaagcctgtctcctctctgcacataaaggcacagaggctctgccctcctc<br>ccacccaagactcaaggatgccctgggcagagttctctgcaccaggaaccttggaaccca |
| SEQ ID NO: 178 | TRBV6-7*01 | cacagcgctgcaaggctgtctcctctctgcacataaaggcaagggaaggtgctgccctcc<br>tccccacccaagactcaaggatgccctgtgcagagatctctgcaccaggaaccttggaa |
| SEQ ID NO: 179 | TRBV6-5*01 | cacagcgctacaaggccgtctcctctctgcacataaaggcagggaggttctgccctcctc<br>ccccacccaagactcagggatgccctgggcagagatctctgcgccaggaaccttggaacc |
| SEQ ID NO: 180 | TRBV19*02 | gccagtagtatagacacagtgaagcacggatgtcgcctctctgtgcataaatgtgcccag<br>tcctgcttccccgaccaggtggcagggctcctctgcactctatgatggcagg |
| SEQ ID NO: 181 | TRBV19*01 | cacagtgaagcacggatgtcgcctctctgtgcataaatgtgcccagtcctgcttcccga<br>ccaggtgacagggctcctctgcactctatgatggcaggaaacgccactcagccactaagc |
| SEQ ID NO: 182 | TRBVA*01 | cacagcactgcacaggcatgtgctcacctcacaaaatggcagtctcaaagggaggagtgc<br>ccaccacaagaggctccacccctattctgagaaagaacttcttcagaggaggagagaat |
| SEQ ID NO: 183 | TRBV26/OR9-2*01 | cacagcactgcatagctgccacatcctctccacataaaaaaaggtgcataccaaagagga<br>aaagcctgccctcaaaattcctcaccgcaaataagagaagttacctcacaggtattgaca |
| SEQ ID NO: 184 | TRBV25/OR9-2*01 | cacagtgctacatagataccgacactctgcacagaaagggtcgcctctaaggtgaggaca<br>tcttgccttcagaaacccttatcttaaactacagaaacccctgcaaatcttcccagactcc |
| SEQ ID NO: 185 | TRBV27*01 | cacagtgttgcacagccagctgctctctgcacaaaaacagagggtagctgcaagaacaag<br>gagactcctccttcaggagaccctcaccgaccaacaggataaacttcctccatcatccc |
| SEQ ID NO: 186 | TRBV8-2*01 | cgcagccctgcacagccagctgccctctgcacaaaaagggcagtcacaggctggaggtgg<br>gcactcctttatggaagcccgtgtctcaaccagaagaaaaagctgccctttctgaagctct |
| SEQ ID NO: 187 | TRBV24-1*01 | cacagtgcttcttggccacctgctctctacacagaaagacagacacatgggtgagttgtt<br>tgctctgaagggtacctggatgtgggttgtgggatgtggggtgtttagagctttcagtgg |
| SEQ ID NO: 188 | TRBV2*01 | cacagccttgcaaagacaactccagcctgtgcaaaatccctcacagagctgcctccctcc<br>cagccgccagctcccacttcctgcctaagaaaaggaagtctctggtttgggtttgttcttg |
| SEQ ID NO: 189 | TRBV11-1*01 | cacagcgttcagagactttctctcctgtgcacaaaactccagggctctctccgctctac<br>tcagctcacagcagcctttccttattcctcatcctctcagggaagaagtgagttttcaga |
| SEQ ID NO: 190 | TRBV11-2*01 | cacagtgtagcagagacacttccctcctgtgcagaaaaccagaaaaccgcaggactctct<br>cctctctactcagctcacagcagcctttccttattcctcatcctcccaaggaagaagtga |
| SEQ ID NO: 191 | TRBV11-3*01 | cacagtgtagcagagacacttccctcctgtgcagaaaaccgcaggactctctcctctcta<br>ctcagctcacagcagcctttccttattcctcatcctcccaggaaagaagtgagttttcag |
| SEQ ID NO: 192 | TRBV15*01 | cacagagctgcagtgcttcctgctctctgttcataaacctcattgtttcccagatccagg<br>tgcttctctaggacttctccctcaccacctcttacaacaataggaagtgggttggtggc |
| SEQ ID NO: 193 | TRBV12-5*01 | cacagcgctgcagaatcacctgctccctgtgcagaaacctggtgcttcctcttctcctc<br>cagtacccagcagctctcagcagcctttcttgctcctccctagcacaggaagtacatag |
| SEQ ID NO: 194 | TRBV12-1*02 | cacagcactgcagaatctccccatctctgtgcagaaacctggtgcttcctcttctcccc<br>acagctctcagcagtcgtcagcaaagtctttcctgctctctgtcaccatggctcacgcc |
| SEQ ID NO: 195 | TRBV7-3*01 | cacagcatgacacaatcgcctccttcctgctcataaacctcctcctctctctccttgctt<br>ccttatgatactattttgcaccaggggatcctcatctcacaccactccactgcctcttcc |
| SEQ ID NO: 196 | TRBV7-9*01 | cacagcatggcacagtcgcctccttcctgctcacaaaccctcaggcacttacttctcctt<br>ccagctctcagaagccctgaacaaaggagctgccctgctctttcctcagcaaggagaatg |
| SEQ ID NO: 197 | TRBV7-2*01 | cacagcatggcacagtcgcctccttcctgctcataaacctcatccttctctctccttgca<br>gctcctagacacccttaacagaggcttctctttgcttctccctccccatgggaaacaagt |
| SEQ ID NO: 198 | TRBV7-5*01 | cacagtgtggcatagtcgcctccttcctgttcacaaacctcatccttctctctccttgca<br>cctcctagagacccttaacagaggcctctctttgctcctcacttttgatgggaagaagt |
| SEQ ID NO: 199 | TRBV17*01 | cacagcatggctgagtcagttccctccagggtgcaaacctctggctgctcttctcccag<br>ttgaactccaagaaaacatttgaaaaagcctcttccttatcttcctacccagaagaaag |
| SEQ ID NO: 200 | TRBV5-7*01 | cacagcccagcagagtcactgacattctgtatataaacttccgccttagctttgacttga<br>gaactgcaggcccacccaggtttcactccttcaagggaagcttttagttgtttggaagg |
| SEQ ID NO: 201 | TRBV5-6*01 | cacagcccatcagagtcactgacgttctgtatataaacttcctgccttagctttgccttg<br>agagctgcaggcccacccagatttcactccttcaagggaagcttttagttgtttggaag |
| SEQ ID NO: 202 | TRBV5-1*01 | cacagccctacaaagccaaccacattctgtgcacaaacctccctggcccaatgtggagca<br>acctcagccctgacatatctgtgagaacctggggactgcagggagaaagaaaggcaattt |

TABLE D-continued

| SEQ ID NO | Name | Sequence |
|---|---|---|
| SEQ ID NO: 203 | TRBV5-3*01 | cacagccctgcagagtcactggaactctgtgcactaatctctctgcttccgtgtacagca gtctcagaccagacagctgtgagaacctggggccttcaggggaaagataaacaatttca |
| SEQ ID NO: 204 | TRBV5-2*01 | atgcaggcctgcagagccaagaacattctgtgtacaaacatccctgccccagtgtggaga acttcagccctaacatatctgtgagaacttgaggactgtagtgggaaagaaaagcagttt |
| SEQ ID NO: 205 | TRBV4-1*01 | cacagccttgcagagtcaccgctttcctgtgcagaaaccttcggggcctgccaggaagcc gtgggggccacggagggctcgggtgaacatttcctccaagagcccgaagaagcttcaga |
| SEQ ID NO: 206 | TRBV1*01 | cacagccctgcagagtcaccgcctccctgtgcacaaacctcctggatctaatcagaaaac cgtgggggcaacgcatccagctgagcctcagcactcggttcagcattctgtaagacctca |
| SEQ ID NO: 207 | TRBV3-2*02 | acacagccttacagagccactgcatccctgtgcacaaacctcccggctcagccaggaagc tgtgggccgtgtgtgcacctgcacccaaggctccagtctccattccctgatggcctctga |
| SEQ ID NO: 208 | TRBV18*01 | cacattgatgcagagccacatcctctcagtccacaaacatcctccagacctgccttggaa acagcggtgggccaggaagggaaacgcgttacctgtacagtgaacaggtcagctctacgg |
| SEQ ID NO: 209 | TRBV9*01 | cacagccctgcatgagcatcagccttctgtgcaataacattcctgccccactcaggaagt gacggtgaggggagggctgccagccagaggggctcaggccctggagagtggacaggcctt |
| SEQ ID NO: 210 | TRBV13*01 | cacagaccctggagaattactggctttctgtacccaaaccctcctatctcacttgaggat gtaataggagaaggaggtggggctgccacacaactttagccaagccccagagatgctt |
| SEQ ID NO: 211 | TRAV34*01 | cacagcgattttcaggcctctatcagctgtctccaaacctgcagctgggcacatatgct cttctgacatggggtcctgagatgtggctgggacctttgccaagacatgaagtctcaga |
| SEQ ID NO: 212 | TRAV30*01 | cacagtgatacccaggcctccaagacctgtactcaaacctaaagctgagccgcagatgct cccctagcacagatgccaccacaggagtatggggaacttaccagaaggttcatccatga |
| SEQ ID NO: 213 | TRAV7*01 | cacagtactccctaggcacctgcaacctgtatccaaacatgcagctgggtagaagtacca taacagaagcatcagcaataggggccctgagcctgagtagacgtgaagaactaaggcatg |
| SEQ ID NO: 214 | TRAV22*01 | cacagtgctcccaggcacctgcggcctgtacacaaaccctcatccgggctcggttcctc taccagtaacaaccacatcacgaggccaccgcagcagcattttgcacagcttaatattcc |
| SEQ ID NO: 215 | TRAV6*01 | cacagtagtgccctggcagctgcttcctgcacccaaactctgctaactctcacaatcaga gctcatggctgtgctgtctcccaaaggctaatcacagctcctgacagaatgggggggtgt |
| SEQ ID NO: 216 | TRAV27*01 | cacagtgctcttgaggcacctgctgcctgcacccaaaccctgctgccagcccagtcacg aggctgccacatgcctccagctccgcctcgcacagcttatggcatgaatagagagaacaa |
| SEQ ID NO: 217 | TRAV20*01 | cacagcgttcccaggcacctgcaacttgtatcaaaaccctgcagctgaggatctgaaat gatggcagaggtatctctgctgttcttcctcttgaaggagtatttatttaatgcccagga |
| SEQ ID NO: 218 | TRAV36/DV7*01 | cacagtgctcccagtcacctgcagcctgtactcaaattctacagctgaggctctgcaac tgtaagatggggaacttgctacattgagcaagccctcaaaaataaactatacggaaaagc |
| SEQ ID NO: 219 | TRAV21*01 | cacagtgcacaacaggcacctgcaaccaataccccaaactctatagctggggctctaactg catgttttatcttgagactgagcaatgttttttgcattaagaggacttctaaattgacact |
| SEQ ID NO: 220 | TRAV41*01 | cacagtgctcccaggcacctggagcccgtacctaaactctaaagttgaggcatcatttc ttactcctgtctttcagacttgtctgtctctatccttggtcagatgatgtaaaatgttta |
| SEQ ID NO: 221 | TRAV37*01 | cacagtgcccacagtcacctgcacccgtgtacctaaagcttgctgaggggcctgggcacac ctccttttataagggccctggggcactgactataactctgctgcatacaaaggaaatat |
| SEQ ID NO: 222 | TRAV11*01 | agtagtgtctccccagcacctgcagcctgtaccataacctgcagccgggacccttgacac aggctagccttgcaggtgggagtgaagatttttttttttttttgtatagagggaacttt |
| SEQ ID NO: 223 | TRAV15*01 | cacagggtccccaagcacctgcagcctgtaccacaacctgcatccgggacccttgacaca gccttgccttgcaggtgggagtgaaggtgttgtctttatatgtagagagaacttcttat |
| SEQ ID NO: 224 | TRAV17*01 | cacagtgttcccaggaacctgcagcctctacgcaaaccctgccaaagcagcttcttaga agccctaatagtgggtagaattagtggttatgtctttcagtcaagaagagtctacaaaca |
| SEQ ID NO: 225 | TRAV10*01 | cactgtgctccacaggcacttgaagccagtatgcaaacctgcacctggaggttatcaagg aggcataggagttagagtagaccgttatttttatgcagaatatgatttcactagtgaat |
| SEQ ID NO: 226 | TRBV7-1*01 | cacagcactactgctccagtgtcagcttggttcccctaggaaatggggtttctagaacctg aatgctgacaaataagagttgtatatgtgtataccatgcaacctgcgtttaaaaatgtat |
| SEQ ID NO: 227 | TRAV24*01 | cacagtgctgttcaggcacctgcagcccatacgcaaacctgtgtctggtgttgcactgtt accagcattgacaaagaaccatgagtaggatggaaaagacaagttcgttgaattacagtt |
| SEQ ID NO: 228 | TRAV39*01 | cacagtgctcccctgacgccaccagtctgtacccaaacctgcagctggtgggcccactcc tcctgcaggaactatgactgtgaggcttcgttcactgtctgtacatttctttctgcaagg |

TABLE D-continued

| SEQ ID NO | Name | Sequence |
| --- | --- | --- |
| SEQ ID NO: 229 | TRAV35*01 | cacagtgctccccaaacacctgcagcctgtactcaaacttgcagctggaactctagtctc<br>tatgctgccttcagctcttagtcctcttggcatgaaatgtgattatgcatgccacctttg |
| SEQ ID NO: 230 | TRAV12-2*01 | cacagtgctccccagacacctgcagtctgtacccaaacctgccatgccccaggaatgcct<br>gatgtagagcttagactgcagggtagtgaaactccccttgctctctagtttcaagtggaa |
| SEQ ID NO: 231 | TRAV29/DV5*01 | cacagtgctctccaggcacctgcagcccgtactcaaacctgctttggggactcagactgg<br>gagacacatagactcgcttccatttacacatgccaatatgagagattatgctttgaagta |
| SEQ ID NO: 232 | TRAV23/DV6*01 | cacagtgctccccaggcacctgaagcctgtacccaaacctgcagttgaggttccagccaa<br>accccacagtgggagcttacgtaggcagagatgtagcctagttttcatctgcatatgcaa |
| SEQ ID NO: 233 | TRAV28*01 | cactgtgctcttcagacacctgcagcctatacatgaaaccatagctgaaggcctaaccca<br>tccccgagagtggcagtaggtcccgatgtgattagcattgcattcccactgcctacatct |
| SEQ ID NO: 234 | TRAV25*01 | cacagtgctccccaagcacctgctgcctgtctccaaatcttgccctgggtcttcaggagc<br>agatcatcctactctccccaaagagcgggcgccagagaaagccaaagtcacaatgtctgt |
| SEQ ID NO: 235 | TRAV32*01 | cacagaactcttcaggcacctgcaacctgtactcaaacctgcaactgggagtccagtcac<br>attctttgtctttgaacgggttttgggttagaatggtttaccataatgtgcttgtttcta |
| SEQ ID NO: 236 | TRAV5*01 | cacattgcttctcaggcacctgtaccctgtacccaaacctgcacctgggactaaagccac<br>actctatttcctttacctttaagtcagggattttgctgtaaggtacttttaatgtacgga |
| SEQ ID NO: 237 | TRAV13-2*01 | cacattgctttccaggcatctgtaaccatcacccaaacctgagatgggaggtgaagcagc<br>atcccttccctttgcaataaattttagttatagcacttgtcattttgtttgttcataagt |
| SEQ ID NO: 238 | TRAV13-1*01 | gcagcaagtacacattgcttcccaggcacctgctaccgtacacaaacctgagactggag<br>ctgaagctgcaccccctttcctttgtcatagatcgtcaattatagcatttgtcatattgt |

The invention claimed is:

1. A library of nucleic acid probes for hybrid capture of double stranded DNA fragments, the library consisting of probes designed to hybridize to substantially all V gene segments and all J gene segments within the B cell receptor genomic loci, immunoglobulin genomic loci, or the combination thereof, wherein each probe hybridizes either to a 3' end of the V gene segment or a 5' end of the J gene segment, and wherein each probe comprises a label for distinguishing between double stranded DNA fragments bound to the probes and unbound double stranded fragments.

2. The library of claim 1, wherein the library consists of probes designed to hybridize to all V gene segments and all J gene segments within the B cell receptor genomic loci, immunoglobulin genomic loci, or the combination thereof, wherein each probe hybridizes either to a 3' end of the V gene segment or a 5' end of the J gene segment.

3. The library of claim 1, wherein the probes of the library consist of substantially all of the probes encoded by the nucleic acid sequences of SEQ ID NOs:239-826 and SEQ ID NOs:872-872.

4. The library of claim 1, wherein the probes of the library consist of all of the probes encoded by the nucleic acid sequences of SEQ ID NOs:239-826 and SEQ ID NOs:872-872.

5. The library of claim 1, wherein the label is biotin.

6. A method of capturing DNA fragments existing in a patient sample using a collection of nucleic acid hybrid capture probes, comprising:
   obtaining a sample from a patient;
   obtaining a library of nucleic acid probes of claim 1, wherein each capture probe is designed to hybridize to a known V gene segment and/or a J gene segment within a B cell receptor and/or immunoglobulin genomic loci; and
   using the library of nucleic acid probes to capture DNA fragments in the patient sample.

7. The method of claim 6, further comprising sequencing the captured DNA fragments, wherein the sequencing can be used to determine clonotypes within the patient sample.

8. The method of claim 7, wherein said sequencing is optimized for short read sequencing.

9. The method of claim 7, further comprising amplifying a population of sequences using nucleic acid amplification probes/oligonucleotides that recognize an adapter prior to said sequencing.

10. The method of claim 6, wherein the patient sample comprises tissue, urine, cerebral spinal fluid, saliva, feces, ascities, pleural effusion, blood or blood plasma.

11. The method of claim 6, wherein the patient sample comprises cell-free nucleic acids in blood plasma.

12. The method of claim 6, wherein the hybrid capture probes are immobilized on an array.

13. The method of claim 6, further comprising immunologically classifying a population of B-Cell receptor and/or immunoglobulin sequences by:
   (a) identifying all sequences containing a V gene segment from the sequences of the DNA fragments by aligning the sequences of the DNA fragments to a library of known V gene segment sequences;
   (b) trimming the identified sequences in (a) to remove any sequences corresponding to V gene segments to produce a collection of V-trimmed nucleotide sequences;
   (c) identifying all sequences containing a J gene segment in the population of V-trimmed nucleotide sequences by aligning the V-trimmed nucleotide sequences to a library of known J gene segment sequences;
   (d) trimming the V-trimmed nucleotide sequences identified in (c) to remove any sequences corresponding to J gene segments to produce VJ-trimmed nucleotide sequences;
   (e) identifying any D gene segment comprised in the VJ-trimmed nucleotide sequences identified in (d) by aligning the VJ-trimmed nucleotide sequences to a library of known D gene segment sequences;
   (f) for each VJ-trimmed nucleotides sequence identified in (d), assembling a nucleotide sequence comprising the V gene segment, any D gene segment, and the J gene segment identified in steps (a), (e) and (c) respectively;
   (g) selecting from the nucleotide sequence assembled in step (f) a junction nucleotide sequence comprising at least the junction between the V gene segment and the J gene segment, including any D gene segment, the junction nucleotide sequence comprising between 18 bp and 140 bp, preferably 40-100 bp, further preferably about 80 bp;
   and optionally (h) and (i):
   (h) translating each reading frame of the junction nucleotide sequence and its complementary strand to produce 6 translated sequences; and
   (i) comparing the 6 translated sequences to a library of known CDR3 regions of T-Cell receptor and/or immunoglobulin sequences to identify the CDR3 region in the DNA fragments.

14. The method of claim 13, further comprising, prior to step (a), aligning left and right reads of overlapping initial DNA fragments to produce the DNA fragments on which step (a) is performed.

15. The method of claim 13, wherein steps (a), (c), (e) are performed with BLASTn and step (i) is performed using expression pattern matching to known sequences and IMGT annotated data.

16. The method of claim 6, further comprising identifying CDR3 regions in B-Cell receptor and/or immunoglobulin sequences by:
   (a) identifying a V gene segment comprised in the immunoglobulin sequence by aligning the immunoglobulin sequence to a library of known V gene segment sequences;
   (b) identifying a J gene segment comprised in the immunoglobulin sequence by aligning the immunoglobulin sequence to a library of known J gene segment sequences;
   (c) if V and J gene segments are identified, then comparing the immunoglobulin sequence to a library of known CDR3 regions of T-Cell receptor and/or immunoglobulin sequences to identify any CDR3 region in the immunoglobulin sequence.

17. The method of claim 16, wherein steps (a) and (b) are performed using the Burrows-Wheeler Alignment or other sequence alignment algorithm.

18. The method of claim 16, wherein if a CDR3 region is identified in step (c), then the method further comprises determining whether the identified V and J gene segments could be rearranged in the same locus using a heuristic approach.

19. The method of claim 16, further defined as a method for characterizing B-cell clonality as a feature of disease in the patient.

20. The method of claim 19, wherein the patient has cancer.

21. The method of claim 19, wherein the patient has a B-cell related disease, plasma cell disorder, or a B-cell lymphoma.

* * * * *

SEQUENCE LISTING

<160> NUMBER OF SEQ ID NOS: 1958

<210> SEQ ID NO 1
<211> LENGTH: 120
<212> TYPE: DNA
<213> ORGANISM: Homo sapiens

<400> SEQUENCE: 1
cccagtgcga caagtcataa catcaaccgc taggatagca gatgagtgag gccgggttgc     60
cctagatgct cctcctggtg cctcaatctg ctgagttgtt ttccagatgc agccaagttt    120

<210> SEQ ID NO 2
<211> LENGTH: 120
<212> TYPE: DNA
<213> ORGANISM: Homo sapiens

<400> SEQUENCE: 2
cctagagtgt tacaggtcat aaaataaacc cccagggaag cagaagtatg actcatggct     60
gccccaggtg cttccactgg tgcctccatc tgctgagagt gtttctcagg tgcagccaag    120

<210> SEQ ID NO 3
<211> LENGTH: 120
<212> TYPE: DNA
<213> ORGANISM: Homo sapiens

<400> SEQUENCE: 3
cactgtgata caagcccgaa cataaaccat ggagggaagt agatgtgtga ggctgggctg     60
ccccagctgc tcctcctggt gccgccctct gctgacagca gttctcagat gcagccaagg    120

<210> SEQ ID NO 4
<211> LENGTH: 120
<212> TYPE: DNA

<213> ORGANISM: Homo sapiens

<400> SEQUENCE: 4

| cacagtgtta caaggcataa cataaacccc caaggaagc agatgtatgg ggctggcctg | 60 |
| cccagatac tcctcctact gcctccagct gctcagagcg tttctcatat tccagtcaag | 120 |

<210> SEQ ID NO 5
<211> LENGTH: 120
<212> TYPE: DNA
<213> ORGANISM: Homo sapiens

<400> SEQUENCE: 5

| cacagtgtta caagtcataa cataaacctc caaggaagca gatgtgtgag gacgagccac | 60 |
| cccagatgct cctcctggtg cctccatctg ctgagagcat ttctcaaact cagtcaggtt | 120 |

<210> SEQ ID NO 6
<211> LENGTH: 120
<212> TYPE: DNA
<213> ORGANISM: Homo sapiens

<400> SEQUENCE: 6

| cacagtgtta caaaccataa caaaccccc ccaggaaagc agacatgtga cgctgggctg | 60 |
| ccccacctgc tcttctttgt gcagccatct ggtgacaaca cttctcagac tcagcctgag | 120 |

<210> SEQ ID NO 7
<211> LENGTH: 120
<212> TYPE: DNA
<213> ORGANISM: Homo sapiens

<400> SEQUENCE: 7

| cacagtgtta caaacccaat aagctcccca aggaagcaga tatgtgaggg tgggctgccc | 60 |
| cagctgcttc tcctgtttcc tccatctgct gagagtgttt ctcagactca gccacactct | 120 |

<210> SEQ ID NO 8
<211> LENGTH: 120
<212> TYPE: DNA
<213> ORGANISM: Homo sapiens

<400> SEQUENCE: 8

| caccatgtgg aaacccacat cctgagagtg tcagaaatcc tgatgtggga ggcagctgtg | 60 |
| ctgagctgag gcagtgatgc agcagtttcc ttaacttcca tcttatctca ttttgcatcg | 120 |

<210> SEQ ID NO 9
<211> LENGTH: 120
<212> TYPE: DNA
<213> ORGANISM: Homo sapiens

<400> SEQUENCE: 9

| cacagtgtga aaacccacat cctgagagag tcagaaatcc tgagggaggt ggcagcagtg | 60 |
| ctaggcttga gagatgacag ggattttatt tgctttaaag ctttttttta gaaagcgagg | 120 |

<210> SEQ ID NO 10
<211> LENGTH: 120
<212> TYPE: DNA
<213> ORGANISM: Homo sapiens

<400> SEQUENCE: 10

| gacacagtgt gaaacccac atcctgagag tgtcagaaac cctgagggag aaggcagctg | 60 |
| tgccgggctg aggagatgac agggtttatt aggtttaagg ctgtttacaa aatgggttat | 120 |

<210> SEQ ID NO 11
<211> LENGTH: 120
<212> TYPE: DNA
<213> ORGANISM: Homo sapiens

<400> SEQUENCE: 11
cacagtgtga aaactcatat cctgagagtg tcagtaaccc tgagggagga agcagctgtc    60
ccagttttca ggatatgaca ggattttatgg ggtttaatgt tgtttagaaa ataggttata   120

<210> SEQ ID NO 12
<211> LENGTH: 120
<212> TYPE: DNA
<213> ORGANISM: Homo sapiens

<400> SEQUENCE: 12
cacaatgtga aacccacat cttgagagtt tcagaaactg caggaggag gcagctgtgt      60 tcctgcagag gagatgacag ggaagatgag gtttaaagtt gtttagaaaa tgggtcaagt   120

<210> SEQ ID NO 13
<211> LENGTH: 120
<212> TYPE: DNA
<213> ORGANISM: Homo sapiens

<400> SEQUENCE: 13
gacacagagt gaaaacccac atcctgagag tgtcagaaac cccaaggagg agcagctgta    60
ctggagctga ggaaatggac aaagattatt cagattgaag actttctacg aaaatgactt   120

<210> SEQ ID NO 14
<211> LENGTH: 120
<212> TYPE: DNA
<213> ORGANISM: Homo sapiens

<400> SEQUENCE: 14
cacagtgtga aacccacat cctgagagtg tcagaaaccc caggggggaa gcagctgtgc     60
tggcatggag gaaatgacaa agattattag attgaagact ttctcagaaa atgatattaa   120

<210> SEQ ID NO 15
<211> LENGTH: 111
<212> TYPE: DNA
<213> ORGANISM: Homo sapiens

<400> SEQUENCE: 15
gacacagtgc gaaaacccac atcctgagag tgtcagaaac cccaggaagg aggcacctgt    60
gctgacacag agggagatga caaagattat tagattaacg attttcttag a            111

<210> SEQ ID NO 16
<211> LENGTH: 120
<212> TYPE: DNA
<213> ORGANISM: Homo sapiens

<400> SEQUENCE: 16
cacagtgcga aacccacat cctgagagtg tcagaaaccc caggaaggag gcacctgtgc     60
tgacacagag gagatgacaa agattattag attaaagatt tccttagaaa atgacactaa   120

<210> SEQ ID NO 17
<211> LENGTH: 120
<212> TYPE: DNA
<213> ORGANISM: Homo sapiens

```
<400> SEQUENCE: 17
cacagtgtga aacccacat cctgagagtg tcagaaagcc tgaggaagga ggcagctgtg    60
ctggggctga ggagatgaca gggattactt gattgaagac tttcttagaa aacgaggtta   120

<210> SEQ ID NO 18
<211> LENGTH: 120
<212> TYPE: DNA
<213> ORGANISM: Homo sapiens

<400> SEQUENCE: 18
cacagtgaga gaaaccagcc ccgagcccgt ctaaaaccct ccacaccgca ggtgcagaat    60
gagctgctag agactcactc cccaggggcc tctctattca tctggggagg aaacactggc   120

<210> SEQ ID NO 19
<211> LENGTH: 120
<212> TYPE: DNA
<213> ORGANISM: Homo sapiens

<400> SEQUENCE: 19
gaccatctaa aaccttccgc ggtgcaggtg cagagtgagc tgccagacac accctcccca    60
ggggcctctc tattcatccg gggaggaaac actggctgtt tgtgtcctca ggagcaaaaa   120

<210> SEQ ID NO 20
<211> LENGTH: 120
<212> TYPE: DNA
<213> ORGANISM: Homo sapiens

<400> SEQUENCE: 20
gcgaataatg gagaacttga gatatggagt gtgagtggat atgagtgaaa aaacagtgat    60
tctgtgtggc aggttctgac tcagatgtct ctgtgcttgt aggtgtctag tgtggggtgc   120

<210> SEQ ID NO 21
<211> LENGTH: 120
<212> TYPE: DNA
<213> ORGANISM: Homo sapiens

<400> SEQUENCE: 21
cacaggagat atccgtgtgg caacctaaca caggggacac ctgtatttgt gtctgagccc    60
agacacaaac ctccctgcag ggagacagga ggggaccgtg tgacagacac tgctcagaac   120

<210> SEQ ID NO 22
<211> LENGTH: 120
<212> TYPE: DNA
<213> ORGANISM: Homo sapiens

<400> SEQUENCE: 22
ccaagtgaga gctgaggaca tggctgtgca tggctgtaca taaggtccca agtgagcaaa    60
catcggtgtg agtccagaca caacacttcc tgcaaaaaca agaaaggagt ctgggccgaa   120

<210> SEQ ID NO 23
<211> LENGTH: 120
<212> TYPE: DNA
<213> ORGANISM: Homo sapiens

<400> SEQUENCE: 23
acaagagtca gaaaagtgtg caggaggccg ggtgaggctg tagacactgt cagcccacta    60
tgccaatccc accacgagtg ctggagaagg tgggagtctg atgaagctta ctaacaaacc   120
```

```
<210> SEQ ID NO 24
<211> LENGTH: 120
<212> TYPE: DNA
<213> ORGANISM: Homo sapiens

<400> SEQUENCE: 24
gccgagattg cgccactgca ctcagcctgg gcgacagagc gagacttcgt ctcaaaaaaa      60
caaaaaaaaa aatcaatcat tggaatactg ttgttcatta caattaatga acgtttgata     120

<210> SEQ ID NO 25
<211> LENGTH: 120
<212> TYPE: DNA
<213> ORGANISM: Homo sapiens

<400> SEQUENCE: 25
cacaggtggg gaagtgggac aaaatctcag cctgctcaga gtcttgttct ctgatgaaat      60
ttagatctta aaataactta tatcacttgt gtgggatgag tgagatatcc cgagctcaca     120

<210> SEQ ID NO 26
<211> LENGTH: 103
<212> TYPE: DNA
<213> ORGANISM: Homo sapiens

<400> SEQUENCE: 26
cacagcgagg ggaagccatt gtgcgctcag aacactctac aaattttcct ccctagtgtt      60
ttaccaaaac tggtatatat ttcagatact gaaatattta caa                       103

<210> SEQ ID NO 27
<211> LENGTH: 120
<212> TYPE: DNA
<213> ORGANISM: Homo sapiens

<400> SEQUENCE: 27
agtaagacca aaaccctcct gagattcctg gcttgtgtcc tgacactggg gctgttggga      60
ttcctgtctt tccttcaaga ttgttcaaat aagcaccgac aatcacttcc atgtgagata     120

<210> SEQ ID NO 28
<211> LENGTH: 120
<212> TYPE: DNA
<213> ORGANISM: Homo sapiens

<400> SEQUENCE: 28
aaggcaaagt gaccccagtg aatgaggaag caggacaaaa actgttttct ctgctccact      60
atgaaggctg ccacgtggcc ctgagaaaca gtgcctgttt tccttactac tcaagaaga     120

<210> SEQ ID NO 29
<211> LENGTH: 120
<212> TYPE: DNA
<213> ORGANISM: Homo sapiens

<400> SEQUENCE: 29
ccgtttgggt aaagcacaga taaatgggga aatgaggcaa aaactgtttt tctactctgc      60
taccaaggtt gaaaaatggc tctcagaacc agtgtctgct gacctgcata ctcaaatatg     120

<210> SEQ ID NO 30
<211> LENGTH: 120
<212> TYPE: DNA
<213> ORGANISM: Homo sapiens

<400> SEQUENCE: 30
```

```
taaaataaaa taaaatgtaa aaaatgatca ataaatgaaa ttactatcag ttgaaactca    60
ttaaatttaa agacattttc tactcaagta actataagaa catgaatgtc aagtttcaga   120
```

<210> SEQ ID NO 31
<211> LENGTH: 120
<212> TYPE: DNA
<213> ORGANISM: Homo sapiens

<400> SEQUENCE: 31

```
cacaggcaga tgagaaagtg agacgaaact cagcctacta agaatggaac tatggctctt    60
tttccaattg tcaaataatt ttcacataca caaactattt tggaagtagc tactgattca   120
```

<210> SEQ ID NO 32
<211> LENGTH: 120
<212> TYPE: DNA
<213> ORGANISM: Homo sapiens

<400> SEQUENCE: 32

```
cacagtgaca gacccatgag aggaaccaag acataaacct ccctcggccc ttgtgatgtg    60
gagatcacat gatcagacat gccagatccc aagatagcct acatgtggac cagccataga   120
```

<210> SEQ ID NO 33
<211> LENGTH: 120
<212> TYPE: DNA
<213> ORGANISM: Homo sapiens

<400> SEQUENCE: 33

```
cacagtgatt taaacctatg aggaagtgca actaaaacct ctttatatac tgagaacagt    60
tcagccctta cagacaggag ggaaagtgag agggtggaaa tggtcaacac ggtgagtgag   120
```

<210> SEQ ID NO 34
<211> LENGTH: 120
<212> TYPE: DNA
<213> ORGANISM: Homo sapiens

<400> SEQUENCE: 34

```
tttaaaccca tgaggaggtg caactaaaac ctctttacat actcagaaag attcagccct    60
tagaagcaag agagaagttg agagggtggg aatgtcaaca ccatgagctg ggaacctcct   120
```

<210> SEQ ID NO 35
<211> LENGTH: 120
<212> TYPE: DNA
<213> ORGANISM: Homo sapiens

<400> SEQUENCE: 35

```
ttctctgatt atctggatgc tctgtgactc cttctgtgca tctctgggat catcattcag    60
actcacctgc accctgagca gtaacatcaa tgttgtttgc tatgacattt actggaaaca   120
```

<210> SEQ ID NO 36
<211> LENGTH: 120
<212> TYPE: DNA
<213> ORGANISM: Homo sapiens

<400> SEQUENCE: 36

```
cacagtgatt ccacaggaaa ccaaacctcc acaagacagc tggtgttttt tcctcaagcc    60
ttctgtttac ttatgggaag ctactatggt ggctgcttag ttattgagag aaaacaatgg   120
```

<210> SEQ ID NO 37
<211> LENGTH: 120

```
<212> TYPE: DNA
<213> ORGANISM: Homo sapiens

<400> SEQUENCE: 37
cacagtaatt caacatgaaa caaaaacttt cacaaaacca ttgatttttt ttttctaaaa      60
ccagcagctt tatgggctgc agctatgatg gctgctcagt tttagcaact gtgcctctat     120

<210> SEQ ID NO 38
<211> LENGTH: 120
<212> TYPE: DNA
<213> ORGANISM: Homo sapiens

<400> SEQUENCE: 38
catactgatt caacatgcaa caaaaacctc caggagacct aaggtgttta tttgattata      60
ccacctgctt cctttttagt catctgatgt ggtgctgctc agttttagca tctctgcttt     120

<210> SEQ ID NO 39
<211> LENGTH: 120
<212> TYPE: DNA
<213> ORGANISM: Homo sapiens

<400> SEQUENCE: 39
cacagtgatt ccacatgaaa caaaaacccc aacaagacca tcagtgttta ctagattatt      60
ataccagctg cttcctttac agacagctag tggggtggcc actcagtgtt agcatctcag     120

<210> SEQ ID NO 40
<211> LENGTH: 120
<212> TYPE: DNA
<213> ORGANISM: Homo sapiens

<400> SEQUENCE: 40
cacagagaca cagcccaggg cgcttcctgt acaagaaccc aggtgttttt cagtggtgct      60
ccctccccac ttctgcagaa caggatagtg tggctgagat gccatttcct gcccagggcg     120

<210> SEQ ID NO 41
<211> LENGTH: 120
<212> TYPE: DNA
<213> ORGANISM: Homo sapiens

<400> SEQUENCE: 41
cacagagaca cagcccaggg cgcctcctgt acaagaaccc aggctgcttc tcagtggtgc      60
tccctcccca cctctgcaga acaggatagt gtggctgaga tgccatttcc tgccagggcc     120

<210> SEQ ID NO 42
<211> LENGTH: 120
<212> TYPE: DNA
<213> ORGANISM: Homo sapiens

<400> SEQUENCE: 42
agtaagacca aaaccctcct gagattcctg acttgtgtcc tgacaccagg tctgttcttc      60
cctcccctag aataaaacat ctcttaagca caaggctgaa gaaatgtggc ctcctccttt     120

<210> SEQ ID NO 43
<211> LENGTH: 120
<212> TYPE: DNA
<213> ORGANISM: Homo sapiens

<400> SEQUENCE: 43
cacagcgagg ggaagccatt gtgcgctcag aacactctac aaattttcct ccctagtgtt      60
```

```
ttaccaaaac tggtatatat ttcagatact gaaatattta caacctacgt tattatgcta    120

<210> SEQ ID NO 44
<211> LENGTH: 120
<212> TYPE: DNA
<213> ORGANISM: Homo sapiens

<400> SEQUENCE: 44
caaacaaaac gacacaaaaa attccaaagt tgtgcaccct ctaaaagcat atgtacttaa    60
ttctcatttt taatttatta aacagctcta ataagttcaa tgttcctgcc ttctcagttg    120

<210> SEQ ID NO 45
<211> LENGTH: 120
<212> TYPE: DNA
<213> ORGANISM: Homo sapiens

<400> SEQUENCE: 45
aaaacttgaa cttccatcaa tgataaatat tccttttgcc tcaagcacat atttgaggaa    60
ttttccattg agtagatcta ccgataaggt cacattttc tgtctgtttt aatctgaata    120

<210> SEQ ID NO 46
<211> LENGTH: 120
<212> TYPE: DNA
<213> ORGANISM: Homo sapiens

<400> SEQUENCE: 46
tagttatttg agagattttt catacaacat ttattctgta agcaaatttc agggattgtt    60
gaatgaatca tattaacaaa tctgacacag aacttcctct gaatcaatct ttgtaaacat    120

<210> SEQ ID NO 47
<211> LENGTH: 120
<212> TYPE: DNA
<213> ORGANISM: Homo sapiens

<400> SEQUENCE: 47
tgcctggccg taagttacca tgtgcttttt aaaaaaatca tagcaaaggg gtgtcttctg    60
gaaatgacat tttgaaatgg tgttattaga ccaccctgg aagggacaca gtaaccacac    120

<210> SEQ ID NO 48
<211> LENGTH: 120
<212> TYPE: DNA
<213> ORGANISM: Homo sapiens

<400> SEQUENCE: 48
agtgatggtg ggggtcctac tagcctgtgg caaatggaag catctctttt ttatcagact    60
gaataatatt gtagtgtttt cttataccac atttacttca tcccttttgtg cattaacact    120

<210> SEQ ID NO 49
<211> LENGTH: 120
<212> TYPE: DNA
<213> ORGANISM: Homo sapiens

<400> SEQUENCE: 49
aaaatccatt gctagtggtg gtgggagtcc atttgtcttg tggaaaatgg cagcatttcc    60
ttattttata aggcataata atgctatgtt gtgtacacat accacattgt ctttatccat    120

<210> SEQ ID NO 50
<211> LENGTH: 120
<212> TYPE: DNA
<213> ORGANISM: Homo sapiens
```

<400> SEQUENCE: 50
aaaatgcatg gctagtgctg ctggaaaccc attcctactg tggcaaatgg cagcatctct    60
tttaaaaggc taaataatat tctattctgt atacatacca cattgccatt atcctttttg    120

<210> SEQ ID NO 51
<211> LENGTH: 120
<212> TYPE: DNA
<213> ORGANISM: Homo sapiens

<400> SEQUENCE: 51
atagatggat aaactaacct aggcctttga aaataaaccc ttatctgaga gtgaaaagat    60
aagccataga tttggagagt ttgcttgcaa atcaaatatt tggaaaagga cttttattac    120

<210> SEQ ID NO 52
<211> LENGTH: 120
<212> TYPE: DNA
<213> ORGANISM: Homo sapiens

<400> SEQUENCE: 52
taggcactgg atggaaagca caggagtggg tcaggtgcat acgtgatgag tggaggatga    60
attccagccc acttatcatg aattcagaca agcccacatg ttcccacatg cactatatct    120

<210> SEQ ID NO 53
<211> LENGTH: 120
<212> TYPE: DNA
<213> ORGANISM: Homo sapiens

<400> SEQUENCE: 53
cactgtgact cgaatccaga gtgaactcag acacaaacct gccctgcagg ggttcttggg    60
accacaaggg gaaggatcag gtcaccaggg tgtacttagg aaccactgaa ctgggtcagg    120

<210> SEQ ID NO 54
<211> LENGTH: 120
<212> TYPE: DNA
<213> ORGANISM: Homo sapiens

<400> SEQUENCE: 54
cgcaatgaag ggccttcatt gtgagcctag acacaaccct ccctgcaggg gtgaatagga    60
gcagcagggg gcattcgggg cagtatgggg gcttaggatg attgttaggg gtcaggatga    120

<210> SEQ ID NO 55
<211> LENGTH: 120
<212> TYPE: DNA
<213> ORGANISM: Homo sapiens

<400> SEQUENCE: 55
cattgtgagc ctagacacaa ccctccctgc aggggtgaat aggagcagca gggggcattc    60
ggggcagtat gggggcttag gatgattgtt aggggtcagg atgagcagga tcaaggcttc    120

<210> SEQ ID NO 56
<211> LENGTH: 120
<212> TYPE: DNA
<213> ORGANISM: Homo sapiens

<400> SEQUENCE: 56
cacaacgagg ggaagtcatt gtgagcccag atacaaacct ccctgcaggg gagctcagaa    60
agagcaggag gcactcagga caccagggaa cactctggac acatcaaggc aggtgcaatg    120

```
<210> SEQ ID NO 57
<211> LENGTH: 120
<212> TYPE: DNA
<213> ORGANISM: Homo sapiens

<400> SEQUENCE: 57
aacagaagag atgtcagtgt gatcccagac acaaacttcc ctggagaggg gcccaggacc      60
accaaagagc actcaggccc atgaaaacag ggcccaagct ggagaacggg tttcctgtca     120

<210> SEQ ID NO 58
<211> LENGTH: 120
<212> TYPE: DNA
<213> ORGANISM: Homo sapiens

<400> SEQUENCE: 58
cacagaaggg gaggtcattg tgaggccaga cacaaacctc cctgcaggga agctcaggac      60 accaggggt gctcagacac caagggctct caggacacat caaggcaggt gcaagagggg     120

<210> SEQ ID NO 59
<211> LENGTH: 120
<212> TYPE: DNA
<213> ORGANISM: Homo sapiens

<400> SEQUENCE: 59
cacagtgagg ggaagtcagt gtgagcccag acacaaacct ccctgcaggg atgctcagga      60
ccccagaagg cacccagcac taccagcgca gggcccagac caggagcagg tgtggagtta     120

<210> SEQ ID NO 60
<211> LENGTH: 120
<212> TYPE: DNA
<213> ORGANISM: Homo sapiens

<400> SEQUENCE: 60
cagagtgagg ggaccacggt gcgagctcac acccaaacct tcctggaggg gtgcacagga      60
cagcaggagt cccgatgatg aaggggtg gtctggattc caggtcactc tcaagatcat     120

<210> SEQ ID NO 61
<211> LENGTH: 120
<212> TYPE: DNA
<213> ORGANISM: Homo sapiens

<400> SEQUENCE: 61
cacagtaagg taaccacagt gggaactcac acccaaacct ccctgtgggg gtgcacagga      60
cagccacagt tactcaggac cccaggattc ctcaggacac caaggggcac tcaaggccat     120

<210> SEQ ID NO 62
<211> LENGTH: 120
<212> TYPE: DNA
<213> ORGANISM: Homo sapiens

<400> SEQUENCE: 62
cacagtgagg ggacatcagt gtgagcccag acacaaacct ccctatgcgg gttcacagga      60
cagcatgggg tgctgaggac agaggtgggc actcaggaac cagcagggaa acccaggggg     120

<210> SEQ ID NO 63
<211> LENGTH: 120
<212> TYPE: DNA
<213> ORGANISM: Homo sapiens

<400> SEQUENCE: 63
```

-continued agtgagagga agtccgtgtg agcccagaca caaacctccc tgcaggggca cgcggggcca    60
ccagagggtg cccaggatcc cctgaagaca gggacagccc aaaggcaggt gcagatggat    120

<210> SEQ ID NO 64
<211> LENGTH: 120
<212> TYPE: DNA
<213> ORGANISM: Homo sapiens

<400> SEQUENCE: 64
cacagtgagg ggaggtcagt gtgagcccag acacaaacct cctgcaggggg catctggagc    60 cacaaggggg cgctcaggat acacagagga caggggcagc cccagggcag gtgcaggtgg    120

<210> SEQ ID NO 65
<211> LENGTH: 120
<212> TYPE: DNA
<213> ORGANISM: Homo sapiens

<400> SEQUENCE: 65
cacagtgagg ggaggtcagt gtgagcccgg acacaaacct ccctgcaggg gcgcgcgggg    60
ctaccagggg gcgctcggga ctcactgagg gcgggacagg tcccaggaac aggtgcagcg    120

<210> SEQ ID NO 66
<211> LENGTH: 120
<212> TYPE: DNA
<213> ORGANISM: Homo sapiens

<400> SEQUENCE: 66
cagtgagggg gaggttaacg taggcccata cacaaatctc cctgcagggg cgcgcagggc    60
caactggggg cgctcgggac ccactgagga tgggacaggt cccaggggcg ggtgcagggg    120

<210> SEQ ID NO 67
<211> LENGTH: 120
<212> TYPE: DNA
<213> ORGANISM: Homo sapiens

<400> SEQUENCE: 67
tacggtaagg agaagtcagt gtgagcccag acacaaacct cccttcaggg tacctgggac    60
aaccagggaa agcctgggac actgtgcact gtgctgaccc caggggcaag tgcaggtgct    120

<210> SEQ ID NO 68
<211> LENGTH: 120
<212> TYPE: DNA
<213> ORGANISM: Homo sapiens

<400> SEQUENCE: 68
cacagagtga ggggaagtca gtgagagccc aggcacaaac ctccctgaag gggtcccaga    60
aacgactagg gggcgccagg acactgtgca cggggctgtc tccagggcag gtgcaggtgc    120

<210> SEQ ID NO 69
<211> LENGTH: 120
<212> TYPE: DNA
<213> ORGANISM: Homo sapiens

<400> SEQUENCE: 69
aacagtgaga ggaagtcaat gtgagtccag acataaacct tcctgctgag aacaatggaa    60
agcttttctt ctaagataag gaataagaaa agaatgccca gtcttaataa ttctaatcag    120

<210> SEQ ID NO 70

```
<211> LENGTH: 120
<212> TYPE: DNA
<213> ORGANISM: Homo sapiens

<400> SEQUENCE: 70
cacagtgagg ggaggtcagt gtgagcccag acacaaacct ccctgcaggg ccatgcgggt    60
ggtttccttt ctcagctgca ggaggcgggc ttattgttgc aggactctgg agacttatta   120

<210> SEQ ID NO 71
<211> LENGTH: 120
<212> TYPE: DNA
<213> ORGANISM: Homo sapiens

<400> SEQUENCE: 71
ctcagtgagg aggtgtcctt atgagccctg acacaaacct gtcagggcac ttaggacctc    60
caggaagact caagaccacc aagggactc acgaccactg gggaagggca ggttgcagta    120

<210> SEQ ID NO 72
<211> LENGTH: 120
<212> TYPE: DNA
<213> ORGANISM: Homo sapiens

<400> SEQUENCE: 72
cacagcgagg gacatttctg tgagtccaga cagaaacctc cctgcaggga gacaagagag    60
gactttgtga taaatggtgc ttaggacacc aggggcact caggacagca gagggtgctc   120

<210> SEQ ID NO 73
<211> LENGTH: 120
<212> TYPE: DNA
<213> ORGANISM: Homo sapiens

<400> SEQUENCE: 73
cacggtgagg ggacatctgt gtgagctcag acacaaacct gcctgcaggg agacacaaac    60
ctccctgcat ggtagatgct tctcagaacc accgggggt gcacaggaaa ccagaaggtg    120

<210> SEQ ID NO 74
<211> LENGTH: 120
<212> TYPE: DNA
<213> ORGANISM: Homo sapiens

<400> SEQUENCE: 74
cataggagca ggaacatctg cgtgagccca gacacaaaat cctctgcagg gagacaggag    60
ggaatcgcat ggtagatgct gattggaact accatgtgtc gctcagaact accaggaggt   120

<210> SEQ ID NO 75
<211> LENGTH: 120
<212> TYPE: DNA
<213> ORGANISM: Homo sapiens

<400> SEQUENCE: 75
cacaggagag agattatctg cacaagccca gacacaaaaa tctgcaggga gacaggaggg    60
aactgcatgg tagatgctgc tcagaagcac cagggggcac tcaacacaag ggggcgctca   120

<210> SEQ ID NO 76
<211> LENGTH: 120
<212> TYPE: DNA
<213> ORGANISM: Homo sapiens

<400> SEQUENCE: 76
agacacagga gagggaatat ctgcgtgagc ccagacagaa aaatctctgc aggaagacag    60
```
gagggagctg catggtagat gctcctcaga accaccaggg caccttgggg acaacctggg    120

<210> SEQ ID NO 77
<211> LENGTH: 120
<212> TYPE: DNA
<213> ORGANISM: Homo sapiens

<400> SEQUENCE: 77
cacaggagag ggaatatctg tgtgagccca gacacaaaaa tctctgcaga gagacaggag    60
ggaactgcat ggtagatgct cctcataacc acaaagggc agtcaggacc atcaggagga    120

<210> SEQ ID NO 78
<211> LENGTH: 120
<212> TYPE: DNA
<213> ORGANISM: Homo sapiens

<400> SEQUENCE: 78
cacatgagga aaggccggtg tgagacacaa acctccagga acacctgggc taatgagctg    60 caggggcgc tcaggaccca ctgatcagtc aaccacagag gggagtgcaa aggttaggac    120

<210> SEQ ID NO 79
<211> LENGTH: 120
<212> TYPE: DNA
<213> ORGANISM: Homo sapiens

<400> SEQUENCE: 79
ccaagtgagg aaacatcggt gtgagtccag acacaaaatt tcctgcagaa agaagaaagg    60
attctgggcc gaagggaca ctcagcactc acaaaacagg tggagcccca gggcaggtac    120

<210> SEQ ID NO 80
<211> LENGTH: 116
<212> TYPE: DNA
<213> ORGANISM: Homo sapiens

<400> SEQUENCE: 80
gtcaccaggt aagaagacat cagtgtgatc acagacacag aatttcctga aataagggag    60
gagtctgggc taaaagggca ctcaggaccc acagaaaaca gcggaagctc tagggc       116

<210> SEQ ID NO 81
<211> LENGTH: 120
<212> TYPE: DNA
<213> ORGANISM: Homo sapiens

<400> SEQUENCE: 81
caccaggtaa gaagacatca gtgtgaacac agacacagaa tttcctgaaa taagggagga    60
gtctggccta aagggcact caggacccac agaaaacagg ggaagctcta ggcaggtgc     120

<210> SEQ ID NO 82
<211> LENGTH: 120
<212> TYPE: DNA
<213> ORGANISM: Homo sapiens

<400> SEQUENCE: 82
agaagacatc agtgtgaaca cagacacaga ggttcctgta atgataaggg aggaggctgg    60
gataaaggga gcactcaaga cccacagaaa cagggggaag ctctagggca ggtgcagacg    120

<210> SEQ ID NO 83
<211> LENGTH: 120
<212> TYPE: DNA

<213> ORGANISM: Homo sapiens

<400> SEQUENCE: 83

```
caccaggtaa aagacatca gtgtgaacac agacacagag tttcctgcaa tgataaggga    60
ggaggctggg ctaaaagggg cactcaggac ccactgaaaa cgggcagctc tagggcaggt   120
```

<210> SEQ ID NO 84
<211> LENGTH: 120
<212> TYPE: DNA
<213> ORGANISM: Homo sapiens

<400> SEQUENCE: 84

```
ccaggtaaga agacatcagt gtgaacacag acacagtttc ctgcaatgat aagggaggag    60
gctgggctaa aggggcact caggacccac tgaaaacggg cagctctagg gcaggtacag   120
```

<210> SEQ ID NO 85
<211> LENGTH: 120
<212> TYPE: DNA
<213> ORGANISM: Homo sapiens

<400> SEQUENCE: 85

```
cacagtgagg ggaagtcagc gagagcccag acaaaaacct cctgcaggaa gacaggaggg    60
gcctgggctg cagagggcac tcaagacaca ctgaaaacac ggttaacact gggacaagtt   120
```

<210> SEQ ID NO 86
<211> LENGTH: 120
<212> TYPE: DNA
<213> ORGANISM: Homo sapiens

<400> SEQUENCE: 86

```
catcgtgatg ggaagtccac gtgggctcag agacagactg ccatgcagga cacagggggt    60
ggcttggctg aaggggcac tcagcaccca cagaagacag gagcagccca gggcaggggc   120
```

<210> SEQ ID NO 87
<211> LENGTH: 120
<212> TYPE: DNA
<213> ORGANISM: Homo sapiens

<400> SEQUENCE: 87

```
cgcagtgaga agtcagtgtg agcccagaca caaacctcct gcagggtacc tgggacaatc    60
agggaaagcc tgggacactg tatactgggc tgtccccagg ggcaagtcca ggtgatataa   120
```

<210> SEQ ID NO 88
<211> LENGTH: 120
<212> TYPE: DNA
<213> ORGANISM: Homo sapiens

<400> SEQUENCE: 88

```
cactgtgaga ggacggaagt gtgagcccag acacaaacct cctgcaggaa cgttggggga    60
aatcagctgc aggggcgct caagacccac tcatcagagt caaccccaga gcaggtgcac   120
```

<210> SEQ ID NO 89
<211> LENGTH: 120
<212> TYPE: DNA
<213> ORGANISM: Homo sapiens

<400> SEQUENCE: 89

```
cacagtgagg agaagtcagt gtgagcccag tcacaaacct cctacaggaa cgctgggagg    60
aaaatcagct acagggctca ctcaaggccc actgatcaga gtccactcca gagggaggtt   120
```

<210> SEQ ID NO 90
<211> LENGTH: 120
<212> TYPE: DNA
<213> ORGANISM: Homo sapiens

<400> SEQUENCE: 90
catggtgagg ggaaatcagt atgagcccag ccagaaacct ccctgcagga accctggggt      60 gggggaaat cagctgcagg gggcactcag gacccactga tcagaatcaa ccccagaagg      120

<210> SEQ ID NO 91
<211> LENGTH: 120
<212> TYPE: DNA
<213> ORGANISM: Homo sapiens

<400> SEQUENCE: 91
cacagtgagg ggaagtcatt gtgagcccag acacaaacct ccctgcagga acgatggggg      60
tgaaatcagc ggcaggggc gctcaggacc cgctgatcag agtcatccgc agaggcaggt      120

<210> SEQ ID NO 92
<211> LENGTH: 120
<212> TYPE: DNA
<213> ORGANISM: Homo sapiens

<400> SEQUENCE: 92
cacagtgagg ggaggccatt gtgcgcccag acacaaacct ccctgcagga acgctgggga      60
aatcagcggc aggggcgct caggagccac tgatcagagt cagccccgga ggcaggtgca      120

<210> SEQ ID NO 93
<211> LENGTH: 120
<212> TYPE: DNA
<213> ORGANISM: Homo sapiens

<400> SEQUENCE: 93
cacagtgagg ggaggtgagt gtgagcccag acaaaaacct ccctgcaggg aggctgaggg      60
cgcggtcgca ggtgcagctc agggccagca ggggcgcgc ggagctcacg gaatacaagg      120

<210> SEQ ID NO 94
<211> LENGTH: 120
<212> TYPE: DNA
<213> ORGANISM: Homo sapiens

<400> SEQUENCE: 94
tacacagtga ggggaggtga gtgtgagccc agacacaaac ctccctacag ataggcagag      60
ggggcgggca caggtgctgc tcaggaccaa caggggcgc gcgaggcaca gagcccgagg      120

<210> SEQ ID NO 95
<211> LENGTH: 120
<212> TYPE: DNA
<213> ORGANISM: Homo sapiens

<400> SEQUENCE: 95
cacagtgaga cagatgagga agtcggacaa aaaccaaggt tttaagcttg tcatttttac      60
tgaactggtt aagaacttca gtggttaata aaatcacatt aaatacagga ttgttgttaa      120

<210> SEQ ID NO 96
<211> LENGTH: 120
<212> TYPE: DNA
<213> ORGANISM: Homo sapiens

<400> SEQUENCE: 96
cactgtgctc taggccaatg ggaaaatccc ctctgcttgt gctgcctggg ctcccactag    60 gccctgctg tttgtgacaa cagccagcac tggtggtgac gcttcagcca tgtatgccct    120

<210> SEQ ID NO 97
<211> LENGTH: 120
<212> TYPE: DNA
<213> ORGANISM: Homo sapiens

<400> SEQUENCE: 97
cactgtgcta aacccaaaa caaaaattag ctcagcctgg cggaacagag aaactgaaca    60 atacccgtt tttatgatcc ttgcaggtgc agttgggaa ataatttacc aaataccatc    120

<210> SEQ ID NO 98
<211> LENGTH: 120
<212> TYPE: DNA
<213> ORGANISM: Homo sapiens

<400> SEQUENCE: 98
cacagtgctt taggtctaaa caaaaacctc cccaggcagc tgctccctga ggctcaaatc    60
cctcagatgt ggcttttat gcaggtccat cagcctgctg tcataggctt gtttgaacaa    120

<210> SEQ ID NO 99
<211> LENGTH: 120
<212> TYPE: DNA
<213> ORGANISM: Homo sapiens

<400> SEQUENCE: 99
cacaatggtt cagcaccaaa caaaagcctc ctgcttggat tgtcccagct gcccaaatta    60
gttccttcac tgaggagtag acagggtata tgctctaaat ctatgtaaca ggaagatgtt    120

<210> SEQ ID NO 100
<211> LENGTH: 120
<212> TYPE: DNA
<213> ORGANISM: Homo sapiens

<400> SEQUENCE: 100
cacagtggta caaccctgaa cagaaacctc ccttcttgct gtggttcagc tgcccaaatg    60
tgttgtttat ctggaaagca gacactgtct attatcttgg gagagtaaag agaggaagat    120

<210> SEQ ID NO 101
<211> LENGTH: 120
<212> TYPE: DNA
<213> ORGANISM: Homo sapiens

<400> SEQUENCE: 101
cacagtggta aaaccctgaa cacaaacctc cctacttggg atggcccagc catccacaag    60
tgtttgcacg tggactgtct gcatggcaga ttctgagttg cttcacagg tagatgttag    120

<210> SEQ ID NO 102
<211> LENGTH: 120
<212> TYPE: DNA
<213> ORGANISM: Homo sapiens

<400> SEQUENCE: 102
cacagtgcta catcctcgaa cagaaacctc cctgctggtt gacccagctc gcgcatgggc    60
tgcttgtctg agggaacagc tgagcagagt ctttgagtct gcagaggaga aggctgttgg    120

```
<210> SEQ ID NO 103
<211> LENGTH: 120
<212> TYPE: DNA
<213> ORGANISM: Homo sapiens

<400> SEQUENCE: 103
cacagtgctt cagcctcgaa cacaaacctc ctccccatac gctgggccag taggtctttg      60
ctgcagcagc tgcttcctct gcacacagcc cccaacatgc atgcttcctc tgtgtgttgg     120

<210> SEQ ID NO 104
<211> LENGTH: 120
<212> TYPE: DNA
<213> ORGANISM: Homo sapiens

<400> SEQUENCE: 104
gggaggcgga gggggcgggc gcaggtgccg ctcaggacca gcaggggcg cgcggggccc      60 acagagcagg aggccgggtc aggagcaggt gcagggaggg cggggcttcc tcatctgctc    120

<210> SEQ ID NO 105
<211> LENGTH: 120
<212> TYPE: DNA
<213> ORGANISM: Homo sapiens

<400> SEQUENCE: 105
ctcagcctcc tcactcaggg cacaggtgac acctccaggg aaagggtcac aggggtctct     60
gggctgatcc ttggtctcct gctcctcagg ctcacctggg cccagcactg actcactaga    120

<210> SEQ ID NO 106
<211> LENGTH: 120
<212> TYPE: DNA
<213> ORGANISM: Homo sapiens

<400> SEQUENCE: 106
tgcccttggc ctgtcccgag gctgatcact ccatacttgc ctatgacaaa caaagagggt     60
gcctgtggct gatcgtacag tttaagcaag ggaggaagtg agactcagcc acaggcccct    120

<210> SEQ ID NO 107
<211> LENGTH: 120
<212> TYPE: DNA
<213> ORGANISM: Homo sapiens

<400> SEQUENCE: 107
cactgtgctc cagacttacg gggaagtgag attagaacct cccctgcatt ctctctgcct     60
tgtgcaggca acaatacact gtctgggacc gagtgtggct catcagtagc agctttgttg    120

<210> SEQ ID NO 108
<211> LENGTH: 120
<212> TYPE: DNA
<213> ORGANISM: Homo sapiens

<400> SEQUENCE: 108
cacagtgctc cagacccatg aggaagtaag acaaaaccct cccctctact ctcctggtct     60
agtgaaatca cccctgctgg tggctctgac caaatctagc tcaggggtg acatctgttg    120

<210> SEQ ID NO 109
<211> LENGTH: 120
<212> TYPE: DNA
<213> ORGANISM: Homo sapiens

<400> SEQUENCE: 109
```

```
tacagtgctc caggcttgca ggggagtgag acaagaaccc ccttcctcct ttcccaggag    60
ggtgagtgcc cagcagctac tgcacaggcc tggcctgtgg cttctgcagt tgctgtttcc   120

<210> SEQ ID NO 110
<211> LENGTH: 120
<212> TYPE: DNA
<213> ORGANISM: Homo sapiens

<400> SEQUENCE: 110
cacagtgctc cagacccatg gggaagtgag acagaaactc cccagagcat ctctacctgg    60
gccagtctca gcctgtctcc accagagagg gtagctctcc catctctcct gtctaagtgc   120

<210> SEQ ID NO 111
<211> LENGTH: 120
<212> TYPE: DNA
<213> ORGANISM: Homo sapiens

<400> SEQUENCE: 111
caccgtggtc caagttcatg gggaattgag acccaaacct gccctgggct ctcagcctct    60
ctcttgttct gaagatgctt cctcaccctg tgcaggggc ttcttgcagc actgccttga   120

<210> SEQ ID NO 112
<211> LENGTH: 120
<212> TYPE: DNA
<213> ORGANISM: Homo sapiens

<400> SEQUENCE: 112
tccacagtga tttaaaccca tgaggaggtg caactaaaac ctctttacat actcagaaag    60
attcagccct tagaagcaag agagaagttg agagggtggg aatgtcaaca ccatgagctg   120

<210> SEQ ID NO 113
<211> LENGTH: 120
<212> TYPE: DNA
<213> ORGANISM: Homo sapiens

<400> SEQUENCE: 113
cacagtgaca cagacagatt ggaaagtgag atctaaagac cttcactgtc tgtatcaccc    60
tctttctcca gccatagcag gactgagcag ggctggcccg ggtcacctgg atcgaagccc   120

<210> SEQ ID NO 114
<211> LENGTH: 120
<212> TYPE: DNA
<213> ORGANISM: Homo sapiens

<400> SEQUENCE: 114
cactcatggg acagcagtgc tactcacctc acaatgacac agacagattg ggaagtgaga    60
tctaaagacc ttcactgtct gtgtcaccct cttcctccag ccatagcagg actgtggaga   120

<210> SEQ ID NO 115
<211> LENGTH: 120
<212> TYPE: DNA
<213> ORGANISM: Homo sapiens

<400> SEQUENCE: 115
cacagtgaca gaggcagaca aggaagtaag acacagaccc cttccccatc tgtgctgctg    60
tcgtcctcca gcccggcaac actgtggaca aagccatgag catgcatgac ccagttcacc   120

<210> SEQ ID NO 116
<211> LENGTH: 120
```

<212> TYPE: DNA
<213> ORGANISM: Homo sapiens

<400> SEQUENCE: 116
cacagtgata caggcagatg aggaagtggg acaaaatcct caacctgctg aggctattgt    60
tcagtgacaa tttttaattt taaaacattt tctgtatgta aaaatctat ctggatgcat    120

<210> SEQ ID NO 117
<211> LENGTH: 120
<212> TYPE: DNA
<213> ORGANISM: Homo sapiens

<400> SEQUENCE: 117
cacagtgcct caggccagtg gggaagtgag ataaaaactc aagagctccc tcggcctcac    60
tgaacaggcc tcacagagca ctgtttaaac tggaccaccc aaaagacaag ggatgcattc    120

<210> SEQ ID NO 118
<211> LENGTH: 120
<212> TYPE: DNA
<213> ORGANISM: Homo sapiens

<400> SEQUENCE: 118
cacagcgcct caggggaagt gagacgaaaa ctcaggagct cccctagctt cactcggtat    60
gcgggggcgt catagagcac tgtttaaact aaaccaaaaa tgacaagggc tggtttccac    120

<210> SEQ ID NO 119
<211> LENGTH: 120
<212> TYPE: DNA
<213> ORGANISM: Homo sapiens

<400> SEQUENCE: 119
aacagtgctg cagtctggga aagtgagatg agaacacgcc aggtctccta ggagcatgac    60
cttccaatgg caccacccac aaccaggaca cgctggtctt gttttaccat ttgtgtggat    120

<210> SEQ ID NO 120
<211> LENGTH: 120
<212> TYPE: DNA
<213> ORGANISM: Homo sapiens

<400> SEQUENCE: 120
cacagtggac ataagattga ttctcaggct ccaagtctgg ccagtgagct tctttgagac    60
tccctgggat cccagcagtg acactgatca ctattgctgt cccacacatc ccaagtgatg    120

<210> SEQ ID NO 121
<211> LENGTH: 120
<212> TYPE: DNA
<213> ORGANISM: Homo sapiens

<400> SEQUENCE: 121
cagcactcca gacccactgg gaggttacaa aaacctcttc tctgatctcc tggcctggtg    60
tagtcactcc tgctggtggc tctaataaag tctatctcac tgggtgactt atattttaga    120

<210> SEQ ID NO 122
<211> LENGTH: 120
<212> TYPE: DNA
<213> ORGANISM: Homo sapiens

<400> SEQUENCE: 122
cacagtgctc cgggttgaag taagtcagac caaaacacac agtgtgccca gccatgaagc    60

```
tctcccatgc accccctact ctgcagctaa gtcaatgtgt tctctcactt gtttgtccta    120
```

<210> SEQ ID NO 123
<211> LENGTH: 120
<212> TYPE: DNA
<213> ORGANISM: Homo sapiens

<400> SEQUENCE: 123

```
ggcagtactt caggccagtg gggaagtggg agaaaaagct gctgcccatc cagcaatgga    60
gcttctctgt gcagccccca cttcttgggc aagtcagctg attaacgttg cttttcattt   120
```

<210> SEQ ID NO 124
<211> LENGTH: 120
<212> TYPE: DNA
<213> ORGANISM: Homo sapiens

<400> SEQUENCE: 124

```
acacctggcc tcttcgtttt tattcatata ttccttcagc agccactatg tcttcccact    60
gatttcttca gtttctgcct tttccttttg aataaggctg ttactcctga gggaagatgg   120
```

<210> SEQ ID NO 125
<211> LENGTH: 120
<212> TYPE: DNA
<213> ORGANISM: Homo sapiens

<400> SEQUENCE: 125

```
ggcaggccac caagtccagc taattttttgt attttttagta gacactgggt ttcacaatat   60
tggtctggct ggtctcaaac tcctgatctc agcctcccaa agtgctggga ttaaagccgt   120
```

<210> SEQ ID NO 126
<211> LENGTH: 120
<212> TYPE: DNA
<213> ORGANISM: Homo sapiens

<400> SEQUENCE: 126

```
attgtgtgca tcccttgttt aggtacatgc agagatgctg ctttggtgtg ttcaggggct    60
cctgttttgg ggacaccaat tttggagttt gcagtatcct tgagtccagt acgttcatgg   120
```

<210> SEQ ID NO 127
<211> LENGTH: 120
<212> TYPE: DNA
<213> ORGANISM: Homo sapiens

<400> SEQUENCE: 127

```
atggtctcac tgatatcttt acttcttttta tcacttttgt tatgtaaatc acaatgaata    60
gtgtattcct catctattat acatttgtta agtctttttt ggtgtcttta aaaaaactga   120
```

<210> SEQ ID NO 128
<211> LENGTH: 120
<212> TYPE: DNA
<213> ORGANISM: Homo sapiens

<400> SEQUENCE: 128

```
cacaatgaat agtgtattcc tcatctatta tacatttgtt aagtcttttt tggtgtcttt    60
aaaaaaactg ataactttat agtatgtaat atccttaagt cctgaaagtg ttttttgatg   120
```

<210> SEQ ID NO 129
<211> LENGTH: 120
<212> TYPE: DNA
<213> ORGANISM: Homo sapiens

<400> SEQUENCE: 129
cttcatctat tatacacttg ttaagtctttt tttggcatct tttaaaaaac tggtaacttt    60
atcctgtgta atatccctgt taagtcctaa aagtcttttt tgatgtctat tttttcttaa   120

<210> SEQ ID NO 130
<211> LENGTH: 120
<212> TYPE: DNA
<213> ORGANISM: Homo sapiens

<400> SEQUENCE: 130
tacctaaatg tgtgtggggg aagcaggggg tgttattctg ttgttctgtg ttctctgaga    60
tgcatggatt caccatttac tctgcctcca ttttggggaa cacagttaga aaaaatgtca   120

<210> SEQ ID NO 131
<211> LENGTH: 120
<212> TYPE: DNA
<213> ORGANISM: Homo sapiens

<400> SEQUENCE: 131
tggttttcag cagttttaat aagattcacc taaatgtgtg tgtgtgtgtc gaggggtgtt    60
atgctattgt tctgtgttct ctgagatgca tggattcacc gtttactctg tctccatttt   120

<210> SEQ ID NO 132
<211> LENGTH: 120
<212> TYPE: DNA
<213> ORGANISM: Homo sapiens

<400> SEQUENCE: 132
cacagtgatt cagacactga aaatctgcct gtggttgctt ctggtacaca agatagacca    60
gccaactctc atttcctgcc ctgaatttac tgtattctgt acaaagagaa acacagctta   120

<210> SEQ ID NO 133
<211> LENGTH: 120
<212> TYPE: DNA
<213> ORGANISM: Homo sapiens

<400> SEQUENCE: 133
cacagtgatt cagatccgcc ctacaccaca ctgaaaacct gccttgtggc tgcttctggt    60
acacaagata gagctgcccc ctctcatttc ctgccaccaa atttaccgtg tgctgaacaa   120

<210> SEQ ID NO 134
<211> LENGTH: 120
<212> TYPE: DNA
<213> ORGANISM: Homo sapiens

<400> SEQUENCE: 134
cacagcagca gacagtttga gccatcccat tcaataaatg tttattgagt ctttgtttat    60
aattacgaat tgggaagcca cagttaccac cagtgtgctt gtaaacagtt tttaagataa   120

<210> SEQ ID NO 135
<211> LENGTH: 120
<212> TYPE: DNA
<213> ORGANISM: Homo sapiens

<400> SEQUENCE: 135
cgcagccttg catgctgccc cagccctaca caaaaggact cttcctcccg atccaacaag    60
gccttgggca ttttcactta ctcttggtcc cttgggtttc cctgtggcat agaagaaaaa   120

<210> SEQ ID NO 136
<211> LENGTH: 120
<212> TYPE: DNA
<213> ORGANISM: Homo sapiens

<400> SEQUENCE: 136
caataatggc aatgtggcag tttccataca tatgtttgtg ctagcttttt tattattata      60
tagtaaactt ctttgcctct ttttatagtt attgtcttga aatatatttt atctgatata     120

<210> SEQ ID NO 137
<211> LENGTH: 120
<212> TYPE: DNA
<213> ORGANISM: Homo sapiens

<400> SEQUENCE: 137
cacaatggaa gcacaaccat tgtctctctg tgcggaaatg tgtcctcacc ctacagcccc      60
caccacatcc tctagcttaa tttttcatt tttaatattt tcttgagatt ttactatgtc     120

<210> SEQ ID NO 138
<211> LENGTH: 120
<212> TYPE: DNA
<213> ORGANISM: Homo sapiens

<400> SEQUENCE: 138
cacagtgact atgaggcctc cttaactgtg ccaaaattca aaagacaatc agtggagtac      60
aggtgggctt gagaagttct agaacttcct gagtgtatct ttgcttaccg tctaattta      120

<210> SEQ ID NO 139
<211> LENGTH: 120
<212> TYPE: DNA
<213> ORGANISM: Homo sapiens

<400> SEQUENCE: 139
cacggtgact atgaggcctc tttagctgca ccaaaattca aaaggcaacc acagcagcga      60
gaagctgtat ttcctgagtg tatgcctgct gtgagttaag actggggact ttggaaccag     120

<210> SEQ ID NO 140
<211> LENGTH: 120
<212> TYPE: DNA
<213> ORGANISM: Homo sapiens

<400> SEQUENCE: 140
tcaggaccct gtgataattg tgttaactgc acaaattata gagcatgtgt gttcaaacaa      60
tatgaaatct gggcaccttg aaaaaagaac aggataacag caatgttcag ggataagag     120

<210> SEQ ID NO 141
<211> LENGTH: 120
<212> TYPE: DNA
<213> ORGANISM: Homo sapiens

<400> SEQUENCE: 141
cacagtgccg aatgttagcc cttcttagaa cacaaactca ttatggaccc agctcaggaa      60
ataagtgtat gtcaggttgg tacacactat aataacagaa agccaacttg aaagacaata     120

<210> SEQ ID NO 142
<211> LENGTH: 120
<212> TYPE: DNA
<213> ORGANISM: Homo sapiens

<400> SEQUENCE: 142
cacaatgtta aatattagct aatcttagga cacagactca tcacggactc agctcaggaa    60
gcaggtggta tactaggttg aaggaaata acagaaacta gagctagctt aagccaaagg   120

<210> SEQ ID NO 143
<211> LENGTH: 120
<212> TYPE: DNA
<213> ORGANISM: Homo sapiens

<400> SEQUENCE: 143
cacagcactg aaatgtcagt tcctcttagc acacaaactt gtcacagacc cagctcagga    60
agcaggtgat gtattaggct ggaagggagt aacagaaaat aactggagcc agcttaagcc   120

<210> SEQ ID NO 144
<211> LENGTH: 120
<212> TYPE: DNA
<213> ORGANISM: Homo sapiens

<400> SEQUENCE: 144
cactgtgtta aaagcacagt gggagctata caaaaacctc aaaggctcag aggaagtatg    60
tagtgaggct ggaaaaccca ggttgtagag ccctgttctc tctttcacag acagtcctgt   120

<210> SEQ ID NO 145
<211> LENGTH: 120
<212> TYPE: DNA
<213> ORGANISM: Homo sapiens

<400> SEQUENCE: 145
cactatgatg caggtgccca ggaagtcata acacaaactc ctggggcaca gctcagcaga    60
gctgcctctt agggcaggtc atgtctggga cttggcatcc ttctcttagc cattttgggt   120

<210> SEQ ID NO 146
<211> LENGTH: 120
<212> TYPE: DNA
<213> ORGANISM: Homo sapiens

<400> SEQUENCE: 146
cacagaggca gggaacccat gaagagctga acagaaacag agatcacagc ctttgcagga    60
ggcaaaacag agatgagcaa taacttttc ctccttaatt cagtattacc caagcttttt   120

<210> SEQ ID NO 147
<211> LENGTH: 120
<212> TYPE: DNA
<213> ORGANISM: Homo sapiens

<400> SEQUENCE: 147
cacagtagct ggttttgcaa ggaagcagaa cacaaaccct ttaaatacag gaaatatttc    60
tttgcaaact ctctgtatgg ccacagcagg gcattctttc tccagaaatt aatattgagt   120

<210> SEQ ID NO 148
<211> LENGTH: 120
<212> TYPE: DNA
<213> ORGANISM: Homo sapiens

<400> SEQUENCE: 148
gactgtgcct gggactgcag gaggagctga acacaaactt cctgagacac tgaggttttc    60
aggaactcaa gggcacagcc tgacctattt gtagcaaggt ctctcatttg atgaaagtga   120

<210> SEQ ID NO 149

```
<211> LENGTH: 120
<212> TYPE: DNA
<213> ORGANISM: Homo sapiens

<400> SEQUENCE: 149
cacagtgcct gagactgcag gagagctgaa cacaaacctc ctgagatgct gagactttct      60
gtgactcaag aactcaacct gtggagcttt caagagggtc cctttttct gtgcccgttt     120

<210> SEQ ID NO 150
<211> LENGTH: 120
<212> TYPE: DNA
<213> ORGANISM: Homo sapiens

<400> SEQUENCE: 150
cacactgata ggggctgcag ggggagcaga acacaaactc ttgagtctgg taaagcccat      60
tttcttgaag tctttgttcc ttcacatgag aacggtgtgc ttccaggata tgtcacttat     120

<210> SEQ ID NO 151
<211> LENGTH: 120
<212> TYPE: DNA
<213> ORGANISM: Homo sapiens

<400> SEQUENCE: 151
cacagtgtct gggactgcaa agggagctga acacaaactt cctaaggtgc tagggagaat      60
aactgcctct gaaagatttt ggattctgtc acagtagaaa ccatgatgtt agtatttta     120

<210> SEQ ID NO 152
<211> LENGTH: 120
<212> TYPE: DNA
<213> ORGANISM: Homo sapiens

<400> SEQUENCE: 152
cagagtggga gggactgcag cgagagccca gcacaaaccc tggggaacgc aggtggggcc      60
tgggtgtgag ccgctttggg agatgaatga atatggactc ttgttcgctg gaccccaaa     120

<210> SEQ ID NO 153
<211> LENGTH: 120
<212> TYPE: DNA
<213> ORGANISM: Homo sapiens

<400> SEQUENCE: 153
cacagtgaca gggactgcag gggaagctga gcacaaactc tgagcagcac gaggggcctg      60
gctgctgagt gtaagccact gtgatcccct ctggttaggg accaggaact actctactat     120

<210> SEQ ID NO 154
<211> LENGTH: 120
<212> TYPE: DNA
<213> ORGANISM: Homo sapiens

<400> SEQUENCE: 154
cactgtgaag aacatgttag aagagcctta caaaagatc ggaactcaac ctgaggcaat      60
tgcctattcc cacattctca ggaaaaactc acaaaccta cccaggcatt gttagcagc     120

<210> SEQ ID NO 155
<211> LENGTH: 120
<212> TYPE: DNA
<213> ORGANISM: Homo sapiens

<400> SEQUENCE: 155
cacaatgaga tgagcagcag ggagaggctt acagaaacct cagacctcag catctgtgca      60
```

```
aaggtcacag ggtgagaggg aagtggtagg gtaataggta tagaaaatca ttgacttctc    120
```

<210> SEQ ID NO 156
<211> LENGTH: 120
<212> TYPE: DNA
<213> ORGANISM: Homo sapiens

<400> SEQUENCE: 156

```
cacagtgaga tgggtgcctg tgggagccct acaaaaacct caacaagagg cagggctcct    60
ggggagagac tctgtcacag acaggaagaa gcaaggaggg tctgtgtcag cacaggtggt    120
```

<210> SEQ ID NO 157
<211> LENGTH: 114
<212> TYPE: DNA
<213> ORGANISM: Homo sapiens

<400> SEQUENCE: 157

```
cacagtgaca gaactgtcgg agggaggtgt acaaaagccc tggggacctg cttgagacct    60
ccacctgctg gagaaccaag gcgggaaatc aacatcacag acaggaagtg gcta          114
```

<210> SEQ ID NO 158
<211> LENGTH: 120
<212> TYPE: DNA
<213> ORGANISM: Homo sapiens

<400> SEQUENCE: 158

```
cacagaagta gaaatgacag tggaagataa acaaaaacct tagcactcca taaaggaagc    60
cacctgctca ggagcttagg gaaaatacat gaagcacaga caggaagaag gcacattagt    120
```

<210> SEQ ID NO 159
<211> LENGTH: 120
<212> TYPE: DNA
<213> ORGANISM: Homo sapiens

<400> SEQUENCE: 159

```
cacagtgttt gaagtgatag taaaagcaaa acaaaaaccc tagggctcaa taagagaacc    60
cctctactcc ccatcctttg ctacaggagc caatctgaaa tgcacacctg cagatctcag    120
```

<210> SEQ ID NO 160
<211> LENGTH: 120
<212> TYPE: DNA
<213> ORGANISM: Homo sapiens

<400> SEQUENCE: 160

```
caccctgctg cagctctact tctgagcagc tcaaaaacca ctgaccaggc gcggtggctc    60
acacctgtaa tcccagcact ttgggaggcc gaggtgggtg gatcacgagg tcaggagatc    120
```

<210> SEQ ID NO 161
<211> LENGTH: 120
<212> TYPE: DNA
<213> ORGANISM: Homo sapiens

<400> SEQUENCE: 161

```
cacactgagc tgggtggggc agacatctgt gcaaaaccc caccctctcc tgagccctaa     60
ccatactccc caggggcctt cacttaggga ctgggtggag gatatttgta agtaggtttc    120
```

<210> SEQ ID NO 162
<211> LENGTH: 120
<212> TYPE: DNA

```
<213> ORGANISM: Homo sapiens

<400> SEQUENCE: 162
cacagcgcca ggaggggatc agacaccgcg gcaagaaccc ctgcagctgc cctccgcccc      60
agcgggcccc ctgagtgctg agaggggaag cgtggagaat ggaaaaccac agctttcctg    120

<210> SEQ ID NO 163
<211> LENGTH: 120
<212> TYPE: DNA
<213> ORGANISM: Homo sapiens

<400> SEQUENCE: 163
cacagtgcag ggcacagatc aaagatctaa gcaagaacct cagctcccct ctacccagct      60
cccctcacat gaacctgagg gccctgtcaa ggtgggacag aagaggaaac cacagctctt    120

<210> SEQ ID NO 164
<211> LENGTH: 120
<212> TYPE: DNA
<213> ORGANISM: Homo sapiens

<400> SEQUENCE: 164
gccacacaca ctcaagatgc cccagacacc ctgcactccg atcttactcg ttcctttact      60
gttttcatcc taattgccct cttacacatt tgaccacaca ttttggtct tggtggttgt    120

<210> SEQ ID NO 165
<211> LENGTH: 120
<212> TYPE: DNA
<213> ORGANISM: Homo sapiens

<400> SEQUENCE: 165
accatactag aactgttgaa acaacatgca caaaatcccc tcccagggtc tgtgcccacc      60
acatccttcc caacaggggc aaccacagcc agtccccagc tgggctccca gactcaggct    120

<210> SEQ ID NO 166
<211> LENGTH: 120
<212> TYPE: DNA
<213> ORGANISM: Homo sapiens

<400> SEQUENCE: 166
cacagcatca gtgccacact gtcccacaca acaacctctg ttgggtctct gcccaaccac      60
atccttccca tgggagcaaa ctctatggac tcctagctgg gctcccaccc tcagccttgc    120

<210> SEQ ID NO 167
<211> LENGTH: 120
<212> TYPE: DNA
<213> ORGANISM: Homo sapiens

<400> SEQUENCE: 167
cacagtgtta gagttgtcaa gataacctac acagaaacta tctccgagtc tgtgcctgtc      60
cacatccttc tccatgtggg caaccacagc ggtttgctca gctgggtgcc cagccggagc    120

<210> SEQ ID NO 168
<211> LENGTH: 120
<212> TYPE: DNA
<213> ORGANISM: Homo sapiens

<400> SEQUENCE: 168
ctcgtgggtg acacacagtg agacagatgg gcctgcacct gtgccgtttt cctctgtggg      60
gtgggagtca cagcctagaa agaagtccaa aagtgctttc taaaattttt attttcaaaa    120
```

<210> SEQ ID NO 169
<211> LENGTH: 120
<212> TYPE: DNA
<213> ORGANISM: Homo sapiens

<400> SEQUENCE: 169
cacactggga cagatggggc tgcacctgtg caatatctcc ctggtggcaa gtgaggagga      60
gggtagcatt cacctagagc aaaatgtcga taggagtcaa aaagtaacaa gaaaagagga     120

<210> SEQ ID NO 170
<211> LENGTH: 120
<212> TYPE: DNA
<213> ORGANISM: Homo sapiens

<400> SEQUENCE: 170
cacagtggga cagatggggc tgcagctgtg caatatctcc ctggtgatga agggaaggc      60 atctaacgag gccactgcac aagaaggagc agaagtttaa tagaggaaga agaaaattta    120

<210> SEQ ID NO 171
<211> LENGTH: 120
<212> TYPE: DNA
<213> ORGANISM: Homo sapiens

<400> SEQUENCE: 171
cacagtgctg cacagctgcc tcctctctgc acataaaggg cagttagaat gactgaggtt     60
gcctgtgctc ccaagtccca gccttcacag gagtcggaga gccctggcta gctgggggc    120

<210> SEQ ID NO 172
<211> LENGTH: 120
<212> TYPE: DNA
<213> ORGANISM: Homo sapiens

<400> SEQUENCE: 172
cacagtgctg cacagctgcc tcctctctgc acggaaacgg cagttagaaa aactgaggtt     60
gcctgtgcac ccaagtctgg gccccaccct gggacgtctc agcccccata ggagtcacag    120

<210> SEQ ID NO 173
<211> LENGTH: 120
<212> TYPE: DNA
<213> ORGANISM: Homo sapiens

<400> SEQUENCE: 173
cacagtgctg catggctgcc tcctctctgc acgtaaacag cagttagaaa gactgaggtt     60
gctctgtgtc tatccccacc cttggaagtc caggcctcca tagaagtcag agggccctgg   120

<210> SEQ ID NO 174
<211> LENGTH: 120
<212> TYPE: DNA
<213> ORGANISM: Homo sapiens

<400> SEQUENCE: 174
cacagcgcag cacagctgca tcctctctgc acaaaaagag cggacgtaag agagaagggg     60
ccctaactca gggctggtgc tggctccgat ggcacattcg tgctaaatag aaaaaaagcg    120

<210> SEQ ID NO 175
<211> LENGTH: 120
<212> TYPE: DNA
<213> ORGANISM: Homo sapiens

```
<400> SEQUENCE: 175
cacagtgctg cacggctgtc tcctctctgc acagaaaggc aagggaaggt gctgccctcc    60
tccgcagcac agattcagcg atgcccttgg tcctagcacc gaaaactttg gagcccaat    120

<210> SEQ ID NO 176
<211> LENGTH: 120
<212> TYPE: DNA
<213> ORGANISM: Homo sapiens

<400> SEQUENCE: 176
cacagtgctg cacagccatc tcctctctgt acataaatgc aggggaggct ctgccctcct    60
ccccgacccc agactcaacc atgtccttgg cagagttctc agcactggga atcttggaag   120

<210> SEQ ID NO 177
<211> LENGTH: 120
<212> TYPE: DNA
<213> ORGANISM: Homo sapiens

<400> SEQUENCE: 177
cacagcgctg caagcctgtc tcctctctgc acataaaggc acagaggctc tgccctcctc    60
ccacccaaga ctcaaggatg ccctgggcag agttctctgc accaggaacc ttggaaccca   120

<210> SEQ ID NO 178
<211> LENGTH: 120
<212> TYPE: DNA
<213> ORGANISM: Homo sapiens

<400> SEQUENCE: 178
cacagcgctg caaggctgtc tcctctctgc acataaaggc aagggaaggt gctgccctcc    60
tcccccaccc aagactcaag gatgccctgt gcagagatct ctgcaccagg aaccttggaa   120

<210> SEQ ID NO 179
<211> LENGTH: 120
<212> TYPE: DNA
<213> ORGANISM: Homo sapiens

<400> SEQUENCE: 179
cacagcgcta caaggccgtc tcctctctgc acataaaggc agggaggttc tgccctcctc    60
ccccacccaa gactcaggga tgccctgggc agagatctct gcgccaggaa ccttggaacc   120

<210> SEQ ID NO 180
<211> LENGTH: 112
<212> TYPE: DNA
<213> ORGANISM: Homo sapiens

<400> SEQUENCE: 180
gccagtagta tagacacagt gaagcacgga tgtcgcctct ctgtgcataa atgtgcccag    60
tcctgcttcc ccgaccaggt ggcagggctc ctctgcactc tatgatggca gg           112

<210> SEQ ID NO 181
<211> LENGTH: 120
<212> TYPE: DNA
<213> ORGANISM: Homo sapiens

<400> SEQUENCE: 181
cacagtgaag cacggatgtc gcctctctgt gcataaatgt gcccagtcct gcttccccga    60
ccaggtgaca gggctcctct gcactctatg atggcaggaa acgccactca gccactaagc   120
```

```
<210> SEQ ID NO 182
<211> LENGTH: 120
<212> TYPE: DNA
<213> ORGANISM: Homo sapiens

<400> SEQUENCE: 182
cacagcactg cacaggcatg tgctcacctc acaaaatggc agtctcaaag ggaggagtgc    60
ccacccacaa gaggctccac cctattctga gaaagaactt ctttcagagg aggagagaat   120

<210> SEQ ID NO 183
<211> LENGTH: 120
<212> TYPE: DNA
<213> ORGANISM: Homo sapiens

<400> SEQUENCE: 183
cacagcactg catagctgcc acatcctctc cacataaaaa aaggtgcata ccaaagagga    60
aaagcctgcc ctcaaaattc ctcaccgcaa ataagagaag ttacctcaca ggtattgaca   120

<210> SEQ ID NO 184
<211> LENGTH: 120
<212> TYPE: DNA
<213> ORGANISM: Homo sapiens

<400> SEQUENCE: 184
cacagtgcta catagatacc gacactctgc acagaaaggg tcgcctctaa ggtgaggaca    60
tcttgccttc agaaacctta tcttaaacta cagaaacccc tgcaaatctt cccagactcc   120

<210> SEQ ID NO 185
<211> LENGTH: 120
<212> TYPE: DNA
<213> ORGANISM: Homo sapiens

<400> SEQUENCE: 185
cacagtgttg cacagccagc tgctctctgc acaaaaacag agggtagctg caagaacaag    60
gagactcctc cttcaggaga cccctcaccg accaacagga taaacttcct ccatcatccc   120

<210> SEQ ID NO 186
<211> LENGTH: 120
<212> TYPE: DNA
<213> ORGANISM: Homo sapiens

<400> SEQUENCE: 186
cgcagccctg cacagccagc tgccctctgc acaaaaaggg cagtcacagg ctggaggtgg    60
gcactcctta tggaagcccg tgtctcaacc agaagaaaaa gctgcccttt ctgaagctct   120

<210> SEQ ID NO 187
<211> LENGTH: 120
<212> TYPE: DNA
<213> ORGANISM: Homo sapiens

<400> SEQUENCE: 187
cacagtgctt cttggccacc tgctctctac acagaaagac agacacatgg gtgagttgtt    60
tgctctgaag ggtacctgga tgtgggttgt gggatgtggg gtgtttagag ctttcagtgg   120

<210> SEQ ID NO 188
<211> LENGTH: 120
<212> TYPE: DNA
<213> ORGANISM: Homo sapiens

<400> SEQUENCE: 188
```

```
cacagccttg caaagacaac tccagcctgt gcaaaatccc tcacagagct gcctccctcc    60
cagccgccag ctcccacttc ctgcctaaga aaggaagtc tctggttggg tttgttcttg    120

<210> SEQ ID NO 189
<211> LENGTH: 120
<212> TYPE: DNA
<213> ORGANISM: Homo sapiens

<400> SEQUENCE: 189
cacagcgttg cagagacttt ctctcctgtg cacaaaactc cagggctctc tccgctctac    60
tcagctcaca gcagccttc cttattcctc atcctctcag ggaagaagtg agttttcaga    120

<210> SEQ ID NO 190
<211> LENGTH: 120
<212> TYPE: DNA
<213> ORGANISM: Homo sapiens

<400> SEQUENCE: 190
cacagtgtag cagagacact tccctcctgt gcagaaaacc agaaaccgc aggactctct    60 cctctctact cagctcacag cagccttcc ttattcctca tcctcccaag gaagaagtga    120

<210> SEQ ID NO 191
<211> LENGTH: 120
<212> TYPE: DNA
<213> ORGANISM: Homo sapiens

<400> SEQUENCE: 191
cacagtgtag cagagacact tccctcctgt gcagaaaacc gcaggactct ctcctctcta    60
ctcagctcac agcagccttt ccttattcct catcctccca ggaaagaagt gagttttcag    120

<210> SEQ ID NO 192
<211> LENGTH: 120
<212> TYPE: DNA
<213> ORGANISM: Homo sapiens

<400> SEQUENCE: 192
cacagagctg cagtgcttcc tgctctctgt tcataaacct cattgtttcc cagatccagg    60
tgctttctct aggacttctc cctcaccacc tcttacaaca ataggaagtg ggttggtggc    120

<210> SEQ ID NO 193
<211> LENGTH: 120
<212> TYPE: DNA
<213> ORGANISM: Homo sapiens

<400> SEQUENCE: 193
cacagcgctg cagaatcacc tgctccctgt gcagaaaccc tggtgcttcc tcttctcctc    60
cagtacccag cagctctcag cagcctttct tgctcctccc ctagcacagg aagtacatag    120

<210> SEQ ID NO 194
<211> LENGTH: 120
<212> TYPE: DNA
<213> ORGANISM: Homo sapiens

<400> SEQUENCE: 194
cacagcactg cagaatctcc ccatctctgt gcagaaaccc tggtgcttcc tcttctcccc    60
acagctctca gcagtcgtca gcaaagtctt tcctgctctc tgctcaccat ggctcacgcc    120

<210> SEQ ID NO 195
<211> LENGTH: 120
```

```
<212> TYPE: DNA
<213> ORGANISM: Homo sapiens

<400> SEQUENCE: 195
cacagcatga cacaatcgcc tccttcctgc tcataaacct cctcctctct ctccttgctt    60
ccttatgata ctattttgca ccaggggatc ctcatctcac accactccac tgcctcttcc   120

<210> SEQ ID NO 196
<211> LENGTH: 120
<212> TYPE: DNA
<213> ORGANISM: Homo sapiens

<400> SEQUENCE: 196
cacagcatgg cacagtcgcc tccttcctgc tcacaaaccc tcaggcactt acttctcctt    60
ccagctctca gaagccctga acaaaggagc tgccctgctc tttcctcagc aaggagaatg   120

<210> SEQ ID NO 197
<211> LENGTH: 120
<212> TYPE: DNA
<213> ORGANISM: Homo sapiens

<400> SEQUENCE: 197
cacagcatgg cacagtcgcc tccttcctgc tcataaacct catccttctc tctccttgca    60
gctcctagac cccttaaca gaggcttctc tttgcttctc cctccccatg ggaaacaagt   120

<210> SEQ ID NO 198
<211> LENGTH: 120
<212> TYPE: DNA
<213> ORGANISM: Homo sapiens

<400> SEQUENCE: 198
cacagtgtgg catagtcgcc tccttcctgt tcacaaacct catccttctc tctccttgca    60
cctcctagag cccttaaca gaggcctctc tttgctcctc acttttgatg ggaaagaagt   120

<210> SEQ ID NO 199
<211> LENGTH: 120
<212> TYPE: DNA
<213> ORGANISM: Homo sapiens

<400> SEQUENCE: 199
cacagcatgg ctgagtcagt tccctccagg gtgcaaaccc tctggctgct cttctcccag    60
ttgaactcca agaaaacatt tgaaaagcc tcttccttat cttcctaccc cagaagaaag   120

<210> SEQ ID NO 200
<211> LENGTH: 120
<212> TYPE: DNA
<213> ORGANISM: Homo sapiens

<400> SEQUENCE: 200
cacagcccag cagagtcact gacattctgt atataaactt ccgccttagc tttgacttga    60
gaactgcagg ccccacccag gtttcactcc ttcaagggaa gcttttagtt gtttggaagg   120

<210> SEQ ID NO 201
<211> LENGTH: 120
<212> TYPE: DNA
<213> ORGANISM: Homo sapiens

<400> SEQUENCE: 201
cacagcccat cagagtcact gacgttctgt atataaactt cctgccttag ctttgccttg    60
```
agagctgcag gccccaccca gatttcactc cttcaaggga agcttttagt tgtttggaag    120

<210> SEQ ID NO 202
<211> LENGTH: 120
<212> TYPE: DNA
<213> ORGANISM: Homo sapiens

<400> SEQUENCE: 202
cacagcccta caaagccaac cacattctgt gcacaaacct ccctggccca atgtggagca    60
acctcagccc tgacatatct gtgagaacct ggggactgca gggagaaaga aaggcaattt    120

<210> SEQ ID NO 203
<211> LENGTH: 120
<212> TYPE: DNA
<213> ORGANISM: Homo sapiens

<400> SEQUENCE: 203
cacagccctg cagagtcact ggaactctgt gcactaatct ctctgcttcc gtgtacagca    60
gtctcagacc agacagctgt gagaacctgg ggccttcagg gggaaagata aacaatttca    120

<210> SEQ ID NO 204
<211> LENGTH: 120
<212> TYPE: DNA
<213> ORGANISM: Homo sapiens

<400> SEQUENCE: 204
atgcaggcct gcagagccaa gaacattctg tgtacaaaca tccctgcccc agtgtggaga    60
acttcagccc taacatatct gtgagaactt gaggactgta gtgggaaaga aaagcagttt    120

<210> SEQ ID NO 205
<211> LENGTH: 120
<212> TYPE: DNA
<213> ORGANISM: Homo sapiens

<400> SEQUENCE: 205
cacagccttg cagagtcacc gctttcctgt gcagaaacct tcggggcctg ccaggaagcc    60
gtgggggcca cggagggctc gggtgaacat ttcctccaag agcccgaag aagcttcaga    120

<210> SEQ ID NO 206
<211> LENGTH: 120
<212> TYPE: DNA
<213> ORGANISM: Homo sapiens

<400> SEQUENCE: 206
cacagccctg cagagtcacc gcctccctgt gcacaaacct cctggatcta atcagaaaac    60
cgtgggggca acgcatccag ctgagcctca gcactcggtt cagcattctg taagacctca    120

<210> SEQ ID NO 207
<211> LENGTH: 120
<212> TYPE: DNA
<213> ORGANISM: Homo sapiens

<400> SEQUENCE: 207
acacagcctt acagagccac tgcatccctg tgcacaaacc tccggctca gccaggaagc    60 tgtgggccgt gtgtgcacct gcacccaagg ctccagtctc cattccctga tggcctctga    120

<210> SEQ ID NO 208
<211> LENGTH: 120
<212> TYPE: DNA
<213> ORGANISM: Homo sapiens

<400> SEQUENCE: 208

```
cacattgatg cagagccaca tcctctcagt ccacaaacat cctccagacc tgccttggaa    60
acagcggtgg gccaggaagg gaaacgcgtt acctgtacag tgaacaggtc agctctacgg   120
```

<210> SEQ ID NO 209
<211> LENGTH: 120
<212> TYPE: DNA
<213> ORGANISM: Homo sapiens

<400> SEQUENCE: 209

```
cacagccctg catgagcatc agccttctgt gcaataacat tcctgcccca ctcaggaagt    60
gacggtgagg ggagggctgc cagccagagg ggctcaggcc ctggagagtg acaggcctt   120
```

<210> SEQ ID NO 210
<211> LENGTH: 120
<212> TYPE: DNA
<213> ORGANISM: Homo sapiens

<400> SEQUENCE: 210

```
cacagaccct ggagaattac tggctttctg tacccaaacc ctcctatctc acttgaggat    60
gtaataggga gaaggaggtg ggggctgcca cacaacttta gccaagcccc agagatgctt   120
```

<210> SEQ ID NO 211
<211> LENGTH: 120
<212> TYPE: DNA
<213> ORGANISM: Homo sapiens

<400> SEQUENCE: 211

```
cacagcgatc ttcaggcctc tatcagctgt ctccaaacct gcagctgggc cacatatgct    60
cttctgacat ggggctcctg agatgtggct gggacctttg ccaagacatg aagtctcaga   120
```

<210> SEQ ID NO 212
<211> LENGTH: 120
<212> TYPE: DNA
<213> ORGANISM: Homo sapiens

<400> SEQUENCE: 212

```
cacagtgata cccaggcctc caagacctgt actcaaacct aaagctgagc cgcagatgct    60
cccctagcac agatgccacc acaggagta tggggaactt accagaaggt tcatccatga   120
```

<210> SEQ ID NO 213
<211> LENGTH: 120
<212> TYPE: DNA
<213> ORGANISM: Homo sapiens

<400> SEQUENCE: 213

```
cacagtactc cctaggcacc tgcaacctgt atccaaacat gcagctgggt agaagtacca    60
taacagaagc atcagcaata ggggccctga gcctgagtag acgtgaagaa ctaaggcatg   120
```

<210> SEQ ID NO 214
<211> LENGTH: 120
<212> TYPE: DNA
<213> ORGANISM: Homo sapiens

<400> SEQUENCE: 214

```
cacagtgctc cccaggcacc tgcggcctgt acacaaaccc tcatccgggc tcggttcctc    60
taccagtaac aaccacatca cgaggccacc gcagcagcat tttgcacagc ttaatattcc   120
```

<210> SEQ ID NO 215
<211> LENGTH: 120
<212> TYPE: DNA
<213> ORGANISM: Homo sapiens

<400> SEQUENCE: 215
cacagtagtg ccctggcagc tgcttcctgc acccaaactc tgctaactct cacaatcaga     60
gctcatggct gtgctgtctc ccaaaggcta atcacagctc ctgacagaat ggggggtgt    120

<210> SEQ ID NO 216
<211> LENGTH: 120
<212> TYPE: DNA
<213> ORGANISM: Homo sapiens

<400> SEQUENCE: 216
cacagtgctc ttgaggcacc tgctgcctgc acccaaaccc tgctgccagc cccagtcacg     60
aggctgccac atgcctccag ctccgcctcg cacagcttat ggcatgaata gagagaacaa    120

<210> SEQ ID NO 217
<211> LENGTH: 120
<212> TYPE: DNA
<213> ORGANISM: Homo sapiens

<400> SEQUENCE: 217
cacagcgttc cccaggcacc tgcaacttgt atcaaaaccc tgcagctgag gatctgaaat     60
gatggcagag gtatctctgc tgttcttcct cttgaaggag tatttattta atgcccagga    120

<210> SEQ ID NO 218
<211> LENGTH: 120
<212> TYPE: DNA
<213> ORGANISM: Homo sapiens

<400> SEQUENCE: 218
cacagtgctc cctagtcacc tgcagcctgt actcaaattc tacagctgag gctctgcaac     60
tgtaagatgg ggaacttgct acattgagca agccctcaaa aataaactat acggaaaagc    120

<210> SEQ ID NO 219
<211> LENGTH: 120
<212> TYPE: DNA
<213> ORGANISM: Homo sapiens

<400> SEQUENCE: 219
cacagtgcac aacaggcacc tgcaaccaat acccaaactc tatagctggg gctctaactg     60
catgttttat cttgagactg agcaatgttt ttgcattaag aggacttcta aattgacact    120

<210> SEQ ID NO 220
<211> LENGTH: 120
<212> TYPE: DNA
<213> ORGANISM: Homo sapiens

<400> SEQUENCE: 220
cacagtgctc cccaggcacc tggagcccgt acctaaactc taaagttgag gcatcatttc     60
ttactcctgt ctttcagact tgtctgtctc tatccttggt cagatgatgt aaaatgttta    120

<210> SEQ ID NO 221
<211> LENGTH: 120
<212> TYPE: DNA
<213> ORGANISM: Homo sapiens

<400> SEQUENCE: 221

```
cacagtgccc acagtcacct gcacccggta cctaaagctt gctgaggggc ctgggcacac    60 ctcctttat aagggccctg ggcactgac tataactctg ctgcatacaa agggaaatat    120
```

<210> SEQ ID NO 222
<211> LENGTH: 120
<212> TYPE: DNA
<213> ORGANISM: Homo sapiens

<400> SEQUENCE: 222

```
agtagtgtct ccccagcacc tgcagcctgt accataacct gcagccggga cccttgacac    60
aggctagcct tgcaggtggg agtgaagatt tttttttttt ttttgtatag agggaacttt    120
```

<210> SEQ ID NO 223
<211> LENGTH: 120
<212> TYPE: DNA
<213> ORGANISM: Homo sapiens

<400> SEQUENCE: 223

```
cacagggtcc ccaagcacct gcagcctgta ccacaacctg catccgggac ccttgacaca    60
gccttgcctt gcaggtggga gtgaaggtgt tgtctttata tgtagagaga acttctttat    120
```

<210> SEQ ID NO 224
<211> LENGTH: 120
<212> TYPE: DNA
<213> ORGANISM: Homo sapiens

<400> SEQUENCE: 224

```
cacagtgttc cccaggaacc tgcagcctct acgcaaaccc tgccaaagca gcttcttaga    60
agccctaata gtgggtagaa ttagtggtta tgtctttcag tcaagaagag tctacaaaca    120
```

<210> SEQ ID NO 225
<211> LENGTH: 120
<212> TYPE: DNA
<213> ORGANISM: Homo sapiens

<400> SEQUENCE: 225

```
cactgtgctc cacaggcact tgaagccagt atgcaaacct gcacctggag gttatcaagg    60
aggcatagga gttagagtag accgttattt tttatgcaga atatgatttc actagtgaat    120
```

<210> SEQ ID NO 226
<211> LENGTH: 120
<212> TYPE: DNA
<213> ORGANISM: Homo sapiens

<400> SEQUENCE: 226

```
cacagcacta ctgctccagt gtcagcttgg ttccctagga atgggggttt ctagaacctg    60
aatgctgaca aataagagtt gtatatgtgt ataccatgca acctgcgttt aaaaatgtat    120
```

<210> SEQ ID NO 227
<211> LENGTH: 120
<212> TYPE: DNA
<213> ORGANISM: Homo sapiens

<400> SEQUENCE: 227

```
cacagtgctg ttcaggcacc tgcagcccat acgcaaacct gtgtctggtg ttgcactgtt    60
accagcattg acaaagaacc atgagtagga tggaaaagac aagttcgttg aattacagtt    120
```

<210> SEQ ID NO 228

```
<211> LENGTH: 120
<212> TYPE: DNA
<213> ORGANISM: Homo sapiens

<400> SEQUENCE: 228
cacagtgctc ccctgacgcc accagtctgt acccaaacct gcagctggtg ggcccactcc    60
tcctgcagga actatgactg tgaggcttcg ttcactgtct gtacatttct ttctgcaagg   120

<210> SEQ ID NO 229
<211> LENGTH: 120
<212> TYPE: DNA
<213> ORGANISM: Homo sapiens

<400> SEQUENCE: 229
cacagtgctc cccaaacacc tgcagcctgt actcaaactt gcagctggaa ctctagtctc    60
tatgctgcct tcagctctta gtcctcttgg catgaaatgt gattatgcat gccacctttg   120

<210> SEQ ID NO 230
<211> LENGTH: 120
<212> TYPE: DNA
<213> ORGANISM: Homo sapiens

<400> SEQUENCE: 230
cacagtgctc cccagacacc tgcagtctgt acccaaacct gccatgcccc aggaatgcct    60
gatgtagagc ttagactgca gggtagtgaa actccccttg ctctctagtt tcaagtggaa   120

<210> SEQ ID NO 231
<211> LENGTH: 120
<212> TYPE: DNA
<213> ORGANISM: Homo sapiens

<400> SEQUENCE: 231
cacagtgctc tccaggcacc tgcagcccgt actcaaacct gctttgggga ctcagactgg    60
gagacacata gactcgcttc catttacaca tgccaatatg agagattatg ctttgaagta   120

<210> SEQ ID NO 232
<211> LENGTH: 120
<212> TYPE: DNA
<213> ORGANISM: Homo sapiens

<400> SEQUENCE: 232
cacagtgctc cccaggcacc tgaagcctgt acccaaacct gcagttgagg ttccagccaa    60
accccacagt gggagcttac gtaggcagag atgtagccta gttttcatct gcatatgcaa   120

<210> SEQ ID NO 233
<211> LENGTH: 120
<212> TYPE: DNA
<213> ORGANISM: Homo sapiens

<400> SEQUENCE: 233
cactgtgctc ttcagacacc tgcagcctat acatgaaacc atagctgaag gcctaaccca    60
tccccgagag tggcagtagg tcccgatgtg attagcattg cattcccact gcctacatct   120

<210> SEQ ID NO 234
<211> LENGTH: 120
<212> TYPE: DNA
<213> ORGANISM: Homo sapiens

<400> SEQUENCE: 234
cacagtgctc cccaagcacc tgctgcctgt ctccaaatct tgccctgggt cttcaggagc    60
```
agatcatcct actctcccca aagagcgggc gccagagaaa gccaaagtca caatgtctgt    120

<210> SEQ ID NO 235
<211> LENGTH: 120
<212> TYPE: DNA
<213> ORGANISM: Homo sapiens

<400> SEQUENCE: 235
cacagaactc ttcaggcacc tgcaacctgt actcaaacct gcaactggga gtccagtcac    60
attctttgtc tttgaacggg ttttgggtta gaatggttta ccataatgtg cttgtttcta    120

<210> SEQ ID NO 236
<211> LENGTH: 120
<212> TYPE: DNA
<213> ORGANISM: Homo sapiens

<400> SEQUENCE: 236
cacattgctt ctcaggcacc tgtatcctgt acccaaacct gcacctggga ctaaagccac    60
actctatttc ctttaccttt aagtcaggga ttttgctgta aggtattttt aatgtacgga    120

<210> SEQ ID NO 237
<211> LENGTH: 120
<212> TYPE: DNA
<213> ORGANISM: Homo sapiens

<400> SEQUENCE: 237
cacattgctt tccaggcatc tgtaaccatc acccaaacct gagatgggag gtgaagcagc    60 atcccttttcc tttgcaataa attttagtta tagcacttgt cattttgttt gttcataagt    120

<210> SEQ ID NO 238
<211> LENGTH: 120
<212> TYPE: DNA
<213> ORGANISM: Homo sapiens

<400> SEQUENCE: 238
gcagcaagta cacattgctt cccaggcacc tgctacccgt acacaaacct gagactggag    60
ctgaagctgc acccccttc ctttgtcata gatcgtcaat tatagcattt gtcatattgt    120

<210> SEQ ID NO 239
<211> LENGTH: 120
<212> TYPE: DNA
<213> ORGANISM: Homo sapiens

<400> SEQUENCE: 239
cacacttcag cccagccttt ctgggccaac tctccatctg tagagacaca tccaaggccc    60
agttatccct gcagctgagc tccgtgatgg ccaagggcag ggccgcacat tcccgtggga    120

<210> SEQ ID NO 240
<211> LENGTH: 120
<212> TYPE: DNA
<213> ORGANISM: Homo sapiens

<400> SEQUENCE: 240
gcttgttgct catgtagctc agccatagga agagctgccc cggcggacat agatctggag    60
gtggcgactg gactcttgag gagtgggttg gaattttttgc tgccttcatg acctgtgcac    120

<210> SEQ ID NO 241
<211> LENGTH: 120
<212> TYPE: DNA

<213> ORGANISM: Homo sapiens

<400> SEQUENCE: 241
aatccaaccc actcctcaag agtccagtca ccatctccag atccacatcc aaaaaacagt    60
ttctcctaca gctgagctac cttaacaagg agtacacaac catgattttt atacaaaaga   120

<210> SEQ ID NO 242
<211> LENGTH: 120
<212> TYPE: DNA
<213> ORGANISM: Homo sapiens

<400> SEQUENCE: 242
catcatgcac cctccaccca ggtccatgtc cccatcaaca gtgactcaac caagagccag    60
ttctctgtga agctcagctc catgaccacc taggacacgg ctgagtatta ctgtgaaaga   120

<210> SEQ ID NO 243
<211> LENGTH: 120
<212> TYPE: DNA
<213> ORGANISM: Homo sapiens

<400> SEQUENCE: 243
gtgaagggag cacaaattac aacccactgc tcaagagtcc atatccagat ccaagaaaca    60
gttcttacag ctgagctctg tgcccagtga acacacaact acgcattttt aagcaaaaga   120

<210> SEQ ID NO 244
<211> LENGTH: 120
<212> TYPE: DNA
<213> ORGANISM: Homo sapiens

<400> SEQUENCE: 244
ttactcccct cttctcaaga gtccagtcac catctccaga tccatgtcca aaaagtagtt    60
cttcttacag ctgaactatg tgaggaacaa acacatagcc atgtatttta gagcaaaaga   120

<210> SEQ ID NO 245
<211> LENGTH: 120
<212> TYPE: DNA
<213> ORGANISM: Homo sapiens

<400> SEQUENCE: 245
ttacaaccca cttctcaaga gtccatatcc ggatccaaga aacagttctt acagctgagc    60
tctgtgccca gtgaacacac aactacgcat tttgaagcaa aagatgcaat gaagggcctt   120

<210> SEQ ID NO 246
<211> LENGTH: 120
<212> TYPE: DNA
<213> ORGANISM: Homo sapiens

<400> SEQUENCE: 246
ttacaaccca ctgctcaaga gtccatatcc agatccaaga aacagttctt acagctgagc    60
tctgtgccca gtgaacacac aactacgcat ttttaagcaa aagacgcaat gaagggcctt   120

<210> SEQ ID NO 247
<211> LENGTH: 120
<212> TYPE: DNA
<213> ORGANISM: Homo sapiens

<400> SEQUENCE: 247
ttactcccct cttctcaaga gtccagtcac catctccaga tccatgtcca aaaagtactt    60
cttcttacag gtgaactatg tgagcaacaa acacatagcc atgtatttta gagcaaaaga   120

<210> SEQ ID NO 248
<211> LENGTH: 120
<212> TYPE: DNA
<213> ORGANISM: Homo sapiens

<400> SEQUENCE: 248
ttacatccca cttctcaaga gtccatatcc agatccaaga aacagttctt acagctgagc    60
tctgtgccca gtgaacacac aactacacat tttgaagcaa agacgcaat gaagggcctt    120

<210> SEQ ID NO 249
<211> LENGTH: 77
<212> TYPE: DNA
<213> ORGANISM: Homo sapiens

<400> SEQUENCE: 249
agcctggtga agcccttgca aaccccctca ctcacctgtg ctgcctctgg attctctgtc    60
acaatcagtg cttcctg                                                   77

<210> SEQ ID NO 250
<211> LENGTH: 120
<212> TYPE: DNA
<213> ORGANISM: Homo sapiens

<400> SEQUENCE: 250
catgaaggga gcacaaattc taacccactc ctcaagagtc cagtcaccac ctccagatct    60
atgtccaaaa acagctcttc gtatggctga gtgacattag caacaagcac acagccatgt   120

<210> SEQ ID NO 251
<211> LENGTH: 120
<212> TYPE: DNA
<213> ORGANISM: Homo sapiens

<400> SEQUENCE: 251
catgaaggga gcacaaattc taacccactc ctcaagagtc cagtcaccac ctccagatct    60
atgtccaaaa acagctcttc gtatggctga gtgacattag caacaagcac acaaccatgt   120

<210> SEQ ID NO 252
<211> LENGTH: 120
<212> TYPE: DNA
<213> ORGANISM: Homo sapiens

<400> SEQUENCE: 252
acgatgatcc atctctgcag agccaactct ccttctccag agattcatcc aagaaacaat    60
tttgactata cctgagctct gtgacatctg aggacatggt ttgtattact gtgcaagaca   120

<210> SEQ ID NO 253
<211> LENGTH: 120
<212> TYPE: DNA
<213> ORGANISM: Homo sapiens

<400> SEQUENCE: 253
gacctgaata gcacacactt accctctgcc tcacctacac tgttactggc cactccgtca    60
caaccagtcc ttactagtgg acctggatct gccggctctc agggaggggc tgcaatggat   120

<210> SEQ ID NO 254
<211> LENGTH: 120
<212> TYPE: DNA
<213> ORGANISM: Homo sapiens

<400> SEQUENCE: 254
acgcaaccca cgcctcaaga gtccagtcac catctccaga tccacatcca aaacacagtt      60
tcttctacag ctgagctacc tgagcaacga gtacacaacc atgaattttt acacaaaaga     120

<210> SEQ ID NO 255
<211> LENGTH: 120
<212> TYPE: DNA
<213> ORGANISM: Homo sapiens

<400> SEQUENCE: 255
aattctaacc cactcctcat gagctcagtc accatctcca gatccacgtc caagaaccaa      60
attttctttt agctgagttc tgtgaccaac aatgccacaa ccttgtatta ctgtgagagg     120

<210> SEQ ID NO 256
<211> LENGTH: 120
<212> TYPE: DNA
<213> ORGANISM: Homo sapiens

<400> SEQUENCE: 256
attccaaccc actcctcaag agtccagtca ccatctccag atccatgtcc aaaaagcagt      60
tcttcctaca gccgagctaa gtgagtcaca agcacacagc catgtatttt taacaaaaga     120

<210> SEQ ID NO 257
<211> LENGTH: 120
<212> TYPE: DNA
<213> ORGANISM: Homo sapiens

<400> SEQUENCE: 257
aaattcccac ccactcctta tgaatccagt caccatctcc aaattcgggt ccaaaaaaca      60 cttgtttta cagtggagct atgtgagcaa caagctcaca gccatgtttt aaagaagaga     120

<210> SEQ ID NO 258
<211> LENGTH: 120
<212> TYPE: DNA
<213> ORGANISM: Homo sapiens

<400> SEQUENCE: 258
attactcccc tttcctcaag agtccagtca ccatcccag atccatgtcc aaaaacagtt       60
cttcctacag ctgagctaca tgagcaacaa tcacatagcc atatatttt cagcaataga     120

<210> SEQ ID NO 259
<211> LENGTH: 120
<212> TYPE: DNA
<213> ORGANISM: Homo sapiens

<400> SEQUENCE: 259
ttccaaccca ctcctcaaga gtccagtcac tatctccaga tccacatcca aaaacagtg      60 tttcctgtag ctgagctacc tgagcaacaa gtacacaacc atgaatttta atacaaaaga     120

<210> SEQ ID NO 260
<211> LENGTH: 120
<212> TYPE: DNA
<213> ORGANISM: Homo sapiens

<400> SEQUENCE: 260
atgcctaggt gtgaagatca cacactgacc tcacccatgc tgtctctggc cacttcatca      60
caaccaatgc ttaatattgg acgtggatct gccagtcccc ggggaatggg ttgaatggat     120

<210> SEQ ID NO 261
<211> LENGTH: 120
<212> TYPE: DNA
<213> ORGANISM: Homo sapiens

<400> SEQUENCE: 261

```
ggcagcaaca gggagaaatt caagaggaag ttcttacatg caccettacg tgcacggtct      60
cactgagatc tttacttcct ttatcacgtt tgttctgtaa atcacaacga atggtgcatt     120
```

<210> SEQ ID NO 262
<211> LENGTH: 120
<212> TYPE: DNA
<213> ORGANISM: Homo sapiens

<400> SEQUENCE: 262

```
tgggactctc cttgagtaaa aagatgatta acaatcctca aatacactca gttcaggaga      60
ttctctttta agatgattaa cctgagagct caggaaaagt ccgtgtatta ctttgaggga     120
```

<210> SEQ ID NO 263
<211> LENGTH: 120
<212> TYPE: DNA
<213> ORGANISM: Homo sapiens

<400> SEQUENCE: 263

```
tcagagttac tctccatgag tacaaataaa ttaacagtcc caagcgacac cttttcatgt      60
gcagtctacc ttaaagggac caaactgaaa gtcaaggaca aggccttgta atactgtgag     120
```

<210> SEQ ID NO 264
<211> LENGTH: 120
<212> TYPE: DNA
<213> ORGANISM: Homo sapiens

<400> SEQUENCE: 264

```
accagaagaa tgctatcatc atcttttctg ttcttttgga aggaatgccc cctctactca      60
cctccacttg cctgcatata tttctatttg tctttgcttt tcagcagttt taataagatt     120
```

<210> SEQ ID NO 265
<211> LENGTH: 120
<212> TYPE: DNA
<213> ORGANISM: Homo sapiens

<400> SEQUENCE: 265

```
gggttacttt ccatgagtac aaataaatta acaatctcaa gcaacaccct tttaagtgca      60
gtctgcctta caatgaccaa tctgaaagcc aaggacaagg tcatgtatta ctgtgagtga     120
```

<210> SEQ ID NO 266
<211> LENGTH: 120
<212> TYPE: DNA
<213> ORGANISM: Homo sapiens

<400> SEQUENCE: 266

```
gcaagctcca ggaccagggt tgatgtgggc agcaacaggg agaaattgaa gaggaagctc      60
tcagtggtgc cctccatgaa tacaaagaat cttcacagtc cccaggacac ccttacgtgc     120
```

<210> SEQ ID NO 267
<211> LENGTH: 120
<212> TYPE: DNA
<213> ORGANISM: Homo sapiens

<400> SEQUENCE: 267

```
agaggaagct ctcagtggtg ccctccatga atacaaagaa tcttcacagt ccccaggaca    60
cccttacgtg catggtctca ctgatatctt tacttccttt atcacttttg ttatgtaaat   120
```

<210> SEQ ID NO 268
<211> LENGTH: 120
<212> TYPE: DNA
<213> ORGANISM: Homo sapiens

<400> SEQUENCE: 268

```
gggttactct ccatgagtac agataaatca acattcccaa gtgacaccct ttcaagtgca    60
gtctacctta caaggaccaa cctgaaagcc aagggcaagg ccgtatatta cagtgaggga   120
```

<210> SEQ ID NO 269
<211> LENGTH: 120
<212> TYPE: DNA
<213> ORGANISM: Homo sapiens

<400> SEQUENCE: 269

```
aatgggactc gccttcagta caaagaagat taacagtcct cagagacact gttcagaaga    60
ttctctttta agataataaa actgagagcc caagacaagt ctgtgtatta ctgtgaggga   120
```

<210> SEQ ID NO 270
<211> LENGTH: 120
<212> TYPE: DNA
<213> ORGANISM: Homo sapiens

<400> SEQUENCE: 270

```
aatgggactc gccttcagta caaagaagat taacagtcct cagagacact gttcagaaga    60
ttctctttta agataataaa accgagagcc caagacaagt ctgtgtatta ctgtgaggga   120
```

<210> SEQ ID NO 271
<211> LENGTH: 120
<212> TYPE: DNA
<213> ORGANISM: Homo sapiens

<400> SEQUENCE: 271

```
agtgggactc tccttcagta caaagaagat taacagtcct cagagacact gttcagaaga    60
ttctctttta agataattaa accaagagcc caggacaagt ctgtgtatta ctgtgaggga   120
```

<210> SEQ ID NO 272
<211> LENGTH: 120
<212> TYPE: DNA
<213> ORGANISM: Homo sapiens
<220> FEATURE:
<221> NAME/KEY: misc_feature
<222> LOCATION: (80)..(80)
<223> OTHER INFORMATION: n is a, c, g, or t

<400> SEQUENCE: 272

```
tttaggaaga atgccccctc aactcatctc cacttgtctg catgtatttc tatttgtctt    60
ggacgttccc aacagcctcn cgaacactca cctcacccta caatgctgct cgaggggtc   120
```

<210> SEQ ID NO 273
<211> LENGTH: 120
<212> TYPE: DNA
<213> ORGANISM: Homo sapiens

<400> SEQUENCE: 273

```
attttcctct tgcttataag gttttaacca gaagaatgct gtcatcatct ttcctgttct    60
tttagaagga atgccccctc aactcatctc cacttgtctg catgtatttc tatttgtctt   120
```

<210> SEQ ID NO 274
<211> LENGTH: 99
<212> TYPE: DNA
<213> ORGANISM: Homo sapiens

<400> SEQUENCE: 274
gatttatcat ctcaagagac aatgtcaaga agatgctgtt tctgcaaatg ggcaatctgc    60
aaaccaagga cacgtcacta cattactgtg caagagaag                           99

<210> SEQ ID NO 275
<211> LENGTH: 120
<212> TYPE: DNA
<213> ORGANISM: Homo sapiens

<400> SEQUENCE: 275
caatgcagac tatgttaggg gcagactcac cacttccaga gacaacacca agtacatgct    60
gtacatgcaa atgaacagcc tgagaaccca gaacatggca gcatttaact gtgcaggaaa   120

<210> SEQ ID NO 276
<211> LENGTH: 120
<212> TYPE: DNA
<213> ORGANISM: Homo sapiens

<400> SEQUENCE: 276
ggtgctctgc tccagcacaa agaagattca cagttcctgg ggacaacact taacatcaca    60
atctccctta aaattatcta ctggaaagct gaggagtagg cagtgtatta ctgtgagaga   120

<210> SEQ ID NO 277
<211> LENGTH: 99
<212> TYPE: DNA
<213> ORGANISM: Homo sapiens

<400> SEQUENCE: 277
gatttattgt ctccagagac aatgtcaaga atatgctata tctgcaaatg ggcgatctgt    60
aaaccaagaa cacatcagta tatcactgtg caagaggag                           99

<210> SEQ ID NO 278
<211> LENGTH: 120
<212> TYPE: DNA
<213> ORGANISM: Homo sapiens

<400> SEQUENCE: 278
agcataatga agattcacaa ttcccaggga caccaattac cagcacagtc tcccttaaaa    60
taatctactt ggaagctgag ggggctctca caggggtagg cagtgtatta ctgtgagaga   120

<210> SEQ ID NO 279
<211> LENGTH: 120
<212> TYPE: DNA
<213> ORGANISM: Homo sapiens

<400> SEQUENCE: 279
aggtttactc ttcatgagta caaataaatt aactggtcca gcgacaccct ttcacgtgca    60
ctctacctta caatgactaa cctgaaagcc aaggacaagg ttgtgtaata ctgtgagctt   120

<210> SEQ ID NO 280
<211> LENGTH: 120
<212> TYPE: DNA
<213> ORGANISM: Homo sapiens

<400> SEQUENCE: 280
tggtaccctc catcaataca agaaaaatc ataatcctca gggacaccct tgtcagcaca       60
gtctccctca aaatgaccaa cctgagagcc gaggagaagg ccatgtatta ctgtgagaga     120

<210> SEQ ID NO 281
<211> LENGTH: 120
<212> TYPE: DNA
<213> ORGANISM: Homo sapiens

<400> SEQUENCE: 281
gggttactct ccatgagtac aagtaaatta acagtcccaa gcaacaccct ttcaagtgca      60
gtctacctta aaatgaccaa tgtgaaagcc aaggacaaga ccttgtatta ctgtgagtga    120

<210> SEQ ID NO 282
<211> LENGTH: 120
<212> TYPE: DNA
<213> ORGANISM: Homo sapiens

<400> SEQUENCE: 282
ctaagcccca accttcaggg cagagctagc atctccagaa acacatagta aaaaacaaga     60
aaacttacag ctgagaagtg tgatggctgg ggatgcaggc gtgtattact gtgctcaagg   120

<210> SEQ ID NO 283
<211> LENGTH: 120
<212> TYPE: DNA
<213> ORGANISM: Homo sapiens

<400> SEQUENCE: 283
aactatgcac agaagtttca gggcagagtc accatgacca gggacacgtc catcagcaca     60
gcctacacgg agctgagcag cctgagatct gaggacacgg ccacgtatta ctgtgcgaga   120

<210> SEQ ID NO 284
<211> LENGTH: 120
<212> TYPE: DNA
<213> ORGANISM: Homo sapiens

<400> SEQUENCE: 284
ctatgcacag aagtttcagg gcagagtcac catgaccagg gacacgtcca tcagcacagc     60
ctgcacggag ctgagcagcc tgagatctga ggacacggcc acgtattact gtgcgagaga   120

<210> SEQ ID NO 285
<211> LENGTH: 120
<212> TYPE: DNA
<213> ORGANISM: Homo sapiens

<400> SEQUENCE: 285
ctatgcacag aagtttcagg gcagagtcac catgaccagg gacacgtcca tcagcacagc     60
ctacacggag ctgagcagcc tgagatctga ggacacagcc acgtattact gtgcgagaga   120

<210> SEQ ID NO 286
<211> LENGTH: 120
<212> TYPE: DNA
<213> ORGANISM: Homo sapiens

<400> SEQUENCE: 286
ctatgcacag aagtttcagg gcagagtcac catgaccagg gacacgtcca tcagcacagc     60
ctacatggag ctgagcagcc tgagatctga ggacacggcc acgtattact gtgcgagaga   120

```
<210> SEQ ID NO 287
<211> LENGTH: 120
<212> TYPE: DNA
<213> ORGANISM: Homo sapiens

<400> SEQUENCE: 287
aactacccac agaagctcca gggcagagtc accatgacca gagacacatc cacgagcaca      60
gcctacatgg agctgagcag cctgagatct gacgacatgg ccgtgtatta ctgtgcgaga     120

<210> SEQ ID NO 288
<211> LENGTH: 120
<212> TYPE: DNA
<213> ORGANISM: Homo sapiens

<400> SEQUENCE: 288
ctacccacag aagctccagg gcagagtcac catgaccaga gacacatcca cgagcacagc      60
ctacatggag ctgagcagcc tgagatctga cgacatggcc gtgtattact gtgcgagaga     120

<210> SEQ ID NO 289
<211> LENGTH: 120
<212> TYPE: DNA
<213> ORGANISM: Homo sapiens

<400> SEQUENCE: 289
aaatattcac agaagctcca gggcagagtc accattacca gggacacatc ttcgagcaca      60
gcctacatgc agctgagcag cctgagatct gaggacacgg ccgtgtatta ctgtgcgaga     120

<210> SEQ ID NO 290
<211> LENGTH: 120
<212> TYPE: DNA
<213> ORGANISM: Homo sapiens

<400> SEQUENCE: 290
atattcacag aagctccagg gcagagtcac cattaccagg gacacatctg cgagcacagc      60
ctacatgcag ctgagcagcc tgagatctga ggacacggcc gtgtattact gtgcgagaga     120

<210> SEQ ID NO 291
<211> LENGTH: 120
<212> TYPE: DNA
<213> ORGANISM: Homo sapiens

<400> SEQUENCE: 291
aagtattcac agaagctcca gggcagagtc accattacca gggacacatc tgcgagcaca      60
gcctacatgc agctgagcag cctgagatct gaggacacgg ccgtgtatta ctgtgcgaga     120

<210> SEQ ID NO 292
<211> LENGTH: 120
<212> TYPE: DNA
<213> ORGANISM: Homo sapiens

<400> SEQUENCE: 292
cgtttctctg gctccaggtc tggcaacacg gcctccctga caatctctgg gctccaggct      60
gaggacgagg gagattatta ctgcagttca tatacagcca ctcctcatat tcctgtgatt     120

<210> SEQ ID NO 293
<211> LENGTH: 120
<212> TYPE: DNA
<213> ORGANISM: Homo sapiens

<400> SEQUENCE: 293
```
agctatgcac aaaagttcca ggccagagtc accataacca gggacacatc catgagcaca    60
gcctacatgg agctaagcag tctgagatct gaggacacgg ccatgtatta ctgtgtgaga   120

<210> SEQ ID NO 294
<211> LENGTH: 120
<212> TYPE: DNA
<213> ORGANISM: Homo sapiens

<400> SEQUENCE: 294
tatatgcaca gaattccagg gcagagtcac cacgacctgg gacacgtcta cagacacagc    60
ctacatggag ctgagcagcc tgagatctga ggacacagcc gtatattaat gtgcaagaca   120

<210> SEQ ID NO 295
<211> LENGTH: 120
<212> TYPE: DNA
<213> ORGANISM: Homo sapiens

<400> SEQUENCE: 295
ctatgcacag aagttccagg gcagagtcac cataaccagg gacacatcca tgggcacagc    60
ctacatggag ctaagcagcc tgagatctga ggacacggcc atgtattact gtgtgagaga   120

<210> SEQ ID NO 296
<211> LENGTH: 120
<212> TYPE: DNA
<213> ORGANISM: Homo sapiens

<400> SEQUENCE: 296
ctatgcacag aagtttcagg gcagagtcac catgaccagg gacatgtcca cgagcacagc    60
ctacatggag ctgagcagtc agagatctga ggacatagat gtgtactact gtgcgagaca   120

<210> SEQ ID NO 297
<211> LENGTH: 120
<212> TYPE: DNA
<213> ORGANISM: Homo sapiens

<400> SEQUENCE: 297
ctatgcacag aagttccagg ccagagtcac cataaccagg gacacatcca tgagcacagc    60
ctacatggag ctaagcagtc tgagatctga ggacacggcc atgtattact gtgtgagaga   120

<210> SEQ ID NO 298
<211> LENGTH: 120
<212> TYPE: DNA
<213> ORGANISM: Homo sapiens

<400> SEQUENCE: 298
gtccctgacc gattctctgg ctccaagtct ggcacctcaa cctccctggc catcagtggg    60
ctccggtccg aggtagaggc tgattattac tgtgcagcat gggatgacag cctgagtggt   120

<210> SEQ ID NO 299
<211> LENGTH: 120
<212> TYPE: DNA
<213> ORGANISM: Homo sapiens

<400> SEQUENCE: 299
gtgaagaagc ctggggcctc agtgaaggtc tcctgcaagg cttctggata caccttcacc    60
tactgctact tgcactgggt atgacaggcc cctggacaag gcttgaatg gacaggattt   120

<210> SEQ ID NO 300
<211> LENGTH: 120

```
<212> TYPE: DNA
<213> ORGANISM: Homo sapiens

<400> SEQUENCE: 300
ctatgcacag aagtttcagg gcagagtcac catgaccagg gacacgtcca cgagcacagc      60
ctacatggag ctgagcagtc agagatctga ggacatagat gtgtactact gtgcgagaca    120

<210> SEQ ID NO 301
<211> LENGTH: 120
<212> TYPE: DNA
<213> ORGANISM: Homo sapiens

<400> SEQUENCE: 301
ctacgcacag aagttccggg gcagagtcac cattaccagt gacaggtccg tgagcacagc      60
ctacatggag ctgagcagcc tgagatctga agacatggtc gtgtattcct gtgtgagaga    120

<210> SEQ ID NO 302
<211> LENGTH: 120
<212> TYPE: DNA
<213> ORGANISM: Homo sapiens

<400> SEQUENCE: 302
cactgcactg aacctccggg gcagagtctc catgaccaca gacacatcca caaacacagt      60
ctacatggag gtgaagagcc taagatctga cgacacggcc atatatttct gtgcgcgaga    120

<210> SEQ ID NO 303
<211> LENGTH: 120
<212> TYPE: DNA
<213> ORGANISM: Homo sapiens

<400> SEQUENCE: 303
ctatgcacag aagctccagg gcagagtcac catgaccaca gacacatcca cgagcacagc      60
ctacatggag ctgaggagcc tgagatctga cgacatggcc gtgtattact gtgcgagaga    120

<210> SEQ ID NO 304
<211> LENGTH: 120
<212> TYPE: DNA
<213> ORGANISM: Homo sapiens

<400> SEQUENCE: 304
ctatgcacag aagctccagg gcagagtcac catgaccaca gacacatcca cgagcacagc      60
ctacatggag ctgaggagcc tgagatctga cgacacggcc gtgtattact gtgcgagaga    120

<210> SEQ ID NO 305
<211> LENGTH: 120
<212> TYPE: DNA
<213> ORGANISM: Homo sapiens

<400> SEQUENCE: 305
cctgaccgat tctctggctc caagtctggc acctcagcct ccctggccat cactgggctc      60
caggctgacg atgaggcaga ttattactgc cagtcctatg acaggggtct gagtggtctc    120

<210> SEQ ID NO 306
<211> LENGTH: 120
<212> TYPE: DNA
<213> ORGANISM: Homo sapiens

<400> SEQUENCE: 306
aactatgcac agaagtttca gggcagggtc accacgacca gggacacgtc catcagcaca      60
```
gcctacatgg agctgagcag gctgagatct gacgcacagg ccgtgtatta ctgtgcgaga    120

<210> SEQ ID NO 307
<211> LENGTH: 120
<212> TYPE: DNA
<213> ORGANISM: Homo sapiens

<400> SEQUENCE: 307
ctatgcacag aagtttcagg gcagggtcac cgtgaccagg gacacgtcca tcaacacagt    60
ctacatggag ctgagcagac tgagatctga cgacacggcc gtgtattact gtgcgagaga    120

<210> SEQ ID NO 308
<211> LENGTH: 120
<212> TYPE: DNA
<213> ORGANISM: Homo sapiens

<400> SEQUENCE: 308
ctatgcacag aagtttcagg gctgggtcac catgaccagg gacacgtcca tcagcacagc    60
ctacatggag ctgagcaggc tgagatctga cgacacggcc gtgtattact gtgcgagaga    120

<210> SEQ ID NO 309
<211> LENGTH: 120
<212> TYPE: DNA
<213> ORGANISM: Homo sapiens

<400> SEQUENCE: 309
atccctgagc gattctctgg ctccagctca gggacaacag tcacgttgac catcagtgga    60
gtccaggcag aagacgaggt tgactattac tgtcaatcag cagacagcag tggtactccg    120

<210> SEQ ID NO 310
<211> LENGTH: 120
<212> TYPE: DNA
<213> ORGANISM: Homo sapiens

<400> SEQUENCE: 310
gtacgcacag aagttccagg gcagagtcac catgaccgag gacacatcta cagacacagc    60
ctacatggag ccggtcagcc tgagatctga cgacacggcc gtctattact gtgcaacaga    120

<210> SEQ ID NO 311
<211> LENGTH: 120
<212> TYPE: DNA
<213> ORGANISM: Homo sapiens

<400> SEQUENCE: 311
aagtattcac agaagtttca ggggagagtc accattacca gggacacatc ggcgaacaca    60
gcctacatgg agctgagtag cctaagatct gaagacacgg ctgtgtatta ctgtgcgaga    120

<210> SEQ ID NO 312
<211> LENGTH: 120
<212> TYPE: DNA
<213> ORGANISM: Homo sapiens

<400> SEQUENCE: 312
atattcacag gagttccagg gcagagtcac cattaccagg gacacatccg cgagcacagc    60
ctacatggag ctgagcagcc tgagatctga ggacatggct gtgtattact gtgcgagaga    120

<210> SEQ ID NO 313
<211> LENGTH: 120
<212> TYPE: DNA
<213> ORGANISM: Homo sapiens

<400> SEQUENCE: 313
cggggtccct gacaggttca gtggcagtgg atcgggcaca gattttacac tgaagatcag    60
cagagtggag cctgaggaca ttggggttta ttactgtatg cagtctctcc aaactcctca   120

<210> SEQ ID NO 314
<211> LENGTH: 120
<212> TYPE: DNA
<213> ORGANISM: Homo sapiens
<220> FEATURE:
<221> NAME/KEY: misc_feature
<222> LOCATION: (119)..(119)
<223> OTHER INFORMATION: n is a, c, g, or t

<400> SEQUENCE: 314
ctacgcacag aaattccagg acagagtcac cattactagg gacaggtcta tgagcacagc    60
ctacatggag ctgagcagcc tgagatctga ggacacagcc atgtattact gtgcaagana   120

<210> SEQ ID NO 315
<211> LENGTH: 120
<212> TYPE: DNA
<213> ORGANISM: Homo sapiens

<400> SEQUENCE: 315
ccaactacgc acagaaattc caggacagag tcaccattac cagggacagg tctatgagca    60
cagcctacat ggagctgagc agcctgagat ctgaggacac agccatgtat tactgtgcaa   120

<210> SEQ ID NO 316
<211> LENGTH: 120
<212> TYPE: DNA
<213> ORGANISM: Homo sapiens

<400> SEQUENCE: 316
gctacgcaca gaagttccag ggcagagtca ccatgaccag ggacacgtcc acgagcacag    60
tctacatgga gctgagcagc ctgagatctg aggacacggc cgtgtattac tgtgcgagag   120

<210> SEQ ID NO 317
<211> LENGTH: 120
<212> TYPE: DNA
<213> ORGANISM: Homo sapiens

<400> SEQUENCE: 317
atccctgaga gattctctgg ctccagctca gggacaatgg ccaccttgac cattagtggg    60
gcccaggtgg aggatgaagc tgactactac tgttactcaa cagacactaa tgataatcgg   120

<210> SEQ ID NO 318
<211> LENGTH: 120
<212> TYPE: DNA
<213> ORGANISM: Homo sapiens

<400> SEQUENCE: 318
aagttcgcac agaaattcca gggcagggtc accattacga gggacacgtc cacgagcaca    60
gtctacatga agctgagcag cttaagatct gaggacacgg ccgtgtatta ctgtgcgaca   120

<210> SEQ ID NO 319
<211> LENGTH: 120
<212> TYPE: DNA
<213> ORGANISM: Homo sapiens

<400> SEQUENCE: 319

```
ctacgcacag aagttccagg aaagagtcac cattaccagg acatgtcca caagtacagc    60 ctacatggag ctgagcagcc tgagatccga ggacacggcc gtgtattact gtgcggcaga   120
```

<210> SEQ ID NO 320
<211> LENGTH: 120
<212> TYPE: DNA
<213> ORGANISM: Homo sapiens

<400> SEQUENCE: 320

```
ctacgcacag aagttccagg aaagagtcac cattaccagg acatgtcca caagcacagc    60 ctacatggag ctgagcagcc tgagatccga ggacacggcc gtgtattact gtgcggcaga   120
```

<210> SEQ ID NO 321
<211> LENGTH: 120
<212> TYPE: DNA
<213> ORGANISM: Homo sapiens

<400> SEQUENCE: 321

```
agctacgcag agaagttcca gggcagagtc accatgacca gggacacatc cacgagcaca    60
gcctacatgg agctgagcag cctgagatct gaagacacgg ccatgtatta ctgtgggaga   120
```

<210> SEQ ID NO 322
<211> LENGTH: 120
<212> TYPE: DNA
<213> ORGANISM: Homo sapiens

<400> SEQUENCE: 322

```
ctatgcaaag aagttccagg gcagagtcac cattaccagg acatgtccc tgaggacagc    60 ctacatagag ctgagcagcc tgagatctga ggactcggct gtgtattact gggcaagata   120
```

<210> SEQ ID NO 323
<211> LENGTH: 120
<212> TYPE: DNA
<213> ORGANISM: Homo sapiens

<400> SEQUENCE: 323

```
atcccagcca ggttcagtgg cagtgggtct gggacagact tcactctcac catcagcagc    60
ctggagcctg aagattttgc agtttattac tgtcagcacc ggagcaactg gctaatcgcc   120
```

<210> SEQ ID NO 324
<211> LENGTH: 120
<212> TYPE: DNA
<213> ORGANISM: Homo sapiens

<400> SEQUENCE: 324

```
tccggggtcc ctgacaggtt cagtggcagt ggatcaggca cagatttac actgaaaatc    60 agtagagtgg aggctgagga tgttgggggtt tattattgca tgcaagctct acaaacccca   120
```

<210> SEQ ID NO 325
<211> LENGTH: 120
<212> TYPE: DNA
<213> ORGANISM: Homo sapiens

<400> SEQUENCE: 325

```
aataccgcac agaggttcga ggacagagtc acgattaccg cggacacatc gacgagcaca    60
gtcttcatgg aactgagcag cctgagatct gaagacacgg ccgtgtatta ctgtgcgaga   120
```

<210> SEQ ID NO 326
<211> LENGTH: 120

```
<212> TYPE: DNA
<213> ORGANISM: Homo sapiens

<400> SEQUENCE: 326
agactacgca cagaaattcc agggcagagt cacgattgtc acggacgaat cgacgagcac    60
atcctacatg gaagtgaaga gcctgagatc tgaagacacg gccgtgtatt attgtgcgag   120

<210> SEQ ID NO 327
<211> LENGTH: 120
<212> TYPE: DNA
<213> ORGANISM: Homo sapiens

<400> SEQUENCE: 327
actacgcaca gaagttccag ggcagagtca cgattaccgc ggacaaatcc acgagcacag    60
cctacatgga gctgagcagc ctgagatctg aggacacggc cgtgtattac tgtgcgagag   120

<210> SEQ ID NO 328
<211> LENGTH: 120
<212> TYPE: DNA
<213> ORGANISM: Homo sapiens

<400> SEQUENCE: 328
gactacgcac agaagtttca ggccagagtc acaataagcg cgcacgaatt cacgcccata    60
gtttatatgg agttgagaag cctgagatcc gaccagcacg ccacatatta ctgtgcgaca   120

<210> SEQ ID NO 329
<211> LENGTH: 120
<212> TYPE: DNA
<213> ORGANISM: Homo sapiens

<400> SEQUENCE: 329
agactacgca cagaacttcc aggatagagt caacattaat gcggaccaat ctacgaacac    60
agtctacatg gaactgagca ggctgacatc tgacgacacg gccgtctatt actgtgcgag   120

<210> SEQ ID NO 330
<211> LENGTH: 120
<212> TYPE: DNA
<213> ORGANISM: Homo sapiens

<400> SEQUENCE: 330
ctccgctcag aagttccaag accgagtcac cattagtgtc gacgagtccg cgggcacagt    60
atacatggac ctggacagcc tgacctctga agacacggcc atgtattact gtgcgaaaga   120

<210> SEQ ID NO 331
<211> LENGTH: 120
<212> TYPE: DNA
<213> ORGANISM: Homo sapiens

<400> SEQUENCE: 331
aactacgcac cgaagttcca gggcagagtc acgattaccg cggacaaaac cactagtact    60
gcttacatgg agctgagcag cctgagatct gaggacacgc tcgtgtatta ctgtgcgaga   120

<210> SEQ ID NO 332
<211> LENGTH: 120
<212> TYPE: DNA
<213> ORGANISM: Homo sapiens

<400> SEQUENCE: 332
ctacgcacag aagttccagg gcagagtcac gattaccgcg gacgaatcca cgagcacagc    60
```

```
ctacatggag ctgagcagcc tgagatctga ggacacggcc gtgtattact gtgcgagaga      120

<210> SEQ ID NO 333
<211> LENGTH: 120
<212> TYPE: DNA
<213> ORGANISM: Homo sapiens

<400> SEQUENCE: 333
actacgcaca gaagttccag ggcagagtca cgattaccgc ggacgaatcc acgagcacag       60
cctacatgga gctgagcagc ctgagatctg aggacacggc cgtgtattac tgtgcgagag      120

<210> SEQ ID NO 334
<211> LENGTH: 120
<212> TYPE: DNA
<213> ORGANISM: Homo sapiens

<400> SEQUENCE: 334
ctacgcacag aagttccagg gcagagtcac gattaccgcg gacaaatcca cgagcacagc       60
ctacatggag ctgagcagcc tgagatctga ggacacggcc gtgtattact gtgcgagaga      120

<210> SEQ ID NO 335
<211> LENGTH: 120
<212> TYPE: DNA
<213> ORGANISM: Homo sapiens

<400> SEQUENCE: 335
tgctcgcaca gaaattccgg ggcagaatct ccataaccgc ggacacgtcc acagacacaa       60
cttacatggc gctgagcagc ctgacctctg atgacacggc cgtctattac tgttcaacag      120

<210> SEQ ID NO 336
<211> LENGTH: 120
<212> TYPE: DNA
<213> ORGANISM: Homo sapiens

<400> SEQUENCE: 336
ggctatgcac agaagttcca gggcagagtc accatgacca ggaacacctc cataagcaca       60
gcctacatgg agctgagcag cctgagatct gaggacacgg ccgtgtatta ctgtgcgaga      120

<210> SEQ ID NO 337
<211> LENGTH: 120
<212> TYPE: DNA
<213> ORGANISM: Homo sapiens

<400> SEQUENCE: 337
ctatgcacag aagttccagg gcagagtcac catgaccagg aacacctcca taagcacagc       60
ctacatggag ctgagcagcc tgagatctga ggacacggcc gtgtattact gtgcgagagg      120

<210> SEQ ID NO 338
<211> LENGTH: 120
<212> TYPE: DNA
<213> ORGANISM: Homo sapiens

<400> SEQUENCE: 338
acagcacgtc tctgaagaac aggctcatca tctccaagga cacctccaaa agccaggtgg       60
tccttaccat gaccaacatg gaccctgtgg acacagccac gtattactgt gcatggagag      120

<210> SEQ ID NO 339
<211> LENGTH: 120
<212> TYPE: DNA
<213> ORGANISM: Homo sapiens
```

<400> SEQUENCE: 339
acagcccatc tctgaagagt aggctcatta tctccaagga cacctccaag aatgaagtgg    60
ttctaacagt gatcaacatg gacattgtgg acacagccac acattactgt gcaaggagac   120

<210> SEQ ID NO 340
<211> LENGTH: 120
<212> TYPE: DNA
<213> ORGANISM: Homo sapiens

<400> SEQUENCE: 340
tacaggacat ctctgaagag caggctctcc atctccaagg acacctccaa aagcctggtg    60
gtccttacca tgaccaacat ggaccctgtg acacagcca cgtattattg tgcacggata   120

<210> SEQ ID NO 341
<211> LENGTH: 120
<212> TYPE: DNA
<213> ORGANISM: Homo sapiens

<400> SEQUENCE: 341
tccggggtcc ctgacaggtt cagtggcagt ggatcaggca cagattttac actgaaaatc    60
agtagagtgg aggctgagga tgttgggatt tattactgca tgcaagctct acaaacccca   120

<210> SEQ ID NO 342
<211> LENGTH: 120
<212> TYPE: DNA
<213> ORGANISM: Homo sapiens

<400> SEQUENCE: 342
acagcccatc tctgaagagc aggctcacca tcaccaagga cacctccaaa accaggtgg    60 tccttacaat gaccaacatg gaccctgtgg acacagccac atattactgt gcacacagac   120

<210> SEQ ID NO 343
<211> LENGTH: 120
<212> TYPE: DNA
<213> ORGANISM: Homo sapiens

<400> SEQUENCE: 343
acggcccatc tctgaagagc aggctcacca tcaccaagga cacctccaaa accaggtgg    60 tccttacaat gaccaacatg gaccctgtgg acacagccac atattactgt gcacacagac   120

<210> SEQ ID NO 344
<211> LENGTH: 120
<212> TYPE: DNA
<213> ORGANISM: Homo sapiens

<400> SEQUENCE: 344
tacggcccat ctctgaagag caggctcacc atcaccaagg acacctccaa aaaccaggtg    60
gtccttacaa tgaccaacat ggaccctgtg acacagcca catattactg tgcacacaga   120

<210> SEQ ID NO 345
<211> LENGTH: 120
<212> TYPE: DNA
<213> ORGANISM: Homo sapiens

<400> SEQUENCE: 345
aggcgctaca gaccctctct gaagaccaga ctcaccatca cccaggacat gtccaggaac    60
caggtggtcc ttagactgac caacttggac ccactggaca caggcacata ttttgtgca   120

<210> SEQ ID NO 346
<211> LENGTH: 120
<212> TYPE: DNA
<213> ORGANISM: Homo sapiens

<400> SEQUENCE: 346
agcgctacag cccatctctg aagagcaggc tcaccatcac caaggacacc tccaaaaacc      60
aggtggtcct tacaatgacc aacgtggacc ctgtggacac agccacatat tactgtgcac     120

<210> SEQ ID NO 347
<211> LENGTH: 120
<212> TYPE: DNA
<213> ORGANISM: Homo sapiens

<400> SEQUENCE: 347
ctacagcaca tctctgaaga ccaggctcac catctccaag gacacctcca aaaccaggt      60 ggtccttaca atgaccaaca tggaccctgt ggacacagcc acgtattact gtgcacggat    120

<210> SEQ ID NO 348
<211> LENGTH: 120
<212> TYPE: DNA
<213> ORGANISM: Homo sapiens

<400> SEQUENCE: 348
tacagcacat ctctgaagac caggctcacc atctccaagg acacctccaa aaccaggtg      60 gtccttacaa tgaccaacat ggaccctgtg gacacagcca cgtattactg tgcacggata    120

<210> SEQ ID NO 349
<211> LENGTH: 120
<212> TYPE: DNA
<213> ORGANISM: Homo sapiens

<400> SEQUENCE: 349
tgataaattc tacagcacat ccctgaagac caggctcacc atctccaagg acacctccaa      60
aaaccaggtg gtccttacaa tgaccaacat ggaccctgtg gacacggccg tgtattactg    120

<210> SEQ ID NO 350
<211> LENGTH: 120
<212> TYPE: DNA
<213> ORGANISM: Homo sapiens

<400> SEQUENCE: 350
acagcacatc tctgaagacc aggctcacca tctccaagga cacctccaaa aaccaggtgg      60
tccttacaat gaccaacatg gaccctgtgg acacagccac gtattactgt gcacggatac    120

<210> SEQ ID NO 351
<211> LENGTH: 120
<212> TYPE: DNA
<213> ORGANISM: Homo sapiens

<400> SEQUENCE: 351
acagcacatc tctgaagacc aggctcacca tctccaagga cacctccaaa aaccaggtgg      60
tccttacaat gaccaacatg gaccctgtgg acacagccac atattactgt gcacacagac    120

<210> SEQ ID NO 352
<211> LENGTH: 120
<212> TYPE: DNA
<213> ORGANISM: Homo sapiens

<400> SEQUENCE: 352
acagcacatc tctgaagacc aggctcacca tctccaagga cacctccaaa aaccaggtgg    60
tccttacaat gaccaacatg daccctgtgg acacagccac gtattattgt gcacggatac   120

<210> SEQ ID NO 353
<211> LENGTH: 120
<212> TYPE: DNA
<213> ORGANISM: Homo sapiens

<400> SEQUENCE: 353
gaatatgctg cgtctgtgaa aggcagactt accatctcaa gagaggattc aaagaacacg    60
atgtatctgc aaatgagcaa cctgaaaacc gaggacttgg ccgtgtatta ctgtgctaga   120

<210> SEQ ID NO 354
<211> LENGTH: 120
<212> TYPE: DNA
<213> ORGANISM: Homo sapiens

<400> SEQUENCE: 354
gaatatgctg cgtctgtgaa aggcagactt accatctcaa gagaggattc aaagaacacg    60
ctgtatctgc aaatgagcag cctgaaaacc gaggacttgg ccgtgtatta ctgtgctaga   120

<210> SEQ ID NO 355
<211> LENGTH: 120
<212> TYPE: DNA
<213> ORGANISM: Homo sapiens

<400> SEQUENCE: 355
tatgctgcgt ctgtgaaagg ccagacttac catctcaaga gaggattcaa agaacacgct    60
gtatctcaaa tgagacagcc tgaaaaccga ggacttggcc gtgtattact gtgctagaga   120

<210> SEQ ID NO 356
<211> LENGTH: 120
<212> TYPE: DNA
<213> ORGANISM: Homo sapiens

<400> SEQUENCE: 356
atatgctgcg tctgtgaaag gcagacttac catctcaaga gaggattcaa agaacacgct    60
gtatctgcaa atgagcaacc tgaaaaccga ggacttggcc gtgtattact gtgctagaga   120

<210> SEQ ID NO 357
<211> LENGTH: 120
<212> TYPE: DNA
<213> ORGANISM: Homo sapiens

<400> SEQUENCE: 357
ctatgcagac tccgtgaagg gccgattcac catctccaga dacaatgcca agaactcctt    60
gtatcttcaa atgaacagcc tgagagccga ggacatggct gtgtattact gtgcaagaga   120

<210> SEQ ID NO 358
<211> LENGTH: 120
<212> TYPE: DNA
<213> ORGANISM: Homo sapiens

<400> SEQUENCE: 358
tactatgcag actccgtgaa gggccgattc accatctcca gagacaatgc caagaactcc    60
ttgtatcttc aaatgaacag cctgagagcc gaggacatgg ctgtgtatta ctgtgcaaga   120

<210> SEQ ID NO 359

```
<211> LENGTH: 120
<212> TYPE: DNA
<213> ORGANISM: Homo sapiens

<400> SEQUENCE: 359
aactacgcag actctgtgaa gggcagattc accatctcca cagacaactc aaagaacacg    60
ctctacctgc aaatgaacag cctgagagtg gaggacacgg ccgtgtatta ctgtgcaaga   120

<210> SEQ ID NO 360
<211> LENGTH: 120
<212> TYPE: DNA
<213> ORGANISM: Homo sapiens

<400> SEQUENCE: 360
agctacgcag actccatgaa gggccaattc accatctcca gagacaatgc taagaacacg    60
ctgtatctgc aaatgaacag tctgagagct gaggacatgg ctgtgtatta ctgtactaga   120

<210> SEQ ID NO 361
<211> LENGTH: 120
<212> TYPE: DNA
<213> ORGANISM: Homo sapiens

<400> SEQUENCE: 361
agctacgcag actccttgaa gggccaattc accatctcca gagacaatgc taagaacacg    60
ctgtatctgc aaatgaacag tctgagagct gaggacatgg ctgtgtatta ctgtactaga   120

<210> SEQ ID NO 362
<211> LENGTH: 120
<212> TYPE: DNA
<213> ORGANISM: Homo sapiens

<400> SEQUENCE: 362
ctatgtggac tccgtgaagg gccaattttc catctccaga gacaattcca gcaagtccct    60
gtatctgcaa aagaacagac agagagccaa ggacatggcc gtgtattact gtgtgagaaa   120

<210> SEQ ID NO 363
<211> LENGTH: 120
<212> TYPE: DNA
<213> ORGANISM: Homo sapiens

<400> SEQUENCE: 363
cactatgtgg actccgtgaa gggccaattt accatctcca gagacaattc cagcaagtcc    60
ctgtatctgc aaaagaacag acagagagcc aaagacatgg ccgtgtatta ctgtgtgaga   120

<210> SEQ ID NO 364
<211> LENGTH: 120
<212> TYPE: DNA
<213> ORGANISM: Homo sapiens

<400> SEQUENCE: 364
cactatgtgg actccgtgaa gggccaattt accatctcca gagacaattc cagcaagtcc    60
ctgtatctgc aaaagaacag acagagagcc aaggacatgg ccgtgtatta ctgtgtgaga   120

<210> SEQ ID NO 365
<211> LENGTH: 120
<212> TYPE: DNA
<213> ORGANISM: Homo sapiens

<400> SEQUENCE: 365
ctacgctgca cctgtgaaag gcagattcac catctcaaga gttgattcaa aaacacgct    60
```
gtatctgcaa atgaacagcc tgaaaaccga ggacacggcc gtgtattact gtaccacaga    120

<210> SEQ ID NO 366
<211> LENGTH: 120
<212> TYPE: DNA
<213> ORGANISM: Homo sapiens

<400> SEQUENCE: 366
gactacgctg cacctgtgaa aggcagattc accatctcaa gagttgattc aaaaaacacg    60
ctgtatctgc aaatgaacag cctgaaaacc gaggacacgg ccgtgtatta ctgtaccaca    120

<210> SEQ ID NO 367
<211> LENGTH: 120
<212> TYPE: DNA
<213> ORGANISM: Homo sapiens

<400> SEQUENCE: 367
aactacgcag actctgtgaa gggccgattc accatctcca gggacaacgc caataactca    60
ccgtatctgc aaatgaacag cctgagagct gaggacacgg ctgtgtatta ctgtgtgaaa    120

<210> SEQ ID NO 368
<211> LENGTH: 120
<212> TYPE: DNA
<213> ORGANISM: Homo sapiens

<400> SEQUENCE: 368
ctacgcagac tctgtgaagg gccgattcac catctccagg gacaacgcca ataactcacc    60
gtatctgcaa atgaacagct gagagctga ggacacggct gtgtattact gtgtgaaaca    120

<210> SEQ ID NO 369
<211> LENGTH: 120
<212> TYPE: DNA
<213> ORGANISM: Homo sapiens

<400> SEQUENCE: 369
ggggtcccat caaggttcac cgccagtgga tctgggacag aattcactct caatatcagc    60
agcctgcacc ctgacgattt tgcaacttat tactgccagc aatatgagcc ttataccccc    120

<210> SEQ ID NO 370
<211> LENGTH: 120
<212> TYPE: DNA
<213> ORGANISM: Homo sapiens

<400> SEQUENCE: 370
gtatggagac tctgtgaagg gccgattcac catctccaga gacaacgcca agaacgccct    60
gtatttacag atgaacagcc tgagagccga ggacacggct gtctattact gtgcgacaga    120

<210> SEQ ID NO 371
<211> LENGTH: 120
<212> TYPE: DNA
<213> ORGANISM: Homo sapiens

<400> SEQUENCE: 371
gggatccctg atcgcttctc aggctccagc tctggggctg agctctacct caccatctcg    60
agcctccagt ctgaggatga ggctgactat tactgtcaga cctggggcac tgacattcag    120

<210> SEQ ID NO 372
<211> LENGTH: 120
<212> TYPE: DNA

<213> ORGANISM: Homo sapiens

<400> SEQUENCE: 372
aactacgcag actctgtgaa gggccgcttc accatctcca gagacaacgc caacaactca    60
ctgtttctgc aaatgaacag cctgagagcc gaggacgcgg ccgtgtatga ctgtgcgaga   120

<210> SEQ ID NO 373
<211> LENGTH: 120
<212> TYPE: DNA
<213> ORGANISM: Homo sapiens

<400> SEQUENCE: 373
cctgaccgat tctctggctc caagtctggc acctcagcct ccctggccat cagtggcctc    60
cagtctgagg atgaggctga ttattactgt gcaccatggg atgacagcct gaatggtccg   120

<210> SEQ ID NO 374
<211> LENGTH: 120
<212> TYPE: DNA
<213> ORGANISM: Homo sapiens

<400> SEQUENCE: 374
ctacgcagac tctgtgaagg gccgattcac catctccaga gacaacgcca agaactcact    60
gtatctgcaa atgaacagcc tgagagccga ggacacggcc gtgtattact gtgcgagaga   120

<210> SEQ ID NO 375
<211> LENGTH: 120
<212> TYPE: DNA
<213> ORGANISM: Homo sapiens

<400> SEQUENCE: 375
ctacgcagtc tctgtgaagg gccgattcac catctccaga gacgcgccg ctaactcagt    60 gtatctgcaa atgaacagcc tgcgagccga ggacacggct gtgtatttct gtgcgagaga   120

<210> SEQ ID NO 376
<211> LENGTH: 120
<212> TYPE: DNA
<213> ORGANISM: Homo sapiens

<400> SEQUENCE: 376
actatccagg ctccgtgaag ggccgattca ccatctccag agaaaatgcc aagaactcct    60
tgtatcttca aatgaacagc ctgagagccg ggacacggc tgtgtattac tgtgcaagag   120

<210> SEQ ID NO 377
<211> LENGTH: 120
<212> TYPE: DNA
<213> ORGANISM: Homo sapiens

<400> SEQUENCE: 377
ctatccaggc tccgtgaagg ggcgattcac catctccaga gaaaatgcca agaactcctt    60
gtatcttcaa atgaacagcc tgagagccgg ggacacggct gtgtattact gtgcaagaga   120

<210> SEQ ID NO 378
<211> LENGTH: 120
<212> TYPE: DNA
<213> ORGANISM: Homo sapiens

<400> SEQUENCE: 378
tactatccag gctccgtgaa gggccaattc accatctcca gagaaaatgc caagaactcc    60
ttgtatcttc aaatgaacag cctgagagcc ggggacacgg ctgtgtatta ctgtgcaaga   120

<210> SEQ ID NO 379
<211> LENGTH: 120
<212> TYPE: DNA
<213> ORGANISM: Homo sapiens

<400> SEQUENCE: 379
ctatccaggc tccgtgaagg gccgattcac catctccaga gaaaatgcca agaactcctt    60
gtatcttcaa atgaacagcc tgagagccgg ggacacggct gtgtattact gtgcaagaga   120

<210> SEQ ID NO 380
<211> LENGTH: 120
<212> TYPE: DNA
<213> ORGANISM: Homo sapiens

<400> SEQUENCE: 380
actatccaga ctccgtgaag ggccgattca ctatctccag agaaaatgcc aagaactcct    60
tgtatctgca aatgaacagc ctgagagtcg gggacacggc tgtatattac tgtgcaagag   120

<210> SEQ ID NO 381
<211> LENGTH: 120
<212> TYPE: DNA
<213> ORGANISM: Homo sapiens

<400> SEQUENCE: 381
gactacgctg catccgtgaa agacagattc accatctcaa gagatgattc aaaaaatacg    60
gtgtttctgc aactgaacag cctgaaaacc gaggacacag ccgtctatta ctgtaccaca   120

<210> SEQ ID NO 382
<211> LENGTH: 120
<212> TYPE: DNA
<213> ORGANISM: Homo sapiens

<400> SEQUENCE: 382
actacgctgc acccattaaa ggcagattca ccatctcaag agatgattca agaaacacac    60
tgtttctgca aatgaacagc ctgaaaaacg aagacacagc catgtatttt tgtaccacag   120

<210> SEQ ID NO 383
<211> LENGTH: 120
<212> TYPE: DNA
<213> ORGANISM: Homo sapiens

<400> SEQUENCE: 383
ctacgctgca cctgtgaaag gcagattcac catctcaaga gttgattcaa aaacacgct    60 gtatctgcaa atgaacagcc tgaaaaccga ggacacagcc gtgtattact gtaccacaga   120

<210> SEQ ID NO 384
<211> LENGTH: 120
<212> TYPE: DNA
<213> ORGANISM: Homo sapiens

<400> SEQUENCE: 384
ctacgctgca cccgtgaaag gcagattcac catctcaaga gatgattcaa aaacacgct    60 gtatctgcaa atgaacagcc tgaaaaccga ggacacagcc gtgtattact gtaccacaga   120

<210> SEQ ID NO 385
<211> LENGTH: 120
<212> TYPE: DNA
<213> ORGANISM: Homo sapiens

<400> SEQUENCE: 385
atagactatg ctgcacccgt gaaaggcaga ttcatcattt caagagatga ttcaaaaagt    60
acggtgtatt tacaaatgaa cagactgaaa attgaggaca cagccgtata ttattgtgtc   120

<210> SEQ ID NO 386
<211> LENGTH: 120
<212> TYPE: DNA
<213> ORGANISM: Homo sapiens

<400> SEQUENCE: 386
actacgctgc acccgtggaa ggcagattca ccatctcaag agatgattca aagaacacgc    60
tgtatttaac aatgaacagc ctgaaaaccg aggacacagg cgtgtattat tgtctttcag   120

<210> SEQ ID NO 387
<211> LENGTH: 120
<212> TYPE: DNA
<213> ORGANISM: Homo sapiens

<400> SEQUENCE: 387
ctacgctgca cctgtgaaag gcagattcac catctcaaga gatgattcaa aaacacgct    60 gtatctgcaa atgatcagcc tgaaaaccga ggacacggcc gtgtattact gtaccacagg   120

<210> SEQ ID NO 388
<211> LENGTH: 120
<212> TYPE: DNA
<213> ORGANISM: Homo sapiens

<400> SEQUENCE: 388
ctatgtggac tccgtgaagc gccgattcat catctccaga gacaattcca ggaactccct    60
gtatctgcaa aagaacagac ggagagccga ggacatggct gtgtattact gtgtgagaaa   120

<210> SEQ ID NO 389
<211> LENGTH: 120
<212> TYPE: DNA
<213> ORGANISM: Homo sapiens

<400> SEQUENCE: 389
ctatgcagac tctgtgaagg gccgattcat catctccaga gacaattcca ggaacttcct    60
gtatcagcaa atgaacagcc tgaggcccga ggacatggct gtgtattact gtgtgagaaa   120

<210> SEQ ID NO 390
<211> LENGTH: 120
<212> TYPE: DNA
<213> ORGANISM: Homo sapiens

<400> SEQUENCE: 390
ttatgcagac tctgtgcagg gccgattcac catctccaga gacaacgcca agaactccct    60
atatctgcaa atgaacagtc tgagagccga ggacacggcc ttgtattact gtgcgagaga   120

<210> SEQ ID NO 391
<211> LENGTH: 120
<212> TYPE: DNA
<213> ORGANISM: Homo sapiens

<400> SEQUENCE: 391
ttatgcagac tctgtgaagg gccgattcac catctccaga gacaacgcca agaactccct    60
gtatctgcaa atgaacagtc tgagagccga ggacacggcc ttgtatcact gtgcgagaga   120

<210> SEQ ID NO 392
<211> LENGTH: 120
<212> TYPE: DNA
<213> ORGANISM: Homo sapiens

<400> SEQUENCE: 392
attacgcaga ctcagcgaag gggcgattca ccatctccag agacaacgcc aagaactcaa    60
tgtatctgca aatgaacagc ctgagagccg aggacacggc tatgtattac tgtgcgaccg   120

<210> SEQ ID NO 393
<211> LENGTH: 120
<212> TYPE: DNA
<213> ORGANISM: Homo sapiens

<400> SEQUENCE: 393
tatactatgc agactcactg aggggccgat tcaccatctc cagagacaac gccagaaatt    60
cactgtctct gcaaatcaac gacctgcgac ccgacgacac ggctatatat tattgtgcga   120

<210> SEQ ID NO 394
<211> LENGTH: 120
<212> TYPE: DNA
<213> ORGANISM: Homo sapiens

<400> SEQUENCE: 394
ctacgcagac tcagtgaagg gccgattcac catctccaga gacaacgcca agaactcact    60
gtatctgcaa atgaacagcc tgagagccga ggacacagct gtgtattact gtgcgagaga   120

<210> SEQ ID NO 395
<211> LENGTH: 120
<212> TYPE: DNA
<213> ORGANISM: Homo sapiens

<400> SEQUENCE: 395
ctacgcagac tcagtgaagg gccgattcac catctccaga gacaacgcca agaactcact    60
gtatctgcaa atgaacagcc tgagagccga ggacacggcc gtgtattact gtgcgagaga   120

<210> SEQ ID NO 396
<211> LENGTH: 120
<212> TYPE: DNA
<213> ORGANISM: Homo sapiens

<400> SEQUENCE: 396
atagaccacg tctgtgaaag gcagattcac aatctcaaga gatgattcca aaagcatcac    60
ctatctgcaa atgaagagcc tgaaaaccga ggacacggcc gtgtattact gttccagaga   120

<210> SEQ ID NO 397
<211> LENGTH: 120
<212> TYPE: DNA
<213> ORGANISM: Homo sapiens

<400> SEQUENCE: 397
atactacgca gactccgtga agggccggtt caccatctcc agagacaatt ccaagaacac    60
gctgtatctg caaatgaaca gcctgagagc cgaggacacg ccgtatatt actgtgcgaa   120

<210> SEQ ID NO 398
<211> LENGTH: 120
<212> TYPE: DNA
<213> ORGANISM: Homo sapiens

<400> SEQUENCE: 398

```
ctacggagac tccgtgaagg gccggttcac catctcaaga gacaattcca agaacacgct    60
gtatctgcaa atgaacagcc tgagagccga ggacacggcc gtatattact gtgcgaaaga   120
```

<210> SEQ ID NO 399
<211> LENGTH: 120
<212> TYPE: DNA
<213> ORGANISM: Homo sapiens

<400> SEQUENCE: 399

```
atcccagcca ggttcagtgg cagtgggtct gggacagact tcactctcac catcagcagc    60
ctggagcctg aagattttgc agtttattac tgtcagcagc gtagcaactg gctaatcgcc   120
```

<210> SEQ ID NO 400
<211> LENGTH: 120
<212> TYPE: DNA
<213> ORGANISM: Homo sapiens

<400> SEQUENCE: 400

```
actacgcaga ctccgtgaag ggccggttca ccatctccag agacaattcc aagaacacgc    60
tgtatctgca aatgaacagc ctgagagccg aggacacggc cgtgtattac tgtgcgaaag   120
```

<210> SEQ ID NO 401
<211> LENGTH: 120
<212> TYPE: DNA
<213> ORGANISM: Homo sapiens

<400> SEQUENCE: 401

```
tattacgcag actccgtgaa gggccggttc accatctcaa gagacaattc caggaacaca    60
ctgtttgtgc aattgaatag cctgagagtc gaggacacgg ccatatatta ttgtgcgaaa   120
```

<210> SEQ ID NO 402
<211> LENGTH: 120
<212> TYPE: DNA
<213> ORGANISM: Homo sapiens

<400> SEQUENCE: 402

```
ctacgcagac tccgtgaagg gccggttcac catctccaga gacaattcca agaacacgct    60
gtatctgcaa atgaacagcc tgagagccga ggacacggcc gtatattact gtgcgaaaga   120
```

<210> SEQ ID NO 403
<211> LENGTH: 120
<212> TYPE: DNA
<213> ORGANISM: Homo sapiens

<400> SEQUENCE: 403

```
cctcatagac tccggtaagg accgattcaa tacctccaga gataacgcca agaacacact    60
tcatctgcaa atgaacagcc tgaaaaccga ggacacggcc ctctattagt gtaccagaga   120
```

<210> SEQ ID NO 404
<211> LENGTH: 120
<212> TYPE: DNA
<213> ORGANISM: Homo sapiens

<400> SEQUENCE: 404

```
cctcatagac tccggtaagg accgattcaa tacctccaga gataacgcca agaacacact    60
tcatctgcaa atgaacagcc tgaaaaccga ggacacggcc ctgtattagt gtaccagaga   120
```

<210> SEQ ID NO 405
<211> LENGTH: 120

```
<212> TYPE: DNA
<213> ORGANISM: Homo sapiens

<400> SEQUENCE: 405
actggtatcc cagccaggtt cagtggcagt gggtctggga cagagttcac tctcaccatc    60
agcagcctgc agtctgaaga ttttgcagtt tattactgtc agcagtataa taactggcag   120

<210> SEQ ID NO 406
<211> LENGTH: 120
<212> TYPE: DNA
<213> ORGANISM: Homo sapiens

<400> SEQUENCE: 406
atgcagactc tgtgaagggc agattctcca tctccaaaga caatgctaag aactctctgt    60
atctgcaaat gaacagtcag agaactgagg acatggctgt gtatggctgt acataaggtt   120

<210> SEQ ID NO 407
<211> LENGTH: 120
<212> TYPE: DNA
<213> ORGANISM: Homo sapiens

<400> SEQUENCE: 407
ctacgcagac tccgtgaagg gccgattcac catctccaga dacaattcca ggaacacact    60
gtatctggca atgaacagcc tgagagttga ggacacggct gtgtattact gtgtgagaga   120

<210> SEQ ID NO 408
<211> LENGTH: 120
<212> TYPE: DNA
<213> ORGANISM: Homo sapiens

<400> SEQUENCE: 408
ctacgcagag tccgtgaagg gccgattcac catctccaga dacaattcca agaacaccct    60
gtatcttcaa ctgaacagcc tgagagctga ggacacggct gtgtattatt gtgcgaaaga   120

<210> SEQ ID NO 409
<211> LENGTH: 120
<212> TYPE: DNA
<213> ORGANISM: Homo sapiens

<400> SEQUENCE: 409
ctatgcagac tccgtgaagg gccgattcac catctccaga dacaattcca agaacacgct    60
gtatctgcaa atgaacagcc tgagagctga ggacacggct gtgtattact gtgcgagaga   120

<210> SEQ ID NO 410
<211> LENGTH: 120
<212> TYPE: DNA
<213> ORGANISM: Homo sapiens

<400> SEQUENCE: 410
tccggggtcc ctgacaggtt cagtggcagt ggatcaggca cagattttac actgaaaatc    60
agtagagtgg aggctgagga tgttggggtt tattactgca tgcaagctct acaaacccca   120

<210> SEQ ID NO 411
<211> LENGTH: 120
<212> TYPE: DNA
<213> ORGANISM: Homo sapiens

<400> SEQUENCE: 411
cctgagcgat tctctggctc caactctggc aacacagcca ctctgaccat cagcgggacc    60
```
caggctatgg atgaggctga ctattactgt caggcgtggg acagcagcac tgccgatgtg    120

<210> SEQ ID NO 412
<211> LENGTH: 120
<212> TYPE: DNA
<213> ORGANISM: Homo sapiens

<400> SEQUENCE: 412
acactatgca gactccgttc agggccgatt cggcgtctcc agagacaatt ccaactacac    60
ggcgtacgtg caactgaaca gcctgagacc agacgacacg gctgtttatt tttgtgcgag    120

<210> SEQ ID NO 413
<211> LENGTH: 120
<212> TYPE: DNA
<213> ORGANISM: Homo sapiens

<400> SEQUENCE: 413
tctacacaga ctccgtgaag ggccgattca ccatctccag agacaattcc aagaacacag    60
tggatttgca gatgactaac ctgagcgatg acgacacggc tgtgtacttc tgtgcgaaag    120

<210> SEQ ID NO 414
<211> LENGTH: 120
<212> TYPE: DNA
<213> ORGANISM: Homo sapiens

<400> SEQUENCE: 414
ctacgcagac tccgtgaagg gccgattcac catctccaga gacaattcca agaacacgct    60
gtatctgcaa atgaacagcc tgagagccga ggacacggct gtgtattact gtgcgagaga    120

<210> SEQ ID NO 415
<211> LENGTH: 120
<212> TYPE: DNA
<213> ORGANISM: Homo sapiens

<400> SEQUENCE: 415
ttatgcagac tccgtgaagg gccgattcac catctccaga gacaattcca agaacacatt    60
gttcctccaa atgaacagcc tgagagtaga ggacacggct ctctattact gtgcgaaaga    120

<210> SEQ ID NO 416
<211> LENGTH: 120
<212> TYPE: DNA
<213> ORGANISM: Homo sapiens

<400> SEQUENCE: 416
ctacgcagac tccgtgaagg gccgattcac catctccaga gacaattcca agaacacgct    60
gtatctgcaa atgagcagcc tgagagctga ggacacggct gtgtattact gtgcgagaga    120

<210> SEQ ID NO 417
<211> LENGTH: 120
<212> TYPE: DNA
<213> ORGANISM: Homo sapiens

<400> SEQUENCE: 417
tttacgcaga ctccatgaag ggccgcttca ccatctccag agagaactcc aagaacacgc    60
tgcatctgca catgaacagc ctgagacctg aggacacggc tgtctattac tgtgcgagag    120

<210> SEQ ID NO 418
<211> LENGTH: 120
<212> TYPE: DNA
<213> ORGANISM: Homo sapiens

<400> SEQUENCE: 418
ttttactcag actccatgaa ggggcggtgc accatttcca gagacaactc caagcagaca    60
gtgtatttgg aaatagacac cctggaaact gaagacacgg cggtatattc ctgtgtgaaa    120

<210> SEQ ID NO 419
<211> LENGTH: 120
<212> TYPE: DNA
<213> ORGANISM: Homo sapiens

<400> SEQUENCE: 419
ttatgcataa tctttgaaga gcaaattcac catctccaaa gaaaatgcca agaactcact    60
gtatttgcta atgaacagtc tgagagcagc gggcacagct gtgtgttact gtatgtgagg    120

<210> SEQ ID NO 420
<211> LENGTH: 120
<212> TYPE: DNA
<213> ORGANISM: Homo sapiens

<400> SEQUENCE: 420
atgcagactc tgtgaagggc agattctcca tctccaaaga caatgctaag aactctctgt    60
atctgcaaat gaacagtcag agagctgagg acatggacgt gtatggctgt acataaggtc    120

<210> SEQ ID NO 421
<211> LENGTH: 120
<212> TYPE: DNA
<213> ORGANISM: Homo sapiens

<400> SEQUENCE: 421
ctacgcagac tccgtgaagg gccgattcac catctccaga gacaattcca agaacacgct    60
gtatctgcaa atgaacagcc tgagagctga ggacacggct gtgtattact gtgcgagaga    120

<210> SEQ ID NO 422
<211> LENGTH: 120
<212> TYPE: DNA
<213> ORGANISM: Homo sapiens

<400> SEQUENCE: 422
ggggtcccat caaggttcag tggcagtgga tctgggacag atttcactct caccatcagc    60
agtctgcaac ctgaaaattt tgcaacttac tactgtcaac agagttacag tacccttgg    120

<210> SEQ ID NO 423
<211> LENGTH: 120
<212> TYPE: DNA
<213> ORGANISM: Homo sapiens

<400> SEQUENCE: 423
ttatgcataa tctttgaaga gcaaattcac catctccaaa gaaaatgcca agaactcact    60
gtatttgcta atgaacagtc tgagagcaga gggcacagct gtgtgttact gtatgtgagg    120

<210> SEQ ID NO 424
<211> LENGTH: 120
<212> TYPE: DNA
<213> ORGANISM: Homo sapiens

<400> SEQUENCE: 424
ctatgcagac tccgtgaagg gccgattcac catctccaga gacaattcca agaacacgct    60
gtatctgcaa atgaacagcc tgagagctga ggacacggct gtgtattact gtgcgaaaga    120

<210> SEQ ID NO 425
<211> LENGTH: 120
<212> TYPE: DNA
<213> ORGANISM: Homo sapiens

<400> SEQUENCE: 425
atgcagactc tgtgaagggc agattctcca tctccaaaga caatgctaag aactctctgt    60
atctgcaaat gaacactcag agagctgagg acgtggccgt gtatggctat acataaggtc   120

<210> SEQ ID NO 426
<211> LENGTH: 120
<212> TYPE: DNA
<213> ORGANISM: Homo sapiens

<400> SEQUENCE: 426
ctatgcagac tccgtgaagg gccgattcac catccccaga ggcaatttca agaacacgct    60
gtatctgcaa atgaacagcc tgagtgccga ggacgcggct gtgtattact gtgcgagaga   120

<210> SEQ ID NO 427
<211> LENGTH: 120
<212> TYPE: DNA
<213> ORGANISM: Homo sapiens

<400> SEQUENCE: 427
ctatgcagac tccgcgaagg gccgattcac catctccaga gacaattcca cgaacacgct    60
gtttctgcaa atgaacagcc tgagagccga ggacacggct gtgtattact gtgcgagaga   120

<210> SEQ ID NO 428
<211> LENGTH: 120
<212> TYPE: DNA
<213> ORGANISM: Homo sapiens

<400> SEQUENCE: 428
atcccagaca ggttcagtgg cagtgggtct gggacagact tcactctcac catcagcaga    60
ctggagcctg aagattttgc agtgtattac tgtcaacact atcgtagttc acctcggaag   120

<210> SEQ ID NO 429
<211> LENGTH: 120
<212> TYPE: DNA
<213> ORGANISM: Homo sapiens

<400> SEQUENCE: 429
ctatgcagac tccgtgaagg gccgattcac catctccaga gacaattcca agaacacgct    60
gtatctgcaa atgaacagcc tgagagccga ggacacggct gtgtattact gtgcgagaga   120

<210> SEQ ID NO 430
<211> LENGTH: 120
<212> TYPE: DNA
<213> ORGANISM: Homo sapiens

<400> SEQUENCE: 430
ttacgcagac tccgtgaagg gccgattcat cgtctccaga gacaattcca gggacacggt    60
gtttctgcag atgagcagcc tgagactcga ggacacggct gtctattact gtgcgacaga   120

<210> SEQ ID NO 431
<211> LENGTH: 120
<212> TYPE: DNA
<213> ORGANISM: Homo sapiens

<400> SEQUENCE: 431
ctatgcagac tccgtgaagg gccgattcac catctccaga gacaattcca agaacacgct    60
gtatctgcaa atgaacagcc tgagagccga ggacacggct gtgtattact gtgcgaaaga    120

<210> SEQ ID NO 432
<211> LENGTH: 120
<212> TYPE: DNA
<213> ORGANISM: Homo sapiens

<400> SEQUENCE: 432
ttatgcccaa tctgtgaaga gcaaattcac catctccaaa gaaaatgcca agaactcact    60
gtatttgcaa atgaacagtc tgagagcaga gggcacagct gtgtgttact gtatgtgagg    120

<210> SEQ ID NO 433
<211> LENGTH: 120
<212> TYPE: DNA
<213> ORGANISM: Homo sapiens

<400> SEQUENCE: 433
cactatgcag actctgtgaa gggccgattc atcatctcca gagacaattc caggaacacc    60
ctgtatctgc aaacgaatag cctgagggcc gaggacacgg ctgtgtatta ctgtgtgaga    120

<210> SEQ ID NO 434
<211> LENGTH: 120
<212> TYPE: DNA
<213> ORGANISM: Homo sapiens

<400> SEQUENCE: 434
agctatgcag actctgtgaa gggtcgattc accctctcca gagatgatgc caagaaatca    60
ctgtatctgc aaatgaacag cgtcagagcc gaggataggt ctgtgtatta ctgtggtggc    120

<210> SEQ ID NO 435
<211> LENGTH: 120
<212> TYPE: DNA
<213> ORGANISM: Homo sapiens

<400> SEQUENCE: 435
ggtagtctat actatgcaga cactgaaggg tagattcacc atctctagag acaatggcaa    60
gaacatgctg ttcttgcaaa tgaacagtct gagagatgag gactcggttg tgttgagaga    120

<210> SEQ ID NO 436
<211> LENGTH: 120
<212> TYPE: DNA
<213> ORGANISM: Homo sapiens

<400> SEQUENCE: 436
tggtagccta tactatgcag acactgaagg gtagattcac catctctaga acaatggca    60 agaacatgct gtacttgcaa atgaacagtc tgagagatga ggactcggct gtgtgagaga    120

<210> SEQ ID NO 437
<211> LENGTH: 120
<212> TYPE: DNA
<213> ORGANISM: Homo sapiens

<400> SEQUENCE: 437
acgcagactc caggaagggc agattcacca tctccagaga caattccaag aacacgctgt    60
atcttcaaat gaacaacctg agagctgagg cacggccgc gtattactgt gccagatata    120

<210> SEQ ID NO 438

```
<211> LENGTH: 120
<212> TYPE: DNA
<213> ORGANISM: Homo sapiens

<400> SEQUENCE: 438
acgcagactc caggaagggc agattcacca tctccagaga caattccaag aacacgctgt      60
atcttcaaat gaacaacctg agagctgagg gcacggccgt gtattactgt gccagatata    120

<210> SEQ ID NO 439
<211> LENGTH: 120
<212> TYPE: DNA
<213> ORGANISM: Homo sapiens

<400> SEQUENCE: 439
ctacgcagac tccaggaagg gcagattcac catctccaga gacaattcca agaacacgct      60
gcatcttcaa atgaacagcc tgagagctga ggacacggct gtgtattact gtaagaaaga    120

<210> SEQ ID NO 440
<211> LENGTH: 120
<212> TYPE: DNA
<213> ORGANISM: Homo sapiens

<400> SEQUENCE: 440
atactatgca gactctgtga agggccgatt cacaatctcc gagacaattc taagagcatg      60
ctctatctgc aaatggacag tctgaaagct aaggacacgg ccatgtatta ctgtaccaga    120

<210> SEQ ID NO 441
<211> LENGTH: 120
<212> TYPE: DNA
<213> ORGANISM: Homo sapiens

<400> SEQUENCE: 441
atgcgctgca tctgtgaaag gcaggttcac catctcaaga gatgattcaa agaacacact      60
gtatatgcaa atgaataccc tgaaaaccaa gtacacggcc atctattact gtactagaga    120

<210> SEQ ID NO 442
<211> LENGTH: 120
<212> TYPE: DNA
<213> ORGANISM: Homo sapiens

<400> SEQUENCE: 442
atgcgctgca tctgtgaaag gcaggttcac catctcaaga gatgattcaa agaacacact      60
gtatctgcaa gtgaataccc tgaaaaccga gtacacggcc atctattact gtactagaga    120

<210> SEQ ID NO 443
<211> LENGTH: 120
<212> TYPE: DNA
<213> ORGANISM: Homo sapiens

<400> SEQUENCE: 443
attatgcagc ctctgtgaag ggtcgattca ccatctccag agacaactcc aaaaactccc      60 tgttttttgca aatgaacagt ctgagagttg aagattccgc cttctattac tgtggaaaag    120

<210> SEQ ID NO 444
<211> LENGTH: 120
<212> TYPE: DNA
<213> ORGANISM: Homo sapiens

<400> SEQUENCE: 444
tactatgcag actctgtgaa gggccgattc accatctcca gagacaacag caaaaactcc      60
```
ctgtatctgc aaatgaacag tctgagaact gaggacaccg ccttgtatta ctgtgcaaaa    120

<210> SEQ ID NO 445
<211> LENGTH: 120
<212> TYPE: DNA
<213> ORGANISM: Homo sapiens

<400> SEQUENCE: 445
atgcagactc tgtgaagggt cgattcacca tctccagaga caacagcaaa aactccctgt    60
atctgcaaat gaacagtctg agagctgagg acaccgcctt gtattactgt gcaaaagata    120

<210> SEQ ID NO 446
<211> LENGTH: 120
<212> TYPE: DNA
<213> ORGANISM: Homo sapiens

<400> SEQUENCE: 446
tactatgcag actccgtgat gggccgattc accatctcca gagacaacgc caagaagtcc    60
ttgtatcttc atatgaacag cctgatagct gaggacatgg ctgtgtatta ttgtgcaaga    120

<210> SEQ ID NO 447
<211> LENGTH: 120
<212> TYPE: DNA
<213> ORGANISM: Homo sapiens

<400> SEQUENCE: 447
tactatgcag actccgtgat gggccgattc accatctcca gagacaacgc caagaagtcc    60
ttgtatcttc aaatgaacag cctgatagct gaggacatgg ctgtgtatta ttgtgcaaga    120

<210> SEQ ID NO 448
<211> LENGTH: 120
<212> TYPE: DNA
<213> ORGANISM: Homo sapiens

<400> SEQUENCE: 448
tactacgcag actctgtgaa gggccgattc accatctcca gagacaatgc caagaactca    60
ctgtatctgc aaatgaacag cctgagagcc gaggacacgg ctgtgtatta ctgtgcgaga    120

<210> SEQ ID NO 449
<211> LENGTH: 120
<212> TYPE: DNA
<213> ORGANISM: Homo sapiens

<400> SEQUENCE: 449
tactacgcag actctgtgaa gggccgattc accatctcca gagacaatgc caggagctca    60
ctgtatctgc aaatgaccag cctgagagtc gaggacacgg ctgtatatca ctgtgcgagg    120

<210> SEQ ID NO 450
<211> LENGTH: 120
<212> TYPE: DNA
<213> ORGANISM: Homo sapiens

<400> SEQUENCE: 450
tactacgcag actctgtgaa gggccgattc accatctcca gagacagtgc caagaattca    60
ctgtatctgc acatgcacag cctgagagcc gaggacacgg ctgtttatta ctgtgcgaga    120

<210> SEQ ID NO 451
<211> LENGTH: 120
<212> TYPE: DNA

<213> ORGANISM: Homo sapiens

<400> SEQUENCE: 451
ctacgcagac tctgtgaagg gccgattcac catctccaga dacaacgcca agaactcact    60
gtatctgcaa atgaacagcc tgagagccga ggacacggct gtgtattact gtgcgagaga   120

<210> SEQ ID NO 452
<211> LENGTH: 120
<212> TYPE: DNA
<213> ORGANISM: Homo sapiens

<400> SEQUENCE: 452
atacaccgcg tctgtgaaag gcagattcac catctcaaga gatggttcca aaagcatcgc    60
ctatctgcaa atgaacagcc tgaaaaccga ggacacagcc gtgtattact gtactagaga   120

<210> SEQ ID NO 453
<211> LENGTH: 120
<212> TYPE: DNA
<213> ORGANISM: Homo sapiens

<400> SEQUENCE: 453
atacgccgcg tctgtgaaag gcagattcac catctcaaga gatgattcca aaagcatcgc    60
ctatctgcaa atgaacagcc tgaaaaccga ggacacagcc gtgtattact gtactagaga   120

<210> SEQ ID NO 454
<211> LENGTH: 120
<212> TYPE: DNA
<213> ORGANISM: Homo sapiens

<400> SEQUENCE: 454
aaatacgccg cgtctgtgaa aggcagattc accatctcaa gagatgatta caaaagcgtc    60
gtctatctgc aaatgaacag cctgagaagc gaggacacag ccgtatacta ctgtactaga   120

<210> SEQ ID NO 455
<211> LENGTH: 120
<212> TYPE: DNA
<213> ORGANISM: Homo sapiens

<400> SEQUENCE: 455
gaatacgccg cgtctgtgaa aggcagattc accatctcaa gagatgattc caaaagcatc    60
gcctatctgc aaatgaacag cctgaaaacc gaggacacag ccgtgtatta ctgtactaga   120

<210> SEQ ID NO 456
<211> LENGTH: 120
<212> TYPE: DNA
<213> ORGANISM: Homo sapiens

<400> SEQUENCE: 456
atgcagactc tgtgaaggtc agattcacca tctccaaaga caatgccaag cacaggttgt    60
atctgcaaat gaacagtctg agagctgaga atatggctct gtattattga gtcaaaggta   120

<210> SEQ ID NO 457
<211> LENGTH: 120
<212> TYPE: DNA
<213> ORGANISM: Homo sapiens

<400> SEQUENCE: 457
ctatgtagac tctgtgaagg gccgattgac catctccaga dacaatgcca agaactccct    60
ctatctgcaa gtgaacagcc tgagagctga ggacatgacc gtgtattact gtgtgagagg   120

<210> SEQ ID NO 458
<211> LENGTH: 120
<212> TYPE: DNA
<213> ORGANISM: Homo sapiens

<400> SEQUENCE: 458
tactatgtag actctgtgaa gggccgattg accatctcca gagacaatgc caagaactcc    60
ctctatctgc aagtgaacag cctgagagct gaggacatga ccgtgtatta ctgtgtgaga   120

<210> SEQ ID NO 459
<211> LENGTH: 120
<212> TYPE: DNA
<213> ORGANISM: Homo sapiens

<400> SEQUENCE: 459
ctacgcagac tccgtgaagg gccgattcac catctccaga gacaattcca agaacacgct    60
gtatcttcaa atgaacagcc tgagagccga ggacacggcc gtgtattact gtgcgagaga   120

<210> SEQ ID NO 460
<211> LENGTH: 120
<212> TYPE: DNA
<213> ORGANISM: Homo sapiens

<400> SEQUENCE: 460
tactatgcag actctgtgaa gggccgattc accatctcca gagacaacag caaaaactcc    60
ctgtatctgc aaatgaacag tctgaaaact gaggacaccg ccttgtatta ctgtgtgaaa   120

<210> SEQ ID NO 461
<211> LENGTH: 120
<212> TYPE: DNA
<213> ORGANISM: Homo sapiens

<400> SEQUENCE: 461
ctacgcagac tctgtgaagg gccgattcac catctccaga gacaattcca agaacacgct    60
gtatcttcaa atgaacagcc tgagagccga ggacacggcc gtgtattact gtgctaggga   120

<210> SEQ ID NO 462
<211> LENGTH: 120
<212> TYPE: DNA
<213> ORGANISM: Homo sapiens

<400> SEQUENCE: 462
gtttctcatc gcttctctgg ctccaagtct ggcaacacgg cctccctgac catctctggg    60
ctccgggctg aggacgaggg tgattattac tgcacctcat atacaatcaa tagcgatttt   120

<210> SEQ ID NO 463
<211> LENGTH: 120
<212> TYPE: DNA
<213> ORGANISM: Homo sapiens

<400> SEQUENCE: 463
ttatgcacaa tctgtgaaga gcagattcac catctccaaa gaaaatgcca agaactcact    60
ccgtttgcaa atgaacagtc tgagagcaga gggcacggcc gtgtattact gtatgtgagg   120

<210> SEQ ID NO 464
<211> LENGTH: 120
<212> TYPE: DNA
<213> ORGANISM: Homo sapiens

<400> SEQUENCE: 464
ttatgcacaa tctgtgaaga gcagattcac catctccaaa gaaaatgcca agaactcact      60
ctgtttgcaa atgaacagtc tgagagcaga gggcacggcc gtgtattact gtatgtgagt     120

<210> SEQ ID NO 465
<211> LENGTH: 120
<212> TYPE: DNA
<213> ORGANISM: Homo sapiens

<400> SEQUENCE: 465
gaacagcctg agagccgagg gcacaaatta acagtcccaa gcgacacctt ttcatgtgca      60
gtctacctta caatgaccaa cctgaaagcc aaggacaagg ctgtgtatta ctgtgaggga     120

<210> SEQ ID NO 466
<211> LENGTH: 120
<212> TYPE: DNA
<213> ORGANISM: Homo sapiens

<400> SEQUENCE: 466
gagttactct ccatgagtac aaataaatta acagtcccaa gcgacacctt ttcatgtgca      60
gtctacctta caatgaccaa cctgaaagcc aaggacaagg ctgtgtatta ctgtgaggga     120

<210> SEQ ID NO 467
<211> LENGTH: 120
<212> TYPE: DNA
<213> ORGANISM: Homo sapiens

<400> SEQUENCE: 467
ctacgcagac tctgtgaagg gccgattcac catttccaga gacaatacca aaaactcact      60
gtatctgcaa atgaacagac tgagggcaga ggatgcagct gcatatgact ctgtgagaga     120

<210> SEQ ID NO 468
<211> LENGTH: 120
<212> TYPE: DNA
<213> ORGANISM: Homo sapiens

<400> SEQUENCE: 468
ctacacagac tctgtgaagg gctgattcac catctctaga gacaatgccc agaattcact      60
gtatctgcaa atgaacagcc tgagagccga cgacatggct gtgtattact gtgtgaaaga     120

<210> SEQ ID NO 469
<211> LENGTH: 120
<212> TYPE: DNA
<213> ORGANISM: Homo sapiens

<400> SEQUENCE: 469
ctacacagac tctgtgaagg gccgattcac catctccaga gacaatgccc agaattcact      60
gtctctgcaa atgaacagcc tgagagccga gggcacagtt gtgtactact gtgtgaaaga     120

<210> SEQ ID NO 470
<211> LENGTH: 120
<212> TYPE: DNA
<213> ORGANISM: Homo sapiens

<400> SEQUENCE: 470
atgcagactc tgtgaagggc agattcacca tctccaaaga caatgctaag aactcaccgt      60
atctccaaac gaacagtctg agagctgagg acatgaccat gcatggctgt acataaggtt     120

<210> SEQ ID NO 471
<211> LENGTH: 120
<212> TYPE: DNA
<213> ORGANISM: Homo sapiens

<400> SEQUENCE: 471
atttcatgca aactctgtga agggcagatt caccatctcc agagacaatt ccaagaacac      60
actgtatctt caaatgggca gcctgagagc tgaggacatg gctgtgtatt actgtgcgag     120

<210> SEQ ID NO 472
<211> LENGTH: 120
<212> TYPE: DNA
<213> ORGANISM: Homo sapiens

<400> SEQUENCE: 472
ttatgcagac tctgtgaagg gcagattcac catctccaga gacaattcca agaacacgct      60
gtatcttcaa atgggcagcc tgagagctga ggacatggct gtgtattact gtgcgagaga     120

<210> SEQ ID NO 473
<211> LENGTH: 120
<212> TYPE: DNA
<213> ORGANISM: Homo sapiens

<400> SEQUENCE: 473
ctacgcagac tcagtgaagg gcagattcac catctccaga gacaattcca agaacacgct      60
gtatgtccaa atgagcagtc tgagagctga ggacacggct gtgtattact gtgtgaaaga     120

<210> SEQ ID NO 474
<211> LENGTH: 120
<212> TYPE: DNA
<213> ORGANISM: Homo sapiens

<400> SEQUENCE: 474
cattctacgc agactccgcg aagggcagat tcaccatctc cagagacaat tccaagaaca      60
ctctgcatct tcaaatgaac agtctgagac ctgaggactc ggctgtctat tactgtgtga     120

<210> SEQ ID NO 475
<211> LENGTH: 120
<212> TYPE: DNA
<213> ORGANISM: Homo sapiens

<400> SEQUENCE: 475
actacgcaga ctccgtgaag ggcagattca ccgtctccag agacgatgcc acgaagaccc      60
tctttcttca agtgagcggt ctgcgagctg aggacacggc tgtctattac tgcgtgaaag     120

<210> SEQ ID NO 476
<211> LENGTH: 120
<212> TYPE: DNA
<213> ORGANISM: Homo sapiens

<400> SEQUENCE: 476
aagtacgcgg actccgtgaa gggcagattc attacctcca gagacaattc caagaacacg      60
ttgtatcttc aaatgagcag tctgagacct gaggacacgg ctatttatta ttgtgtgaaa     120

<210> SEQ ID NO 477
<211> LENGTH: 120
<212> TYPE: DNA
<213> ORGANISM: Homo sapiens

<400> SEQUENCE: 477

```
ctttctaatc gcttctctgg ctccaagtct ggcaacacgg cctccctgac catctctggg      60
ctccaggctg aggacggggc tgattatttc tgcagctcat atacaaccaa caacaagggg     120

<210> SEQ ID NO 478
<211> LENGTH: 120
<212> TYPE: DNA
<213> ORGANISM: Homo sapiens

<400> SEQUENCE: 478
atacgccgcg tctgtgaaag gcagattcac catctcaagc gatgattcca aaagcatcgc      60
ctatctgcaa atgaacagcc tgaaaaccga ggacacggcc gtgtattact ataccagaga     120

<210> SEQ ID NO 479
<211> LENGTH: 120
<212> TYPE: DNA
<213> ORGANISM: Homo sapiens

<400> SEQUENCE: 479
ctacgcagac tccgtgaagg gcagattcac catctccaga gacaattcca agaacacgct      60
gtatcttcaa atgaacagcc tgagagccga ggacacggct gtgtattact gtgcgagaga     120

<210> SEQ ID NO 480
<211> LENGTH: 120
<212> TYPE: DNA
<213> ORGANISM: Homo sapiens

<400> SEQUENCE: 480
tattacacag actccgtgaa gggccgattc accatctcca gagacaattc caagaacacg      60
ctgtatcttc aaatgaacag cctgagagct gaggacacgg ctgtgtatta ctgtgcgaga     120

<210> SEQ ID NO 481
<211> LENGTH: 120
<212> TYPE: DNA
<213> ORGANISM: Homo sapiens

<400> SEQUENCE: 481
ctacgcagac tccgtgaagg gccgattcac catctccaga gacaattcca agaacacgct      60
gtatcttcaa atgaacagcc tgagagctga ggacacggct gtgtattact gtgcgagaga     120

<210> SEQ ID NO 482
<211> LENGTH: 120
<212> TYPE: DNA
<213> ORGANISM: Homo sapiens

<400> SEQUENCE: 482
ctacgcagac tccgtgaagg gcagattcac catctccaga gacaattcca agaacacgct      60
gtatcttcaa atgaacagcc tgagagccga ggacacggct gtgtattact gtgcgagaca     120

<210> SEQ ID NO 483
<211> LENGTH: 120
<212> TYPE: DNA
<213> ORGANISM: Homo sapiens

<400> SEQUENCE: 483
ggggtttcta atcgcttctc tggctccaag tctgccaaca cggcctccct gacaatctct      60
ggactccagg ctgaggacga ggctgattat tactgctgct catatgcagg aagtaagact     120

<210> SEQ ID NO 484
<211> LENGTH: 120
```

```
<212> TYPE: DNA
<213> ORGANISM: Homo sapiens

<400> SEQUENCE: 484
catcccagac aggttcagtg gcagtgggtc tgggacagac ttcactctca gcatcagcag        60
gctggagcct gaagactttg cagtgtatta ctgtcagcag tatggtagct cacctccgga      120

<210> SEQ ID NO 485
<211> LENGTH: 120
<212> TYPE: DNA
<213> ORGANISM: Homo sapiens

<400> SEQUENCE: 485
ctatgtggac tctgtgaagg gccgattcac catctccaga gacaacgcca agaactcact        60
gtatctgcaa atgaacagcc tgagagccga ggacacggct gtgtattact gtgcgagaga      120

<210> SEQ ID NO 486
<211> LENGTH: 120
<212> TYPE: DNA
<213> ORGANISM: Homo sapiens

<400> SEQUENCE: 486
atactatatg gactctctga agggccgatt caccatctcc agagacaacg ccaagaactc        60
agtgaatctc caaatcaaca gcctgagagg cgaggacacg gctgtctatt actgtgcgag      120

<210> SEQ ID NO 487
<211> LENGTH: 120
<212> TYPE: DNA
<213> ORGANISM: Homo sapiens

<400> SEQUENCE: 487
ctatgtggac tctgtgaagg gccgattcac catctccaga gacaacgcca agaactcact        60
gtatctgcaa atgaacagcc tgagggccga ggacacggcc gtgtatcact gtgcgagaga      120

<210> SEQ ID NO 488
<211> LENGTH: 120
<212> TYPE: DNA
<213> ORGANISM: Homo sapiens

<400> SEQUENCE: 488
gaatagacca cgtctgtgaa aggcagattc acaatctcaa gagatgattc caaaagcatc        60
acctatctgc aaatgaacag cctgagagcc gaggacacgg ccgtgtatta ctgtgcgaga      120

<210> SEQ ID NO 489
<211> LENGTH: 120
<212> TYPE: DNA
<213> ORGANISM: Homo sapiens

<400> SEQUENCE: 489
atagaccacg tctgtgaaag gcagattcac aatctcaaga gatgattcca aaagcatcac        60
ctatctgcaa atgaacagcc tgagagccga ggacatggct gtgtattact gtgcgagaga      120

<210> SEQ ID NO 490
<211> LENGTH: 120
<212> TYPE: DNA
<213> ORGANISM: Homo sapiens

<400> SEQUENCE: 490
atagaccacg tctgtgaaag gcagattcac aatctcaaga gatgattcca aaagcatcac        60
```

```
ctatctgcaa atgaacagcc tgagagccga ggacacggct gtgtattact gtgcgagaga    120
```

<210> SEQ ID NO 491
<211> LENGTH: 120
<212> TYPE: DNA
<213> ORGANISM: Homo sapiens

<400> SEQUENCE: 491

```
aatacgccgc gtctgtgaaa ggcagattca tcatctcaag agatgattca aagaactcac    60
tatatctgga aatgaacagc ctgaaaaccg aggacacggc cgagtattac tgtgctagag    120
```

<210> SEQ ID NO 492
<211> LENGTH: 120
<212> TYPE: DNA
<213> ORGANISM: Homo sapiens

<400> SEQUENCE: 492

```
acatcttacg ctccgtcgat aaaaggcaag ttcatcattt ccagagatga ttccagcaat    60
atgttgtatc ttcaaatgaa caacctgaaa accgaggaca cggccgtcta ttttttgtact   120
```

<210> SEQ ID NO 493
<211> LENGTH: 120
<212> TYPE: DNA
<213> ORGANISM: Homo sapiens

<400> SEQUENCE: 493

```
gcatatactg cgtcggtgag aggcaggttc accatctcca gagatgattc aaagaacacg    60
gcgtggctgc aaatgagcag cctggaaacc gaggacacgg ccgtatatta ctgtattaga    120
```

<210> SEQ ID NO 494
<211> LENGTH: 120
<212> TYPE: DNA
<213> ORGANISM: Homo sapiens

<400> SEQUENCE: 494

```
ctacgcggac tccgtgaagg gccgattcac catctccaga dacaacgcca agaacacgct    60
gtatctgcaa atgaacagtc tgagagccga ggacacggct ttgtattact gtgtaagaga    120
```

<210> SEQ ID NO 495
<211> LENGTH: 120
<212> TYPE: DNA
<213> ORGANISM: Homo sapiens

<400> SEQUENCE: 495

```
aactacgcgg actccgtgaa gggccgattc accatctaca gagacgacgc caagaacaca    60
ctgaatctgc aaatgaacag tctgagagtc gaggacacgg cagtgtatta ttgtgtaaga    120
```

<210> SEQ ID NO 496
<211> LENGTH: 120
<212> TYPE: DNA
<213> ORGANISM: Homo sapiens

<400> SEQUENCE: 496

```
aacttacgcg gactccatga agggccgatt caccatctcc agagacaatg ccaaaaacac    60
gctggatctg caaatgaaca gcctgagagt cgaggacacg gctgtgtatt actgtgtaag    120
```

<210> SEQ ID NO 497
<211> LENGTH: 120
<212> TYPE: DNA
<213> ORGANISM: Homo sapiens

<400> SEQUENCE: 497
tcctactagc ctgtggcaaa tggaagcatc tcttttttat cagactgaat aatattgtag    60
tgttttctta taccacattt acttcatccc tttgtgcatt aacacttagg ttgttttat   120

<210> SEQ ID NO 498
<211> LENGTH: 120
<212> TYPE: DNA
<213> ORGANISM: Homo sapiens

<400> SEQUENCE: 498
tactactcag actctgtgaa gggccggttg accatctcca gagaaaacac caagaactca    60
ctgtatctgc aaataaacag tttcattgct gacaccatgg ccgtctatta ctgtaagaga   120

<210> SEQ ID NO 499
<211> LENGTH: 120
<212> TYPE: DNA
<213> ORGANISM: Homo sapiens

<400> SEQUENCE: 499
taccacccac tcctcaagtg tccagtcacc atccccagat ccgtgtccaa aaaagcagtt    60
cttcctacag ctgagctaca tgagcaacaa gcacatagcc atgtattttt aagccaaaga   120

<210> SEQ ID NO 500
<211> LENGTH: 120
<212> TYPE: DNA
<213> ORGANISM: Homo sapiens

<400> SEQUENCE: 500
taggctatgt ggactctgtg aagggccgat tcaccatctc cagagacaac gccaagaact    60
ccctgtatct gcaaatgaat agtctgagag ctgaggacac ggccttatat tactgtgcaa   120

<210> SEQ ID NO 501
<211> LENGTH: 120
<212> TYPE: DNA
<213> ORGANISM: Homo sapiens

<400> SEQUENCE: 501
atgcggactc tgtgaagggc cgattcacca tctccagaga caacgccaag aactccctgt    60
atctgcaaat gaacagtctg agagctgagg acacggcctt gtattactgt gcaaagata   120

<210> SEQ ID NO 502
<211> LENGTH: 120
<212> TYPE: DNA
<213> ORGANISM: Homo sapiens

<400> SEQUENCE: 502
atgcggactc tgtgaagggc cgattcacca tctccagaga caacgccaag aactccctgt    60
atctgcaaat gaacagtctg agagctgagg acatggcctt gtattactgt gcaaagata   120

<210> SEQ ID NO 503
<211> LENGTH: 120
<212> TYPE: DNA
<213> ORGANISM: Homo sapiens

<400> SEQUENCE: 503
ctacaacccg tccctcaaga gtcgagtcac catatcagta gacaagtcca agaaccagtt    60
ctccctgaag ctgagctctg tgaccgccgc ggacacggcc gtgtattact gtgcgagaga   120

<210> SEQ ID NO 504
<211> LENGTH: 120
<212> TYPE: DNA
<213> ORGANISM: Homo sapiens

<400> SEQUENCE: 504
tactacgcag actctgtgaa gggccgattc accatctcca gggacaacgc caagaactca    60
ctgtatctgc aaatgaacag cctgagagcc gaggacacgg ccgtgtatta ctgtgcgaga   120

<210> SEQ ID NO 505
<211> LENGTH: 120
<212> TYPE: DNA
<213> ORGANISM: Homo sapiens

<400> SEQUENCE: 505
ctacaaccca tccctcaaga gtcgagtcac catatcagta gacaagtcca agaaccagtt    60
ctccctgaag ctgagctctg tgaccgccgc ggacacggcc gtgtattact gtgcgagaga   120

<210> SEQ ID NO 506
<211> LENGTH: 120
<212> TYPE: DNA
<213> ORGANISM: Homo sapiens

<400> SEQUENCE: 506
tactacaacc cgtccctcaa gagtcgagtc accatgtcag tagacacgtc caagaaccag    60
ttctccctga agctgagctc tgtgaccgcc gtggacacgg ccgtgtatta ctgtgcgaga   120

<210> SEQ ID NO 507
<211> LENGTH: 120
<212> TYPE: DNA
<213> ORGANISM: Homo sapiens

<400> SEQUENCE: 507
ctacaacccg tccctcaaga gtcgagtcac catgtcagta gacacgtcca agaaccagtt    60
ctccctgaag ctgagctctg tgaccgccgt ggacacggcc gtgtattact gtgcgagaaa   120

<210> SEQ ID NO 508
<211> LENGTH: 120
<212> TYPE: DNA
<213> ORGANISM: Homo sapiens

<400> SEQUENCE: 508
ctacaacccg tccctcaaga gtcgagtcac catgtcagta gacacgtcca agaaccagtt    60
ctccctgaag ctgagctctg tgaccgccgt ggacacggcc gtgtattact gtgcgagaga   120

<210> SEQ ID NO 509
<211> LENGTH: 120
<212> TYPE: DNA
<213> ORGANISM: Homo sapiens

<400> SEQUENCE: 509
tactacaacc cgtccctcaa gagtcgagtc accatgtcag tagacacgtc caagaaccag    60
ttctccctga agctgagctc tgtgaccgcc gtggacaccg cgtgtatta ctgtgcgaga   120

<210> SEQ ID NO 510
<211> LENGTH: 120
<212> TYPE: DNA
<213> ORGANISM: Homo sapiens

<400> SEQUENCE: 510
ctacaacccg tccctcaaga gtcgagtcac catgtcagta gacacgtcca agaaccagtt    60
ctccctgaag ctgagctctg tgaccgcctt ggacacggcc gtgtattact gtgcgagaaa   120

<210> SEQ ID NO 511
<211> LENGTH: 120
<212> TYPE: DNA
<213> ORGANISM: Homo sapiens

<400> SEQUENCE: 511
acttcaaccc gtccctcaag agtcgagtca ccctatcagt tgacaggtcc gagaaccagt    60
tctccctgaa gctcagctct gtgaccgccg cggacacggc cgtgtattac tgtgccagag   120

<210> SEQ ID NO 512
<211> LENGTH: 120
<212> TYPE: DNA
<213> ORGANISM: Homo sapiens

<400> SEQUENCE: 512
ctacaacccg tccctcaaga gtcgagtcac catatccgta gacacgtcca agaaccagtt    60
ctccctgaag ctgagctctg tgaccgctgc agacacggct gtgtattact gtgcgagaca   120

<210> SEQ ID NO 513
<211> LENGTH: 120
<212> TYPE: DNA
<213> ORGANISM: Homo sapiens

<400> SEQUENCE: 513
ctacaacccg tccctcaaga gtcgagttac catatcagta gacacgtcca agaaccagtt    60
ctccctgaag ctgagctctg tgactgccgc agacacggcc gtgtattact gtgccagaga   120

<210> SEQ ID NO 514
<211> LENGTH: 120
<212> TYPE: DNA
<213> ORGANISM: Homo sapiens

<400> SEQUENCE: 514
ctacaacccg tccctcaaga gtcgagtcac catatcagta gacaggtcca agaaccagtt    60
ctccctgaag ctgagctctg tgaccgccgc ggacacggcc gtgtattact gtgccagaga   120

<210> SEQ ID NO 515
<211> LENGTH: 120
<212> TYPE: DNA
<213> ORGANISM: Homo sapiens

<400> SEQUENCE: 515
ctacaacccg tccctcaaga gtcgagttac catatcagta gacacgtcca agaaccagtt    60
ctccctgaag ctgagctctg tgactgcagc agacacggcc gtgtattact gtgccagaga   120

<210> SEQ ID NO 516
<211> LENGTH: 120
<212> TYPE: DNA
<213> ORGANISM: Homo sapiens

<400> SEQUENCE: 516
attataaccc gccctcagg agtcgagtaa ccatatcagc agacacgtcc aagaatcagg    60
tctccctgga gctgagtcct atgactgccg cggacacggc cgtgtattac tgtgccagag   120

<210> SEQ ID NO 517

<211> LENGTH: 120
<212> TYPE: DNA
<213> ORGANISM: Homo sapiens

<400> SEQUENCE: 517
ctacaacccg tccctcaaga gtcgagttac catatcagta gacacgtcca agaaccagtt    60
ctccctgaag ctgagctctg tgaccgccgc ggacacggcc gtgtattact gtgccagaga   120

<210> SEQ ID NO 518
<211> LENGTH: 120
<212> TYPE: DNA
<213> ORGANISM: Homo sapiens

<400> SEQUENCE: 518
cctactacaa cccgtccctc aagagtctag ttaccatatc agtagacacg tctaagaacc    60
agttctccct gaagctgagc tctgtgactg ctgcggacac ggccgtgtat tactgtgcga   120

<210> SEQ ID NO 519
<211> LENGTH: 120
<212> TYPE: DNA
<213> ORGANISM: Homo sapiens

<400> SEQUENCE: 519
ctacaacccg tccctcaaga gtcgagttac catatcagta gacacgtcta agaaccagtt    60
ctccctgaag ctgagctctg tgactgccgc ggacacggcc gtgtattact gtgcgagaga   120

<210> SEQ ID NO 520
<211> LENGTH: 120
<212> TYPE: DNA
<213> ORGANISM: Homo sapiens

<400> SEQUENCE: 520
ttactacaac ccgtccctca aggggcgagt taccatatca gtagacacgt ctgagaacca    60
gttctccctg aggctgagct ctgtgactgc cgcggacacg tccgtgtatt actgtgcgag   120

<210> SEQ ID NO 521
<211> LENGTH: 120
<212> TYPE: DNA
<213> ORGANISM: Homo sapiens

<400> SEQUENCE: 521
accgactaca acccgtccct caggagtcga gttaccatat cagtagacat gtctaagaac    60
cagttctccc tgaaactgag gtctgtgact gccgcggacg cggccgtcta ttattgtgcg   120

<210> SEQ ID NO 522
<211> LENGTH: 120
<212> TYPE: DNA
<213> ORGANISM: Homo sapiens

<400> SEQUENCE: 522
actacaaccc gtccctcaag agtcgagtta ccatatcagt agacacgcct aagaaccagt    60
tctctctgga gttgagctct gtgactgccg cggacacggc catatattac tgtgcaagag   120

<210> SEQ ID NO 523
<211> LENGTH: 120
<212> TYPE: DNA
<213> ORGANISM: Homo sapiens

<400> SEQUENCE: 523
actataaccc ggctctcaag agtcgagcct ccatctcaca agacacgtct gagaaccggt    60

```
tttccctgag gctgacctct gtgactgccg cggacacggc cgtgtatttc tgtgcgagag    120
```

<210> SEQ ID NO 524
<211> LENGTH: 120
<212> TYPE: DNA
<213> ORGANISM: Homo sapiens

<400> SEQUENCE: 524

```
actacaactc gtccctcaag agtcgactta ccatatccgt agacacgtcc gagaaccagt    60
tctccctgaa gctgagctct gtgaccgctg cggacacggc cgtgtattac tgtgcgagag   120
```

<210> SEQ ID NO 525
<211> LENGTH: 120
<212> TYPE: DNA
<213> ORGANISM: Homo sapiens

<400> SEQUENCE: 525

```
ctacaacccg tccctcaaga gtcgagttac catatcagta gacccgtcca agaaccagtt    60
ctccctgaag ccgagctctg tgactgccgc ggacacggcc gtggattact gtgcgagaga   120
```

<210> SEQ ID NO 526
<211> LENGTH: 120
<212> TYPE: DNA
<213> ORGANISM: Homo sapiens

<400> SEQUENCE: 526

```
actacaaccc gtccctcaag agtcgagtca ccatatcagt agacacgtcc aagaaccagt    60
tctccctgaa gctgagctct gtgaccgccg cggacacggc tgtgtattac tgtgcgagag   120
```

<210> SEQ ID NO 527
<211> LENGTH: 120
<212> TYPE: DNA
<213> ORGANISM: Homo sapiens

<400> SEQUENCE: 527

```
gactacaacc cgtccctcaa gagtcgagtc accatatcag tggacacgtc caagaaccag    60
ttctccctga gctgagctc tgtgaccgcc gcggacacgg ctgtgtatta ctgtgcgaga   120
```

<210> SEQ ID NO 528
<211> LENGTH: 120
<212> TYPE: DNA
<213> ORGANISM: Homo sapiens

<400> SEQUENCE: 528

```
actacaaccc gtccctcaag agtcgagtta ccatatcagt agacacgtct aagaaccagt    60
tctccctgaa gctgagctct gtgactgccg cggacacggc cgtgtattac tgtgcgagag   120
```

<210> SEQ ID NO 529
<211> LENGTH: 120
<212> TYPE: DNA
<213> ORGANISM: Homo sapiens

<400> SEQUENCE: 529

```
gagttcctga tcgcttctca ggctccagct ctggggctga ccgctacctc accatctcca    60
acctccagtc tgaggatgag gctgattatt actgtgagac ctgcgacagt aacactcatg   120
```

<210> SEQ ID NO 530
<211> LENGTH: 120
<212> TYPE: DNA

<213> ORGANISM: Homo sapiens

<400> SEQUENCE: 530
caacaacccg tccctcaaga gtcgagccac catatcagta gacacgtcca agaaccagtt    60
ctccctgaag ctgagctctg tgaccgccgc ggacacggct gtgtattact gtgcgagagg   120

<210> SEQ ID NO 531
<211> LENGTH: 120
<212> TYPE: DNA
<213> ORGANISM: Homo sapiens

<400> SEQUENCE: 531
accaactaca aagtttccct cgagagtcga gtcaccatat acattgacac gtctaagaac    60
cgattctccc tgagggtgag ggccgtgacc gccgcggaca cggctaaata cttctgtgcg   120

<210> SEQ ID NO 532
<211> LENGTH: 120
<212> TYPE: DNA
<213> ORGANISM: Homo sapiens

<400> SEQUENCE: 532
aagtacaacc cgtcgctcga gagtcgggtc accatatcaa tagacacgtc caggaaccac    60
ttctccctga acctgagctc agtgaccgcc gcggacacag ctgtctatta ctgtgcgaga   120

<210> SEQ ID NO 533
<211> LENGTH: 120
<212> TYPE: DNA
<213> ORGANISM: Homo sapiens

<400> SEQUENCE: 533
aactacaacc cgtccctcaa gagtcgagtc accatatcaa tagacacgtc caagaggcaa    60
ttctccctga ggctgacttc tatgaccgcc gcggacacgg ctgcatattt ctgtgcgaga   120

<210> SEQ ID NO 534
<211> LENGTH: 120
<212> TYPE: DNA
<213> ORGANISM: Homo sapiens

<400> SEQUENCE: 534
atcccagcca ggctcagtgg cagtgggtct gggacagact tcactctcac catcagcagc    60
ctggagcctg aagattttgc agtttattac tgtcagcagc gtagcaactg gctaatcgcc   120

<210> SEQ ID NO 535
<211> LENGTH: 120
<212> TYPE: DNA
<213> ORGANISM: Homo sapiens

<400> SEQUENCE: 535
ttacaacccg tccctcgaga gtcgagtcac catatcaata gacacgtcca agcaccaatt    60
ctccctgagg gtgatttctt tgaccgccgc ggacacggct agatatttct gtgcgagagg   120

<210> SEQ ID NO 536
<211> LENGTH: 120
<212> TYPE: DNA
<213> ORGANISM: Homo sapiens

<400> SEQUENCE: 536
actacaaccc gtccctcaag agtcgagtca ccatatcagt agacacgtcc aagaaacagc    60
tctccctgaa gttgagctct gtgaacgccg cggacacggc tgtgtattac tgtgcgagag   120

<210> SEQ ID NO 537
<211> LENGTH: 120
<212> TYPE: DNA
<213> ORGANISM: Homo sapiens

<400> SEQUENCE: 537
cactacaacc cgtccctcaa gagtcgagtc tccatatcag ttgtcacgtc caagaaccag    60
ctctccctga ggctgaggtt tgtgactgcc gcagacacgg ccgtctatta ctgtgcgaga   120

<210> SEQ ID NO 538
<211> LENGTH: 120
<212> TYPE: DNA
<213> ORGANISM: Homo sapiens

<400> SEQUENCE: 538
tactacaacc cgtccctcaa gagtcgagtc accatatcag tagacacgtc caagaaccag    60
ttctccctga agctgagctc tgtgaccgcc gcagacacgg ccgtgtatta ctgtgcgaga   120

<210> SEQ ID NO 539
<211> LENGTH: 120
<212> TYPE: DNA
<213> ORGANISM: Homo sapiens

<400> SEQUENCE: 539
agtggggtcc catcaaggtt cagtgccggt gtgtctggga cagatttcac cctcaccatc    60
agcagtctgc aatctgaaga ttttgcaact tactactgtc aacagagtta tagtcccccg   120

<210> SEQ ID NO 540
<211> LENGTH: 120
<212> TYPE: DNA
<213> ORGANISM: Homo sapiens

<400> SEQUENCE: 540
tactacaatc cctccctcaa gagccgagtc accatatccg tagacacgtt gaagaataac    60
ttctccctga agctgagttc tgtgaccgcc gcagacacgg ctgtttatta ctgtacgaga   120

<210> SEQ ID NO 541
<211> LENGTH: 120
<212> TYPE: DNA
<213> ORGANISM: Homo sapiens

<400> SEQUENCE: 541
gtctacaatc cgtccctcaa gagtcgagtc accatatccg tagacacgtc caagaacctg    60
ttctccctga aactgaccte tgtgaccgcc gcagacaggc tggtatattt ctgtgcgaga   120

<210> SEQ ID NO 542
<211> LENGTH: 120
<212> TYPE: DNA
<213> ORGANISM: Homo sapiens

<400> SEQUENCE: 542
caccttctac aacccgtccc tcaagagtcg agtcaccata tccgtggaca cgtccaaaaa    60
ccagatctcc ctgaggctga actctgtgac cgccgcagac acggctgtgt attattgtgc   120

<210> SEQ ID NO 543
<211> LENGTH: 120
<212> TYPE: DNA
<213> ORGANISM: Homo sapiens

<400> SEQUENCE: 543
ctacaacccg tccctcaaga gtcgagtcac catatcagta gacacgtcca agaaccagtt    60
ccccctgaag ctgagctctg tgaccgccgc ggacacggcc gtgtattact gtgcgagaga   120

<210> SEQ ID NO 544
<211> LENGTH: 120
<212> TYPE: DNA
<213> ORGANISM: Homo sapiens

<400> SEQUENCE: 544
actataaccc gtctctcatg agtcgagtcg ccatatcagt agacacgtcc aggaaccagt    60
tcttcctgaa gctgaactct gtgaccgccg cggacacggc cgtttattac tgtgcgagag   120

<210> SEQ ID NO 545
<211> LENGTH: 120
<212> TYPE: DNA
<213> ORGANISM: Homo sapiens

<400> SEQUENCE: 545
ggggtcccat caaggttcag tggcagtgga tctgggacag atttcactct caccatcagc    60
agtctgcaac ctgaagattt tgcaacttac tactgtcaac agagttacag tacccccccg   120

<210> SEQ ID NO 546
<211> LENGTH: 120
<212> TYPE: DNA
<213> ORGANISM: Homo sapiens

<400> SEQUENCE: 546
actacaaccc gtccctcaag agtcgagtca ccatatcagt agacaagtcc aagaaccagt    60
tctccctgaa gctgagctct gtgaccgccg cggacacggc cgtgtattac tgtgcgagag   120

<210> SEQ ID NO 547
<211> LENGTH: 120
<212> TYPE: DNA
<213> ORGANISM: Homo sapiens

<400> SEQUENCE: 547
ctacaacccc tccctcaaga gtcgagtcac catgtcagta gacacgtcca agaaccagtt    60
ctccctgaag ctgagctctg tgaccgccgc ggacacggcc gtgtattact gtgcgagaga   120

<210> SEQ ID NO 548
<211> LENGTH: 120
<212> TYPE: DNA
<213> ORGANISM: Homo sapiens

<400> SEQUENCE: 548
actacaaccc ctccctcaag agtcgagtca ccatgtcagt agacacgtcc aagaaccagt    60
tctccctgaa gctgagctct gtgaccgccg cggacacggc cgtgtattac tgtgcgagag   120

<210> SEQ ID NO 549
<211> LENGTH: 120
<212> TYPE: DNA
<213> ORGANISM: Homo sapiens

<400> SEQUENCE: 549
ctacaacccc tccctcaaga gtcgagtcac catatccgta gacacgtcca agaaccagtt    60
ctccctgaag ctgagctctg tgaccgccgc agacacggcc gtgtattact gtgcgagaga   120

<210> SEQ ID NO 550
<211> LENGTH: 120
<212> TYPE: DNA
<213> ORGANISM: Homo sapiens

<400> SEQUENCE: 550
ctacaacccg tccctcaaga gtcgaatcac catgtccgta gacacgtcca agaaccagtt      60
ctacctgaag ctgagctctg tgaccgccgc ggacacggcc gtgtattact gtgcgagata     120

<210> SEQ ID NO 551
<211> LENGTH: 120
<212> TYPE: DNA
<213> ORGANISM: Homo sapiens

<400> SEQUENCE: 551
ctacaacccg tccctcaaga gtcgaatcac catgtcagta gacacgtcca agaaccagtt      60
ctacctgaag ctgagctctg tgaccgccgc ggacacggcc gtgtattact gtgcgagata     120

<210> SEQ ID NO 552
<211> LENGTH: 120
<212> TYPE: DNA
<213> ORGANISM: Homo sapiens

<400> SEQUENCE: 552
ctacaacccg tccctcaaga gtcgaatcac catgtcagta gacacgtcca agaaccagtt      60
ctacctgaag ctgagctctg tgaccgccgc ggacacggcc gtgtattact gtgcgagaga     120

<210> SEQ ID NO 553
<211> LENGTH: 120
<212> TYPE: DNA
<213> ORGANISM: Homo sapiens

<400> SEQUENCE: 553
ctacaacccg tccctcaaga gtcgaatcac catgtccgta gacacgtcca agaaccagtt      60
ctccctgaag ctgagctctg tgaccgccgt ggacacggcc gtgtattact gtgcgagaaa     120

<210> SEQ ID NO 554
<211> LENGTH: 120
<212> TYPE: DNA
<213> ORGANISM: Homo sapiens

<400> SEQUENCE: 554
aactacaacc cctccctcaa gagtcgagtc accatatcag tagacacgtc caagaaccag      60
ttctccctga agctgagctc tgtgaccgct gcggacacgg ccgtgtatta ctgtgcgaga     120

<210> SEQ ID NO 555
<211> LENGTH: 120
<212> TYPE: DNA
<213> ORGANISM: Homo sapiens

<400> SEQUENCE: 555
agtataaccc ctccctcaag aatcgagtca ccatatcatt agacacgtcc gagaaccagt      60
tctccctgaa actcagctct gtgaccgccg cggacacggc cgtatattac tgtgccagag     120

<210> SEQ ID NO 556
<211> LENGTH: 120
<212> TYPE: DNA
<213> ORGANISM: Homo sapiens

<400> SEQUENCE: 556

```
actacaaccc ctccgtcaag agtcgggtca ccatatcagc gcacacgtcc acgaatcaat        60
tctccctgaa cctgttctct gtgaccgctg cggacacggc cgtgtattac tgtgcgagag       120

<210> SEQ ID NO 557
<211> LENGTH: 120
<212> TYPE: DNA
<213> ORGANISM: Homo sapiens

<400> SEQUENCE: 557
aagtataacc cgtccctcaa gagtcgactc accctgtcca ttgacacgtc caagagccag        60
ttctccctga agttgaggtc tgtgaccgcc gccgacacgg ccgtctatta ctgtgcgcga       120

<210> SEQ ID NO 558
<211> LENGTH: 120
<212> TYPE: DNA
<213> ORGANISM: Homo sapiens

<400> SEQUENCE: 558
ctttataatc cctccctcga gagtcgagtc accatgtcag tagacacatc caaggaccag        60
ttctccatga agctgaccct gtgaccgcc gcagacacgg ccatatatta ctgtgcgaga       120

<210> SEQ ID NO 559
<211> LENGTH: 120
<212> TYPE: DNA
<213> ORGANISM: Homo sapiens

<400> SEQUENCE: 559
cagttctccc tccctcagga ggcgagtcac catgtcaaca gacacgtcca gaaatcagtt        60
ctccctcaat ttgacttctg tgaccgctgc ggacacggcc gtctattact gtgcgagaga       120

<210> SEQ ID NO 560
<211> LENGTH: 120
<212> TYPE: DNA
<213> ORGANISM: Homo sapiens

<400> SEQUENCE: 560
ctacaacccc tccctcaaga gtcgagtcac catatcagta gacacgtcca agaaccagtt        60
ctccctgaag ctgagctctg tgaccgctgc ggacacggcc gtgtattact gtgcgagaga       120

<210> SEQ ID NO 561
<211> LENGTH: 120
<212> TYPE: DNA
<213> ORGANISM: Homo sapiens

<400> SEQUENCE: 561
caactacaac ccctccctca agagtcgagt caccatatca gtagacacgt ccaagaacca        60
gttctccctg aagctgagct ctgtgaccgc cgcagacacg gccgtgtatt actgtgcgag       120

<210> SEQ ID NO 562
<211> LENGTH: 120
<212> TYPE: DNA
<213> ORGANISM: Homo sapiens

<400> SEQUENCE: 562
aactacaacc cctccctcaa gagtcgagtc accatgtcag tagacacgtc caggaaccac        60
ttctccctga acctgaactc tgtgaccgcc gcagacacgg ccgtctatta ctgtgcgaga       120

<210> SEQ ID NO 563
<211> LENGTH: 120
```

```
<212> TYPE: DNA
<213> ORGANISM: Homo sapiens

<400> SEQUENCE: 563
gggtacacca ggtacaaccc ctccctcaag agtcgagtca ccatatcaat agactcgtcc      60
aagaaccagt tgtccctgaa tctgaactct gtgaccgccg ccgacacggc cgtctactac     120

<210> SEQ ID NO 564
<211> LENGTH: 120
<212> TYPE: DNA
<213> ORGANISM: Homo sapiens

<400> SEQUENCE: 564
aactacaacc cctccctcaa gagtcgagtc accatatcag tagacaagtc caagaaccag      60
ttctccctga agctgagctc tgtgaccgcc gcggacacgg ccgtgtatta ctgtgcgaga     120

<210> SEQ ID NO 565
<211> LENGTH: 120
<212> TYPE: DNA
<213> ORGANISM: Homo sapiens

<400> SEQUENCE: 565
aactacaacc cctccctcaa gagtcgagtc agcatatcag tagacgcgtc taagaaccaa      60
ttctccctga agctgacctc tgtgaccgct gcggacacgg ccgtctatta ctgtgcgaga     120

<210> SEQ ID NO 566
<211> LENGTH: 120
<212> TYPE: DNA
<213> ORGANISM: Homo sapiens

<400> SEQUENCE: 566
attggataca tctattatag tgggaggagc tactacaccc cgtccctcag gagttgagtc      60
accatgtcaa tagaaacgtc caagaaccag ttttccctga agctgagctc tgtgaccgca     120

<210> SEQ ID NO 567
<211> LENGTH: 120
<212> TYPE: DNA
<213> ORGANISM: Homo sapiens

<400> SEQUENCE: 567
aactacagcc cgtccttcca aggccacgtc accatctcaa ctgacaagtc catcaacact      60
gcctacctgc agtggaacag cctgaaggcc tcggacaccg ccatctatta ttgtgcgaga     120

<210> SEQ ID NO 568
<211> LENGTH: 120
<212> TYPE: DNA
<213> ORGANISM: Homo sapiens

<400> SEQUENCE: 568
caatacagcc cgtcctttca aggccacgtc accatctcag ctgacaagtc catcacaact      60
gcctacttgc agtggagcag cctgaaggcc tcggacaccg ccatatatta ttgtgcgaga     120

<210> SEQ ID NO 569
<211> LENGTH: 120
<212> TYPE: DNA
<213> ORGANISM: Homo sapiens

<400> SEQUENCE: 569
aactacagcc cgtccttcca aggccacgtc agcatctcag ctgacaagtc catcagcact      60
```
gcctacctgc agtggagcag cctgaaggcc tcggacaccg ccatgtatta ctgtgcgaga    120

<210> SEQ ID NO 570
<211> LENGTH: 120
<212> TYPE: DNA
<213> ORGANISM: Homo sapiens

<400> SEQUENCE: 570
tacagcccat ctctggaggg tagactcacc atcactaagg acacctccaa aaaccaggtg    60
gtccttacaa tgaccgacat ggaccctgtg gacacaggca catattactg tgcacacaga    120

<210> SEQ ID NO 571
<211> LENGTH: 120
<212> TYPE: DNA
<213> ORGANISM: Homo sapiens

<400> SEQUENCE: 571
atatagcccg tccttccaag gccaggtcac catgtcagcc gacaagtcca tcagcaccgc    60
ctacctacag tggagcagcc tgcgggcctc ggacaccgcc atgtattact gtgcgagaca    120

<210> SEQ ID NO 572
<211> LENGTH: 120
<212> TYPE: DNA
<213> ORGANISM: Homo sapiens

<400> SEQUENCE: 572
gatacagccc gtccttcgaa ggccaggtca ccatgtcagc cgacgagtcc ctcagcaccg    60
tctacctcca atggagcagc ctgaagccct cggacagcgc catgtatttc tgtgcgcggc    120

<210> SEQ ID NO 573
<211> LENGTH: 120
<212> TYPE: DNA
<213> ORGANISM: Homo sapiens

<400> SEQUENCE: 573
agatacagcc cgtccttcca aggccaggtc accatctcag ccgacaagtc catcagcacc    60
gcctacctgc agtggagcag cctgaaggcc tcggacaccg ccatgtattt ctgtgcgaga    120

<210> SEQ ID NO 574
<211> LENGTH: 120
<212> TYPE: DNA
<213> ORGANISM: Homo sapiens

<400> SEQUENCE: 574
agatatagcc cgtccttcca aggccaggtc accatctcag ccgacaagcc catcagtacc    60
gcctacctgc agtggaacag cctgagggcc tcggacaccg ccatttatta ctgtgcgaga    120

<210> SEQ ID NO 575
<211> LENGTH: 120
<212> TYPE: DNA
<213> ORGANISM: Homo sapiens

<400> SEQUENCE: 575
atacagccca tccttccaag gccacgtcac catctcagcc gacagctcca gcagcaccgc    60
ctacctgcag tggagcagcc tgaaggcctc ggacgccgcc atgtattatt gtgtgagagg    120

<210> SEQ ID NO 576
<211> LENGTH: 120
<212> TYPE: DNA
<213> ORGANISM: Homo sapiens

<400> SEQUENCE: 576
cagatacagc ccaccttcca aggccacgtc accatctcag ccgacagctc cagcagcacc      60
gcctacctgc agtggagcag cctgaaggcc tcggacgccg ccatgtatta ttgtgtgaga     120

<210> SEQ ID NO 577
<211> LENGTH: 120
<212> TYPE: DNA
<213> ORGANISM: Homo sapiens

<400> SEQUENCE: 577
attatgcaat atctgtgaaa agtcgaatag ccatcaaccc agacacatcc aagaaccagt      60
tctccctgca gctgaactct gtgactcccg aggacacggc tgtgtattac tgtgcaagag     120

<210> SEQ ID NO 578
<211> LENGTH: 120
<212> TYPE: DNA
<213> ORGANISM: Homo sapiens

<400> SEQUENCE: 578
atcccagaca ggttcagtgg cagtgggtct gggacagact tcactctcac catcagcaga      60
ctggagcctg aagattttgc agtgtattac tgtcagcagt gtagtagctc accctggatg     120

<210> SEQ ID NO 579
<211> LENGTH: 120
<212> TYPE: DNA
<213> ORGANISM: Homo sapiens

<400> SEQUENCE: 579
actgggaacc taacgtatgc ccagggcttc acaggacggt ttgtcttctc catggacacc      60
tccgtcagca tggcatatct tcatatcagc agcctaaagg ctgaggacac gtgcaagagg     120

<210> SEQ ID NO 580
<211> LENGTH: 120
<212> TYPE: DNA
<213> ORGANISM: Homo sapiens

<400> SEQUENCE: 580
gtatacccac ggcttcacag gatggtttgt cttctccatg gacacgtctg tcagcacggc      60
gtgtcttcag atcagcagcc taaaggctga ggacacggcc gagtattact gtgcgaagta     120

<210> SEQ ID NO 581
<211> LENGTH: 120
<212> TYPE: DNA
<213> ORGANISM: Homo sapiens

<400> SEQUENCE: 581
cctgaccgct tctctggctc caagtctggc acgtctgcca ccctgggcat cactggactc      60
cagactggag acgaggccca ttattactgc gccacatggg atagtggcct gagtgccgga     120

<210> SEQ ID NO 582
<211> LENGTH: 120
<212> TYPE: DNA
<213> ORGANISM: Homo sapiens

<400> SEQUENCE: 582
atataccaac ggcttcacag gacggttcct attctccatg gacacctctg tcagcatggc      60
gtatctgcag atcagcagcc taaaggctga ggacacggcc gtgtatgact gtatgagaga     120

<210> SEQ ID NO 583
<211> LENGTH: 120
<212> TYPE: DNA
<213> ORGANISM: Homo sapiens

<400> SEQUENCE: 583 ataticcaac ggcttcacag gacggtttct attctccatg gacacctctg tcagcatggc    60
gtatctgaag atcagcagcc taaaggctga ggacacggcc gtgtatgact gtatgagaga   120

<210> SEQ ID NO 584
<211> LENGTH: 120
<212> TYPE: DNA
<213> ORGANISM: Homo sapiens

<400> SEQUENCE: 584
gtatacccac ggcttcacag gacggtttgt cttctccatg gacacctctg tcagcatggc    60
gtatctgcag atcagcagcc taaaggctga ggacacggcc gtgtatgact ctatgagaga   120

<210> SEQ ID NO 585
<211> LENGTH: 120
<212> TYPE: DNA
<213> ORGANISM: Homo sapiens

<400> SEQUENCE: 585
acgtatgccc agggcttcac aggacggttt gtcttctcct tggacacctc tgtcagcacg    60
gcatatctgc agatctgcag cctaaaggct gaggacactg ccgtgtatta ctgtgcgaga   120

<210> SEQ ID NO 586
<211> LENGTH: 120
<212> TYPE: DNA
<213> ORGANISM: Homo sapiens

<400> SEQUENCE: 586
caacatatgc ccaagacttc acagggcgat ttgtcttctc cctggacacc tctgtcaaca    60
cggcatttct gcagatcagc agcctacagg ctgaagacac tgccgtctat tactgtgcga   120

<210> SEQ ID NO 587
<211> LENGTH: 120
<212> TYPE: DNA
<213> ORGANISM: Homo sapiens

<400> SEQUENCE: 587
gtatgcccag ggcttcacag gacggtttgt cttctccttg gacacctctg tcagcatggc    60
atatctgcag atcagcagcc taaaggctga ggacactgcc gtgtattact gtgcgagaga   120

<210> SEQ ID NO 588
<211> LENGTH: 120
<212> TYPE: DNA
<213> ORGANISM: Homo sapiens

<400> SEQUENCE: 588
gtatgcccag ggcttcacag gacggtttgt cttctccttg gacacctctg tcagcatggc    60
atatctgcag atcagcagcc taaaggctga ggacactgcc gtgtgttact gtgcgagaga   120

<210> SEQ ID NO 589
<211> LENGTH: 120
<212> TYPE: DNA
<213> ORGANISM: Homo sapiens

<400> SEQUENCE: 589

```
tgtatgccca cagattcaca cacggtttgt cttctccatg gacacctctg tcagcacggc    60
ggatctgcag actagctgcc taaagactga ggatgcagcc atttattact gtgtgaggta   120
```

<210> SEQ ID NO 590
<211> LENGTH: 120
<212> TYPE: DNA
<213> ORGANISM: Homo sapiens

<400> SEQUENCE: 590

```
atatgcccag ggcttcacag gacggtttgt cttctccatg gacacctctg ccagcacagc    60
atacctgcag atcagcagcc taaaggctga ggacatggcc atgtattact gtgcgagata   120
```

<210> SEQ ID NO 591
<211> LENGTH: 120
<212> TYPE: DNA
<213> ORGANISM: Homo sapiens

<400> SEQUENCE: 591

```
tgggattccc tctcggttca gtgacagtgg atctgggaca gattacactc tcaccatcag    60
cagcctgcag cctgaagatt ttgcaactta ttactgtcaa cagagtgaca gtacctctcc   120
```

<210> SEQ ID NO 592
<211> LENGTH: 120
<212> TYPE: DNA
<213> ORGANISM: Homo sapiens

<400> SEQUENCE: 592

```
tgggattccc tctcggttca gtgacagtgg atctggggca gactacactc tcaccatccg    60
cagcctgcag cctgaagatt ttgcaactta ttactgtcaa cagagtgaca gtacccctcc   120
```

<210> SEQ ID NO 593
<211> LENGTH: 120
<212> TYPE: DNA
<213> ORGANISM: Homo sapiens

<400> SEQUENCE: 593

```
tgggattccc tctcggttca gtgacagtgg atctggggca gattacactc tcaccatccg    60
cagcctgcag cctgaagatt ttgcaactta ttagtgtcaa cagagtgaca gtacccctcc   120
```

<210> SEQ ID NO 594
<211> LENGTH: 120
<212> TYPE: DNA
<213> ORGANISM: Homo sapiens

<400> SEQUENCE: 594

```
tgggattccc tctcggttca gtgacagtgg atctgggaca gattacactc tcaccatcag    60
cagcctgcag cctgaagatt ttgcaactta ttactgtcaa cagagtgaca gtaaccctcc   120
```

<210> SEQ ID NO 595
<211> LENGTH: 120
<212> TYPE: DNA
<213> ORGANISM: Homo sapiens

<400> SEQUENCE: 595

```
tgggattccc tctcggttca gtgacagtgg atctggggca gattacactc tcaccatccg    60
cagcctgcag cctgaagatt ttgcaactta ttactgtcaa cagagtgaca gtacccctcc   120
```

<210> SEQ ID NO 596

<211> LENGTH: 120
<212> TYPE: DNA
<213> ORGANISM: Homo sapiens

<400> SEQUENCE: 596
tgggattccc tctcggttca gtgacagtgg atctggggca gattacactc tcaccatcag    60
cagcctgcag cctgaagatt ttgcagctta ttactgtcaa cagagtgaca gtacccctcc   120

<210> SEQ ID NO 597
<211> LENGTH: 120
<212> TYPE: DNA
<213> ORGANISM: Homo sapiens

<400> SEQUENCE: 597
gggggtccca tctcggttca gtggcagtgg atctgggaca gatttcactc tcaccatcag    60
cagcctgcag cctgaagatg ttgcaactta ttactgtcta caggattata ctaccccatt   120

<210> SEQ ID NO 598
<211> LENGTH: 120
<212> TYPE: DNA
<213> ORGANISM: Homo sapiens

<400> SEQUENCE: 598
ggcgatgcca tctcagttca gtggcagcgg atatggaaga gatttcactc tcaccgtcag    60
cagcctgcag cctgaagatt ttgcaactta ttaatgtcaa caagagagca ttttccctcc   120

<210> SEQ ID NO 599
<211> LENGTH: 120
<212> TYPE: DNA
<213> ORGANISM: Homo sapiens

<400> SEQUENCE: 599
tgggattccc tctcggttca gtgacagtgg atctggggca gattacactc tcaccatccg    60
cagcctgcag cctgaagatt ttgcaaatta ttactgtcaa cagagtgaca gtacccctcc   120

<210> SEQ ID NO 600
<211> LENGTH: 120
<212> TYPE: DNA
<213> ORGANISM: Homo sapiens

<400> SEQUENCE: 600
ccatcctggt tcagtagcag tcaatctggg acagatttca ctctcaccat cagcagcctg    60
cagcctgcag cgtgatgatt tggccactta ttactatcaa cagcattaca gttaccctcc   120

<210> SEQ ID NO 601
<211> LENGTH: 120
<212> TYPE: DNA
<213> ORGANISM: Homo sapiens

<400> SEQUENCE: 601
tgggattccc tctcagttca gtgacagtgg atctgggaca gattagactc tcaccatcag    60
cagcctgcag cctgaagatt ttgcaactta ttactgtcaa cagagttaca gtacccctcc   120

<210> SEQ ID NO 602
<211> LENGTH: 120
<212> TYPE: DNA
<213> ORGANISM: Homo sapiens

<400> SEQUENCE: 602
tgggattccc tctcagttca gtgacagtgg atctgggaca gattagactc tcaccatcag    60
cagcctgcag cctgaagatt ttacaactta ttactgtcaa cagagttaca gtacccctcc    120

<210> SEQ ID NO 603
<211> LENGTH: 120
<212> TYPE: DNA
<213> ORGANISM: Homo sapiens

<400> SEQUENCE: 603
ggggatgcca tctcagttca gtggcagcgg atatggaaga gatttcactc tcactgtcag    60
cagcctgcag cctgaagatt ttgcaactta ttaatgtcaa caagagagca ttttccctct    120

<210> SEQ ID NO 604
<211> LENGTH: 120
<212> TYPE: DNA
<213> ORGANISM: Homo sapiens

<400> SEQUENCE: 604
gtttgcaaac ggggggttcca tctctgttca gtggtagtga atctgggaca gatttcactc    60
taaccatcag cagcctgcag cctgatgatg atgcaactta ctactgtcaa cagtaactcc    120

<210> SEQ ID NO 605
<211> LENGTH: 120
<212> TYPE: DNA
<213> ORGANISM: Homo sapiens

<400> SEQUENCE: 605
tgggattccc tctcggttca gtgacagtgg atctgggaca gattacactc tcaccatcag    60
cagcctgcag cctgaagatt ttgcagctta ttactgtcaa cagagtgaca gtacccctcc    120

<210> SEQ ID NO 606
<211> LENGTH: 120
<212> TYPE: DNA
<213> ORGANISM: Homo sapiens

<400> SEQUENCE: 606
tgggattccc tctcggttca gtgacagtgg atctgggaca gattacactc tcaccatcag    60
cagcctgcag cctgaagatt ttgcaaccta ttactgtcaa cagagtgaca gtaaccctcc    120

<210> SEQ ID NO 607
<211> LENGTH: 120
<212> TYPE: DNA
<213> ORGANISM: Homo sapiens

<400> SEQUENCE: 607
tgggattccc actcggttca gtgacagtgg atctgggaca gattacactc ccaccatcag    60
cagcctgcag cctgaagatt ttgcaactta ctactgtcaa cagagtgaca gtacccctcc    120

<210> SEQ ID NO 608
<211> LENGTH: 120
<212> TYPE: DNA
<213> ORGANISM: Homo sapiens

<400> SEQUENCE: 608
tggggtccca tcaaggttca gcggcagtgg atctgggaca gatttcactc tcaccatcag    60
cagcctgcag cctgaagatt ttgcaactta ctattgtcaa caggctaaca gtttccctcc    120

<210> SEQ ID NO 609
<211> LENGTH: 120
<212> TYPE: DNA

<213> ORGANISM: Homo sapiens

<400> SEQUENCE: 609
tggggtccca tcaaggttca gcggcagtgg atctgggaca gatttcactc tcaccatcag    60
cagcctgcag cctgaagatt ttgcaactta ctattgtcaa caggctaaca gtttcccttc   120

<210> SEQ ID NO 610
<211> LENGTH: 120
<212> TYPE: DNA
<213> ORGANISM: Homo sapiens

<400> SEQUENCE: 610
tggggtccca tcaaggttca gcggcagtgg atctgggaca gatttcactc tcaccatcag    60
cagcctgcag cctgaagatt ttgcaactta ttactgtcaa cagtttaata attaccctca   120

<210> SEQ ID NO 611
<211> LENGTH: 120
<212> TYPE: DNA
<213> ORGANISM: Homo sapiens

<400> SEQUENCE: 611
tggggtccca tcaaggttca gcggcagtgg atctgggaca gatttcactc tcaccatcag    60
cagcctgcag cctgaagatt ttgcaactta ttactgtcaa cagtttaata gttaccctca   120

<210> SEQ ID NO 612
<211> LENGTH: 120
<212> TYPE: DNA
<213> ORGANISM: Homo sapiens

<400> SEQUENCE: 612
agtggggtcc catccaggtt cagtggcagt ggatctggga cggattacac tctcaccatc    60
agcagcctgc agcctgaaga ttttgcaact tattactgtc aacagtatta gtacctct     120

<210> SEQ ID NO 613
<211> LENGTH: 120
<212> TYPE: DNA
<213> ORGANISM: Homo sapiens

<400> SEQUENCE: 613
aagtggggtc ccatcaaagt tcagcggcag tggatctggg acagatttca ctctcaccat    60
cagcagcctg cagcctgaag attttgcaac ttattactgc aacagtata atagttaccc    120

<210> SEQ ID NO 614
<211> LENGTH: 120
<212> TYPE: DNA
<213> ORGANISM: Homo sapiens

<400> SEQUENCE: 614
aggtggggtc ccatcaaggt tcagcggcag tggatctggg acagaattca ctctcacaat    60
cagcagcctg cagcctgaag attttgcaac ttattactgt ctacagcata atagttaccc   120

<210> SEQ ID NO 615
<211> LENGTH: 120
<212> TYPE: DNA
<213> ORGANISM: Homo sapiens

<400> SEQUENCE: 615
tggggtccca tcaaggttca gcggcagtgg atctgggaca gaattcactc tcacaatcag    60
caacctgcag cctgaagatt ttgcaactta ttactgtcta cagcataata gttaccctcc   120

<210> SEQ ID NO 616
<211> LENGTH: 120
<212> TYPE: DNA
<213> ORGANISM: Homo sapiens

<400> SEQUENCE: 616
tggggtccca tcaaggttca gcggcagtgg atctgggaca gaattcactc tcacaatcag    60
cagcctgcag cctgaagatt ttgcaactta ttactgtcta cagcataata gttaccctcc   120

<210> SEQ ID NO 617
<211> LENGTH: 120
<212> TYPE: DNA
<213> ORGANISM: Homo sapiens

<400> SEQUENCE: 617
gggtcccgtc acggttcagt ggcagtaggt ctgggacaca tttcacacat tctcaccatc    60
aggagcctgc aacctgaaga tgttataact tattgctgtc tatagactta cagcagccat   120

<210> SEQ ID NO 618
<211> LENGTH: 120
<212> TYPE: DNA
<213> ORGANISM: Homo sapiens

<400> SEQUENCE: 618
atcaggggtc ccatctcggt tcagtggcag tggatctggg acagatttca ctctcaccat    60
cagcagcctg cagcctgaag atgttgcaac ttattactgt caaaatata acagtgtccc    120

<210> SEQ ID NO 619
<211> LENGTH: 120
<212> TYPE: DNA
<213> ORGANISM: Homo sapiens

<400> SEQUENCE: 619
ggggtccctg atcgcttctc tggctccaag tctggcaaca cggcctccct gaccgtctct    60
gggctccagg ctgaggatga ggctgattac tactgcagtt catatgctgg cgacaacatt   120

<210> SEQ ID NO 620
<211> LENGTH: 120
<212> TYPE: DNA
<213> ORGANISM: Homo sapiens

<400> SEQUENCE: 620
tgaaaacagg ggtcccatca aggttcaatg gaagtggatc tgggacagat tttactttca    60
ccatcagcag cctgcagcct gaagatattg caacatatta ctgtcaacag tatgataatc   120

<210> SEQ ID NO 621
<211> LENGTH: 120
<212> TYPE: DNA
<213> ORGANISM: Homo sapiens

<400> SEQUENCE: 621
tggggctcct tcgcggttcg gtggcagtgg atctgggaca gatttactc tcaccatcag     60 aatcctgcag cctaaagatg ttgcaactta ttactgtcaa cagtataaaa attaccctat   120

<210> SEQ ID NO 622
<211> LENGTH: 120
<212> TYPE: DNA
<213> ORGANISM: Homo sapiens

```
<400> SEQUENCE: 622
tggagtccca tctcggttca gtggcagtgg atctgggaca gatttcactc tcactatcag    60
cagcctgcag cctgaagatg ttgcaactta ttacggtcaa cggacttaca atgcccctcc   120

<210> SEQ ID NO 623
<211> LENGTH: 120
<212> TYPE: DNA
<213> ORGANISM: Homo sapiens

<400> SEQUENCE: 623
tggggtccca tcaaggttca gtggcagtgg atctgggaca gatttcactc tcaccatcag    60
cagtctgcaa cctgaagatt ttgcaactta ctactgtcaa cagagttaca gtacccctcc   120

<210> SEQ ID NO 624
<211> LENGTH: 120
<212> TYPE: DNA
<213> ORGANISM: Homo sapiens

<400> SEQUENCE: 624
tggggtccca tcaaggttca gtggcagtgg atctgggaca gatttcactc tcaccatcag    60
cagtctgcaa cctgaagatt ttgcaactta ttactgtcag tgtggttaca gtacacctcc   120

<210> SEQ ID NO 625
<211> LENGTH: 120
<212> TYPE: DNA
<213> ORGANISM: Homo sapiens

<400> SEQUENCE: 625
tggggtccca ccaaggttca gcggcagtgg atctgggaca gaattcgctc tcaccatcag    60
cagcctgcag cctgatgatt ttgcaactta ttactgccaa cagtatgata gttattcgac   120

<210> SEQ ID NO 626
<211> LENGTH: 120
<212> TYPE: DNA
<213> ORGANISM: Homo sapiens

<400> SEQUENCE: 626
tggggtccca tcaaggttca gcggcagtgg atctgggaca gaattcactc tcaccatcag    60
cagcctgcag cctgatgatt ttgcaactta ttactgccaa cagtataata gttattctcc   120

<210> SEQ ID NO 627
<211> LENGTH: 120
<212> TYPE: DNA
<213> ORGANISM: Homo sapiens

<400> SEQUENCE: 627
gtccctgatc gcttctctgg ctccatcctt gggaacaaag ctgccctcac catcacgggg    60
gcccaggcag atgatgattc tgactattac tgtgtactat atatgggtga tgcctgggcg   120

<210> SEQ ID NO 628
<211> LENGTH: 120
<212> TYPE: DNA
<213> ORGANISM: Homo sapiens

<400> SEQUENCE: 628
gtggggtccc atcaaggttc agcggcagtg gatttggcac agatttcact ctcaccatca    60
gcagcctaca gcctgaagat tttgcaactt attactgtct acaagattac agttaccctc   120
```

```
<210> SEQ ID NO 629
<211> LENGTH: 120
<212> TYPE: DNA
<213> ORGANISM: Homo sapiens

<400> SEQUENCE: 629
tggggtccca tcaaggttca gcggcagtgg atctggcaca gatttcactc tcaccatcag      60
cagcctgcag cctgaagatt ttgcaactta ttactgtcta caagattaca attaccctcc     120

<210> SEQ ID NO 630
<211> LENGTH: 120
<212> TYPE: DNA
<213> ORGANISM: Homo sapiens

<400> SEQUENCE: 630
gtggggtccc atcaaggttc agcggcagtg gatctgggac agatttcact ctcaccatca      60
gcggcctgca gtctgaagat tttgcaactt attactgtcg acagtattat agttaccctc     120

<210> SEQ ID NO 631
<211> LENGTH: 120
<212> TYPE: DNA
<213> ORGANISM: Homo sapiens

<400> SEQUENCE: 631
ttgggtccca tcaaggttca gcggccgtgg atctgggacc gaattcaccc tcacaatcag      60
cagcctgcag cctgaagatt ttgcaactta ttactgtcaa cagcttaatc gttaccctcc     120

<210> SEQ ID NO 632
<211> LENGTH: 120
<212> TYPE: DNA
<213> ORGANISM: Homo sapiens

<400> SEQUENCE: 632
aagtggggtc ccatcaaggt tcagcggcag tggatctggg acagatttca ctctcactat      60
cagcagcctg cagcctgaag attttgcaac ttactattgt caacaggcta acagtttccc     120

<210> SEQ ID NO 633
<211> LENGTH: 120
<212> TYPE: DNA
<213> ORGANISM: Homo sapiens

<400> SEQUENCE: 633
aagtggggtc ccgtcaaggt tcagcggcag tggatctggg acagatttca ctctcaccat      60
cagcagcctg cagcctgagg attttgcgac ttattactgc aacagtata atagttaccc     120

<210> SEQ ID NO 634
<211> LENGTH: 120
<212> TYPE: DNA
<213> ORGANISM: Homo sapiens

<400> SEQUENCE: 634
tggggtccca tcaaggttca gcggcagtgg atctgggaca gatttcactc tcaccatcag      60
cagcctgcag cctgaagatt ttgcaactta ttactgccaa cagtataata gttaccctcc     120

<210> SEQ ID NO 635
<211> LENGTH: 120
<212> TYPE: DNA
<213> ORGANISM: Homo sapiens

<400> SEQUENCE: 635
```

```
aagtggggtc ccatcgaggt tcagcggcag tggatctggg acagaattca ctctcacaat        60
cagcagcctg cagcctgaag attttgcaac ttattactgt ctacatcata ataattaccc       120
```

<210> SEQ ID NO 636
<211> LENGTH: 120
<212> TYPE: DNA
<213> ORGANISM: Homo sapiens

<400> SEQUENCE: 636

```
gggtcccgtc acggttcagt ggcagtaggt ctgggacaca tttcacacat tctcaccatc        60
aggagcctgc aacctgaaga tgttataact tattactgtc tatagactta cagcagccat       120
```

<210> SEQ ID NO 637
<211> LENGTH: 120
<212> TYPE: DNA
<213> ORGANISM: Homo sapiens

<400> SEQUENCE: 637

```
gggggtccca tctcggttca gtggcagtgg atctgggaca gatttcactc tcaccatcag        60
cagcctgcag cctgaagatg ttgcaactta ttactgtcaa agtataaaca gtgcccctcc       120
```

<210> SEQ ID NO 638
<211> LENGTH: 120
<212> TYPE: DNA
<213> ORGANISM: Homo sapiens

<400> SEQUENCE: 638

```
gtcccattgc agttatgtgg cattggatcc aggacagatt tgattctcac cattagcatc        60
ctccagtctg aagttgctgc aacttcttat tattggtcaa cagtataaaa gtgaccctct       120
```

<210> SEQ ID NO 639
<211> LENGTH: 120
<212> TYPE: DNA
<213> ORGANISM: Homo sapiens

<400> SEQUENCE: 639

```
agcaggggtc ccatcaaggt tcagtggaaa tagatctggg acagattta ctttcaccat        60 caacagcctg cagtctggag atatcgcaac atattactgt caacagtatg atgatctccc       120
```

<210> SEQ ID NO 640
<211> LENGTH: 120
<212> TYPE: DNA
<213> ORGANISM: Homo sapiens

<400> SEQUENCE: 640

```
agtggggtcc catcaaggtt cagtggcagt ggatctggga cagatttcac tctcaccatc        60
aacagtctgc aacctgaaga ttttgcaact tactactgtc aacagagtta cagtaccccc       120
```

<210> SEQ ID NO 641
<211> LENGTH: 120
<212> TYPE: DNA
<213> ORGANISM: Homo sapiens

<400> SEQUENCE: 641

```
tggggtctca tcgaggttca gtggcagggg atctgggacg gatttcactc tcaccatcat        60
cagcctgaag cctgaagatt ttgcagctta ttactgtaaa caggacttca gttaccctcc       120
```

<210> SEQ ID NO 642
<211> LENGTH: 120

```
<212> TYPE: DNA
<213> ORGANISM: Homo sapiens

<400> SEQUENCE: 642
tggggtccca tcaaggttca gcggcagtgg atctgggacg gattacactc tcaccatcag      60
cagcctgcag cctgaagatt ttgcaactta ttactgtcaa cagtattata gtacccctcc     120

<210> SEQ ID NO 643
<211> LENGTH: 120
<212> TYPE: DNA
<213> ORGANISM: Homo sapiens

<400> SEQUENCE: 643
agtggggtcc catcaagatt cagtggcagt ggatctggga cagatttcac tctcaccatt      60
agttgcctgc aatctgaaga ttttgcaact tattactgtc aacaatatta atttccct      120

<210> SEQ ID NO 644
<211> LENGTH: 120
<212> TYPE: DNA
<213> ORGANISM: Homo sapiens

<400> SEQUENCE: 644
tggggtccca tcaaggttca gtggcagtgg atctgggaca gatttcactc tcaccatcag      60
ctgcctgcag tctgaagatt ttgcaactta ttactgtcaa cagtattata gtttccctcc     120

<210> SEQ ID NO 645
<211> LENGTH: 120
<212> TYPE: DNA
<213> ORGANISM: Homo sapiens

<400> SEQUENCE: 645
tggggtccca tccaggttca gtggcagtgg atctgggacg gattacactc tcaccatcag      60
cagcctgcag cctgaagatt ttgcaactta ttactgtcaa cagtattata gtacccctcc     120

<210> SEQ ID NO 646
<211> LENGTH: 120
<212> TYPE: DNA
<213> ORGANISM: Homo sapiens

<400> SEQUENCE: 646
gggtcccaga caggttcagt ggcagtgggt caggcattga tttcacactg aaaatcagcc      60
cggtggaggc tgaggatgtt ggggtttata ttactgcatg caagctacac actggccccc     120

<210> SEQ ID NO 647
<211> LENGTH: 120
<212> TYPE: DNA
<213> ORGANISM: Homo sapiens

<400> SEQUENCE: 647
ctggagtccc agacaggttc aatggcagtg ggtcaggcac tgatttcaca ctgaaaatca      60
gccgggtgga gctgaagatg ttggggttta ttactgcatg caggctctgc agcttcctcc     120

<210> SEQ ID NO 648
<211> LENGTH: 120
<212> TYPE: DNA
<213> ORGANISM: Homo sapiens

<400> SEQUENCE: 648
tgcagtccca gacaggctca gtggcagtgg gtcaggcact gatttcacac tgaaaatcag      60
```

```
ccgggtggag gctgaagatg ttggggttta tcactgcatg caagctctac aaactcctcc    120
```

<210> SEQ ID NO 649
<211> LENGTH: 120
<212> TYPE: DNA
<213> ORGANISM: Homo sapiens

<400> SEQUENCE: 649

```
tggagttcca gacaggttca gtggcagtgg gtcaggcact gatttcactc tgaaaatcag    60
tagggtggag gcttaggatg ttggggttta ttactgcatg caagctctac aaactccgcc    120
```

<210> SEQ ID NO 650
<211> LENGTH: 120
<212> TYPE: DNA
<213> ORGANISM: Homo sapiens

<400> SEQUENCE: 650

```
gggtcccaga caggttcagt ggcagtgggt cgggcattga tttcacactg aaaatcagcc    60
cggtggaggc tgcggatgtt ggggtttata ttactgcatg caagctacac actggtcccc    120
```

<210> SEQ ID NO 651
<211> LENGTH: 120
<212> TYPE: DNA
<213> ORGANISM: Homo sapiens

<400> SEQUENCE: 651

```
ctggagtccc agacaggttc agtggcagtg ggttggggac agatttcatg ctgaaatcag    60
gaggatggat gctgaggatg ttggggttta ttgctgccag caaagtacac attatcctcc    120
```

<210> SEQ ID NO 652
<211> LENGTH: 120
<212> TYPE: DNA
<213> ORGANISM: Homo sapiens

<400> SEQUENCE: 652

```
tggagtccca gacaggttca gtggcagtgg gtcggggaca gatttcatgt ttaaaataag    60
gaggatggat gctgaggatg ttggggttta ttgctgccag caaagtacac attattctcc    120
```

<210> SEQ ID NO 653
<211> LENGTH: 120
<212> TYPE: DNA
<213> ORGANISM: Homo sapiens

<400> SEQUENCE: 653

```
aatcccttct ctggctccaa gtctggcaac acggcctccc tgaccatctc tgggctccag    60
gctgaggacg aggctgatta ttactgcgcc tcatatacaa gcagcagcac tctttatatc    120
```

<210> SEQ ID NO 654
<211> LENGTH: 120
<212> TYPE: DNA
<213> ORGANISM: Homo sapiens

<400> SEQUENCE: 654

```
tctggggtct cggcaggtt cagcagcagt ggttcaggga cagatttcat attgaaaatc     60
agcagggtag aggctgagga cgttgggggtt tattactgcc tgcaaggtac acaagtgcct   120
```

<210> SEQ ID NO 655
<211> LENGTH: 120
<212> TYPE: DNA
<213> ORGANISM: Homo sapiens

```
<400> SEQUENCE: 655
tggtaatgga tacacctatt tgtattagtt cctgcagaag ccaggccact ctccacagct      60
cctgatctgt aggacttcca atcagttttc tgccttccca cacaggttct ccccagtggg    120

<210> SEQ ID NO 656
<211> LENGTH: 120
<212> TYPE: DNA
<213> ORGANISM: Homo sapiens

<400> SEQUENCE: 656
ctctggggtc ccagacagat tcagtggcag tggggcaggg acagatttca cactgaaaat      60
cagcagggtg gaagctgagg atgtcggggt ttattactgc atgcaagcta cacaattccc    120

<210> SEQ ID NO 657
<211> LENGTH: 120
<212> TYPE: DNA
<213> ORGANISM: Homo sapiens

<400> SEQUENCE: 657
tggagtgcca gataggttca gtggcagcgg gtcagggaca gatttcacac tgaaaatcag      60
ccgggtggag gctgaggatg ttggagttta ttactgcatg caagatgcac aagatcctcc    120

<210> SEQ ID NO 658
<211> LENGTH: 120
<212> TYPE: DNA
<213> ORGANISM: Homo sapiens

<400> SEQUENCE: 658
cggggtccct gacaggttca gtggcagtgg atcaggcaca gattttacac tgaaaatcag      60
cagagtggag gctgaggatg ttggggttta ttactgcatg caagctctac aaactcctcc    120

<210> SEQ ID NO 659
<211> LENGTH: 120
<212> TYPE: DNA
<213> ORGANISM: Homo sapiens

<400> SEQUENCE: 659
tggagtgcca gataggttca gtggcagcgg gtcagggaca gatttcacac tgaaaatcag      60
ccgggtggag gctgaggatg ttggggttta ttactgaatg caaggtatac accttcctcc    120

<210> SEQ ID NO 660
<211> LENGTH: 120
<212> TYPE: DNA
<213> ORGANISM: Homo sapiens

<400> SEQUENCE: 660
tggagtgcca gataggttca gtggcagcgg gtcaggaca gatttcacac tgaaaatcag      60
ccgggtggag gctgaggatg ttggggttta ttactgcatg caaggtatac accttcctcc    120

<210> SEQ ID NO 661
<211> LENGTH: 120
<212> TYPE: DNA
<213> ORGANISM: Homo sapiens

<400> SEQUENCE: 661
ctctggggtc ccagacagat tcaccggcag tgggtcaggc actgatttca cactggaaat      60
cagcagggtg gaggctgagg atgttggggt ttattactgc atgcaaggta cacactggcc    120
```

<210> SEQ ID NO 662
<211> LENGTH: 120
<212> TYPE: DNA
<213> ORGANISM: Homo sapiens

<400> SEQUENCE: 662
ctctggggtc ccagacagat tcagcggcag tgggtcaggc actgatttca cactgaaaat      60
cagcagggtg aggctgagg atgttggggt ttattactgc atgcaaggta cacactggcc     120

<210> SEQ ID NO 663
<211> LENGTH: 120
<212> TYPE: DNA
<213> ORGANISM: Homo sapiens

<400> SEQUENCE: 663
atttatgagg tttccaacca agcctccgaa ttctcagaca ggttcagggg taatgggtca      60
ggtactgagt ttacactgaa agtcagtagg acggagacca aggatgttgg agtttattag     120

<210> SEQ ID NO 664
<211> LENGTH: 120
<212> TYPE: DNA
<213> ORGANISM: Homo sapiens

<400> SEQUENCE: 664
tctggagtcc cagacaggtt caatagcagt gggtcaggca catattttaa actcaaaatt      60
agcagggtgg aggctgagga tattcgactt tattaataca tgcaagctac ataatatcct     120

<210> SEQ ID NO 665
<211> LENGTH: 120
<212> TYPE: DNA
<213> ORGANISM: Homo sapiens

<400> SEQUENCE: 665
tggagtccca aacaagttca gtggcagcag gtcaggggaca ggtttcacac ttaaattcag      60
caaagtggag gctgaggatg ttggggttta ttgctgtgaa cagggtctgc aaggtcctca     120

<210> SEQ ID NO 666
<211> LENGTH: 120
<212> TYPE: DNA
<213> ORGANISM: Homo sapiens

<400> SEQUENCE: 666
cctgatcgct tctctggctc caagtctggc aacacggcct ccctgaccat ctctgggctc      60
ctggctgaag atgaggctga ttatcactgc tgctcatatg cgggcagctt cactgtgatc     120

<210> SEQ ID NO 667
<211> LENGTH: 120
<212> TYPE: DNA
<213> ORGANISM: Homo sapiens

<400> SEQUENCE: 667
ctggagtccc agacaagttc agtggcagtg ggtcggggac agatttcatg ctaaaatcag      60
gaggatggat gctgaggatg ttggggttta ttgctgccag caaagtacac attatcctcc     120

<210> SEQ ID NO 668
<211> LENGTH: 120
<212> TYPE: DNA
<213> ORGANISM: Homo sapiens

<400> SEQUENCE: 668
tctggggtcc cagacaggtt tagtggcagt gggtcaggca gtgatttcac actgaaaatc      60
agctgggtgg aggctgagga tgttgggggtt tattactgca tgcaagctac acagtttcct    120

<210> SEQ ID NO 669
<211> LENGTH: 120
<212> TYPE: DNA
<213> ORGANISM: Homo sapiens

<400> SEQUENCE: 669
ggggtttcta atcgcttctc tggctccaag tctggcaaca cggcctccct gaccatctct      60
ggcctccagg ctgaggacga ggctgattat tactgctgct catatgcaaa cagcgactcc    120

<210> SEQ ID NO 670
<211> LENGTH: 120
<212> TYPE: DNA
<213> ORGANISM: Homo sapiens

<400> SEQUENCE: 670
accacataac cgtgagtttg cagtggttgc aggtcaggga cagattttat gcttaagatc      60
agtagggtgg aggctgagga tcttggctat tacaactgcc accacactct acaatatcct    120

<210> SEQ ID NO 671
<211> LENGTH: 120
<212> TYPE: DNA
<213> ORGANISM: Homo sapiens

<400> SEQUENCE: 671
tggggtccca gacagattca gtggcagtgg ggcagggaca gatttcacac tgaaaatcag      60
cagggtggaa gctgaggatg tcggggttta ttactgcacg caagctacac aatttcctca    120

<210> SEQ ID NO 672
<211> LENGTH: 120
<212> TYPE: DNA
<213> ORGANISM: Homo sapiens

<400> SEQUENCE: 672
tggagtgcca gataggttca gtggcagcgg gtcagggaca gatttcacac tgaaaatcag      60
ccgggtggag gctgaggatt ttggagttta ttactgcatg caagatgcac aagatcctcc    120

<210> SEQ ID NO 673
<211> LENGTH: 120
<212> TYPE: DNA
<213> ORGANISM: Homo sapiens

<400> SEQUENCE: 673
tctggagtgc cagataggtt cagtggcagc gggtcaggga cagatttcac actgaaaatc      60
agccgggtgg aggctgagga ttttggagtt tattactgca tgcaagatgc acaagatcct    120

<210> SEQ ID NO 674
<211> LENGTH: 120
<212> TYPE: DNA
<213> ORGANISM: Homo sapiens

<400> SEQUENCE: 674
tccggggtcc ctgacaggtt cagtggcagt ggatcaggca cagatttttac actgaaaatc      60 agcagagtgg aggctgagga tgttgggggtt tattactgca tgcaagctct acaaactcct    120

<210> SEQ ID NO 675

```
<211> LENGTH: 120
<212> TYPE: DNA
<213> ORGANISM: Homo sapiens

<400> SEQUENCE: 675
ctctggagtg ccagataggt tcagtggcgg cgggtcaggg acagatttca cactgaaaat    60
cagccgggtg gaggctgagg atgctgggt ttattactgc atgcaaagta tacagcttcc   120

<210> SEQ ID NO 676
<211> LENGTH: 120
<212> TYPE: DNA
<213> ORGANISM: Homo sapiens

<400> SEQUENCE: 676
acgcagactc cgtgaagggc cggttcacca tctccagaga caattccaag aagaacactc    60
tgtatctgca aatgaacagc ctgagagtcg aggacacggc cgtatattac tgtgcgaaag   120

<210> SEQ ID NO 677
<211> LENGTH: 120
<212> TYPE: DNA
<213> ORGANISM: Homo sapiens

<400> SEQUENCE: 677
ctggggtccc agacagattc agcggcagtg ggtcaggcac tgatttcaca ctgaaaatca    60
gcagggtgga ggctgaggat gttggggttt attactgcat gcaaggtaca tactggcctc   120

<210> SEQ ID NO 678
<211> LENGTH: 120
<212> TYPE: DNA
<213> ORGANISM: Homo sapiens

<400> SEQUENCE: 678
tcttacgctc cgtcgataaa aggcaagttc atcatttcca gagatgattc cagcaatatg    60
ttgtatcttc aaatgaacaa cctgaaaacc gaggacacgg ccgtctattt ttgtactcgc   120

<210> SEQ ID NO 679
<211> LENGTH: 120
<212> TYPE: DNA
<213> ORGANISM: Homo sapiens

<400> SEQUENCE: 679
tggagtccca gacaggttca gtggcagtgg gtcaggcact gatttcacac tgaaaatcag    60
cagggtggag gctgaggatg ttggagttta ttactgcatg caacgtatag agtttccttc   120

<210> SEQ ID NO 680
<211> LENGTH: 120
<212> TYPE: DNA
<213> ORGANISM: Homo sapiens

<400> SEQUENCE: 680
cctggaaaag ctccctggtt cctcatctaa ggcacatcca acagggccac tagcatcctg    60
gggtttagtg gtcatggatt ggagacagac tttactatca ccatcagctg cctgaagcct   120

<210> SEQ ID NO 681
<211> LENGTH: 120
<212> TYPE: DNA
<213> ORGANISM: Homo sapiens

<400> SEQUENCE: 681
tggcatccca gccaggttca gtggtagtgg gtctgggaca gacttcactc tcaccatcag    60
```

```
cagcctgcag cctgaagatt ttgcagttta ttactgtcag caggattata acttacctcc    120
```

<210> SEQ ID NO 682
<211> LENGTH: 120
<212> TYPE: DNA
<213> ORGANISM: Homo sapiens

<400> SEQUENCE: 682

```
tgacatccca gtggggctca gtagctgtga atctgggatg tactttactc tcaccaacag    60
taacctggaa cctgaagatt ttgcacttga ttactcttat ctgtatagta gttggaattt   120
```

<210> SEQ ID NO 683
<211> LENGTH: 120
<212> TYPE: DNA
<213> ORGANISM: Homo sapiens

<400> SEQUENCE: 683

```
ccgctggcgt cccagccagg ttcagtggca gtgggtctgg gacagacttc actctcacca    60
tcagcaccct agaacctgaa gattttgcag tttattactg tcaacactgt aggaactggc   120
```

<210> SEQ ID NO 684
<211> LENGTH: 120
<212> TYPE: DNA
<213> ORGANISM: Homo sapiens

<400> SEQUENCE: 684

```
tactacgcag actccgtgaa gggccgattc accatctcca gacacaattc caagaacacg    60
ctgtatcttc aaatgaacag cctgagagct gaggacacgg ccgtgtatta ctgtgcgaga   120
```

<210> SEQ ID NO 685
<211> LENGTH: 120
<212> TYPE: DNA
<213> ORGANISM: Homo sapiens

<400> SEQUENCE: 685

```
ggtatcccag ccaggttcag tggcagtggg tctgggacag agttcactct caccatcagc    60
agcctgcagt ctgaagattt tgcagtttat tactgtcagc agtataataa ctggcctccg   120
```

<210> SEQ ID NO 686
<211> LENGTH: 120
<212> TYPE: DNA
<213> ORGANISM: Homo sapiens

<400> SEQUENCE: 686

```
cactggcatc ccagacaggt tcagtggcag tgggtctggg acagacttca ctctcaccat    60
cagcagactg gagcctcaag attttgcagt gtattactgt cagcactatg gtaggtcacc   120
```

<210> SEQ ID NO 687
<211> LENGTH: 120
<212> TYPE: DNA
<213> ORGANISM: Homo sapiens

<400> SEQUENCE: 687

```
gtgcatccag cagggccact ggcatcccag caaggttcag tggcagtggg tctgggacag    60
acttcactct caccatcagc agactggagc ctgaagattt tgcagtttat tactgtcagc   120
```

<210> SEQ ID NO 688
<211> LENGTH: 120
<212> TYPE: DNA

<213> ORGANISM: Homo sapiens

<400> SEQUENCE: 688
tacagccctg atttgtgata gtgggtcggg gacagggctt actctcacca tcggcagcct    60
ggagcctgga gcctggagat ttgcacttca tcactgttat cagcatagta gttggtgtcc   120

<210> SEQ ID NO 689
<211> LENGTH: 120
<212> TYPE: DNA
<213> ORGANISM: Homo sapiens

<400> SEQUENCE: 689
atcccagcca ggttcagtgg cagtgggtct gggacagact tcactctcac catcagcagc    60
ctggagcctg aagattttgc agtttattac tgtcagcacc gtagcaactg gctaatcgcc   120

<210> SEQ ID NO 690
<211> LENGTH: 120
<212> TYPE: DNA
<213> ORGANISM: Homo sapiens

<400> SEQUENCE: 690
agcatcccag cccggttcag tggtggtggg cctgaggcag actttacccc aaccatcaac    60
agcctagacc ctgaagatgt cacaatttta ttaccctcat cagtacagca gtgggtgtcc   120

<210> SEQ ID NO 691
<211> LENGTH: 120
<212> TYPE: DNA
<213> ORGANISM: Homo sapiens

<400> SEQUENCE: 691
tagcatccca gccaggttca gtggcagtgg gtctgggaca gacttcactc tcaccatcag    60
cagcctgcag cctgaagatt ttgcagttta ttactgtcag caggatcata acttacctcc   120

<210> SEQ ID NO 692
<211> LENGTH: 120
<212> TYPE: DNA
<213> ORGANISM: Homo sapiens

<400> SEQUENCE: 692
tggcatccca gccaggttca gtggcagtgg gtctgggaca gacttcactc tcaccatcag    60
cagcctgcag cctgaagatt ttgcagttta ttactgtcag caggattata acttacctcc   120

<210> SEQ ID NO 693
<211> LENGTH: 120
<212> TYPE: DNA
<213> ORGANISM: Homo sapiens

<400> SEQUENCE: 693
tagcatccca gccaggttca gtggcagtgg gtctgggaga gacttcactc tcaccatcag    60
cagcctgcag cctgaagatt ttgcagttta ttactgtcag caggatcata acttacctcc   120

<210> SEQ ID NO 694
<211> LENGTH: 120
<212> TYPE: DNA
<213> ORGANISM: Homo sapiens

<400> SEQUENCE: 694
tagcatccca gccaggttca gtggcagtgg gtctgggaca gacttcactc tcaccatcag    60
cagcctgcag cctgaagatt ttgcagttta ttactgtcag caggattata acttacctcc   120

<210> SEQ ID NO 695
<211> LENGTH: 120
<212> TYPE: DNA
<213> ORGANISM: Homo sapiens

<400> SEQUENCE: 695
tggcatccca gccaggttca gtggcagtgg gcctgggaca gacttcactc tcaccatcag    60
cagcctagag cctgaagatt ttgcagttta ttactgtcag cagcgtagca actggcatcc   120

<210> SEQ ID NO 696
<211> LENGTH: 120
<212> TYPE: DNA
<213> ORGANISM: Homo sapiens

<400> SEQUENCE: 696
tggcatccca gccaggttca gtggcagtgg gcctgggaca gacttcactc tcaccatcag    60
cagcctagag cctgaagatt ttgcagtgta ttactgtcag cagcgtagca actggcatcc   120

<210> SEQ ID NO 697
<211> LENGTH: 120
<212> TYPE: DNA
<213> ORGANISM: Homo sapiens

<400> SEQUENCE: 697
tatcccagcc aggttcagtg gcagtgggtc tgggacagag ttcactctca ccatcagtag    60
cctgcagtct gaagattttg cagtttatta ctgtcagcag tataataact ggcctcagag   120

<210> SEQ ID NO 698
<211> LENGTH: 120
<212> TYPE: DNA
<213> ORGANISM: Homo sapiens

<400> SEQUENCE: 698
tggcatccca gccaggttca gtggcagtgg gtctgggaca gagttcactc tcaccatcag    60
cagcctgcag tctgaagatt ttgcagttta ttactgtcag cagtataata actgacctcc   120

<210> SEQ ID NO 699
<211> LENGTH: 120
<212> TYPE: DNA
<213> ORGANISM: Homo sapiens

<400> SEQUENCE: 699
tggcatccca gccaggttca gtggcagtgg gtctgggaca gagttcactc tcaccatcag    60
catcctgcag tctgaagatt ttgcagttta ttactgtcag cagtataata actggcctcc   120

<210> SEQ ID NO 700
<211> LENGTH: 120
<212> TYPE: DNA
<213> ORGANISM: Homo sapiens

<400> SEQUENCE: 700
actggcatct cagacaggtt cagtggcagt gggtctggga cagacttcac tctcaccatc    60
agcagactga agcctgaaga ttctgcagtg tatttctgtc agcaatatgg atcatcccct   120

<210> SEQ ID NO 701
<211> LENGTH: 120
<212> TYPE: DNA
<213> ORGANISM: Homo sapiens

```
<400> SEQUENCE: 701
tggcatccca gacaggttca gtggcagtgg gtctgggaca gacttcactc tcaccatcag      60
cagactggag cctgaagatt ttgcagtcta ttactgtcag cagcgtagca actggcatcc     120

<210> SEQ ID NO 702
<211> LENGTH: 120
<212> TYPE: DNA
<213> ORGANISM: Homo sapiens

<400> SEQUENCE: 702
atctatggta cagccctgat ttgtgatagt gggtcaggac agggcttact ctcaccatcg      60
gcaggctgga gcctgaagat ttgcacttca tcactgttat cagcatagta gttggtgtcc     120

<210> SEQ ID NO 703
<211> LENGTH: 120
<212> TYPE: DNA
<213> ORGANISM: Homo sapiens

<400> SEQUENCE: 703
caatgtccca gcctggtgga gtggcagtgg gttcggggaa agcttcagtc tcattatcag      60
caggctggag catgaagatt ttgcacttta acactgttat cagcatagtg gtgggtattc     120

<210> SEQ ID NO 704
<211> LENGTH: 120
<212> TYPE: DNA
<213> ORGANISM: Homo sapiens

<400> SEQUENCE: 704
atccggggtc cctgaccgat tcagtggcag cgggtctggg acagatttca ctctcaccat      60
tagtagcctg cagactgaag atgtggcagt ttattcttgt cagcaatttc atagttttcc     120

<210> SEQ ID NO 705
<211> LENGTH: 120
<212> TYPE: DNA
<213> ORGANISM: Homo sapiens

<400> SEQUENCE: 705
cctggaatct cacctcgatt cagtggcagc gggtatggaa cagattttac cctcacaatt      60
aataacatag aatctgagga tgctgcatat tacttctgtc tacaacatga taatttcccg     120

<210> SEQ ID NO 706
<211> LENGTH: 120
<212> TYPE: DNA
<213> ORGANISM: Homo sapiens

<400> SEQUENCE: 706
aggggtcccc tcgaggttca gtggcagtgg atctgggaca gatttcaccc tcaccatcaa      60
tagcctggaa gctgaagatg ctgcaacgta ttactgtcat cagagtagta gtttacctca     120

<210> SEQ ID NO 707
<211> LENGTH: 120
<212> TYPE: DNA
<213> ORGANISM: Homo sapiens

<400> SEQUENCE: 707
aggggtcccc tcgaggttca gtggcagtgg atctgggaca gatttcaccc tcaccatcaa      60
tagcctggaa gctgaagatg ctgcagcgta ttactgtcat cagagtagta gtttacctca     120
```

-continued

<210> SEQ ID NO 708
<211> LENGTH: 120
<212> TYPE: DNA
<213> ORGANISM: Homo sapiens

<400> SEQUENCE: 708
tcaggggtcc cctcgaggtt cagtggcagt ggatctggga cagatttcac ctttaccatc    60
agtagcctgg aagctgaaga tgctgcaaca tattactgtc agcagggcaa taagcaccct   120

<210> SEQ ID NO 709
<211> LENGTH: 120
<212> TYPE: DNA
<213> ORGANISM: Homo sapiens

<400> SEQUENCE: 709
tggaatccca cctcgattca gtggcagcgg gtatggaaca gatttacccc tcacaattaa    60
taacatagaa tctgaggatg ctgcatatta cttctgtcta caacatgata atttccctct   120

<210> SEQ ID NO 710
<211> LENGTH: 120
<212> TYPE: DNA
<213> ORGANISM: Homo sapiens

<400> SEQUENCE: 710
gtccctgatg gcttctctgg ctccaagtct ggaaacacag cctccatgac catctctggg    60
ttccaggctg aggatgaggc tgattattac tgcaactcac ataggagagg tggcactttc   120

<210> SEQ ID NO 711
<211> LENGTH: 120
<212> TYPE: DNA
<213> ORGANISM: Homo sapiens

<400> SEQUENCE: 711
tccagaactg attcttgagt gatcagtctg gcaaggaggc cttcctgagc atatctgggc    60
tccaggctga ggacaaggct gatcactaac gttggatttg acagttctc tggaggcccc   120

<210> SEQ ID NO 712
<211> LENGTH: 120
<212> TYPE: DNA
<213> ORGANISM: Homo sapiens

<400> SEQUENCE: 712
ttcaggacag acgctcaggc taccagtctt gcatgaagcc cttcctaagc atctctgggc    60
tttaggctga ggacaaggct gatcactcct gttggcttca gacagccccc tggaggtcca   120

<210> SEQ ID NO 713
<211> LENGTH: 120
<212> TYPE: DNA
<213> ORGANISM: Homo sapiens

<400> SEQUENCE: 713
cctcagggaa tttcccagcc ccatgttagg cagtttggcc tccctggcca tctctgggct    60
ccaggctggc gacggtgctg attttcacta tttagcacag aatggcagcc tcgctgatta   120

<210> SEQ ID NO 714
<211> LENGTH: 120
<212> TYPE: DNA
<213> ORGANISM: Homo sapiens

<400> SEQUENCE: 714

```
tccctgacaa ttctctggct tcaagtctgg caactccatt ttcgtgacca tcactgtgct      60
acagcctgaa gatgaggctg attatcactg ccaattctac aaaaacagcc tgagtgcttt     120
```

<210> SEQ ID NO 715
<211> LENGTH: 120
<212> TYPE: DNA
<213> ORGANISM: Homo sapiens

<400> SEQUENCE: 715

```
cataggccca atgctgaggc tccaggttgg agaacatggc ctctctgagc atctctggac      60
tccaggcaga ggaaaaggct gatttttatt ctcagcttgg gacacaagca ccaaggctca     120
```

<210> SEQ ID NO 716
<211> LENGTH: 120
<212> TYPE: DNA
<213> ORGANISM: Homo sapiens

<400> SEQUENCE: 716

```
ccctgaccgc ttctctggct caaagtctgg gaccacagcc tccctgacta tctcgggcct      60
ctagcctgag gacgaggctg attattactg ttcaacatgg gactacagcc tcagtgctca     120
```

<210> SEQ ID NO 717
<211> LENGTH: 120
<212> TYPE: DNA
<213> ORGANISM: Homo sapiens

<400> SEQUENCE: 717

```
cagacaattc tctgggttga gaggctcctc cagagtctca agttatttgg tcgtctctgg      60
ccttcacctt gaggatggag cagatcatct ctctcagatg ggctgacagg gcatggctta     120
```

<210> SEQ ID NO 718
<211> LENGTH: 120
<212> TYPE: DNA
<213> ORGANISM: Homo sapiens

<400> SEQUENCE: 718

```
ctaaatccaa agatgccttg gccagtgcag gcaatttgct catctctggg gtccagccag      60
aggacaagac tatctgttct atctattact gtcagacctg ggatattgat acttcagtta     120
```

<210> SEQ ID NO 719
<211> LENGTH: 120
<212> TYPE: DNA
<213> ORGANISM: Homo sapiens

<400> SEQUENCE: 719

```
tctggattaa tggaaggccg gtccaataaa gggctcttgc tcatatctga tctccagtct      60
gaggatgagg cttactatta ctgtatgatc gagcacagca gagcttctca tgctgacaca     120
```

<210> SEQ ID NO 720
<211> LENGTH: 120
<212> TYPE: DNA
<213> ORGANISM: Homo sapiens

<400> SEQUENCE: 720

```
gttcccatcc acttctctgg atccaatgat acattagcca atgcagggat tctgtacatt      60
cctgggctga agcctgaggg tgaggctatt actgttgtac gtgtcacagc agctccaagt     120
```

<210> SEQ ID NO 721
<211> LENGTH: 120

```
<212> TYPE: DNA
<213> ORGANISM: Homo sapiens

<400> SEQUENCE: 721
gtcacttctg tgaatccaaa gatccctcgg gcaatgtgca gggattctgc acatttctga     60
gcagcctgag atcaagtccg actattacta ttttacatat cacagcaaca gtggcacttt    120

<210> SEQ ID NO 722
<211> LENGTH: 120
<212> TYPE: DNA
<213> ORGANISM: Homo sapiens

<400> SEQUENCE: 722
tacagttctc aggatccagc tatggggctg atcggtaggt caccatctcc aacatccagt     60
ttgaggatga agctgattgt atctgtggtg cagatcatag cattggtgtg acatatgggt    120

<210> SEQ ID NO 723
<211> LENGTH: 120
<212> TYPE: DNA
<213> ORGANISM: Homo sapiens

<400> SEQUENCE: 723
attcccagtc actagttctc agtctccagg actggagctg accactatag tgtcatttct     60
acaatcccgt ctgaggatgg agctgactat atctgtggta cagattgtag cattggtgtg    120

<210> SEQ ID NO 724
<211> LENGTH: 120
<212> TYPE: DNA
<213> ORGANISM: Homo sapiens

<400> SEQUENCE: 724
agagacataa gactcattct caggctccaa gtctggccag tgagcttctt tgagactccc     60
tgggatccca gcagtgacac tgatcactat tgctgtccca cacatcccaa gtgatgagga    120

<210> SEQ ID NO 725
<211> LENGTH: 120
<212> TYPE: DNA
<213> ORGANISM: Homo sapiens

<400> SEQUENCE: 725
agagacataa gattgattct caggctccaa gtctgacaag tgagcttctt tgagactccc     60
tgggatccca gcagtgacac tgatcactgt tgctgttcca cacatcccaa gtgatgagga    120

<210> SEQ ID NO 726
<211> LENGTH: 120
<212> TYPE: DNA
<213> ORGANISM: Homo sapiens

<400> SEQUENCE: 726
ctcagagaga ttatctgcat ccatatcagg aaacacagcc tccctgacca ttactggact     60
ccagcctgag gacgaggctg actattactg ctcagcatgg gacagcagcc tcagtgctca    120

<210> SEQ ID NO 727
<211> LENGTH: 120
<212> TYPE: DNA
<213> ORGANISM: Homo sapiens

<400> SEQUENCE: 727
atctcagaga gaatctctgc atccaggtca ggaaacacag cctccctgac cattactgga     60
```

```
ctccagcctg aggacgaggc tgactattac tgctcagcat gggacagcag cctcagtgct    120

<210> SEQ ID NO 728
<211> LENGTH: 120
<212> TYPE: DNA
<213> ORGANISM: Homo sapiens

<400> SEQUENCE: 728
aaagaaaaag agatattcc tgaggggtac agtgtctcta gagagaagaa ggagcgcttc    60
tccctgattc tggagtccgc cagcaccaac cagacatcta tgtacctctg tgccagcagc    120

<210> SEQ ID NO 729
<211> LENGTH: 120
<212> TYPE: DNA
<213> ORGANISM: Homo sapiens

<400> SEQUENCE: 729
gcttctaatc gcttctctgg ctccaagtct ggcaacacgg cctccctgac catctctggg    60
cttcaggctg agaacgaggc tgattattac tgcagttcat atacaagcac caccactctc    120

<210> SEQ ID NO 730
<211> LENGTH: 120
<212> TYPE: DNA
<213> ORGANISM: Homo sapiens

<400> SEQUENCE: 730
tctcagagag attccctggc tccgggttag gaacatggca tctctgacca tctctggcct    60
ccagaccaag gacaagcctg cctattactg ctcagcctgg gacagcagcc tcagtgctca    120

<210> SEQ ID NO 731
<211> LENGTH: 120
<212> TYPE: DNA
<213> ORGANISM: Homo sapiens

<400> SEQUENCE: 731
cccagtcgag tctctggctc caaggagacc tcaagtaaca cagcgttttt gctcatctct    60
gggctccagc ctgaggacga ggccgattat tactgccagg tgtacgaaag tagtgctaat    120

<210> SEQ ID NO 732
<211> LENGTH: 120
<212> TYPE: DNA
<213> ORGANISM: Homo sapiens

<400> SEQUENCE: 732
ctctgaccga ttctctggct ccaagtctgg cacctcagcc tccctggcca tcagtgggct    60
ccagtctgag gatgaggctg attattactg tgcagcatgg gatgacagcc tgaatggtcc    120

<210> SEQ ID NO 733
<211> LENGTH: 120
<212> TYPE: DNA
<213> ORGANISM: Homo sapiens

<400> SEQUENCE: 733
ccctgaccga ttctctggct ccaagtctgg cacctcagcc tccctggcca tcactggact    60
ccaggctgag gatgaggctg attattactg ccagtcctat gacagcagcc tgagtggttc    120

<210> SEQ ID NO 734
<211> LENGTH: 120
<212> TYPE: DNA
<213> ORGANISM: Homo sapiens
```

<400> SEQUENCE: 734
gtccctgacc gattctctgg ctccaagtct ggcacctcag cctccctggc catcactggg      60
ctccaggctg aggatgaggc tgattattac tgccagtcct atgacagcag cctgagtggt     120

<210> SEQ ID NO 735
<211> LENGTH: 120
<212> TYPE: DNA
<213> ORGANISM: Homo sapiens

<400> SEQUENCE: 735
gtccctgacc gattctctgg ctccaagtct ggcgcctcag cctccctggc catcactggg      60
ctccaggctg aggatgaggc tgattattac tgccagtcct atgacagcag cctgagtggt     120

<210> SEQ ID NO 736
<211> LENGTH: 120
<212> TYPE: DNA
<213> ORGANISM: Homo sapiens

<400> SEQUENCE: 736
attcctgacc gattctctgg ctccaagtct ggcacctcag ccaccctggg catcactggc      60
ctctggcctg aggacgaggc cgattattac tgcttagcat gggataccag cccgagagct     120

<210> SEQ ID NO 737
<211> LENGTH: 120
<212> TYPE: DNA
<213> ORGANISM: Homo sapiens

<400> SEQUENCE: 737
tcctgaccga ttctctggct ccaagtctgg cacctcagcc accctgggca tcactggcct      60
ctggcctgag gactaggccg attattactg cttagcatgg gataccagcc tgagagcttg     120

<210> SEQ ID NO 738
<211> LENGTH: 120
<212> TYPE: DNA
<213> ORGANISM: Homo sapiens

<400> SEQUENCE: 738
ccctgaccga ttctctggct ccaagtctgg cacctcagcc tccctggcca tcagtgggct      60
ccagtctgag gatgaggctg attattactg tgcagcatgg gatgacagcc tgaatggtcc     120

<210> SEQ ID NO 739
<211> LENGTH: 120
<212> TYPE: DNA
<213> ORGANISM: Homo sapiens

<400> SEQUENCE: 739
gtccctgccc gattctctgg ctccaggtct ggcacctcag cctccctggc catccgtggg      60
ctccagtctg acgatgaggg tgattatttc tgttcggcat gggatgacag cctgaatcat     120

<210> SEQ ID NO 740
<211> LENGTH: 120
<212> TYPE: DNA
<213> ORGANISM: Homo sapiens

<400> SEQUENCE: 740
gggtccctga ccgattctct ggctccaagt ctggcacctc agcctccctg gccatcagtg      60
ggctccggtc cgaagatgag gctgtttatt actgtggagc gtgggatggc ggcctgagtg     120

<210> SEQ ID NO 741
<211> LENGTH: 120
<212> TYPE: DNA
<213> ORGANISM: Homo sapiens

<400> SEQUENCE: 741
ccctgaccga ttctctggct ccaagtctgg cacctcagcc tccctggcca tcagtgggct    60
ccggtccgag gatgaggctg attattactg tgcagcatgg gatgacagcc tgagtggtcc    120

<210> SEQ ID NO 742
<211> LENGTH: 120
<212> TYPE: DNA
<213> ORGANISM: Homo sapiens

<400> SEQUENCE: 742
ccctgaccaa ttctctggct ccaagtctgg cacctcagcc tccctggcca tcactggact    60
ccagtctgag gatgaggctg attattactg caaagcatgg gataacagcc tgaatgctca    120

<210> SEQ ID NO 743
<211> LENGTH: 120
<212> TYPE: DNA
<213> ORGANISM: Homo sapiens

<400> SEQUENCE: 743
attcctgacc gattctctgg ctccaagtct ggcacgtcag ccaccctggg catcaccgga    60
ctccagactg ggacgaggc cgattattac tgcggaacat gggatagcag cctgagtgct    120

<210> SEQ ID NO 744
<211> LENGTH: 120
<212> TYPE: DNA
<213> ORGANISM: Homo sapiens

<400> SEQUENCE: 744
tcctgaccga ttctctggct ccaagtctgg cacgtctgcc accctgggca tcaccggact    60
ccagactggg gacgaggccg attattattg cggaacatgg gataacaatc tgcgtgcggg    120

<210> SEQ ID NO 745
<211> LENGTH: 120
<212> TYPE: DNA
<213> ORGANISM: Homo sapiens

<400> SEQUENCE: 745
tatctgacca attctctggt tccaagtctg gcagcttggc ctccctgggc accactgggc    60
tctgggctga ggacaagact gattatcact gccagtcccg tgacatctgc tgagtgcttg    120

<210> SEQ ID NO 746
<211> LENGTH: 120
<212> TYPE: DNA
<213> ORGANISM: Homo sapiens

<400> SEQUENCE: 746
gggtccctga tcgcttctct ggctccaagt ctggcaacac ggcctccctg accatctctg    60
ggctccaggc tgaggatgag gctgattatt actgctgctc atatgcaggc agctacactt    120

<210> SEQ ID NO 747
<211> LENGTH: 120
<212> TYPE: DNA
<213> ORGANISM: Homo sapiens

<400> SEQUENCE: 747

```
gtccctgatc gcttctctgg ctccaagtct ggcaacacgg cctccctgac catctctggg      60
ctccaggctg aggatgaggc tgattattac tgctgctcat atgcaggcag ctacactttc     120
```

<210> SEQ ID NO 748
<211> LENGTH: 120
<212> TYPE: DNA
<213> ORGANISM: Homo sapiens

<400> SEQUENCE: 748

```
gtctctaatc gcttctctgg ttccaagtct ggcaacacgg cctccctgac catctctggg      60
ctccaggctg aggacgaggc tgattattac tgcaactcat atacaaccag cgacactctc     120
```

<210> SEQ ID NO 749
<211> LENGTH: 120
<212> TYPE: DNA
<213> ORGANISM: Homo sapiens

<400> SEQUENCE: 749

```
gtttctaatc gcttctctgg ctccaagtct gccaacacgg cctccctgac aatctctggg      60
ctccaggctg aggacgaggc tgattattac tgcagctcat atacaagcag cagcactctc     120
```

<210> SEQ ID NO 750
<211> LENGTH: 120
<212> TYPE: DNA
<213> ORGANISM: Homo sapiens

<400> SEQUENCE: 750

```
aagtacgcgg actccgtgaa gggccgattc accatctcca gagacaacgc caggaacacg      60
ctgtatctgc agatgaacag tctgagagcc gaggacacgg ctgtgtatta ttgtgcaaga     120
```

<210> SEQ ID NO 751
<211> LENGTH: 120
<212> TYPE: DNA
<213> ORGANISM: Homo sapiens

<400> SEQUENCE: 751

```
tcttggaccc ctgcccggtt ctcaggctcc ctcctcgggg gcaaagctgt cctgacactg      60
tcaggtgtgc agcctgagga cgaggctgag tattactgca tgctctactc tagtggtcct     120
```

<210> SEQ ID NO 752
<211> LENGTH: 120
<212> TYPE: DNA
<213> ORGANISM: Homo sapiens

<400> SEQUENCE: 752

```
gtccctgatc gcttctctgg gtccaagtct ggcaacacgg cctccctgac cacctctggg      60
ctccaggctg aggacgaggc tgattattac tgcagctcat atacaagcag cagcactttc     120
```

<210> SEQ ID NO 753
<211> LENGTH: 120
<212> TYPE: DNA
<213> ORGANISM: Homo sapiens

<400> SEQUENCE: 753

```
gtccctgatc gctcctctgg gtccaagtcc ggcaacacgg cctccctgac catctctggg      60
ctccaggctg aggacgaggc tgattattac tgcagctcat atacaagcag cagcactttc     120
```

<210> SEQ ID NO 754

```
<211> LENGTH: 120
<212> TYPE: DNA
<213> ORGANISM: Homo sapiens

<400> SEQUENCE: 754
tttctaatcg cttctctggc tccaagtctg gcaacacggc ctccctgaca atctctgggc    60
tccaggctga ggacgaggct gattattact gctgctcata tgcaggtagt agcactttac   120

<210> SEQ ID NO 755
<211> LENGTH: 120
<212> TYPE: DNA
<213> ORGANISM: Homo sapiens

<400> SEQUENCE: 755
gtttctaatc gcttctctgg ctccaagtct ggcaacacgg cctccctgac aatctctggg    60
ctccaggctg aggacgaggc tgattattac tgctgctcat atgcaggtag tagcactttc   120

<210> SEQ ID NO 756
<211> LENGTH: 120
<212> TYPE: DNA
<213> ORGANISM: Homo sapiens

<400> SEQUENCE: 756
gggtttctga tcgcttctct ggctccaagt ctggcagcac ggcctccctg acaatttctg    60
ggctccaggc tgaggatgag gctgattatt actgctgctc atatgttggc agtcacactt   120

<210> SEQ ID NO 757
<211> LENGTH: 120
<212> TYPE: DNA
<213> ORGANISM: Homo sapiens

<400> SEQUENCE: 757
tctctgatca cttctctggc tccagctct ggcaacatgg cctccatgac catctctggg     60
ctccaggctg aggacgaggc tgattattac tgcagttcat atacaagcag caacattttc   120

<210> SEQ ID NO 758
<211> LENGTH: 120
<212> TYPE: DNA
<213> ORGANISM: Homo sapiens

<400> SEQUENCE: 758
atctctgacc tcttctcagg ctccaagtct ggcaacatgg cttccctgac catctctggg    60
ctcaagtccg aggttgaggc taattatcac tgcagcttat attcaagtag ttacactttc   120

<210> SEQ ID NO 759
<211> LENGTH: 120
<212> TYPE: DNA
<213> ORGANISM: Homo sapiens

<400> SEQUENCE: 759
atctctgacc tcttctcagg ctccaagtct ggcaacgtgg cttccctgac catctctggg    60
ctcaagtccg aggttgaggc taattatcac tgcagcttat attcaagtag ttacactttc   120

<210> SEQ ID NO 760
<211> LENGTH: 120
<212> TYPE: DNA
<213> ORGANISM: Homo sapiens

<400> SEQUENCE: 760 gccctggtt gcttctctgg ctccaagtct ggcaacacgg cctccctgac catctctggg     60
```
ctccaggctg aggacgaggc tgattattac tgcagctcat atgcaggcag ctacaatttc    120

<210> SEQ ID NO 761
<211> LENGTH: 120
<212> TYPE: DNA
<213> ORGANISM: Homo sapiens

<400> SEQUENCE: 761
gtccctgatc gtttctctgg ctccaagtct ggcaatacgg cctccatgac catctctgga    60
ctccaggctg aggacgaggc tgattattag tgctgctcat atacaagcag tgccacttaa    120

<210> SEQ ID NO 762
<211> LENGTH: 120
<212> TYPE: DNA
<213> ORGANISM: Homo sapiens

<400> SEQUENCE: 762
tccctgatcg tttctctggc tccaagtctg gcaacacggc tccatgacc atctctggac    60 tccaggctga ggacgaggct gattattagt gctgctcata tacaagcagt gccacttaac    120

<210> SEQ ID NO 763
<211> LENGTH: 120
<212> TYPE: DNA
<213> ORGANISM: Homo sapiens

<400> SEQUENCE: 763
ggtccctgat cgcttctctg gctccaagtc tggcaacacg gcctccctga ccgtctctgg    60
gctccaggct gaggacgagg ctgattatta ctgcagctca tatgcaggca gcaacaattt    120

<210> SEQ ID NO 764
<211> LENGTH: 120
<212> TYPE: DNA
<213> ORGANISM: Homo sapiens

<400> SEQUENCE: 764
gtccctgatc gcttctctgg ctccaagtct ggcaacacgg cctccctgac cgtctctggg    60
ctccaggctg aggatgaggc tgattattac tgcagctcat atgcaggcag caacaatttc    120

<210> SEQ ID NO 765
<211> LENGTH: 120
<212> TYPE: DNA
<213> ORGANISM: Homo sapiens

<400> SEQUENCE: 765
agggatccct gagcgaatct ctggctccaa gtctgggaac acagccactc tgaccatcag    60
cgggacccag gctatggatg aggctgacta ttactgtcag gcgtgggaca gcagggctgc    120

<210> SEQ ID NO 766
<211> LENGTH: 120
<212> TYPE: DNA
<213> ORGANISM: Homo sapiens

<400> SEQUENCE: 766
ccctgagaga ttctctggct ccagctcagg gacaatggcc accttgacta tcagtggggc    60
ccaggtggag gatgaagctg actactactg ttactcaaca gacagcagtg gtaatcattg    120

<210> SEQ ID NO 767
<211> LENGTH: 120
<212> TYPE: DNA

<213> ORGANISM: Homo sapiens

<400> SEQUENCE: 767
ccctgagcga ttctctggct ccaacccagg aacaccacc accctaacca tcagcaggat    60
cgaggctggg gatgaggctg actattactg tcaggtgtgg gacagtagta gtgatccccc   120

<210> SEQ ID NO 768
<211> LENGTH: 120
<212> TYPE: DNA
<213> ORGANISM: Homo sapiens

<400> SEQUENCE: 768
ccctgagcga ttctctggct ccaacccagg aacaccgcc accctaacca tcagcaggat    60
cgaggctggg gatgaggctg actattactg tcaggtgtgg gacagtagta gtgatcatcc   120

<210> SEQ ID NO 769
<211> LENGTH: 120
<212> TYPE: DNA
<213> ORGANISM: Homo sapiens

<400> SEQUENCE: 769
tggaatccct gagcgattct ctgggtccac ctcagggaac acaaccgccc tgaccattag    60
cagggtcctg accaaaggcg gggctgacta ttactgtttt tctggtgatt agaacaatct   120

<210> SEQ ID NO 770
<211> LENGTH: 120
<212> TYPE: DNA
<213> ORGANISM: Homo sapiens

<400> SEQUENCE: 770
ggatctctga gagattctct ggctccaact tggggaacgt ggccaccctg accatcaaca    60
ggacccaggg tggggacaag gctattactg taagatgtgg gacattagca ctcctcatcc   120

<210> SEQ ID NO 771
<211> LENGTH: 120
<212> TYPE: DNA
<213> ORGANISM: Homo sapiens

<400> SEQUENCE: 771
atccctgagc gattctctgg ctccagctca gggacaatag tcacattgac catcagtgga    60
gtccaggcag aagacgaggc tgactattac tgtctatcag cagacagcag tggtacttat   120

<210> SEQ ID NO 772
<211> LENGTH: 120
<212> TYPE: DNA
<213> ORGANISM: Homo sapiens

<400> SEQUENCE: 772
tcccagaccg attctctggc tccaagtcag gaacacagcc accctgacca tcactggggc    60
tcaggttgaa catgaagctg actattaccg tcactcatgg gacaacagtg gtactcatct   120

<210> SEQ ID NO 773
<211> LENGTH: 120
<212> TYPE: DNA
<213> ORGANISM: Homo sapiens

<400> SEQUENCE: 773
cgggcctccg gggtccctga caggttcagt ggcagtggat caggcacaga ttttacactg    60
aaaatcagca gagtggaggc tgaggatgtt ggggtttatt actgcatgca agctctacat   120

<210> SEQ ID NO 774
<211> LENGTH: 120
<212> TYPE: DNA
<213> ORGANISM: Homo sapiens

<400> SEQUENCE: 774
agtgattcct gagcaatttt ctgactgcat atcagaggac atggccacct tgattattaa    60
tggggcacag gatggaaaca aggctattac tgtcgctcgg aacagcactg cttctcatct   120

<210> SEQ ID NO 775
<211> LENGTH: 120
<212> TYPE: DNA
<213> ORGANISM: Homo sapiens

<400> SEQUENCE: 775
ggatccctga ccgattctct ggctccaatt ctgggaacac ggccaccccg accatcagca    60
gggtcgaagc cggggatgag gccgactatt actgtcaggt gtgggatgtg aatagtgatc   120

<210> SEQ ID NO 776
<211> LENGTH: 120
<212> TYPE: DNA
<213> ORGANISM: Homo sapiens

<400> SEQUENCE: 776
atccctgagc gattctctgg ctccaactct gggaacacgg ccaccctgac catcagcagg    60
gtcgaagccg gggatgaggc cgactattac tgtcaggtgt gggatagtag tagtgatcat   120

<210> SEQ ID NO 777
<211> LENGTH: 120
<212> TYPE: DNA
<213> ORGANISM: Homo sapiens

<400> SEQUENCE: 777
ccctgagcgt ttctctggct ccaactctgg gaacacggcc accctgacca tcagcagggt    60
cgaagccggg gatgaggccg actattactg tcaggtgtgg gagagtagta gtgaaccacc   120

<210> SEQ ID NO 778
<211> LENGTH: 120
<212> TYPE: DNA
<213> ORGANISM: Homo sapiens

<400> SEQUENCE: 778
tggaatccct gaacgattct ctgggtccac ctcagggaac acgaccaccc tgaccatcag    60
cagggtcctg accgaagacg aggctgacta ttactgtttg tctggggatg aggacaatcc   120

<210> SEQ ID NO 779
<211> LENGTH: 120
<212> TYPE: DNA
<213> ORGANISM: Homo sapiens

<400> SEQUENCE: 779
tggaatccct gaacgattct ctgggtccac ctcagggaac acgaccaccc tgaccatcag    60
cagggtcctg accgaagacg aggctgacta ttactgtttg tctgggaatg aggataatcc   120

<210> SEQ ID NO 780
<211> LENGTH: 120
<212> TYPE: DNA
<213> ORGANISM: Homo sapiens

```
<400> SEQUENCE: 780
cagggatctc tgagattctc tggctcaaac tcagggaaca ggaccaccct ggccatcaac      60
agggcccagg ctgggacgag ctattactg taagatgtgg gacattagga ctcctcatcc     120

<210> SEQ ID NO 781
<211> LENGTH: 120
<212> TYPE: DNA
<213> ORGANISM: Homo sapiens

<400> SEQUENCE: 781
agggatctct gagattctct ggctcaaact cagggaacag gaccaccctg gccatcaaca      60
gggcccaggc tggggaccag ctattactg taagatgtgg gacattagga ctcctcatcc     120

<210> SEQ ID NO 782
<211> LENGTH: 120
<212> TYPE: DNA
<213> ORGANISM: Homo sapiens

<400> SEQUENCE: 782
ccctgagcga ttctctggct ccagctcagg acaacagtc acgttgacca tcagtggagt      60
ccaggcagaa gatgaggctg actattactg tcaatcagca gacagcagtg gtacttatcc     120

<210> SEQ ID NO 783
<211> LENGTH: 120
<212> TYPE: DNA
<213> ORGANISM: Homo sapiens

<400> SEQUENCE: 783
gcgacaatat atcgtgcgtc ggtgaaaggc agattcacca tctccagaga tgattcaaaa      60
aacatggcgt ttctgcaaat ggacagcctg agacccgacg acacggccct gtattactgt    120

<210> SEQ ID NO 784
<211> LENGTH: 120
<212> TYPE: DNA
<213> ORGANISM: Homo sapiens

<400> SEQUENCE: 784
ctcagggatc cctgagcgat tctatggctc cacctcaggg acaacagtca cgttgaccat      60
cagtggagtc caggcagaag acgaggctga ctattactgt caatcaattg acaaaagtgg    120

<210> SEQ ID NO 785
<211> LENGTH: 120
<212> TYPE: DNA
<213> ORGANISM: Homo sapiens

<400> SEQUENCE: 785
tcccagacca attctctggc tccaagtcag gaacacagcc accctgacca tcactggggc      60
tcaggttgaa catgaagctg actattacca tcactcatgg gacagcagtg ctactcacct    120

<210> SEQ ID NO 786
<211> LENGTH: 120
<212> TYPE: DNA
<213> ORGANISM: Homo sapiens

<400> SEQUENCE: 786
agggatccct gagcgattct ccggctccag ctcaggggacc acagtcacct tgaccatcag      60
cggggcccag gttgaggatg aggctgacta ttactgttac tctgcggctg acaacaatct    120
```

```
<210> SEQ ID NO 787
<211> LENGTH: 120
<212> TYPE: DNA
<213> ORGANISM: Homo sapiens

<400> SEQUENCE: 787
cttcagggat ctctaagtga ttctccagct ccaactcggg gaacatggtc accctgacca      60
tcagtggagc ccaggctggg gacgaggctt cctctcagg tgtggggcag tggcactgca      120

<210> SEQ ID NO 788
<211> LENGTH: 120
<212> TYPE: DNA
<213> ORGANISM: Homo sapiens

<400> SEQUENCE: 788
agtgattctc tggctccaac ttgtggaaca cagccactct gaccattagt ggggcccagg      60
ccagggacga ggctattact gtagcaccta tgatggctga gggagcagca gccagtggct      120

<210> SEQ ID NO 789
<211> LENGTH: 120
<212> TYPE: DNA
<213> ORGANISM: Homo sapiens

<400> SEQUENCE: 789
agtgattctc tggctccaac ttgtggaaca cagccactct gaccattagt ggggcccagg      60
ccagggacga ggctattact gtagcaccta tgatggctga gggagcagca ggcagtggct      120

<210> SEQ ID NO 790
<211> LENGTH: 120
<212> TYPE: DNA
<213> ORGANISM: Homo sapiens

<400> SEQUENCE: 790
tcctaagaaa ttctctggct ccagctcagg gaacatggcc accctgacca tcactgggat      60
tcaggttgaa gacaaggctg actattactg tcagtcatgg gacagcagtc gtactcattc      120

<210> SEQ ID NO 791
<211> LENGTH: 120
<212> TYPE: DNA
<213> ORGANISM: Homo sapiens

<400> SEQUENCE: 791
aaggatccct gagcgattct ctggctccaa atcaggcaac acaaccaccc tgaccatcac      60
tggggcccag gctgaggatg aggctgatta ttactatcag ttgatagaca accatgctac      120

<210> SEQ ID NO 792
<211> LENGTH: 120
<212> TYPE: DNA
<213> ORGANISM: Homo sapiens

<400> SEQUENCE: 792
gctcagagat cactgagcga ttctctggtt cctgctcagg gggaacagcc acactgacca      60
ttactggggc tcacgttgaa gacgaggcta tttttgtttt tctggagata aaaacacatt      120

<210> SEQ ID NO 793
<211> LENGTH: 120
<212> TYPE: DNA
<213> ORGANISM: Homo sapiens

<400> SEQUENCE: 793
```

```
gaatttctga ttttctgagt ccagctcagg gaacatggcc accctgacca tcagcagggc      60
tcagactgag gacgaggctg actattactg tcacaggtac aatagaaaca gtgatgagcc     120

<210> SEQ ID NO 794
<211> LENGTH: 120
<212> TYPE: DNA
<213> ORGANISM: Homo sapiens

<400> SEQUENCE: 794
gaatttctga ttttctgagt ccagctcagg gaacatggcc accctgacca tcatcagggc      60
tcagactgag gacgaggctg actattactg tcacaggtac aacagaaaca gtgatgagcc     120

<210> SEQ ID NO 795
<211> LENGTH: 120
<212> TYPE: DNA
<213> ORGANISM: Homo sapiens

<400> SEQUENCE: 795
tgattcctga acaactctct gactccatat cagagaacat ggccaccctg ataatcaatg      60
ggccccaggc tggaaacaag gctattactg tcaatcatga gacagcactg atactcatct     120

<210> SEQ ID NO 796
<211> LENGTH: 120
<212> TYPE: DNA
<213> ORGANISM: Homo sapiens

<400> SEQUENCE: 796
gggatccctg agcgattctc tggctccaac tcggggaaca cggccaccct gaccatcagc      60
agagcccaag ccggggatga ggctgactat tactgtcagg tgtgggacag cagcactgca     120

<210> SEQ ID NO 797
<211> LENGTH: 120
<212> TYPE: DNA
<213> ORGANISM: Homo sapiens

<400> SEQUENCE: 797
ccctgagcga ttctctggct ccaactcggg gaacacggcc accctgacca tcagcagagc      60
ccaagccggg gatgaggctg actattactg tcaggtgtgg gacagcagca ctgcacaccc     120

<210> SEQ ID NO 798
<211> LENGTH: 120
<212> TYPE: DNA
<213> ORGANISM: Homo sapiens

<400> SEQUENCE: 798
tactacgcag actcagtgaa gggccgattc accatctcca gagacaacgc caagaactca      60
ctgtatctgc aaatgaacag cctgagagcc gaggacacgg ctgtgtatta ctgtgcgaga     120

<210> SEQ ID NO 799
<211> LENGTH: 120
<212> TYPE: DNA
<213> ORGANISM: Homo sapiens

<400> SEQUENCE: 799
agcggagttc ctgatcgctt ctcaggctcc agctctgggg ctgaccgcta cctcaccatc      60
tccaacctcc agttagagga tgaggctgat tattactgtg agacctggga cagtaacact     120

<210> SEQ ID NO 800
<211> LENGTH: 120
```

```
<212> TYPE: DNA
<213> ORGANISM: Homo sapiens

<400> SEQUENCE: 800
ggagcggagt tcctgatcgc ttctcaggct ccagctctgg ggctgaccgc tacctcacca    60
tctccaacct ccagtttgag gatgagggtg attattactg tgagacctgg gacactaaca   120

<210> SEQ ID NO 801
<211> LENGTH: 120
<212> TYPE: DNA
<213> ORGANISM: Homo sapiens

<400> SEQUENCE: 801
ggcggagatc cgaatcgctt ctcaggctcc agctctgggg ctgaccgcta cctcaccatc    60
tccaacctcc agtctgacga tcaggctgat tattactgtg agacctggga cagtgacact   120

<210> SEQ ID NO 802
<211> LENGTH: 120
<212> TYPE: DNA
<213> ORGANISM: Homo sapiens

<400> SEQUENCE: 802
gagacgggat ccctgatcgc ttctcaggct ccagttctgg ggctgagcgc tacctcacca    60
tctccagcct ccagtctgaa gatgaggctg agtattactg tcagacctgg ggccctggca   120

<210> SEQ ID NO 803
<211> LENGTH: 120
<212> TYPE: DNA
<213> ORGANISM: Homo sapiens

<400> SEQUENCE: 803
gggtcccatc aaggttcagt ggcagtggat ctgggacaga tttcactctc accatcagca    60
gtctgcaacc tgaagatttt gcaacttact actgtcaaca gagttacagt accccctggat  120

<210> SEQ ID NO 804
<211> LENGTH: 120
<212> TYPE: DNA
<213> ORGANISM: Homo sapiens

<400> SEQUENCE: 804
cccagccgct tctctggatc caaagatgct tcagccaata cagggatttt actcatctcc    60
gggctccagt ctgaggatga ggctgactat tactgtatga tttggccaag caatgcttct   120

<210> SEQ ID NO 805
<211> LENGTH: 120
<212> TYPE: DNA
<213> ORGANISM: Homo sapiens

<400> SEQUENCE: 805
tccccagccg cttctctgga tccaaagatg tttcaaccaa tgcaggcctg ttactcatct    60
ctgggctcca gtctgaagat gaggctgact attactgtgc catttggtac agcagctctt   120

<210> SEQ ID NO 806
<211> LENGTH: 120
<212> TYPE: DNA
<213> ORGANISM: Homo sapiens

<400> SEQUENCE: 806
cccagccgct tctctggatc caaagatgct tcaaccaatg caggcctttt actcatctct    60
```
gggctccagt ctgaagatga ggctgactat tactgtgcca tttggtacag cagcacttct    120

<210> SEQ ID NO 807
<211> LENGTH: 120
<212> TYPE: DNA
<213> ORGANISM: Homo sapiens

<400> SEQUENCE: 807
ctggcatccc agacaggttc agtggcagtg ggtctgggac agacttcact ctcaccatca    60
gcagactgga gcctgaagat tttgcagtgt attactgtca gcagtatggt gactcacctc    120

<210> SEQ ID NO 808
<211> LENGTH: 120
<212> TYPE: DNA
<213> ORGANISM: Homo sapiens

<400> SEQUENCE: 808
tccccagccg cttctctgga tccaaagatg cttcggccaa tgcagggatt ttactcatct    60
ctgggctcca gtctgaggat gaggctgact attactgtat gatttggcac agcagcgctt    120

<210> SEQ ID NO 809
<211> LENGTH: 120
<212> TYPE: DNA
<213> ORGANISM: Homo sapiens

<400> SEQUENCE: 809
agtggggtcc catcaaggtt cagtggcagt gggtctggga cagacttcac tctcaccata    60
agcagtctgc aacctgaaga ttttgcaact tactactgtc aacagactta tcgaagccgg    120

<210> SEQ ID NO 810
<211> LENGTH: 120
<212> TYPE: DNA
<213> ORGANISM: Homo sapiens

<400> SEQUENCE: 810
cccagccgct tctctggatc caaagatgct tcggccaatg cagggatttt actcatctct    60
gggctccagt ctgaggatga ggctgactat tactgtatga tttggcacag cagcgcttct    120

<210> SEQ ID NO 811
<211> LENGTH: 120
<212> TYPE: DNA
<213> ORGANISM: Homo sapiens

<400> SEQUENCE: 811
cccagccgct tctctggatc caaagatgct tcgagcaatg cagggatttt agtcatctct    60
gggctccagt ctgaggatga ggctgactat tactgtatga tttggcacag cagtgcttct    120

<210> SEQ ID NO 812
<211> LENGTH: 120
<212> TYPE: DNA
<213> ORGANISM: Homo sapiens

<400> SEQUENCE: 812
cccagccgct tctctggatc caaagatgct tcgaccaatg cagggatttt attcatctct    60
gggctctagt ctgaggatga ggctgactat tactgtatga tttggcacag cagtgcttct    120

<210> SEQ ID NO 813
<211> LENGTH: 120
<212> TYPE: DNA
<213> ORGANISM: Homo sapiens

<400> SEQUENCE: 813
cgcttctctg gatccaacga tgcatcagcc aatgcaggga ttctgcgtat ctctgggctc    60
cagcctgagg atgaggctga ctattactgt ggtacatggc acagcaactc taagacccct   120

<210> SEQ ID NO 814
<211> LENGTH: 120
<212> TYPE: DNA
<213> ORGANISM: Homo sapiens

<400> SEQUENCE: 814
ccctgatcgg ttctctggct ccatcgacag ctcctccaac tctgcctccc tcaccatctc    60
tggactgaag actgaggacg aggctgacta ctactgtcag tcttatgata gcagcaatca   120

<210> SEQ ID NO 815
<211> LENGTH: 120
<212> TYPE: DNA
<213> ORGANISM: Homo sapiens

<400> SEQUENCE: 815
ggacccctgc ccagttctca ggctcagtcc ttgggagcaa agctgcccag acactcttgg    60
gtgtgcagcc cgagaggtga agctgagtac tactgcttac tgcaccatag tcgtgcttgg   120

<210> SEQ ID NO 816
<211> LENGTH: 120
<212> TYPE: DNA
<213> ORGANISM: Homo sapiens

<400> SEQUENCE: 816
tggacccctg cccggttctc aggctccctc cttgggggca agctgccct gacactgtca    60 ggtgtgcagc ctgaggacga ggctgagtat tactgcctgc tctactatgg tggtgctcag   120

<210> SEQ ID NO 817
<211> LENGTH: 120
<212> TYPE: DNA
<213> ORGANISM: Homo sapiens

<400> SEQUENCE: 817
tggacacctg cccggttctc aggctccctc cttgggggca agctgccct gacccttttg    60 ggtgcgcagc ctgaggatga ggctgagtat tactgcttgc tctcctatag tggtgctcgg   120

<210> SEQ ID NO 818
<211> LENGTH: 120
<212> TYPE: DNA
<213> ORGANISM: Homo sapiens

<400> SEQUENCE: 818
ctggacacct gcccggttct caggctccct ccttgggggc aaagctgccc tgacctttcg    60
ggtgcgcagc ctgaggatga ggctgagtat tactgcttgc tctcctatag tggtgctcgg   120

<210> SEQ ID NO 819
<211> LENGTH: 120
<212> TYPE: DNA
<213> ORGANISM: Homo sapiens

<400> SEQUENCE: 819
cctggtcgct tctctggctc catccttggg aacaaagctg ccctcaccat cacggggact    60
cagtagatga tgactctgat cattactgtg tgctgtacat gggtagtggc aattccacag   120

<210> SEQ ID NO 820
<211> LENGTH: 120
<212> TYPE: DNA
<213> ORGANISM: Homo sapiens

<400> SEQUENCE: 820
ggggtccctg gtcgcttctc tggctccatc cttgggaaca aagctgccct caccatcacg      60
gggactcagg tagatgatga ctctgatcat tactgtgtgc tgtacatggg tagtggcaat     120

<210> SEQ ID NO 821
<211> LENGTH: 120
<212> TYPE: DNA
<213> ORGANISM: Homo sapiens

<400> SEQUENCE: 821
cttctggggt ccctgatcgc ttctctggct ccatccttgg gaacaaagct gccctcacca      60 tcacggggc ccaggcagat gatgaatctg attattactg tgtgctgtat atgggtggtg     120

<210> SEQ ID NO 822
<211> LENGTH: 120
<212> TYPE: DNA
<213> ORGANISM: Homo sapiens

<400> SEQUENCE: 822
ggtccctgat tgcttctctg gctccatcct tgggaacaaa gctgccctca ccatcacggg      60
ggcccaggca gatgatgaat ctgattatta ctgtgtgctg tatatgggta gtggcatttc     120

<210> SEQ ID NO 823
<211> LENGTH: 120
<212> TYPE: DNA
<213> ORGANISM: Homo sapiens

<400> SEQUENCE: 823
tgatcgcttc tcagtcttgg gctcaggcct gaatcggtac ctgaccatcg agaacatcca      60
ggaagaggat gacagtgact ccactgtggg gcagaccat ggcagtggga gcaacttcgt     120

<210> SEQ ID NO 824
<211> LENGTH: 120
<212> TYPE: DNA
<213> ORGANISM: Homo sapiens

<400> SEQUENCE: 824
cttctcagtc ttgggctcag gcctgaatcg gtacctgacc atcaagaaca tccaggaaga      60
agatgagagt gactaccact gtggggcaga ccatggcagt gggagcaact cgtgtaacc     120

<210> SEQ ID NO 825
<211> LENGTH: 120
<212> TYPE: DNA
<213> ORGANISM: Homo sapiens

<400> SEQUENCE: 825
cttctcagtc ttgggctcag gcctgaatcg gtacctgacc atcaagaaca tccaggaaga      60
ggatgagagt gactaccact gtggggcaga ccatggcagt gggagcaact cgtgtaacc     120

<210> SEQ ID NO 826
<211> LENGTH: 120
<212> TYPE: DNA
<213> ORGANISM: Homo sapiens

<400> SEQUENCE: 826

```
tccaaagatg tggccaggaa caggggggtat ttgagcatct ctgagctgca gcctgaggac    60
gaggctatgt attactgtgc tatgggggcc cgcagctcgg agaaggagga gagggagagg   120

<210> SEQ ID NO 827
<211> LENGTH: 118
<212> TYPE: DNA
<213> ORGANISM: Homo sapiens

<400> SEQUENCE: 827 tacactttg gccaggggac caagctggaa atcagacgta agtactttt tccactgatt    60 cttcactgtt gctaattagt ttactttgtg ttcctttgtg tggattttca ttagtcgg   118

<210> SEQ ID NO 828
<211> LENGTH: 120
<212> TYPE: DNA
<213> ORGANISM: Homo sapiens

<400> SEQUENCE: 828
gatcaccttc ggccaaggga cacgactgga gattaaacgt aagtaatttt tcactattgt    60
cttctgaaat tgggtctga tggccagtat tgactttag aggcttaaat aggagtttgg   120

<210> SEQ ID NO 829
<211> LENGTH: 120
<212> TYPE: DNA
<213> ORGANISM: Homo sapiens

<400> SEQUENCE: 829
gctcactttc ggcggaggga ccaaggtgga gatcaaacgt aagtgcactt tcctaatgct    60
ttttcttata aggttttaaa tttggagcgt ttttgtgttt gagatattag ctcaggtcaa   120

<210> SEQ ID NO 830
<211> LENGTH: 120
<212> TYPE: DNA
<213> ORGANISM: Homo sapiens

<400> SEQUENCE: 830
attcactttc ggccctggga ccaaagtgga tatcaaacgt aagtacatct gtctcaatta    60
ttcgtgagat tttagtgcca ttgtatcatt tgtgcaagtt ttgtgatatt ttggttgaat   120

<210> SEQ ID NO 831
<211> LENGTH: 120
<212> TYPE: DNA
<213> ORGANISM: Homo sapiens

<400> SEQUENCE: 831
tgtacacttt tggccagggg accaagctgg agatcaaacg taagtacttt tttccactga    60
ttcttcactg ttgctaatta gtttactttg tgttcctttg tgtggatttt cattagtcgg   120

<210> SEQ ID NO 832
<211> LENGTH: 120
<212> TYPE: DNA
<213> ORGANISM: Homo sapiens

<400> SEQUENCE: 832
gtggacgttc ggccaaggga ccaaggtgga aatcaaacgt gagtagaatt taaactttgc    60
ttcctcagtt gtctgtgtct tctgttccct gtgtctatga agtgatctat aaggtgactc   120

<210> SEQ ID NO 833
```

-continued

```
<211> LENGTH: 120
<212> TYPE: DNA
<213> ORGANISM: Homo sapiens

<400> SEQUENCE: 833
ggacgttcgg ccaagggacc aaggtggaaa tcaaacgtga gtagaattta aactttgctt      60
cctcagttgt ctgtgtcttc tgttccctgt gtctatgaag tgatctataa ggtgactctg     120

<210> SEQ ID NO 834
<211> LENGTH: 120
<212> TYPE: DNA
<213> ORGANISM: Homo sapiens

<400> SEQUENCE: 834
ggctcctgct ccagcccagc ccccagagag cagaccccag gtgctggccc cgggggtttt      60
ggtctgagcc tcagtcactg tgttatgtct tcggaactgg gaccaaggtc accgtcctag     120

<210> SEQ ID NO 835
<211> LENGTH: 120
<212> TYPE: DNA
<213> ORGANISM: Homo sapiens

<400> SEQUENCE: 835
ttatgtcttc ggaactggga ccaaggtcac cgtcctaggt aagtggctct caacctttcc      60
cagcctgtct caccctctgc tgtccctgga aaatctgttt tctctctctg gggcttcctc     120

<210> SEQ ID NO 836
<211> LENGTH: 120
<212> TYPE: DNA
<213> ORGANISM: Homo sapiens

<400> SEQUENCE: 836
cagcttcctc cttcacagct gcagtggggg ctggggctgg ggcatcccag ggagggtttt      60
tgtatgagcc tgtgtcacag tgtgtggtat tcggcggagg gaccaagctg accgtcctag     120

<210> SEQ ID NO 837
<211> LENGTH: 120
<212> TYPE: DNA
<213> ORGANISM: Homo sapiens

<400> SEQUENCE: 837
tgtggtattc ggcggaggga ccaagctgac cgtcctaggt gagtctcttc tcccctctcc      60
ttccccactc ttgggacaat ttctgctgtt tttgtttgtt tctgtatctt gtctcaactt     120

<210> SEQ ID NO 838
<211> LENGTH: 120
<212> TYPE: DNA
<213> ORGANISM: Homo sapiens

<400> SEQUENCE: 838
cagcttcctc cttcacagct gcagtggggg ctggggctgg ggcatcccag ggagggtttt      60
tgtatgagcc tgtgtcacag tgttgggtgt tcggcggagg gaccaagctg accgtcctag     120

<210> SEQ ID NO 839
<211> LENGTH: 120
<212> TYPE: DNA
<213> ORGANISM: Homo sapiens

<400> SEQUENCE: 839
ttgggtgttc ggcggaggga ccaagctgac cgtcctaggt gagtctcttc tcccctctcc      60
```

```
ttccccgctc ttgggacaat ttctgctgtt tttgtttgtt tctgtatctt gtctcaactt    120
```

<210> SEQ ID NO 840
<211> LENGTH: 120
<212> TYPE: DNA
<213> ORGANISM: Homo sapiens

<400> SEQUENCE: 840

```
agcttcctcc ttcacagctg cagtgggggc tggggctagg ggcatcccag ggagggtttt    60
tgtatgagcc tgtgtcacag tgttgggtgt tcggcggagg gaccaagctg accgtcctag   120
```

<210> SEQ ID NO 841
<211> LENGTH: 120
<212> TYPE: DNA
<213> ORGANISM: Homo sapiens

<400> SEQUENCE: 841

```
ttgggtgttc ggcggaggga ccaagctgac cgtcctaggt gagtctcttc tcccctctcc    60
ttccccgctc ttgggacaat ttctgctgtt tttgtttgtt tctgtatctt gtctcaactt   120
```

<210> SEQ ID NO 842
<211> LENGTH: 120
<212> TYPE: DNA
<213> ORGANISM: Homo sapiens

<400> SEQUENCE: 842

```
agcttcctcc ttcacagctg cagtgggggc tggggctagg ggcatcccag ggagggtttt    60
tgtatgagcc tgtgtcacag tgtgtggtat tcggcggagg gaccaagctg accgtcctag   120
```

<210> SEQ ID NO 843
<211> LENGTH: 120
<212> TYPE: DNA
<213> ORGANISM: Homo sapiens

<400> SEQUENCE: 843

```
tgtggtattc ggcggaggga ccaagctgac cgtcctaggt gagtctcttc tcccctctcc    60
ttccccgctc ttgggacaat ttctgctgtt tttgtttgtt tctgtatctt gtctcaactt   120
```

<210> SEQ ID NO 844
<211> LENGTH: 120
<212> TYPE: DNA
<213> ORGANISM: Homo sapiens

<400> SEQUENCE: 844

```
gtatttggtg gaggaaccca gctgatcatt ttagatgagt ctcttcttcc ctttctttcc    60
ctgccaagtt ggtgacaatt ttattctgat ttcgatcttt gtctgtgact tgccacagcc   120
```

<210> SEQ ID NO 845
<211> LENGTH: 120
<212> TYPE: DNA
<213> ORGANISM: Homo sapiens

<400> SEQUENCE: 845

```
ttttgtattt ggtggaggaa cccagctgat cattttagat gagtctcttc ttcccttttct   60 ttccctgcca agttggtgac aatttttattc tgatttcgat cttttgtctgt gacttgccac  120
```

<210> SEQ ID NO 846
<211> LENGTH: 120
<212> TYPE: DNA

```
<213> ORGANISM: Homo sapiens

<400> SEQUENCE: 846
cagagagggt ttttgtatga gcctgtgtca cagcactggg tgtttggtga ggggacggag    60
ctgaccgtcc tagatgagtc ttttcccct ccttccctgg tctccccaag gtactgggaa   120

<210> SEQ ID NO 847
<211> LENGTH: 120
<212> TYPE: DNA
<213> ORGANISM: Homo sapiens

<400> SEQUENCE: 847
ctgggtgttt ggtgagggga cggagctgac cgtcctagga tgagtctttt ccccctcctt    60
ccctggtctc cccaaggtac tgggaaattt tctgctgctt tgttcttttt ctgtatcttg   120

<210> SEQ ID NO 848
<211> LENGTH: 120
<212> TYPE: DNA
<213> ORGANISM: Homo sapiens

<400> SEQUENCE: 848
ggagggtttg tgtgcagggt tatatcacag tgtaatgtgt tcggcagtgg caccaaggtg    60
accgtcctcg gtgagtcccc ttttctattc ttttgggtct agggtgagat ctggggagac   120

<210> SEQ ID NO 849
<211> LENGTH: 120
<212> TYPE: DNA
<213> ORGANISM: Homo sapiens

<400> SEQUENCE: 849
taatgtgttc ggcagtggca ccaaggtgac cgtcctcggt gagtcccctt ttctattctt    60
ttgggtctag ggtgagatct ggggagactt ttctgtcctt tctgttctct ctagggtaga   120

<210> SEQ ID NO 850
<211> LENGTH: 120
<212> TYPE: DNA
<213> ORGANISM: Homo sapiens

<400> SEQUENCE: 850
tcactgtgtg ctgtgttcgg aggaggcacc cagctgaccg tcctcggtaa gtctccccgc    60
ttctctcctc tttgagatcc caagttaaac acggggagtt tttcccttc ctgtctgtcg   120

<210> SEQ ID NO 851
<211> LENGTH: 120
<212> TYPE: DNA
<213> ORGANISM: Homo sapiens

<400> SEQUENCE: 851
tgctgtgttc ggaggaggca cccagctgac cgtcctcggt aagtctcccc gcttctctcc    60
tctttgagat cccaagttaa acacggggag ttttttccctt cctgtctgt cgaaggctaa   120

<210> SEQ ID NO 852
<211> LENGTH: 120
<212> TYPE: DNA
<213> ORGANISM: Homo sapiens

<400> SEQUENCE: 852
tcactgtgtg ctgtgttcgg aggaggcacc cagctgaccg ccctcggtaa gtctccccgc    60
ttctctcctc tttgagatcc caagttaaac acggggagtt tttcccttc ctgtctgtcg   120
```

<210> SEQ ID NO 853
<211> LENGTH: 120
<212> TYPE: DNA
<213> ORGANISM: Homo sapiens

<400> SEQUENCE: 853

```
tgctgtgttc ggaggaggca cccagctgac cgccctcggt aagtctcccc gcttctctcc    60
tctttgagat cccaagttaa acacggggag ttttcccctt cctgtctgt cgaaggctaa   120
```

<210> SEQ ID NO 854
<211> LENGTH: 120
<212> TYPE: DNA
<213> ORGANISM: Homo sapiens

<400> SEQUENCE: 854

```
tactactact actactacat ggacgtctgg ggcaaaggga ccacggtcac cgtctcctca    60
ggtaagaatg gccactctag ggcctttgtt ttctgctact gcctgtgggg tttcctgagc   120
```

<210> SEQ ID NO 855
<211> LENGTH: 117
<212> TYPE: DNA
<213> ORGANISM: Homo sapiens

<400> SEQUENCE: 855

```
attactacta ctactactac atggacgtct ggggcaaagg gaccacggtc accgtctcct    60
caggtaagaa tggccactct agggcctttg ttttctgcta ctgcctgtgg ggaattc     117
```

<210> SEQ ID NO 856
<211> LENGTH: 120
<212> TYPE: DNA
<213> ORGANISM: Homo sapiens

<400> SEQUENCE: 856

```
attactacta ctactacggt atggacgtct ggggcaaagg gaccacggtc accgtctcct    60
caggtaagaa tggccactct agggcctttg ttttctgcta ctgcctgtgg ggtttcctga   120
```

<210> SEQ ID NO 857
<211> LENGTH: 120
<212> TYPE: DNA
<213> ORGANISM: Homo sapiens

<400> SEQUENCE: 857

```
tgatgctttt gatatctggg gccaagggac aatggtcacc gtctcttcag gtaagatggc    60
tttccttctg cctcctttct ctgggcccag cgtcctctgt cctggagctg ggagataatg   120
```

<210> SEQ ID NO 858
<211> LENGTH: 120
<212> TYPE: DNA
<213> ORGANISM: Homo sapiens

<400> SEQUENCE: 858

```
cttgcagttg gacttcccag gccgacagtg gtctggcttc tgagggtca ggccagaatg    60
tggggtacgt gggaggccag cagagggttc catgagaagg gcaggacagg gccacggaca   120
```

<210> SEQ ID NO 859
<211> LENGTH: 120
<212> TYPE: DNA
<213> ORGANISM: Homo sapiens

<400> SEQUENCE: 859
gactattggg gccagggaac cctggtcacc gtctcctcag gtgagtcctc acaagctctc    60
tcctacttta actcagaaga ctctcactgc attttggggg ggagataagg gtgctgggtc   120

<210> SEQ ID NO 860
<211> LENGTH: 120
<212> TYPE: DNA
<213> ORGANISM: Homo sapiens

<400> SEQUENCE: 860
actactttga ctactggggc cagggaaccc tggtcaccgt ctcctcaggt gagtcctcac    60
aacctctctc ctgctttaac tctgaagggt tttgctgcat ttttgggggg aaataagggt   120

<210> SEQ ID NO 861
<211> LENGTH: 120
<212> TYPE: DNA
<213> ORGANISM: Homo sapiens

<400> SEQUENCE: 861
aactggttcg acccctgggg ccagggaacc ctggtcaccg tctcctcagg tgagtcctca    60 ccacccctc tctgagtcca cttagggaga ctcagcttgc cagggtctca gggtcagagt   120

<210> SEQ ID NO 862
<211> LENGTH: 120
<212> TYPE: DNA
<213> ORGANISM: Homo sapiens

<400> SEQUENCE: 862
cagtgcttcg acccctgggg ccagggaacc ctggtcaccg tctcctcagg agattcctca    60 ccacccctc tctgagtcct cttagtgaga ctcagtttgc cggactctca gggtcagagt   120

<210> SEQ ID NO 863
<211> LENGTH: 120
<212> TYPE: DNA
<213> ORGANISM: Homo sapiens

<400> SEQUENCE: 863
acaactggtt cgacccctgg ggccagggaa ccctggtcac cgtctcctca ggtgagtcct    60
caccaccccc tctctgagtc cacttaggga gactcagctt gccagggtct cagggtcaga   120

<210> SEQ ID NO 864
<211> LENGTH: 120
<212> TYPE: DNA
<213> ORGANISM: Homo sapiens

<400> SEQUENCE: 864
tactttgact actggggcca gggaaccctg gtcaccgtct cctcaggtga gtcctcacaa    60
cctctctcct gctttaactc tgaagggttt tgctgcattt ctgggggaa ataagggtgc    120

<210> SEQ ID NO 865
<211> LENGTH: 120
<212> TYPE: DNA
<213> ORGANISM: Homo sapiens

<400> SEQUENCE: 865
tttgactgct ggggccaggg aaccctggtc accgtctcct caggtgagcc ctcacaacct    60
ctctcctggg ttaactctga agggttttgc tgcattttg ggggaaata agggtgctgg    120

<210> SEQ ID NO 866
<211> LENGTH: 120
<212> TYPE: DNA
<213> ORGANISM: Homo sapiens

<400> SEQUENCE: 866
tgatgctttt gatgtctggg gccaagggac aatggtcacc gtctcttcag gtaagatggg      60
ctttccttct gcctcctttc tctggcccca gcgtcctctg tcctggagct gggagataat     120

<210> SEQ ID NO 867
<211> LENGTH: 120
<212> TYPE: DNA
<213> ORGANISM: Homo sapiens

<400> SEQUENCE: 867
tgatgctttt gatatctggg gccaagggac aatggtcacc gtctcttcag gtaagatggc      60
tttccttctg cctcctttct ctgggcccag cgtcctctgt cctggagctg ggagataatg     120

<210> SEQ ID NO 868
<211> LENGTH: 120
<212> TYPE: DNA
<213> ORGANISM: Homo sapiens

<400> SEQUENCE: 868
gatgcttttg atatctgggg ccaagggaca atggtcaccg tctcttcagg taagatggct      60
ttccttctgc ctcctttctc tgggcccagc gtcctctgtc ctggagctgg gagataatgt     120

<210> SEQ ID NO 869
<211> LENGTH: 120
<212> TYPE: DNA
<213> ORGANISM: Homo sapiens

<400> SEQUENCE: 869
gctacaagtg cttggagcac tggggccagg gcagcccggc caccgtctcc ctgggaacgt      60 caccccctccc tgcctgggtc tcagcccggg ggtctgtgtg gctggggaca gggacgccgg    120

<210> SEQ ID NO 870
<211> LENGTH: 120
<212> TYPE: DNA
<213> ORGANISM: Homo sapiens

<400> SEQUENCE: 870
ctactggtac ttcgatctct ggggccgtgg caccctggtc actgtctcct caggtgagtc      60
ccactgcagc cccctcccag tcttctctgt ccaggcacca ggccaggtat ctggggtctg     120

<210> SEQ ID NO 871
<211> LENGTH: 120
<212> TYPE: DNA
<213> ORGANISM: Homo sapiens

<400> SEQUENCE: 871
gctgaatact tccagcactg gggccagggc accctggtca ccgtctcctc aggtgagtct      60
gctgtctggg gatagcgggg agccaggtgt actgggccag gcaagggctt tggcttcaga     120

<210> SEQ ID NO 872
<211> LENGTH: 120
<212> TYPE: DNA
<213> ORGANISM: Homo sapiens

<400> SEQUENCE: 872

```
aaaggtgctg ggggcccctg acccgaccc gccctggaga ccgcagccac atcaagcccc    60
cagccccaca ggcccctac cagccgcagg gttttggctg agctgagaac cactgtgcta   120
```

<210> SEQ ID NO 873
<211> LENGTH: 100
<212> TYPE: DNA
<213> ORGANISM: Homo sapiens

<400> SEQUENCE: 873

```
ggacaaagcc ttgagcagcc ctctgaagtg acagctgtgg aaggagccat tgtccagata    60
aactgcacgt accagacatc tgggttttat gggctgtcct                         100
```

<210> SEQ ID NO 874
<211> LENGTH: 100
<212> TYPE: DNA
<213> ORGANISM: Homo sapiens

<400> SEQUENCE: 874

```
gttttcttc attccttagt cgctctgata gttatggtta cctccttcta caggagctcc    60
agatgaaaga ctctgcctct tacttctgcg ctgtgagaga                         100
```

<210> SEQ ID NO 875
<211> LENGTH: 100
<212> TYPE: DNA
<213> ORGANISM: Homo sapiens

<400> SEQUENCE: 875

```
ggacaaagcc ttgagcagcc ctctgaagtg acagctgtgg aaggagccat tgtccagata    60
aactgcacgt accagacatc tgggttttat gggctgtcct                         100
```

<210> SEQ ID NO 876
<211> LENGTH: 100
<212> TYPE: DNA
<213> ORGANISM: Homo sapiens

<400> SEQUENCE: 876

```
caggtcgttt ttcttcattc cttagtcgct ctgatagtta tggttacctc cttctacagg    60
agctccagat gaaagactct gcctcttact tctgcgctgt                         100
```

<210> SEQ ID NO 877
<211> LENGTH: 100
<212> TYPE: DNA
<213> ORGANISM: Homo sapiens

<400> SEQUENCE: 877

```
ggacaaaaca ttgaccagcc cactgagatg acagctacgg aaggtgccat tgtccagatc    60
aactgcacgt accagacatc tgggttcaac gggctgttct                         100
```

<210> SEQ ID NO 878
<211> LENGTH: 100
<212> TYPE: DNA
<213> ORGANISM: Homo sapiens

<400> SEQUENCE: 878

```
gttttcttc attccttagt cggtctaaag ggtacagtta cctcctttg aaggagctcc    60 agatgaaaga ctctgcctct tacctctgtg ctgtgagaga                         100
```

<210> SEQ ID NO 879
<211> LENGTH: 100

```
<212> TYPE: DNA
<213> ORGANISM: Homo sapiens

<400> SEQUENCE: 879
ggacaaaaca ttgaccagcc cactgagatg acagctacgg aaggtgccat tgtccagatc    60
aactgcacgt accagacatc tgggttcaac gggctgttct                         100

<210> SEQ ID NO 880
<211> LENGTH: 100
<212> TYPE: DNA
<213> ORGANISM: Homo sapiens

<400> SEQUENCE: 880
catctgggtt caacgggctg ttctggtacc agcaacatgc tggcgaagca cccacatttc    60
tgtcttacaa tgttctggat ggtctggagg agaaaggtcg                         100

<210> SEQ ID NO 881
<211> LENGTH: 100
<212> TYPE: DNA
<213> ORGANISM: Homo sapiens

<400> SEQUENCE: 881
aaaaaccaag tggagcagag tcctcagtcc ctgatcatcc tggagggaaa gaactgcact    60
cttcaatgca attatacagt gagccccttc agcaacttaa                         100

<210> SEQ ID NO 882
<211> LENGTH: 100
<212> TYPE: DNA
<213> ORGANISM: Homo sapiens

<400> SEQUENCE: 882
agatatacag caactctgga tgcagacaca aagcaaagct ctctgcacat cacagcctcc    60
cagctcagcg attcagcctc ctacatctgt gtggtgagcg                         100

<210> SEQ ID NO 883
<211> LENGTH: 100
<212> TYPE: DNA
<213> ORGANISM: Homo sapiens

<400> SEQUENCE: 883
ctacatacac tggagcagag tccttcattc ctgaatattc aggagggaat gcatgccgtt    60
cttaattgta cttatcagga gagaacactc ttcaatttcc                         100

<210> SEQ ID NO 884
<211> LENGTH: 100
<212> TYPE: DNA
<213> ORGANISM: Homo sapiens

<400> SEQUENCE: 884
caaatatttt aaagaactgc ttggaaaaga aaaattttat agtgtttgga atatcgcagc    60
ctctcatctg ggagattcag ccacctactt ctgtgctttg                         100

<210> SEQ ID NO 885
<211> LENGTH: 100
<212> TYPE: DNA
<213> ORGANISM: Homo sapiens

<400> SEQUENCE: 885
cggaaggagg tggagcagga tcctggaccc ttcaatgttc cagagggagc cactgtcgct    60
```
ttcaactgta cttacagcaa cagtgcttct cagtctttct                          100

<210> SEQ ID NO 886
<211> LENGTH: 100
<212> TYPE: DNA
<213> ORGANISM: Homo sapiens

<400> SEQUENCE: 886
aggtttacag cacagctcaa tagagccagc cagtatattt ccctgctcat cagagactcc   60
aagctcagtg attcagccac ctacctctgt gtggtgaaca                         100

<210> SEQ ID NO 887
<211> LENGTH: 100
<212> TYPE: DNA
<213> ORGANISM: Homo sapiens

<400> SEQUENCE: 887
cggaaggagg tggagcagga tcctggaccc ttcaatgttc cagagggagc cactgtcgct   60
ttcaactgta cttacagcaa cagtgcttct cagtctttct                         100

<210> SEQ ID NO 888
<211> LENGTH: 100
<212> TYPE: DNA
<213> ORGANISM: Homo sapiens

<400> SEQUENCE: 888
acagcacacg tcaatagagc cagccagtat atttccctgc tcatcagaga ctccaagctc   60
agtgattcag ccacctacct ctgtgtggtg aacattcgcc                         100

<210> SEQ ID NO 889
<211> LENGTH: 100
<212> TYPE: DNA
<213> ORGANISM: Homo sapiens

<400> SEQUENCE: 889
cagaaggagg tggagcagaa ttctggaccc ctcagtgttc cagagggagc cattgcctct   60
ctcaactgca cttacagtga ccgaggttcc cagtccttct                         100

<210> SEQ ID NO 890
<211> LENGTH: 100
<212> TYPE: DNA
<213> ORGANISM: Homo sapiens

<400> SEQUENCE: 890
aggtttacag cacagctcaa taaagccagc cagtatgttt ctctgctcat cagagactcc   60
cagcccagtg attcagccac ctacctctgt gccgtgaaca                         100

<210> SEQ ID NO 891
<211> LENGTH: 100
<212> TYPE: DNA
<213> ORGANISM: Homo sapiens

<400> SEQUENCE: 891
cagaaggagg tggagcagaa ttctggaccc ctcagtgttc cagagggagc cattgcctct   60
ctcaactgca cttacagtga ccgaggttcc cagtccttct                         100

<210> SEQ ID NO 892
<211> LENGTH: 100
<212> TYPE: DNA
<213> ORGANISM: Homo sapiens

<400> SEQUENCE: 892
gtttacagca cagctcaata aagccagcca gtatgtttct ctgctcatca gagactccca        60
gcccagtgat tcagccacct acctctgtgc cgtgtaccac        100

<210> SEQ ID NO 893
<211> LENGTH: 100
<212> TYPE: DNA
<213> ORGANISM: Homo sapiens

<400> SEQUENCE: 893
ggacccctca gtgttccaga gggagccatt gcctctctca actgcactta cagtgaccga        60
gtttcccagt ccttcttctg gtacagacaa tattctggga        100

<210> SEQ ID NO 894
<211> LENGTH: 100
<212> TYPE: DNA
<213> ORGANISM: Homo sapiens

<400> SEQUENCE: 894
aaggtttaca gcacagctca ataaagccag ccagtatgtt tctctgctca tcagagactc        60
ccagcccagt gattcagcca cctacctctg tgccgtgaac        100

<210> SEQ ID NO 895
<211> LENGTH: 100
<212> TYPE: DNA
<213> ORGANISM: Homo sapiens

<400> SEQUENCE: 895
cagaaggagg tggagcagga tcctggacca ctcagtgttc cagagggagc cattgtttct        60
ctcaactgca cttacagcaa cagtgctttt caatacttca        100

<210> SEQ ID NO 896
<211> LENGTH: 100
<212> TYPE: DNA
<213> ORGANISM: Homo sapiens

<400> SEQUENCE: 896
aggtttacag cacaggtcga taaatccagc aagtatatct ccttgttcat cagagactca        60
cagcccagtg attcagccac ctacctctgt gcaatgagcg        100

<210> SEQ ID NO 897
<211> LENGTH: 100
<212> TYPE: DNA
<213> ORGANISM: Homo sapiens

<400> SEQUENCE: 897
cagaaggagg tggagcagga tcctggacca ctcagtgttc cagagggagc cattgtttct        60
ctcaactgca cttacagcaa cagtgctttt caatacttca        100

<210> SEQ ID NO 898
<211> LENGTH: 100
<212> TYPE: DNA
<213> ORGANISM: Homo sapiens

<400> SEQUENCE: 898
aggtttacag cacaggtcga taaatccagc aagtatatct ccttgttcat cagagactca        60
cagcccagtg attcagccac ctacctctgt gcaatgagcg        100

<210> SEQ ID NO 899
<211> LENGTH: 100
<212> TYPE: DNA
<213> ORGANISM: Homo sapiens

<400> SEQUENCE: 899
ggagagaatg tggagcagca tccttcaacc ctgagtgtcc aggagggaga cagcgctgtt    60
atcaagtgta cttattcaga cagtgcctca aactacttcc                         100

<210> SEQ ID NO 900
<211> LENGTH: 100
<212> TYPE: DNA
<213> ORGANISM: Homo sapiens

<400> SEQUENCE: 900
cgaattgctg ttacattgaa caagacagcc aaacatttct ccctgcacat cacagagacc    60
caacctgaag actcggctgt ctacttctgt gcagcaagta                         100

<210> SEQ ID NO 901
<211> LENGTH: 100
<212> TYPE: DNA
<213> ORGANISM: Homo sapiens

<400> SEQUENCE: 901
ggagagaatg tggagcagca tccttcaacc ctgagtgtcc aggagggaga cagcgctgtt    60
atcaagtgta cttattcaga cagtgcctca aactacttcc                         100

<210> SEQ ID NO 902
<211> LENGTH: 100
<212> TYPE: DNA
<213> ORGANISM: Homo sapiens

<400> SEQUENCE: 902
tgttacattg aacaagacag ccaaacattt ctccctgcac atcacagaga cccaacctga    60
agactcggct gtctacttct gtgcagcaag taggaaggac                         100

<210> SEQ ID NO 903
<211> LENGTH: 100
<212> TYPE: DNA
<213> ORGANISM: Homo sapiens

<400> SEQUENCE: 903
ggagagaatg tggagcagca tccttcaacc ctgagtgtcc aggagggaga cagcgctgtt    60
atcaagtgta cttattcaga cagtgcctca aactacttcc                         100

<210> SEQ ID NO 904
<211> LENGTH: 100
<212> TYPE: DNA
<213> ORGANISM: Homo sapiens

<400> SEQUENCE: 904
gcttattata gacattcgtt caaatgtggg cgaaaagaaa gaccaacgaa ttgctgttac    60
attgaacaag acagccaaac atttctccct gcagatcaca                         100

<210> SEQ ID NO 905
<211> LENGTH: 100
<212> TYPE: DNA
<213> ORGANISM: Homo sapiens

<400> SEQUENCE: 905

```
ggagagagtg tggggctgca tcttcctacc ctgagtgtcc aggagggtga caactctatt    60
atcaactgtg cttattcaaa cagcgcctca gactacttca                         100

<210> SEQ ID NO 906
<211> LENGTH: 100
<212> TYPE: DNA
<213> ORGANISM: Homo sapiens

<400> SEQUENCE: 906
agagtcaccg ttttattgaa taagacagtg aaacatctct ctctgcaaat tgcagctact    60
caacctggag actcagctgt ctactttgt gcagagaata                          100

<210> SEQ ID NO 907
<211> LENGTH: 100
<212> TYPE: DNA
<213> ORGANISM: Homo sapiens

<400> SEQUENCE: 907
ggagagagtg tggggctgca tcttcctacc ctgagtgtcc aggagggtga caactctatt    60
atcaactgtg cttattcaaa cagcgcctca gactacttca                         100

<210> SEQ ID NO 908
<211> LENGTH: 100
<212> TYPE: DNA
<213> ORGANISM: Homo sapiens

<400> SEQUENCE: 908
caaagagtca ccgttttatt gaataagaca gtgaaacatc tctctctgca aattgcagct    60
actcaacctg gagactcagc tgtctacttt tgtgcagaga                         100

<210> SEQ ID NO 909
<211> LENGTH: 100
<212> TYPE: DNA
<213> ORGANISM: Homo sapiens

<400> SEQUENCE: 909
gcccagaaga taactcaaac ccaaccagga atgttcgtgc aggaaaagga ggctgtgact    60
ctggactgca catatgacac cagtgatcca agttatggtc                         100

<210> SEQ ID NO 910
<211> LENGTH: 100
<212> TYPE: DNA
<213> ORGANISM: Homo sapiens

<400> SEQUENCE: 910
actcattgaa tttccagaag gcaagaaaat ccgccaacct tgtcatctcc gcttcacaac    60
tgggggactc agcaatgtac ttctgtgcaa tgagagaggg                         100

<210> SEQ ID NO 911
<211> LENGTH: 100
<212> TYPE: DNA
<213> ORGANISM: Homo sapiens

<400> SEQUENCE: 911
gcccagaaga taactcaaac ccaaccagga atgttcgtgc aggaaaagga ggctgtgact    60
ctggactgca catatgacac cagtgatcaa agttatggtc                         100

<210> SEQ ID NO 912
```

```
<211> LENGTH: 100
<212> TYPE: DNA
<213> ORGANISM: Homo sapiens

<400> SEQUENCE: 912
actcattgaa tttccagaag gcaagaaaat ccgccaacct tgtcatctcc gcttcacaac      60
tgggggactc agcaatgtat ttctgtgcaa tgagagaggg                           100

<210> SEQ ID NO 913
<211> LENGTH: 100
<212> TYPE: DNA
<213> ORGANISM: Homo sapiens

<400> SEQUENCE: 913
gcccagaaga taactcaaac ccaaccagga atgttcgtgc aggaaaagga ggctgtgact      60
ctggactgca catatgacac cagtgatcca agttatggtc                           100

<210> SEQ ID NO 914
<211> LENGTH: 100
<212> TYPE: DNA
<213> ORGANISM: Homo sapiens

<400> SEQUENCE: 914
aggtcgctac tcattgaatt tccagaaggc aagaaaatcc gccaaccttg tcatctccgc      60
ttcacaactg ggggactcag caatgtattt ctgtgcaatg                           100

<210> SEQ ID NO 915
<211> LENGTH: 100
<212> TYPE: DNA
<213> ORGANISM: Homo sapiens

<400> SEQUENCE: 915
cagaagataa ctcaaaccca accaggaatg ttcgtgcagg aaaaggaggc tgtgactctg      60
gactgcacat atgacaccag tgatcaaagt tatggtctct                           100

<210> SEQ ID NO 916
<211> LENGTH: 100
<212> TYPE: DNA
<213> ORGANISM: Homo sapiens

<400> SEQUENCE: 916
gcaacagaag gtcgctactc attgaatttc cagaaggcaa gaaaatccgc caaccttgtc      60
atctccgctt cacaactggg ggactcagca atgtacttct                           100

<210> SEQ ID NO 917
<211> LENGTH: 100
<212> TYPE: DNA
<213> ORGANISM: Homo sapiens

<400> SEQUENCE: 917
ctccatattc tggagtagag tccttcattc attcctgagt atccgggagg gaatgcacaa      60
cattcttaat tgcacttatg aggagagaac gttctcttaa                           100

<210> SEQ ID NO 918
<211> LENGTH: 100
<212> TYPE: DNA
<213> ORGANISM: Homo sapiens

<400> SEQUENCE: 918
acattttaaa gaagcgcttg gaaaagagaa gttttatagt gttttgaata tgctggtctc      60
```

```
tcatcctgga gattcaggca cctacttctg tgctttgagg                   100
```

<210> SEQ ID NO 919
<211> LENGTH: 100
<212> TYPE: DNA
<213> ORGANISM: Homo sapiens

<400> SEQUENCE: 919

```
gcccagagag tgactcagcc cgagaagctc ctctctgtct ttaaaggggc cccagtggag   60
ctgaagtgca actattccta ttctgggagt cctgaactct                        100
```

<210> SEQ ID NO 920
<211> LENGTH: 100
<212> TYPE: DNA
<213> ORGANISM: Homo sapiens

<400> SEQUENCE: 920

```
gcttcactgc tgaccttaac aaaggcgaga catctttcca cctgaagaaa ccatttgctc   60
aagaggaaga ctcagccatg tattactgtg ctctaagtgg                        100
```

<210> SEQ ID NO 921
<211> LENGTH: 100
<212> TYPE: DNA
<213> ORGANISM: Homo sapiens

<400> SEQUENCE: 921

```
agtcaacagg gagaagagga tcctcaggcc ttgagcatcc aggagggtga aaatgccacc   60
atgaactgca gttacaaaac tagtataaac aatttacagt                        100
```

<210> SEQ ID NO 922
<211> LENGTH: 100
<212> TYPE: DNA
<213> ORGANISM: Homo sapiens

<400> SEQUENCE: 922

```
agattaagag tcacgcttga cacttccaag aaaagcagtt ccttgttgat cacggcttcc   60
cgggcagcag acactgcttc ttacttctgt gctacggacg                        100
```

<210> SEQ ID NO 923
<211> LENGTH: 100
<212> TYPE: DNA
<213> ORGANISM: Homo sapiens

<400> SEQUENCE: 923

```
ggagactcgg ttacccagac agaaggccca gttaccctcc ctgagagggc agctctgaca   60
ttaaactgca cttatcagtc cagctattca acttttctat                        100
```

<210> SEQ ID NO 924
<211> LENGTH: 100
<212> TYPE: DNA
<213> ORGANISM: Homo sapiens

<400> SEQUENCE: 924

```
gttttcaggc cagtcctatc aagagtgaca gttccttcca cctggagaag ccctcggtgc   60
agctgtcgga ctctgccgtg tactactgcg ctctgagaga                        100
```

<210> SEQ ID NO 925
<211> LENGTH: 100
<212> TYPE: DNA

-continued

<213> ORGANISM: Homo sapiens

<400> SEQUENCE: 925
gctcagaagg taactcaagc gcagactgaa atttctgtgg tggagaagga ggatgtgacc    60
ttggactgtg tgtatgaaac ccgtgatact acttattact                          100

<210> SEQ ID NO 926
<211> LENGTH: 100
<212> TYPE: DNA
<213> ORGANISM: Homo sapiens

<400> SEQUENCE: 926
attcttggaa cttccagaaa tccaccagtt ccttcaactt caccatcaca gcctcacaag    60
tcgtggactc agcagtatac ttctgtgctc tgagtgaggc                          100

<210> SEQ ID NO 927
<211> LENGTH: 100
<212> TYPE: DNA
<213> ORGANISM: Homo sapiens

<400> SEQUENCE: 927
aaggaccaag tgtttcagcc ttccacagtg gcatcttcag agggagctgt ggtggaaatc    60
ttctgtaatc actctgtgtc caatgcttac aacttcttct                          100

<210> SEQ ID NO 928
<211> LENGTH: 100
<212> TYPE: DNA
<213> ORGANISM: Homo sapiens

<400> SEQUENCE: 928
agggacgata caacatgacc tatgaacggt tctcttcatc gctgctcatc ctccaggtgc    60
gggaggcaga tgctgctgtt tactactgtg ctgtggagga                          100

<210> SEQ ID NO 929
<211> LENGTH: 100
<212> TYPE: DNA
<213> ORGANISM: Homo sapiens

<400> SEQUENCE: 929
aaggaccaag tgtttcagcc ttccacagtg gcatcttcag agggagctgt ggtggaaatc    60
ttctgtaatc actctgtgtc caatgcttac aacttcttct                          100

<210> SEQ ID NO 930
<211> LENGTH: 100
<212> TYPE: DNA
<213> ORGANISM: Homo sapiens

<400> SEQUENCE: 930
gggacgatac aacatgacct atgaacggtt ctcttcatcg ctgctcatcc tccaggtgcg    60
ggaggcagat gctgctgttt actactgtgc tgtggcctgg                          100

<210> SEQ ID NO 931
<211> LENGTH: 100
<212> TYPE: DNA
<213> ORGANISM: Homo sapiens

<400> SEQUENCE: 931
gaagaccagg tgacgcagag tcccgaggcc ctgagactcc aggagggaga gagtagcagt    60
cttaactgca gttacacagt cagcggttta agagggctgt                          100

```
<210> SEQ ID NO 932
<211> LENGTH: 100
<212> TYPE: DNA
<213> ORGANISM: Homo sapiens

<400> SEQUENCE: 932
aaagaaaggc taaaagccac attaacaaag aaggaaagct ttctgcacat cacagccct      60 aaacctgaag actcagccac ttatctctgt gctgtgcagg                          100

<210> SEQ ID NO 933
<211> LENGTH: 100
<212> TYPE: DNA
<213> ORGANISM: Homo sapiens

<400> SEQUENCE: 933
gaagaccagg tgacgcagag tcccgaggcc ctgagactcc aggagggaga gagtagcagt     60
ctcaactgca gttacacagt cagcggttta agagggctgt                          100

<210> SEQ ID NO 934
<211> LENGTH: 100
<212> TYPE: DNA
<213> ORGANISM: Homo sapiens

<400> SEQUENCE: 934
aaaggagaaa gaaaggctaa aagccacatt aacaaagaag gaaagctttc tgcacatcac     60
agcccctaaa cctgaagact cagccactta tctctgtgct                          100

<210> SEQ ID NO 935
<211> LENGTH: 100
<212> TYPE: DNA
<213> ORGANISM: Homo sapiens

<400> SEQUENCE: 935
gaagaccagg tgacgcagag tcccgaggcc ctgagactcc aggagggaga gagtcgcagt     60
ctcaactgca gttacacagt cagcggttta agagggctgt                          100

<210> SEQ ID NO 936
<211> LENGTH: 100
<212> TYPE: DNA
<213> ORGANISM: Homo sapiens

<400> SEQUENCE: 936
agaaaaggag aaagaaaggc taaaagccac attaacaaag aaggaaagct ttctgcacat     60
cacagcccct aaacctgaag actcagccac ttatctctgt                          100

<210> SEQ ID NO 937
<211> LENGTH: 100
<212> TYPE: DNA
<213> ORGANISM: Homo sapiens

<400> SEQUENCE: 937
gaagaccagg tgacgcagag tcccgaggcc ctgagactcc aggagggaga gagtagcagt     60
ctcaactgca gttgcacagt cagcggttta agagggctgt                          100

<210> SEQ ID NO 938
<211> LENGTH: 100
<212> TYPE: DNA
<213> ORGANISM: Homo sapiens
```

```
<400> SEQUENCE: 938
aaaggagaaa gaaaggctaa aagccacatt aacaaagaag gaaagctttc tgcacatcac      60
agcccctaaa cctgaagact cagccactta tctctgtgct                           100

<210> SEQ ID NO 939
<211> LENGTH: 100
<212> TYPE: DNA
<213> ORGANISM: Homo sapiens

<400> SEQUENCE: 939
aaacaggagg tgacgcagat tcctgcagct ctgagtgtcc cagaaggaga aaacttggtt      60
ctcaactgca gtttcactga tagcgctatt tacaacctcc                           100

<210> SEQ ID NO 940
<211> LENGTH: 100
<212> TYPE: DNA
<213> ORGANISM: Homo sapiens

<400> SEQUENCE: 940
aagacttaat gcctcgctgg ataaatcatc aggacgtagt actttataca ttgcagcttc      60
tcagcctggt gactcagcca cctacctctg tgctgtgagg                           100

<210> SEQ ID NO 941
<211> LENGTH: 100
<212> TYPE: DNA
<213> ORGANISM: Homo sapiens

<400> SEQUENCE: 941
aaacaggagg tgacacagat tcctgcagct ctgagtgtcc cagaaggaga aaacttggtt      60
ctcaactgca gtttcactga tagcgctatt tacaacctcc                           100

<210> SEQ ID NO 942
<211> LENGTH: 100
<212> TYPE: DNA
<213> ORGANISM: Homo sapiens

<400> SEQUENCE: 942
aagtggaaga cttaatgcct cgctggataa atcatcagga cgtagtactt tatacattgc      60
agcttctcag cctggtgact cagccaccta cctctgtgct                           100

<210> SEQ ID NO 943
<211> LENGTH: 100
<212> TYPE: DNA
<213> ORGANISM: Homo sapiens

<400> SEQUENCE: 943
ggaatacaag tggagcagag tcctccagac ctgattctcc aggagggagc caattccacg      60
ctgcggtgca ttttttctga ctctgtgaac aatttgcagt                           100

<210> SEQ ID NO 944
<211> LENGTH: 100
<212> TYPE: DNA
<213> ORGANISM: Homo sapiens

<400> SEQUENCE: 944
agattaagcg ccacgactgt cgctacggaa cgctacagct tattgtacat ttcctcttcc      60
cagaccacag actcaggcgt ttatttctgt gctgtggagc                           100
```

```
<210> SEQ ID NO 945
<211> LENGTH: 100
<212> TYPE: DNA
<213> ORGANISM: Homo sapiens

<400> SEQUENCE: 945
cagcagcagg tgaaacaaag tcctcaatct ttgatagtcc agaaaggagg gatttcaatt      60
ataaactgtg cttatgagaa cactgcgttt gactactttc                           100

<210> SEQ ID NO 946
<211> LENGTH: 100
<212> TYPE: DNA
<213> ORGANISM: Homo sapiens

<400> SEQUENCE: 946
agattcacaa tctccttcaa taaaagtgcc aagcagttct cattgcatat catggattcc      60
cagcctggag actcagccac ctacttctgt gcagcaagca                           100

<210> SEQ ID NO 947
<211> LENGTH: 100
<212> TYPE: DNA
<213> ORGANISM: Homo sapiens

<400> SEQUENCE: 947
cagcagcagg tgaaacaaag tcctcaatct ttgatagtcc agaaaggagg gattccaatt      60
ataaactgtg cttatgagaa cactgcgttt gactactttc                           100

<210> SEQ ID NO 948
<211> LENGTH: 100
<212> TYPE: DNA
<213> ORGANISM: Homo sapiens

<400> SEQUENCE: 948
agattcacaa tctccttcaa taaaagtgcc aagcagttct cattgcatat catggattcc      60
cagcctggag actcagccac ctacttctgt gcagcaagcg                           100

<210> SEQ ID NO 949
<211> LENGTH: 100
<212> TYPE: DNA
<213> ORGANISM: Homo sapiens

<400> SEQUENCE: 949
cagcagcagg tgaaacaaag tcctcaatct ttgatagtcc agaaaggagg gatttcaatt      60
ataaactgtg cttatgagaa cactgcgttt gactactttc                           100

<210> SEQ ID NO 950
<211> LENGTH: 100
<212> TYPE: DNA
<213> ORGANISM: Homo sapiens

<400> SEQUENCE: 950
agattcacaa tctccttcaa taaaagtgcc aagcagttct cattgcatat catggattcc      60
cagcctggag actcagccac ctacttctgt gcagcaagca                           100

<210> SEQ ID NO 951
<211> LENGTH: 100
<212> TYPE: DNA
<213> ORGANISM: Homo sapiens

<400> SEQUENCE: 951
```

```
cagcaggtga aacaaagtcc tcaatctttg atagtccaga aaggagggat ttcaattata    60
aactgtgctt atgagaacac tgcgtttgac tactttccat                         100

<210> SEQ ID NO 952
<211> LENGTH: 100
<212> TYPE: DNA
<213> ORGANISM: Homo sapiens

<400> SEQUENCE: 952
gaaagaagga agattcacaa tctccttcaa taaaagtgcc aagcagttct cattgcatat    60
catggattcc cagcctggag actcagccac ctacttctgt                        100

<210> SEQ ID NO 953
<211> LENGTH: 100
<212> TYPE: DNA
<213> ORGANISM: Homo sapiens

<400> SEQUENCE: 953
aggacgaata agtgccactc ttaataccaa ggagggttac agctatttgt acatcaaagg    60
atcccagcct gaagactcag ccacatacct ctgtgccttt                        100

<210> SEQ ID NO 954
<211> LENGTH: 100
<212> TYPE: DNA
<213> ORGANISM: Homo sapiens

<400> SEQUENCE: 954
ggacgaataa gtgccactct taataccaag gagggttaca gctatttgta catcaaagga    60
tcccagcctg aagactcagc cacatacctc tgtgccttta                        100

<210> SEQ ID NO 955
<211> LENGTH: 100
<212> TYPE: DNA
<213> ORGANISM: Homo sapiens

<400> SEQUENCE: 955
atactgaacg tggaacaagg tcctcagtca ctgcatgttc aggagggaga cagcaccaat    60
ttcacctgca gcttcccttc cagcaatttt tatgccttac                        100

<210> SEQ ID NO 956
<211> LENGTH: 100
<212> TYPE: DNA
<213> ORGANISM: Homo sapiens

<400> SEQUENCE: 956
ggacgaataa gtgccactct taataccaag gagggttaca gctatttgta catcaaagga    60
tcccagcctg aagattcagc cacatacctc tgtgccttta                        100

<210> SEQ ID NO 957
<211> LENGTH: 100
<212> TYPE: DNA
<213> ORGANISM: Homo sapiens

<400> SEQUENCE: 957
ggacaacagg taatgcaaat tcctcagtac cagcatgtac aagaaggaga ggacttcacc    60
acgtactgca attcctcaac tactttaagc aatatacagt                        100

<210> SEQ ID NO 958
<211> LENGTH: 100
```

```
<212> TYPE: DNA
<213> ORGANISM: Homo sapiens

<400> SEQUENCE: 958
gaaaagactg acatttcagt ttggagaagc aaaaaagaac agctccctgc acatcacagc    60
cacccagact acagatgtag gaacctactt ctgtgcaggg                         100

<210> SEQ ID NO 959
<211> LENGTH: 100
<212> TYPE: DNA
<213> ORGANISM: Homo sapiens

<400> SEQUENCE: 959
gatgctaaga ccacccagcc ccctccatg gattgcgctg aaggaagagc tgcaaacctg     60
ccttgtaatc actctaccat cagtggaaat gagtatgtgt                         100

<210> SEQ ID NO 960
<211> LENGTH: 100
<212> TYPE: DNA
<213> ORGANISM: Homo sapiens

<400> SEQUENCE: 960
gcctctctga tcatcacaga agacagaaag tccagcacct tgatcctgcc ccacgctacg    60
ctgagagaca ctgctgtgta ctattgcatc gtcagagtcg                         100

<210> SEQ ID NO 961
<211> LENGTH: 100
<212> TYPE: DNA
<213> ORGANISM: Homo sapiens

<400> SEQUENCE: 961
gatgctaaga ccacccagcc cacctccatg gattgcgctg aaggaagagc tgcaaacctg    60
ccttgtaatc actctaccat cagtggaaat gagtatgtgt                         100

<210> SEQ ID NO 962
<211> LENGTH: 100
<212> TYPE: DNA
<213> ORGANISM: Homo sapiens

<400> SEQUENCE: 962
ctctgatcat cacagaagac agaaagtcca gcaccttgat cctgccccac gctacgctga    60
gagacactgc tgtgtactat tgcatcgtca gagattgggt                         100

<210> SEQ ID NO 963
<211> LENGTH: 100
<212> TYPE: DNA
<213> ORGANISM: Homo sapiens

<400> SEQUENCE: 963
gatgctaaga ccacccagcc ccctccatg gattgcgctg aaggaagagc tgcaaacctg     60
ccttgtaatc actctaccat cagtggaaat gagtatgtgt                         100

<210> SEQ ID NO 964
<211> LENGTH: 100
<212> TYPE: DNA
<213> ORGANISM: Homo sapiens

<400> SEQUENCE: 964
caatgaaatg gcctctctga tcatcacaga agacagaaag tccagcacct tgatcctgcc    60
```

| | |
|---|---|
| ccacgctacg ctgagagaca ctgctgtgta ctattgcatc | 100 |

<210> SEQ ID NO 965
<211> LENGTH: 100
<212> TYPE: DNA
<213> ORGANISM: Homo sapiens

<400> SEQUENCE: 965

| | |
|---|---|
| gatgctaaga ccacacagcc aaattcaatg gagagtaacg aagaagagcc tgttcacttg | 60 |
| ccttgtaacc actccacaat cagtggaact gattacatac | 100 |

<210> SEQ ID NO 966
<211> LENGTH: 100
<212> TYPE: DNA
<213> ORGANISM: Homo sapiens

<400> SEQUENCE: 966

| | |
|---|---|
| ggcctctctg gcaatcgctg aagacagaaa gtccagtacc ttgatcctgc accgtgctac | 60 |
| cttgagagat gctgctgtgt actactgcat cctgagagac | 100 |

<210> SEQ ID NO 967
<211> LENGTH: 100
<212> TYPE: DNA
<213> ORGANISM: Homo sapiens

<400> SEQUENCE: 967

| | |
|---|---|
| gatgctaaga ccacacagcc aaattcaatg gagagtaacg aagaagagcc tgttcacttg | 60 |
| ccttgtaacc actccacaat cagtggaact gattacatac | 100 |

<210> SEQ ID NO 968
<211> LENGTH: 100
<212> TYPE: DNA
<213> ORGANISM: Homo sapiens

<400> SEQUENCE: 968

| | |
|---|---|
| ccctcccagg gtccagagta cgtgattcat ggtcttacaa gcaatgtgaa caacagaatg | 60 |
| gcctgtgtgg caatcgctga agacagaaag tccagtacct | 100 |

<210> SEQ ID NO 969
<211> LENGTH: 100
<212> TYPE: DNA
<213> ORGANISM: Homo sapiens

<400> SEQUENCE: 969

| | |
|---|---|
| acccagctgc tggagcagag ccctcagttt ctaagcatcc aagagggaga aaatctcact | 60 |
| gtgtactgca actcctcaag tgttttttcc agcttacaat | 100 |

<210> SEQ ID NO 970
<211> LENGTH: 100
<212> TYPE: DNA
<213> ORGANISM: Homo sapiens

<400> SEQUENCE: 970

| | |
|---|---|
| aagagactaa cctttcagtt tggtgatgca agaaaggaca gttctctcca catcactgca | 60 |
| gcccagcctg gtgatacagg cctctacctc tgtgcaggag | 100 |

<210> SEQ ID NO 971
<211> LENGTH: 100
<212> TYPE: DNA
<213> ORGANISM: Homo sapiens

```
<400> SEQUENCE: 971
acccagctgc tggagcagag ccctcagttt ctaagcatcc aagagggaga aaatctcact    60
gtgtactgca actcctcaag tgttttttcc agcttacaat                         100

<210> SEQ ID NO 972
<211> LENGTH: 100
<212> TYPE: DNA
<213> ORGANISM: Homo sapiens

<400> SEQUENCE: 972
tgaagagact aacctttcag tttggtgatg caagaaagga cagttctctc cacatcactg    60
cggcccagcc tggtgataca ggccactacc tctgtgcagg                         100

<210> SEQ ID NO 973
<211> LENGTH: 100
<212> TYPE: DNA
<213> ORGANISM: Homo sapiens

<400> SEQUENCE: 973
acccagctgc tggagcagag ccctcagttt ctaagcatcc aagagggaga aaatctcact    60
gtgtactgca actcctcaag tgttttttcc agcttacaat                         100

<210> SEQ ID NO 974
<211> LENGTH: 100
<212> TYPE: DNA
<213> ORGANISM: Homo sapiens

<400> SEQUENCE: 974
gctgaagaga ctaacctttc agtttggtga tgcaagaaag gacagttctc tccacatcac    60
tgcagcccag actggtgata caggcctcta cctctgtgca                         100

<210> SEQ ID NO 975
<211> LENGTH: 100
<212> TYPE: DNA
<213> ORGANISM: Homo sapiens

<400> SEQUENCE: 975
aaagtggagc agagtcctca ggtcctgatc ctccaagagg gaagaaattc attcctggtg    60
tgcagttgtt ctatttacat gatccgtgtg cagtggtttc                         100

<210> SEQ ID NO 976
<211> LENGTH: 100
<212> TYPE: DNA
<213> ORGANISM: Homo sapiens

<400> SEQUENCE: 976
gaagactaaa atccgcagtc aaagctgagg aactttatgg ccacctatac atcagattcc    60
cagcctgagg actcagctat ttacttctgt gctgtgggga                         100

<210> SEQ ID NO 977
<211> LENGTH: 100
<212> TYPE: DNA
<213> ORGANISM: Homo sapiens

<400> SEQUENCE: 977
gaccagcaag ttaagcaaaa ttcaccatcc ctgagcgtcc aggaaggaag aatttctatt    60
ctgaactgtg actatactaa cagcatgttt gattatttcc                         100
```

```
<210> SEQ ID NO 978
<211> LENGTH: 100
<212> TYPE: DNA
<213> ORGANISM: Homo sapiens

<400> SEQUENCE: 978
agattcactg tcttcttaaa caaaagtgcc aagcacctct ctctgcacat tgtgccctcc    60
cagcctggag actctgcagt gtacttctgt gcagcaagcg                         100

<210> SEQ ID NO 979
<211> LENGTH: 100
<212> TYPE: DNA
<213> ORGANISM: Homo sapiens

<400> SEQUENCE: 979
gaccagcaag ttaagcaaaa ttcaccatcc ctgagcgtcc aggaaggaag aatttctatt    60
ctgaactgtg actatactaa cagcatgttt gattatttcc                         100

<210> SEQ ID NO 980
<211> LENGTH: 100
<212> TYPE: DNA
<213> ORGANISM: Homo sapiens

<400> SEQUENCE: 980
aagattcact gttttcttaa acaaaagtgc caagcacctc tctctcgaca ttgtgccctc    60
ccagcctgga gactctgcag tgtacttctg tgcagcaagc                         100

<210> SEQ ID NO 981
<211> LENGTH: 100
<212> TYPE: DNA
<213> ORGANISM: Homo sapiens

<400> SEQUENCE: 981
gaccagcaag ttaagcaaaa ttcaccatcc ctgagcgtcc aggaaggaag aatttctatt    60
ctgaactgtg actatactaa cagcatgttt gattatttcc                         100

<210> SEQ ID NO 982
<211> LENGTH: 100
<212> TYPE: DNA
<213> ORGANISM: Homo sapiens

<400> SEQUENCE: 982
agattcactg ttttcttaaa caaaagtgcc aagcacctct ctctgcacat tgtgccctcc    60
cagcctggag actctgcagt gtacttctgt gcagcaagcg                         100

<210> SEQ ID NO 983
<211> LENGTH: 100
<212> TYPE: DNA
<213> ORGANISM: Homo sapiens

<400> SEQUENCE: 983
gctcagtcag tggctcagcc ggaagatcag gtcaacgttg ctgaagggaa tcctctgact    60
gtgaaatgca cctattcagt ctctggaaac ccttatcttt                         100

<210> SEQ ID NO 984
<211> LENGTH: 100
<212> TYPE: DNA
<213> ORGANISM: Homo sapiens

<400> SEQUENCE: 984
```

```
tttgaagctg aatttaacaa gagccaaacc tccttccacc tgaagaaacc atctgccctt    60
gtgagcgact ccgctttgta cttctgtgct gtgagagaca                         100

<210> SEQ ID NO 985
<211> LENGTH: 100
<212> TYPE: DNA
<213> ORGANISM: Homo sapiens

<400> SEQUENCE: 985
gctcagtcag tggctcagcg aagatcagg tcaacgttgc tgaagggaat cctctgactg    60
tgaaatgcac ctattcagtc tctggaaacc cttatctttt                         100

<210> SEQ ID NO 986
<211> LENGTH: 100
<212> TYPE: DNA
<213> ORGANISM: Homo sapiens

<400> SEQUENCE: 986
ctttgaagct gaatttaaca agagccaaac ctccttccac ctgaagaaac catctgccct    60
tgtgagcgac tccgctttgt acttctgtgc tgtgagaccc                         100

<210> SEQ ID NO 987
<211> LENGTH: 100
<212> TYPE: DNA
<213> ORGANISM: Homo sapiens

<400> SEQUENCE: 987
caacaaccag tgcagagtcc tcaagccgtg atcctccgag aaggggaaga tgctgtcatc    60
aactgcagtt cctccaaggc tttatattct gtacactggt                         100

<210> SEQ ID NO 988
<211> LENGTH: 100
<212> TYPE: DNA
<213> ORGANISM: Homo sapiens

<400> SEQUENCE: 988
aaaatatctg cttcatttaa tgaaaaaaag cagcaaagct ccctgtacct tacggcctcc    60
cagctcagtt actcaggaac ctacttctgc ggcacagaga                         100

<210> SEQ ID NO 989
<211> LENGTH: 100
<212> TYPE: DNA
<213> ORGANISM: Homo sapiens

<400> SEQUENCE: 989
caacaaccag tgcagagtcc tcaagccgtg atcctccgag aaggggaaga tgctgtcacc    60
aactgcagtt cctccaaggc tttatattct gtacactggt                         100

<210> SEQ ID NO 990
<211> LENGTH: 100
<212> TYPE: DNA
<213> ORGANISM: Homo sapiens

<400> SEQUENCE: 990
tcgtgaaaaa atatctgctt catttaatga aaaaagcag caaagctccc tgtaccttac    60
ggcctcccag ctcagttact caggaaccta cttctgcggg                         100

<210> SEQ ID NO 991
```

```
<211> LENGTH: 100
<212> TYPE: DNA
<213> ORGANISM: Homo sapiens

<400> SEQUENCE: 991
caacaaccag tgcagagtcc tcaagccgtg atcctccgag aaggggaaga tgctgtcatc      60
aactgcagtt cctccaaggc tttatattct gtacactggt                           100

<210> SEQ ID NO 992
<211> LENGTH: 100
<212> TYPE: DNA
<213> ORGANISM: Homo sapiens

<400> SEQUENCE: 992
tcatgaaaaa atatctgctt catttaatga aaaaagcgg caaagctccc tgtaccttac       60
ggcctcccag ctcagttact caggaaccta cttctgcggc                           100

<210> SEQ ID NO 993
<211> LENGTH: 100
<212> TYPE: DNA
<213> ORGANISM: Homo sapiens

<400> SEQUENCE: 993
caacaaccag tgcagagtcc tcaagccgtg atcctccgag aaggggaaga tgctgtcatc      60
aactgcagtt cctccaaggc tttatattct gtacactggt                           100

<210> SEQ ID NO 994
<211> LENGTH: 100
<212> TYPE: DNA
<213> ORGANISM: Homo sapiens

<400> SEQUENCE: 994
tcctgatgat attactgaag ggtggagaac agaagcgtca tgaaaaaata tctgcttcat      60
ttaatgaaaa aaagcagcaa agctccctgt accttacggc                           100

<210> SEQ ID NO 995
<211> LENGTH: 100
<212> TYPE: DNA
<213> ORGANISM: Homo sapiens

<400> SEQUENCE: 995
cagagggtca ttcaatccca accagcaata tctacgcagg agggtgagac cgtgaaactg      60
gactgtgcat acaaaactaa tattgtatat tacatattgt                           100

<210> SEQ ID NO 996
<211> LENGTH: 100
<212> TYPE: DNA
<213> ORGANISM: Homo sapiens

<400> SEQUENCE: 996
tattctgtga gcttccagaa aacaactaaa actattcagc ttatcatatc atcatcacag      60
ccagaagacc tgcaacatat ttctgttgtc tcaaagagcc                           100

<210> SEQ ID NO 997
<211> LENGTH: 100
<212> TYPE: DNA
<213> ORGANISM: Homo sapiens

<400> SEQUENCE: 997
aaggatgtga tacagagtta ttcaaatcta aatgtctagg agagagaaat ggccgttatt      60
```

```
aatgacagtt atacagatgg agctttgaat tatttctgtt                  100
```

<210> SEQ ID NO 998
<211> LENGTH: 100
<212> TYPE: DNA
<213> ORGANISM: Homo sapiens

<400> SEQUENCE: 998

```
aggctcactg tactgttgaa taaaaatgct aaacatgtct ccctgcatat tacagccacc   60
caaccaggag actcattcct gtacttctgt gcagtgagaa                       100
```

<210> SEQ ID NO 999
<211> LENGTH: 100
<212> TYPE: DNA
<213> ORGANISM: Homo sapiens

<400> SEQUENCE: 999

```
gctcagaaag taacccaagt tcagaccaca gtaactaggc agaaaggagt agctgtgacc   60
ttggactgca tgtttgaaac cagatagaat tcgtacactt                       100
```

<210> SEQ ID NO 1000
<211> LENGTH: 100
<212> TYPE: DNA
<213> ORGANISM: Homo sapiens

<400> SEQUENCE: 1000

```
gcaaagcctg tgaactttga aaaaagaaa aagttcatca acctcaccat caattcctta    60
aaactgactc agccaagtac ttctgtgctc tcaggaatcc                       100
```

<210> SEQ ID NO 1001
<211> LENGTH: 100
<212> TYPE: DNA
<213> ORGANISM: Homo sapiens

<400> SEQUENCE: 1001

```
agccaagaac tggagcagag tcctcagtcc ttgatcgtcc aagagggaaa gaatctcacc    60
ataaactgca cgtcatcaaa gacgttatat ggcttatact                       100
```

<210> SEQ ID NO 1002
<211> LENGTH: 100
<212> TYPE: DNA
<213> ORGANISM: Homo sapiens

<400> SEQUENCE: 1002

```
aagataactg ccaagttgga tgagaaaaag cagcaaagtt ccctgcatat cacagcctcc   60
cagcccagcc atgcaggcat ctacctctgt ggagcagaca                       100
```

<210> SEQ ID NO 1003
<211> LENGTH: 100
<212> TYPE: DNA
<213> ORGANISM: Homo sapiens

<400> SEQUENCE: 1003

```
ggtcaacagc tgaatcagag tcctcaatct atgtttatcc aggaaggaga agatgtctcc   60
atgaactgca cttcttcaag catatttaac acctggctat                       100
```

<210> SEQ ID NO 1004
<211> LENGTH: 100
<212> TYPE: DNA

<213> ORGANISM: Homo sapiens

<400> SEQUENCE: 1004

```
aagactgact gctcagtttg gtataaccag aaaggacagc ttcctgaata tctcagcatc    60
catacctagt gatgtaggca tctacttctg tgctgggcag                         100
```

<210> SEQ ID NO 1005
<211> LENGTH: 100
<212> TYPE: DNA
<213> ORGANISM: Homo sapiens

<400> SEQUENCE: 1005

```
ggtcaacagc tgaatcagag tcctcaatct atgtttatcc aggaaggaga agatgtctcc    60
atgaactgca cttcttcaag catatttaac acctggctat                         100
```

<210> SEQ ID NO 1006
<211> LENGTH: 100
<212> TYPE: DNA
<213> ORGANISM: Homo sapiens

<400> SEQUENCE: 1006

```
aaatggaaga ctgactgctc agtttggtat aaccagaaag gacagcttcc tgaatatctc    60
agcatccata cctagtgatg taggcatcta cttctgtgct                         100
```

<210> SEQ ID NO 1007
<211> LENGTH: 100
<212> TYPE: DNA
<213> ORGANISM: Homo sapiens

<400> SEQUENCE: 1007

```
gaagacaagg tggtacaaag ccctctatct ctggttgtcc acgagggaga caccgtaact    60
ctcaattgca gttatgaagt gactaacttt cgaagcctac                         100
```

<210> SEQ ID NO 1008
<211> LENGTH: 100
<212> TYPE: DNA
<213> ORGANISM: Homo sapiens

<400> SEQUENCE: 1008

```
agactaagta gcatattaga taagaaagaa cttccagca tcctgaacat cacagccacc     60
cagaccggag actcggccat ctacctctgt gctgtggagg                         100
```

<210> SEQ ID NO 1009
<211> LENGTH: 100
<212> TYPE: DNA
<213> ORGANISM: Homo sapiens

<400> SEQUENCE: 1009

```
gaagacaagg tggtacaaag ccctcaatct ctggttgtcc acgagggaga cactgtaact    60
ctcaattgca gttatgaaat gactaacttt cgaagcctac                         100
```

<210> SEQ ID NO 1010
<211> LENGTH: 100
<212> TYPE: DNA
<213> ORGANISM: Homo sapiens

<400> SEQUENCE: 1010

```
ggaagactaa gtagcatatt agataagaaa gaacttttca gcatcctgaa catcacagcc    60
acccagaccg gagactcggc cgtctacctc tgtgctgtgg                         100
```

<210> SEQ ID NO 1011
<211> LENGTH: 100
<212> TYPE: DNA
<213> ORGANISM: Homo sapiens

<400> SEQUENCE: 1011
gaagacaagg tggtacaaag ccctctatct ctggttgtcc acgagggaga cactgtaact    60
cccaattgca gttatgaagt gactaactt cgaagcctac                          100

<210> SEQ ID NO 1012
<211> LENGTH: 100
<212> TYPE: DNA
<213> ORGANISM: Homo sapiens

<400> SEQUENCE: 1012
gtcaggaaga ctaagtagca tattagataa gaaagaactt ttcagcatcc tgaacatcac    60
agccacccag accggagact cggccgtcta cctctgtgct                          100

<210> SEQ ID NO 1013
<211> LENGTH: 100
<212> TYPE: DNA
<213> ORGANISM: Homo sapiens

<400> SEQUENCE: 1013
gaagacaagg tggtacaaag ccctctatct ctggttgtcc acgagggaga cactgtaact    60
ctcaattgca gttatgaagt gactaactt cgaagcctac                          100

<210> SEQ ID NO 1014
<211> LENGTH: 100
<212> TYPE: DNA
<213> ORGANISM: Homo sapiens

<400> SEQUENCE: 1014
tcaggaagac taagtagcat attagataag aaagaacttt tcagcatcct gaacatcaca    60
gccacccaga ccggagactc ggccgtctac ctctgtgctg                          100

<210> SEQ ID NO 1015
<211> LENGTH: 100
<212> TYPE: DNA
<213> ORGANISM: Homo sapiens

<400> SEQUENCE: 1015
caactgccag tggaacagaa tgctccttcc ctgaaagtca aggaaggtga cagcgtcaca    60
ctgaactgca gttacagaga cagcccttca gatttcttca                          100

<210> SEQ ID NO 1016
<211> LENGTH: 100
<212> TYPE: DNA
<213> ORGANISM: Homo sapiens

<400> SEQUENCE: 1016
agattcacag ccaggcttaa aaaaggagac cagcacattt ccctgcacat acaggattcc    60
cagctccatg actcaaccac attcttctgc gcagcaagca                          100

<210> SEQ ID NO 1017
<211> LENGTH: 100
<212> TYPE: DNA
<213> ORGANISM: Homo sapiens

<400> SEQUENCE: 1017
gcccagacag tcactcagtc tcaaccagag atgtctgtgc aggaggcaga gactgtgacc    60
ctgagttgca catatgacac cagtgagaat aattattatt                         100

<210> SEQ ID NO 1018
<211> LENGTH: 100
<212> TYPE: DNA
<213> ORGANISM: Homo sapiens

<400> SEQUENCE: 1018
tctctgtgaa cttccagaaa gcagccaaat ccttcagtct caagatctca gactcacagc    60
tgggggacac tgcgatgtat ttctgtgctt tcatgaagca                         100

<210> SEQ ID NO 1019
<211> LENGTH: 100
<212> TYPE: DNA
<213> ORGANISM: Homo sapiens

<400> SEQUENCE: 1019
gcccagacag tcactcagtc tcaaccagag atgtctgtgc aggaggcaga gactgtgacc    60
ctgagttgca catatgacac cagtgagaat gattattatt                         100

<210> SEQ ID NO 1020
<211> LENGTH: 100
<212> TYPE: DNA
<213> ORGANISM: Homo sapiens

<400> SEQUENCE: 1020
gagaatcgtt tctctgtgaa cttccagaaa gcagccaaat ccttcagtct caagatctca    60
gactcacagc tgggggacac tgcgatgtat ttctgtgctt                         100

<210> SEQ ID NO 1021
<211> LENGTH: 100
<212> TYPE: DNA
<213> ORGANISM: Homo sapiens

<400> SEQUENCE: 1021
gcccagacag tcactcagtc tcaaccagag atgtctgtgc aggaggcaga gactgtgacc    60
ctgagttgca catatgacac cagtgagagt aattattatt                         100

<210> SEQ ID NO 1022
<211> LENGTH: 100
<212> TYPE: DNA
<213> ORGANISM: Homo sapiens

<400> SEQUENCE: 1022
aatcgtttct ctgtgaactt ccagaaagca gccaaatcct tcagtctcaa gatctcagac    60
tcacagctgg gggacactgc gatgtatttc tgtgctttca                         100

<210> SEQ ID NO 1023
<211> LENGTH: 100
<212> TYPE: DNA
<213> ORGANISM: Homo sapiens

<400> SEQUENCE: 1023
gcccagacag tcactcagtc ccagccagag atgtctgtgc aggaggcaga gactgtgacc    60
ctgagttgca catatgacac cagtgagaat aattattatt                         100

```
<210> SEQ ID NO 1024
<211> LENGTH: 100
<212> TYPE: DNA
<213> ORGANISM: Homo sapiens

<400> SEQUENCE: 1024
ggagaatcgt ttctctgtga acttccagaa agcagccaaa tccttcagtc tcaagatctc      60
agactcacag ctgggggaca ctgcgatgta tttctgtgca                           100

<210> SEQ ID NO 1025
<211> LENGTH: 100
<212> TYPE: DNA
<213> ORGANISM: Homo sapiens

<400> SEQUENCE: 1025
gctcagacag tcactcagtc tcaaccagag atgtctgtgc aggaggcaga gaccgtgacc      60
ctgagctgca catatgacac cagtgagagt gattattatt                           100

<210> SEQ ID NO 1026
<211> LENGTH: 100
<212> TYPE: DNA
<213> ORGANISM: Homo sapiens

<400> SEQUENCE: 1026
ttctctgtga acttccagaa agcagccaaa tccttcagtc tcaagatctc agactcacag      60
ctgggggatg ccgcgatgta tttctgtgct tataggagcg                           100

<210> SEQ ID NO 1027
<211> LENGTH: 100
<212> TYPE: DNA
<213> ORGANISM: Homo sapiens

<400> SEQUENCE: 1027
gagctgaaag tggaacaaaa ccctctgttc ctgagcatgc aggagggaaa aaactatacc      60
atctactgca attattcaac cacttcagac agactgtatt                           100

<210> SEQ ID NO 1028
<211> LENGTH: 100
<212> TYPE: DNA
<213> ORGANISM: Homo sapiens

<400> SEQUENCE: 1028
cgattaatgg cctcacttga taccaaagcc cgtctcagca ccctccacat cacagctgcc      60
gtgcatgacc tctctgccac ctacttctgt gccgtggaca                           100

<210> SEQ ID NO 1029
<211> LENGTH: 100
<212> TYPE: DNA
<213> ORGANISM: Homo sapiens

<400> SEQUENCE: 1029
cttgctaaga ccacccagcc catctccatg gactcatatg aaggacaaga agtgaacata      60
acctgtagcc acaacaacat tgctacaaat gattatatca                           100

<210> SEQ ID NO 1030
<211> LENGTH: 100
<212> TYPE: DNA
<213> ORGANISM: Homo sapiens

<400> SEQUENCE: 1030
```

```
gcctccctgt ttatccctgc cgacagaaag tccagcactc tgagcctgcc ccgggtttcc    60
ctgagcgaca ctgctgtgta ctactgcctc gtgggtgaca                         100

<210> SEQ ID NO 1031
<211> LENGTH: 100
<212> TYPE: DNA
<213> ORGANISM: Homo sapiens

<400> SEQUENCE: 1031
agcaattcag tcaagcagac gggccaaata accgtctcgg agggagcatc tgtgactatg    60
aactgcacat acacatccac ggggtaccct acccttttct                         100

<210> SEQ ID NO 1032
<211> LENGTH: 100
<212> TYPE: DNA
<213> ORGANISM: Homo sapiens

<400> SEQUENCE: 1032
aaaacttcgg aggcggaaat attaaagaca aaaactcccc cattgtgaaa tattcagtcc    60
aggtatcaga ctcagccgtg tactactgtc ttctgggaga                         100

<210> SEQ ID NO 1033
<211> LENGTH: 100
<212> TYPE: DNA
<213> ORGANISM: Homo sapiens

<400> SEQUENCE: 1033
aaaaatgaag tggagcagag tcctcagaac ctgactgccc aggaaggaga atttatcaca    60
atcaactgca gttactcggt aggaataagt gccttacact                         100

<210> SEQ ID NO 1034
<211> LENGTH: 100
<212> TYPE: DNA
<213> ORGANISM: Homo sapiens

<400> SEQUENCE: 1034
aagattaatt gccacaataa acatacagga aaagcacagc tccctgcaca tcacagcctc    60
ccatcccaga gactctgccg tctacatctg tgctgtcaga                         100

<210> SEQ ID NO 1035
<211> LENGTH: 100
<212> TYPE: DNA
<213> ORGANISM: Homo sapiens

<400> SEQUENCE: 1035
ggagaggatg tggagcagag tcttttcctg agtgtccgag agggagacag ctccgttata    60
aactgcactt acacagacag ctcctccacc tacttatact                         100

<210> SEQ ID NO 1036
<211> LENGTH: 100
<212> TYPE: DNA
<213> ORGANISM: Homo sapiens

<400> SEQUENCE: 1036
agactcactg ttctattgaa taaaaaggat aaacatctgt ctctgcgcat tgcagacacc    60
cagactgggg actcagctat ctacttctgt gcagagagta                         100

<210> SEQ ID NO 1037
<211> LENGTH: 100
```

```
<212> TYPE: DNA
<213> ORGANISM: Homo sapiens

<400> SEQUENCE: 1037
agccaaaaga tagaacagaa ttccgaggcc ctgaacattc aggagggtaa aacggccacc      60
ctgacctgca actatacaaa ctattcccca gcatacttac                           100

<210> SEQ ID NO 1038
<211> LENGTH: 100
<212> TYPE: DNA
<213> ORGANISM: Homo sapiens

<400> SEQUENCE: 1038
agactgaagg tcacctttga taccacccct aaacagagtt tgtttcatat cacagcctcc      60
cagcctgcag actcagctac ctacctctgt gctctagaca                           100

<210> SEQ ID NO 1039
<211> LENGTH: 100
<212> TYPE: DNA
<213> ORGANISM: Homo sapiens

<400> SEQUENCE: 1039
agccaaaaga tagaacagaa ttccgaggcc ctgaacattc aggagggtaa aacggccacc      60
ctgacctgca actatacaaa ctattctcca gcatacttac                           100

<210> SEQ ID NO 1040
<211> LENGTH: 100
<212> TYPE: DNA
<213> ORGANISM: Homo sapiens

<400> SEQUENCE: 1040
gaaagaaaga ctgaaggtca cctttgatac caccccttaaa cagagtttgt ttcatatcac     60
agcctcccag cctgcagact cagctaccta cctctgtgct                           100

<210> SEQ ID NO 1041
<211> LENGTH: 100
<212> TYPE: DNA
<213> ORGANISM: Homo sapiens

<400> SEQUENCE: 1041
gaggccctga acattcagga gggtaaaacg gccaccctga cctgcaacta tacaaactat      60
tctccagcat acttacagtg gtaccgacaa gatccaggaa                           100

<210> SEQ ID NO 1042
<211> LENGTH: 100
<212> TYPE: DNA
<213> ORGANISM: Homo sapiens

<400> SEQUENCE: 1042
gaaagaaaga ctgaaggtca cctttgatac caccccttaaa cagagtttgt ttcatatcac     60
agcctcccag cctgcagact cagctaccta cctctgtgct                           100

<210> SEQ ID NO 1043
<211> LENGTH: 100
<212> TYPE: DNA
<213> ORGANISM: Homo sapiens

<400> SEQUENCE: 1043
gaggccctga acattcagga gggtaaaacg gccaccctga cctgcaacta tacaaactat      60
```

```
tctccagcat acttacagtg gtaccgacaa gatccaggaa              100

<210> SEQ ID NO 1044
<211> LENGTH: 100
<212> TYPE: DNA
<213> ORGANISM: Homo sapiens

<400> SEQUENCE: 1044
gaaagaaaga ctgaaggtca cctttgatac caccccttaaa cagagtttgt ttcatgtcac   60
agcctcccag cctgcagact cagctaccta cctctgtgct                          100

<210> SEQ ID NO 1045
<211> LENGTH: 100
<212> TYPE: DNA
<213> ORGANISM: Homo sapiens

<400> SEQUENCE: 1045
gaggccctga acattcagga gggtaaaacg gccaccctga cctgcaacta tacgaactat   60
tctccagcat acttacagtg gtaccgacaa gatccaggaa                          100

<210> SEQ ID NO 1046
<211> LENGTH: 100
<212> TYPE: DNA
<213> ORGANISM: Homo sapiens

<400> SEQUENCE: 1046
gaaagaaaga ctgaaggtca cctttgatac caccccttaaa cagagtttgt ttcatatcac   60
agcctcccag cctgcagact cagctaccta cctctgtgct                          100

<210> SEQ ID NO 1047
<211> LENGTH: 100
<212> TYPE: DNA
<213> ORGANISM: Homo sapiens

<400> SEQUENCE: 1047
agccaaaaga tagaacagaa ttccgaggcc ctgaacattc aggagggtaa aacggccacc   60
ctgacctgca actatacaaa ctattctcca gcatacttac                          100

<210> SEQ ID NO 1048
<211> LENGTH: 100
<212> TYPE: DNA
<213> ORGANISM: Homo sapiens

<400> SEQUENCE: 1048
ccaggaagag gccctgtttt cttgctactc atacgtgaaa atgagaaaga aaaaggaaa    60 gaaagactga aggtcacctt tgataccacc cttaaccaga                          100

<210> SEQ ID NO 1049
<211> LENGTH: 100
<212> TYPE: DNA
<213> ORGANISM: Homo sapiens

<400> SEQUENCE: 1049
gaaaaccagg tggagcacag ccctcatttt ctgggacccc agcagggaga cgttgcctcc   60
atgagctgca cgtactctgt cagtcgtttt aacaatttgc                          100

<210> SEQ ID NO 1050
<211> LENGTH: 100
<212> TYPE: DNA
<213> ORGANISM: Homo sapiens
```

<400> SEQUENCE: 1050
aaaggaagac taaatgctac attactgaag aatggaagca gcttgtacat tacagccgtg    60
cagcctgaag attcagccac ctatttctgt gctgtagatg                          100

<210> SEQ ID NO 1051
<211> LENGTH: 100
<212> TYPE: DNA
<213> ORGANISM: Homo sapiens

<400> SEQUENCE: 1051
gcccagtctg tgagccagca taaccaccac gtaattctct ctgaagcagc ctcactggag    60
ttgggatgca actattccta tggtggaact gttaatctct                          100

<210> SEQ ID NO 1052
<211> LENGTH: 100
<212> TYPE: DNA
<213> ORGANISM: Homo sapiens

<400> SEQUENCE: 1052
gctttgaggc tgaatttata aagagtaaat tctcctttaa tctgaggaaa ccctctgtgc    60
agtggagtga cacagctgag tacttctgtg ccgtgaatgc                          100

<210> SEQ ID NO 1053
<211> LENGTH: 100
<212> TYPE: DNA
<213> ORGANISM: Homo sapiens

<400> SEQUENCE: 1053
gcccagtctg tgagccagca taaccaccac gtaattctct ctgaagcagc ctcactggag    60
ttgggatgca actattccta tggtggaact gttaatctct                          100

<210> SEQ ID NO 1054
<211> LENGTH: 100
<212> TYPE: DNA
<213> ORGANISM: Homo sapiens

<400> SEQUENCE: 1054
ttttcagggg atccactggt taaaggcatc aagggcgttg aggctgaatt tataaagagt    60
aaattctcct ttaatctgag gaaaccctct gtgcagtgga                          100

<210> SEQ ID NO 1055
<211> LENGTH: 100
<212> TYPE: DNA
<213> ORGANISM: Homo sapiens

<400> SEQUENCE: 1055
gcccagtcgg tgacccagct tgacagccac gtctctgtct ctgaaggaac cccggtgctg    60
ctgaggtgca actactcatc ttcttattca ccatctctct                          100

<210> SEQ ID NO 1056
<211> LENGTH: 100
<212> TYPE: DNA
<213> ORGANISM: Homo sapiens

<400> SEQUENCE: 1056
gttttgaggc tgaatttaag aagagtgaaa cctccttcca cctgacgaaa ccctcagccc    60
atatgagcga cgcggctgag tacttctgtg ttgtgagtga                          100

<210> SEQ ID NO 1057
<211> LENGTH: 100
<212> TYPE: DNA
<213> ORGANISM: Homo sapiens

<400> SEQUENCE: 1057
gcccagtcgg tgacccagct tagcagccac gtctctgtct ctgaaggaac cccggtgctg    60
ctgaggtgca actactcatc ttcttattca ccatctctct                         100

<210> SEQ ID NO 1058
<211> LENGTH: 100
<212> TYPE: DNA
<213> ORGANISM: Homo sapiens

<400> SEQUENCE: 1058
tttaagaaga gtgaaacctc cttccacctg acgaaaccct cagcccatat gagcgacgcg    60
gctgagtact tctgtgttgt gacccgtcac gagctttcag                         100

<210> SEQ ID NO 1059
<211> LENGTH: 100
<212> TYPE: DNA
<213> ORGANISM: Homo sapiens

<400> SEQUENCE: 1059
gcccagtcag tgacccagcc tgacatccac atcactgtct ctgaaggagc ctcactggag    60
ttgagatgta actattccta tggggcaaca ccttatctct                         100

<210> SEQ ID NO 1060
<211> LENGTH: 100
<212> TYPE: DNA
<213> ORGANISM: Homo sapiens

<400> SEQUENCE: 1060
gctttgaggc tgaatttaag aggagtcaat cttccttcaa tctgaggaaa ccctctgtgc    60
attggagtga tgctgctgag tacttctgtg ctgtgggtgc                         100

<210> SEQ ID NO 1061
<211> LENGTH: 100
<212> TYPE: DNA
<213> ORGANISM: Homo sapiens

<400> SEQUENCE: 1061
gcccagtcag tgacccagcc tgacatccac atcactgtct ctgaaggagc ctcactggag    60
ttgagatgta actattccta tggggcaaca ccttatctct                         100

<210> SEQ ID NO 1062
<211> LENGTH: 100
<212> TYPE: DNA
<213> ORGANISM: Homo sapiens

<400> SEQUENCE: 1062
aggctttgag gctgaattta agaggagtca atcttccttc aacctgagga aaccctctgt    60
gcattggagt gatgctgctg agtacttctg tgctgtggtt                         100

<210> SEQ ID NO 1063
<211> LENGTH: 100
<212> TYPE: DNA
<213> ORGANISM: Homo sapiens

<400> SEQUENCE: 1063

```
gcccagtcag tgacccagcc tgacatccac atcactgtct ctgaaggagc ctcactggag    60
ttgagatgta actattccta tggggcaaca ccttatctct                         100
```

<210> SEQ ID NO 1064
<211> LENGTH: 100
<212> TYPE: DNA
<213> ORGANISM: Homo sapiens

<400> SEQUENCE: 1064

```
tattaaaggc tttgaggctg aatttaagag gagtcaatct tccttcaatc tgaggaaacc    60
ctctgtgcat tggagtgatg cgtctgagta cttctgtgct                         100
```

<210> SEQ ID NO 1065
<211> LENGTH: 100
<212> TYPE: DNA
<213> ORGANISM: Homo sapiens

<400> SEQUENCE: 1065

```
gcccagtcgg tgacccagct tggcagccac gtctctgtct ctgaaggagc cctggttctg    60
ctgaggtgca actactcatc gtctgttcca ccatatctct                         100
```

<210> SEQ ID NO 1066
<211> LENGTH: 100
<212> TYPE: DNA
<213> ORGANISM: Homo sapiens

<400> SEQUENCE: 1066

```
gttttgaggc tgaatttaag aagagtgaaa cctccttcca cctgacgaaa ccctcagccc    60
atatgagcga cgcggctgag tacttctgtg ctgtgagtga                         100
```

<210> SEQ ID NO 1067
<211> LENGTH: 100
<212> TYPE: DNA
<213> ORGANISM: Homo sapiens

<400> SEQUENCE: 1067

```
gcccagtcgg tgacccagct tggcagccac gtctctgtct ctgaaggagc cctggttctg    60
ctgaggtgca actactcatc gtctgttcca ccatatctct                         100
```

<210> SEQ ID NO 1068
<211> LENGTH: 100
<212> TYPE: DNA
<213> ORGANISM: Homo sapiens

<400> SEQUENCE: 1068

```
gaatttaaga agagtgaaac ctccttccac ctgacaaaac cctcagccca tatgagcgac    60
gcggctgagt acttctgtgc tgtgagtgat ctcgaaccga                         100
```

<210> SEQ ID NO 1069
<211> LENGTH: 100
<212> TYPE: DNA
<213> ORGANISM: Homo sapiens

<400> SEQUENCE: 1069

```
gcccagtcgg tgacccagct tggcagccac gtctctgtct ctgagggagc cctggttctg    60
ctgaggtgca actactcatc gtctgttcca ccatatctct                         100
```

<210> SEQ ID NO 1070

```
<211> LENGTH: 100
<212> TYPE: DNA
<213> ORGANISM: Homo sapiens

<400> SEQUENCE: 1070
catcaacggt tttgaggctg aatttaagaa gagtgaaacc tccttccacc tgacgaaacc      60
ctcagcccat atgagcgacg cggctgagta cttctgtgct                          100

<210> SEQ ID NO 1071
<211> LENGTH: 100
<212> TYPE: DNA
<213> ORGANISM: Homo sapiens

<400> SEQUENCE: 1071
gcccagtcgg tgacccagct tggcagccac gtctctgtct ctgaacgagc cctggttctg      60
ctgaggtgca actactcatc gtctgttcca ccatatctct                          100

<210> SEQ ID NO 1072
<211> LENGTH: 100
<212> TYPE: DNA
<213> ORGANISM: Homo sapiens

<400> SEQUENCE: 1072
aggcatcaac ggttttgagg ctgaatttaa gaagagtgaa acctccttcc acctgacgaa      60
accctcagcc catatgagcg acgcggctga gtacttctgt                          100

<210> SEQ ID NO 1073
<211> LENGTH: 100
<212> TYPE: DNA
<213> ORGANISM: Homo sapiens

<400> SEQUENCE: 1073
gcccagtcgg tgacccagct tggcagccac gtctctgtct ctgaaggagc cctggttctg      60
ctgaggtgca actactcatc gtctgttcca ccatatctct                          100

<210> SEQ ID NO 1074
<211> LENGTH: 100
<212> TYPE: DNA
<213> ORGANISM: Homo sapiens

<400> SEQUENCE: 1074
ggctgaattt aagaagagtg aaacctcctt ccacctgacg aaaccctcag cccatatgag      60
cgacgcggct gagtacttct gtgctgtgag tgagtctcca                          100

<210> SEQ ID NO 1075
<211> LENGTH: 100
<212> TYPE: DNA
<213> ORGANISM: Homo sapiens

<400> SEQUENCE: 1075
ctcttctggt atgtgcaata ccccaaccaa ggactccagc ttctcctgaa gtacacatca      60
gcggccaccc tggttaaagg catcaacggt tttgaggctg                          100

<210> SEQ ID NO 1076
<211> LENGTH: 100
<212> TYPE: DNA
<213> ORGANISM: Homo sapiens

<400> SEQUENCE: 1076
gaatttaaga agagtgaaac ctccttccac ctgacgaaac ccgcagccca tatgagcgac      60
```

```
gcggctgagt acttctgtgc tgtgagtgat ctcgaaccga                  100
```

<210> SEQ ID NO 1077
<211> LENGTH: 100
<212> TYPE: DNA
<213> ORGANISM: Homo sapiens

<400> SEQUENCE: 1077

```
gttgaaccat atctcttctg gtatgtgcaa taccccaacc aaggactcca gcttctcctg   60
aagtacacaa caggggccac cctggttaaa ggcatcaacg                        100
```

<210> SEQ ID NO 1078
<211> LENGTH: 100
<212> TYPE: DNA
<213> ORGANISM: Homo sapiens

<400> SEQUENCE: 1078

```
acggttttga ggctgaattt aaaaagagtg aaacctcctt ccacctgacg aaaccctcag   60
cccatatgac cgacccggct gagtacttct gtgctgtgag                        100
```

<210> SEQ ID NO 1079
<211> LENGTH: 100
<212> TYPE: DNA
<213> ORGANISM: Homo sapiens

<400> SEQUENCE: 1079

```
gcccagtcag tgacccagcc tgacatccgc atcactgtct ctgaaggagc ctcactggag   60
ttgagatgta actattccta tggggcgatg ttgtgggaag                        100
```

<210> SEQ ID NO 1080
<211> LENGTH: 100
<212> TYPE: DNA
<213> ORGANISM: Homo sapiens

<400> SEQUENCE: 1080

```
tggacactta tcacttcccc aatcaatacc cctgtgattt cctatgcctg tctttacttt   60
aatctcttaa tcctgtcagc tgaggaggat gtatgtcacc                        100
```

<210> SEQ ID NO 1081
<211> LENGTH: 100
<212> TYPE: DNA
<213> ORGANISM: Homo sapiens

<400> SEQUENCE: 1081

```
gcccagtctg tgacccagct tgacagccaa gtccctgtct ttgaagaagc ccctgtggag   60
ctgaggtgca actactcatc gtctgtttca gtgtatctct                        100
```

<210> SEQ ID NO 1082
<211> LENGTH: 100
<212> TYPE: DNA
<213> ORGANISM: Homo sapiens

<400> SEQUENCE: 1082

```
gttttgaggc tgaatttaac aagagtcaaa cttccttcca cttgaggaaa ccctcagtcc   60
atataagcga cacggctgag tacttctgtg ctgtgagtga                        100
```

<210> SEQ ID NO 1083
<211> LENGTH: 100
<212> TYPE: DNA

```
<213> ORGANISM: Homo sapiens

<400> SEQUENCE: 1083
gcccagtctg tgacccagct tgacagccaa gtccctgtct ttgaagaagc ccctgtggag    60
ctgaggtgca actactcatc gtctgtttca gtgtatctct                         100

<210> SEQ ID NO 1084
<211> LENGTH: 100
<212> TYPE: DNA
<213> ORGANISM: Homo sapiens

<400> SEQUENCE: 1084
gttttgaggc tgaatttaac aagagtcaaa cttccttcca cttgaggaaa ccctcagtcc    60
atataagcga cacggctgag tacttctgtg ctgtgagtga                         100

<210> SEQ ID NO 1085
<211> LENGTH: 100
<212> TYPE: DNA
<213> ORGANISM: Homo sapiens

<400> SEQUENCE: 1085
acccagtcgg tgacccagct tgatggccac atcactgtct ctgaagaagc ccctctggaa    60
ctgaagtgca actattccta tagtggagtt ccttctctct                         100

<210> SEQ ID NO 1086
<211> LENGTH: 100
<212> TYPE: DNA
<213> ORGANISM: Homo sapiens

<400> SEQUENCE: 1086
aggctgaatt taagaagagc gaaacctcct tctacctgag gaaaccatca acccatgtga    60
gtgatgctgc tgagtacttc tgtgctgtgg gtgacaggag                         100

<210> SEQ ID NO 1087
<211> LENGTH: 100
<212> TYPE: DNA
<213> ORGANISM: Homo sapiens

<400> SEQUENCE: 1087
ggagattcag tggtccagac agaaggccaa gtgctcccct ctgaagggga ttccctgatt    60
gtgaactgct cctatgaaac cacacagtac ccttcccttt                         100

<210> SEQ ID NO 1088
<211> LENGTH: 100
<212> TYPE: DNA
<213> ORGANISM: Homo sapiens

<400> SEQUENCE: 1088
gttttgaagc catgtaccgt aaagaaacca cttctttcca cttggagaaa gactcagttc    60
aagagtcaga ctccgctgtg tacttctgtg ctctgagtga                         100

<210> SEQ ID NO 1089
<211> LENGTH: 100
<212> TYPE: DNA
<213> ORGANISM: Homo sapiens

<400> SEQUENCE: 1089
ggaaattcag tgacccagat ggaagggcca gtgactctct cagaagaggc cttcctgact    60
ataaactgca cgtacacagc cacaggatac ccttcccttt                         100
```

<210> SEQ ID NO 1090
<211> LENGTH: 100
<212> TYPE: DNA
<213> ORGANISM: Homo sapiens

<400> SEQUENCE: 1090
gttttgaagc cacataccgt aaagaaacca cttctttcca cttggagaaa ggctcagttc    60
aagtgtcaga ctcagcggtg tacttctgtg ctctgagtga                         100

<210> SEQ ID NO 1091
<211> LENGTH: 100
<212> TYPE: DNA
<213> ORGANISM: Homo sapiens

<400> SEQUENCE: 1091
ggagattcag tgacccagat ggaagggcca gtgactctct cagaagaggc cttcctgact    60
ataaactgca cgtacacagc cacaggatac ccttcccttt                         100

<210> SEQ ID NO 1092
<211> LENGTH: 100
<212> TYPE: DNA
<213> ORGANISM: Homo sapiens

<400> SEQUENCE: 1092
caacaaaggt tttgaagcca cataccgtaa agaaaccact tctttccact tggagaaagg    60
ctcagttcaa gtgtcagact cagcggtgta cttctgtgct                         100

<210> SEQ ID NO 1093
<211> LENGTH: 100
<212> TYPE: DNA
<213> ORGANISM: Homo sapiens

<400> SEQUENCE: 1093
ggagattcag tgacccagat ggaagggcca gtgactctct cagaagaggc cttcctgact    60
ataaactgca cgtacacagc cacaggatac ccttcccttt                         100

<210> SEQ ID NO 1094
<211> LENGTH: 100
<212> TYPE: DNA
<213> ORGANISM: Homo sapiens

<400> SEQUENCE: 1094
caacaaaggt tttgaagcca cataccgtaa ggaaaccact tctttccact tggagaaagg    60
ctcagttcaa gtgtcagact cagcggtgta cttctgtgct                         100

<210> SEQ ID NO 1095
<211> LENGTH: 100
<212> TYPE: DNA
<213> ORGANISM: Homo sapiens

<400> SEQUENCE: 1095
ggaaattcag tgacccagat ggaagggcca gtgactctct cagaagaggc cttcctgact    60
ataaactgca cgtacacagc cacaggatac ccttcccttt                         100

<210> SEQ ID NO 1096
<211> LENGTH: 100
<212> TYPE: DNA
<213> ORGANISM: Homo sapiens

<400> SEQUENCE: 1096
caacaaaggt tttgaagcca cataccgtaa ggaaaccact tctttccact tggagaaagg    60
ctcagttcaa gtgtcagact cagcggtgta cttctgtgct                         100

<210> SEQ ID NO 1097
<211> LENGTH: 100
<212> TYPE: DNA
<213> ORGANISM: Homo sapiens

<400> SEQUENCE: 1097
gatactggaa ttacccagac accaaaatac ctggtcacag caatggggag taaaaggaca    60
atgaaacgtg agcatctggg acatgattct atgtattggt                         100

<210> SEQ ID NO 1098
<211> LENGTH: 100
<212> TYPE: DNA
<213> ORGANISM: Homo sapiens

<400> SEQUENCE: 1098
acttcacacc tgaatgccct gacagctctc gcttatacct tcatgtggtc gcactgcagc    60
aagaagactc agctgcgtat ctctgcacca gcagccaaga                         100

<210> SEQ ID NO 1099
<211> LENGTH: 100
<212> TYPE: DNA
<213> ORGANISM: Homo sapiens

<400> SEQUENCE: 1099
gatgctgaaa tcacccagag cccaagacac aagatcacag agacaggaag gcaggtgacc    60
ttggcgtgtc accagacttg gaaccacaac aatatgttct                         100

<210> SEQ ID NO 1100
<211> LENGTH: 100
<212> TYPE: DNA
<213> ORGANISM: Homo sapiens

<400> SEQUENCE: 1100
gctacagtgt ctctagatca aacacagagg acctcccct cactctggag tctgctgcct     60
cctcccagac atctgtatat ttctgcgcca gcagtgagtc                         100

<210> SEQ ID NO 1101
<211> LENGTH: 100
<212> TYPE: DNA
<213> ORGANISM: Homo sapiens

<400> SEQUENCE: 1101
gatgctgaaa tcacccagag cccaagacac aagatcacag agacaggaag gcaggtgacc    60
ttggcgtgtc accagacttg gaaccacaac aatatgttct                         100

<210> SEQ ID NO 1102
<211> LENGTH: 100
<212> TYPE: DNA
<213> ORGANISM: Homo sapiens

<400> SEQUENCE: 1102
agatggctac agtgtctcta gatcaaacac agaggacctc ccctcactc tggagtctgc     60 tgcctcctcc cagacatctg tatatttctg cgccagcagt                         100

```
<210> SEQ ID NO 1103
<211> LENGTH: 100
<212> TYPE: DNA
<213> ORGANISM: Homo sapiens

<400> SEQUENCE: 1103
aggcaggtga ccttggcgtg tcaccagact tggaaccaca acaatatgtt ctggtatcga    60
caagacctgg gacatgggct gaggctgatc cattactcat                         100

<210> SEQ ID NO 1104
<211> LENGTH: 100
<212> TYPE: DNA
<213> ORGANISM: Homo sapiens

<400> SEQUENCE: 1104
ctaacaaagg agaagtctca gatggctaca gtgtctctag atcaaacaca gaggacctcc    60
ccctcactct gtagtctgct gcctcctccc agacatctgt                         100

<210> SEQ ID NO 1105
<211> LENGTH: 100
<212> TYPE: DNA
<213> ORGANISM: Homo sapiens

<400> SEQUENCE: 1105
gatgctggaa tcacccagag cccaagatac aagatcacag agacaggaag gcaggtgacc    60
ttgatgtgtc accagacttg gagccacagc tatatgttct                         100

<210> SEQ ID NO 1106
<211> LENGTH: 100
<212> TYPE: DNA
<213> ORGANISM: Homo sapiens

<400> SEQUENCE: 1106
gctatgttgt ctccagatcc aagacagaga atttccccct cactctggag tcagctaccc    60
gctcccagac atctgtgtat ttctgcgcca gcagtgagtc                         100

<210> SEQ ID NO 1107
<211> LENGTH: 100
<212> TYPE: DNA
<213> ORGANISM: Homo sapiens

<400> SEQUENCE: 1107
aaggcaggtg accttgatgt gtcaccagac ttggagccac agctatatgt tctggtatcg    60
acaagacctg ggacatgggc tgaggctgat ctattactca                         100

<210> SEQ ID NO 1108
<211> LENGTH: 100
<212> TYPE: DNA
<213> ORGANISM: Homo sapiens

<400> SEQUENCE: 1108
agataaagga gaagtccccg atggctacgt tgtctccaga tccaagacag agaatttccc    60
cctcactctg gagtcagcta cccgctccca gacatctgtg                         100

<210> SEQ ID NO 1109
<211> LENGTH: 100
<212> TYPE: DNA
<213> ORGANISM: Homo sapiens

<400> SEQUENCE: 1109
```

```
gatgctggaa tcacccagag cccaagacac aaggtcacag agacaggaac accagtgact    60
ctgagatgtc accagactga gaaccaccgc tatatgtact                         100
```

<210> SEQ ID NO 1110
<211> LENGTH: 100
<212> TYPE: DNA
<213> ORGANISM: Homo sapiens

<400> SEQUENCE: 1110

```
gctatagtgt ctctagatca aagacagagg atttcctcct cactctggag tccgctacca    60
gctcccagac atctgtgtac ttctgtgcca tcagtgagtc                         100
```

<210> SEQ ID NO 1111
<211> LENGTH: 100
<212> TYPE: DNA
<213> ORGANISM: Homo sapiens

<400> SEQUENCE: 1111

```
gatgctggaa tcacccagag cccaagacac aaggtcacag agacaggaac accagtgact    60
ctgagatgtc atcagactga gaaccaccgc tatatgtact                         100
```

<210> SEQ ID NO 1112
<211> LENGTH: 100
<212> TYPE: DNA
<213> ORGANISM: Homo sapiens

<400> SEQUENCE: 1112

```
gctatagtgt ctctagatca aagacagagg atttcctcct cactctggag tccgctacca    60
gctcccagac atctgtgtac ttctgtgcca tcagtgagtc                         100
```

<210> SEQ ID NO 1113
<211> LENGTH: 100
<212> TYPE: DNA
<213> ORGANISM: Homo sapiens

<400> SEQUENCE: 1113

```
gatgctggaa tcacccagag cccaagacac aaggtcacag agacaggaac accagtgact    60
ctgagatgtc accagactga gaaccaccgc tacatgtact                         100
```

<210> SEQ ID NO 1114
<211> LENGTH: 100
<212> TYPE: DNA
<213> ORGANISM: Homo sapiens

<400> SEQUENCE: 1114

```
agaagtctca gatggctata gtgtctctag atcaaagaca gaggatttcc tcctcactct    60
ggagtccgct accagctccc agacatctgt gtacttctgt                         100
```

<210> SEQ ID NO 1115
<211> LENGTH: 100
<212> TYPE: DNA
<213> ORGANISM: Homo sapiens

<400> SEQUENCE: 1115

```
gatgctggaa tcacccagag cccaagacac aaggtcacag agacaggaac accagtgact    60
ctgagatgtc accagactga gaaccaccgc tacatgtact                         100
```

<210> SEQ ID NO 1116
<211> LENGTH: 100

```
<212> TYPE: DNA
<213> ORGANISM: Homo sapiens

<400> SEQUENCE: 1116
agaagtctca gatggctata gtgtctctag atcaaagaca gaggatttcc tcctcactct    60
ggagtccgct accagctccc agacatctgt gtacttctgt                         100

<210> SEQ ID NO 1117
<211> LENGTH: 100
<212> TYPE: DNA
<213> ORGANISM: Homo sapiens

<400> SEQUENCE: 1117
gaagctgaag ttgcccagtc ccccagatat aagattacag agaaaagcca ggctgtggct    60
ttttggtgtg atcctatttc tggccatgct acccttact                          100

<210> SEQ ID NO 1118
<211> LENGTH: 100
<212> TYPE: DNA
<213> ORGANISM: Homo sapiens

<400> SEQUENCE: 1118
gattttctgc agagaggctc aaaggagtag actccactct caagatccag cctgcagagc    60
ttggggactc ggccatgtat ctctgtgcca gcagcttagc                         100

<210> SEQ ID NO 1119
<211> LENGTH: 100
<212> TYPE: DNA
<213> ORGANISM: Homo sapiens

<400> SEQUENCE: 1119
gaagctggag ttgcccagtc tcccagatat aagattatag agaaaaggca gagtgtggct    60
ttttggtgca atcctatatc tggccatgct acccttact                          100

<210> SEQ ID NO 1120
<211> LENGTH: 100
<212> TYPE: DNA
<213> ORGANISM: Homo sapiens

<400> SEQUENCE: 1120
gattttctgc agagaggctc aaaggagtag actccactct caagatccag cctgcaaagc    60
ttgaggactc ggccgtgtat ctctgtgcca gcagcttaga                         100

<210> SEQ ID NO 1121
<211> LENGTH: 100
<212> TYPE: DNA
<213> ORGANISM: Homo sapiens

<400> SEQUENCE: 1121
gaagctggag ttgcccagtc tcccagatat aagattatag agaaaaggca gagtgtggct    60
ttttggtgca atcctatatc tggccatgct acccttact                          100

<210> SEQ ID NO 1122
<211> LENGTH: 100
<212> TYPE: DNA
<213> ORGANISM: Homo sapiens

<400> SEQUENCE: 1122
ggatcgattt tctgcagaga ggctcaaagg agtagactcc actctcaaga tccagcctgc    60
```

```
aaagcttgag aactcggccg tgtatctctg tgccagcagt          100
```

\<210\> SEQ ID NO 1123
\<211\> LENGTH: 100
\<212\> TYPE: DNA
\<213\> ORGANISM: Homo sapiens

\<400\> SEQUENCE: 1123

```
gaagctggag ttgcccagtc tcccagatat aagattatag agaaaaggca gagtgtggct   60
ttttggtgca atcctatatc tggccatgct acccttact                          100
```

\<210\> SEQ ID NO 1124
\<211\> LENGTH: 100
\<212\> TYPE: DNA
\<213\> ORGANISM: Homo sapiens

\<400\> SEQUENCE: 1124

```
ggatcgattt tctgcagaga ggctcaaagg agtagactcc actctcaaga tccaacctgc   60
aaagcttgag gactcggccg tgtatctctg tgccagcagc                         100
```

\<210\> SEQ ID NO 1125
\<211\> LENGTH: 100
\<212\> TYPE: DNA
\<213\> ORGANISM: Homo sapiens

\<400\> SEQUENCE: 1125

```
gaagctggag tggttcagtc tcccagatat aagattatag agaaaaaaca gcctgtggct   60
ttttggtgca atcctatttc tggccacaat acccttttact                        100
```

\<210\> SEQ ID NO 1126
\<211\> LENGTH: 100
\<212\> TYPE: DNA
\<213\> ORGANISM: Homo sapiens

\<400\> SEQUENCE: 1126

```
gattttctgc agagaggctc aaaggagtag actccactct caagatccag cctgcagagc   60
ttggggactc ggccgtgtat ctctgtgcca gcagcttaga                         100
```

\<210\> SEQ ID NO 1127
\<211\> LENGTH: 100
\<212\> TYPE: DNA
\<213\> ORGANISM: Homo sapiens

\<400\> SEQUENCE: 1127

```
gaagctggag tggttcagtc tcccagatat aagattatag agaaaaagca gcctgtggct   60
ttttggtgca atcctatttc tggccacaat acccttttact                        100
```

\<210\> SEQ ID NO 1128
\<211\> LENGTH: 100
\<212\> TYPE: DNA
\<213\> ORGANISM: Homo sapiens

\<400\> SEQUENCE: 1128

```
ggatcgattt tctgcagaga ggctcaaagg agtagactcc actctcaaga tccagcctgc   60
agagcttggg gactcggccg tgtatctctg tgccagcagc                         100
```

\<210\> SEQ ID NO 1129
\<211\> LENGTH: 100
\<212\> TYPE: DNA
\<213\> ORGANISM: Homo sapiens

<400> SEQUENCE: 1129
ggtctcccag atataagatt atagagaaga aacagcctgt ggcttttttgg tgcaatccaa    60 tttctggcca caatacccctt tactggtacc tgcagaactt    100

<210> SEQ ID NO 1130
<211> LENGTH: 100
<212> TYPE: DNA
<213> ORGANISM: Homo sapiens

<400> SEQUENCE: 1130
ggatcgattt tctgcagaga ggctcaaagg agtagactcc actctcaaga tccagccagc    60
agagcttggg gactcggcca tgtatctctg tgccagcagc    100

<210> SEQ ID NO 1131
<211> LENGTH: 100
<212> TYPE: DNA
<213> ORGANISM: Homo sapiens

<400> SEQUENCE: 1131
gatgctggtg ttatccagtc acccaggcac aaagtgacag agatgggaca atcagtaact    60
ctgagatgcg aaccaatttc aggccacaat gatcttctct    100

<210> SEQ ID NO 1132
<211> LENGTH: 100
<212> TYPE: DNA
<213> ORGANISM: Homo sapiens

<400> SEQUENCE: 1132
gattctcagc acagatgcct gatgtatcat tctccactct gaggatccag cccatggaac    60
ccagggactt gggcctatat ttctgtgcca gcagctttgc    100

<210> SEQ ID NO 1133
<211> LENGTH: 100
<212> TYPE: DNA
<213> ORGANISM: Homo sapiens

<400> SEQUENCE: 1133
gatgctggca ttatccagtc acccaagcat gaggtgacag aaatgggaca aacagtgact    60
ctgagatgtg agccaatttt tggccacaat ttccttttct    100

<210> SEQ ID NO 1134
<211> LENGTH: 100
<212> TYPE: DNA
<213> ORGANISM: Homo sapiens

<400> SEQUENCE: 1134
gattctcagc tgagaggcct gatggatcat tctctactct gaagatccag cctgcagagc    60
agggggactc ggccgtgtat gtctgtgcaa gtcgcttagc    100

<210> SEQ ID NO 1135
<211> LENGTH: 100
<212> TYPE: DNA
<213> ORGANISM: Homo sapiens

<400> SEQUENCE: 1135
gatgctggag ttatccagtc accccgccat gaggtgacag agatgggaca agaagtgact    60
ctgagatgta aaccaatttc aggccacaac tcccttttct    100

<210> SEQ ID NO 1136
<211> LENGTH: 100
<212> TYPE: DNA
<213> ORGANISM: Homo sapiens

<400> SEQUENCE: 1136
gattctcagc taagatgcct aatgcatcat tctccactct gaagatccag ccctcagaac     60
ccagggactc agctgtgtac ttctgtgcca gcagtttagc                           100

<210> SEQ ID NO 1137
<211> LENGTH: 100
<212> TYPE: DNA
<213> ORGANISM: Homo sapiens

<400> SEQUENCE: 1137
gatgctggag ttatccagtc accccggcac gaggtgacag agatgggaca agaagtgact     60
ctgagatgta aaccaatttc aggacacgac tacctttct                            100

<210> SEQ ID NO 1138
<211> LENGTH: 100
<212> TYPE: DNA
<213> ORGANISM: Homo sapiens

<400> SEQUENCE: 1138
gattctcagc taagatgcct aatgcatcat tctccactct gaagatccag ccctcagaac     60
ccagggactc agctgtgtac ttctgtgcca gcagtttagc                           100

<210> SEQ ID NO 1139
<211> LENGTH: 100
<212> TYPE: DNA
<213> ORGANISM: Homo sapiens

<400> SEQUENCE: 1139
gatgctggag ttatccagtc accccggcac gaggtgacag agatgggaca agaagtgact     60
ctgagatgta aaccaatttc aggacatgac tacctttct                            100

<210> SEQ ID NO 1140
<211> LENGTH: 100
<212> TYPE: DNA
<213> ORGANISM: Homo sapiens

<400> SEQUENCE: 1140
tcgattctca gctaagatgc ctaatgcatc attctccact ctgaggatcc agccctcaga     60
acccagggac tcagctgtgt acttctgtgc cagcagttta                           100

<210> SEQ ID NO 1141
<211> LENGTH: 100
<212> TYPE: DNA
<213> ORGANISM: Homo sapiens

<400> SEQUENCE: 1141
gatgctagag tcacccagac accaaggcac aaggtgacag agatgggaca agaagtaaca     60
atgagatgtc agccaatttt aggccacaat actgttttct                           100

<210> SEQ ID NO 1142
<211> LENGTH: 100
<212> TYPE: DNA
<213> ORGANISM: Homo sapiens

<400> SEQUENCE: 1142

```
gattctcagc agagatgcct gatgcaactt tagccactct gaagatccag ccctcagaac    60
ccagggactc agctgtgtat ttttgtgcta gtggtttggt                         100

<210> SEQ ID NO 1143
<211> LENGTH: 100
<212> TYPE: DNA
<213> ORGANISM: Homo sapiens

<400> SEQUENCE: 1143
gctgctggag tcatccagtc cccaagacat ctgatcaaag aaaagaggga aacagccact    60
ctgaaatgct atcctatccc tagacacgac actgtctact                         100

<210> SEQ ID NO 1144
<211> LENGTH: 100
<212> TYPE: DNA
<213> ORGANISM: Homo sapiens

<400> SEQUENCE: 1144
gattctcagc tcaacagttc agtgactatc attctgaact gaacatgagc tccttggagc    60
tgggggactc agccctgtac ttctgtgcca gcagcttagg                         100

<210> SEQ ID NO 1145
<211> LENGTH: 100
<212> TYPE: DNA
<213> ORGANISM: Homo sapiens

<400> SEQUENCE: 1145
gctgctggag tcatccagtc cccaagacat ctgatcagag aaaagaggga aacagccact    60
ctgaaatgct atcctatccc tagacacgac actgtctact                         100

<210> SEQ ID NO 1146
<211> LENGTH: 100
<212> TYPE: DNA
<213> ORGANISM: Homo sapiens

<400> SEQUENCE: 1146
tgatcgattc tcagctcaac agttcagtga ctatcattct gaactgaaca tgagctcctt    60
ggagctgggg gactcagccc tgtacttctg tgccagcagc                         100

<210> SEQ ID NO 1147
<211> LENGTH: 100
<212> TYPE: DNA
<213> ORGANISM: Homo sapiens

<400> SEQUENCE: 1147
gaagctggag ttactcagtt ccccagccac agcgtaatag agaagggcca gactgtgact    60
ctgagatgtg acccaatttc tggacatgat aatctttatt                         100

<210> SEQ ID NO 1148
<211> LENGTH: 100
<212> TYPE: DNA
<213> ORGANISM: Homo sapiens

<400> SEQUENCE: 1148
gattcttagc tgaaaggact ggagggacgt attctactct gaaggtgcag cctgcagaac    60
tggaggattc tggagtttat ttctgtgcca gcagccaaga                         100

<210> SEQ ID NO 1149
```

```
<211> LENGTH: 100
<212> TYPE: DNA
<213> ORGANISM: Homo sapiens

<400> SEQUENCE: 1149
gaagctggag ttactcagtt ccccagccac agcgtaatag agaagggcca gactgtgact      60
ctgagatgtg acccaatttc tggacatgat aatctttatt                          100

<210> SEQ ID NO 1150
<211> LENGTH: 100
<212> TYPE: DNA
<213> ORGANISM: Homo sapiens

<400> SEQUENCE: 1150
caatcgattc ttagctgaaa ggactggagg gacgtattct actctgaagg tgcagcctgc     60
agaactggag gattctggag tttatttctg tgccagcagc                          100

<210> SEQ ID NO 1151
<211> LENGTH: 100
<212> TYPE: DNA
<213> ORGANISM: Homo sapiens

<400> SEQUENCE: 1151
gatgccatgg tcatccagaa cccaagatac caggttaccc agtttggaaa gccagtgacc     60
ctgagttgtt ctcagacttt gaaccataac gtcatgtact                          100

<210> SEQ ID NO 1152
<211> LENGTH: 100
<212> TYPE: DNA
<213> ORGANISM: Homo sapiens

<400> SEQUENCE: 1152
acttccaatc caggaggccg aacacttctt tctgctttct tgacatccgc tcaccaggcc     60
tgggggacac agccatgtac ctgtgtgcca ccagcagaga                          100

<210> SEQ ID NO 1153
<211> LENGTH: 100
<212> TYPE: DNA
<213> ORGANISM: Homo sapiens

<400> SEQUENCE: 1153
gatgccatgg tcatccagaa cccaagatac caggttaccc agtttggaaa gccagtgacc     60
ctgagttgtt ctcagacttt gaaccataac gtcatgtact                          100

<210> SEQ ID NO 1154
<211> LENGTH: 100
<212> TYPE: DNA
<213> ORGANISM: Homo sapiens

<400> SEQUENCE: 1154
tgataacttc caatccagga ggccgaacac ttctttctgc tttcttgaca tccgctcacc     60
aggcctgggg gacgcagcca tgtacctgtg tgccaccagc                          100

<210> SEQ ID NO 1155
<211> LENGTH: 100
<212> TYPE: DNA
<213> ORGANISM: Homo sapiens

<400> SEQUENCE: 1155
gatgccatgg tcatccagaa cccaagatac cgggttaccc agtttggaaa gccagtgacc     60
```
ctgagttgtt ctcagacttt gaaccataac gtcatgtact                100

<210> SEQ ID NO 1156
<211> LENGTH: 100
<212> TYPE: DNA
<213> ORGANISM: Homo sapiens

<400> SEQUENCE: 1156
tgataacttc aatccagga ggccgaacac ttctttctgc tttctagaca tccgctcacc    60
aggcctgggg gacgcagcca tgtaccagtg tgccaccagc                        100

<210> SEQ ID NO 1157
<211> LENGTH: 100
<212> TYPE: DNA
<213> ORGANISM: Homo sapiens

<400> SEQUENCE: 1157
ggtgaagaag tcgcccagac tccaaaacat cttgtcagag gggaaggaca gaaagcaaaa    60
ttatattgtg ccccaataaa aggacacagt tatgtttttt                        100

<210> SEQ ID NO 1158
<211> LENGTH: 100
<212> TYPE: DNA
<213> ORGANISM: Homo sapiens

<400> SEQUENCE: 1158
gattttcagc taagtgcctc ccaaattcac cctgtagcct tgagatccag gctacgaagc    60
ttgaggattc agcagtgtat ttttgtgcca gcagccaatc                        100

<210> SEQ ID NO 1159
<211> LENGTH: 100
<212> TYPE: DNA
<213> ORGANISM: Homo sapiens

<400> SEQUENCE: 1159
ggtgaagaag tcgcccagac tccaaaacat cttgtcagag gggaaggaca gaaagcaaaa    60
ttatattgtg ccccaataaa aggacacagt taggtttttt                        100

<210> SEQ ID NO 1160
<211> LENGTH: 100
<212> TYPE: DNA
<213> ORGANISM: Homo sapiens

<400> SEQUENCE: 1160
gattttcagc taagtgcctc ccaaattcac cctgtagcct tgagatccag gctacgaagc    60
ttgaggattc agcagtgtat ttttgtgcca gcagccaatc                        100

<210> SEQ ID NO 1161
<211> LENGTH: 100
<212> TYPE: DNA
<213> ORGANISM: Homo sapiens

<400> SEQUENCE: 1161
ggtgaagaag tcgcccagac tccaaaacat cttgtcagag gggaaggaca gaaagcaaaa    60
ttatattgtg ccccaataaa aggacacagt tatgtttttt                        100

<210> SEQ ID NO 1162
<211> LENGTH: 100
<212> TYPE: DNA

<213> ORGANISM: Homo sapiens

<400> SEQUENCE: 1162

```
ggaaagattt tcagctaagt gcctcccaaa ttcaccctgt agccttgaga tccaggctac    60
gaagcttgag gattcagcag tgtattttg tgccagcagc                          100
```

<210> SEQ ID NO 1163
<211> LENGTH: 100
<212> TYPE: DNA
<213> ORGANISM: Homo sapiens

<400> SEQUENCE: 1163

```
gagcctggag tcagccagac ccccagacac aaggtcacca acatgggaca ggaggtgatt    60
ctgaggtgcg atccatcttc tggtcacatg tttgttcact                          100
```

<210> SEQ ID NO 1164
<211> LENGTH: 100
<212> TYPE: DNA
<213> ORGANISM: Homo sapiens

<400> SEQUENCE: 1164

```
aacgattcac agctgaaaga cctaacggaa cgtcttccac gctgaagatc catcccgcag    60
agccgaggga ctcagccgtg tatctctaca gtagcggtgg                          100
```

<210> SEQ ID NO 1165
<211> LENGTH: 100
<212> TYPE: DNA
<213> ORGANISM: Homo sapiens

<400> SEQUENCE: 1165

```
aatgccggcg tcatgcagaa cccaagacac ctggtcagga ggaggggaca ggaggcaaga    60
ctgagatgca gcccaatgaa aggacacagt catgtttact                          100
```

<210> SEQ ID NO 1166
<211> LENGTH: 100
<212> TYPE: DNA
<213> ORGANISM: Homo sapiens

<400> SEQUENCE: 1166

```
gattttctgc tgaatttccc aaagagggcc ccagcatcct gaggatccag caggtagtgc    60
gaggagattc ggcagcttat ttctgtgcca gctcaccacc                          100
```

<210> SEQ ID NO 1167
<211> LENGTH: 100
<212> TYPE: DNA
<213> ORGANISM: Homo sapiens

<400> SEQUENCE: 1167

```
gatggtggaa tcactcagtc cccaaagtac ctgttcagaa aggaaggaca gaatgtgacc    60
ctgagttgtg aacagaattt gaaccacgat gccatgtact                          100
```

<210> SEQ ID NO 1168
<211> LENGTH: 100
<212> TYPE: DNA
<213> ORGANISM: Homo sapiens

<400> SEQUENCE: 1168

```
ggtacagcgt ctctcgggag aagaaggaat cctttcctct cactgtgaca tcggcccaaa    60
agaacccgac agctttctat ctctgtgcca gtagtataga                          100
```

```
<210> SEQ ID NO 1169
<211> LENGTH: 100
<212> TYPE: DNA
<213> ORGANISM: Homo sapiens

<400> SEQUENCE: 1169
gatggtggaa tcactcagtc cccaaagtac ctgttcagaa aggaaggaca gaatgtgacc      60
ctgagttgtg aacagaattt gaaccacgat gccatgtact                          100

<210> SEQ ID NO 1170
<211> LENGTH: 100
<212> TYPE: DNA
<213> ORGANISM: Homo sapiens

<400> SEQUENCE: 1170
ggtacagcgt ctctcgggag aagaaggaat cctttcctct cactgtgaca tcggcccaaa     60
agaacccgac agctttctat ctctgtgcca gtagtataga                          100

<210> SEQ ID NO 1171
<211> LENGTH: 100
<212> TYPE: DNA
<213> ORGANISM: Homo sapiens

<400> SEQUENCE: 1171
gatggtggaa tcactcagtc cccaaagtac ctgttcagaa aggaaggaca gaatgtgacc     60
ctgagttgtg aacagaattt gaaccacgat gccatgtact                          100

<210> SEQ ID NO 1172
<211> LENGTH: 100
<212> TYPE: DNA
<213> ORGANISM: Homo sapiens

<400> SEQUENCE: 1172
tgaagggtac agcgtctctc gggagaagaa ggaatccttt cctctcactg tgacatcggc     60
ccaaaagaac ccgacagctt tctatctctg tgccagtagc                          100

<210> SEQ ID NO 1173
<211> LENGTH: 100
<212> TYPE: DNA
<213> ORGANISM: Homo sapiens

<400> SEQUENCE: 1173
gaacctgaag tcacccagac tcccagccat caggtcacac agatgggaca ggaagtgatc     60
ttgcgctgtg tccccatctc taatcactta tacttctatt                          100

<210> SEQ ID NO 1174
<211> LENGTH: 100
<212> TYPE: DNA
<213> ORGANISM: Homo sapiens

<400> SEQUENCE: 1174
aattctcagt tgaaaggcct gatggatcaa atttcactct gaagatccgg tccacaaagc     60
tggaggactc agccatgtac ttctgtgcca gcagtgaagc                          100

<210> SEQ ID NO 1175
<211> LENGTH: 100
<212> TYPE: DNA
<213> ORGANISM: Homo sapiens
```

<400> SEQUENCE: 1175
gaacctgaag tcacccagac tcccagccat caggtcacac agatgggaca ggaagtgatc      60
ttgcactgtg tccccatctc taatcactta tacttctatt                           100

<210> SEQ ID NO 1176
<211> LENGTH: 100
<212> TYPE: DNA
<213> ORGANISM: Homo sapiens

<400> SEQUENCE: 1176
tgatcaattc tcagttgaaa ggcctgatgg atcaaatttc actctgaaga tccggtccac      60
aaagctggag gactcagcca tgtacttctg tgccagcagt                           100

<210> SEQ ID NO 1177
<211> LENGTH: 100
<212> TYPE: DNA
<213> ORGANISM: Homo sapiens

<400> SEQUENCE: 1177
gaacctgaag tcacccagac tcccagccat caggtcacac agatgggaca ggaagtgatc      60
ttgcgctgtg tccccatctc taatcactta tacttctatt                           100

<210> SEQ ID NO 1178
<211> LENGTH: 100
<212> TYPE: DNA
<213> ORGANISM: Homo sapiens

<400> SEQUENCE: 1178
tcaattctca gttgagaggc ctgatggatc aaatttcact ctgaagatcc ggtccacaaa      60
gctggaggac tcagccatgt acttctgtgc cagcagtgaa                           100

<210> SEQ ID NO 1179
<211> LENGTH: 100
<212> TYPE: DNA
<213> ORGANISM: Homo sapiens

<400> SEQUENCE: 1179
ggtgctgtcg tctctcaaca tccgagctgg gttatctgta agagtggaac ctctgtgaag      60
atcgagtgcc gttccctgga ctttcaggcc acaactatgt                           100

<210> SEQ ID NO 1180
<211> LENGTH: 100
<212> TYPE: DNA
<213> ORGANISM: Homo sapiens

<400> SEQUENCE: 1180
acaagtttct catcaaccat gcaagcctga ccttgtccac tctgacagtg accagtgccc      60
atcctgaaga cagcagcttc tacatctgca gtgctagaga                           100

<210> SEQ ID NO 1181
<211> LENGTH: 100
<212> TYPE: DNA
<213> ORGANISM: Homo sapiens

<400> SEQUENCE: 1181
ggtgctgtcg tctctcaaca tccgagcagg gttatctgta agagtggaac ctctgtgaag      60
atcgagtgcc gttccctgga ctttcaggcc acaactatgt                           100

```
<210> SEQ ID NO 1182
<211> LENGTH: 100
<212> TYPE: DNA
<213> ORGANISM: Homo sapiens

<400> SEQUENCE: 1182
gaaggacaag tttctcatca accatgcaag cctgaccttg tccactctga cagtgaccag      60
tgcccatcct gaagacagca gcttctacat ctgcagtgct                           100

<210> SEQ ID NO 1183
<211> LENGTH: 100
<212> TYPE: DNA
<213> ORGANISM: Homo sapiens

<400> SEQUENCE: 1183
ggtgctgtcg tctctcaaca tccgagctgg gttatctgta agagtggaac ctctgtgaag      60
atcgagtgcc gttccctgga cttcaggcc acaactatgt                            100

<210> SEQ ID NO 1184
<211> LENGTH: 100
<212> TYPE: DNA
<213> ORGANISM: Homo sapiens

<400> SEQUENCE: 1184
gaaggacaag tttctcatca accatgcaag cctgaccttg tccactctga cagtgaccag      60
tgcccatcct gaagacagca gcttctacat ctgcagtgct                           100

<210> SEQ ID NO 1185
<211> LENGTH: 100
<212> TYPE: DNA
<213> ORGANISM: Homo sapiens

<400> SEQUENCE: 1185
ggtgctgtcg tctctcaaca tccgagcagg gttatctgta agagtggaac ctctgtgaag      60
atcgagtgcc gttccttgga cttcaggcc acaactatgt                            100

<210> SEQ ID NO 1186
<211> LENGTH: 100
<212> TYPE: DNA
<213> ORGANISM: Homo sapiens

<400> SEQUENCE: 1186
ggacaagttt ctcatcaacc atgcaagcct gaccttgtcc actctgacag tgaccagtgc      60
ccatcctgaa gacagcagct tctacatctg cagtgctagt                           100

<210> SEQ ID NO 1187
<211> LENGTH: 100
<212> TYPE: DNA
<213> ORGANISM: Homo sapiens

<400> SEQUENCE: 1187
ggtgctgtcg tctctcaaca tccgagcagg gttatctgta agagtggaac ctctgtgaag      60
atcgagtgcc gttccctgga ctttcaggcc acaactatgt                           100

<210> SEQ ID NO 1188
<211> LENGTH: 100
<212> TYPE: DNA
<213> ORGANISM: Homo sapiens

<400> SEQUENCE: 1188
```

```
ggacaagttt ctcatcaacc atgcaagcct gaccttgtcc actctgacag tgaccagtgc    60
ccatcctgaa gacagcagct tctacatctg cagtgctaga                          100

<210> SEQ ID NO 1189
<211> LENGTH: 100
<212> TYPE: DNA
<213> ORGANISM: Homo sapiens

<400> SEQUENCE: 1189
ggtgctgtcg tctctcaaca tccgagtagg gttatctgta agagtggaac ctctgtgaag    60
atcgagtgcc gttccctgga ctttcaggcc acaactatgt                          100

<210> SEQ ID NO 1190
<211> LENGTH: 100
<212> TYPE: DNA
<213> ORGANISM: Homo sapiens

<400> SEQUENCE: 1190
gaaggacaag tttctcatca accatgcaag cctgaccttg tccactctga cagtgaccag    60
tgcccatcct gaagacagca gcttctacat ctgcagtgct                          100

<210> SEQ ID NO 1191
<211> LENGTH: 100
<212> TYPE: DNA
<213> ORGANISM: Homo sapiens

<400> SEQUENCE: 1191
ggtgctgtcg tctctcaaca tccgagcagg gttatctgta agagtggaac ctctgtgaag    60
atcgagtgcc gttccctgga ctttcaggcc acaactatgt                          100

<210> SEQ ID NO 1192
<211> LENGTH: 100
<212> TYPE: DNA
<213> ORGANISM: Homo sapiens

<400> SEQUENCE: 1192
ggacaagttt ctcatcaacc atgcaagcct gaccttgtcc actctgacag tgaccagtgc    60
ccatcctgaa gacagcagct tctacatctg cagtgctaga                          100

<210> SEQ ID NO 1193
<211> LENGTH: 100
<212> TYPE: DNA
<213> ORGANISM: Homo sapiens

<400> SEQUENCE: 1193
agtgctgtcg tctctcaaca tccgagcagg gttatctgta agagtggaac ctctgtgaac    60
atcgagtgcc gttccctgga ctttcaggcc acaactatgt                          100

<210> SEQ ID NO 1194
<211> LENGTH: 100
<212> TYPE: DNA
<213> ORGANISM: Homo sapiens

<400> SEQUENCE: 1194
acaagtttcc catcaaccat ccaaacctga ccttctccgc tctgacagtg accagtgccc    60
atcctgaaga cagcagcttc tacatctgca gtgctagaga                          100

<210> SEQ ID NO 1195
<211> LENGTH: 100
```

```
<212> TYPE: DNA
<213> ORGANISM: Homo sapiens

<400> SEQUENCE: 1195
ggtgctgtcg tctctcaaca tccgagcagg gttatctgta agagtggaac ctctgtgaac    60
atcgagtgcc gttccctgga ctttcaggcc acaactatgt                          100

<210> SEQ ID NO 1196
<211> LENGTH: 100
<212> TYPE: DNA
<213> ORGANISM: Homo sapiens

<400> SEQUENCE: 1196
gaaggacaag tttcccatca accatccaaa cctgaccttc tccgctctga cagtgacctg    60
tgcccatcct gaagacagca gcttctacat ctgcagtgct                          100

<210> SEQ ID NO 1197
<211> LENGTH: 100
<212> TYPE: DNA
<213> ORGANISM: Homo sapiens

<400> SEQUENCE: 1197
agtgctgtcg tctctcaaca tccgagcagg gttatctgta agagtggaac ctctgtgaac    60
atcgagtgcc gttccctgga ctttcaggcc acaactatgt                          100

<210> SEQ ID NO 1198
<211> LENGTH: 100
<212> TYPE: DNA
<213> ORGANISM: Homo sapiens

<400> SEQUENCE: 1198
acaagtttcc catcaaccat ccaaacctga ccttctccgc tctgacagtg accagtgccc    60
atcctgaaga cagcagcttc tacatctgca gtgctagaga                          100

<210> SEQ ID NO 1199
<211> LENGTH: 100
<212> TYPE: DNA
<213> ORGANISM: Homo sapiens

<400> SEQUENCE: 1199
gacaccaagg tcacccagag acctagactt ctggtcaaag caagtgaaca gaaagcaaag    60
atggattgtg ttcctataaa agcacatagt tatgtttact                          100

<210> SEQ ID NO 1200
<211> LENGTH: 100
<212> TYPE: DNA
<213> ORGANISM: Homo sapiens

<400> SEQUENCE: 1200 gattttagc ccaatgctcc aaaaactcat cctgtacctt ggagatccag tccacggagt    60
caggggacac agcactgtat ttctgtgcca gcagcaaagc                          100

<210> SEQ ID NO 1201
<211> LENGTH: 100
<212> TYPE: DNA
<213> ORGANISM: Homo sapiens

<400> SEQUENCE: 1201
gacaccaagg tcacccagag acctagattt ctggtcaaag caaatgaaca gaaagcaaag    60
```
atggactgtg ttcctataaa aagacatagt tatgtttact    100

<210> SEQ ID NO 1202
<211> LENGTH: 100
<212> TYPE: DNA
<213> ORGANISM: Homo sapiens

<400> SEQUENCE: 1202
gattttcagc ccaatgcccc caaaactcac cctgtacctt ggagatccag tccacggagt    60
caggagacac agcacggtat ttctgtgcca acagcaaagc    100

<210> SEQ ID NO 1203
<211> LENGTH: 100
<212> TYPE: DNA
<213> ORGANISM: Homo sapiens

<400> SEQUENCE: 1203
gatgctgaca tctatcagat gccattccag ctcactgggg ctggatggga tgtgactctg    60
gagtggaaac ggaatttgag acacaatgac atgtactgct    100

<210> SEQ ID NO 1204
<211> LENGTH: 100
<212> TYPE: DNA
<213> ORGANISM: Homo sapiens

<400> SEQUENCE: 1204
aggctacgtg tctgccaaga ggagaagggg ctatttcttc tcagggtgaa gttggcccac    60
accagccaaa cagctttgta cttctgtcct gggagcgcac    100

<210> SEQ ID NO 1205
<211> LENGTH: 100
<212> TYPE: DNA
<213> ORGANISM: Homo sapiens

<400> SEQUENCE: 1205
gatgctgaca tctatcagac gccattccag ctcactgggg ctggatggga tgtgaccctg    60
gagtagaaac aatttgagac acaatgacat gtactggtac    100

<210> SEQ ID NO 1206
<211> LENGTH: 100
<212> TYPE: DNA
<213> ORGANISM: Homo sapiens

<400> SEQUENCE: 1206
ggctacggtg tctcccgaga ggagaagggg ctgtttcttc tcatggtgaa gctggcccac    60
accagccaaa cagctctgta cttctgtcct gggagtgcac    100

<210> SEQ ID NO 1207
<211> LENGTH: 100
<212> TYPE: DNA
<213> ORGANISM: Homo sapiens

<400> SEQUENCE: 1207
catgccaaag tcacacagac tccaggacat ttggtcaaag gaaaaggaca gaaaacaaag    60
atggattgta cccccgaaaa aggacatact tttgtttatt    100

<210> SEQ ID NO 1208
<211> LENGTH: 100
<212> TYPE: DNA
<213> ORGANISM: Homo sapiens

<400> SEQUENCE: 1208
gattctcatc tcaatgcccc aagaacgcac cctgcagcct ggcaatcctg tcctcagaac    60
cgggagacac ggcactgtat ctctgcgcca gcagtcaatc                          100

<210> SEQ ID NO 1209
<211> LENGTH: 100
<212> TYPE: DNA
<213> ORGANISM: Homo sapiens

<400> SEQUENCE: 1209
catgccaaag tcacacagac tccaggatat ttggtcaaag gaaaggaag gaaaacaaag     60 atgtattgta cccccaaaaa cggacatact tttgtttgtt                          100

<210> SEQ ID NO 1210
<211> LENGTH: 100
<212> TYPE: DNA
<213> ORGANISM: Homo sapiens

<400> SEQUENCE: 1210
gatgcacaag aagcgattct catctcaatg ccccaagaac ccaccctgca gcctggcaat    60
cctgtcctcg gaaccgggag acaccgcact gtatctctgt                          100

<210> SEQ ID NO 1211
<211> LENGTH: 100
<212> TYPE: DNA
<213> ORGANISM: Homo sapiens

<400> SEQUENCE: 1211
catgccaaag tcacacagac tccaggatat ttggtcaaag gaaaggaag gaaaacaaag     60 atgtattgta cccccaaaaa cggacatact tttgtttgtt                          100

<210> SEQ ID NO 1212
<211> LENGTH: 100
<212> TYPE: DNA
<213> ORGANISM: Homo sapiens

<400> SEQUENCE: 1212
gtttttgatt tcctttcaga atgaacaagt tcttcaagaa atggagatgc acaagaagcg    60
attctcatct caatgcccca agaacgcacc ctgcagcctg                          100

<210> SEQ ID NO 1213
<211> LENGTH: 100
<212> TYPE: DNA
<213> ORGANISM: Homo sapiens

<400> SEQUENCE: 1213
gatgctgatg ttacccagac cccaaggaat aggatcacaa agacaggaaa gaggattatg    60
ctggaatgtt ctcagactaa gggtcatgat agaatgtact                          100

<210> SEQ ID NO 1214
<211> LENGTH: 100
<212> TYPE: DNA
<213> ORGANISM: Homo sapiens

<400> SEQUENCE: 1214
atacagtgtc tctcgacagg cacaggctaa attctccctg tccctagagt ctgccatccc    60
caaccagaca gctctttact tctgtgccac cagtgatttg                          100

```
<210> SEQ ID NO 1215
<211> LENGTH: 100
<212> TYPE: DNA
<213> ORGANISM: Homo sapiens

<400> SEQUENCE: 1215
gatgctgatg ttacccagac cccaaggaat aggatcacaa agacaggaaa gaggattatg    60
ctggaatgtt ctcagactaa gggtcatgat agaatgtact                          100

<210> SEQ ID NO 1216
<211> LENGTH: 100
<212> TYPE: DNA
<213> ORGANISM: Homo sapiens

<400> SEQUENCE: 1216
atacagtgtc tctcgacagg cacaggctaa attctccctg tccctagagt ctgccatccc    60
caaccagaca gctctttact tctgtgccac cagtgatttg                          100

<210> SEQ ID NO 1217
<211> LENGTH: 100
<212> TYPE: DNA
<213> ORGANISM: Homo sapiens

<400> SEQUENCE: 1217
gatgctgatg ttatccagac cccaaggaat aggatcacaa agacaggaaa gaggattatg    60
ctggcatgtt ctcagactaa gggtcatgat ggaatgtact                          100

<210> SEQ ID NO 1218
<211> LENGTH: 100
<212> TYPE: DNA
<213> ORGANISM: Homo sapiens

<400> SEQUENCE: 1218
cagttgatct attgctcctt tgatgtcaaa atatataaac aaaagagaga tctctgatgg    60
atacagtgtc tcttgacagg aacaggctaa attctccctg                          100

<210> SEQ ID NO 1219
<211> LENGTH: 100
<212> TYPE: DNA
<213> ORGANISM: Homo sapiens

<400> SEQUENCE: 1219
gatgctgatg ttatccagac cccaaggaat aggatcacaa agacaggaaa gaggattatg    60
ctggaatgtt ctcagactaa gggtcatgat ggaatgtact                          100

<210> SEQ ID NO 1220
<211> LENGTH: 100
<212> TYPE: DNA
<213> ORGANISM: Homo sapiens

<400> SEQUENCE: 1220
agtgtctctt gacaggaaca ggctaaattc tccctgtccc tagagcctgc cacccccaac    60
cagacagctt ctaggttact tcagtgccac cagtgatttc                          100

<210> SEQ ID NO 1221
<211> LENGTH: 100
<212> TYPE: DNA
<213> ORGANISM: Homo sapiens

<400> SEQUENCE: 1221
```

```
gaagctgaca tctaccagac cccaagatac cttgttatag ggacaggaaa gaagatcact    60
ctggaatgtt ctcaaaccat gggccatgac aaaatgtact                        100

<210> SEQ ID NO 1222
<211> LENGTH: 100
<212> TYPE: DNA
<213> ORGANISM: Homo sapiens

<400> SEQUENCE: 1222
agtcaacagt ctccagaata aggacggagc attttcccct gaccctggag tctgccaggc    60
cctcacatac ctctcagtac ctctgtgcca gcagtgaata                        100

<210> SEQ ID NO 1223
<211> LENGTH: 100
<212> TYPE: DNA
<213> ORGANISM: Homo sapiens

<400> SEQUENCE: 1223
gaagctgaaa tctaccagac cccaagacac cgtgttatag gggcaggaaa gaagatcact    60
ctggaatgtt ctcaaaccat gggccatgac aaaatgtact                        100

<210> SEQ ID NO 1224
<211> LENGTH: 100
<212> TYPE: DNA
<213> ORGANISM: Homo sapiens

<400> SEQUENCE: 1224
agtcaacagt ctccagaata aggatagagc gttttcccct gaccctggag tctgccagcc    60
cctcacatac ctctcagtac ctctgtgcca gcagtgaata                        100

<210> SEQ ID NO 1225
<211> LENGTH: 100
<212> TYPE: DNA
<213> ORGANISM: Homo sapiens

<400> SEQUENCE: 1225
gaagctgaaa tctaccagac cccaagacac cgtgttatag gggcaggaaa gaagatcact    60
ctggaatgtt ctcaaaccat gggccatgac aaaatgtact                        100

<210> SEQ ID NO 1226
<211> LENGTH: 100
<212> TYPE: DNA
<213> ORGANISM: Homo sapiens

<400> SEQUENCE: 1226
gagttaattc cacagagaag ggagatcttt gctctgagtc aacagtctcc agaataagga    60
tagagcgttt tcccctgacc ctggagtctg ccagcccctc                        100

<210> SEQ ID NO 1227
<211> LENGTH: 100
<212> TYPE: DNA
<213> ORGANISM: Homo sapiens

<400> SEQUENCE: 1227
gatgctgtag ttacacaatt cccaagacac agaatcattg ggacaggaaa ggaattcatt    60
ctacagtgtt cccagaatat gaatcatgtt acaatgtact                        100

<210> SEQ ID NO 1228
```

```
<211> LENGTH: 100
<212> TYPE: DNA
<213> ORGANISM: Homo sapiens

<400> SEQUENCE: 1228
ggtatcatgt ttcttgaaat actatagcat cttttcccct gaccctgaag tctgccagca     60
ccaaccagac atctgtgtat ctctatgcca gcagttcatc                          100

<210> SEQ ID NO 1229
<211> LENGTH: 100
<212> TYPE: DNA
<213> ORGANISM: Homo sapiens

<400> SEQUENCE: 1229
gatgctgtag ttacacaatt ctcaagacac agaatcattg ggacaggaaa ggaattcatt     60
ctactgtgtc cccagaatat gaatcatgtt gcaatgtact                          100

<210> SEQ ID NO 1230
<211> LENGTH: 100
<212> TYPE: DNA
<213> ORGANISM: Homo sapiens

<400> SEQUENCE: 1230
ggtatcatgt ttcttgaaat actatagcat cttttctcct gaccctgaag tctgctagca     60
ccaaccagac atgtgtgtat ctctgcgcca gcagttcatc                          100

<210> SEQ ID NO 1231
<211> LENGTH: 100
<212> TYPE: DNA
<213> ORGANISM: Homo sapiens

<400> SEQUENCE: 1231
gatgctgtag ttacacaatt cccaagacac agaatcattg ggacaggaaa ggaattcatt     60
ctactgtgtc cccagaatat gaatcatgtt gcaatgtact                          100

<210> SEQ ID NO 1232
<211> LENGTH: 100
<212> TYPE: DNA
<213> ORGANISM: Homo sapiens

<400> SEQUENCE: 1232
ggtatcatgt ttcttgaaat actatagcat cttttctcct gaccctgaag tctgctagca     60
ccaaccagac atgtgtgtat ctctgcgcca gcagttcatc                          100

<210> SEQ ID NO 1233
<211> LENGTH: 100
<212> TYPE: DNA
<213> ORGANISM: Homo sapiens

<400> SEQUENCE: 1233
gaagcccaag tgacccagaa cccaagatac ctcatcacag tgactggaaa gaagttaaca     60
gtgacttgtt ctcagaatat gaaccatgag tatatgtcct                          100

<210> SEQ ID NO 1234
<211> LENGTH: 100
<212> TYPE: DNA
<213> ORGANISM: Homo sapiens

<400> SEQUENCE: 1234
ggtacaaagt ctctcgaaaa gagaagagga atttcccccct gatcctggag tcgcccagcc    60
```

```
ccaaccagac ctctctgtac ttctgtgcca gcagtttatc                          100
```

<210> SEQ ID NO 1235
<211> LENGTH: 100
<212> TYPE: DNA
<213> ORGANISM: Homo sapiens

<400> SEQUENCE: 1235

```
gatgtgaaag taacccagag ctcgagatat ctagtcaaaa ggacgggaga gaaagttttt    60
ctggaatgtg tccaggatat ggaccatgaa aatatgttct                          100
```

<210> SEQ ID NO 1236
<211> LENGTH: 100
<212> TYPE: DNA
<213> ORGANISM: Homo sapiens

<400> SEQUENCE: 1236

```
ggtacagtgt ctctagagag aagaaggagc gcttctccct gattctggag tccgccagca    60
ccaaccagac atctatgtac ctctgtgcca gcagtttatg                          100
```

<210> SEQ ID NO 1237
<211> LENGTH: 100
<212> TYPE: DNA
<213> ORGANISM: Homo sapiens

<400> SEQUENCE: 1237

```
agtgctgtca tctctcaaaa gccaagcagg gatatctgtc aacgtggaac ctccctgacg    60
atccagtgtc aagtcgatag ccaagtcacc atgatgttct                          100
```

<210> SEQ ID NO 1238
<211> LENGTH: 100
<212> TYPE: DNA
<213> ORGANISM: Homo sapiens

<400> SEQUENCE: 1238

```
acaagtttcc catcagccgc ccaaacctaa cattctcaac tctgactgtg agcaacatga    60
gccctgaaga cagcagcata tatctctgca gcgttgaaga                          100
```

<210> SEQ ID NO 1239
<211> LENGTH: 99
<212> TYPE: DNA
<213> ORGANISM: Homo sapiens

<400> SEQUENCE: 1239

```
agtgctgtca tctctcaaaa gccaagcagg gatatctgtc aacgtggaac ctccctgacg    60
atccagtgtc aagtcgatag ccaagtcacc atgatgttc                           99
```

<210> SEQ ID NO 1240
<211> LENGTH: 100
<212> TYPE: DNA
<213> ORGANISM: Homo sapiens

<400> SEQUENCE: 1240

```
tgacaagttt cccatcagcc gcccaaacct aacattctca gtctgactg tgagcaacat     60
gagccctgaa gacagcagca tatatctctg cagcgttgaa                          100
```

<210> SEQ ID NO 1241
<211> LENGTH: 100
<212> TYPE: DNA

```
<213> ORGANISM: Homo sapiens

<400> SEQUENCE: 1241
acgatccagt gtcaagtcga tagccaagtc accatgatat tctggtaccg tcagcaacct      60
ggacagagcc tgacactgat cgcaactgca aatcagggct                           100

<210> SEQ ID NO 1242
<211> LENGTH: 100
<212> TYPE: DNA
<213> ORGANISM: Homo sapiens

<400> SEQUENCE: 1242
tgacaagttt cccatcagcc gcccaaacct aacattctca actctgactg tgagcaacat      60
gagccctgaa gacagcagca tatatctctg cagcgcgggc                           100

<210> SEQ ID NO 1243
<211> LENGTH: 100
<212> TYPE: DNA
<213> ORGANISM: Homo sapiens

<400> SEQUENCE: 1243
agtgctgtca tctctcaaaa gccaagcagg gatatctgtc aacgtggaac ctccatgatg      60
atccagtgtc aagtcgacag ccaagtcacc atgatgttct                           100

<210> SEQ ID NO 1244
<211> LENGTH: 100
<212> TYPE: DNA
<213> ORGANISM: Homo sapiens

<400> SEQUENCE: 1244
acaagtttcc catcagccgc ccaaacctaa cattctcaac tctgactgtg agcaacagga      60
gacctgaaga cagcagcata tacctctgca gcgttgaaga                           100

<210> SEQ ID NO 1245
<211> LENGTH: 100
<212> TYPE: DNA
<213> ORGANISM: Homo sapiens

<400> SEQUENCE: 1245
agtgctgtca tctctcaaaa gccaagcagg gatatctgtc aacgtggaac ctccatgatg      60
atccagtgtc aagtcgacag ccaagtcacc atgatgttct                           100

<210> SEQ ID NO 1246
<211> LENGTH: 100
<212> TYPE: DNA
<213> ORGANISM: Homo sapiens

<400> SEQUENCE: 1246
acaagtttcc catcagccgc ccaaacctaa cattctcaac tctgactgtg agcaacagga      60
gacctgaaga cagcagcata tacctctgca gcgttgaaga                           100

<210> SEQ ID NO 1247
<211> LENGTH: 100
<212> TYPE: DNA
<213> ORGANISM: Homo sapiens

<400> SEQUENCE: 1247
gacacagctg tttcccagac tccaaaatac ctggtcacac agatgggaaa cgacaagtcc      60
attaaatgtg aacaaaatct gggccatgat actatgtatt                           100
```

<210> SEQ ID NO 1248
<211> LENGTH: 100
<212> TYPE: DNA
<213> ORGANISM: Homo sapiens

<400> SEQUENCE: 1248

```
gcttctcacc taaatctcca gacaaagctc acttaaatct tcacatcaat tccctggagc    60
ttggtgactc tgctgtgtat ttctgtgcca gcagccaaga                         100
```

<210> SEQ ID NO 1249
<211> LENGTH: 100
<212> TYPE: DNA
<213> ORGANISM: Homo sapiens

<400> SEQUENCE: 1249

```
gacacagctg tttcccagac tccaaaatac ctggtcacac agatgggaaa cgacaagtcc    60
attaaatgtg aacaaaatct gggccatgat actatgtatt                         100
```

<210> SEQ ID NO 1250
<211> LENGTH: 100
<212> TYPE: DNA
<213> ORGANISM: Homo sapiens

<400> SEQUENCE: 1250

```
tccaaatcga ttctcaccta aatctccaga caaagctaaa ttaaatcttc acatcaattc    60
cctggagctt ggtgactctg ctgtgtattt ctgtgccagc                         100
```

<210> SEQ ID NO 1251
<211> LENGTH: 100
<212> TYPE: DNA
<213> ORGANISM: Homo sapiens

<400> SEQUENCE: 1251

```
gacacagccg tttcccagac tccaaaatac ctggtcacac agatgggaaa aaaggagtct    60
cttaaatgag aacaaaatct gggccataat gctatgtatt                         100
```

<210> SEQ ID NO 1252
<211> LENGTH: 100
<212> TYPE: DNA
<213> ORGANISM: Homo sapiens

<400> SEQUENCE: 1252

```
gcttctcacc tgactctcca gacaaagctc atttaaatct tcacatcaat tccctggagc    60
ttggtgactc tgctgtgtat ttctgtgcca gcagccaaga                         100
```

<210> SEQ ID NO 1253
<211> LENGTH: 100
<212> TYPE: DNA
<213> ORGANISM: Homo sapiens

<400> SEQUENCE: 1253

```
gacacagccg tttcccagac tccaaaatac ctggtcacac agatgggaaa aaaggagtct    60
cttaaatgag aacaaaatct gggccataat gctatgtatt                         100
```

<210> SEQ ID NO 1254
<211> LENGTH: 100
<212> TYPE: DNA
<213> ORGANISM: Homo sapiens

<400> SEQUENCE: 1254
gcttctcacc tgactctcca gacaaagttc atttaaatct tcacatcaat tccctggagc    60
ttggtgactc tgctgtgtat ttctgtgcca gcagccaaga                          100

<210> SEQ ID NO 1255
<211> LENGTH: 100
<212> TYPE: DNA
<213> ORGANISM: Homo sapiens

<400> SEQUENCE: 1255
gacacagccg tttcccagac tccaaaatac ctggtcacac agacgggaaa aaaggagtct    60
cttaaatgag aacaaaatct gggccataat gctatgtatt                          100

<210> SEQ ID NO 1256
<211> LENGTH: 100
<212> TYPE: DNA
<213> ORGANISM: Homo sapiens

<400> SEQUENCE: 1256
tcgcttctca cctgactctc cagacaaagt tcatttaaat cttcacatca attccctgga    60
gcttggtgac tctgctgtgt atttctgtgc cagcagccaa                          100

<210> SEQ ID NO 1257
<211> LENGTH: 100
<212> TYPE: DNA
<213> ORGANISM: Homo sapiens

<400> SEQUENCE: 1257
tctcagacta ttcatcaatg gccagcgacc ctggtgcagc ctgtgggcag cccgctctct    60
ctggagtgca ctgtggaggg aacatcaaac cccaacctat                          100

<210> SEQ ID NO 1258
<211> LENGTH: 100
<212> TYPE: DNA
<213> ORGANISM: Homo sapiens

<400> SEQUENCE: 1258
agaatctctc agcctccaga ccccaggacc ggcagttcat cctgagttct aagaagctcc    60
ttctcagtga ctctggcttc tatctctgtg cctggagtgt                          100

<210> SEQ ID NO 1259
<211> LENGTH: 100
<212> TYPE: DNA
<213> ORGANISM: Homo sapiens

<400> SEQUENCE: 1259
tctcagacta ttcatcaatg gccagcgacc ctggtgcagc ctgtgggcag cccgctctct    60
ctggagtgca ctgtggaggg aacatcaaac cccaacctat                          100

<210> SEQ ID NO 1260
<211> LENGTH: 100
<212> TYPE: DNA
<213> ORGANISM: Homo sapiens

<400> SEQUENCE: 1260
agaatctctc agcctccaga ccccaggacc ggcagttcat cctgagttct aagaagctcc    60
tcctcagtga ctctggcttc tatctctgtg cctggagtgt                          100

```
<210> SEQ ID NO 1261
<211> LENGTH: 100
<212> TYPE: DNA
<213> ORGANISM: Homo sapiens

<400> SEQUENCE: 1261
actattcatc aatggccagc gaccctggtg cagcctgtgg gcagcccgct ctctctggag      60
tgcactgtgg agggaacatc aaacccaac ctatactggt                           100

<210> SEQ ID NO 1262
<211> LENGTH: 100
<212> TYPE: DNA
<213> ORGANISM: Homo sapiens

<400> SEQUENCE: 1262
ccagaatctc tcagcctcca gaccccagga ccggcagttc attctgagtt ctaagaagct      60
cctcctcagt gactctggct tctatctctg tgcctggagt                           100

<210> SEQ ID NO 1263
<211> LENGTH: 100
<212> TYPE: DNA
<213> ORGANISM: Homo sapiens

<400> SEQUENCE: 1263
tctcagacta ttcatcaatg gccagcgacc ctggtgcagc ctgtgggcag cccgctctcc      60
ctggagtgca ctgtggaggg aacatcaaac cccaacctat                           100

<210> SEQ ID NO 1264
<211> LENGTH: 100
<212> TYPE: DNA
<213> ORGANISM: Homo sapiens

<400> SEQUENCE: 1264
ccagaatctc tcagcctcca gaccccagga ccggcagttc atcctgagtt ctaagaagct      60
ccttctcagt gactctggct tctatctctg tgcctgggga                           100

<210> SEQ ID NO 1265
<211> LENGTH: 100
<212> TYPE: DNA
<213> ORGANISM: Homo sapiens

<400> SEQUENCE: 1265
gacactgaag ttacccagac accaaaacac ctggtcatgg gaatgacaaa taagaagtct      60
ttgaaatgtg aacaacatat ggggcacagg gctatgtatt                           100

<210> SEQ ID NO 1266
<211> LENGTH: 100
<212> TYPE: DNA
<213> ORGANISM: Homo sapiens

<400> SEQUENCE: 1266
gcttctcacc tgaatgcccc aacagctctc tcttaaacct tcacctacac gccctgcagc      60
cagaagactc agccctgtat ctctgcgcca gcagccaaga                           100

<210> SEQ ID NO 1267
<211> LENGTH: 100
<212> TYPE: DNA
<213> ORGANISM: Homo sapiens

<400> SEQUENCE: 1267
```

-continued

```
cacctggtca tgggaatgac aaataagaag tctttgaaat gtgaacaaca tatggggcac     60
agggcaatgt attggtacaa gcagaaagct aagaagccac                          100
```

<210> SEQ ID NO 1268
<211> LENGTH: 100
<212> TYPE: DNA
<213> ORGANISM: Homo sapiens

<400> SEQUENCE: 1268

```
tcgcttctca cctgaatgcc ccaacagctc tctcttaaac cttcacctac acgccctgca     60
gccagaagac tcagccctgt atctctgcgc cagcagccaa                          100
```

<210> SEQ ID NO 1269
<211> LENGTH: 100
<212> TYPE: DNA
<213> ORGANISM: Homo sapiens

<400> SEQUENCE: 1269

```
gaaacgggag ttacgcagac accaagacac ctggtcatgg gaatgacaaa taagaagtct     60
ttgaaatgtg aacaacatct ggggcataac gctatgtatt                          100
```

<210> SEQ ID NO 1270
<211> LENGTH: 100
<212> TYPE: DNA
<213> ORGANISM: Homo sapiens

<400> SEQUENCE: 1270

```
gcttctcacc tgaatgcccc aacagctctc acttattcct tcacctacac accctgcagc     60
cagaagactc ggccctgtat ctctgtgcca gcagccaaga                          100
```

<210> SEQ ID NO 1271
<211> LENGTH: 100
<212> TYPE: DNA
<213> ORGANISM: Homo sapiens

<400> SEQUENCE: 1271

```
gaaacgggag ttacgcagac accaagacac ctggtcatgg gaatgacaaa taagaagtct     60
ttgaaatgtg aacaacatct ggggcataac gctatgtatt                          100
```

<210> SEQ ID NO 1272
<211> LENGTH: 100
<212> TYPE: DNA
<213> ORGANISM: Homo sapiens

<400> SEQUENCE: 1272

```
aagtcgcttc tcacctgaat gccccaacag ctctcactta tgccttcacc tacacaccct     60
gcagccagaa gactcggccc tgtatctctg tgccagcacc                          100
```

<210> SEQ ID NO 1273
<211> LENGTH: 100
<212> TYPE: DNA
<213> ORGANISM: Homo sapiens

<400> SEQUENCE: 1273

```
gaaacgggag ttacgcagac accaagacac ctggtcatgg gaatgacaaa taagaagtct     60
ttgaaatgtg aacaacatct gggtcataac gctatgtatt                          100
```

<210> SEQ ID NO 1274
<211> LENGTH: 100

```
<212> TYPE: DNA
<213> ORGANISM: Homo sapiens

<400> SEQUENCE: 1274
gcttctcacc tgaatgcccc aacagctctc acttattcct tcacctacac accctgcagc    60
cagaagactc ggccctgtat ctctgcgcca gcagccaaga                         100

<210> SEQ ID NO 1275
<211> LENGTH: 100
<212> TYPE: DNA
<213> ORGANISM: Homo sapiens

<400> SEQUENCE: 1275
gaaacgggag ttacgcagac accaagacac ctggtcatgg gaatgacaaa taagaagtct    60
ttgaaatgtg aacaacatct gggtcataac gctatgtatt                         100

<210> SEQ ID NO 1276
<211> LENGTH: 100
<212> TYPE: DNA
<213> ORGANISM: Homo sapiens

<400> SEQUENCE: 1276
aagtcgcttc tcacctgaat gccccaacag ctctcactta tcccttcacc tacacaccct    60
gcagccagaa gactcggccc tgtatctctg cgccagcagc                         100

<210> SEQ ID NO 1277
<211> LENGTH: 100
<212> TYPE: DNA
<213> ORGANISM: Homo sapiens

<400> SEQUENCE: 1277
gaaacgggag ttacgcagac accaagacac ctggtcatgg gaatgacaaa taagaagtct    60
ttgaaatgtg aacaacatct gggtcataac gctatgtatt                         100

<210> SEQ ID NO 1278
<211> LENGTH: 100
<212> TYPE: DNA
<213> ORGANISM: Homo sapiens

<400> SEQUENCE: 1278
aagtcgcttc tcacctgaat gccccaacag ctctcactta ttccttcacc tacacaccct    60
gcagccagaa gactcggccc tgtatctctg cgccagcagc                         100

<210> SEQ ID NO 1279
<211> LENGTH: 100
<212> TYPE: DNA
<213> ORGANISM: Homo sapiens

<400> SEQUENCE: 1279
aagaagtctt tgaaatgtga acaacatctg gggcataacg ctatgtattg gtacaagcaa    60
agtgctaaga agccactgga gctcatgttt gtctacagtc                         100

<210> SEQ ID NO 1280
<211> LENGTH: 100
<212> TYPE: DNA
<213> ORGANISM: Homo sapiens

<400> SEQUENCE: 1280
aagtcgcttc tcacctgaat gccccaacag ctctcactta ttccttcacc tacacaccct    60
```

```
gcagccagaa gactcggccc tgtatctctg cgccagcagc                            100

<210> SEQ ID NO 1281
<211> LENGTH: 100
<212> TYPE: DNA
<213> ORGANISM: Homo sapiens

<400> SEQUENCE: 1281
aaggctggag tcactcaaac tccaagatat ctgatcaaaa cgagaggaca gcaagtgaca     60
ctgagctgct cccctatctc tgggcatagg agtgtatcct                          100

<210> SEQ ID NO 1282
<211> LENGTH: 100
<212> TYPE: DNA
<213> ORGANISM: Homo sapiens

<400> SEQUENCE: 1282
cgattctcag ggcgccagtt ctctaactct cgctctgaga tgaatgtgag caccttggag     60
ctgggggact cggcccttta tctttgcgcc agcagcttgg                          100

<210> SEQ ID NO 1283
<211> LENGTH: 100
<212> TYPE: DNA
<213> ORGANISM: Homo sapiens

<400> SEQUENCE: 1283
agggctgggg tcactcaaac tccaagacat ctgatcaaaa cgagaggaca gcaagtgaca     60
ctgggctgct cccctatctc tgggcatagg agtgtatcct                          100

<210> SEQ ID NO 1284
<211> LENGTH: 100
<212> TYPE: DNA
<213> ORGANISM: Homo sapiens

<400> SEQUENCE: 1284
tcgattctca gggcgccagt tctctaactc tcgctctgag atgaatgtga gcaccttgga     60
gctgggggac tcggcccttt atctttgcgc cagcgcttgc                          100

<210> SEQ ID NO 1285
<211> LENGTH: 100
<212> TYPE: DNA
<213> ORGANISM: Homo sapiens

<400> SEQUENCE: 1285
gaggctggaa tcacccaagc tccaagacac ctgatcaaaa caagagacca gcaagtgaca     60
ctgagatgct cccctgcctc tgggcataac tgtgtgtcct                          100

<210> SEQ ID NO 1286
<211> LENGTH: 100
<212> TYPE: DNA
<213> ORGANISM: Homo sapiens

<400> SEQUENCE: 1286
aacttgccta attgattctc agctcaccac gtccataact attactgagt caaacacgga     60
gctaggggac tcagccctgt atctctgtgc cagcaacttg                          100

<210> SEQ ID NO 1287
<211> LENGTH: 100
<212> TYPE: DNA
<213> ORGANISM: Homo sapiens
```

<400> SEQUENCE: 1287
gaggctggag tcacccaaag tcccacacac ctgatcaaaa cgagaggaca gcaagtgact    60
ctgagatgct ctcctatctc tgggcacagc agtgtgtcct                        100

<210> SEQ ID NO 1288
<211> LENGTH: 100
<212> TYPE: DNA
<213> ORGANISM: Homo sapiens

<400> SEQUENCE: 1288
cgattctcag ggcgccagtt ccatgactgt tgctctgaga tgaatgtgag tgccttggag    60
ctgggggact cggccctgta tctctgtgcc agaagcttgg                        100

<210> SEQ ID NO 1289
<211> LENGTH: 100
<212> TYPE: DNA
<213> ORGANISM: Homo sapiens

<400> SEQUENCE: 1289
gaggctggag tcacccaaag tcccacacac ctgatcaaaa cgagaggaca gcaagtgact    60
ctgagatgct ctcctatctc tgggcacagc agtgtgtcct                        100

<210> SEQ ID NO 1290
<211> LENGTH: 100
<212> TYPE: DNA
<213> ORGANISM: Homo sapiens

<400> SEQUENCE: 1290
cgattctcag ggcgccagtt ccatgactat tgctctgaga tgaatgtgag tgccttggag    60
ctgggggact cggccctgta tctctgtgcc agaagcttgg                        100

<210> SEQ ID NO 1291
<211> LENGTH: 100
<212> TYPE: DNA
<213> ORGANISM: Homo sapiens

<400> SEQUENCE: 1291
gagactggag tcacccaaag tcccacacac ctgatcaaaa cgagaggaca gcaagtgact    60
ctgagatgct cttctcagtc tgggcacaac actgtgtcct                        100

<210> SEQ ID NO 1292
<211> LENGTH: 100
<212> TYPE: DNA
<213> ORGANISM: Homo sapiens

<400> SEQUENCE: 1292
agattctcag gtctccagtt ccctaattat agctctgagc tgaatgtgaa cgccttggag    60
ctggacgact cggccctgta tctctgtgcc agcagcttgg                        100

<210> SEQ ID NO 1293
<211> LENGTH: 100
<212> TYPE: DNA
<213> ORGANISM: Homo sapiens

<400> SEQUENCE: 1293
gagactggag tcacccaaag tcccacacac ctgatcaaaa cgagaggaca gcaagtgact    60
ctgagatgct cttctcagtc tgggcacaac actgtgtcct                        100

<210> SEQ ID NO 1294
<211> LENGTH: 100
<212> TYPE: DNA
<213> ORGANISM: Homo sapiens

<400> SEQUENCE: 1294
tcctagattc tcaggtctcc agttccctaa ttataactct gagctgaatg tgaacgcctt    60
ggagctggac gactcggccc tgtatctctg tgccagcagc                         100

<210> SEQ ID NO 1295
<211> LENGTH: 100
<212> TYPE: DNA
<213> ORGANISM: Homo sapiens

<400> SEQUENCE: 1295
cagcaagtga cactgagatg ctcttctcag tctgggcaca acactgtgtc ctggtaccaa    60
caggccctgg gtcaggggcc ccagtttatc tttcagtatt                         100

<210> SEQ ID NO 1296
<211> LENGTH: 100
<212> TYPE: DNA
<213> ORGANISM: Homo sapiens

<400> SEQUENCE: 1296
tcctagattc tcaggtctcc agttccctaa ttatagctct gagctgaatg tgaacgcctt    60
ggagctggac gactcggccc tgtatctctg tgccagcagc                         100

<210> SEQ ID NO 1297
<211> LENGTH: 100
<212> TYPE: DNA
<213> ORGANISM: Homo sapiens

<400> SEQUENCE: 1297
actgtgtcct ggtaccaaca ggccctgggt caggggcccc agtttatctt tcagtattat    60
agggaggaag agaatggcag aggaaactcc cctcctagat                         100

<210> SEQ ID NO 1298
<211> LENGTH: 100
<212> TYPE: DNA
<213> ORGANISM: Homo sapiens

<400> SEQUENCE: 1298
tcctagattc tcaggtctcc agttccctaa ttatagctct gagctgaatg tgaacgcctt    60
ggagctggac gactcggccc tgtatctctg tgccagcagc                         100

<210> SEQ ID NO 1299
<211> LENGTH: 100
<212> TYPE: DNA
<213> ORGANISM: Homo sapiens

<400> SEQUENCE: 1299
gacgctggag tcacccaaag tcccacacac ctgatcaaaa cgagaggaca gcaagtgact    60
ctgagatgct ctcctatctc tgggcacaag agtgtgtcct                         100

<210> SEQ ID NO 1300
<211> LENGTH: 100
<212> TYPE: DNA
<213> ORGANISM: Homo sapiens

<400> SEQUENCE: 1300

```
cgattctcag ctcgccagtt ccctaactat agctctgagc tgaatgtgaa cgccttgttg    60
ctgggggact cggccctgta tctctgtgcc agcagcttgg                          100
```

<210> SEQ ID NO 1301
<211> LENGTH: 100
<212> TYPE: DNA
<213> ORGANISM: Homo sapiens

<400> SEQUENCE: 1301

```
gacgctggag tcacccaaag tcccacacac ctgatcaaaa cgagaggaca gcacgtgact    60
ctgagatgct ctcctatctc tgggcacaag agtgtgtcct                          100
```

<210> SEQ ID NO 1302
<211> LENGTH: 100
<212> TYPE: DNA
<213> ORGANISM: Homo sapiens

<400> SEQUENCE: 1302

```
tgatcgattc tcagctcgcc agttccctaa ctatagctct gagctgaatg tgaacgcctt    60
gttgctgggg gactcggccc tgtatctctg tgccagcagc                          100
```

<210> SEQ ID NO 1303
<211> LENGTH: 100
<212> TYPE: DNA
<213> ORGANISM: Homo sapiens

<400> SEQUENCE: 1303

```
gacgctggag tcacccaaag tcccacacac ctgatcaaaa cgagaggaca gcaagtgact    60
ctgagatgct ctcctatctc tgagcacaag agtgtgtcct                          100
```

<210> SEQ ID NO 1304
<211> LENGTH: 100
<212> TYPE: DNA
<213> ORGANISM: Homo sapiens

<400> SEQUENCE: 1304

```
tgatcgattc tcagctcgcc agttccctaa ctatagctct gagctgaatg tgaacgcctt    60
gttgctgggg gactcggccc tgtatctctg tgccagcagc                          100
```

<210> SEQ ID NO 1305
<211> LENGTH: 100
<212> TYPE: DNA
<213> ORGANISM: Homo sapiens

<400> SEQUENCE: 1305

```
gacgctggag tcacccaaag tcccacacac ctgatcaaaa cgagaggaca gcaagtgact    60
ctgagatgct ctcctaagtc tgggcatgac actgtgtcct                          100
```

<210> SEQ ID NO 1306
<211> LENGTH: 100
<212> TYPE: DNA
<213> ORGANISM: Homo sapiens

<400> SEQUENCE: 1306

```
cgattctcag gtcaccagtt ccctaactat agctctgagc tgaatgtgaa cgccttgttg    60
ctgggggact cggccctcta tctctgtgcc agcagcttgg                          100
```

<210> SEQ ID NO 1307

```
<211> LENGTH: 100
<212> TYPE: DNA
<213> ORGANISM: Homo sapiens

<400> SEQUENCE: 1307
gacgctggag tcacccaaag tcccacacac ctgatcaaaa cgagaggaca gcacgtgact      60
ctgagatgct ctcctatctc tgggcacacc agtgtgtcct                          100

<210> SEQ ID NO 1308
<211> LENGTH: 100
<212> TYPE: DNA
<213> ORGANISM: Homo sapiens

<400> SEQUENCE: 1308
caattctcag gtcaccagtt ccctaactat agctctgagc tgaatgtgaa cgccttgttg      60
ctaggggact cggccctcta tctctgtgcc agcagcttgg                          100

<210> SEQ ID NO 1309
<211> LENGTH: 100
<212> TYPE: DNA
<213> ORGANISM: Homo sapiens

<400> SEQUENCE: 1309
gaggctggag tcacacaaag tcccacacac ctgatcaaaa cgagaggaca gcaagcgact      60
ctgagatgct ctcctatctc tgggcacacc agtgtgtact                          100

<210> SEQ ID NO 1310
<211> LENGTH: 100
<212> TYPE: DNA
<213> ORGANISM: Homo sapiens

<400> SEQUENCE: 1310
agattttcag gtcgccagtt ccctaattat agctctgagc tgaatgtgaa cgccttggag      60
ctggaggact cggccctgta tctctgtgcc agcagcttgg                          100

<210> SEQ ID NO 1311
<211> LENGTH: 100
<212> TYPE: DNA
<213> ORGANISM: Homo sapiens

<400> SEQUENCE: 1311
aggacagcaa gcgactctga gatgctctcc tatctctggg cacaccagtg tgtactggta      60
ccaacaggcc ctgggtctgg gcctccagct cctcctttgg                          100

<210> SEQ ID NO 1312
<211> LENGTH: 100
<212> TYPE: DNA
<213> ORGANISM: Homo sapiens

<400> SEQUENCE: 1312
tcctagattt tcaggtcgcc agttccctaa ttatagctct gagctgaatg tgaacgcctt      60
ggagctggag gactcggccc tgtatctctg tgccagcagc                          100

<210> SEQ ID NO 1313
<211> LENGTH: 100
<212> TYPE: DNA
<213> ORGANISM: Homo sapiens

<400> SEQUENCE: 1313
aatgctggtg tcactcagac cccaaaattc caggtcctga agacaggaca gagcatgaca      60
```

```
ctgcagtgtg cccaggatat gaaccataac tccatgtact                100
```

<210> SEQ ID NO 1314
<211> LENGTH: 100
<212> TYPE: DNA
<213> ORGANISM: Homo sapiens

<400> SEQUENCE: 1314

```
gctacaatgt ctccagatta aacaaacggg agttctcgct caggctggag tcggctgctc    60
cctcccagac atctgtgtac ttctgtgcca gcagtgaagc                         100
```

<210> SEQ ID NO 1315
<211> LENGTH: 100
<212> TYPE: DNA
<213> ORGANISM: Homo sapiens

<400> SEQUENCE: 1315

```
aatgctggtg tcactcagac cccaaaattc cgggtcctga agacaggaca gagcatgaca    60
ctgctgtgtg cccaggatat gaaccatgaa tacatgtact                         100
```

<210> SEQ ID NO 1316
<211> LENGTH: 100
<212> TYPE: DNA
<213> ORGANISM: Homo sapiens

<400> SEQUENCE: 1316

```
gctacaatgt ctccagatta aaaaaacaga atttcctgct ggggttggag tcggctgctc    60
cctcccaaac atctgtgtac ttctgtgcca gcagttactc                         100
```

<210> SEQ ID NO 1317
<211> LENGTH: 100
<212> TYPE: DNA
<213> ORGANISM: Homo sapiens

<400> SEQUENCE: 1317

```
aatgctggtg tcactcagac cccaaaattc cgggtcctga agacaggaca gagcatgaca    60
ctgctgtgtg cccaggatat gaaccatgaa tacatgtact                         100
```

<210> SEQ ID NO 1318
<211> LENGTH: 100
<212> TYPE: DNA
<213> ORGANISM: Homo sapiens

<400> SEQUENCE: 1318

```
tggctacaat gtctccagat taaaaaaaca gaatttcctg ctggggttgg agtcggctgc    60
tccctcccaa acatctgtgt acttctgtgc cagcagccct                         100
```

<210> SEQ ID NO 1319
<211> LENGTH: 100
<212> TYPE: DNA
<213> ORGANISM: Homo sapiens

<400> SEQUENCE: 1319

```
aatgctggtg tcactcagac cccaaaattc cgggtcctga agacaggaca gagcatgaca    60
ctgctgtgtg cccaggatat gaaccatgaa tacatgtact                         100
```

<210> SEQ ID NO 1320
<211> LENGTH: 100
<212> TYPE: DNA

<213> ORGANISM: Homo sapiens

<400> SEQUENCE: 1320
gctacaatgt ctccagatta aaaaaacaga atttcctgct ggggttggag tcggctgctc    60
cctcccaaac atctgtgtac ttctgtgcca gcagttactc                         100

<210> SEQ ID NO 1321
<211> LENGTH: 100
<212> TYPE: DNA
<213> ORGANISM: Homo sapiens

<400> SEQUENCE: 1321
attgctggga tcacccaggc accaacatct cagatcctgg cagcaggacg gcgcatgaca    60
ctgagatgta cccaggatat gagacataat gccatgtact                         100

<210> SEQ ID NO 1322
<211> LENGTH: 100
<212> TYPE: DNA
<213> ORGANISM: Homo sapiens

<400> SEQUENCE: 1322
gttatagtgt ctccagagca aacacagatg atttccccct cacgttggcg tctgctgtac    60
cctctcagac atctgtgtac ttctgtgcca gcagtgactc                         100

<210> SEQ ID NO 1323
<211> LENGTH: 100
<212> TYPE: DNA
<213> ORGANISM: Homo sapiens

<400> SEQUENCE: 1323
actgctggga tcacccaggc accaacatct cagatcctgg cagcaggacg gagcatgaca    60
ctgagatgta cccaggatat gagacataat gccatgtact                         100

<210> SEQ ID NO 1324
<211> LENGTH: 100
<212> TYPE: DNA
<213> ORGANISM: Homo sapiens

<400> SEQUENCE: 1324
gttatagtgt ctccagagca aacacagatg atttccccct cacgttggcg tctgctgtac    60
cctctcagac atctgtgtac ttctgtgcca gcagtgactc                         100

<210> SEQ ID NO 1325
<211> LENGTH: 100
<212> TYPE: DNA
<213> ORGANISM: Homo sapiens

<400> SEQUENCE: 1325
aatgctggtg tcactcagac cccaaaattc caggtcctga agacaggaca gagcatgaca    60
ctgcagtgtg cccaggatat gaaccatgaa tacatgtcct                         100

<210> SEQ ID NO 1326
<211> LENGTH: 100
<212> TYPE: DNA
<213> ORGANISM: Homo sapiens

<400> SEQUENCE: 1326
gctacaatgt ctccagatca accacagagg atttcccgct caggctgctg tcggctgctc    60
cctcccagac atctgtgtac ttctgtgcca gcagttactc                         100

<210> SEQ ID NO 1327
<211> LENGTH: 100
<212> TYPE: DNA
<213> ORGANISM: Homo sapiens

<400> SEQUENCE: 1327
aatgctggtg tcactcagac cccaaaattc cgcatcctga agataggaca gagcatgaca    60
ctgcagtgta cccaggatat gaaccataac tacatgtact                         100

<210> SEQ ID NO 1328
<211> LENGTH: 100
<212> TYPE: DNA
<213> ORGANISM: Homo sapiens

<400> SEQUENCE: 1328
gctacaacgt ctccagatca accacagagg atttcccgct caggctggag ttggctgctc    60
cctcccagac atctgtgtac ttctgtgcca gcagttactc                         100

<210> SEQ ID NO 1329
<211> LENGTH: 100
<212> TYPE: DNA
<213> ORGANISM: Homo sapiens

<400> SEQUENCE: 1329
aatgctggtg tcactcagac cccaaaattc cgcatcctga agataggaca gagcatgaca    60
ctgcagtgtg cccaggatat gaaccataac tacatgtact                         100

<210> SEQ ID NO 1330
<211> LENGTH: 100
<212> TYPE: DNA
<213> ORGANISM: Homo sapiens

<400> SEQUENCE: 1330
gaatggctac aacgtctcca gatcaaccac agaggatttc ccgctcaggc tggagttggc    60
tgctccctcc cagacatctg tgtacttctg tgccagcagt                         100

<210> SEQ ID NO 1331
<211> LENGTH: 100
<212> TYPE: DNA
<213> ORGANISM: Homo sapiens

<400> SEQUENCE: 1331
aatgctggtg tcactcagac cccaaaattc cgcatcctga agataggaca gagcatgaca    60
ctgcagtgtg cccaggatat gaaccataac tacatgtact                         100

<210> SEQ ID NO 1332
<211> LENGTH: 100
<212> TYPE: DNA
<213> ORGANISM: Homo sapiens

<400> SEQUENCE: 1332
gaatggctac aacgtctcca gatcaaccac agaggatttc ccgctcaggc tggagttggc    60
tgctccctcc cagacatctg tgtacttctg tgccagcagt                         100

<210> SEQ ID NO 1333
<211> LENGTH: 100
<212> TYPE: DNA
<213> ORGANISM: Homo sapiens

```
<400> SEQUENCE: 1333
aatgctggtg tcactcagac cccaaaattc cgcatcctga agataggaca gagcatgaca    60
ctgcagtgta cccaggatat gaaccatgaa tacatgtact                          100

<210> SEQ ID NO 1334
<211> LENGTH: 100
<212> TYPE: DNA
<213> ORGANISM: Homo sapiens

<400> SEQUENCE: 1334
tggctacaat gtctccagat caaccacaga ggatttcccg ctcaggctgg agttggctgc    60
tccctcccag acatctgtgt acttctgtgc cagcagtcga                          100

<210> SEQ ID NO 1335
<211> LENGTH: 100
<212> TYPE: DNA
<213> ORGANISM: Homo sapiens

<400> SEQUENCE: 1335
aatgctggtg tcactcagac cccaaaattc cgcatcctga agataggaca gagcatgaca    60
ctgcagtgtg cccaggatat gaaccataac tacatgtact                          100

<210> SEQ ID NO 1336
<211> LENGTH: 100
<212> TYPE: DNA
<213> ORGANISM: Homo sapiens

<400> SEQUENCE: 1336
gaatggctac aacgtctcca gatcaaccac agaggatttc ccgctcaggc tggagttggc    60
tgctgcctcc cagacatctg tgtacttctg tgccagcagc                          100

<210> SEQ ID NO 1337
<211> LENGTH: 100
<212> TYPE: DNA
<213> ORGANISM: Homo sapiens

<400> SEQUENCE: 1337
aatgctggtg tcactcagac cccaaaattc cacgtcctga agacaggaca gagcatgact    60
ctgctgtgtg cccaggatat gaaccatgaa tacatgtatc                          100

<210> SEQ ID NO 1338
<211> LENGTH: 100
<212> TYPE: DNA
<213> ORGANISM: Homo sapiens

<400> SEQUENCE: 1338
gctacaatgt ctccagatca aacacagagg atttccccct caagctggag tcagctgctc    60
cctctcagac ttctgtttac ttctgtgcca gcagttactc                          100

<210> SEQ ID NO 1339
<211> LENGTH: 100
<212> TYPE: DNA
<213> ORGANISM: Homo sapiens

<400> SEQUENCE: 1339
aatgctggtg tcactcagac cccaaaattc cacatcctga agacaggaca gagcatgaca    60
ctgcagtgtg cccaggatat gaaccatgga tacatgtcct                          100
```

```
<210> SEQ ID NO 1340
<211> LENGTH: 100
<212> TYPE: DNA
<213> ORGANISM: Homo sapiens

<400> SEQUENCE: 1340
gctacaatgt ctctagatta aacacagagg atttcccact caggctggtg tcggctgctc      60
cctcccagac atctgtgtac ttgtgtgcca gcagttactc                           100

<210> SEQ ID NO 1341
<211> LENGTH: 100
<212> TYPE: DNA
<213> ORGANISM: Homo sapiens

<400> SEQUENCE: 1341
aatgctggtg tcactcagac cccaaaattc cacatcctga agacaggaca gagcatgaca      60
ctgcagtgtg cccaggatat gaaccatgga tacttgtcct                          100

<210> SEQ ID NO 1342
<211> LENGTH: 100
<212> TYPE: DNA
<213> ORGANISM: Homo sapiens

<400> SEQUENCE: 1342
gctacaatgt atccagatca aacacagagg atttcccgct caggctggag tcagctgctc      60
cctcccagac atctgtatac ttctgtgcca gcagttattc                          100

<210> SEQ ID NO 1343
<211> LENGTH: 100
<212> TYPE: DNA
<213> ORGANISM: Homo sapiens

<400> SEQUENCE: 1343
ggtgctggag tctcccagtc cctgagacac aaggtagcaa agaagggaaa ggatgtagct      60
ctcagatatg atccaatttc aggtcataat gcccttatt                           100

<210> SEQ ID NO 1344
<211> LENGTH: 100
<212> TYPE: DNA
<213> ORGANISM: Homo sapiens

<400> SEQUENCE: 1344
ggttctctgc acagaggtct gagggatcca tctccactct gaagttccag cgcacacagc      60
agggggactt ggctgtgtat ctctgtgcca gcagctcagc                          100

<210> SEQ ID NO 1345
<211> LENGTH: 100
<212> TYPE: DNA
<213> ORGANISM: Homo sapiens

<400> SEQUENCE: 1345
ggagctggag tctcccagtc ccccagtaac aaggtcacag agaagggaaa ggatgtagag      60
ctcaggtgtg atccaatttc aggtcatact gcccttact                           100

<210> SEQ ID NO 1346
<211> LENGTH: 100
<212> TYPE: DNA
<213> ORGANISM: Homo sapiens

<400> SEQUENCE: 1346
```

```
gcttctctgc agagaggact gggggatccg tctccactct gacgatccag cgcacacagc    60
aggaggactc ggccgtgtat ctctgtgcca gcagcttagc                         100
```

<210> SEQ ID NO 1347
<211> LENGTH: 100
<212> TYPE: DNA
<213> ORGANISM: Homo sapiens

<400> SEQUENCE: 1347

```
ggagctggag tctcccagtc ccccagtaac aaggtcacag agaagggaaa ggatgtagag    60
ctcaggtgtg atccaatttc aggtcatact gcccttact                          100
```

<210> SEQ ID NO 1348
<211> LENGTH: 100
<212> TYPE: DNA
<213> ORGANISM: Homo sapiens

<400> SEQUENCE: 1348

```
gcttctctgc agagaggact ggggaatccg tctccactct gacgatccag cgcacacagc    60
aggaggactc ggccgtgtat ctctgtgcca gcagcttagc                         100
```

<210> SEQ ID NO 1349
<211> LENGTH: 100
<212> TYPE: DNA
<213> ORGANISM: Homo sapiens

<400> SEQUENCE: 1349

```
ggagctggag tctcccagtc ccccagtaac aaggtcacag agaagggaaa ggatgtagag    60
ctcaggtgtg atccaatttc aggtcatact gcccttact                          100
```

<210> SEQ ID NO 1350
<211> LENGTH: 100
<212> TYPE: DNA
<213> ORGANISM: Homo sapiens

<400> SEQUENCE: 1350

```
gcttctctgc agagaggact ggggaatccg tctccactct gacgatccag cgcacacagc    60
aggaggactc ggccgtgtat ctctgtacca gcagcttagc                         100
```

<210> SEQ ID NO 1351
<211> LENGTH: 100
<212> TYPE: DNA
<213> ORGANISM: Homo sapiens

<400> SEQUENCE: 1351

```
ggagctggag tttcccagtc ccccagtaac aaggtcacag agaagggaaa ggatgtagag    60
ctcaggtgtg atccaatttc aggtcatact gcccttact                          100
```

<210> SEQ ID NO 1352
<211> LENGTH: 100
<212> TYPE: DNA
<213> ORGANISM: Homo sapiens

<400> SEQUENCE: 1352

```
tcgcttctct gcagagagga ctgggggatc cgtctccact ctgacgatcc agcgcacaca    60
gcaggaggac tcggccgtgt atctctgtgc cagcagctta                         100
```

<210> SEQ ID NO 1353
<211> LENGTH: 100

<212> TYPE: DNA
<213> ORGANISM: Homo sapiens

<400> SEQUENCE: 1353

```
ggtgctggag tctcccagac ccccagtaac aaggtcacag agaagggaaa atatgtagag    60
ctcaggtgtg atccaatttc aggtcatact gccctttact                         100
```

<210> SEQ ID NO 1354
<211> LENGTH: 100
<212> TYPE: DNA
<213> ORGANISM: Homo sapiens

<400> SEQUENCE: 1354

```
ggttctttgc agtcaggcct gagggatccg tctctactct gaagatccag cgcacagagc    60
gggggactc agccgtgtat ctctgtgcca gcagcttaac                          100
```

<210> SEQ ID NO 1355
<211> LENGTH: 100
<212> TYPE: DNA
<213> ORGANISM: Homo sapiens

<400> SEQUENCE: 1355

```
ggtgctggag tctcccagac ccccagtaac aaggtcacag agaagggaaa agatgtagag    60
ctcaggtgtg atccaatttc aggtcatact gccctttact                         100
```

<210> SEQ ID NO 1356
<211> LENGTH: 100
<212> TYPE: DNA
<213> ORGANISM: Homo sapiens

<400> SEQUENCE: 1356

```
ggttctttgc agtcaggcct gagggatccg tctctactct gaagatccag cgcacagagc    60
aggggactc agccgtgtat ctccgtgcca gcagcttaac                          100
```

<210> SEQ ID NO 1357
<211> LENGTH: 100
<212> TYPE: DNA
<213> ORGANISM: Homo sapiens

<400> SEQUENCE: 1357

```
ggtgctggag tctcccagac ccccagtaac aaggtcacag agaagggaaa agatgtagag    60
ctcaggtgtg atccaatttc aggtcatact gccctttact                         100
```

<210> SEQ ID NO 1358
<211> LENGTH: 100
<212> TYPE: DNA
<213> ORGANISM: Homo sapiens

<400> SEQUENCE: 1358

```
ggttctttgc agtcaggcct gagggatccg tctctactct gaagatccag cgcacagagc    60
aggggactc agccgcgtat ctccgtgcca gcagcttaac                          100
```

<210> SEQ ID NO 1359
<211> LENGTH: 100
<212> TYPE: DNA
<213> ORGANISM: Homo sapiens

<400> SEQUENCE: 1359

```
ggtgctggag tctcccagac ccccagtaac aaggtcacag agaagggaaa atatgtagag    60
```

```
ctcaggtgtg atccaatttc aggtcatact gcccttact                    100
```

<210> SEQ ID NO 1360
<211> LENGTH: 100
<212> TYPE: DNA
<213> ORGANISM: Homo sapiens

<400> SEQUENCE: 1360

```
cgatcggttc tttgcagtca ggcctgaggg atccgtctct actctgaaga tccagcgcac    60
agagcggggg gactctgccg tgtatctctg tgccagcagc                         100
```

<210> SEQ ID NO 1361
<211> LENGTH: 100
<212> TYPE: DNA
<213> ORGANISM: Homo sapiens

<400> SEQUENCE: 1361

```
tgggagctca ggtgtgatcc aatttcaggt catactgccc tttactggta ccgacaaagc    60
ctggggcagg gcccagagct tctaatttac ttccaaggca                         100
```

<210> SEQ ID NO 1362
<211> LENGTH: 100
<212> TYPE: DNA
<213> ORGANISM: Homo sapiens

<400> SEQUENCE: 1362

```
cgatcggttc tttgcagtca ggcctgaggg atccgtctct actctgaaga tccagcgcac    60
agagcggggg gactcagccg tgtatctctg tgccagcagc                         100
```

<210> SEQ ID NO 1363
<211> LENGTH: 100
<212> TYPE: DNA
<213> ORGANISM: Homo sapiens

<400> SEQUENCE: 1363

```
ggtgctggag tctcccagtc cccaaggtac aaagtcgcaa agaggggacg ggatgtagct    60
ctcaggtgtg attcaatttc gggtcatgta acccttatt                          100
```

<210> SEQ ID NO 1364
<211> LENGTH: 100
<212> TYPE: DNA
<213> ORGANISM: Homo sapiens

<400> SEQUENCE: 1364

```
ggttctctgc agagaggcct gagagatccg tctccactct gaagatccag cgcacagagc    60 aggggactc agctgtgtat ctctgtgcca gcagcttagc                          100
```

<210> SEQ ID NO 1365
<211> LENGTH: 100
<212> TYPE: DNA
<213> ORGANISM: Homo sapiens

<400> SEQUENCE: 1365

```
ggtgctggag tctcccagtc cccaaggtac aaagtcgcaa agaggggacg ggatgtagct    60
ctcaggtgtg attcaatttc gggtcatgta acccttatt                          100
```

<210> SEQ ID NO 1366
<211> LENGTH: 100
<212> TYPE: DNA
<213> ORGANISM: Homo sapiens

```
<400> SEQUENCE: 1366
aacgagacaa atcagggcgg cccagtggtc ggttctctgc agagaggcct gagagatcgt    60
ctccactccg aagatccagc gcacagagca gggggactca                         100

<210> SEQ ID NO 1367
<211> LENGTH: 100
<212> TYPE: DNA
<213> ORGANISM: Homo sapiens

<400> SEQUENCE: 1367
ggtgctggag tctcccagtc cccaaggtac gaagtcacac agaggggaca ggatgtagct    60
cccaggtgtg atccaatttc gggtcaggta acccttattt                        100

<210> SEQ ID NO 1368
<211> LENGTH: 100
<212> TYPE: DNA
<213> ORGANISM: Homo sapiens

<400> SEQUENCE: 1368
tcaattctcc acagagaggt ctgaggatct ttctccacct gaagatccag cgcacagagc    60
aagggcgact cggctgtgta tctctgtgcc agaagcttag                        100

<210> SEQ ID NO 1369
<211> LENGTH: 100
<212> TYPE: DNA
<213> ORGANISM: Homo sapiens

<400> SEQUENCE: 1369
ggtgctggag tctcccagtc cccaaggtac gaagtcacac agaggggaca ggatgtagct    60
cccaggtgtg atccaatttc gggtcaggta acccttattt                        100

<210> SEQ ID NO 1370
<211> LENGTH: 100
<212> TYPE: DNA
<213> ORGANISM: Homo sapiens

<400> SEQUENCE: 1370
caattctcca cagagaggtc tgaggatctt tctccacctg aagatccagc gcacagagca    60
agggcgactc ggctgtgtat ctctgtgtca gaagcttagc                        100

<210> SEQ ID NO 1371
<211> LENGTH: 100
<212> TYPE: DNA
<213> ORGANISM: Homo sapiens

<400> SEQUENCE: 1371
ggtgctggag tctcccagtc tcccaggtac aaagtcacaa agaggggaca ggatgtagct    60
ctcaggtgtg atccaatttc gggtcatgta tcccttattt                        100

<210> SEQ ID NO 1372
<211> LENGTH: 100
<212> TYPE: DNA
<213> ORGANISM: Homo sapiens

<400> SEQUENCE: 1372
ggttctctgc agagaggcct gagggatcca tctccactct gacgatccag cgcacagagc    60
agcgggactc ggccatgtat cgctgtgcca gcagcttagc                        100
```

```
<210> SEQ ID NO 1373
<211> LENGTH: 100
<212> TYPE: DNA
<213> ORGANISM: Homo sapiens

<400> SEQUENCE: 1373
ggtgctggag tctcccagtc tcccaggtac aaagtcacaa agaggggaca ggatgtagct    60
ctcaggtgtg atccaatctc gggtcatgta tccctttatt                         100

<210> SEQ ID NO 1374
<211> LENGTH: 100
<212> TYPE: DNA
<213> ORGANISM: Homo sapiens

<400> SEQUENCE: 1374
tgatcggttc tctgcagaga ggcctgaggg atccatctcc actctgacga tccagcgcac    60
agagcagcgg gactcggcca tgtatcgctg tgccagcagc                         100

<210> SEQ ID NO 1375
<211> LENGTH: 100
<212> TYPE: DNA
<213> ORGANISM: Homo sapiens

<400> SEQUENCE: 1375
ggtgctggag tctcccagtc tcccaggtac aaagtcacaa agaggggaca ggatgtaact    60
ctcaggtgtg atccaatttc gagtcatgca accctttatt                         100

<210> SEQ ID NO 1376
<211> LENGTH: 100
<212> TYPE: DNA
<213> ORGANISM: Homo sapiens

<400> SEQUENCE: 1376
ggttctctgc agagaggcct gagggatcca tctccactct gacgattcag cgcacagagc    60
agcgggactc agccatgtat cgctgtgcca gcagcttagc                         100

<210> SEQ ID NO 1377
<211> LENGTH: 100
<212> TYPE: DNA
<213> ORGANISM: Homo sapiens

<400> SEQUENCE: 1377
ggtgctggag tctcccagtc tcccaggtac aaagtcacaa agaggggaca ggatgtaact    60
ctcaggtgtg atccaatttc gagtcatgta accctttatt                         100

<210> SEQ ID NO 1378
<211> LENGTH: 100
<212> TYPE: DNA
<213> ORGANISM: Homo sapiens

<400> SEQUENCE: 1378
tgatcggttc tctgcagaga ggcctgaggg atccatctcc actctgacga ttcagcgcac    60
agagcagcgg gactcagcca tgtatcgctg tgccagcagc                         100

<210> SEQ ID NO 1379
<211> LENGTH: 100
<212> TYPE: DNA
<213> ORGANISM: Homo sapiens

<400> SEQUENCE: 1379
```
ggtgctggag tctcccagtc ccctaggtac aaagtcgcaa agagaggaca ggatgtagct    60
ctcaggtgtg atccaatttc gggtcatgta tcccttttt                          100

<210> SEQ ID NO 1380
<211> LENGTH: 100
<212> TYPE: DNA
<213> ORGANISM: Homo sapiens

<400> SEQUENCE: 1380
gcttctttgc agaaaggcct gagggatccg tctccactct gaagatccag cgcacacagc    60
aggaggactc cgccgtgtat ctctgtgcca gcagcttagc                         100

<210> SEQ ID NO 1381
<211> LENGTH: 100
<212> TYPE: DNA
<213> ORGANISM: Homo sapiens

<400> SEQUENCE: 1381
ggtgctggag tctcccagtc ccctaggtac aaagtcgcaa agagaggaca ggatgtagct    60
ctcaggtgtg atccaatttc gggtcatgta tcccttttt                          100

<210> SEQ ID NO 1382
<211> LENGTH: 100
<212> TYPE: DNA
<213> ORGANISM: Homo sapiens

<400> SEQUENCE: 1382
gcttctttgc agaaaggcct gagggatccg tctccactct gaagatccag cgcacacaga    60
aggaggactc cgccgtgtat ctctgtgcca gcagcttagc                         100

<210> SEQ ID NO 1383
<211> LENGTH: 100
<212> TYPE: DNA
<213> ORGANISM: Homo sapiens

<400> SEQUENCE: 1383
ggtgctggag tctcccagtc ccctaggtac aaagtcgcaa agagaggaca ggatgtagct    60
ctcaggtgtg atccaatttc gggtcatgta tcccttttt                          100

<210> SEQ ID NO 1384
<211> LENGTH: 100
<212> TYPE: DNA
<213> ORGANISM: Homo sapiens

<400> SEQUENCE: 1384
tcgcttcttt gcagaaaggc ctgagggatc cgtctccact ctgaagatcc agcgcacaca    60
gcaggaggac tccgccgtgt atctctgtgc cagcagccga                         100

<210> SEQ ID NO 1385
<211> LENGTH: 100
<212> TYPE: DNA
<213> ORGANISM: Homo sapiens

<400> SEQUENCE: 1385
gatactggag tctcccagaa ccccagacac aagatcacaa agaggggaca gaatgtaact    60
ttcaggtgtg atccaatttc tgaacacaac cgcctttatt                         100

<210> SEQ ID NO 1386

<211> LENGTH: 100
<212> TYPE: DNA
<213> ORGANISM: Homo sapiens

<400> SEQUENCE: 1386
ggttctctgc agagaggcct aagggatctt tctccaccct tggagatccag cgcacagagc     60 aggggactc ggccatgtat ctctgtgcca gcagcttagc                             100

<210> SEQ ID NO 1387
<211> LENGTH: 100
<212> TYPE: DNA
<213> ORGANISM: Homo sapiens

<400> SEQUENCE: 1387
gatactggag tctcccagaa ccccagacac aacatcacaa agaggggaca gaatgtaact     60
ttcaggtgtg atccaatttc tgaacacaac cgcctttatt                            100

<210> SEQ ID NO 1388
<211> LENGTH: 100
<212> TYPE: DNA
<213> ORGANISM: Homo sapiens

<400> SEQUENCE: 1388
tcggttctct gcagagaggc ctaagggatc tttctccacc ttggagatcc agcgcacaga     60 gcaggggac tcggccatgt atctctgtgc cagcagctta                             100

<210> SEQ ID NO 1389
<211> LENGTH: 100
<212> TYPE: DNA
<213> ORGANISM: Homo sapiens

<400> SEQUENCE: 1389
gatactggag tctcccagga ccccagacac aagatcacaa agaggggaca gaatgtaact     60
ttcaggtgtg atccaatttc tgaacacaac cgcctttatt                            100

<210> SEQ ID NO 1390
<211> LENGTH: 100
<212> TYPE: DNA
<213> ORGANISM: Homo sapiens

<400> SEQUENCE: 1390
tgatcggttc tctgcagaga ggcctaaggg atctttctcc accttggaga tccagcgcac     60
agagcagggg gactcggcca tgtatctctg tgccagcagc                            100

<210> SEQ ID NO 1391
<211> LENGTH: 100
<212> TYPE: DNA
<213> ORGANISM: Homo sapiens

<400> SEQUENCE: 1391
atatctggag tctcccacaa ccccagacac aagatcacaa agaggggaca gaatgtaact     60
ttcaggtgtg atccaatttc tgaacacaac cgcctttatt                            100

<210> SEQ ID NO 1392
<211> LENGTH: 100
<212> TYPE: DNA
<213> ORGANISM: Homo sapiens

<400> SEQUENCE: 1392
tcggatctct gcagagaggc ctaagggatc tttctccacc ttggagatcc agcgcacaga     60

```
gcaggggggac tcggccatgt atctctgtgc cagcagctct                 100
```

<210> SEQ ID NO 1393
<211> LENGTH: 100
<212> TYPE: DNA
<213> ORGANISM: Homo sapiens

<400> SEQUENCE: 1393

```
gatactggag tctcccagaa ccccagacac aagatcacaa agaggggaca gaatgtaact   60
ttcaggtgtg atccaatttc tgaacacaac cgcctttatt                       100
```

<210> SEQ ID NO 1394
<211> LENGTH: 100
<212> TYPE: DNA
<213> ORGANISM: Homo sapiens

<400> SEQUENCE: 1394

```
tcggttctct gcagagaggc ctaagggatc tctctccacc ttggagatcc agcgcacaga   60 gcaggggggac tcggccatgt atctctgtgc cagcaccaaa                      100
```

<210> SEQ ID NO 1395
<211> LENGTH: 100
<212> TYPE: DNA
<213> ORGANISM: Homo sapiens

<400> SEQUENCE: 1395

```
gatactggag tctcccagaa ccccagacac aagatcacaa agaggggaca gaatgtaact   60
ttcaggtgtg atccaatttc tgaacacaac cgcctttatt                       100
```

<210> SEQ ID NO 1396
<211> LENGTH: 100
<212> TYPE: DNA
<213> ORGANISM: Homo sapiens

<400> SEQUENCE: 1396

```
tcggttctct gcagagaggc ctaagggatc tctttccacc ttggagatcc agcgcacaga   60 gcaggggggac tcggccatgt atctctgtgc cagcacgttg                      100
```

<210> SEQ ID NO 1397
<211> LENGTH: 100
<212> TYPE: DNA
<213> ORGANISM: Homo sapiens

<400> SEQUENCE: 1397

```
cacaaccgcc tttattggta ccgacagacc ctggggcagg gcccagagtt tctgacttac   60
ttccagaatg aagctcaact agaaaaatca aggctgctca                       100
```

<210> SEQ ID NO 1398
<211> LENGTH: 100
<212> TYPE: DNA
<213> ORGANISM: Homo sapiens

<400> SEQUENCE: 1398

```
gttctctgca gagaggccta agggatcttt ctccaccttg gagatccagc gcacagagga   60
gggggactcg gccatgtatc tctgtgccag cagcagcagt                       100
```

<210> SEQ ID NO 1399
<211> LENGTH: 100
<212> TYPE: DNA

<213> ORGANISM: Homo sapiens

<400> SEQUENCE: 1399
gaggcaggga tcagccagat accaagatat cacagacaca cagggaaaaa gatcatcctg    60
aaatatgctc agattaggaa ccattattca gtgttctgtt                         100

<210> SEQ ID NO 1400
<211> LENGTH: 100
<212> TYPE: DNA
<213> ORGANISM: Homo sapiens

<400> SEQUENCE: 1400
ggaagggtac aatgtctctg gaaacaagct caagcatttt ccctcaaccc tggagtctac    60
tagcaccagc cagacctctg tacctctgtg gcagtgcatc                         100

<210> SEQ ID NO 1401
<211> LENGTH: 100
<212> TYPE: DNA
<213> ORGANISM: Homo sapiens

<400> SEQUENCE: 1401
gatgctggga tcacccagat gccaagatat cacattgtac agaagaaaga gatgatcctg    60
gaatgtgctc aggttaggaa cagtgttctg atatcgacag                         100

<210> SEQ ID NO 1402
<211> LENGTH: 100
<212> TYPE: DNA
<213> ORGANISM: Homo sapiens

<400> SEQUENCE: 1402
agaggggtac tgtgtttctt gaaacaagct tgagcatttc cccaatcctg gcatccacca    60
gcaccagcca gacctatctg taccactgtg gcagcacatc                         100

<210> SEQ ID NO 1403
<211> LENGTH: 100
<212> TYPE: DNA
<213> ORGANISM: Homo sapiens

<400> SEQUENCE: 1403
gattctggag tcacacaaac cccaaagcac ctgatcacag caactggaca gcgagtgacg    60
ctgagatgct cccctaggtc tggagacctc tctgtgtact                         100

<210> SEQ ID NO 1404
<211> LENGTH: 100
<212> TYPE: DNA
<213> ORGANISM: Homo sapiens

<400> SEQUENCE: 1404
cgattctccg cacaacagtt ccctgacttg cactctgaac taaacctgag ctctctggag    60 ctggggact cagctttgta tttctgtgcc agcagcgtag                          100

<210> SEQ ID NO 1405
<211> LENGTH: 100
<212> TYPE: DNA
<213> ORGANISM: Homo sapiens

<400> SEQUENCE: 1405
gattctggag tcacacaaac cccaaagcac ctgatcacag caactggaca gcgagtgacg    60
ctgagatgct cccctaggtc tggagacctc tctgtgtact                         100

<210> SEQ ID NO 1406
<211> LENGTH: 100
<212> TYPE: DNA
<213> ORGANISM: Homo sapiens

<400> SEQUENCE: 1406
cgattctccg cacaacagtt ccctgacttg cactctgaac taaacctgag ctctctggag    60
ctgggggact cagctttgta tttctgtgcc agcagcgtag                         100

<210> SEQ ID NO 1407
<211> LENGTH: 100
<212> TYPE: DNA
<213> ORGANISM: Homo sapiens

<400> SEQUENCE: 1407
gattctggag tcacacaaac cccaaagcac ctgatcacag caactggaca gcgagtgacg    60
ctgagatgct cccctaggtc tggagacctc tctgtgtact                         100

<210> SEQ ID NO 1408
<211> LENGTH: 100
<212> TYPE: DNA
<213> ORGANISM: Homo sapiens

<400> SEQUENCE: 1408
tgaacgattc tccgcacaac agttccctga cttgcactct gaactaaacc tgagctctct    60
ggagctgggg gactcagctt tgtatttctg tgccagcagc                         100

<210> SEQ ID NO 1409
<211> LENGTH: 100
<212> TYPE: DNA
<213> ORGANISM: Homo sapiens

<400> SEQUENCE: 1409
gaagctgaag ccacctagac tctaagacac ctgattgcag agacaggaaa ggagttctca    60
agataagtgc caagatttca tactggtttt cacaagaatc                         100

<210> SEQ ID NO 1410
<211> LENGTH: 100
<212> TYPE: DNA
<213> ORGANISM: Homo sapiens

<400> SEQUENCE: 1410
tccctattga aaatatttcc tggcaaaaaa tagaagttct ctttggctct gaaatctgca    60 actcccttc aggtgtccct gtgtccttgt accgtcactc                          100

<210> SEQ ID NO 1411
<211> LENGTH: 100
<212> TYPE: DNA
<213> ORGANISM: Homo sapiens

<400> SEQUENCE: 1411
gaagctgaag tcacctagac tccaagacac ctgattgtag agacaggaaa ggagttctca    60
ggatatgtgc cataatttca tactggtttc tacaagaatc                         100

<210> SEQ ID NO 1412
<211> LENGTH: 100
<212> TYPE: DNA
<213> ORGANISM: Homo sapiens

```
<400> SEQUENCE: 1412
tccctgttga aaatatttcc cggcaaaaaa cagaagttcc ctttggctct gaaatctgca    60
aagccctttc agatgtccct gtgtccttgt gccgtcactc                         100

<210> SEQ ID NO 1413
<211> LENGTH: 100
<212> TYPE: DNA
<213> ORGANISM: Homo sapiens

<400> SEQUENCE: 1413
aatgtcaaag taacacagac cctgagatga ggcaggaaag ttgtatcgga atgttttcag    60
actatcaacc agaccaaacg ttctggaatc cataagatcc                         100

<210> SEQ ID NO 1414
<211> LENGTH: 100
<212> TYPE: DNA
<213> ORGANISM: Homo sapiens

<400> SEQUENCE: 1414
gactctgaga ccctctgcag cagcagccta tcagtgcagc cacatcctct ctgagcggat    60
atgacaaacc ccagggttga agcgacctaa cctatgagcc                         100

<210> SEQ ID NO 1415
<211> LENGTH: 100
<212> TYPE: DNA
<213> ORGANISM: Homo sapiens

<400> SEQUENCE: 1415
agtgacttct aaattggtct atgaaggaga atctcccccca ttcctggagt cgcccagtcc   60
agacctctct gtacatttgc accagcagtt tatccacagt                         100

<210> SEQ ID NO 1416
<211> LENGTH: 100
<212> TYPE: DNA
<213> ORGANISM: Homo sapiens

<400> SEQUENCE: 1416
gcccagaagg ttactcaagc ccagtcatca gtatccatgc cagtgaggaa agcagtcacc    60
ctgaactgcc tgtatgaaac aagttggtgg tcatattata                         100

<210> SEQ ID NO 1417
<211> LENGTH: 100
<212> TYPE: DNA
<213> ORGANISM: Homo sapiens

<400> SEQUENCE: 1417
attctgtcaa cttcaagaaa gcagcgaaat ccgtcgcctt aaccatttca gccttacagc    60
tagaagattc agcaaagtac ttttgtgctc ttggggaact                         100

<210> SEQ ID NO 1418
<211> LENGTH: 100
<212> TYPE: DNA
<213> ORGANISM: Homo sapiens

<400> SEQUENCE: 1418
gccattgagt tggtgcctga acaccaaaca gtgcctgtgt caatagtggt ccctgccacc    60
ctcaggtgct ccatgaaagg agaagcgatc ggtaactact                         100
```

```
<210> SEQ ID NO 1419
<211> LENGTH: 100
<212> TYPE: DNA
<213> ORGANISM: Homo sapiens

<400> SEQUENCE: 1419
tttccaaggt gacattgata ttgcaaagaa cctggctgta cttaagatac ttgcaccatc      60
agagagagat gaagggtctt actactgtgc ctgtgacacc                           100

<210> SEQ ID NO 1420
<211> LENGTH: 100
<212> TYPE: DNA
<213> ORGANISM: Homo sapiens

<400> SEQUENCE: 1420
attgagttgg tgcctgaaca ccaaacagtg cctgtgtcaa tagggatccc tgccaccctc      60
aggtgctcca tgaaaggaga agcgatcggt aactactata                           100

<210> SEQ ID NO 1421
<211> LENGTH: 100
<212> TYPE: DNA
<213> ORGANISM: Homo sapiens

<400> SEQUENCE: 1421
aatttccaag gtgacattga tattgcaaag aacctggctg tacttaagat acttgcacca      60
tcagagagag atgaagggtc ttactactgt gcctgtgaca                           100

<210> SEQ ID NO 1422
<211> LENGTH: 100
<212> TYPE: DNA
<213> ORGANISM: Homo sapiens

<400> SEQUENCE: 1422
gccattgagt tggtgcctga acaccaaaca gtgcctgtgt caatagggggt ccctgccacc     60 ctcaggtgct ccatgaaagg agaagcgatc ggtaactact                           100

<210> SEQ ID NO 1423
<211> LENGTH: 100
<212> TYPE: DNA
<213> ORGANISM: Homo sapiens

<400> SEQUENCE: 1423
tttccaaggt gacattgata ttgcaaagaa cctggctgta cttaagatac ttgcaccatc      60
agagagagat gaagggtctt actactgtgc ctgtgacacc                           100

<210> SEQ ID NO 1424
<211> LENGTH: 100
<212> TYPE: DNA
<213> ORGANISM: Homo sapiens

<400> SEQUENCE: 1424
tgtgacaaag taacccagag ttccccggac cagacggtgg cgagtggcag tgaggtggta      60
ctgctctgca cttacgacac tgtatattca aatccagatt                           100

<210> SEQ ID NO 1425
<211> LENGTH: 100
<212> TYPE: DNA
<213> ORGANISM: Homo sapiens

<400> SEQUENCE: 1425
```

```
gacggttttc tgtgaaacac attctgaccc agaaagcctt tcacttggtg atctctccag    60
taaggactga agacagtgcc acttactact gtgcctttag                         100

<210> SEQ ID NO 1426
<211> LENGTH: 100
<212> TYPE: DNA
<213> ORGANISM: Homo sapiens

<400> SEQUENCE: 1426
tgtgacaaag taacccagag ttccccggac cagacggtgg cgagtggcag tgaggtggta    60
ctgctctgca cttacgacac tgtatattca aatccagatt                         100

<210> SEQ ID NO 1427
<211> LENGTH: 100
<212> TYPE: DNA
<213> ORGANISM: Homo sapiens

<400> SEQUENCE: 1427
gacggttttc tgtgaaacac attctgaccc agaaagcctt tcacttggtg atctctccag    60
taaggactga agacagtgcc acttactact gtgcctttag                         100

<210> SEQ ID NO 1428
<211> LENGTH: 100
<212> TYPE: DNA
<213> ORGANISM: Homo sapiens

<400> SEQUENCE: 1428
tcttccaact tggaagggag aacgaagtca gtcaccaggc tgactgggtc atctgctgaa    60
atcacctgtg atcttcctgg agcaagtacc ttatacatcc                         100

<210> SEQ ID NO 1429
<211> LENGTH: 100
<212> TYPE: DNA
<213> ORGANISM: Homo sapiens

<400> SEQUENCE: 1429
aaagtatgac actggaagca caaggagcaa ttggaatttg agactgcaaa atctaattaa    60
aaatgattct gggttctatt actgtgccac ctgggacagg                         100

<210> SEQ ID NO 1430
<211> LENGTH: 100
<212> TYPE: DNA
<213> ORGANISM: Homo sapiens

<400> SEQUENCE: 1430
ttatcaaaag tggagcagtt ccagctatcc atttccacgg aagtcaagaa aagtattgac    60
ataccttgca agatatcgag cacaaggttt gaaacagatg                         100

<210> SEQ ID NO 1431
<211> LENGTH: 100
<212> TYPE: DNA
<213> ORGANISM: Homo sapiens

<400> SEQUENCE: 1431
aggcaagaaa gaattctcaa actctcactt caatccttac catcaagtcc gtagagaaag    60
aagacatggc cgtttactac tgtgctgcgt ggtgggtggc                         100

<210> SEQ ID NO 1432
<211> LENGTH: 100
```

```
<212> TYPE: DNA
<213> ORGANISM: Homo sapiens

<400> SEQUENCE: 1432
ttatcaaaag tggagcagtt ccagctatcc atttccacgg aagtcaagaa aagtattgac    60
ataccttgca agatatcgag cacaaggttt gaaacagatg                         100

<210> SEQ ID NO 1433
<211> LENGTH: 100
<212> TYPE: DNA
<213> ORGANISM: Homo sapiens

<400> SEQUENCE: 1433
tggaggcaag aaagaattct caaactctca cttcaatcct taccatcaag tccgtagaga    60
aagaagacat ggccgtttac tactgtgctg cgtgggatta                         100

<210> SEQ ID NO 1434
<211> LENGTH: 100
<212> TYPE: DNA
<213> ORGANISM: Homo sapiens

<400> SEQUENCE: 1434
cttgggcagt tggaacaacc tgaaatatct atttccagac cagcaaataa gagtgcccac    60
atatcttgga aggcatccat ccaaggcttt agcagtaaaa                         100

<210> SEQ ID NO 1435
<211> LENGTH: 100
<212> TYPE: DNA
<213> ORGANISM: Homo sapiens

<400> SEQUENCE: 1435
ggtaagtaaa aatgctcaca cttccacttc cactttgaaa ataaagttct tagagaaaga    60
agatgaggtg gtgtaccact gtgcctgctg gattaggcac                         100

<210> SEQ ID NO 1436
<211> LENGTH: 100
<212> TYPE: DNA
<213> ORGANISM: Homo sapiens

<400> SEQUENCE: 1436
cttgggcagt tggaacaacc tgaaatatct atttccagac cagcaaataa gagtgcccac    60
atatcttgga aggcatccat ccaaggcttt agcagtaaaa                         100

<210> SEQ ID NO 1437
<211> LENGTH: 100
<212> TYPE: DNA
<213> ORGANISM: Homo sapiens

<400> SEQUENCE: 1437
gataagtaaa aatgctcaca cttccacttc cactttgaaa ataaagttct tagagaaaga    60
agatgaggtg gtgtaccact gtgcctgctg gattaggcac                         100

<210> SEQ ID NO 1438
<211> LENGTH: 100
<212> TYPE: DNA
<213> ORGANISM: Homo sapiens

<400> SEQUENCE: 1438
tcttccaact tggaagggag aacgaagtca gtcatcaggc agactgggtc atctgctgaa    60
```

```
atcacttgtg atcttgctga aggaagtaac ggctacatcc                    100
```

<210> SEQ ID NO 1439
<211> LENGTH: 100
<212> TYPE: DNA
<213> ORGANISM: Homo sapiens

<400> SEQUENCE: 1439

```
gtattatact tacgcaagca caaggaacaa cttgagattg atactgcgaa atctaattga    60
aaatgactct ggggtctatt actgtgccac ctgggacggg                   100
```

<210> SEQ ID NO 1440
<211> LENGTH: 100
<212> TYPE: DNA
<213> ORGANISM: Homo sapiens

<400> SEQUENCE: 1440

```
tcttccaact tggaagggag aacgaagtca gtcatcaggc agactgggtc atctgctgaa    60
atcacttgtg atcttgctga aggaagtaac ggctacatcc                   100
```

<210> SEQ ID NO 1441
<211> LENGTH: 100
<212> TYPE: DNA
<213> ORGANISM: Homo sapiens

<400> SEQUENCE: 1441

```
gaagtattat acttacgcaa gcacaaggaa caacttgaga ttgatactgc aaaatctaat    60
tgaaaatgac tctggggtct attactgtgc cacctgggac                   100
```

<210> SEQ ID NO 1442
<211> LENGTH: 100
<212> TYPE: DNA
<213> ORGANISM: Homo sapiens

<400> SEQUENCE: 1442

```
tcttccaact tggaagggag aacgaagtca gtcaccaggc agactgggtc atctgctgaa    60
atcacttgcg atcttactgt aacaaatacc ttctacatcc                   100
```

<210> SEQ ID NO 1443
<211> LENGTH: 100
<212> TYPE: DNA
<213> ORGANISM: Homo sapiens

<400> SEQUENCE: 1443

```
gtattatact catacaccca ggaggtggag ctggatattg agactgcaaa atctaattga    60
aaatgattct ggggtctatt actgtgccac ctgggacagg                   100
```

<210> SEQ ID NO 1444
<211> LENGTH: 100
<212> TYPE: DNA
<213> ORGANISM: Homo sapiens

<400> SEQUENCE: 1444

```
tcttccaact tggaagggag aacgaagtca gtcaccaggc agactgggtc atctgctgaa    60
atcacttgcg atcttactgt aacaaatacc ttctacatcc                   100
```

<210> SEQ ID NO 1445
<211> LENGTH: 100
<212> TYPE: DNA
<213> ORGANISM: Homo sapiens

<400> SEQUENCE: 1445
agtattatac tcatacaccc aggaggtgga gctggatatt gagactgcaa aatctaattg    60
aaaatgattc tggggtctat tactgtgcca cctgggacag                          100

<210> SEQ ID NO 1446
<211> LENGTH: 100
<212> TYPE: DNA
<213> ORGANISM: Homo sapiens

<400> SEQUENCE: 1446
tcttccaact tggaagggag aacgaagtca gtcatcaggc agactgggtc atctgctgaa    60
atcacttgtg atcttgctga aggaagtacc ggctacatcc                          100

<210> SEQ ID NO 1447
<211> LENGTH: 100
<212> TYPE: DNA
<213> ORGANISM: Homo sapiens

<400> SEQUENCE: 1447
gtatgatact tatggaagca caaggaagaa cttgagaatg atactgcgaa atcttattga    60
aaatgactct ggagtctatt actgtgccac ctgggatggg                          100

<210> SEQ ID NO 1448
<211> LENGTH: 100
<212> TYPE: DNA
<213> ORGANISM: Homo sapiens

<400> SEQUENCE: 1448
tcttccaact tggaagggag aacgaagtca gtcatcaggc agactgggtc atctgctgaa    60
atcacttgtg atcttgctga aggaagtacc ggctacatcc                          100

<210> SEQ ID NO 1449
<211> LENGTH: 100
<212> TYPE: DNA
<213> ORGANISM: Homo sapiens

<400> SEQUENCE: 1449
gtatgatact tacggaagca caaggaagaa cttgagaatg atactgcgaa atcttattga    60
aaatgactct ggagtctatt actgtgccac ctgggatggg                          100

<210> SEQ ID NO 1450
<211> LENGTH: 100
<212> TYPE: DNA
<213> ORGANISM: Homo sapiens

<400> SEQUENCE: 1450
tcttccaact tggaaggggg aacgaagtca gtcacgaggc cgactaggtc atctgctgaa    60
atcacttgtg accttactgt aataaatgcc ttctacatcc                          100

<210> SEQ ID NO 1451
<211> LENGTH: 100
<212> TYPE: DNA
<213> ORGANISM: Homo sapiens

<400> SEQUENCE: 1451
gtattatact catacaccca ggaggtggag ctggatattg atactacgaa atctaattga    60
aaatgattct ggggtctatt actgtgccac ctgggacagg                          100

<210> SEQ ID NO 1452
<211> LENGTH: 100
<212> TYPE: DNA
<213> ORGANISM: Homo sapiens

<400> SEQUENCE: 1452
tcttccaact tggaagggag aatgaagtca gtcaccaggc cgactgggtc atctgctgaa    60
atcacttgtg accttactgt aataaatgcc gtctacatcc                         100

<210> SEQ ID NO 1453
<211> LENGTH: 100
<212> TYPE: DNA
<213> ORGANISM: Homo sapiens

<400> SEQUENCE: 1453
gtattatact catacaccga ggaggtggag ctggaatttg agactgcaaa atctaattga    60
aaatgattct ggggtctatt actgtgccac ctggggcagg                         100

<210> SEQ ID NO 1454
<211> LENGTH: 100
<212> TYPE: DNA
<213> ORGANISM: Homo sapiens

<400> SEQUENCE: 1454
tcttccaact tggaagggag aatgaagtca gtcaccaggc cgactgggtc atctgctgaa    60
atcacttgtg accttactgt aataaatgcc gtctacatcc                         100

<210> SEQ ID NO 1455
<211> LENGTH: 100
<212> TYPE: DNA
<213> ORGANISM: Homo sapiens

<400> SEQUENCE: 1455
gtattatact catacaccga ggaggtggag ctggaatttg agactgcaaa atctaattga    60
aaatgattct ggggtctatt actgtgccac ctggggcagg                         100

<210> SEQ ID NO 1456
<211> LENGTH: 100
<212> TYPE: DNA
<213> ORGANISM: Homo sapiens

<400> SEQUENCE: 1456
tctactaact tggaagcgaa aataaagtca ggcaccaggc agatggggtc atctgctgta    60
atcacctgtg atcttcctgt agaaaatgcc ttctacatcc                         100

<210> SEQ ID NO 1457
<211> LENGTH: 100
<212> TYPE: DNA
<213> ORGANISM: Homo sapiens

<400> SEQUENCE: 1457
gcatgatact tatggaagta gaaggataag ctggaaattt atacctccaa aactaaatga    60
aaatgcctct ggggtctatt actgtgccac ctaggacagg                         100

<210> SEQ ID NO 1458
<211> LENGTH: 100
<212> TYPE: DNA
<213> ORGANISM: Homo sapiens

<400> SEQUENCE: 1458

```
tctactaact tggaagcgaa aataaagtca ggcaccaggc agatgggtc atctgctgta        60 atcacctgtg atcttcctgt agaaaatgcc ttctacatcc                            100

<210> SEQ ID NO 1459
<211> LENGTH: 100
<212> TYPE: DNA
<213> ORGANISM: Homo sapiens

<400> SEQUENCE: 1459
gcatgatact tatggaagta gaaggataag ctggaaattt atacctccaa aactaaatga      60
aaatgcctct ggggtctatt actgtgccac ctaggacagg                            100

<210> SEQ ID NO 1460
<211> LENGTH: 100
<212> TYPE: DNA
<213> ORGANISM: Homo sapiens

<400> SEQUENCE: 1460
tcttccaact tgcaagggag aaggaagtca gtcaccaggc cagctgggtc atctgctgta      60
atcacttgtg atcttactgt aataaatacc ttctacatcc                            100

<210> SEQ ID NO 1461
<211> LENGTH: 100
<212> TYPE: DNA
<213> ORGANISM: Homo sapiens

<400> SEQUENCE: 1461
agtattttac ttatgcaagc atgaggagga gctggaaatt gatactgcaa aatctaattg      60
aaaatgattc tggatctatt actgtgccac ctgggacagg                            100

<210> SEQ ID NO 1462
<211> LENGTH: 100
<212> TYPE: DNA
<213> ORGANISM: Homo sapiens

<400> SEQUENCE: 1462
tcttccaact tggaagggag aacaaagtca gtcaccaggc caactgggtc atcagctgta      60
atcacttgtg atcttcctgt agaaaatgcc gtctacaccc                            100

<210> SEQ ID NO 1463
<211> LENGTH: 100
<212> TYPE: DNA
<213> ORGANISM: Homo sapiens

<400> SEQUENCE: 1463
gtatcatact tatgcaagca cagggaagag ccttaaattt atactggaaa atctaattga      60
acgtgactct ggggtctatt actgtgccac ctgggatagg                            100

<210> SEQ ID NO 1464
<211> LENGTH: 100
<212> TYPE: DNA
<213> ORGANISM: Homo sapiens

<400> SEQUENCE: 1464
gcaggtcacc tagagcaacc tcaaatttcc agtactaaaa cgctgtcaaa aacagcccgc      60
ctggaatgtg tggtgtctgg aataacaatt tctgcaacat                            100

<210> SEQ ID NO 1465
```

```
<211> LENGTH: 100
<212> TYPE: DNA
<213> ORGANISM: Homo sapiens

<400> SEQUENCE: 1465
tgaggtggat aggatacctg aaacgtctac atccactctc accattcaca atgtagagaa      60
acaggacata gctacctact actgtgcctt gtgggaggtg                           100

<210> SEQ ID NO 1466
<211> LENGTH: 100
<212> TYPE: DNA
<213> ORGANISM: Homo sapiens

<400> SEQUENCE: 1466
gcaggtcacc tagagcaacc tcaaatttcc agtactaaaa cgctgtcaaa aacagcccgc      60
ctggaatgtg tggtgtctgg aataaaaatt tctgcaacat                           100

<210> SEQ ID NO 1467
<211> LENGTH: 100
<212> TYPE: DNA
<213> ORGANISM: Homo sapiens

<400> SEQUENCE: 1467
tgaggtggat aggatacctg aaacgtctac atccactctc accattcaca atgtagagaa      60
acaggacata gctacctact actgtgcctt gtgggaggtg                           100

<210> SEQ ID NO 1468
<211> LENGTH: 100
<212> TYPE: DNA
<213> ORGANISM: Homo sapiens

<400> SEQUENCE: 1468
ctcatcaggc cggagcagct ggcccatgtc ctggggcact agggaagctt ggtcatcctg      60
cagtgcgtgg tccgcaccag gatcagctac acccactggt                           100

<210> SEQ ID NO 1469
<211> LENGTH: 100
<212> TYPE: DNA
<213> ORGANISM: Homo sapiens

<400> SEQUENCE: 1469
agataaaatc atagccaagg atggcagcag ctctatcttg gcagtactga agttggagac      60
aggcatcgag ggcatgaact actgcacaac ctgggccctg                           100

<210> SEQ ID NO 1470
<211> LENGTH: 100
<212> TYPE: DNA
<213> ORGANISM: Homo sapiens

<400> SEQUENCE: 1470
tttaaagcaa taaaaatgt caactacatt tttgtcaaca gagcaacaga taaaagtgtc       60
taggtatctt gtgtggtgtc cactgaagac tttgtaaata                           100

<210> SEQ ID NO 1471
<211> LENGTH: 100
<212> TYPE: DNA
<213> ORGANISM: Homo sapiens

<400> SEQUENCE: 1471
cttgaggcaa gaacaaattt tcaaatgtct acttcagtct ttaccataaa cttcatagga      60
```

```
aaggaagatg aggccattta ctactgcact gcttaggacc                          100
```

<210> SEQ ID NO 1472
<211> LENGTH: 100
<212> TYPE: DNA
<213> ORGANISM: Homo sapiens

<400> SEQUENCE: 1472

```
aatagagaca cggggcatgg tatgaaagta ttacctccca gttgcaattt ggcaaaggaa     60
ccagagtttc cacttctccc cgtacgtctg cccatgccca                         100
```

<210> SEQ ID NO 1473
<211> LENGTH: 100
<212> TYPE: DNA
<213> ORGANISM: Homo sapiens

<400> SEQUENCE: 1473

```
gaggcatcaa acactgtgat actcacggga ggaggaaaca aactcacctt tgggacaggc     60
actcagctaa aagtggaact cagtaagtat gagattctat                         100
```

<210> SEQ ID NO 1474
<211> LENGTH: 100
<212> TYPE: DNA
<213> ORGANISM: Homo sapiens

<400> SEQUENCE: 1474

```
tatggggatt tgctatagtg tgaattcagg atacagcacc ctcacctttg ggaaggggac     60
tatgcttcta gtctctccag gtacatgttg accccatccc                         100
```

<210> SEQ ID NO 1475
<211> LENGTH: 100
<212> TYPE: DNA
<213> ORGANISM: Homo sapiens

<400> SEQUENCE: 1475

```
actgactaag aaacactgtg ggatggatag cagctataaa ttgatcttcg ggagtgggac     60
cagactgctg gtcaggcctg gtaagtaagg tgtcagagag                         100
```

<210> SEQ ID NO 1476
<211> LENGTH: 100
<212> TYPE: DNA
<213> ORGANISM: Homo sapiens

<400> SEQUENCE: 1476

```
aaggcaggca ttacagtgtg aattctgggg gttaccagaa agttaccttt ggaattggaa     60
caaagctcca agtcatccca agtgagtcca atttcctatg                         100
```

<210> SEQ ID NO 1477
<211> LENGTH: 100
<212> TYPE: DNA
<213> ORGANISM: Homo sapiens

<400> SEQUENCE: 1477

```
aaaggcaggc attacagtgt gaattctggg ggttaccaga agttacctt tggaactgga      60
acaaagctcc aagtcatccc aagtgagtcc aatttcctat                         100
```

<210> SEQ ID NO 1478
<211> LENGTH: 100
<212> TYPE: DNA

<213> ORGANISM: Homo sapiens

<400> SEQUENCE: 1478
tttgtcaggc agcacagtgc tgtgatttat agcacattca tctttgggag tgggacaaga    60
ttatcagtaa aacctggtaa gtaggcaata tgtcactaaa                         100

<210> SEQ ID NO 1479
<211> LENGTH: 100
<212> TYPE: DNA
<213> ORGANISM: Homo sapiens

<400> SEQUENCE: 1479
cagggcctca tttcactgtg ccaaccaggc aggaactgct ctgatctttg ggaagggaac    60
caccttatca gtgagttcca gtaagtacct gataattatt                         100

<210> SEQ ID NO 1480
<211> LENGTH: 100
<212> TYPE: DNA
<213> ORGANISM: Homo sapiens

<400> SEQUENCE: 1480
cagggcctca tttcactgtg ccaaccaggc aggaactgct ctgatctttg ggaagggaac    60
ccacctatca gtgagttcca gtaagtacct gataattatt                         100

<210> SEQ ID NO 1481
<211> LENGTH: 100
<212> TYPE: DNA
<213> ORGANISM: Homo sapiens

<400> SEQUENCE: 1481
tggtacaata gatcactgtg ggttttcaga tggccagaag ctgctctttg caagggggaac   60 catgttaaag gtggatctta gtaagtatta ttactaatga                         100

<210> SEQ ID NO 1482
<211> LENGTH: 100
<212> TYPE: DNA
<213> ORGANISM: Homo sapiens

<400> SEQUENCE: 1482
cctgtggttt tgctgggcc ttaaatcatt gtgtgatcaa agctgcaggc aacaagctaa     60
cttttggagg aggaaccagg gtgctagtta aaccaagtga                         100

<210> SEQ ID NO 1483
<211> LENGTH: 100
<212> TYPE: DNA
<213> ORGANISM: Homo sapiens

<400> SEQUENCE: 1483
aggggaccag cattgtgccg acagaggctc aaccctgggg aggctatact ttggaagagg     60
aactcagttg actgtctggc ctggtgagtg agtcgctttc                         100

<210> SEQ ID NO 1484
<211> LENGTH: 100
<212> TYPE: DNA
<213> ORGANISM: Homo sapiens

<400> SEQUENCE: 1484
ttttgcagag gacagatgtg gctatcaaag attttacaat ttcacctttg gaaagggatc     60
caaacataat gtcactccaa gtaagtgagc agccttttgt                         100

<210> SEQ ID NO 1485
<211> LENGTH: 100
<212> TYPE: DNA
<213> ORGANISM: Homo sapiens

<400> SEQUENCE: 1485

```
tggtgtcacc tacggtatga atactggagg aacaattgat aaactcacat ttgggaaagg      60
gacccatgta ttcattatat ctggtgagtc atcccaggtg                          100
```

<210> SEQ ID NO 1486
<211> LENGTH: 100
<212> TYPE: DNA
<213> ORGANISM: Homo sapiens

<400> SEQUENCE: 1486

```
tgtaggcgac ctcgcactgt ggttctaacg actacaagct cagctttgga gccggaacca      60
cagtaactgt aagagcaagt aagtaagaaa gaaaagtcca                          100
```

<210> SEQ ID NO 1487
<211> LENGTH: 100
<212> TYPE: DNA
<213> ORGANISM: Homo sapiens

<400> SEQUENCE: 1487

```
tgtaatgcca ataaacatgg tgtacaactt caacaaattt tactttggat ctgggaccaa      60
actcaatgta aaaccaagta agttatagtt gcctagaaga                          100
```

<210> SEQ ID NO 1488
<211> LENGTH: 100
<212> TYPE: DNA
<213> ORGANISM: Homo sapiens

<400> SEQUENCE: 1488

```
gttgagcaaa tcatagtgtt tcttctggtt ctgcaaggca actgaccttt ggatctggga      60
cacaattgac tgttttacct ggtaggctgc ctcaattaaa                          100
```

<210> SEQ ID NO 1489
<211> LENGTH: 100
<212> TYPE: DNA
<213> ORGANISM: Homo sapiens

<400> SEQUENCE: 1489

```
aggatatgta acacagtgtg atttataacc agggaggaaa gcttatcttc ggacagggaa      60
cggagttatc tgtgaaaccc agtaagtata aaattgtatc                          100
```

<210> SEQ ID NO 1490
<211> LENGTH: 100
<212> TYPE: DNA
<213> ORGANISM: Homo sapiens

<400> SEQUENCE: 1490

```
gactggatgt gttttttgaca ggatatgtaa cacagtgtga tttataacca gggaggaaag      60
cttatcttcg gacagggaac ggagctatct gtgaaaccca                          100
```

<210> SEQ ID NO 1491
<211> LENGTH: 100
<212> TYPE: DNA
<213> ORGANISM: Homo sapiens

<400> SEQUENCE: 1491
gaggtgtttg tcacagtgtg acaactgaca gctgggggaa attcgagttt ggagcaggga    60
cccaggttgt ggtcacccca ggtaagccca ttcctggagc    100

<210> SEQ ID NO 1492
<211> LENGTH: 100
<212> TYPE: DNA
<213> ORGANISM: Homo sapiens

<400> SEQUENCE: 1492
gaggtgtttg tcacagtgtg acaactgaca gctgggggaa attgcagttt ggagcaggga    60
cccaggttgt ggtcacccca ggtaagcccc attccctgga    100

<210> SEQ ID NO 1493
<211> LENGTH: 100
<212> TYPE: DNA
<213> ORGANISM: Homo sapiens

<400> SEQUENCE: 1493
atgctgagat aatcactatg cagaaggaca aggcttctcc tttatctttg ggaaggggac    60
aaggctgctt gtcaagccaa gtaagtgaca tataatttat    100

<210> SEQ ID NO 1494
<211> LENGTH: 100
<212> TYPE: DNA
<213> ORGANISM: Homo sapiens

<400> SEQUENCE: 1494
ctgagcccag aaacactgtg gggataacta tggtcagaat tttgtctttg gtcccggaac    60
cagattgtcc gtgctgccct gtaagtacag ttaagtggag    100

<210> SEQ ID NO 1495
<211> LENGTH: 100
<212> TYPE: DNA
<213> ORGANISM: Homo sapiens

<400> SEQUENCE: 1495
caatagcact aaagactgtg taacaccaat gcaggcaaat caacctttgg ggatgggact    60
acgctcactg tgaagccaag taagttgtgt tcttctttgc    100

<210> SEQ ID NO 1496
<211> LENGTH: 100
<212> TYPE: DNA
<213> ORGANISM: Homo sapiens

<400> SEQUENCE: 1496
agaaaggaaa ctctgtgcat actctggggc tgggagttac caactcactt tcgggaaggg    60
gaccaaactc tcggtcatac caagtaagtt cttctttctg    100

<210> SEQ ID NO 1497
<211> LENGTH: 100
<212> TYPE: DNA
<213> ORGANISM: Homo sapiens

<400> SEQUENCE: 1497
ttatggagga aatcactgtg ggaattcagg aaacacacct cttgtctttg gaaagggcac    60
aagactttct gtgattgcaa gtaagtgttt ctagccatcc    100

<210> SEQ ID NO 1498
<211> LENGTH: 100
<212> TYPE: DNA
<213> ORGANISM: Homo sapiens

<400> SEQUENCE: 1498
aaagacctta cccacagtgg gggtacagca gtgcttccaa gataatcttt ggatcaggga    60
ccagactcag catccggcca agtaagtaga atgaagcagg                         100

<210> SEQ ID NO 1499
<211> LENGTH: 100
<212> TYPE: DNA
<213> ORGANISM: Homo sapiens

<400> SEQUENCE: 1499
gttatggtcc caatcacagt gtgaacagag atgacaagat catctttgga aaagggacac    60
gacttcatat tctccccagt aagtgctgtt tatgtgattt                          100

<210> SEQ ID NO 1500
<211> LENGTH: 100
<212> TYPE: DNA
<213> ORGANISM: Homo sapiens

<400> SEQUENCE: 1500
agtaaaggca ggaagtgctg tggaataaca atgccagact catgtttgga gatggaactc    60
agctggtggt gaagcccagt aagtggccat gttttattga                         100

<210> SEQ ID NO 1501
<211> LENGTH: 100
<212> TYPE: DNA
<213> ORGANISM: Homo sapiens

<400> SEQUENCE: 1501
ggctctgaag gactgtgtga attatggcgg tgctacaaac aagctcatct ttggaactgg    60
cactctgctt gctgtccagc caagtacgta agtagtggca                         100

<210> SEQ ID NO 1502
<211> LENGTH: 100
<212> TYPE: DNA
<213> ORGANISM: Homo sapiens

<400> SEQUENCE: 1502
gtgattcagc cacctacctc tgtgccgatg gtggtgctac aaacaagctc atctttggaa    60
ctggcactct gcttgctgtc cagccaaata tccagaaccc                         100

<210> SEQ ID NO 1503
<211> LENGTH: 100
<212> TYPE: DNA
<213> ORGANISM: Homo sapiens

<400> SEQUENCE: 1503
gttaaggttt ttgtgtctgt gtggatagca actatcagtt aatctggggc gctgggacca    60
agctaattat aaagccaggt aagtctcaga gatgtgactg                         100

<210> SEQ ID NO 1504
<211> LENGTH: 89
<212> TYPE: DNA
<213> ORGANISM: Homo sapiens

<400> SEQUENCE: 1504

```
aggttttttgt agatctcagt atcactgtgt cttataacac cgacaagctc atctttggga    60
ctgggaccag attacaagtc tttccaagt                                      89

<210> SEQ ID NO 1505
<211> LENGTH: 100
<212> TYPE: DNA
<213> ORGANISM: Homo sapiens

<400> SEQUENCE: 1505
taaaagaatg agccattgtg ataggctttt gggaatgtgc tgcattgcgg gtccggcact    60
caagtgattg ttttaccacg taagtatatc ttttctcatt                          100

<210> SEQ ID NO 1506
<211> LENGTH: 100
<212> TYPE: DNA
<213> ORGANISM: Homo sapiens

<400> SEQUENCE: 1506
tactgggcag aaacactgtg tcaaactggg gcaaacaacc tcttctttgg gactggaacg    60
agactcaccg ttattccctg taagtcctta cctcttgaca                          100

<210> SEQ ID NO 1507
<211> LENGTH: 100
<212> TYPE: DNA
<213> ORGANISM: Homo sapiens

<400> SEQUENCE: 1507
aaagtacagc attagagtgt ggctctggca acacaggcaa actaatcttt gggcaaggga    60
caactttaca agtaaaacca ggtaggtctg gatgtttcca                          100

<210> SEQ ID NO 1508
<211> LENGTH: 100
<212> TYPE: DNA
<213> ORGANISM: Homo sapiens

<400> SEQUENCE: 1508
ctcagcggtg tacttctgtg ctcttcatgg ctctagcaac acaggcaaac taatctttgg    60
gcaagggaca actttacaag taaaaccaga tatccagaac                          100

<210> SEQ ID NO 1509
<211> LENGTH: 100
<212> TYPE: DNA
<213> ORGANISM: Homo sapiens

<400> SEQUENCE: 1509
aaagctttct atgactgtgt aatgctggca acaaccgtaa gctgatttgg ggattgggaa    60
caagcctggc agtaaatccg agtgagtctt cgtgttaact                          100

<210> SEQ ID NO 1510
<211> LENGTH: 100
<212> TYPE: DNA
<213> ORGANISM: Homo sapiens

<400> SEQUENCE: 1510
cagccgaaga tcactgtgtg aataataatg caggcaacat gctcacccttt ggagggggaa   60 caaggttaat ggtcaaaccc cgtgagtatc tctgctgaat                          100

<210> SEQ ID NO 1511
<211> LENGTH: 100
```

<212> TYPE: DNA
<213> ORGANISM: Homo sapiens

<400> SEQUENCE: 1511
aagcaccatc tgattgtgtg ttttctggtg gctacaataa gctgattttt ggagcaggga    60
ccaggctggc tgtacaccca tgtgagtatg accctgcaag                         100

<210> SEQ ID NO 1512
<211> LENGTH: 97
<212> TYPE: DNA
<213> ORGANISM: Homo sapiens

<400> SEQUENCE: 1512
tatgttggtt tatgtagaga cacataacac tgtgactacc tcaggaacct acaaatacat    60
ctttggaaca ggcaccaggc tgaaggtttt agcaagt                             97

<210> SEQ ID NO 1513
<211> LENGTH: 100
<212> TYPE: DNA
<213> ORGANISM: Homo sapiens

<400> SEQUENCE: 1513
ttagggagaa cgcactgtgg aactcaaatt ccgggtatgc actcaacttc ggcaaaggca    60
cctcgctgtt ggtcacaccc cgtgagtttt tgtggtttac                         100

<210> SEQ ID NO 1514
<211> LENGTH: 100
<212> TYPE: DNA
<213> ORGANISM: Homo sapiens

<400> SEQUENCE: 1514
agccccatag gactgtgtga attatggagg aagccaagga aatctcatct ttggaaaagg    60
cactaaactc tctgttaaac caagtaagtg ttggggattc                         100

<210> SEQ ID NO 1515
<211> LENGTH: 100
<212> TYPE: DNA
<213> ORGANISM: Homo sapiens

<400> SEQUENCE: 1515
ttgttagagc atgtattact gtgacaataa caatgacatg cgctttggag cagggaccag    60
actgacagta aaaccaagta agttggggga atgggtcaat                         100

<210> SEQ ID NO 1516
<211> LENGTH: 94
<212> TYPE: DNA
<213> ORGANISM: Homo sapiens

<400> SEQUENCE: 1516
aggtttctgt tatgaagcat ctcacagtgt aaataccggc actgccagta aactcacctt    60
tgggactgga acaagacttc aggtcacgct cggt                                94

<210> SEQ ID NO 1517
<211> LENGTH: 100
<212> TYPE: DNA
<213> ORGANISM: Homo sapiens

<400> SEQUENCE: 1517
agggttggcc cagagtgtgt attcaggagg aggtgctgac ggactcacct ttggcaaagg    60

```
gactcatcta atcatccagc cctgtaagtg cttttgcctg                           100
```

<210> SEQ ID NO 1518
<211> LENGTH: 100
<212> TYPE: DNA
<213> ORGANISM: Homo sapiens

<400> SEQUENCE: 1518

```
aagctgctga cagccgtgag aagaaaagca gcggagacaa gctgactttt gggaccggga    60
ctcgtttagc agttaggccc agtaagtctg agcagaaagt                          100
```

<210> SEQ ID NO 1519
<211> LENGTH: 100
<212> TYPE: DNA
<213> ORGANISM: Homo sapiens

<400> SEQUENCE: 1519

```
gtagaggagt ttgacgctgt gtggaatatg gaaacaaact ggtctttggc gcaggaacca    60
ttctgagagt caagtcctgt gagtataaaa cacactcaag                          100
```

<210> SEQ ID NO 1520
<211> LENGTH: 100
<212> TYPE: DNA
<213> ORGANISM: Homo sapiens

<400> SEQUENCE: 1520

```
gtgtactatt gcatctcggc cctggaatat ggaaacaagc tggtctttgg cgcaggaacc    60
attctgagag tcaagtccta tatccagaac cctgaccctg                          100
```

<210> SEQ ID NO 1521
<211> LENGTH: 100
<212> TYPE: DNA
<213> ORGANISM: Homo sapiens

<400> SEQUENCE: 1521

```
atgacttaga acactgtgta tctaactttg gaaatgagaa attaaccttt gggactggaa    60
caagactcac catcataccc agtaagttct tcatccttgg                          100
```

<210> SEQ ID NO 1522
<211> LENGTH: 100
<212> TYPE: DNA
<213> ORGANISM: Homo sapiens

<400> SEQUENCE: 1522

```
tgttgagctt cctatcacag tggaacaccg gtaaccagtt ctattttggg acagggacaa    60
gtttgacggt cattccaagt aagtcaaaga aaattttcca                          100
```

<210> SEQ ID NO 1523
<211> LENGTH: 100
<212> TYPE: DNA
<213> ORGANISM: Homo sapiens

<400> SEQUENCE: 1523

```
tactgtgatg taccagggtg tggacacggg caggagagca cttactttg ggagtggaac    60
aagactccaa gtgcaaccaa gtaagtaccc aaacttaggc                          100
```

<210> SEQ ID NO 1524
<211> LENGTH: 100
<212> TYPE: DNA
<213> ORGANISM: Homo sapiens

<400> SEQUENCE: 1524
taaaggtttg gatggctgtg tgaaaacctc ctacgacaag gtgatatttg ggccagggac    60
aagcttatca gtcattccaa gtaagtgtcc ctggggtgct                         100

<210> SEQ ID NO 1525
<211> LENGTH: 100
<212> TYPE: DNA
<213> ORGANISM: Homo sapiens

<400> SEQUENCE: 1525
aaactccctg aagcagggag atgcgtgaca gctatgagaa gctgatattt ggaaaggaga    60
catgactaac tgtgaagcca agcaagctgg aaagacctaa                         100

<210> SEQ ID NO 1526
<211> LENGTH: 100
<212> TYPE: DNA
<213> ORGANISM: Homo sapiens

<400> SEQUENCE: 1526
gcctccagtg cagtgctaat gctggtggta ctagctatgg aaagctgaca tttggacaag    60
ggaccatctt gactgtccat ccaagtaagt gtaacaagac                         100

<210> SEQ ID NO 1527
<211> LENGTH: 100
<212> TYPE: DNA
<213> ORGANISM: Homo sapiens

<400> SEQUENCE: 1527
agccttctgt ggctgtgaga atagtggagg tagcaactat aaactgacat ttggaaaagg    60
aactctctta accgtgaatc caagtaagtt tgaagggagt                         100

<210> SEQ ID NO 1528
<211> LENGTH: 100
<212> TYPE: DNA
<213> ORGANISM: Homo sapiens

<400> SEQUENCE: 1528
taaagcctcg tgctgtggtg taattcaggg agcccagaag ctggtatttg gccaaggaac    60
caggctgact atcaacccaa gtaagtatga cagggtgaag                         100

<210> SEQ ID NO 1529
<211> LENGTH: 100
<212> TYPE: DNA
<213> ORGANISM: Homo sapiens

<400> SEQUENCE: 1529
gaggatggat ccctgttagt gacaagtgct ggtaatgctc ctgttgggga aagggaatga    60
gtacaaaaat aaatccaagt aagtgtggag ggacaagaag                         100

<210> SEQ ID NO 1530
<211> LENGTH: 100
<212> TYPE: DNA
<213> ORGANISM: Homo sapiens

<400> SEQUENCE: 1530
agatcctcgt gtcattgtgt tatactggag ccaatagtaa gctgacattt ggaaaaggaa    60
taactctgag tgttagacca ggtatgtttt aatgaatgtt                         100

<210> SEQ ID NO 1531
<211> LENGTH: 100
<212> TYPE: DNA
<213> ORGANISM: Homo sapiens

<400> SEQUENCE: 1531
aagcagtctg tgggggtgta actcagggcg gatctgaaaa gctggtcttt ggaaagggaa    60
cgaaactgac agtaaaccca tgtaagtctg aataatgctt                         100

<210> SEQ ID NO 1532
<211> LENGTH: 100
<212> TYPE: DNA
<213> ORGANISM: Homo sapiens

<400> SEQUENCE: 1532
aagcccctca gcacagtgtt taagaaacca gtggctctag gttgaccttt ggggaaggaa    60
cacagctcac agtgaatcct ggtaagtgga ggggagcatt                         100

<210> SEQ ID NO 1533
<211> LENGTH: 100
<212> TYPE: DNA
<213> ORGANISM: Homo sapiens

<400> SEQUENCE: 1533
atgtaaaggc agcagctcct gtgggaagga aggaaacagg aaatttacat ttggaatggg    60
gacgcaagtg agagtgaagc tatctttaaa ccaaaggtgt                         100

<210> SEQ ID NO 1534
<211> LENGTH: 98
<212> TYPE: DNA
<213> ORGANISM: Homo sapiens

<400> SEQUENCE: 1534
caggttttat caaaggctgt cctcactgtg tgcatcagga ggaagctaca tacctacatt    60
tggaagagga accagcctta ttgttcatcc gtgtaagt                           98

<210> SEQ ID NO 1535
<211> LENGTH: 100
<212> TYPE: DNA
<213> ORGANISM: Homo sapiens

<400> SEQUENCE: 1535
gtaaagggcc tgggcactat gtgaagatca cctagatgct caactttggg aaggggactg    60
agttaattgt gagcctgggt gagtacctca actccagagg                         100

<210> SEQ ID NO 1536
<211> LENGTH: 100
<212> TYPE: DNA
<213> ORGANISM: Homo sapiens

<400> SEQUENCE: 1536
taaaggtgcc cactcctgtg ggtaccgggt taataggaaa ctgacatttg gagccaacac    60
tagaggaatc atgaaactca gcaagtaata tttggcagaa                         100

<210> SEQ ID NO 1537
<211> LENGTH: 100
<212> TYPE: DNA
<213> ORGANISM: Homo sapiens

<400> SEQUENCE: 1537

```
tgtaatacac ttacacagtg tgactatggg aacaacagac tcgcttttgg gaagggaac        60 caagtggtgg tcataccaag taagtgagct gggatcctcc                            100

<210> SEQ ID NO 1538
<211> LENGTH: 100
<212> TYPE: DNA
<213> ORGANISM: Homo sapiens

<400> SEQUENCE: 1538
tacagagtta tgtcagagtg tgaacacagg cttcagaaa cttgtatttg gaactggcac        60
ccgacttctg gtcagtccaa gtaagtcaaa tctgcagaaa                            100

<210> SEQ ID NO 1539
<211> LENGTH: 100
<212> TYPE: DNA
<213> ORGANISM: Homo sapiens

<400> SEQUENCE: 1539
cgcagtgcaa atcactgtgg gaaatactgg aggcttcaaa actatctttg gagcaggaac       60
aagactattt gttaaagcaa gtaagttcca tgaaataacc                            100

<210> SEQ ID NO 1540
<211> LENGTH: 100
<212> TYPE: DNA
<213> ORGANISM: Homo sapiens

<400> SEQUENCE: 1540
ttttcacctt gaccctgtc actgtgtgaa cactgaagct ttctttggac aaggcaccag        60
actcacagtt gtaggtaaga cattttttcag gttcttttgc                           100

<210> SEQ ID NO 1541
<211> LENGTH: 100
<212> TYPE: DNA
<213> ORGANISM: Homo sapiens

<400> SEQUENCE: 1541 tttagagtg gctatattct tatgtgctaa ctatggctac accttcggtt cggggaccag        60
gttaaccgtt gtaggtaagg ctgggggtct ctaggagggg                            100

<210> SEQ ID NO 1542
<211> LENGTH: 100
<212> TYPE: DNA
<213> ORGANISM: Homo sapiens

<400> SEQUENCE: 1542
tttgaagtgg ccctgggagg ctgtgctctg gaaacaccat atatttggga gagggaagtt      60
ggctcactgt tgtaggtgag taagtcaagg ctggacagct                            100

<210> SEQ ID NO 1543
<211> LENGTH: 100
<212> TYPE: DNA
<213> ORGANISM: Homo sapiens

<400> SEQUENCE: 1543
ttccttccag tctttaatgt tgtgcaacta atgaaaaact gttttttggc agtggaaccc      60
agctctctgt cttgggtatg taaaagactt ctttcgggat                            100

<210> SEQ ID NO 1544
```

```
<211> LENGTH: 100
<212> TYPE: DNA
<213> ORGANISM: Homo sapiens

<400> SEQUENCE: 1544
tttgccacac tcatgatgca ctgtgtagca atcagcccca gcattttggt gatgggactc    60
gactctccat cctaggtaag ttggcagaat cagggtggta                         100

<210> SEQ ID NO 1545
<211> LENGTH: 100
<212> TYPE: DNA
<213> ORGANISM: Homo sapiens

<400> SEQUENCE: 1545
ttatctaagc ctctgcagct gtgctcctat aattcacccc tccactttgg gaatgggacc    60
aggctcactg tgacaggtat gggggctcca ctcttgactc                         100

<210> SEQ ID NO 1546
<211> LENGTH: 100
<212> TYPE: DNA
<213> ORGANISM: Homo sapiens

<400> SEQUENCE: 1546
ttatctaagc ctctgcagct gtgctcctat aattcacccc tccactttgg gaacgggacc    60
aggctcactg tgacaggtat gggggctcca ctcttgactc                         100

<210> SEQ ID NO 1547
<211> LENGTH: 100
<212> TYPE: DNA
<213> ORGANISM: Homo sapiens

<400> SEQUENCE: 1547
ttctgggcag ccccttccca ctgtgctcct acaatgagca gttcttcggg ccagggacac    60
ggctcaccgt gctaggtaag aagggggctc caggtgggag                         100

<210> SEQ ID NO 1548
<211> LENGTH: 100
<212> TYPE: DNA
<213> ORGANISM: Homo sapiens

<400> SEQUENCE: 1548
tgcgccaggg tccccagggc tgtgcgaaca ccggggagct gttttttgga gaaggctcta    60
ggctgaccgt actgggtaag gaggcggctg gggctccgga                         100

<210> SEQ ID NO 1549
<211> LENGTH: 100
<212> TYPE: DNA
<213> ORGANISM: Homo sapiens

<400> SEQUENCE: 1549
agctgcccca ctctgagagg ggctgtgctg agaggcgctg ctgggcgtct gggcggagga    60
ctcctggttc tgggtgctgg gagagcgatg gggctctcag                         100

<210> SEQ ID NO 1550
<211> LENGTH: 100
<212> TYPE: DNA
<213> ORGANISM: Homo sapiens

<400> SEQUENCE: 1550
ttttgtcctg ggcctccagg ctgtgagcac agatacgcag tattttggcc caggcacccg    60
```

```
gctgacagtg ctcggtaagc gggggctccc gctgaagccc                    100

<210> SEQ ID NO 1551
<211> LENGTH: 100
<212> TYPE: DNA
<213> ORGANISM: Homo sapiens

<400> SEQUENCE: 1551
ttctgtgccg cgtctcgggg ctgtgagcca aaaacattca gtacttcggc gccgggaccc    60
ggctctcagt gctgggtaag ctggggccgc cgggggaccg                    100

<210> SEQ ID NO 1552
<211> LENGTH: 100
<212> TYPE: DNA
<213> ORGANISM: Homo sapiens

<400> SEQUENCE: 1552
tttttgtgcg gggctcgggg gccgtgacca agagacccag tacttcgggc caggcacgcg    60
gctcctggtg ctcggtgagc gcgggctgct ggggcgcggg                    100

<210> SEQ ID NO 1553
<211> LENGTH: 100
<212> TYPE: DNA
<213> ORGANISM: Homo sapiens

<400> SEQUENCE: 1553
ttgcggggag tccccgggct gtgctctggg gccaacgtcc tgactttcgg ggccggcagc    60
aggctgaccg tgctgggtga gttttcgcgg gaccacccgg                    100

<210> SEQ ID NO 1554
<211> LENGTH: 100
<212> TYPE: DNA
<213> ORGANISM: Homo sapiens

<400> SEQUENCE: 1554
tttgcatgcg ggggtgcacc tccgtgctcc tacgagcagt acttcgggcc gggcaccagg    60
ctcacggtca caggtgagat tcgggcgtct ccccaccttc                    100

<210> SEQ ID NO 1555
<211> LENGTH: 100
<212> TYPE: DNA
<213> ORGANISM: Homo sapiens

<400> SEQUENCE: 1555
tttgcatgcg gggatgcacc tccgtgctcc tacgagcagt acgtcgggcc gggcaccagg    60
ctcacggtca caggtgagat tcgggcgtct ccccaccttc                    100

<210> SEQ ID NO 1556
<211> LENGTH: 100
<212> TYPE: DNA
<213> ORGANISM: Homo sapiens

<400> SEQUENCE: 1556
ttttggaacg tcctcaagtg ctgtgacacc gataaactca tctttggaaa aggaacccgt    60
gtgactgtgg aaccaagtaa gtaactcatt atttatctga                    100

<210> SEQ ID NO 1557
<211> LENGTH: 100
<212> TYPE: DNA
```

<213> ORGANISM: Homo sapiens

<400> SEQUENCE: 1557
tttttcgtaa tgacgcctgt ggtagtgctt tgacagcaca actcttcttt ggaaagggaa    60
cacaactcat cgtggaacca ggtaagttat gcattttact                         100

<210> SEQ ID NO 1558
<211> LENGTH: 100
<212> TYPE: DNA
<213> ORGANISM: Homo sapiens

<400> SEQUENCE: 1558
tgaggcactg tcataatgtg ctcctgggac acccgacaga tgttttttcgg aactggcatc   60 aaactcttcg tggagccccg tgagttgatc ttttttcctat                        100

<210> SEQ ID NO 1559
<211> LENGTH: 76
<212> TYPE: DNA
<213> ORGANISM: Homo sapiens

<400> SEQUENCE: 1559
atgagacata caaaaaggta atgccgcccc agacccctga tctttggcaa aggaacctat    60
ctggaggtac aacaac                                                    76

<210> SEQ ID NO 1560
<211> LENGTH: 100
<212> TYPE: DNA
<213> ORGANISM: Homo sapiens

<400> SEQUENCE: 1560
ttttgatatg gactgaatca ctgtggaatt attataagaa actctttggc agtggaacaa    60
cactggttgt cacaggtaag tatcggaaga atacaacatt                         100

<210> SEQ ID NO 1561
<211> LENGTH: 71
<212> TYPE: DNA
<213> ORGANISM: Homo sapiens

<400> SEQUENCE: 1561
tactgtgcct tgtgggaggt gcttattata agaaactctt tggcagtgga acaacacttg    60
ttgtcacagg t                                                         71

<210> SEQ ID NO 1562
<211> LENGTH: 100
<212> TYPE: DNA
<213> ORGANISM: Homo sapiens

<400> SEQUENCE: 1562
ttttgatatg gactgaatca ctgtggaatt attataagaa actctttggc agtggaacaa    60
cacttgttgt cacaggtaag tatcggaaga atacaacatt                         100

<210> SEQ ID NO 1563
<211> LENGTH: 100
<212> TYPE: DNA
<213> ORGANISM: Homo sapiens

<400> SEQUENCE: 1563
ataaaggctt ctcaggtggt gggcaagagt tgggcaaaaa aatcaaggta tttggtcccg    60
gaacaaagct tatcattaca ggtaagtttt ctttaaattt                         100

<210> SEQ ID NO 1564
<211> LENGTH: 94
<212> TYPE: DNA
<213> ORGANISM: Homo sapiens

<400> SEQUENCE: 1564

```
gatttttcta gaagcttaga ccggtgtgat accactggtt ggttcaagat atttgctgaa    60
gggactaagc tcatagtaac ttcacctggt aagt                                94
```

<210> SEQ ID NO 1565
<211> LENGTH: 94
<212> TYPE: DNA
<213> ORGANISM: Homo sapiens

<400> SEQUENCE: 1565

```
gatttttgta gaagcttaga ccagtgtgat agtagtgatt ggatcaagac gtttgcaaaa    60
gggactaggc tcatagtaac ttcgcctggt aagt                                94
```

<210> SEQ ID NO 1566
<211> LENGTH: 100
<212> TYPE: DNA
<213> ORGANISM: Homo sapiens

<400> SEQUENCE: 1566

```
caggtcgttt ttcttcattc cttagtcgct ctgatagtta tggttacctc cttctacagg    60
agctccagat gaaagactct gcctcttact tctgcgctgt                         100
```

<210> SEQ ID NO 1567
<211> LENGTH: 100
<212> TYPE: DNA
<213> ORGANISM: Homo sapiens

<400> SEQUENCE: 1567

```
catctgggtt caacgggctg ttctggtacc agcaacatgc tggcgaagca cccacatttc    60
tgtcttacaa tgttctggat ggtctggagg agaaaggtcg                         100
```

<210> SEQ ID NO 1568
<211> LENGTH: 100
<212> TYPE: DNA
<213> ORGANISM: Homo sapiens

<400> SEQUENCE: 1568

```
acagcacacg tcaatagagc cagccagtat atttccctgc tcatcagaga ctccaagctc    60
agtgattcag ccacctacct ctgtgtggtg aacattcgcc                         100
```

<210> SEQ ID NO 1569
<211> LENGTH: 100
<212> TYPE: DNA
<213> ORGANISM: Homo sapiens

<400> SEQUENCE: 1569

```
gtttacagca cagctcaata aagccagcca gtatgtttct ctgctcatca gagactccca    60
gcccagtgat tcagccacct acctctgtgc cgtgtaccac                         100
```

<210> SEQ ID NO 1570
<211> LENGTH: 100
<212> TYPE: DNA
<213> ORGANISM: Homo sapiens

<400> SEQUENCE: 1570
aaggtttaca gcacagctca ataaagccag ccagtatgtt tctctgctca tcagagactc    60
ccagcccagt gattcagcca cctacctctg tgccgtgaac                         100

<210> SEQ ID NO 1571
<211> LENGTH: 100
<212> TYPE: DNA
<213> ORGANISM: Homo sapiens

<400> SEQUENCE: 1571
aggtttacag cacaggtcga taaatccagc aagtatatct ccttgttcat cagagactca    60
cagcccagtg attcagccac ctacctctgt gcaatgagcg                         100

<210> SEQ ID NO 1572
<211> LENGTH: 100
<212> TYPE: DNA
<213> ORGANISM: Homo sapiens

<400> SEQUENCE: 1572
tgttacattg aacaagacag ccaaacattt ctccctgcac atcacagaga cccaacctga    60
agactcggct gtctacttct gtgcagcaag taggaaggac                         100

<210> SEQ ID NO 1573
<211> LENGTH: 100
<212> TYPE: DNA
<213> ORGANISM: Homo sapiens

<400> SEQUENCE: 1573
gcttattata gacattcgtt caaatgtggg cgaaaagaaa gaccaacgaa ttgctgttac    60
attgaacaag acagccaaac atttctccct gcagatcaca                         100

<210> SEQ ID NO 1574
<211> LENGTH: 100
<212> TYPE: DNA
<213> ORGANISM: Homo sapiens

<400> SEQUENCE: 1574
caaagagtca ccgttttatt gaataagaca gtgaaacatc tctctctgca aattgcagct    60
actcaacctg gagactcagc tgtctacttt tgtgcagaga                         100

<210> SEQ ID NO 1575
<211> LENGTH: 100
<212> TYPE: DNA
<213> ORGANISM: Homo sapiens

<400> SEQUENCE: 1575
aggtcgctac tcattgaatt tccagaaggc aagaaaatcc gccaaccttg tcatctccgc    60
ttcacaactg ggggactcag caatgtattt ctgtgcaatg                         100

<210> SEQ ID NO 1576
<211> LENGTH: 100
<212> TYPE: DNA
<213> ORGANISM: Homo sapiens

<400> SEQUENCE: 1576
gcaacagaag gtcgctactc attgaatttc cagaaggcaa gaaaatccgc caaccttgtc    60
atctccgctt cacaactggg ggactcagca atgtacttct                         100

<210> SEQ ID NO 1577
<211> LENGTH: 100
<212> TYPE: DNA
<213> ORGANISM: Homo sapiens

<400> SEQUENCE: 1577
gggacgatac aacatgacct atgaacggtt ctcttcatcg ctgctcatcc tccaggtgcg    60
ggaggcagat gctgctgttt actactgtgc tgtggcctgg                         100

<210> SEQ ID NO 1578
<211> LENGTH: 100
<212> TYPE: DNA
<213> ORGANISM: Homo sapiens

<400> SEQUENCE: 1578
aaaggagaaa gaaaggctaa aagccacatt aacaaagaag gaaagctttc tgcacatcac    60
agcccctaaa cctgaagact cagccactta tctctgtgct                         100

<210> SEQ ID NO 1579
<211> LENGTH: 100
<212> TYPE: DNA
<213> ORGANISM: Homo sapiens

<400> SEQUENCE: 1579
agaaaaggag aaagaaaggc taaaagccac attaacaaag aaggaaagct ttctgcacat    60
cacagcccct aaacctgaag actcagccac ttatctctgt                         100

<210> SEQ ID NO 1580
<211> LENGTH: 100
<212> TYPE: DNA
<213> ORGANISM: Homo sapiens

<400> SEQUENCE: 1580
aaaggagaaa gaaaggctaa aagccacatt aacaaagaag gaaagctttc tgcacatcac    60
agcccctaaa cctgaagact cagccactta tctctgtgct                         100

<210> SEQ ID NO 1581
<211> LENGTH: 100
<212> TYPE: DNA
<213> ORGANISM: Homo sapiens

<400> SEQUENCE: 1581
aagtggaaga cttaatgcct cgctggataa atcatcagga cgtagtactt tatacattgc    60
agcttctcag cctggtgact cagccaccta cctctgtgct                         100

<210> SEQ ID NO 1582
<211> LENGTH: 100
<212> TYPE: DNA
<213> ORGANISM: Homo sapiens

<400> SEQUENCE: 1582
agattcacaa tctccttcaa taaaagtgcc aagcagttct cattgcatat catggattcc    60
cagcctggag actcagccac ctacttctgt gcagcaagcg                         100

<210> SEQ ID NO 1583
<211> LENGTH: 100
<212> TYPE: DNA
<213> ORGANISM: Homo sapiens

<400> SEQUENCE: 1583

```
agattcacaa tctccttcaa taaaagtgcc aagcagttct cattgcatat catggattcc    60
cagcctggag actcagccac ctacttctgt gcagcaagca                         100

<210> SEQ ID NO 1584
<211> LENGTH: 100
<212> TYPE: DNA
<213> ORGANISM: Homo sapiens

<400> SEQUENCE: 1584
gaaagaagga agattcacaa tctccttcaa taaaagtgcc aagcagttct cattgcatat    60
catggattcc cagcctggag actcagccac ctacttctgt                        100

<210> SEQ ID NO 1585
<211> LENGTH: 100
<212> TYPE: DNA
<213> ORGANISM: Homo sapiens

<400> SEQUENCE: 1585
ggacgaataa gtgccactct aataccaag gagggttaca gctatttgta catcaaagga    60
tcccagcctg aagattcagc cacataccte tgtgccttta                        100

<210> SEQ ID NO 1586
<211> LENGTH: 100
<212> TYPE: DNA
<213> ORGANISM: Homo sapiens

<400> SEQUENCE: 1586
ctctgatcat cacagaagac agaaagtcca gcaccttgat cctgccccac gctacgctga    60
gagacactgc tgtgtactat tgcatcgtca gagattgggt                        100

<210> SEQ ID NO 1587
<211> LENGTH: 100
<212> TYPE: DNA
<213> ORGANISM: Homo sapiens

<400> SEQUENCE: 1587
caatgaaatg gcctctctga tcatcacaga agacagaaag tccagcacct tgatcctgcc    60
ccacgctacg ctgagagaca ctgctgtgta ctattgcatc                        100

<210> SEQ ID NO 1588
<211> LENGTH: 100
<212> TYPE: DNA
<213> ORGANISM: Homo sapiens

<400> SEQUENCE: 1588
ccctcccagg gtccagagta cgtgattcat ggtcttacaa gcaatgtgaa caacagaatg    60
gcctgtgtgg caatcgctga agacagaaag tccagtacct                        100

<210> SEQ ID NO 1589
<211> LENGTH: 100
<212> TYPE: DNA
<213> ORGANISM: Homo sapiens

<400> SEQUENCE: 1589
tgaagagact aacctttcag tttggtgatg caagaaagga cagttctctc cacatcactg    60
cggcccagcc tggtgataca ggccactacc tctgtgcagg                        100

<210> SEQ ID NO 1590
<211> LENGTH: 100
```

```
<212> TYPE: DNA
<213> ORGANISM: Homo sapiens

<400> SEQUENCE: 1590
gctgaagaga ctaacctttc agtttggtga tgcaagaaag gacagttctc tccacatcac      60
tgcagcccag actggtgata caggcctcta cctctgtgca                            100

<210> SEQ ID NO 1591
<211> LENGTH: 100
<212> TYPE: DNA
<213> ORGANISM: Homo sapiens

<400> SEQUENCE: 1591
aagattcact gttttcttaa acaaaagtgc caagcacctc tctctcgaca ttgtgccctc      60
ccagcctgga gactctgcag tgtacttctg tgcagcaagc                            100

<210> SEQ ID NO 1592
<211> LENGTH: 100
<212> TYPE: DNA
<213> ORGANISM: Homo sapiens

<400> SEQUENCE: 1592
agattcactg ttttcttaaa caaaagtgcc aagcacctct ctctgcacat tgtgccctcc      60
cagcctggag actctgcagt gtacttctgt gcagcaagcg                            100

<210> SEQ ID NO 1593
<211> LENGTH: 100
<212> TYPE: DNA
<213> ORGANISM: Homo sapiens

<400> SEQUENCE: 1593
ctttgaagct gaatttaaca agagccaaac ctccttccac ctgaagaaac catctgccct      60
tgtgagcgac tccgctttgt acttctgtgc tgtgagaccc                            100

<210> SEQ ID NO 1594
<211> LENGTH: 100
<212> TYPE: DNA
<213> ORGANISM: Homo sapiens

<400> SEQUENCE: 1594
tcgtgaaaaa atatctgctt catttaatga aaaaaagcag caaagctccc tgtaccttac      60
ggcctcccag ctcagttact caggaaccta cttctgcggg                            100

<210> SEQ ID NO 1595
<211> LENGTH: 100
<212> TYPE: DNA
<213> ORGANISM: Homo sapiens

<400> SEQUENCE: 1595
tcatgaaaaa atatctgctt catttaatga aaaaaagcgg caaagctccc tgtaccttac      60
ggcctcccag ctcagttact caggaaccta cttctgcggc                            100

<210> SEQ ID NO 1596
<211> LENGTH: 100
<212> TYPE: DNA
<213> ORGANISM: Homo sapiens

<400> SEQUENCE: 1596
tcctgatgat attactgaag ggtggagaac agaagcgtca tgaaaaaata tctgcttcat      60
```

```
ttaatgaaaa aaagcagcaa agctccctgt accttacggc                          100

<210> SEQ ID NO 1597
<211> LENGTH: 100
<212> TYPE: DNA
<213> ORGANISM: Homo sapiens

<400> SEQUENCE: 1597
aaatggaaga ctgactgctc agtttggtat aaccagaaag gacagcttcc tgaatatctc    60
agcatccata cctagtgatg taggcatcta cttctgtgct                          100

<210> SEQ ID NO 1598
<211> LENGTH: 100
<212> TYPE: DNA
<213> ORGANISM: Homo sapiens

<400> SEQUENCE: 1598
ggaagactaa gtagcatatt agataagaaa gaactttca gcatcctgaa catcacagcc     60
acccagaccg gagactcggc cgtctacctc tgtgctgtgg                          100

<210> SEQ ID NO 1599
<211> LENGTH: 100
<212> TYPE: DNA
<213> ORGANISM: Homo sapiens

<400> SEQUENCE: 1599
gtcaggaaga ctaagtagca tattagataa gaaagaactt ttcagcatcc tgaacatcac    60
agccacccag accggagact cggccgtcta cctctgtgct                          100

<210> SEQ ID NO 1600
<211> LENGTH: 100
<212> TYPE: DNA
<213> ORGANISM: Homo sapiens

<400> SEQUENCE: 1600
tcaggaagac taagtagcat attagataag aaagaacttt tcagcatcct gaacatcaca    60
gccacccaga ccggagactc ggccgtctac ctctgtgctg                          100

<210> SEQ ID NO 1601
<211> LENGTH: 100
<212> TYPE: DNA
<213> ORGANISM: Homo sapiens

<400> SEQUENCE: 1601
gagaatcgtt tctctgtgaa cttccagaaa gcagccaaat ccttcagtct caagatctca    60
gactcacagc tgggggacac tgcgatgtat ttctgtgctt                          100

<210> SEQ ID NO 1602
<211> LENGTH: 100
<212> TYPE: DNA
<213> ORGANISM: Homo sapiens

<400> SEQUENCE: 1602
aatcgtttct ctgtgaactt ccagaaagca gccaaatcct tcagtctcaa gatctcagac    60
tcacagctgg gggacactgc gatgtatttc tgtgctttca                          100

<210> SEQ ID NO 1603
<211> LENGTH: 100
<212> TYPE: DNA
<213> ORGANISM: Homo sapiens
```

<400> SEQUENCE: 1603
ggagaatcgt tctctgtga acttccagaa agcagccaaa tccttcagtc tcaagatctc    60
agactcacag ctgggggaca ctgcgatgta tttctgtgca    100

<210> SEQ ID NO 1604
<211> LENGTH: 100
<212> TYPE: DNA
<213> ORGANISM: Homo sapiens

<400> SEQUENCE: 1604
gaaagaaaga ctgaaggtca cctttgatac caccttaaa cagagtttgt ttcatatcac    60
agcctcccag cctgcagact cagctaccta cctctgtgct    100

<210> SEQ ID NO 1605
<211> LENGTH: 100
<212> TYPE: DNA
<213> ORGANISM: Homo sapiens

<400> SEQUENCE: 1605
gaaagaaaga ctgaaggtca cctttgatac cacccttaaa cagagtttgt ttcatatcac    60
agcctcccag cctgcagact cagctaccta cctctgtgct    100

<210> SEQ ID NO 1606
<211> LENGTH: 100
<212> TYPE: DNA
<213> ORGANISM: Homo sapiens

<400> SEQUENCE: 1606
gaaagaaaga ctgaaggtca cctttgatac cacccttaaa cagagtttgt ttcatgtcac    60
agcctcccag cctgcagact cagctaccta cctctgtgct    100

<210> SEQ ID NO 1607
<211> LENGTH: 100
<212> TYPE: DNA
<213> ORGANISM: Homo sapiens

<400> SEQUENCE: 1607
gaaagaaaga ctgaaggtca cctttgatac cacccttaaa cagagtttgt ttcatatcac    60
agcctcccag cctgcagact cagctaccta cctctgtgct    100

<210> SEQ ID NO 1608
<211> LENGTH: 100
<212> TYPE: DNA
<213> ORGANISM: Homo sapiens

<400> SEQUENCE: 1608
ccaggaagag gccctgtttt cttgctactc atacgtgaaa atgagaaaga aaaaggaaa    60 gaaagactga aggtcaccttt tgataccacc cttaaccaga    100

<210> SEQ ID NO 1609
<211> LENGTH: 100
<212> TYPE: DNA
<213> ORGANISM: Homo sapiens

<400> SEQUENCE: 1609
ttttcagggg atccactggt taaaggcatc aagggcgttg aggctgaatt tataaagagt    60
aaattctcct ttaatctgag gaaaccctct gtgcagtgga    100

```
<210> SEQ ID NO 1610
<211> LENGTH: 100
<212> TYPE: DNA
<213> ORGANISM: Homo sapiens

<400> SEQUENCE: 1610
tttaagaaga gtgaaacctc cttccacctg acgaaaccct cagcccatat gagcgacgcg    60
gctgagtact tctgtgttgt gacccgtcac gagctttcag                         100

<210> SEQ ID NO 1611
<211> LENGTH: 100
<212> TYPE: DNA
<213> ORGANISM: Homo sapiens

<400> SEQUENCE: 1611
aggctttgag gctgaattta agaggagtca atcttccttc aacctgagga aaccctctgt    60
gcattggagt gatgctgctg agtacttctg tgctgtggtt                         100

<210> SEQ ID NO 1612
<211> LENGTH: 100
<212> TYPE: DNA
<213> ORGANISM: Homo sapiens

<400> SEQUENCE: 1612
tattaaaggc tttgaggctg aatttaagag gagtcaatct tccttcaatc tgaggaaacc    60
ctctgtgcat tggagtgatg cgtctgagta cttctgtgct                         100

<210> SEQ ID NO 1613
<211> LENGTH: 100
<212> TYPE: DNA
<213> ORGANISM: Homo sapiens

<400> SEQUENCE: 1613
gaatttaaga agagtgaaac ctccttccac ctgacaaaac cctcagccca tatgagcgac    60
gcggctgagt acttctgtgc tgtgagtgat ctcgaaccga                         100

<210> SEQ ID NO 1614
<211> LENGTH: 100
<212> TYPE: DNA
<213> ORGANISM: Homo sapiens

<400> SEQUENCE: 1614
catcaacggt tttgaggctg aatttaagaa gagtgaaacc tccttccacc tgacgaaacc    60
ctcagcccat atgagcgacg cggctgagta cttctgtgct                         100

<210> SEQ ID NO 1615
<211> LENGTH: 100
<212> TYPE: DNA
<213> ORGANISM: Homo sapiens

<400> SEQUENCE: 1615
aggcatcaac ggttttgagg ctgaatttaa gaagagtgaa acctccttcc acctgacgaa    60
accctcagcc catatgagcg acgcggctga gtacttctgt                         100

<210> SEQ ID NO 1616
<211> LENGTH: 100
<212> TYPE: DNA
<213> ORGANISM: Homo sapiens

<400> SEQUENCE: 1616
```

```
ggctgaattt aagaagagtg aaacctcctt ccacctgacg aaaccctcag cccatatgag    60
cgacgcggct gagtacttct gtgctgtgag tgagtctcca                         100
```

<210> SEQ ID NO 1617
<211> LENGTH: 100
<212> TYPE: DNA
<213> ORGANISM: Homo sapiens

<400> SEQUENCE: 1617

```
gaatttaaga agagtgaaac ctccttccac ctgacgaaac ccgcagccca tatgagcgac    60
gcggctgagt acttctgtgc tgtgagtgat ctcgaaccga                         100
```

<210> SEQ ID NO 1618
<211> LENGTH: 100
<212> TYPE: DNA
<213> ORGANISM: Homo sapiens

<400> SEQUENCE: 1618

```
acggttttga ggctgaattt aaaaagagtg aaacctcctt ccacctgacg aaaccctcag    60
cccatatgac cgacccggct gagtacttct gtgctgtgag                         100
```

<210> SEQ ID NO 1619
<211> LENGTH: 100
<212> TYPE: DNA
<213> ORGANISM: Homo sapiens

<400> SEQUENCE: 1619

```
caacaaaggt tttgaagcca cataccgtaa agaaaccact tctttccact tggagaaagg    60
ctcagttcaa gtgtcagact cagcggtgta cttctgtgct                         100
```

<210> SEQ ID NO 1620
<211> LENGTH: 100
<212> TYPE: DNA
<213> ORGANISM: Homo sapiens

<400> SEQUENCE: 1620

```
caacaaaggt tttgaagcca cataccgtaa ggaaaccact tctttccact tggagaaagg    60
ctcagttcaa gtgtcagact cagcggtgta cttctgtgct                         100
```

<210> SEQ ID NO 1621
<211> LENGTH: 100
<212> TYPE: DNA
<213> ORGANISM: Homo sapiens

<400> SEQUENCE: 1621

```
caacaaaggt tttgaagcca cataccgtaa ggaaaccact tctttccact tggagaaagg    60
ctcagttcaa gtgtcagact cagcggtgta cttctgtgct                         100
```

<210> SEQ ID NO 1622
<211> LENGTH: 100
<212> TYPE: DNA
<213> ORGANISM: Homo sapiens

<400> SEQUENCE: 1622

```
ctaacaaagg agaagtctca gatggctaca gtgtctctag atcaaacaca gaggacctcc    60
ccctcactct gtagtctgct gcctcctccc agacatctgt                         100
```

<210> SEQ ID NO 1623

-continued

```
<211> LENGTH: 100
<212> TYPE: DNA
<213> ORGANISM: Homo sapiens

<400> SEQUENCE: 1623
agataaagga gaagtccccg atggctacgt tgtctccaga tccaagacag agaatttccc    60
cctcactctg gagtcagcta cccgctccca gacatctgtg                         100

<210> SEQ ID NO 1624
<211> LENGTH: 100
<212> TYPE: DNA
<213> ORGANISM: Homo sapiens

<400> SEQUENCE: 1624
agaagtctca gatggctata gtgtctctag atcaaagaca gaggatttcc tcctcactct    60
ggagtccgct accagctccc agacatctgt gtacttctgt                         100

<210> SEQ ID NO 1625
<211> LENGTH: 100
<212> TYPE: DNA
<213> ORGANISM: Homo sapiens

<400> SEQUENCE: 1625
agaagtctca gatggctata gtgtctctag atcaaagaca gaggatttcc tcctcactct    60
ggagtccgct accagctccc agacatctgt gtacttctgt                         100

<210> SEQ ID NO 1626
<211> LENGTH: 100
<212> TYPE: DNA
<213> ORGANISM: Homo sapiens

<400> SEQUENCE: 1626
ggatcgattt tctgcagaga ggctcaaagg agtagactcc actctcaaga tccagcctgc    60
aaagcttgag aactcggccg tgtatctctg tgccagcagt                         100

<210> SEQ ID NO 1627
<211> LENGTH: 100
<212> TYPE: DNA
<213> ORGANISM: Homo sapiens

<400> SEQUENCE: 1627
ggatcgattt tctgcagaga ggctcaaagg agtagactcc actctcaaga tccaacctgc    60
aaagcttgag gactcggccg tgtatctctg tgccagcagc                         100

<210> SEQ ID NO 1628
<211> LENGTH: 100
<212> TYPE: DNA
<213> ORGANISM: Homo sapiens

<400> SEQUENCE: 1628
ggatcgattt tctgcagaga ggctcaaagg agtagactcc actctcaaga tccagcctgc    60
agagcttggg gactcggccg tgtatctctg tgccagcagc                         100

<210> SEQ ID NO 1629
<211> LENGTH: 100
<212> TYPE: DNA
<213> ORGANISM: Homo sapiens

<400> SEQUENCE: 1629
ggatcgattt tctgcagaga ggctcaaagg agtagactcc actctcaaga tccagccagc    60
```

```
agagcttggg gactcggcca tgtatctctg tgccagcagc                    100

<210> SEQ ID NO 1630
<211> LENGTH: 100
<212> TYPE: DNA
<213> ORGANISM: Homo sapiens

<400> SEQUENCE: 1630
tcgattctca gctaagatgc ctaatgcatc attctccact ctgaggatcc agccctcaga    60
acccagggac tcagctgtgt acttctgtgc cagcagttta                   100

<210> SEQ ID NO 1631
<211> LENGTH: 100
<212> TYPE: DNA
<213> ORGANISM: Homo sapiens

<400> SEQUENCE: 1631
tgatcgattc tcagctcaac agttcagtga ctatcattct gaactgaaca tgagctcctt    60
ggagctgggg gactcagccc tgtacttctg tgccagcagc                   100

<210> SEQ ID NO 1632
<211> LENGTH: 100
<212> TYPE: DNA
<213> ORGANISM: Homo sapiens

<400> SEQUENCE: 1632
caatcgattc ttagctgaaa ggactggagg gacgtattct actctgaagg tgcagcctgc    60
agaactggag gattctggag tttatttctg tgccagcagc                   100

<210> SEQ ID NO 1633
<211> LENGTH: 100
<212> TYPE: DNA
<213> ORGANISM: Homo sapiens

<400> SEQUENCE: 1633
tgataacttc caatccagga ggccgaacac ttctttctgc tttcttgaca tccgctcacc    60
aggcctgggg gacgcagcca tgtacctgtg tgccaccagc                   100

<210> SEQ ID NO 1634
<211> LENGTH: 100
<212> TYPE: DNA
<213> ORGANISM: Homo sapiens

<400> SEQUENCE: 1634
tgataacttc caatccagga ggccgaacac ttctttctgc tttctagaca tccgctcacc    60
aggcctgggg gacgcagcca tgtaccagtg tgccaccagc                   100

<210> SEQ ID NO 1635
<211> LENGTH: 100
<212> TYPE: DNA
<213> ORGANISM: Homo sapiens

<400> SEQUENCE: 1635
ggaaagattt tcagctaagt gcctcccaaa ttcaccctgt agccttgaga tccaggctac    60
gaagcttgag gattcagcag tgtatttttg tgccagcagc                   100

<210> SEQ ID NO 1636
<211> LENGTH: 100
<212> TYPE: DNA
```

<213> ORGANISM: Homo sapiens

<400> SEQUENCE: 1636
tgaagggtac agcgtctctc gggagaagaa ggaatccttt cctctcactg tgacatcggc    60
ccaaaagaac ccgacagctt tctatctctg tgccagtagc                          100

<210> SEQ ID NO 1637
<211> LENGTH: 100
<212> TYPE: DNA
<213> ORGANISM: Homo sapiens

<400> SEQUENCE: 1637
tgatcaattc tcagttgaaa ggcctgatgg atcaaatttc actctgaaga tccggtccac    60
aaagctggag gactcagcca tgtacttctg tgccagcagt                          100

<210> SEQ ID NO 1638
<211> LENGTH: 100
<212> TYPE: DNA
<213> ORGANISM: Homo sapiens

<400> SEQUENCE: 1638
tcaattctca gttgagaggc ctgatggatc aaatttcact ctgaagatcc ggtccacaaa    60
gctggaggac tcagccatgt acttctgtgc cagcagtgaa                          100

<210> SEQ ID NO 1639
<211> LENGTH: 100
<212> TYPE: DNA
<213> ORGANISM: Homo sapiens

<400> SEQUENCE: 1639
gaaggacaag tttctcatca accatgcaag cctgaccttg tccactctga cagtgaccag    60
tgcccatcct gaagacagca gcttctacat ctgcagtgct                          100

<210> SEQ ID NO 1640
<211> LENGTH: 100
<212> TYPE: DNA
<213> ORGANISM: Homo sapiens

<400> SEQUENCE: 1640
ggacaagttt ctcatcaacc atgcaagcct gaccttgtcc actctgacag tgaccagtgc    60
ccatcctgaa gacagcagct tctacatctg cagtgctagt                          100

<210> SEQ ID NO 1641
<211> LENGTH: 100
<212> TYPE: DNA
<213> ORGANISM: Homo sapiens

<400> SEQUENCE: 1641
ggacaagttt ctcatcaacc atgcaagcct gaccttgtcc actctgacag tgaccagtgc    60
ccatcctgaa gacagcagct tctacatctg cagtgctaga                          100

<210> SEQ ID NO 1642
<211> LENGTH: 100
<212> TYPE: DNA
<213> ORGANISM: Homo sapiens

<400> SEQUENCE: 1642
gaaggacaag tttctcatca accatgcaag cctgaccttg tccactctga cagtgaccag    60
tgcccatcct gaagacagca gcttctacat ctgcagtgct                          100

<210> SEQ ID NO 1643
<211> LENGTH: 100
<212> TYPE: DNA
<213> ORGANISM: Homo sapiens

<400> SEQUENCE: 1643
ggacaagttt ctcatcaacc atgcaagcct gaccttgtcc actctgacag tgaccagtgc    60
ccatcctgaa gacagcagct tctacatctg cagtgctaga                         100

<210> SEQ ID NO 1644
<211> LENGTH: 100
<212> TYPE: DNA
<213> ORGANISM: Homo sapiens

<400> SEQUENCE: 1644
gaaggacaag tttcccatca accatccaaa cctgaccttc tccgctctga cagtgacctg    60
tgcccatcct gaagacagca gcttctacat ctgcagtgct                         100

<210> SEQ ID NO 1645
<211> LENGTH: 100
<212> TYPE: DNA
<213> ORGANISM: Homo sapiens

<400> SEQUENCE: 1645
gtttttgatt tcctttcaga atgaacaagt tcttcaagaa atggagatgc acaagaagcg    60
attctcatct caatgcccca agaacgcacc ctgcagcctg                         100

<210> SEQ ID NO 1646
<211> LENGTH: 100
<212> TYPE: DNA
<213> ORGANISM: Homo sapiens

<400> SEQUENCE: 1646
cagttgatct attgctcctt tgatgtcaaa atatataaac aaaagagaga tctctgatgg    60
atacagtgtc tcttgacagg aacaggctaa attctccctg                         100

<210> SEQ ID NO 1647
<211> LENGTH: 100
<212> TYPE: DNA
<213> ORGANISM: Homo sapiens

<400> SEQUENCE: 1647
gagttaattc cacagagaag ggagatcttt gctctgagtc aacagtctcc agaataagga    60
tagagcgttt tccctgacc ctggagtctg ccagcccctc                          100

<210> SEQ ID NO 1648
<211> LENGTH: 100
<212> TYPE: DNA
<213> ORGANISM: Homo sapiens

<400> SEQUENCE: 1648
tgacaagttt cccatcagcc gcccaaacct aacattctca gtctgactg tgagcaacat     60 gagccctgaa gacagcagca tatatctctg cagcgttgaa                         100

<210> SEQ ID NO 1649
<211> LENGTH: 100
<212> TYPE: DNA
<213> ORGANISM: Homo sapiens

```
<400> SEQUENCE: 1649
tgacaagttt cccatcagcc gcccaaacct aacattctca actctgactg tgagcaacat    60
gagccctgaa gacagcagca tatatctctg cagcgcgggc                         100

<210> SEQ ID NO 1650
<211> LENGTH: 100
<212> TYPE: DNA
<213> ORGANISM: Homo sapiens

<400> SEQUENCE: 1650
tccaaatcga ttctcaccta aatctccaga caaagctaaa ttaaatcttc acatcaattc    60
cctggagctt ggtgactctg ctgtgtattt ctgtgccagc                         100

<210> SEQ ID NO 1651
<211> LENGTH: 100
<212> TYPE: DNA
<213> ORGANISM: Homo sapiens

<400> SEQUENCE: 1651
tcgcttctca cctgactctc cagacaaagt tcatttaaat cttcacatca attccctgga    60
gcttggtgac tctgctgtgt atttctgtgc cagcagccaa                         100

<210> SEQ ID NO 1652
<211> LENGTH: 100
<212> TYPE: DNA
<213> ORGANISM: Homo sapiens

<400> SEQUENCE: 1652
agaatctctc agcctccaga ccccaggacc ggcagttcat cctgagttct aagaagctcc    60
tcctcagtga ctctggcttc tatctctgtg cctggagtgt                         100

<210> SEQ ID NO 1653
<211> LENGTH: 100
<212> TYPE: DNA
<213> ORGANISM: Homo sapiens

<400> SEQUENCE: 1653
ccagaatctc tcagcctcca gaccccagga ccggcagttc attctgagtt ctaagaagct    60
cctcctcagt gactctggct tctatctctg tgcctggagt                         100

<210> SEQ ID NO 1654
<211> LENGTH: 100
<212> TYPE: DNA
<213> ORGANISM: Homo sapiens

<400> SEQUENCE: 1654
ccagaatctc tcagcctcca gaccccagga ccggcagttc atcctgagtt ctaagaagct    60
ccttctcagt gactctggct tctatctctg tgcctgggga                         100

<210> SEQ ID NO 1655
<211> LENGTH: 100
<212> TYPE: DNA
<213> ORGANISM: Homo sapiens

<400> SEQUENCE: 1655
tcgcttctca cctgaatgcc ccaacagctc tctcttaaac cttcacctac acgccctgca    60
gccagaagac tcagccctgt atctctgcgc cagcagccaa                         100
```

```
<210> SEQ ID NO 1656
<211> LENGTH: 100
<212> TYPE: DNA
<213> ORGANISM: Homo sapiens

<400> SEQUENCE: 1656
aagtcgcttc tcacctgaat gccccaacag ctctcactta tgccttcacc tacacaccct      60
gcagccagaa gactcggccc tgtatctctg tgccagcacc                            100

<210> SEQ ID NO 1657
<211> LENGTH: 100
<212> TYPE: DNA
<213> ORGANISM: Homo sapiens

<400> SEQUENCE: 1657
aagtcgcttc tcacctgaat gccccaacag ctctcactta tcccttcacc tacacaccct      60
gcagccagaa gactcggccc tgtatctctg cgccagcagc                            100

<210> SEQ ID NO 1658
<211> LENGTH: 100
<212> TYPE: DNA
<213> ORGANISM: Homo sapiens

<400> SEQUENCE: 1658
aagtcgcttc tcacctgaat gccccaacag ctctcactta ttccttcacc tacacaccct      60
gcagccagaa gactcggccc tgtatctctg cgccagcagc                            100

<210> SEQ ID NO 1659
<211> LENGTH: 100
<212> TYPE: DNA
<213> ORGANISM: Homo sapiens

<400> SEQUENCE: 1659
aagtcgcttc tcacctgaat gccccaacag ctctcactta ttccttcacc tacacaccct      60
gcagccagaa gactcggccc tgtatctctg cgccagcagc                            100

<210> SEQ ID NO 1660
<211> LENGTH: 100
<212> TYPE: DNA
<213> ORGANISM: Homo sapiens

<400> SEQUENCE: 1660
tcgattctca gggcgccagt tctctaactc tcgctctgag atgaatgtga gcaccttgga      60 gctggggac tcggcccttt atctttgcgc cagcgcttgc                             100

<210> SEQ ID NO 1661
<211> LENGTH: 100
<212> TYPE: DNA
<213> ORGANISM: Homo sapiens

<400> SEQUENCE: 1661
tcctagattc tcaggtctcc agttccctaa ttataactct gagctgaatg tgaacgcctt      60
ggagctggac gactcggccc tgtatctctg tgccagcagc                            100

<210> SEQ ID NO 1662
<211> LENGTH: 100
<212> TYPE: DNA
<213> ORGANISM: Homo sapiens

<400> SEQUENCE: 1662
```

```
tcctagattc tcaggtctcc agttccctaa ttatagctct gagctgaatg tgaacgcctt    60
ggagctggac gactcggccc tgtatctctg tgccagcagc                         100

<210> SEQ ID NO 1663
<211> LENGTH: 100
<212> TYPE: DNA
<213> ORGANISM: Homo sapiens

<400> SEQUENCE: 1663
tcctagattc tcaggtctcc agttccctaa ttatagctct gagctgaatg tgaacgcctt    60
ggagctggac gactcggccc tgtatctctg tgccagcagc                         100

<210> SEQ ID NO 1664
<211> LENGTH: 100
<212> TYPE: DNA
<213> ORGANISM: Homo sapiens

<400> SEQUENCE: 1664
tgatcgattc tcagctcgcc agttccctaa ctatagctct gagctgaatg tgaacgcctt    60
gttgctgggg gactcggccc tgtatctctg tgccagcagc                         100

<210> SEQ ID NO 1665
<211> LENGTH: 100
<212> TYPE: DNA
<213> ORGANISM: Homo sapiens

<400> SEQUENCE: 1665
tgatcgattc tcagctcgcc agttccctaa ctatagctct gagctgaatg tgaacgcctt    60
gttgctgggg gactcggccc tgtatctctg tgccagcagc                         100

<210> SEQ ID NO 1666
<211> LENGTH: 100
<212> TYPE: DNA
<213> ORGANISM: Homo sapiens

<400> SEQUENCE: 1666
tcctagattt tcaggtcgcc agttccctaa ttatagctct gagctgaatg tgaacgcctt    60
ggagctggag gactcggccc tgtatctctg tgccagcagc                         100

<210> SEQ ID NO 1667
<211> LENGTH: 100
<212> TYPE: DNA
<213> ORGANISM: Homo sapiens

<400> SEQUENCE: 1667
tggctacaat gtctccagat taaaaaaaca gaatttcctg ctggggttgg agtcggctgc    60
tccctcccaa acatctgtgt acttctgtgc cagcagccct                         100

<210> SEQ ID NO 1668
<211> LENGTH: 100
<212> TYPE: DNA
<213> ORGANISM: Homo sapiens

<400> SEQUENCE: 1668
gaatggctac aacgtctcca gatcaaccac agaggatttc ccgctcaggc tggagttggc    60 tgctcccctcc cagacatctg tgtacttctg tgccagcagt                        100

<210> SEQ ID NO 1669
<211> LENGTH: 100
```

```
<212> TYPE: DNA
<213> ORGANISM: Homo sapiens

<400> SEQUENCE: 1669
tggctacaat gtctccagat caaccacaga ggatttcccg ctcaggctgg agttggctgc      60
tccctcccag acatctgtgt acttctgtgc cagcagtcga                          100

<210> SEQ ID NO 1670
<211> LENGTH: 100
<212> TYPE: DNA
<213> ORGANISM: Homo sapiens

<400> SEQUENCE: 1670
gaatggctac aacgtctcca gatcaaccac agaggatttc ccgctcaggc tggagttggc      60
tgctgcctcc cagacatctg tgtacttctg tgccagcagc                          100

<210> SEQ ID NO 1671
<211> LENGTH: 100
<212> TYPE: DNA
<213> ORGANISM: Homo sapiens

<400> SEQUENCE: 1671
gcttctctgc agagaggact ggggaatccg tctccactct gacgatccag cgcacacagc      60
aggaggactc ggccgtgtat ctctgtacca gcagcttagc                          100

<210> SEQ ID NO 1672
<211> LENGTH: 100
<212> TYPE: DNA
<213> ORGANISM: Homo sapiens

<400> SEQUENCE: 1672
tcgcttctct gcagagagga ctgggggatc cgtctccact ctgacgatcc agcgcacaca      60
gcaggaggac tcggccgtgt atctctgtgc cagcagctta                          100

<210> SEQ ID NO 1673
<211> LENGTH: 100
<212> TYPE: DNA
<213> ORGANISM: Homo sapiens

<400> SEQUENCE: 1673
cgatcggttc tttgcagtca ggcctgaggg atccgtctct actctgaaga tccagcgcac      60
agagcggggg gactctgccg tgtatctctg tgccagcagc                          100

<210> SEQ ID NO 1674
<211> LENGTH: 100
<212> TYPE: DNA
<213> ORGANISM: Homo sapiens

<400> SEQUENCE: 1674
cgatcggttc tttgcagtca ggcctgaggg atccgtctct actctgaaga tccagcgcac      60
agagcggggg gactcagccg tgtatctctg tgccagcagc                          100

<210> SEQ ID NO 1675
<211> LENGTH: 100
<212> TYPE: DNA
<213> ORGANISM: Homo sapiens

<400> SEQUENCE: 1675
aacgagacaa atcagggcgg cccagtggtc ggttctctgc agagaggcct gagagatcgt      60
```

```
ctccactccg aagatccagc gcacagagca gggggactca                    100
```

<210> SEQ ID NO 1676
<211> LENGTH: 100
<212> TYPE: DNA
<213> ORGANISM: Homo sapiens

<400> SEQUENCE: 1676

```
tgatcggttc tctgcagaga ggcctgaggg atccatctcc actctgacga tccagcgcac    60
agagcagcgg gactcggcca tgtatcgctg tgccagcagc                         100
```

<210> SEQ ID NO 1677
<211> LENGTH: 100
<212> TYPE: DNA
<213> ORGANISM: Homo sapiens

<400> SEQUENCE: 1677

```
tgatcggttc tctgcagaga ggcctgaggg atccatctcc actctgacga ttcagcgcac    60
agagcagcgg gactcagcca tgtatcgctg tgccagcagc                         100
```

<210> SEQ ID NO 1678
<211> LENGTH: 100
<212> TYPE: DNA
<213> ORGANISM: Homo sapiens

<400> SEQUENCE: 1678

```
tcgcttcttt gcagaaaggc ctgagggatc cgtctccact ctgaagatcc agcgcacaca    60
gcaggaggac tccgccgtgt atctctgtgc cagcagccga                         100
```

<210> SEQ ID NO 1679
<211> LENGTH: 100
<212> TYPE: DNA
<213> ORGANISM: Homo sapiens

<400> SEQUENCE: 1679

```
tcggttctct gcagagaggc ctaagggatc tttctccacc ttggagatcc agcgcacaga    60
gcaggggac tcggccatgt atctctgtgc cagcagctta                          100
```

<210> SEQ ID NO 1680
<211> LENGTH: 100
<212> TYPE: DNA
<213> ORGANISM: Homo sapiens

<400> SEQUENCE: 1680

```
tcggatctct gcagagaggc ctaagggatc tttctccacc ttggagatcc agcgcacaga    60
gcaggggac tcggccatgt atctctgtgc cagcagctct                          100
```

<210> SEQ ID NO 1681
<211> LENGTH: 100
<212> TYPE: DNA
<213> ORGANISM: Homo sapiens

<400> SEQUENCE: 1681

```
tcggttctct gcagagaggc ctaagggatc tctctccacc ttggagatcc agcgcacaga    60
gcaggggac tcggccatgt atctctgtgc cagcaccaaa                          100
```

<210> SEQ ID NO 1682
<211> LENGTH: 100
<212> TYPE: DNA
<213> ORGANISM: Homo sapiens

<400> SEQUENCE: 1682
tcggttctct gcagagaggc ctaagggatc tctttccacc ttggagatcc agcgcacaga    60 gcaggggac tcggccatgt atctctgtgc cagcacgttg    100

<210> SEQ ID NO 1683
<211> LENGTH: 100
<212> TYPE: DNA
<213> ORGANISM: Homo sapiens

<400> SEQUENCE: 1683
gttctctgca gagaggccta agggatcttt ctccaccttg gagatccagc gcacagagga    60 ggggactcg gccatgtatc tctgtgccag cagcagcagt    100

<210> SEQ ID NO 1684
<211> LENGTH: 100
<212> TYPE: DNA
<213> ORGANISM: Homo sapiens

<400> SEQUENCE: 1684
tgaacgattc tccgcacaac agttccctga cttgcactct gaactaaacc tgagctctct    60
ggagctgggg gactcagctt tgtatttctg tgccagcagc    100

<210> SEQ ID NO 1685
<211> LENGTH: 100
<212> TYPE: DNA
<213> ORGANISM: Homo sapiens

<400> SEQUENCE: 1685
gaagtattat acttacgcaa gcacaaggaa caacttgaga ttgatactgc aaaatctaat    60
tgaaaatgac tctggggtct attactgtgc cacctgggac    100

<210> SEQ ID NO 1686
<211> LENGTH: 100
<212> TYPE: DNA
<213> ORGANISM: Homo sapiens

<400> SEQUENCE: 1686
gaaggacaag tttctcatca accatgcaag cctgaccttg tccactctga cagtgaccag    60
tgcccatcct gaagacagca gcttctacat ctgcagtgct    100

<210> SEQ ID NO 1687
<211> LENGTH: 100
<212> TYPE: DNA
<213> ORGANISM: Homo sapiens

<400> SEQUENCE: 1687
gcatgatact tatggaagta gaaggataag ctggaaattt atacctccaa aactaaatga    60
aaatgcctct ggggtctatt actgtgccac ctaggacagg    100

<210> SEQ ID NO 1688
<211> LENGTH: 100
<212> TYPE: DNA
<213> ORGANISM: Homo sapiens

<400> SEQUENCE: 1688
gtatgatact tacggaagca caaggaagaa cttgagaatg atactgcgaa atcttattga    60
aaatgactct ggagtctatt actgtgccac ctgggatggg    100

<210> SEQ ID NO 1689
<211> LENGTH: 100
<212> TYPE: DNA
<213> ORGANISM: Homo sapiens

<400> SEQUENCE: 1689
gtattatact catacaccga ggaggtggag ctggaatttg agactgcaaa atctaattga    60
aaatgattct ggggtctatt actgtgccac ctggggcagg                        100

<210> SEQ ID NO 1690
<211> LENGTH: 100
<212> TYPE: DNA
<213> ORGANISM: Homo sapiens

<400> SEQUENCE: 1690
gctatagtgt ctctagatca aagacagagg atttcctcct cactctggag tccgctacca    60
gctcccagac atctgtgtac ttctgtgcca tcagtgagtc                        100

<210> SEQ ID NO 1691
<211> LENGTH: 100
<212> TYPE: DNA
<213> ORGANISM: Homo sapiens

<400> SEQUENCE: 1691
atacagtgtc tctcgacagg cacaggctaa attctccctg tccctagagt ctgccatccc    60
caaccagaca gctctttact tctgtgccac cagtgatttg                        100

<210> SEQ ID NO 1692
<211> LENGTH: 100
<212> TYPE: DNA
<213> ORGANISM: Homo sapiens

<400> SEQUENCE: 1692
acaagtttcc catcaaccat ccaaacctga ccttctccgc tctgacagtg accagtgccc    60
atcctgaaga cagcagcttc tacatctgca gtgctagaga                        100

<210> SEQ ID NO 1693
<211> LENGTH: 100
<212> TYPE: DNA
<213> ORGANISM: Homo sapiens

<400> SEQUENCE: 1693
ggtaagtaaa aatgctcaca cttccacttc cactttgaaa ataaagttct tagagaaaga    60
agatgaggtg gtgtaccact gtgcctgctg gattaggcac                        100

<210> SEQ ID NO 1694
<211> LENGTH: 100
<212> TYPE: DNA
<213> ORGANISM: Homo sapiens

<400> SEQUENCE: 1694
gcttctttgc agaaaggcct gagggatccg tctccactct gaagatccag cgcacacaga    60
aggaggactc cgccgtgtat ctctgtgcca gcagcttagc                        100

<210> SEQ ID NO 1695
<211> LENGTH: 100
<212> TYPE: DNA
<213> ORGANISM: Homo sapiens

<400> SEQUENCE: 1695

```
ggttctttgc agtcaggcct gagggatccg tctctactct gaagatccag cgcacagagc    60
agggggactc agccgtgtat ctccgtgcca gcagcttaac                         100

<210> SEQ ID NO 1696
<211> LENGTH: 100
<212> TYPE: DNA
<213> ORGANISM: Homo sapiens

<400> SEQUENCE: 1696
aggcaagaaa gaattctcaa actctcactt caatccttac catcaagtcc gtagagaaag    60
aagacatggc cgtttactac tgtgctgcgt ggtgggtggc                         100

<210> SEQ ID NO 1697
<211> LENGTH: 100
<212> TYPE: DNA
<213> ORGANISM: Homo sapiens

<400> SEQUENCE: 1697
tgaggtggat aggatacctg aaacgtctac atccactctc accattcaca atgtagagaa    60
acaggacata gctacctact actgtgcctt gtgggaggtg                         100

<210> SEQ ID NO 1698
<211> LENGTH: 100
<212> TYPE: DNA
<213> ORGANISM: Homo sapiens

<400> SEQUENCE: 1698
gacggttttc tgtgaaacac attctgaccc agaaagcctt tcacttggtg atctctccag    60
taaggactga agacagtgcc acttactact gtgcctttag                         100

<210> SEQ ID NO 1699
<211> LENGTH: 100
<212> TYPE: DNA
<213> ORGANISM: Homo sapiens

<400> SEQUENCE: 1699
aatttccaag gtgacattga tattgcaaag aacctggctg tacttaagat acttgcacca    60
tcagagagag atgaagggtc ttactactgt gcctgtgaca                         100

<210> SEQ ID NO 1700
<211> LENGTH: 100
<212> TYPE: DNA
<213> ORGANISM: Homo sapiens

<400> SEQUENCE: 1700
agtattatac tcatacaccc aggaggtgga gctggatatt gagactgcaa aatctaattg    60
aaaatgattc tggggtctat tactgtgcca cctgggacag                         100

<210> SEQ ID NO 1701
<211> LENGTH: 100
<212> TYPE: DNA
<213> ORGANISM: Homo sapiens

<400> SEQUENCE: 1701
tttccaaggt gacattgata ttgcaaagaa cctggctgta cttaagatac ttgcaccatc    60
agagagagat gaagggtctt actactgtgc ctgtgacacc                         100

<210> SEQ ID NO 1702
```

```
<211> LENGTH: 100
<212> TYPE: DNA
<213> ORGANISM: Homo sapiens

<400> SEQUENCE: 1702
ggtacagcgt ctctcgggag aagaaggaat cctttcctct cactgtgaca tcggcccaaa      60
agaacccgac agctttctat ctctgtgcca gtagtataga                            100

<210> SEQ ID NO 1703
<211> LENGTH: 100
<212> TYPE: DNA
<213> ORGANISM: Homo sapiens

<400> SEQUENCE: 1703
actcattgaa tttccagaag gcaagaaaat ccgccaacct tgtcatctcc gcttcacaac      60
tgggggactc agcaatgtac ttctgtgcaa tgagagaggg                            100

<210> SEQ ID NO 1704
<211> LENGTH: 100
<212> TYPE: DNA
<213> ORGANISM: Homo sapiens

<400> SEQUENCE: 1704
gcttctcacc tgactctcca gacaaagttc atttaaatct tcacatcaat tccctggagc      60
ttggtgactc tgctgtgtat ttctgtgcca gcagccaaga                            100

<210> SEQ ID NO 1705
<211> LENGTH: 100
<212> TYPE: DNA
<213> ORGANISM: Homo sapiens

<400> SEQUENCE: 1705
tggaggcaag aaagaattct caaactctca cttcaatcct taccatcaag tccgtagaga      60
aagaagacat ggccgtttac tactgtgctg cgtgggatta                            100

<210> SEQ ID NO 1706
<211> LENGTH: 100
<212> TYPE: DNA
<213> ORGANISM: Homo sapiens

<400> SEQUENCE: 1706
caaatatttt aaagaactgc ttggaaaaga aaaattttat agtgtttgga atatcgcagc      60
ctctcatctg ggagattcag ccacctactt ctgtgctttg                            100

<210> SEQ ID NO 1707
<211> LENGTH: 100
<212> TYPE: DNA
<213> ORGANISM: Homo sapiens

<400> SEQUENCE: 1707
aacttgccta attgattctc agctcaccac gtccataact attactgagt caaacacgga      60
gctaggggac tcagccctgt atctctgtgc cagcaacttg                            100

<210> SEQ ID NO 1708
<211> LENGTH: 100
<212> TYPE: DNA
<213> ORGANISM: Homo sapiens

<400> SEQUENCE: 1708
ggaagggtac aatgtctctg gaaacaagct caagcatttt ccctcaaccc tggagtctac      60
```

```
tagcaccagc cagacctctg tacctctgtg gcagtgcatc                          100
```

<210> SEQ ID NO 1709
<211> LENGTH: 100
<212> TYPE: DNA
<213> ORGANISM: Homo sapiens

<400> SEQUENCE: 1709

```
tctctgtgaa cttccagaaa gcagccaaat ccttcagtct caagatctca gactcacagc    60
tgggggacac tgcgatgtat ttctgtgctt tcatgaagca                          100
```

<210> SEQ ID NO 1710
<211> LENGTH: 100
<212> TYPE: DNA
<213> ORGANISM: Homo sapiens

<400> SEQUENCE: 1710

```
aggctacgtg tctgccaaga ggagaagggg ctatttcttc tcagggtgaa gttggcccac    60
accagccaaa cagctttgta cttctgtcct gggagcgcac                          100
```

<210> SEQ ID NO 1711
<211> LENGTH: 100
<212> TYPE: DNA
<213> ORGANISM: Homo sapiens

<400> SEQUENCE: 1711

```
gattttcagc taagtgcctc ccaaattcac cctgtagcct tgagatccag gctacgaagc    60
ttgaggattc agcagtgtat ttttgtgcca gcagccaatc                          100
```

<210> SEQ ID NO 1712
<211> LENGTH: 100
<212> TYPE: DNA
<213> ORGANISM: Homo sapiens

<400> SEQUENCE: 1712

```
agaatctctc agcctccaga ccccaggacc ggcagttcat cctgagttct aagaagctcc    60
ttctcagtga ctctggcttc tatctctgtg cctggagtgt                          100
```

<210> SEQ ID NO 1713
<211> LENGTH: 100
<212> TYPE: DNA
<213> ORGANISM: Homo sapiens

<400> SEQUENCE: 1713

```
tttgaagctg aatttaacaa gagccaaacc tccttccacc tgaagaaacc atctgccctt    60
gtgagcgact ccgctttgta cttctgtgct gtgagagaca                          100
```

<210> SEQ ID NO 1714
<211> LENGTH: 100
<212> TYPE: DNA
<213> ORGANISM: Homo sapiens

<400> SEQUENCE: 1714

```
gcctctctga tcatcacaga agacagaaag tccagcacct tgatcctgcc ccacgctacg    60
ctgagagaca ctgctgtgta ctattgcatc gtcagagtcg                          100
```

<210> SEQ ID NO 1715
<211> LENGTH: 100
<212> TYPE: DNA

<213> ORGANISM: Homo sapiens

<400> SEQUENCE: 1715
aggctcactg tactgttgaa taaaaatgct aaacatgtct ccctgcatat tacagccacc    60
caaccaggag actcattcct gtacttctgt gcagtgagaa    100

<210> SEQ ID NO 1716
<211> LENGTH: 100
<212> TYPE: DNA
<213> ORGANISM: Homo sapiens

<400> SEQUENCE: 1716
gcaaagcctg tgaactttga aaaaagaaa aagttcatca acctcaccat caattcctta    60
aaactgactc agccaagtac ttctgtgctc tcaggaatcc    100

<210> SEQ ID NO 1717
<211> LENGTH: 100
<212> TYPE: DNA
<213> ORGANISM: Homo sapiens

<400> SEQUENCE: 1717
gattctcagc tcaacagttc agtgactatc attctgaact gaacatgagc tccttggagc    60
tgggggactc agccctgtac ttctgtgcca gcagcttagg    100

<210> SEQ ID NO 1718
<211> LENGTH: 100
<212> TYPE: DNA
<213> ORGANISM: Homo sapiens

<400> SEQUENCE: 1718
acttccaatc caggaggccg aacacttctt tctgctttct tgacatccgc tcaccaggcc    60
tgggggacac agccatgtac ctgtgtgcca ccagcagaga    100

<210> SEQ ID NO 1719
<211> LENGTH: 100
<212> TYPE: DNA
<213> ORGANISM: Homo sapiens

<400> SEQUENCE: 1719
agggacgata caacatgacc tatgaacggt tctcttcatc gctgctcatc ctccaggtgc    60
gggaggcaga tgctgctgtt tactactgtg ctgtggagga    100

<210> SEQ ID NO 1720
<211> LENGTH: 100
<212> TYPE: DNA
<213> ORGANISM: Homo sapiens

<400> SEQUENCE: 1720
ggttctctgc acagaggtct gagggatcca tctccactct gaagttccag cgcacacagc    60
agggggactt ggctgtgtat ctctgtgcca gcagctcagc    100

<210> SEQ ID NO 1721
<211> LENGTH: 100
<212> TYPE: DNA
<213> ORGANISM: Homo sapiens

<400> SEQUENCE: 1721
gattctcatc tcaatgcccc aagaacgcac cctgcagcct ggcaatcctg tcctcagaac    60
cgggagacac ggcactgtat ctctgcgcca gcagtcaatc    100

<210> SEQ ID NO 1722
<211> LENGTH: 100
<212> TYPE: DNA
<213> ORGANISM: Homo sapiens

<400> SEQUENCE: 1722
gatgcacaag aagcgattct catctcaatg ccccaagaac ccaccctgca gcctggcaat    60
cctgtcctcg gaaccgggag acaccgcact gtatctctgt                         100

<210> SEQ ID NO 1723
<211> LENGTH: 100
<212> TYPE: DNA
<213> ORGANISM: Homo sapiens

<400> SEQUENCE: 1723
tccctattga aaatatttcc tggcaaaaaa tagaagttct ctttggctct gaaatctgca    60
actccctttc aggtgtccct gtgtccttgt accgtcactc                         100

<210> SEQ ID NO 1724
<211> LENGTH: 100
<212> TYPE: DNA
<213> ORGANISM: Homo sapiens

<400> SEQUENCE: 1724
tccctgttga aaatatttcc cggcaaaaaa cagaagttcc ctttggctct gaaatctgca    60 aagcccttc agatgtccct gtgtccttgt gccgtcactc                          100

<210> SEQ ID NO 1725
<211> LENGTH: 100
<212> TYPE: DNA
<213> ORGANISM: Homo sapiens

<400> SEQUENCE: 1725
gattctcagc acagatgcct gatgtatcat tctccactct gaggatccag cccatggaac    60
ccagggactt gggcctatat ttctgtgcca gcagctttgc                         100

<210> SEQ ID NO 1726
<211> LENGTH: 100
<212> TYPE: DNA
<213> ORGANISM: Homo sapiens

<400> SEQUENCE: 1726
ggtatcatgt ttcttgaaat actatagcat cttttctcct gaccctgaag tctgctagca    60
ccaaccagac atgtgtgtat ctctgcgcca gcagttcatc                         100

<210> SEQ ID NO 1727
<211> LENGTH: 100
<212> TYPE: DNA
<213> ORGANISM: Homo sapiens

<400> SEQUENCE: 1727
tgaggtggat aggatacctg aaacgtctac atccactctc accattcaca atgtagagaa    60
acaggacata gctacctact actgtgcctt gtgggaggtg                         100

<210> SEQ ID NO 1728
<211> LENGTH: 100
<212> TYPE: DNA
<213> ORGANISM: Homo sapiens

<400> SEQUENCE: 1728
cttgaggcaa gaacaaattt tcaaatgtct acttcagtct ttaccataaa cttcatagga    60
aaggaagatg aggccattta ctactgcact gcttaggacc                         100

<210> SEQ ID NO 1729
<211> LENGTH: 100
<212> TYPE: DNA
<213> ORGANISM: Homo sapiens

<400> SEQUENCE: 1729
ggttctttgc agtcaggcct gagggatccg tctctactct gaagatccag cgcacagagc    60 gggggggactc agccgtgtat ctctgtgcca gcagcttaac                        100

<210> SEQ ID NO 1730
<211> LENGTH: 100
<212> TYPE: DNA
<213> ORGANISM: Homo sapiens

<400> SEQUENCE: 1730
ggttctctgc agagaggcct aagggatctt tctccacctt ggagatccag cgcacagagc    60 aggggggactc ggccatgtat ctctgtgcca gcagcttagc                        100

<210> SEQ ID NO 1731
<211> LENGTH: 100
<212> TYPE: DNA
<213> ORGANISM: Homo sapiens

<400> SEQUENCE: 1731
gcttctctgc agagaggact gggggatccg tctccactct gacgatccag cgcacacagc    60
aggaggactc ggccgtgtat ctctgtgcca gcagcttagc                         100

<210> SEQ ID NO 1732
<211> LENGTH: 100
<212> TYPE: DNA
<213> ORGANISM: Homo sapiens

<400> SEQUENCE: 1732
gcttctctgc agagaggact ggggaatccg tctccactct gacgatccag cgcacacagc    60
aggaggactc ggccgtgtat ctctgtgcca gcagcttagc                         100

<210> SEQ ID NO 1733
<211> LENGTH: 100
<212> TYPE: DNA
<213> ORGANISM: Homo sapiens

<400> SEQUENCE: 1733
ggttctctgc agagaggcct gagggatcca tctccactct gacgattcag cgcacagagc    60
agcgggactc agccatgtat cgctgtgcca gcagcttagc                         100

<210> SEQ ID NO 1734
<211> LENGTH: 100
<212> TYPE: DNA
<213> ORGANISM: Homo sapiens

<400> SEQUENCE: 1734
gcttctttgc agaaaggcct gagggatccg tctccactct gaagatccag cgcacacagc    60
aggaggactc cgccgtgtat ctctgtgcca gcagcttagc                         100

<210> SEQ ID NO 1735
<211> LENGTH: 100
<212> TYPE: DNA
<213> ORGANISM: Homo sapiens

<400> SEQUENCE: 1735
aacgattcac agctgaaaga cctaacggaa cgtcttccac gctgaagatc catcccgcag    60
agccgaggga ctcagccgtg tatctctaca gtagcggtgg                         100

<210> SEQ ID NO 1736
<211> LENGTH: 100
<212> TYPE: DNA
<213> ORGANISM: Homo sapiens

<400> SEQUENCE: 1736
agattttcag gtcgccagtt ccctaattat agctctgagc tgaatgtgaa cgccttggag    60
ctggaggact cggccctgta tctctgtgcc agcagcttgg                         100

<210> SEQ ID NO 1737
<211> LENGTH: 100
<212> TYPE: DNA
<213> ORGANISM: Homo sapiens

<400> SEQUENCE: 1737
caattctcag gtcaccagtt ccctaactat agctctgagc tgaatgtgaa cgccttgttg    60
ctaggggact cggccctcta tctctgtgcc agcagcttgg                         100

<210> SEQ ID NO 1738
<211> LENGTH: 100
<212> TYPE: DNA
<213> ORGANISM: Homo sapiens

<400> SEQUENCE: 1738
cgattctcag gtcaccagtt ccctaactat agctctgagc tgaatgtgaa cgccttgttg    60
ctgggggact cggccctcta tctctgtgcc agcagcttgg                         100

<210> SEQ ID NO 1739
<211> LENGTH: 100
<212> TYPE: DNA
<213> ORGANISM: Homo sapiens

<400> SEQUENCE: 1739
cgattctcag ctcgccagtt ccctaactat agctctgagc tgaatgtgaa cgccttgttg    60
ctgggggact cggccctgta tctctgtgcc agcagcttgg                         100

<210> SEQ ID NO 1740
<211> LENGTH: 100
<212> TYPE: DNA
<213> ORGANISM: Homo sapiens

<400> SEQUENCE: 1740
agattctcag gtctccagtt ccctaattat agctctgagc tgaatgtgaa cgccttggag    60
ctggacgact cggccctgta tctctgtgcc agcagcttgg                         100

<210> SEQ ID NO 1741
<211> LENGTH: 100
<212> TYPE: DNA
<213> ORGANISM: Homo sapiens

<400> SEQUENCE: 1741

```
cgattctcag ggcgccagtt ctctaactct cgctctgaga tgaatgtgag caccttggag      60
ctgggggact cggcccttta tctttgcgcc agcagcttgg                           100
```

<210> SEQ ID NO 1742
<211> LENGTH: 100
<212> TYPE: DNA
<213> ORGANISM: Homo sapiens

<400> SEQUENCE: 1742

```
gcttctcacc taaatctcca gacaaagctc acttaaatct tcacatcaat tccctggagc      60
ttggtgactc tgctgtgtat ttctgtgcca gcagccaaga                           100
```

<210> SEQ ID NO 1743
<211> LENGTH: 100
<212> TYPE: DNA
<213> ORGANISM: Homo sapiens

<400> SEQUENCE: 1743

```
acttcacacc tgaatgccct gacagctctc gcttatacct tcatgtggtc gcactgcagc      60
aagaagactc agctgcgtat ctctgcacca gcagccaaga                           100
```

<210> SEQ ID NO 1744
<211> LENGTH: 100
<212> TYPE: DNA
<213> ORGANISM: Homo sapiens

<400> SEQUENCE: 1744

```
cgattctcag ggcgccagtt ccatgactgt tgctctgaga tgaatgtgag tgccttggag      60
ctgggggact cggccctgta tctctgtgcc agaagcttgg                           100
```

<210> SEQ ID NO 1745
<211> LENGTH: 100
<212> TYPE: DNA
<213> ORGANISM: Homo sapiens

<400> SEQUENCE: 1745

```
cgattctcag ggcgccagtt ccatgactat tgctctgaga tgaatgtgag tgccttggag      60
ctgggggact cggccctgta tctctgtgcc agaagcttgg                           100
```

<210> SEQ ID NO 1746
<211> LENGTH: 100
<212> TYPE: DNA
<213> ORGANISM: Homo sapiens

<400> SEQUENCE: 1746

```
cgattctccg cacaacagtt ccctgacttg cactctgaac taaacctgag ctctctggag      60
ctgggggact cagctttgta tttctgtgcc agcagcgtag                           100
```

<210> SEQ ID NO 1747
<211> LENGTH: 100
<212> TYPE: DNA
<213> ORGANISM: Homo sapiens

<400> SEQUENCE: 1747

```
gcttctcacc tgactctcca gacaaagctc atttaaatct tcacatcaat tccctggagc      60
ttggtgactc tgctgtgtat ttctgtgcca gcagccaaga                           100
```

<210> SEQ ID NO 1748
<211> LENGTH: 100

```
<212> TYPE: DNA
<213> ORGANISM: Homo sapiens

<400> SEQUENCE: 1748
aattctcagt tgaaaggcct gatggatcaa atttcactct gaagatccgg tccacaaagc    60
tggaggactc agccatgtac ttctgtgcca gcagtgaagc                         100

<210> SEQ ID NO 1749
<211> LENGTH: 100
<212> TYPE: DNA
<213> ORGANISM: Homo sapiens

<400> SEQUENCE: 1749
gcttctcacc tgaatgcccc aacagctctc acttattcct tcacctacac accctgcagc    60
cagaagactc ggccctgtat ctctgcgcca gcagccaaga                         100

<210> SEQ ID NO 1750
<211> LENGTH: 100
<212> TYPE: DNA
<213> ORGANISM: Homo sapiens

<400> SEQUENCE: 1750
gcttctcacc tgaatgcccc aacagctctc tcttaaacct tcacctacac gccctgcagc    60
cagaagactc agccctgtat ctctgcgcca gcagccaaga                         100

<210> SEQ ID NO 1751
<211> LENGTH: 100
<212> TYPE: DNA
<213> ORGANISM: Homo sapiens

<400> SEQUENCE: 1751
gcttctcacc tgaatgcccc aacagctctc acttattcct tcacctacac accctgcagc    60
cagaagactc ggccctgtat ctctgtgcca gcagccaaga                         100

<210> SEQ ID NO 1752
<211> LENGTH: 100
<212> TYPE: DNA
<213> ORGANISM: Homo sapiens

<400> SEQUENCE: 1752
aagataactg ccaagttgga tgagaaaaag cagcaaagtt ccctgcatat cacagcctcc    60
cagcccagcc atgcaggcat ctacctctgt ggagcagaca                         100

<210> SEQ ID NO 1753
<211> LENGTH: 100
<212> TYPE: DNA
<213> ORGANISM: Homo sapiens

<400> SEQUENCE: 1753
ggtacagtgt ctctagagag aagaaggagc gcttctccct gattctggag tccgccagca    60
ccaaccagac atctatgtac ctctgtgcca gcagtttatg                         100

<210> SEQ ID NO 1754
<211> LENGTH: 100
<212> TYPE: DNA
<213> ORGANISM: Homo sapiens

<400> SEQUENCE: 1754
acaagtttct catcaaccat gcaagcctga ccttgtccac tctgacagtg accagtgccc    60
```
atcctgaaga cagcagcttc tacatctgca gtgctagaga                                    100

<210> SEQ ID NO 1755
<211> LENGTH: 100
<212> TYPE: DNA
<213> ORGANISM: Homo sapiens

<400> SEQUENCE: 1755
acaagtttcc catcaaccat ccaaacctga ccttctccgc tctgacagtg accagtgccc              60
atcctgaaga cagcagcttc tacatctgca gtgctagaga                                    100

<210> SEQ ID NO 1756
<211> LENGTH: 100
<212> TYPE: DNA
<213> ORGANISM: Homo sapiens

<400> SEQUENCE: 1756
gaatggctac aacgtctcca gatcaaccac agaggatttc ccgctcaggc tggagttggc              60
tgctccctcc cagacatctg tgtacttctg tgccagcagt                                    100

<210> SEQ ID NO 1757
<211> LENGTH: 100
<212> TYPE: DNA
<213> ORGANISM: Homo sapiens

<400> SEQUENCE: 1757
gctacaacgt ctccagatca accacagagg atttcccgct caggctggag ttggctgctc              60
cctcccagac atctgtgtac ttctgtgcca gcagttactc                                    100

<210> SEQ ID NO 1758
<211> LENGTH: 100
<212> TYPE: DNA
<213> ORGANISM: Homo sapiens

<400> SEQUENCE: 1758
gctacaatgt ctccagatca accacagagg atttcccgct caggctgctg tcggctgctc              60
cctcccagac atctgtgtac ttctgtgcca gcagttactc                                    100

<210> SEQ ID NO 1759
<211> LENGTH: 100
<212> TYPE: DNA
<213> ORGANISM: Homo sapiens

<400> SEQUENCE: 1759
gctacaatgt ctctagatta aacacagagg atttcccact caggctggtg tcggctgctc              60
cctcccagac atctgtgtac ttgtgtgcca gcagttactc                                    100

<210> SEQ ID NO 1760
<211> LENGTH: 100
<212> TYPE: DNA
<213> ORGANISM: Homo sapiens

<400> SEQUENCE: 1760
gctacaatgt atccagatca aacacagagg atttcccgct caggctggag tcagctgctc              60
cctcccagac atctgtatac ttctgtgcca gcagttattc                                    100

<210> SEQ ID NO 1761
<211> LENGTH: 100
<212> TYPE: DNA
<213> ORGANISM: Homo sapiens

<400> SEQUENCE: 1761
gctacaatgt ctccagatca aacacagagg atttccccct caagctggag tcagctgctc    60
cctctcagac ttctgtttac ttctgtgcca gcagttactc                          100

<210> SEQ ID NO 1762
<211> LENGTH: 100
<212> TYPE: DNA
<213> ORGANISM: Homo sapiens

<400> SEQUENCE: 1762
gattctcagc taagatgcct aatgcatcat tctccactct gaagatccag ccctcagaac    60
ccagggactc agctgtgtac ttctgtgcca gcagtttagc                          100

<210> SEQ ID NO 1763
<211> LENGTH: 100
<212> TYPE: DNA
<213> ORGANISM: Homo sapiens

<400> SEQUENCE: 1763
gattctcagc taagatgcct aatgcatcat tctccactct gaagatccag ccctcagaac    60
ccagggactc agctgtgtac ttctgtgcca gcagtttagc                          100

<210> SEQ ID NO 1764
<211> LENGTH: 100
<212> TYPE: DNA
<213> ORGANISM: Homo sapiens

<400> SEQUENCE: 1764
gattctcagc agagatgcct gatgcaactt tagccactct gaagatccag ccctcagaac    60
ccagggactc agctgtgtat ttttgtgcta gtggtttggt                          100

<210> SEQ ID NO 1765
<211> LENGTH: 100
<212> TYPE: DNA
<213> ORGANISM: Homo sapiens

<400> SEQUENCE: 1765
gattctcagc tgagaggcct gatggatcat tctctactct gaagatccag cctgcagagc    60 aggggggactc ggccgtgtat gtctgtgcaa gtcgcttagc                         100

<210> SEQ ID NO 1766
<211> LENGTH: 100
<212> TYPE: DNA
<213> ORGANISM: Homo sapiens

<400> SEQUENCE: 1766
gctacaatgt ctccagatta aacaaacggg agttctcgct caggctggag tcggctgctc    60
cctcccagac atctgtgtac ttctgtgcca gcagtgaagc                          100

<210> SEQ ID NO 1767
<211> LENGTH: 100
<212> TYPE: DNA
<213> ORGANISM: Homo sapiens

<400> SEQUENCE: 1767
ggttctctgc agagaggcct gagagatccg tctccactct gaagatccag cgcacagagc    60 aggggggactc agctgtgtat ctctgtgcca gcagcttagc                         100

-continued

```
<210> SEQ ID NO 1768
<211> LENGTH: 100
<212> TYPE: DNA
<213> ORGANISM: Homo sapiens

<400> SEQUENCE: 1768
tcaattctcc acagagaggt ctgaggatct ttctccacct gaagatccag cgcacagagc    60
aagggcgact cggctgtgta tctctgtgcc agaagcttag                         100

<210> SEQ ID NO 1769
<211> LENGTH: 100
<212> TYPE: DNA
<213> ORGANISM: Homo sapiens

<400> SEQUENCE: 1769
aaagaaaggc taaaagccac attaacaaag aaggaaagct ttctgcacat cacagcccct    60
aaacctgaag actcagccac ttatctctgt gctgtgcagg                         100

<210> SEQ ID NO 1770
<211> LENGTH: 100
<212> TYPE: DNA
<213> ORGANISM: Homo sapiens

<400> SEQUENCE: 1770
gattttctgc agagaggctc aaaggagtag actccactct caagatccag cctgcagagc    60
ttggggactc ggccatgtat ctctgtgcca gcagcttagc                         100

<210> SEQ ID NO 1771
<211> LENGTH: 100
<212> TYPE: DNA
<213> ORGANISM: Homo sapiens

<400> SEQUENCE: 1771
acattttaaa gaagcgcttg gaaaagagaa gttttatagt gttttgaata tgctggtctc    60
tcatcctgga gattcaggca cctacttctg tgctttgagg                         100

<210> SEQ ID NO 1772
<211> LENGTH: 100
<212> TYPE: DNA
<213> ORGANISM: Homo sapiens

<400> SEQUENCE: 1772
aaaggaagac taaatgctac attactgaag aatggaagca gcttgtacat tacagccgtg    60
cagcctgaag attcagccac ctatttctgt gctgtagatg                         100

<210> SEQ ID NO 1773
<211> LENGTH: 100
<212> TYPE: DNA
<213> ORGANISM: Homo sapiens

<400> SEQUENCE: 1773
gcttcactgc tgaccttaac aaaggcgaga catctttcca cctgaagaaa ccatttgctc    60
aagaggaaga ctcagccatg tattactgtg ctctaagtgg                         100

<210> SEQ ID NO 1774
<211> LENGTH: 100
<212> TYPE: DNA
<213> ORGANISM: Homo sapiens

<400> SEQUENCE: 1774
```

-continued agactgaagg tcacctttga taccaccctt aaacagagtt tgtttcatat cacagcctcc    60
cagcctgcag actcagctac ctacctctgt gctctagaca                          100

<210> SEQ ID NO 1775
<211> LENGTH: 100
<212> TYPE: DNA
<213> ORGANISM: Homo sapiens

<400> SEQUENCE: 1775
ggtacagcgt ctctcgggag aagaaggaat cctttcctct cactgtgaca tcggcccaaa    60
agaacccgac agctttctat ctctgtgcca gtagtataga                          100

<210> SEQ ID NO 1776
<211> LENGTH: 100
<212> TYPE: DNA
<213> ORGANISM: Homo sapiens

<400> SEQUENCE: 1776
actcattgaa tttccagaag gcaagaaaat ccgccaacct tgtcatctcc gcttcacaac    60
tgggggactc agcaatgtat ttctgtgcaa tgagagaggg                          100

<210> SEQ ID NO 1777
<211> LENGTH: 100
<212> TYPE: DNA
<213> ORGANISM: Homo sapiens

<400> SEQUENCE: 1777
gttttgaagc catgtaccgt aaagaaacca cttctttcca cttggagaaa gactcagttc    60
aagagtcaga ctccgctgtg tacttctgtg ctctgagtga                          100

<210> SEQ ID NO 1778
<211> LENGTH: 100
<212> TYPE: DNA
<213> ORGANISM: Homo sapiens

<400> SEQUENCE: 1778
gttttgaagc cacataccgt aaagaaacca cttctttcca cttggagaaa ggctcagttc    60
aagtgtcaga ctcagcggtg tacttctgtg ctctgagtga                          100

<210> SEQ ID NO 1779
<211> LENGTH: 100
<212> TYPE: DNA
<213> ORGANISM: Homo sapiens

<400> SEQUENCE: 1779
gtttttcttc attccttagt cgctctgata gttatggtta cctccttcta caggagctcc    60
agatgaaaga ctctgcctct tacttctgcg ctgtgagaga                          100

<210> SEQ ID NO 1780
<211> LENGTH: 100
<212> TYPE: DNA
<213> ORGANISM: Homo sapiens

<400> SEQUENCE: 1780
ttctctgtga acttccagaa agcagccaaa tccttcagtc tcaagatctc agactcacag    60
ctgggggatg ccgcgatgta tttctgtgct tataggagcg                          100

<210> SEQ ID NO 1781

```
<211> LENGTH: 100
<212> TYPE: DNA
<213> ORGANISM: Homo sapiens

<400> SEQUENCE: 1781
attcttggaa cttccagaaa tccaccagtt ccttcaactt caccatcaca gcctcacaag      60
tcgtggactc agcagtatac ttctgtgctc tgagtgaggc                          100

<210> SEQ ID NO 1782
<211> LENGTH: 100
<212> TYPE: DNA
<213> ORGANISM: Homo sapiens

<400> SEQUENCE: 1782
aaaatatctg cttcatttaa tgaaaaaaag cagcaaagct ccctgtacct tacggcctcc     60
cagctcagtt actcaggaac ctacttctgc ggcacagaga                          100

<210> SEQ ID NO 1783
<211> LENGTH: 100
<212> TYPE: DNA
<213> ORGANISM: Homo sapiens

<400> SEQUENCE: 1783
agtattttac ttatgcaagc atgaggagga gctggaaatt gatactgcaa aatctaattg     60
aaaatgattc tggatctatt actgtgccac ctgggacagg                          100

<210> SEQ ID NO 1784
<211> LENGTH: 100
<212> TYPE: DNA
<213> ORGANISM: Homo sapiens

<400> SEQUENCE: 1784
aaagtatgac actggaagca caaggagcaa ttggaatttg agactgcaaa atctaattaa     60
aaatgattct gggttctatt actgtgccac ctgggacagg                          100

<210> SEQ ID NO 1785
<211> LENGTH: 100
<212> TYPE: DNA
<213> ORGANISM: Homo sapiens

<400> SEQUENCE: 1785
gtattatact catacaccca ggaggtggag ctggatattg agactgcaaa atctaattga     60
aaatgattct ggggtctatt actgtgccac ctgggacagg                          100

<210> SEQ ID NO 1786
<211> LENGTH: 100
<212> TYPE: DNA
<213> ORGANISM: Homo sapiens

<400> SEQUENCE: 1786
gtattatact catacaccca ggaggtggag ctggatattg atactacgaa atctaattga     60
aaatgattct ggggtctatt actgtgccac ctgggacagg                          100

<210> SEQ ID NO 1787
<211> LENGTH: 100
<212> TYPE: DNA
<213> ORGANISM: Homo sapiens

<400> SEQUENCE: 1787
gtatcatact tatgcaagca caggaagag ccttaaattt atactggaaa atctaattga     60
```

```
acgtgactct ggggtctatt actgtgccac ctgggatagg                         100
```

<210> SEQ ID NO 1788
<211> LENGTH: 100
<212> TYPE: DNA
<213> ORGANISM: Homo sapiens

<400> SEQUENCE: 1788

```
gtatgatact tatggaagca caaggaagaa cttgagaatg atactgcgaa atcttattga    60
aaatgactct ggagtctatt actgtgccac ctgggatggg                        100
```

<210> SEQ ID NO 1789
<211> LENGTH: 100
<212> TYPE: DNA
<213> ORGANISM: Homo sapiens

<400> SEQUENCE: 1789

```
gtattatact tacgcaagca caaggaacaa cttgagattg atactgcgaa atctaattga    60
aaatgactct ggggtctatt actgtgccac ctgggacggg                        100
```

<210> SEQ ID NO 1790
<211> LENGTH: 100
<212> TYPE: DNA
<213> ORGANISM: Homo sapiens

<400> SEQUENCE: 1790

```
gtattatact catacaccga ggaggtggag ctggaatttg agactgcaaa atctaattga    60
aaatgattct ggggtctatt actgtgccac ctggggcagg                        100
```

<210> SEQ ID NO 1791
<211> LENGTH: 100
<212> TYPE: DNA
<213> ORGANISM: Homo sapiens

<400> SEQUENCE: 1791

```
aagacttaat gcctcgctgg ataaatcatc aggacgtagt actttataca ttgcagcttc    60
tcagcctggt gactcagcca cctacctctg tgctgtgagg                        100
```

<210> SEQ ID NO 1792
<211> LENGTH: 100
<212> TYPE: DNA
<213> ORGANISM: Homo sapiens

<400> SEQUENCE: 1792

```
acaagtttcc catcagccgc ccaaacctaa cattctcaac tctgactgtg agcaacagga    60
gacctgaaga cagcagcata tacctctgca gcgttgaaga                        100
```

<210> SEQ ID NO 1793
<211> LENGTH: 100
<212> TYPE: DNA
<213> ORGANISM: Homo sapiens

<400> SEQUENCE: 1793

```
agattcacag ccaggcttaa aaaggagac cagcacattt ccctgcacat acaggattcc    60
cagctccatg actcaaccac attcttctgc gcagcaagca                        100
```

<210> SEQ ID NO 1794
<211> LENGTH: 100
<212> TYPE: DNA

<213> ORGANISM: Homo sapiens

<400> SEQUENCE: 1794
gattttcagc ccaatgcccc caaaactcac cctgtacctt ggagatccag tccacggagt    60
caggagacac agcacggtat ttctgtgcca acagcaaagc    100

<210> SEQ ID NO 1795
<211> LENGTH: 100
<212> TYPE: DNA
<213> ORGANISM: Homo sapiens

<400> SEQUENCE: 1795
gatttttagc ccaatgctcc aaaaactcat cctgtacctt ggagatccag tccacggagt    60
caggggacac agcactgtat ttctgtgcca gcagcaaagc    100

<210> SEQ ID NO 1796
<211> LENGTH: 100
<212> TYPE: DNA
<213> ORGANISM: Homo sapiens

<400> SEQUENCE: 1796
gttttgaggc tgaatttaac aagagtcaaa cttccttcca cttgaggaaa ccctcagtcc    60
atataagcga cacggctgag tacttctgtg ctgtgagtga    100

<210> SEQ ID NO 1797
<211> LENGTH: 100
<212> TYPE: DNA
<213> ORGANISM: Homo sapiens

<400> SEQUENCE: 1797
gctttgaggc tgaatttaag aggagtcaat cttccttcaa tctgaggaaa ccctctgtgc    60
attggagtga tgctgctgag tacttctgtg ctgtgggtgc    100

<210> SEQ ID NO 1798
<211> LENGTH: 100
<212> TYPE: DNA
<213> ORGANISM: Homo sapiens

<400> SEQUENCE: 1798
acaagtttcc catcagccgc ccaaacctaa cattctcaac tctgactgtg agcaacatga    60
gccctgaaga cagcagcata tatctctgca gcgttgaaga    100

<210> SEQ ID NO 1799
<211> LENGTH: 100
<212> TYPE: DNA
<213> ORGANISM: Homo sapiens

<400> SEQUENCE: 1799
agtcaacagt ctccagaata aggatagagc gttttcccct gaccctggag tctgccagcc    60
cctcacatac ctctcagtac ctctgtgcca gcagtgaata    100

<210> SEQ ID NO 1800
<211> LENGTH: 100
<212> TYPE: DNA
<213> ORGANISM: Homo sapiens

<400> SEQUENCE: 1800
agtcaacagt ctccagaata aggacggagc attttcccct gaccctggag tctgccaggc    60
cctcacatac ctctcagtac ctctgtgcca gcagtgaata    100

```
<210> SEQ ID NO 1801
<211> LENGTH: 100
<212> TYPE: DNA
<213> ORGANISM: Homo sapiens

<400> SEQUENCE: 1801
aagactgact gctcagtttg gtataaccag aaaggacagc ttcctgaata tctcagcatc      60 cataccctagt gatgtaggca tctacttctg tgctgggcag                          100

<210> SEQ ID NO 1802
<211> LENGTH: 100
<212> TYPE: DNA
<213> ORGANISM: Homo sapiens

<400> SEQUENCE: 1802
gaaaagactg acatttcagt ttggagaagc aaaaaagaac agctccctgc acatcacagc      60
cacccagact acagatgtag gaacctactt ctgtgcaggg                            100

<210> SEQ ID NO 1803
<211> LENGTH: 100
<212> TYPE: DNA
<213> ORGANISM: Homo sapiens

<400> SEQUENCE: 1803
aggtttacag cacagctcaa taaagccagc cagtatgttt ctctgctcat cagagactcc      60
cagcccagtg attcagccac ctacctctgt gccgtgaaca                            100

<210> SEQ ID NO 1804
<211> LENGTH: 100
<212> TYPE: DNA
<213> ORGANISM: Homo sapiens

<400> SEQUENCE: 1804
aggtttacag cacagctcaa tagagccagc cagtatattt ccctgctcat cagagactcc      60
aagctcagtg attcagccac ctacctctgt gtggtgaaca                            100

<210> SEQ ID NO 1805
<211> LENGTH: 100
<212> TYPE: DNA
<213> ORGANISM: Homo sapiens

<400> SEQUENCE: 1805
aggtttacag cacaggtcga taaatccagc aagtatatct ccttgttcat cagagactca      60
cagcccagtg attcagccac ctacctctgt gcaatgagcg                            100

<210> SEQ ID NO 1806
<211> LENGTH: 100
<212> TYPE: DNA
<213> ORGANISM: Homo sapiens

<400> SEQUENCE: 1806
agattcacaa tctccttcaa taaaagtgcc aagcagttct cattgcatat catggattcc      60
cagcctggag actcagccac ctacttctgt gcagcaagca                            100

<210> SEQ ID NO 1807
<211> LENGTH: 100
<212> TYPE: DNA
<213> ORGANISM: Homo sapiens
```

<400> SEQUENCE: 1807
agattaagcg ccacgactgt cgctacggaa cgctacagct tattgtacat ttcctcttcc    60
cagaccacag actcaggcgt ttatttctgt gctgtggagc                          100

<210> SEQ ID NO 1808
<211> LENGTH: 100
<212> TYPE: DNA
<213> ORGANISM: Homo sapiens

<400> SEQUENCE: 1808
aagattaatt gccacaataa acatacagga aaagcacagc tccctgcaca tcacagcctc    60
ccatcccaga gactctgccg tctacatctg tgctgtcaga                          100

<210> SEQ ID NO 1809
<211> LENGTH: 100
<212> TYPE: DNA
<213> ORGANISM: Homo sapiens

<400> SEQUENCE: 1809
cgattaatgg cctcacttga taccaaagcc cgtctcagca ccctccacat cacagctgcc    60
gtgcatgacc tctctgccac ctacttctgt gccgtggaca                          100

<210> SEQ ID NO 1810
<211> LENGTH: 100
<212> TYPE: DNA
<213> ORGANISM: Homo sapiens

<400> SEQUENCE: 1810
agactaagta gcatattaga taagaaagaa ctttccagca tcctgaacat cacagccacc    60
cagaccggag actcggccat ctacctctgt gctgtggagg                          100

<210> SEQ ID NO 1811
<211> LENGTH: 100
<212> TYPE: DNA
<213> ORGANISM: Homo sapiens

<400> SEQUENCE: 1811
agattcactg tcttcttaaa caaaagtgcc aagcacctct ctctgcacat tgtgccctcc    60
cagcctggag actctgcagt gtacttctgt gcagcaagcg                          100

<210> SEQ ID NO 1812
<211> LENGTH: 100
<212> TYPE: DNA
<213> ORGANISM: Homo sapiens

<400> SEQUENCE: 1812
aagagactaa cctttcagtt tggtgatgca agaaaggaca gttctctcca catcactgca    60
gcccagcctg gtgatacagg cctctacctc tgtgcaggag                          100

<210> SEQ ID NO 1813
<211> LENGTH: 100
<212> TYPE: DNA
<213> ORGANISM: Homo sapiens

<400> SEQUENCE: 1813
gttatagtgt ctccagagca aaacacagatg atttcccct cacgttggcg tctgctgtac    60
cctctcagac atctgtgtac ttctgtgcca gcagtgactc                          100

```
<210> SEQ ID NO 1814
<211> LENGTH: 100
<212> TYPE: DNA
<213> ORGANISM: Homo sapiens

<400> SEQUENCE: 1814
gctacagtgt ctctagatca aacacagagg acctcccct cactctggag tctgctgcct      60
cctcccagac atctgtatat ttctgcgcca gcagtgagtc                          100

<210> SEQ ID NO 1815
<211> LENGTH: 100
<212> TYPE: DNA
<213> ORGANISM: Homo sapiens

<400> SEQUENCE: 1815
gctatgttgt ctccagatcc aagacagaga atttcccct cactctggag tcagctaccc      60
gctcccagac atctgtgtat ttctgcgcca gcagtgagtc                          100

<210> SEQ ID NO 1816
<211> LENGTH: 100
<212> TYPE: DNA
<213> ORGANISM: Homo sapiens

<400> SEQUENCE: 1816
gctacaatgt ctccagatta aaaaaacaga atttcctgct ggggttggag tcggctgctc      60
cctcccaaac atctgtgtac ttctgtgcca gcagttactc                          100

<210> SEQ ID NO 1817
<211> LENGTH: 100
<212> TYPE: DNA
<213> ORGANISM: Homo sapiens

<400> SEQUENCE: 1817
gctatagtgt ctctagatca aagacagagg atttcctcct cactctggag tccgctacca      60
gctcccagac atctgtgtac ttctgtgcca tcagtgagtc                          100

<210> SEQ ID NO 1818
<211> LENGTH: 100
<212> TYPE: DNA
<213> ORGANISM: Homo sapiens

<400> SEQUENCE: 1818
ggacgaataa gtgccactct taataccaag gagggttaca gctatttgta catcaaagga      60
tcccagcctg aagactcagc cacatacctc tgtgccttta                          100

<210> SEQ ID NO 1819
<211> LENGTH: 100
<212> TYPE: DNA
<213> ORGANISM: Homo sapiens

<400> SEQUENCE: 1819
gattcttagc tgaaaggact ggagggacgt attctactct gaaggtgcag cctgcagaac      60
tggaggattc tggagtttat ttctgtgcca gcagccaaga                          100

<210> SEQ ID NO 1820
<211> LENGTH: 100
<212> TYPE: DNA
<213> ORGANISM: Homo sapiens

<400> SEQUENCE: 1820
```

```
atacagtgtc tctcgacagg cacaggctaa attctccctg tccctagagt ctgccatccc    60
caaccagaca gctctttact tctgtgccac cagtgatttg                         100
```

<210> SEQ ID NO 1821
<211> LENGTH: 100
<212> TYPE: DNA
<213> ORGANISM: Homo sapiens

<400> SEQUENCE: 1821

```
agtgtctctt gacaggaaca ggctaaattc tccctgtccc tagagcctgc caccccaac    60 cagacagctt ctaggttact tcagtgccac cagtgatttc                         100
```

<210> SEQ ID NO 1822
<211> LENGTH: 100
<212> TYPE: DNA
<213> ORGANISM: Homo sapiens

<400> SEQUENCE: 1822

```
gttttgaggc tgaatttaag aagagtgaaa cctccttcca cctgacgaaa ccctcagccc    60
atatgagcga cgcggctgag tacttctgtg ttgtgagtga                          100
```

<210> SEQ ID NO 1823
<211> LENGTH: 100
<212> TYPE: DNA
<213> ORGANISM: Homo sapiens

<400> SEQUENCE: 1823

```
gttttgaggc tgaatttaag aagagtgaaa cctccttcca cctgacgaaa ccctcagccc    60
atatgagcga cgcggctgag tacttctgtg ctgtgagtga                          100
```

<210> SEQ ID NO 1824
<211> LENGTH: 100
<212> TYPE: DNA
<213> ORGANISM: Homo sapiens

<400> SEQUENCE: 1824

```
ggctacggtg tctcccgaga ggagaagggg ctgtttcttc tcatggtgaa gctggcccac    60
accagccaaa cagctctgta cttctgtcct gggagtgcac                          100
```

<210> SEQ ID NO 1825
<211> LENGTH: 100
<212> TYPE: DNA
<213> ORGANISM: Homo sapiens

<400> SEQUENCE: 1825

```
ggcctctctg gcaatcgctg aagacagaaa gtccagtacc ttgatcctgc accgtgctac    60
cttgagagat gctgctgtgt actactgcat cctgagagac                          100
```

<210> SEQ ID NO 1826
<211> LENGTH: 100
<212> TYPE: DNA
<213> ORGANISM: Homo sapiens

<400> SEQUENCE: 1826

```
gattttctgc agagaggctc aaaggagtag actccactct caagatccag cctgcaaagc    60
ttgaggactc ggccgtgtat ctctgtgcca gcagcttaga                          100
```

<210> SEQ ID NO 1827
<211> LENGTH: 100

```
<212> TYPE: DNA
<213> ORGANISM: Homo sapiens

<400> SEQUENCE: 1827
gattttctgc agagaggctc aaaggagtag actccactct caagatccag cctgcagagc    60
ttggggactc ggccgtgtat ctctgtgcca gcagcttaga                         100

<210> SEQ ID NO 1828
<211> LENGTH: 100
<212> TYPE: DNA
<213> ORGANISM: Homo sapiens

<400> SEQUENCE: 1828
gctttgaggc tgaatttata aagagtaaat tctcctttaa tctgaggaaa ccctctgtgc    60
agtggagtga cacagctgag tacttctgtg ccgtgaatgc                         100

<210> SEQ ID NO 1829
<211> LENGTH: 100
<212> TYPE: DNA
<213> ORGANISM: Homo sapiens

<400> SEQUENCE: 1829
caattctcca cagagaggtc tgaggatctt tctccacctg aagatccagc gcacagagca    60
agggcgactc ggctgtgtat ctctgtgtca gaagcttagc                         100

<210> SEQ ID NO 1830
<211> LENGTH: 100
<212> TYPE: DNA
<213> ORGANISM: Homo sapiens

<400> SEQUENCE: 1830
ggttctctgc agagaggcct gagggatcca tctccactct gacgatccag cgcacagagc    60
agcgggactc ggccatgtat cgctgtgcca gcagcttagc                         100

<210> SEQ ID NO 1831
<211> LENGTH: 100
<212> TYPE: DNA
<213> ORGANISM: Homo sapiens

<400> SEQUENCE: 1831
gataagtaaa aatgctcaca cttccacttc cactttgaaa ataaagttct tagagaaaga    60
agatgaggtg gtgtaccact gtgcctgctg gattaggcac                         100

<210> SEQ ID NO 1832
<211> LENGTH: 100
<212> TYPE: DNA
<213> ORGANISM: Homo sapiens

<400> SEQUENCE: 1832
agattaagag tcacgcttga cacttccaag aaaagcagtt ccttgttgat cacggcttcc    60
cgggcagcag acactgcttc ttacttctgt gctacggacg                         100

<210> SEQ ID NO 1833
<211> LENGTH: 100
<212> TYPE: DNA
<213> ORGANISM: Homo sapiens

<400> SEQUENCE: 1833
ggtacaaagt ctctcgaaaa gagaagagga atttcccccct gatcctggag tcgcccagcc   60
```

| | |
|---|---|
| ccaaccagac ctctctgtac ttctgtgcca gcagtttatc | 100 |

<210> SEQ ID NO 1834
<211> LENGTH: 100
<212> TYPE: DNA
<213> ORGANISM: Homo sapiens

<400> SEQUENCE: 1834

| | |
|---|---|
| attctgtcaa cttcaagaaa gcagcgaaat ccgtcgcctt aaccatttca gccttacagc | 60 |
| tagaagattc agcaaagtac ttttgtgctc ttggggaact | 100 |

<210> SEQ ID NO 1835
<211> LENGTH: 100
<212> TYPE: DNA
<213> ORGANISM: Homo sapiens

<400> SEQUENCE: 1835

| | |
|---|---|
| gattttctgc tgaatttccc aaagagggcc ccagcatcct gaggatccag caggtagtgc | 60 |
| gaggagattc ggcagcttat ttctgtgcca gctcaccacc | 100 |

<210> SEQ ID NO 1836
<211> LENGTH: 100
<212> TYPE: DNA
<213> ORGANISM: Homo sapiens

<400> SEQUENCE: 1836

| | |
|---|---|
| agactcactg ttctattgaa taaaaggat aaacatctgt ctctgcgcat tgcagacacc | 60 |
| cagactgggg actcagctat ctacttctgt gcagagagta | 100 |

<210> SEQ ID NO 1837
<211> LENGTH: 100
<212> TYPE: DNA
<213> ORGANISM: Homo sapiens

<400> SEQUENCE: 1837

| | |
|---|---|
| agagtcaccg ttttattgaa taagacagtg aaacatctct ctctgcaaat tgcagctact | 60 |
| caacctggag actcagctgt ctacttttgt gcagagaata | 100 |

<210> SEQ ID NO 1838
<211> LENGTH: 100
<212> TYPE: DNA
<213> ORGANISM: Homo sapiens

<400> SEQUENCE: 1838

| | |
|---|---|
| tttccaaggt gacattgata ttgcaaagaa cctggctgta cttaagatac ttgcaccatc | 60 |
| agagagagat gaagggtctt actactgtgc ctgtgacacc | 100 |

<210> SEQ ID NO 1839
<211> LENGTH: 100
<212> TYPE: DNA
<213> ORGANISM: Homo sapiens

<400> SEQUENCE: 1839

| | |
|---|---|
| gtttttcttc attccttagt cggtctaaag ggtacagtta cctccttttg aaggagctcc | 60 |
| agatgaaaga ctctgcctct tacctctgtg ctgtgagaga | 100 |

<210> SEQ ID NO 1840
<211> LENGTH: 100
<212> TYPE: DNA
<213> ORGANISM: Homo sapiens

<400> SEQUENCE: 1840
gacggttttc tgtgaaacac attctgaccc agaaagcctt tcacttggtg atctctccag    60
taaggactga agacagtgcc acttactact gtgcctttag    100

<210> SEQ ID NO 1841
<211> LENGTH: 100
<212> TYPE: DNA
<213> ORGANISM: Homo sapiens

<400> SEQUENCE: 1841
tattctgtga gcttccagaa aacaactaaa actattcagc ttatcatatc atcatcacag    60
ccagaagacc tgcaacatat ttctgttgtc tcaaagagcc    100

<210> SEQ ID NO 1842
<211> LENGTH: 100
<212> TYPE: DNA
<213> ORGANISM: Homo sapiens

<400> SEQUENCE: 1842
agatatacag caactctgga tgcagacaca aagcaaagct ctctgcacat cacagcctcc    60
cagctcagcg attcagcctc ctacatctgt gtggtgagcg    100

<210> SEQ ID NO 1843
<211> LENGTH: 100
<212> TYPE: DNA
<213> ORGANISM: Homo sapiens

<400> SEQUENCE: 1843
gaagactaaa atccgcagtc aaagctgagg aactttatgg ccacctatac atcagattcc    60
cagcctgagg actcagctat ttacttctgt gctgtgggga    100

<210> SEQ ID NO 1844
<211> LENGTH: 100
<212> TYPE: DNA
<213> ORGANISM: Homo sapiens

<400> SEQUENCE: 1844
aaaacttcgg aggcggaaat attaaagaca aaaactcccc cattgtgaaa tattcagtcc    60
aggtatcaga ctcagccgtg tactactgtc ttctgggaga    100

<210> SEQ ID NO 1845
<211> LENGTH: 100
<212> TYPE: DNA
<213> ORGANISM: Homo sapiens

<400> SEQUENCE: 1845
gcatgatact tatggaagta gaaggataag ctggaaattt atacctccaa aactaaatga    60
aaatgcctct ggggtctatt actgtgccac ctaggacagg    100

<210> SEQ ID NO 1846
<211> LENGTH: 100
<212> TYPE: DNA
<213> ORGANISM: Homo sapiens

<400> SEQUENCE: 1846
gttttcaggc cagtcctatc aagagtgaca gttccttcca cctggagaag ccctcggtgc    60
agctgtcgga ctctgccgtg tactactgcg ctctgagaga    100

<210> SEQ ID NO 1847
<211> LENGTH: 100
<212> TYPE: DNA
<213> ORGANISM: Homo sapiens

<400> SEQUENCE: 1847
ggtatcatgt ttcttgaaat actatagcat cttttcccct gaccctgaag tctgccagca    60
ccaaccagac atctgtgtat ctctatgcca gcagttcatc                          100

<210> SEQ ID NO 1848
<211> LENGTH: 100
<212> TYPE: DNA
<213> ORGANISM: Homo sapiens

<400> SEQUENCE: 1848
agaggggtac tgtgtttctt gaaacaagct tgagcatttc cccaatcctg gcatccacca    60
gcaccagcca gacctatctg taccactgtg gcagcacatc                          100

<210> SEQ ID NO 1849
<211> LENGTH: 100
<212> TYPE: DNA
<213> ORGANISM: Homo sapiens

<400> SEQUENCE: 1849
agataaaatc atagccaagg atggcagcag ctctatcttg gcagtactga agttggagac    60
aggcatcgag ggcatgaact actgcacaac ctgggccctg                          100

<210> SEQ ID NO 1850
<211> LENGTH: 100
<212> TYPE: DNA
<213> ORGANISM: Homo sapiens

<400> SEQUENCE: 1850
gcctccctgt ttatccctgc cgacagaaag tccagcactc tgagcctgcc ccgggtttcc    60
ctgagcgaca ctgctgtgta ctactgcctc gtgggtgaca                          100

<210> SEQ ID NO 1851
<211> LENGTH: 100
<212> TYPE: DNA
<213> ORGANISM: Homo sapiens

<400> SEQUENCE: 1851
aggctgaatt taagaagagc gaaacctcct tctacctgag gaaaccatca acccatgtga    60
gtgatgctgc tgagtacttc tgtgctgtgg gtgacaggag                          100

<210> SEQ ID NO 1852
<211> LENGTH: 100
<212> TYPE: DNA
<213> ORGANISM: Homo sapiens

<400> SEQUENCE: 1852
cgaattgctg ttacattgaa caagacagcc aaacatttct ccctgcacat cacagagacc    60
caacctgaag actcggctgt ctacttctgt gcagcaagta                          100

<210> SEQ ID NO 1853
<211> LENGTH: 100
<212> TYPE: DNA
<213> ORGANISM: Homo sapiens

<400> SEQUENCE: 1853

```
gactctgaga ccctctgcag cagcagccta tcagtgcagc cacatcctct ctgagcggat    60
atgacaaacc ccagggttga agcgacctaa cctatgagcc                         100

<210> SEQ ID NO 1854
<211> LENGTH: 100
<212> TYPE: DNA
<213> ORGANISM: Homo sapiens

<400> SEQUENCE: 1854
tggacactta tcacttcccc aatcaatacc cctgtgattt cctatgcctg tctttacttt    60
aatctcttaa tcctgtcagc tgaggaggat gtatgtcacc                         100

<210> SEQ ID NO 1855
<211> LENGTH: 100
<212> TYPE: DNA
<213> ORGANISM: Homo sapiens

<400> SEQUENCE: 1855
gattttcagc taagtgcctc ccaaattcac cctgtagcct tgagatccag gctacgaagc    60
ttgaggattc agcagtgtat ttttgtgcca gcagccaatc                         100

<210> SEQ ID NO 1856
<211> LENGTH: 100
<212> TYPE: DNA
<213> ORGANISM: Homo sapiens

<400> SEQUENCE: 1856
ggtatcatgt ttcttgaaat actatagcat cttttctcct gaccctgaag tctgctagca    60
ccaaccagac atgtgtgtat ctctgcgcca gcagttcatc                         100

<210> SEQ ID NO 1857
<211> LENGTH: 100
<212> TYPE: DNA
<213> ORGANISM: Homo sapiens

<400> SEQUENCE: 1857
ggttctttgc agtcaggcct gagggatccg tctctactct gaagatccag cgcacagagc    60 aggggactc agccgcgtat ctccgtgcca gcagcttaac                          100

<210> SEQ ID NO 1858
<211> LENGTH: 100
<212> TYPE: DNA
<213> ORGANISM: Homo sapiens

<400> SEQUENCE: 1858
tgatcggttc tctgcagaga ggcctaaggg atctttctcc accttggaga tccagcgcac    60
agagcagggg gactcggcca tgtatctctg tgccagcagc                         100

<210> SEQ ID NO 1859
<211> LENGTH: 100
<212> TYPE: DNA
<213> ORGANISM: Homo sapiens

<400> SEQUENCE: 1859
cgattctccg cacaacagtt ccctgacttg cactctgaac taaacctgag ctctctggag    60
ctgggggact cagcttttgta tttctgtgcc agcagcgtag                        100

<210> SEQ ID NO 1860
```

```
<211> LENGTH: 100
<212> TYPE: DNA
<213> ORGANISM: Homo sapiens

<400> SEQUENCE: 1860
acaagtttcc catcagccgc ccaaacctaa cattctcaac tctgactgtg agcaacagga    60
gacctgaaga cagcagcata tacctctgca gcgttgaaga                          100

<210> SEQ ID NO 1861
<211> LENGTH: 100
<212> TYPE: DNA
<213> ORGANISM: Homo sapiens

<400> SEQUENCE: 1861
gttttgaggc tgaatttaac aagagtcaaa cttccttcca cttgaggaaa ccctcagtcc    60
atataagcga cacggctgag tacttctgtg ctgtgagtga                          100

<210> SEQ ID NO 1862
<211> LENGTH: 100
<212> TYPE: DNA
<213> ORGANISM: Homo sapiens

<400> SEQUENCE: 1862
gttatagtgt ctccagagca aacacagatg atttcccct cacgttggcg tctgctgtac     60
cctctcagac atctgtgtac ttctgtgcca gcagtgactc                          100

<210> SEQ ID NO 1863
<211> LENGTH: 100
<212> TYPE: DNA
<213> ORGANISM: Homo sapiens

<400> SEQUENCE: 1863
agatggctac agtgtctcta gatcaaacac agaggacctc cccctcactc tggagtctgc    60
tgcctcctcc cagacatctg tatatttctg cgccagcagt                          100

<210> SEQ ID NO 1864
<211> LENGTH: 100
<212> TYPE: DNA
<213> ORGANISM: Homo sapiens

<400> SEQUENCE: 1864
gctacaatgt ctccagatta aaaaaacaga atttcctgct ggggttggag tcggctgctc    60
cctcccaaac atctgtgtac ttctgtgcca gcagttactc                          100

<210> SEQ ID NO 1865
<211> LENGTH: 100
<212> TYPE: DNA
<213> ORGANISM: Homo sapiens

<400> SEQUENCE: 1865
aatagagaca cggggcatgg tatgaaagta ttacctccca gttgcaattt ggcaaaggaa    60
ccagagtttc cacttctccc cgtacgtctg cccatgccca                          100

<210> SEQ ID NO 1866
<211> LENGTH: 100
<212> TYPE: DNA
<213> ORGANISM: Homo sapiens

<400> SEQUENCE: 1866
gaggcatcaa acactgtgat actcacggga ggaggaaaca aactcacctt tgggacaggc    60
```

```
actcagctaa aagtggaact cagtaagtat gagattctat                            100
```

<210> SEQ ID NO 1867
<211> LENGTH: 100
<212> TYPE: DNA
<213> ORGANISM: Homo sapiens

<400> SEQUENCE: 1867

```
tatgggatt tgctatagtg tgaattcagg atacagcacc ctcacctttg ggaagggac        60 tatgcttcta gtctctccag gtacatgttg accccatccc                           100
```

<210> SEQ ID NO 1868
<211> LENGTH: 100
<212> TYPE: DNA
<213> ORGANISM: Homo sapiens

<400> SEQUENCE: 1868

```
actgactaag aaacactgtg ggatggatag cagctataaa ttgatcttcg ggagtgggac      60
cagactgctg gtcaggcctg gtaagtaagg tgtcagagag                           100
```

<210> SEQ ID NO 1869
<211> LENGTH: 100
<212> TYPE: DNA
<213> ORGANISM: Homo sapiens

<400> SEQUENCE: 1869

```
aaggcaggca ttacagtgtg aattctgggg gttaccagaa agttaccttt ggaattggaa     60
caaagctcca agtcatccca agtgagtcca atttcctatg                           100
```

<210> SEQ ID NO 1870
<211> LENGTH: 100
<212> TYPE: DNA
<213> ORGANISM: Homo sapiens

<400> SEQUENCE: 1870

```
aaaggcaggc attacagtgt gaattctggg ggttaccaga agttacctt tggaactgga      60 acaaagctcc aagtcatccc aagtgagtcc aatttcctat                           100
```

<210> SEQ ID NO 1871
<211> LENGTH: 100
<212> TYPE: DNA
<213> ORGANISM: Homo sapiens

<400> SEQUENCE: 1871

```
tttgtcaggc agcacagtgc tgtgatttat agcacattca tctttgggag tgggacaaga     60
ttatcagtaa aacctggtaa gtaggcaata tgtcactaaa                           100
```

<210> SEQ ID NO 1872
<211> LENGTH: 100
<212> TYPE: DNA
<213> ORGANISM: Homo sapiens

<400> SEQUENCE: 1872

```
cagggcctca tttcactgtg ccaaccaggc aggaactgct ctgatctttg ggaagggaac     60
caccttatca gtgagttcca gtaagtacct gataattatt                           100
```

<210> SEQ ID NO 1873
<211> LENGTH: 100
<212> TYPE: DNA

```
<213> ORGANISM: Homo sapiens

<400> SEQUENCE: 1873
cagggcctca tttcactgtg ccaaccaggc aggaactgct ctgatctttg ggaagggaac      60
ccacctatca gtgagttcca gtaagtacct gataattatt                          100

<210> SEQ ID NO 1874
<211> LENGTH: 100
<212> TYPE: DNA
<213> ORGANISM: Homo sapiens

<400> SEQUENCE: 1874
tggtacaata gatcactgtg ggttttcaga tggccagaag ctgctctttg caaggggaac     60
catgttaaag gtggatctta gtaagtatta ttactaatga                         100

<210> SEQ ID NO 1875
<211> LENGTH: 100
<212> TYPE: DNA
<213> ORGANISM: Homo sapiens

<400> SEQUENCE: 1875
cctgtggttt ttgctgggcc ttaaatcatt gtgtgatcaa agctgcaggc aacaagctaa     60
cttttggagg aggaaccagg gtgctagtta aaccaagtga                         100

<210> SEQ ID NO 1876
<211> LENGTH: 100
<212> TYPE: DNA
<213> ORGANISM: Homo sapiens

<400> SEQUENCE: 1876
aggggaccag cattgtgccg acagaggctc aaccctgggg aggctatact ttggaagagg     60
aactcagttg actgtctggc ctggtgagtg agtcgctttc                         100

<210> SEQ ID NO 1877
<211> LENGTH: 100
<212> TYPE: DNA
<213> ORGANISM: Homo sapiens

<400> SEQUENCE: 1877
ttttgcagag gacagatgtg gctatcaaag attttacaat ttcacctttg gaaagggatc     60
caaacataat gtcactccaa gtaagtgagc agccttttgt                         100

<210> SEQ ID NO 1878
<211> LENGTH: 100
<212> TYPE: DNA
<213> ORGANISM: Homo sapiens

<400> SEQUENCE: 1878
tggtgtcacc tacggtatga atactggagg aacaattgat aaactcacat ttgggaaagg     60
gacccatgta ttcattatat ctggtgagtc atcccaggtg                         100

<210> SEQ ID NO 1879
<211> LENGTH: 100
<212> TYPE: DNA
<213> ORGANISM: Homo sapiens

<400> SEQUENCE: 1879
tgtaggcgac ctcgcactgt ggttctaacg actacaagct cagctttgga gccggaacca     60
cagtaactgt aagagcaagt aagtaagaaa gaaaagtcca                         100
```

<210> SEQ ID NO 1880
<211> LENGTH: 100
<212> TYPE: DNA
<213> ORGANISM: Homo sapiens

<400> SEQUENCE: 1880
tgtaatgcca ataaacatgg tgtacaactt caacaaattt tactttggat ctgggaccaa    60
actcaatgta aaaccaagta agttatagtt gcctagaaga                         100

<210> SEQ ID NO 1881
<211> LENGTH: 100
<212> TYPE: DNA
<213> ORGANISM: Homo sapiens

<400> SEQUENCE: 1881
gttgagcaaa tcatagtgtt tcttctggtt ctgcaaggca actgaccttt ggatctggga    60
cacaattgac tgttttacct ggtaggctgc ctcaattaaa                         100

<210> SEQ ID NO 1882
<211> LENGTH: 100
<212> TYPE: DNA
<213> ORGANISM: Homo sapiens

<400> SEQUENCE: 1882
aggatatgta acacagtgtg atttataacc agggaggaaa gcttatcttc ggacagggaa    60
cggagttatc tgtgaaaccc agtaagtata aaattgtatc                         100

<210> SEQ ID NO 1883
<211> LENGTH: 100
<212> TYPE: DNA
<213> ORGANISM: Homo sapiens

<400> SEQUENCE: 1883
gactggatgt gtttttgaca ggatatgtaa cacagtgtga tttataacca gggaggaaag    60
cttatcttcg gacagggaac ggagctatct gtgaaaccca                         100

<210> SEQ ID NO 1884
<211> LENGTH: 100
<212> TYPE: DNA
<213> ORGANISM: Homo sapiens

<400> SEQUENCE: 1884
gaggtgtttg tcacagtgtg acaactgaca gctgggggaa attcgagttt ggagcaggga    60
cccaggttgt ggtcacccca ggtaagccca ttcctggagc                         100

<210> SEQ ID NO 1885
<211> LENGTH: 100
<212> TYPE: DNA
<213> ORGANISM: Homo sapiens

<400> SEQUENCE: 1885
gaggtgtttg tcacagtgtg acaactgaca gctgggggaa attgcagttt ggagcaggga    60
cccaggttgt ggtcacccca ggtaagcccc attccctgga                         100

<210> SEQ ID NO 1886
<211> LENGTH: 100
<212> TYPE: DNA
<213> ORGANISM: Homo sapiens

<400> SEQUENCE: 1886
atgctgagat aatcactatg cagaaggaca aggcttctcc tttatctttg ggaagggggac    60 aaggctgctt gtcaagccaa gtaagtgaca tataatttat                          100

<210> SEQ ID NO 1887
<211> LENGTH: 100
<212> TYPE: DNA
<213> ORGANISM: Homo sapiens

<400> SEQUENCE: 1887
ctgagcccag aaacactgtg gggataacta tggtcagaat tttgtctttg gtcccggaac    60
cagattgtcc gtgctgccct gtaagtacag ttaagtggag                          100

<210> SEQ ID NO 1888
<211> LENGTH: 100
<212> TYPE: DNA
<213> ORGANISM: Homo sapiens

<400> SEQUENCE: 1888
caatagcact aaagactgtg taacaccaat gcaggcaaat caacctttgg ggatgggact    60
acgctcactg tgaagccaag taagttgtgt tcttctttgc                          100

<210> SEQ ID NO 1889
<211> LENGTH: 100
<212> TYPE: DNA
<213> ORGANISM: Homo sapiens

<400> SEQUENCE: 1889
agaaaggaaa ctctgtgcat actctggggc tgggagttac caactcactt tcgggaaggg    60
gaccaaactc tcggtcatac caagtaagtt cttctttctg                          100

<210> SEQ ID NO 1890
<211> LENGTH: 100
<212> TYPE: DNA
<213> ORGANISM: Homo sapiens

<400> SEQUENCE: 1890
ttatggagga aatcactgtg ggaattcagg aaacacacct cttgtctttg gaaagggcac    60
aagactttct gtgattgcaa gtaagtgttt ctagccatcc                          100

<210> SEQ ID NO 1891
<211> LENGTH: 100
<212> TYPE: DNA
<213> ORGANISM: Homo sapiens

<400> SEQUENCE: 1891 aaagaccta cccacagtgg gggtacagca gtgcttccaa gataatcttt ggatcaggga    60
ccagactcag catccggcca agtaagtaga atgaagcagg                          100

<210> SEQ ID NO 1892
<211> LENGTH: 100
<212> TYPE: DNA
<213> ORGANISM: Homo sapiens

<400> SEQUENCE: 1892
gttatggtcc caatcacagt gtgaacagag atgacaagat catctttgga aaagggacac    60
gacttcatat tctcccccagt aagtgctgtt tatgtgattt                          100

<210> SEQ ID NO 1893
<211> LENGTH: 100
<212> TYPE: DNA
<213> ORGANISM: Homo sapiens

<400> SEQUENCE: 1893
agtaaaggca ggaagtgctg tggaataaca atgccagact catgtttgga gatggaactc    60
agctggtggt gaagcccagt aagtggccat gttttattga                         100

<210> SEQ ID NO 1894
<211> LENGTH: 100
<212> TYPE: DNA
<213> ORGANISM: Homo sapiens

<400> SEQUENCE: 1894
ggctctgaag gactgtgtga attatggcgg tgctacaaac aagctcatct ttggaactgg    60
cactctgctt gctgtccagc caagtacgta agtagtggca                         100

<210> SEQ ID NO 1895
<211> LENGTH: 100
<212> TYPE: DNA
<213> ORGANISM: Homo sapiens

<400> SEQUENCE: 1895
gtgattcagc cacctacctc tgtgccgatg gtggtgctac aaacaagctc atctttggaa    60
ctggcactct gcttgctgtc cagccaaata tccagaaccc                         100

<210> SEQ ID NO 1896
<211> LENGTH: 100
<212> TYPE: DNA
<213> ORGANISM: Homo sapiens

<400> SEQUENCE: 1896
gttaaggttt ttgtgtctgt gtggatagca actatcagtt aatctggggc gctgggacca    60
agctaattat aaagccaggt aagtctcaga gatgtgactg                         100

<210> SEQ ID NO 1897
<211> LENGTH: 89
<212> TYPE: DNA
<213> ORGANISM: Homo sapiens

<400> SEQUENCE: 1897 aggttttgt agatctcagt atcactgtgt cttataacac cgacaagctc atctttggga    60
ctgggaccag attacaagtc tttccaagt                                     89

<210> SEQ ID NO 1898
<211> LENGTH: 100
<212> TYPE: DNA
<213> ORGANISM: Homo sapiens

<400> SEQUENCE: 1898
taaaagaatg agccattgtg gataggcttt gggaatgtgc tgcattgcgg gtccggcact    60
caagtgattg ttttaccacg taagtatatc ttttctcatt                         100

<210> SEQ ID NO 1899
<211> LENGTH: 100
<212> TYPE: DNA
<213> ORGANISM: Homo sapiens

<400> SEQUENCE: 1899

| | |
|---|---|
| tactgggcag aaacactgtg tcaaactggg gcaaacaacc tcttctttgg gactggaacg | 60 |
| agactcaccg ttattccctg taagtcctta cctcttgaca | 100 |

<210> SEQ ID NO 1900
<211> LENGTH: 100
<212> TYPE: DNA
<213> ORGANISM: Homo sapiens

<400> SEQUENCE: 1900

| | |
|---|---|
| aaagtacagc attagagtgt ggctctggca acacaggcaa actaatcttt gggcaaggga | 60 |
| caactttaca agtaaaacca ggtaggtctg gatgtttcca | 100 |

<210> SEQ ID NO 1901
<211> LENGTH: 100
<212> TYPE: DNA
<213> ORGANISM: Homo sapiens

<400> SEQUENCE: 1901

| | |
|---|---|
| ctcagcggtg tacttctgtg ctcttcatgg ctctagcaac acaggcaaac taatctttgg | 60 |
| gcaagggaca actttacaag taaaaccaga tatccagaac | 100 |

<210> SEQ ID NO 1902
<211> LENGTH: 100
<212> TYPE: DNA
<213> ORGANISM: Homo sapiens

<400> SEQUENCE: 1902

| | |
|---|---|
| aaagctttct atgactgtgt aatgctggca acaaccgtaa gctgatttgg ggattgggaa | 60 |
| caagcctggc agtaaatccg agtgagtctt cgtgttaact | 100 |

<210> SEQ ID NO 1903
<211> LENGTH: 100
<212> TYPE: DNA
<213> ORGANISM: Homo sapiens

<400> SEQUENCE: 1903

| | |
|---|---|
| cagccgaaga tcactgtgtg aataataatg caggcaacat gctcacccttt ggaggggaa | 60 |
| caaggttaat ggtcaaaccc cgtgagtatc tctgctgaat | 100 |

<210> SEQ ID NO 1904
<211> LENGTH: 100
<212> TYPE: DNA
<213> ORGANISM: Homo sapiens

<400> SEQUENCE: 1904

| | |
|---|---|
| aagcaccatc tgattgtgtg ttttctggtg gctacaataa gctgattttt ggagcaggga | 60 |
| ccaggctggc tgtacaccca tgtgagtatg accctgcaag | 100 |

<210> SEQ ID NO 1905
<211> LENGTH: 97
<212> TYPE: DNA
<213> ORGANISM: Homo sapiens

<400> SEQUENCE: 1905

| | |
|---|---|
| tatgttggtt tatgtagaga cacataacac tgtgactacc tcaggaacct acaaatacat | 60 |
| ctttggaaca ggcaccaggc tgaaggtttt agcaagt | 97 |

<210> SEQ ID NO 1906
<211> LENGTH: 100

<212> TYPE: DNA
<213> ORGANISM: Homo sapiens

<400> SEQUENCE: 1906
ttagggagaa cgcactgtgg aactcaaatt ccgggtatgc actcaacttc ggcaaaggca    60
cctcgctgtt ggtcacaccc cgtgagtttt tgtggtttac                         100

<210> SEQ ID NO 1907
<211> LENGTH: 100
<212> TYPE: DNA
<213> ORGANISM: Homo sapiens

<400> SEQUENCE: 1907
agccccatag gactgtgtga attatggagg aagccaagga aatctcatct ttggaaaagg    60
cactaaactc tctgttaaac caagtaagtg ttggggattc                         100

<210> SEQ ID NO 1908
<211> LENGTH: 100
<212> TYPE: DNA
<213> ORGANISM: Homo sapiens

<400> SEQUENCE: 1908
ttgttagagc atgtattact gtgacaataa caatgacatg cgctttggag cagggaccag    60
actgacagta aaccaagta agttggggga atgggtcaat                          100

<210> SEQ ID NO 1909
<211> LENGTH: 94
<212> TYPE: DNA
<213> ORGANISM: Homo sapiens

<400> SEQUENCE: 1909
aggtttctgt tatgaagcat ctcacagtgt aaataccggc actgccagta aactcacctt    60
tgggactgga acaagacttc aggtcacgct cggt                               94

<210> SEQ ID NO 1910
<211> LENGTH: 100
<212> TYPE: DNA
<213> ORGANISM: Homo sapiens

<400> SEQUENCE: 1910
agggttggcc cagagtgtgt attcaggagg aggtgctgac ggactcacct ttggcaaagg    60
gactcatcta atcatccagc cctgtaagtg cttttgcctg                         100

<210> SEQ ID NO 1911
<211> LENGTH: 100
<212> TYPE: DNA
<213> ORGANISM: Homo sapiens

<400> SEQUENCE: 1911
aagctgctga cagccgtgag aagaaaagca gcggagacaa gctgactttt gggaccggga    60
ctcgtttagc agttaggccc agtaagtctg agcagaaagt                         100

<210> SEQ ID NO 1912
<211> LENGTH: 100
<212> TYPE: DNA
<213> ORGANISM: Homo sapiens

<400> SEQUENCE: 1912
gtagaggagt ttgacgctgt gtggaatatg gaaacaaact ggtctttggc gcaggaacca    60
ttctgagagt caagtcctgt gagtataaaa cacactcaag        100

<210> SEQ ID NO 1913
<211> LENGTH: 100
<212> TYPE: DNA
<213> ORGANISM: Homo sapiens

<400> SEQUENCE: 1913
gtgtactatt gcatctcggc cctggaatat ggaaacaagc tggtctttgg cgcaggaacc        60
attctgagag tcaagtccta tatccagaac cctgaccctg        100

<210> SEQ ID NO 1914
<211> LENGTH: 100
<212> TYPE: DNA
<213> ORGANISM: Homo sapiens

<400> SEQUENCE: 1914
atgacttaga acactgtgta tctaactttg gaaatgagaa attaacctttt gggactggaa        60 caagactcac catcataccc agtaagttct tcatccttgg        100

<210> SEQ ID NO 1915
<211> LENGTH: 100
<212> TYPE: DNA
<213> ORGANISM: Homo sapiens

<400> SEQUENCE: 1915
tgttgagctt cctatcacag tggaacaccg gtaaccagtt ctattttggg acagggacaa        60
gtttgacggt cattccaagt aagtcaaaga aaattttcca        100

<210> SEQ ID NO 1916
<211> LENGTH: 100
<212> TYPE: DNA
<213> ORGANISM: Homo sapiens

<400> SEQUENCE: 1916
tactgtgatg taccagggtg tggacacggg caggagagca cttacttttg ggagtggaac        60
aagactccaa gtgcaaccaa gtaagtaccc aaacttaggc        100

<210> SEQ ID NO 1917
<211> LENGTH: 100
<212> TYPE: DNA
<213> ORGANISM: Homo sapiens

<400> SEQUENCE: 1917
taaaggtttg gatggctgtg tgaaaacctc ctacgacaag gtgatatttg ggccagggac        60
aagcttatca gtcattccaa gtaagtgtcc ctggggtgct        100

<210> SEQ ID NO 1918
<211> LENGTH: 100
<212> TYPE: DNA
<213> ORGANISM: Homo sapiens

<400> SEQUENCE: 1918
aaactccctg aagcagggag atgcgtgaca gctatgagaa gctgatattt ggaaaggaga        60
catgactaac tgtgaagcca agcaagctgg aaagacctaa        100

<210> SEQ ID NO 1919
<211> LENGTH: 100
<212> TYPE: DNA
<213> ORGANISM: Homo sapiens

<400> SEQUENCE: 1919
gcctccagtg cagtgctaat gctggtggta ctagctatgg aaagctgaca tttggacaag   60
ggaccatctt gactgtccat ccaagtaagt gtaacaagac                        100

<210> SEQ ID NO 1920
<211> LENGTH: 100
<212> TYPE: DNA
<213> ORGANISM: Homo sapiens

<400> SEQUENCE: 1920
agccttctgt ggctgtgaga atagtggagg tagcaactat aaactgacat ttggaaaagg   60
aactctctta accgtgaatc caagtaagtt tgaagggagt                        100

<210> SEQ ID NO 1921
<211> LENGTH: 100
<212> TYPE: DNA
<213> ORGANISM: Homo sapiens

<400> SEQUENCE: 1921
taaagcctcg tgctgtggtg taattcaggg agcccagaag ctggtatttg gccaaggaac   60
caggctgact atcaacccaa gtaagtatga cagggtgaag                        100

<210> SEQ ID NO 1922
<211> LENGTH: 100
<212> TYPE: DNA
<213> ORGANISM: Homo sapiens

<400> SEQUENCE: 1922
gaggatggat ccctgttagt gacaagtgct ggtaatgctc ctgttgggga aagggatga   60 gtacaaaaat aaatccaagt aagtgtggag ggacaagaag                        100

<210> SEQ ID NO 1923
<211> LENGTH: 100
<212> TYPE: DNA
<213> ORGANISM: Homo sapiens

<400> SEQUENCE: 1923
agatcctcgt gtcattgtgt tatactggag ccaatagtaa gctgacattt ggaaaaggaa   60
taactctgag tgttagacca ggtatgtttt aatgaatgtt                        100

<210> SEQ ID NO 1924
<211> LENGTH: 100
<212> TYPE: DNA
<213> ORGANISM: Homo sapiens

<400> SEQUENCE: 1924
aagcagtctg tgggggtgta actcagggcg gatctgaaaa gctggtcttt ggaaagggaa   60
cgaaactgac agtaaaccca tgtaagtctg aataatgctt                        100

<210> SEQ ID NO 1925
<211> LENGTH: 100
<212> TYPE: DNA
<213> ORGANISM: Homo sapiens

<400> SEQUENCE: 1925 aagccccctca gcacagtgtt taagaaacca gtggctctag gttgacccttt ggggaaggaa   60 cacagctcac agtgaatcct ggtaagtgga ggggagcatt                        100

<210> SEQ ID NO 1926
<211> LENGTH: 100
<212> TYPE: DNA
<213> ORGANISM: Homo sapiens

<400> SEQUENCE: 1926
atgtaaaggc agcagctcct gtgggaagga aggaaacagg aaatttacat ttggaatggg    60
gacgcaagtg agagtgaagc tatctttaaa ccaaaggtgt                         100

<210> SEQ ID NO 1927
<211> LENGTH: 98
<212> TYPE: DNA
<213> ORGANISM: Homo sapiens

<400> SEQUENCE: 1927
caggttttat caaaggctgt cctcactgtg tgcatcagga ggaagctaca tacctacatt    60
tggaagagga accagcctta ttgttcatcc gtgtaagt                            98

<210> SEQ ID NO 1928
<211> LENGTH: 100
<212> TYPE: DNA
<213> ORGANISM: Homo sapiens

<400> SEQUENCE: 1928
gtaaagggcc tgggcactat gtgaagatca cctagatgct caactttggg aaggggactg    60
agttaattgt gagcctgggt gagtacctca actccagagg                         100

<210> SEQ ID NO 1929
<211> LENGTH: 100
<212> TYPE: DNA
<213> ORGANISM: Homo sapiens

<400> SEQUENCE: 1929
taaaggtgcc cactcctgtg ggtaccgggt taataggaaa ctgacatttg agccaacac     60 tagaggaatc atgaaactca gcaagtaata tttggcagaa                         100

<210> SEQ ID NO 1930
<211> LENGTH: 100
<212> TYPE: DNA
<213> ORGANISM: Homo sapiens

<400> SEQUENCE: 1930
tgtaatacac ttacacagtg tgactatggg aacaacagac tcgcttttgg gaaggggaac    60
caagtggtgg tcataccaag taagtgagct gggatcctcc                         100

<210> SEQ ID NO 1931
<211> LENGTH: 100
<212> TYPE: DNA
<213> ORGANISM: Homo sapiens

<400> SEQUENCE: 1931
tacagagtta tgtcagagtg tgaacacagg ctttcagaaa cttgtatttg gaactggcac    60
ccgacttctg gtcagtccaa gtaagtcaaa tctgcagaaa                         100

<210> SEQ ID NO 1932
<211> LENGTH: 100
<212> TYPE: DNA
<213> ORGANISM: Homo sapiens

<400> SEQUENCE: 1932
cgcagtgcaa atcactgtgg gaaatactgg aggcttcaaa actatctttg gagcaggaac     60
aagactattt gttaaagcaa gtaagttcca tgaaataacc                          100

<210> SEQ ID NO 1933
<211> LENGTH: 100
<212> TYPE: DNA
<213> ORGANISM: Homo sapiens

<400> SEQUENCE: 1933
ttttcacctt gacccctgtc actgtgtgaa cactgaagct ttctttggac aaggcaccag     60
actcacagtt gtaggtaaga cattttttcag gttcttttgc                          100

<210> SEQ ID NO 1934
<211> LENGTH: 100
<212> TYPE: DNA
<213> ORGANISM: Homo sapiens

<400> SEQUENCE: 1934
ttttagagtg gctatattct tatgtgctaa ctatggctac accttcggtt cggggaccag     60
gttaaccgtt gtaggtaagg ctgggggtct ctaggagggg                          100

<210> SEQ ID NO 1935
<211> LENGTH: 100
<212> TYPE: DNA
<213> ORGANISM: Homo sapiens

<400> SEQUENCE: 1935
tttgaagtgg ccctgggagg ctgtgctctg gaaacaccat atattttgga gagggaagtt     60
ggctcactgt tgtaggtgag taagtcaagg ctggacagct                          100

<210> SEQ ID NO 1936
<211> LENGTH: 100
<212> TYPE: DNA
<213> ORGANISM: Homo sapiens

<400> SEQUENCE: 1936
ttccttccag tctttaatgt tgtgcaacta atgaaaaact gttttttggc agtggaaccc     60
agctctctgt cttgggtatg taaaagactt ctttcgggat                          100

<210> SEQ ID NO 1937
<211> LENGTH: 100
<212> TYPE: DNA
<213> ORGANISM: Homo sapiens

<400> SEQUENCE: 1937
tttgccacac tcatgatgca ctgtgtagca atcagcccca gcattttggt gatgggactc     60
gactctccat cctaggtaag ttggcagaat cagggtggta                          100

<210> SEQ ID NO 1938
<211> LENGTH: 100
<212> TYPE: DNA
<213> ORGANISM: Homo sapiens

<400> SEQUENCE: 1938
ttatctaagc ctctgcagct gtgctcctat aattcacccc tccactttgg gaatgggacc     60
aggctcactg tgacaggtat gggggctcca ctcttgactc                          100

<210> SEQ ID NO 1939

<211> LENGTH: 100
<212> TYPE: DNA
<213> ORGANISM: Homo sapiens

<400> SEQUENCE: 1939

```
ttatctaagc ctctgcagct gtgctcctat aattcacccc tccactttgg gaacgggacc      60
aggctcactg tgacaggtat gggggctcca ctcttgactc                           100
```

<210> SEQ ID NO 1940
<211> LENGTH: 100
<212> TYPE: DNA
<213> ORGANISM: Homo sapiens

<400> SEQUENCE: 1940

```
ttctgggcag ccccttccca ctgtgctcct acaatgagca gttcttcggg ccagggacac      60
ggctcaccgt gctaggtaag aaggggctc caggtgggag                            100
```

<210> SEQ ID NO 1941
<211> LENGTH: 100
<212> TYPE: DNA
<213> ORGANISM: Homo sapiens

<400> SEQUENCE: 1941

```
tgcgccaggg tccccagggc tgtgcgaaca ccggggagct gttttttgga gaaggctcta      60
ggctgaccgt actgggtaag gaggcggctg gggctccgga                           100
```

<210> SEQ ID NO 1942
<211> LENGTH: 100
<212> TYPE: DNA
<213> ORGANISM: Homo sapiens

<400> SEQUENCE: 1942

```
agctgcccca ctctgagagg ggctgtgctg agaggcgctg ctgggcgtct gggcggagga      60
ctcctggttc tgggtgctgg gagagcgatg gggctctcag                           100
```

<210> SEQ ID NO 1943
<211> LENGTH: 100
<212> TYPE: DNA
<213> ORGANISM: Homo sapiens

<400> SEQUENCE: 1943

```
ttttgtcctg ggcctccagg ctgtgagcac agatacgcag tattttggcc caggcacccg      60
gctgacagtg ctcggtaagc gggggctccc gctgaagccc                           100
```

<210> SEQ ID NO 1944
<211> LENGTH: 100
<212> TYPE: DNA
<213> ORGANISM: Homo sapiens

<400> SEQUENCE: 1944

```
ttctgtgccg cgtctcgggg ctgtgagcca aaaacattca gtacttcggc gccgggaccc      60
ggctctcagt gctgggtaag ctggggccgc cgggggaccg                           100
```

<210> SEQ ID NO 1945
<211> LENGTH: 100
<212> TYPE: DNA
<213> ORGANISM: Homo sapiens

<400> SEQUENCE: 1945

```
tttttgtgcg gggctcgggg gccgtgacca agagacccag tacttcgggc caggcacgcg      60
```

```
gctcctggtg ctcggtgagc gcgggctgct ggggcgcggg                  100
```

<210> SEQ ID NO 1946
<211> LENGTH: 100
<212> TYPE: DNA
<213> ORGANISM: Homo sapiens

<400> SEQUENCE: 1946

```
ttgcggggag tccccgggct gtgctctggg gccaacgtcc tgactttcgg ggccggcagc   60
aggctgaccg tgctgggtga gttttcgcgg gaccacccgg                        100
```

<210> SEQ ID NO 1947
<211> LENGTH: 100
<212> TYPE: DNA
<213> ORGANISM: Homo sapiens

<400> SEQUENCE: 1947

```
tttgcatgcg ggggtgcacc tccgtgctcc tacgagcagt acttcgggcc gggcaccagg   60
ctcacggtca caggtgagat tcgggcgtct ccccaccttc                        100
```

<210> SEQ ID NO 1948
<211> LENGTH: 100
<212> TYPE: DNA
<213> ORGANISM: Homo sapiens

<400> SEQUENCE: 1948

```
tttgcatgcg gggatgcacc tccgtgctcc tacgagcagt acgtcgggcc gggcaccagg   60
ctcacggtca caggtgagat tcgggcgtct ccccaccttc                        100
```

<210> SEQ ID NO 1949
<211> LENGTH: 100
<212> TYPE: DNA
<213> ORGANISM: Homo sapiens

<400> SEQUENCE: 1949

```
ttttggaacg tcctcaagtg ctgtgacacc gataaactca tctttggaaa aggaacccgt   60
gtgactgtgg aaccaagtaa gtaactcatt atttatctga                        100
```

<210> SEQ ID NO 1950
<211> LENGTH: 100
<212> TYPE: DNA
<213> ORGANISM: Homo sapiens

<400> SEQUENCE: 1950

```
tttttcgtaa tgacgcctgt ggtagtgctt tgacagcaca actcttcttt ggaaagggaa   60
cacaactcat cgtggaacca ggtaagttat gcattttact                        100
```

<210> SEQ ID NO 1951
<211> LENGTH: 100
<212> TYPE: DNA
<213> ORGANISM: Homo sapiens

<400> SEQUENCE: 1951

```
tgaggcactg tcataatgtg ctcctgggac acccgacaga tgttttttcgg aactggcatc   60 aaactcttcg tggagccccg tgagttgatc ttttttcctat                        100
```

<210> SEQ ID NO 1952
<211> LENGTH: 76
<212> TYPE: DNA

<213> ORGANISM: Homo sapiens

<400> SEQUENCE: 1952
atgagacata caaaaaggta atgccgcccc agacccctga tctttggcaa aggaacctat    60
ctggaggtac aacaac    76

<210> SEQ ID NO 1953
<211> LENGTH: 100
<212> TYPE: DNA
<213> ORGANISM: Homo sapiens

<400> SEQUENCE: 1953
ttttgatatg gactgaatca ctgtggaatt attataagaa actctttggc agtggaacaa    60
cactggttgt cacaggtaag tatcggaaga atacaacatt    100

<210> SEQ ID NO 1954
<211> LENGTH: 71
<212> TYPE: DNA
<213> ORGANISM: Homo sapiens

<400> SEQUENCE: 1954
tactgtgcct tgtgggaggt gcttattata agaaactctt tggcagtgga acaacacttg    60
ttgtcacagg t    71

<210> SEQ ID NO 1955
<211> LENGTH: 100
<212> TYPE: DNA
<213> ORGANISM: Homo sapiens

<400> SEQUENCE: 1955
ttttgatatg gactgaatca ctgtggaatt attataagaa actctttggc agtggaacaa    60
cacttgttgt cacaggtaag tatcggaaga atacaacatt    100

<210> SEQ ID NO 1956
<211> LENGTH: 100
<212> TYPE: DNA
<213> ORGANISM: Homo sapiens

<400> SEQUENCE: 1956
ataaaggctt ctcaggtggt gggcaagagt tgggcaaaaa aatcaaggta tttggtcccg    60
gaacaaagct tatcattaca ggtaagtttt ctttaaattt    100

<210> SEQ ID NO 1957
<211> LENGTH: 94
<212> TYPE: DNA
<213> ORGANISM: Homo sapiens

<400> SEQUENCE: 1957 gattttcta gaagcttaga ccggtgtgat accactggtt ggttcaagat atttgctgaa    60
gggactaagc tcatagtaac ttcacctggt aagt    94

<210> SEQ ID NO 1958
<211> LENGTH: 94
<212> TYPE: DNA
<213> ORGANISM: Homo sapiens

```
<400> SEQUENCE: 1958
gatttttgta gaagcttaga ccagtgtgat agtagtgatt ggatcaagac gtttgcaaaa         60
gggactaggc tcatagtaac ttcgcctggt aagt                                    94
```